United States Patent
Rudd et al.

(10) Patent No.: US 10,752,587 B2
(45) Date of Patent: Aug. 25, 2020

(54) HOMOBISPIPERIDINYL DERIVATIVES AS LIVER X RECEPTOR BETA AGONISTS, COMPOSITIONS AND THEIR USE

(71) Applicant: Merck Sharp & Dohme Corp., Rahway, NJ (US)

(72) Inventors: Michael T. Rudd, Collegeville, PA (US); David Jonathan Bennett, Winchester, MA (US); Jenny Wai, Harleysville, PA (US); Zhaoyang Meng, Ambler, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/780,289

(22) PCT Filed: Nov. 29, 2016

(86) PCT No.: PCT/US2016/063891
§ 371 (c)(1),
(2) Date: May 31, 2018

(87) PCT Pub. No.: WO2017/095758
PCT Pub. Date: Jun. 8, 2017

(65) Prior Publication Data
US 2018/0354901 A1     Dec. 13, 2018

Related U.S. Application Data
(60) Provisional application No. 62/261,462, filed on Dec. 1, 2015.

(51) Int. Cl.
| | |
|---|---|
| C07D 211/16 | (2006.01) |
| C07D 401/14 | (2006.01) |
| C07D 409/14 | (2006.01) |
| C07D 401/06 | (2006.01) |
| C07D 487/08 | (2006.01) |
| C07D 413/14 | (2006.01) |
| C07D 451/02 | (2006.01) |
| C07D 417/14 | (2006.01) |
| C07D 211/46 | (2006.01) |
| C07D 211/10 | (2006.01) |
| C07D 211/54 | (2006.01) |
| C07D 211/44 | (2006.01) |

(52) U.S. Cl.
CPC .......... *C07D 211/16* (2013.01); *C07D 211/10* (2013.01); *C07D 211/44* (2013.01); *C07D 211/46* (2013.01); *C07D 211/54* (2013.01); *C07D 401/06* (2013.01); *C07D 401/14* (2013.01); *C07D 409/14* (2013.01); *C07D 413/14* (2013.01); *C07D 417/14* (2013.01); *C07D 451/02* (2013.01); *C07D 487/08* (2013.01)

(58) Field of Classification Search
None
See application file for complete search history.

(56) References Cited

U.S. PATENT DOCUMENTS

| | | | | |
|---|---|---|---|---|
| 6,255,302 | B1 * | 7/2001 | Kelly | C07D 211/26 514/217.05 |
| 7,449,464 | B2 * | 11/2008 | Martin | A61K 31/00 514/218 |
| 7,638,631 | B2 | 12/2009 | Bruton et al. | |
| 2005/0267095 | A1 | 12/2005 | Bemardelli et al. | |
| 2010/0249098 | A1 | 9/2010 | Chao et al. | |

FOREIGN PATENT DOCUMENTS

| | | |
|---|---|---|
| WO | 2005014571 A1 | 2/2005 |
| WO | 2006014136 A1 | 5/2006 |
| WO | 2017083216 A1 | 5/2017 |
| WO | 2017083219 A1 | 5/2017 |
| WO | 2018071313 A1 | 4/2018 |
| WO | 2018071317 A1 | 4/2018 |
| WO | 2918071315 A2 | 4/2018 |

OTHER PUBLICATIONS

Youssef et al. Medicinal Chemistry Research (2011), 20(7), 898-911. (Year: 2011).*
International Search Report for PCT/US16/063891 dated Apr. 10, 2017, 10 pages.
Loren, J, Liver X receptor modulators: a review of recently patented compounds (2009-2012), Expert Opin. Ther. Patents, 2013, 1317-1335, vol. 23, No. 10.

* cited by examiner

*Primary Examiner* — Kamal A Saeed
(74) *Attorney, Agent, or Firm* — Sylvia A. Ayler; Catherine D. Fitch

(57) ABSTRACT

In its many embodiments, the present invention provides certain substituted bispiperidinyl compounds of the Formula (I): and pharmaceutically acceptable salts thereof, wherein ring A, ring B, $R^1$, $R^2$, $R^3$, L, $R^4$, X, Z, $L_i$, Q and R5 are as defined herein. The novel compounds of the invention, and pharmaceutically acceptable compositions comprising a compound thereof, are useful as Liver X-β receptor (LXRβ) agonists, and may be useful for treating or preventing pathologies related thereto. Such pathologies include, but are not limited to, inflammatory diseases and diseases characterized by defects in cholesterol and lipid metabolism, such as Alzheimer's disease.

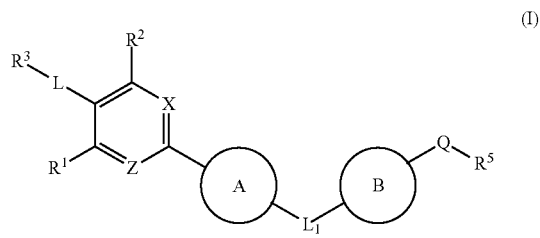

(I)

10 Claims, No Drawings

HOMOBISPIPERIDINYL DERIVATIVES AS LIVER X RECEPTOR BETA AGONISTS, COMPOSITIONS AND THEIR USE

FIELD OF THE INVENTION

The present invention provides certain compounds of formula (I), and compositions comprising these compounds, as Liver X-β receptor (LXRβ) agonists, which may be useful for treating or preventing pathologies related thereto. Such pathologies include, but are not limited to, inflammatory diseases and diseases characterized by defects in cholesterol and lipid metabolism, such as Alzheimer's disease.

BACKGROUND OF THE INVENTION

Alzheimer's disease is a common neurodegenerative disease affecting the elderly, resulting in progressive memory impairment, loss of language and visuospatial skills, and behavior deficits. Clinical, genetic, epidemiological and biochemical evidence suggest that dysfunctional cholesterol metabolism is implicated in the pathogenesis of Alzheimer's Disease. Hypercholesterolemia and low levels of high density lipoprotein are well-established risk factors for Alzheimer's Disease. It has been suggested that vascular, genetic and amyloid factors, in combination with diet and lifestyle, contribute to the cause and progression of Alzheimer's Disease. Hooijmans et al, *Eur J Pharmacol* 585 (2008), 176-196.

The liver X receptor (LXR) is a member of the nuclear receptor family of transcription factors, and is a part of the cholesterol regulation pathway. There are two identified isoforms of LXRs. LXRα is found in liver, intestine and in macrophages, while LXRβ is widely expressed in many tissues and is considered a ubiquitous receptor. Typically, the activity of nuclear receptors is controlled by small lipophilic moieties, such as hormones, fatty acids, bile acids, cholesterol precursors and oxysterols. Lala, *Curr Opinions Invest Drugs* 2005, 6:934-943. Cholesterol precursors such as desmosterol and oxysterols are known to bind and activate LXRs.

LXRs have demonstrated a role in the physiological metabolism of lipid and cholesterol, and thus are believed to have an important role in metabolic disorders such as hyperlipidemia and atherosclerosis. Activation of LXRs reduces cholesterol absorption, thereby reducing the ability of the body to take up cholesterol. Consistently, deletion of LXRs in mice leads to impaired cholesterol and bile acid metabolism. See Peet et al, *Cell* 1998, 93(5): 693-704. Activation of LXRs also increase peripheral cholesterol efflux systems, and impact the elimination of cholesterol by regulating cholesterol excretion into bile. See Cao et al, *Drug News Perspect* 20004, 17(1), 35-41.

LXRs also regulate lipid homeostasis in the brain. The connection between metabolic disorders and Alzheimer's Disease suggests that LXRs may have a role in the Alzheimer's disease pathway. Activation of LXRs also inhibit inflammation and pro-inflammatory expression in the body. Zelcer et al, *J Clin Invest* 2006, 116:3 (607-614). Thus, LXRs may serve as targets for the treatment of inflammatory diseases. However, activation of hepatic LXRα is believed to be the underlying cause of liver steatosis and hyperlipidemia associated with dual LXRα/β small agonist molecules developed to date.

LXRs have also been proposed as possible therapeutics to treat a number of cancers e.g. prostate, breast, ovarian, melanoma, pancreas, lung, colon and hematological malignancy (Lin, C—Y and Gustafsson, J-A, (2015) Nature Reviews Cancer 15, 216-224).

LXRβ is the predominant brain isoform. See Song et al, *Ann NY Acad Sci* 195, 761:38-49. LXRβ knockout male mice demonstrated adult-onset motor neuron degeneration. (Andersson et al, *Proc Natt Acad Sci USA* 2005, 8; 1902 (1)):3857-3862), and the LXRα and LXRβ double knockout mice develop neurodegenerative changes in brain tissue. (Wang et al, Proc Natl Acad Sci USA. 2002, 99(21):13878-83). Therefore development of selective LXRβ agonists could be a therapeutic approach to neurodegenerative diseases such as AD and avoid the peripheral adverse lipid effects that have been linked to LXRα.

Applicants have now discovered a series of LXRβ selective agonists. Thus, the compounds of the invention, which are selective LXRβ agonists, may be useful in the treatment of Alzheimer's disease, inflammatory diseases, and diseases characterized by defects in cholesterol and lipid metabolism.

SUMMARY OF THE INVENTION

The present invention provides certain compounds, which are collectively or individually referred to herein as "compound(s) of the invention", as described herein. The compounds of the invention are selective agonists of LXRβ, and may be useful for treating or preventing diseases or pathologies related thereto.

In one embodiment, the compounds of the invention have the structural Formula (I):

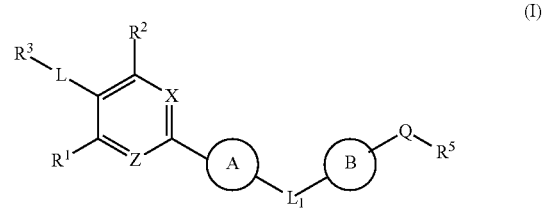

or a pharmaceutically acceptable salt thereof, wherein:

ring A is

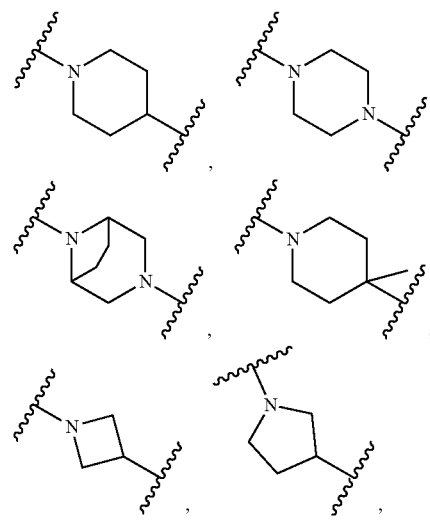

-continued

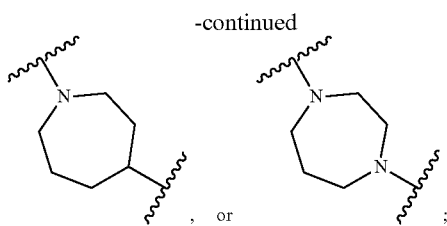
, or ;

ring B is

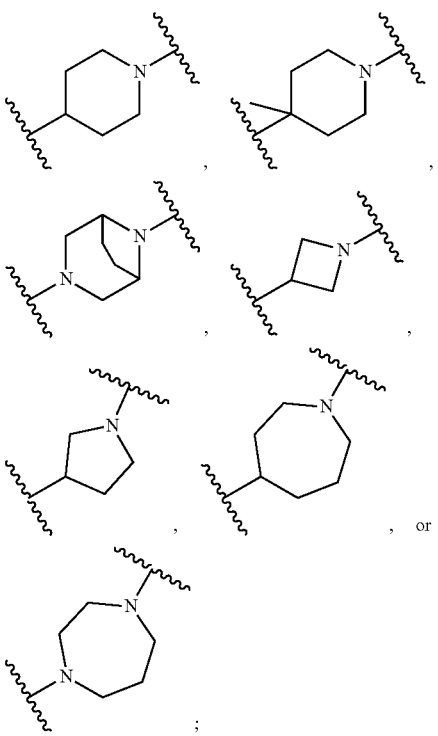
;

-L$_1$- is —CH$_2$—, —CH$_2$CH$_2$—, —C(O)—, —O—, or —S—;

R$^1$ is selected from the group consisting of H, methyl, and halogen;

R$^2$ is selected from the group consisting of H, —S(O)$_2$(C$_1$-C$_6$alkyl), and halogen;

X is selected from the group consisting of —N— and —CH—;

Z is selected from the group consisting of N and C(R$^4$);

R$^4$ is selected from the group consisting of H and methyl;

L is a bond and R$^3$ is selected from the group consisting of H, —(C$_1$-C$_6$)alkyl and —(C$_1$-C$_6$)alkyl-OH;

or, alternatively, L is a divalent moiety selected from the group consisting of —C(O)— and —S(O)$_2$—; and R$^3$ is —N(R$^{N1}$)(R$^{N2}$), wherein:

R$^{N1}$ is selected from the group consisting of H and —(C$_1$-C$_6$)alkyl; and R$^{N2}$ is selected from the group consisting of: H, —(C$_1$-C$_6$)alkyl, —O—(C$_1$-C$_6$)alkyl, —OH, halogen, —CN, and —(C$_1$-C$_6$)alkyl which is substituted with 1 or 2 groups independently selected from the group consisting of:
—OH, halogen, —CN,
—NH$_2$, —NH(C$_1$-C$_6$alkyl, —N((C$_1$-C$_6$)alkyl)$_2$, optionally substituted phenyl, (wherein said optional substitutents on said phenyl are 1 to 3 groups independently selected from OH, CN, —(C$_1$-C$_4$)alkyl, —(C$_1$-C$_4$)alkoxyl), optionally substituted heteroaryl, (wherein said optional substituents on said heteroaryl are 1 to 3 groups independently selected from —(C$_1$-C$_6$)alkyl, —(C$_1$-C$_4$)alkoxyl, and cyclopropyl), optionally substituted cyclopropyl (wherein said optional substituents on said cyclopropyl are 1 to 3 groups independently selected from —(C$_1$-C$_6$)alkyl), and optionally substituted heterocycloalkyl (wherein said optional substitutents on said heterocycloalkyl are 1 to 3 groups independently selected from halogen, —OH, oxo, CN, and —(C$_1$-C$_6$)alkyl, or, alternatively, R$^{N1}$ and R$^{N2}$ are taken together with the nitrogen atom to which they are shown attached to form a 4-, 5-, or 6-membered fully saturated heterocyclic ring comprising (including said nitrogen atom) 1, 2, or 3 ring heteroatoms selected from the group consisting of N, N-oxide, O, S, and S-oxide, wherein said heterocyclic ring is unsubstituted or substituted with 1, 2, or 3 substituents independently selected from the group consisting of halogen, —OH, oxo, CN, —(C$_1$-C$_6$)alkyl, amino-substituted —(C$_1$-C$_6$)alkyl (wherein said amino is 1, 2, or 3 groups independently selected from the group consisting of —NH$_2$, —N(C$_1$-C$_4$alkyl)$_2$, and —NH(C$_1$-C$_4$alkyl)), —O—(C$_1$-C$_6$)alkyl, —(C$_1$-C$_6$)alkyl-OH, —(C$_1$-C$_6$)haloalkyl, —C(O)O—(C$_1$-C$_6$)alkyl, cyclopropyl, spirocyclopropyl, —NHC(O)O—(C$_1$-C$_6$)alkyl, —CH$_2$—NHC(O)O—(C$_1$-C$_6$)alkyl, —CH$_2$—N(CH$_3$)C(O)O—(C$_1$-C$_6$)alkyl, phenyl, benzyl, —NHC(O)-phenyl, heteroaryl, and —(C$_1$-C$_4$)alkylheteroaryl, heterocycloalkyl;

Q is a bond or a divalent moiety selected from the group consisting of —C(O)—, —S(O)$_2$—, and —C(O)O—; and R$^5$ is selected from the group consisting of:
—C(R$^{5A}$)(R$^{5B}$)(R$^{5C}$), wherein:
each of R$^{5A}$ and R$^{5B}$ and R$^{5C}$ is independently selected from the group consisting of: H, halogen, OH, NH$_2$, —(C$_1$-C$_6$)alkyl, —(C$_1$-C$_6$)haloalkyl, —(C$_1$-C$_6$)alkenyl, —(C$_1$-C$_6$)alkynyl, —(C$_3$-C$_6$)cycloalkyl, —(C$_3$-C$_6$)cycloalkyl substituted with —(C$_1$-C$_6$)alkyl, —(C$_1$-C$_6$)alkenyl, —(C$_1$-C$_6$)alkynyl, phenyl, —C(O)phenyl, heteroaryl, heterocycloalkyl, and aryl,
wherein said phenyl, said —C(O)phenyl, said heteroaryl, said heterocycloalkyl, and said aryl are unsubstituted or substituted with from 1, 2, or 3 groups independently selected from halogen, CN, —(C$_1$-C$_6$)alkyl, —(C$_1$-C$_6$)haloalkyl, —O—(C$_1$-C$_6$)alkyl, —O—(C$_1$-C$_6$)haloalkyl, —C(O)O—(C$_1$-C$_6$)alkyl, and —N(C$_1$-C$_6$alkyl)$_2$,

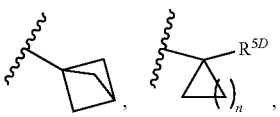
, wherein:
n is an integer from 1 to 4; and R$^{5D}$ is selected from the group consisting of H, —(C$_1$-C$_6$)alkyl, —(C$_1$-C$_6$)haloalkyl, phenyl, and phenyl substituted with from 1 to 3 groups independently selected from the group consisting of OH, halogen, —(C$_1$-C$_6$)alkyl, and —O—(C$_1$-C$_6$)alkyl, and phenyl, benzyl, or thienyl, wherein:
said phenyl and said benzyl are unsubstituted or substituted with 1, 2, or 3 groups, and wherein said thienyl is unsubstituted or substituted with 1 or 2 groups, independently selected from the group consisting of halogen, CN, —($C_1$-$C_6$)alkyl, —O—$C_1$-$C_6$)alkyl, —($C_1$-$C_6$)haloalkyl, and —O—($C_1$-$C_6$)haloalkyl.

In other embodiments, the invention provides compositions, including pharmaceutical compositions, comprising one or more compounds of the invention (e.g., one compound of the invention) or a pharmaceutically acceptable salt thereof, optionally together with one or more additional therapeutic agents, optionally in an acceptable (e.g., pharmaceutically acceptable) carrier or diluent.

In another embodiment, the invention is directed to methods of treating an inflammatory diseases or a disease characterized by defects in cholesterol or lipid metabolism, in a patient in need thereof by administering to the patient a compound of the invention or a pharmaceutically acceptable salt thereof. Non-limiting examples of such inflammatory diseases and diseases characterized by defects in cholesterol or lipid metabolism are described below.

In another embodiment, the invention provides for the use of a compound of the invention in the manufacture of a medicament for treating an inflammatory disease or a disease characterized by defects in cholesterol or lipid metabolism in a patient in need thereof. Non-limiting examples of such inflammatory diseases and diseases characterized by defects in cholesterol or lipid metabolism are described below.

In another embodiment, the invention is directed to a method of treating cancer in a patient in need thereof comprising administering to the patient a compound of the invention or a pharmaceutically acceptable salt thereof. Such cancers include prostate, breast, ovarian, melanoma, pancreas, lung, colon and hematological malignancy.

In another embodiment, the invention provides for the use of a compound of the invention in the manufacture of a medicament for treating cancer in a patient in need thereof comprising administering to the patient a compound of the invention or a pharmaceutically acceptable salt thereof. Such cancers include prostate, breast, ovarian, melanoma, pancreas, lung, colon and hematological malignancy.

In another embodiment, the invention provides for the use of any of the compounds of the invention for use as a medicament, or in medicine, or in therapy.

These and other embodiments of the invention, which are described in detail below or will become readily apparent to those of ordinary skill in the art, are included within the scope of the invention.

DETAILED DESCRIPTION

For each of the following embodiments, any variable not explicitly defined in the embodiment is as defined in Formula (I). In each of the embodiments described herein, each variable is selected independently of the other unless otherwise noted.

In one embodiment, the compounds of the invention have the structural Formula (I) as described above, and pharmaceutically acceptable salts thereof.

In another embodiment, the compounds of the invention have a structural Formula (II)

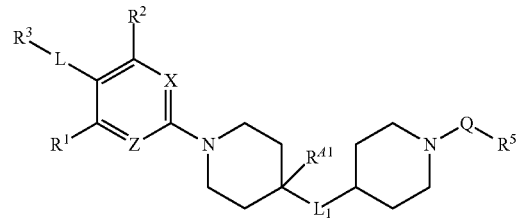

(II)

or a pharmaceutically acceptable salt thereof, wherein:
-$L_1$- is —$CH_2$—, —$CH_2CH_2$—, —O—, or —S—;
$R^{41}$ is H or $CH_3$; and $R^1$, $R^2$, L, $R^3$, $R^4$, Q, and $R^5$ are each as defined in Formula (I).

In an alternative of the immediately preceding embodiment, $R^{41}$ is H. In another alternative of the immediately preceding embodiment, $R^{41}$ is $CH_3$.

In another embodiment, the compounds of the invention have a structural Formula (III)

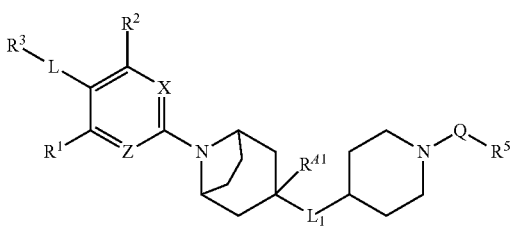

(III)

or a pharmaceutically acceptable salt thereof, wherein:
-$L_1$- is —$CH_2$—, —$CH_2CH_2$—, —O—, or —S—;
$R^{41}$ is H or $CH_3$; and $R^1$, $R^2$, L, $R^3$, $R^4$, Q, and $R^5$ are each as defined in Formula (I).

In an alternative of the immediately preceding embodiment, $R^{41}$ is H. In another alternative of the immediately preceding embodiment, $R^{41}$ is $CH_3$.

In another embodiment, the compounds of the invention have a structural Formula (IV)

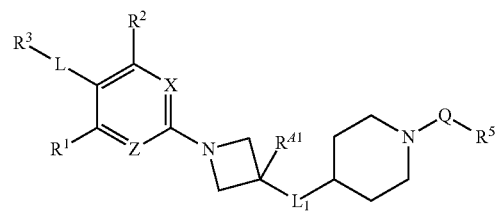

(IV)

or a pharmaceutically acceptable salt thereof, wherein:
-$L_1$- is —$CH_2$—, —$CH_2CH_2$—, —O—, or —S—;
$R^{41}$ is H or $CH_3$;
and $R^1$, $R^2$, L, $R^3$, $R^4$, Q, and $R^5$ are each as defined in Formula (I).

In an alternative of the immediately preceding embodiment, $R^{41}$ is H. In another alternative of the immediately preceding embodiment, $R^{41}$ is $CH_3$.

In another embodiment, the compounds of the invention have a structural Formula (V)

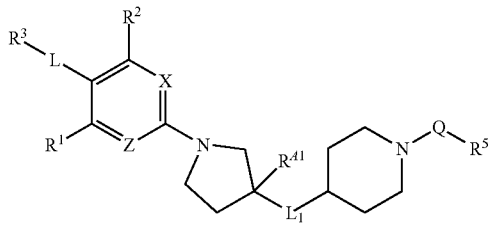

(V)

or a pharmaceutically acceptable salt thereof, wherein:
-$L_1$- is —$CH_2$—, —$CH_2CH_2$—, —O—, or —S—;
$R^{41}$ is H or $CH_3$;
and $R^1$, $R^2$, L, $R^3$, $R^4$, Q, and $R^5$ are each as defined in Formula (I).

In an alternative of the immediately preceding embodiment, $R^{41}$ is H. In another alternative of the immediately preceding embodiment, $R^{41}$ is $CH_3$.

In another embodiment, the compounds of the invention have a structural Formula (VI):

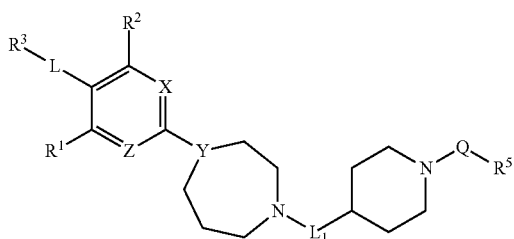

(VI)

or a pharmaceutically acceptable salt thereof, wherein:
-$L_1$- is —$CH_2$—, —$CH_2CH_2$—, —O—, or —S—;
Y is $CR^{41}$ or N;
$R^{41}$ is H or $CH_3$;
and $R^1$, $R^2$, L, $R^3$, $R^4$, Q, and $R^5$ are each as defined in Formula (I).

In an alternative of the immediately preceding embodiment, Y is N.

In another alternative of the immediately preceding embodiment, Y is $CR^{41}$; and $R^{41}$ is H. In another alternative of the immediately preceding embodiment, Y is $C(CH_3)$.

In another embodiment, the compounds of the invention have a structural Formula (VII)

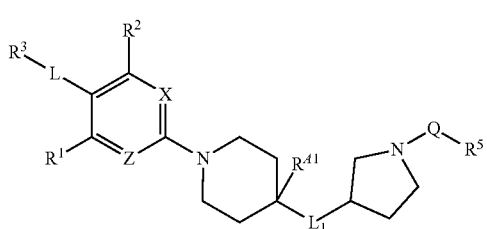

(VII)

or a pharmaceutically acceptable salt thereof, wherein:
-$L_1$- is —$CH_2$—, —$CH_2CH_2$—, —O—, or —S—;
$R^{41}$ is H or $CH_3$; and $R^1$, $R^2$, L, $R^3$, $R^4$, Q, and $R^5$ are each as defined in Formula (I).

In an alternative of the immediately preceding embodiment, $R^{41}$ is H. In another alternative of the immediately preceding embodiment, $R^{41}$ is $CH_3$.

In another embodiment, the compounds of the invention have a structural Formula (VIII)

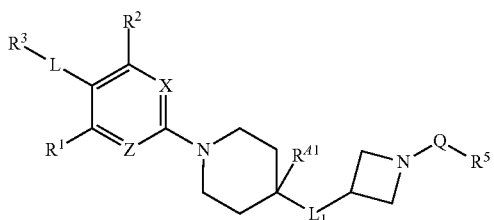

(VIII)

or a pharmaceutically acceptable salt thereof, wherein:
-$L_1$- is —$CH_2$—, —$CH_2CH_2$—, —O—, or —S—;
$R^{41}$ is H or $CH_3$; and $R^1$, $R^2$, L, $R^3$, $R^4$, Q, and $R^5$ are each as defined in Formula (I).

In an alternative of the immediately preceding embodiment, $R^{41}$ is H. In another alternative of the immediately preceding embodiment, $R^{41}$ is $CH_3$.

In another embodiment, the compounds of the invention have a structural Formula (IX)

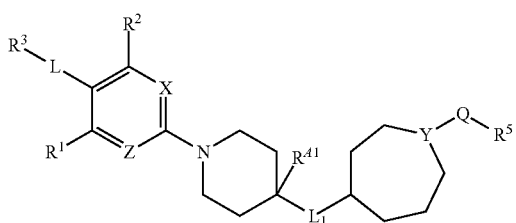

(IX)

or a pharmaceutically acceptable salt thereof, wherein:
-$L_1$- is —$CH_2$—, —$CH_2CH_2$—, —O—, or —S—;
$R^{41}$ is H or $CH_3$;
Y is $CR^{41}$ or N;
$R^{41}$ is H or $CH_3$; and
$R^1$, $R^2$, L, $R^3$, $R^4$, Q, and $R^5$ are each as defined in Formula (I).

In an alternative of the immediately preceding embodiment, $R^{41}$ is H. In another alternative of the immediately preceding embodiment, $R^{41}$ is $CH_3$. In another alternative of the immediately preceding embodiment, Y is N. In another alternative of the immediately preceding embodiment, Y is $CR^{41}$; and $R^{41}$ is H. In another alternative of the immediately preceding embodiment, Y is $C(CH_3)$.

The following alternative embodiments, alone and in combination, are applicable to each of the embodiments described hereinabove.

In another embodiment, in each of Formulas (I), (II), (III), (IV), (V), (VI), (VII), (VIII), and (IX), X is CH; and Z is $C(R^4)$.

In another embodiment, in each of Formulas (I), (II), (III), (IV), (V), (VI), (VII), (VIII), and (IX), X is N; and Z is $C(R^4)$.

In another embodiment, in each of Formulas (I), (II), (III), (IV), (V), (VI), (VII), (VIII), and (IX), X is CH; and Z is N.

In another embodiment, in each of Formulas (I), (II), (III), (IV), (V), (VI), (VII), (VIII), and (IX), X is N; and Z is N.

The following alternative embodiments of $R^1$ apply to each of Formulas (I), (II), (III), (IV), (V), (VI), (VII), (VIII), and (IX), and also to each of the embodiments and alternative embodiments of described hereinabove.

In another embodiment, in each of Formulas (I), (II), (III), (IV), (V), (VI), (VII), (VIII), and (IX), $R^1$ is selected from the group consisting of H, methyl, F, and Cl.

In another embodiment, in each of Formulas (I), (II), (III), (IV), (V), (VI), (VII), (VIII), and (IX), $R^2$ is selected from the group consisting of H, F, and Cl.

In another embodiment, in each of Formulas (I), (II), (III), (IV), (V), (VI), (VII), (VIII), and (IX), $R^4$ is H.

In another embodiment, in each of Formulas (I), (II), (III), (IV), (V), (VI), (VII), (VIII), and (IX), $R^4$ is methyl.

In another embodiment, in each of Formulas (I), (II), (III), (IV), (V), (VI), (VII), (VIII), and (IX), $R^1$ is H and $R^2$ is Cl.

In another embodiment, in each of Formulas (I), (II), (III), (IV), (V), (VI), (VII), (VIII), and (IX), $R^1$ is H and $R^2$ is H.

In another embodiment, in each of Formulas (I), (II), (III), (IV), (V), (VI), (VII), (VIII), and (IX), $R^1$ is methyl and $R^2$ is H.

In another embodiment, in each of Formulas (I), (II), (III), (IV), (V), (VI), (VII), (VIII), and (IX), $R^1$ is Cl and $R^2$ is Cl.

In another embodiment, in each of Formulas (I), (II), (III), (IV), (V), (VI), (VII), (VIII), and (IX), L is a bond; and $R^2$ is selected from the group consisting of H, —S(O)$_2$(C$_1$-C$_6$alkyl), and halogen.

In another embodiment, in each of Formulas (I), (II), (III), (IV), (V), (VI), (VII), (VIII), and (IX), X is —CH—; $R^1$ is H; $R^2$ is Cl; and $R^4$ is H.

In another embodiment, in each of Formulas (I), (II), (III), (IV), (V), (VI), (VII), (VIII), and (IX), X is —N—; $R^1$ is H; $R^2$ is Cl; and $R^4$ is H.

In another embodiment, in each of Formulas (I), (II), (III), (IV), (V), (VI), (VII), (VIII), and (IX), X is —CH—; $R^1$ is H; $R^2$ is H; and $R^4$ is H.

In another embodiment, in each of Formulas (I), (II), (III), (IV), (V), (VI), (VII), (VIII), and (IX), X is —N—; $R^1$ is H; $R^2$ is H; and $R^4$ is H.

In another embodiment, in each of Formulas (I), (II), (III), (IV), (V), (VI), (VII), (VIII), and (IX), X is —CH—; $R^1$ is Cl; $R^2$ is Cl; and $R^4$ is H.

In another embodiment, in each of Formulas (I), (II), (III), (IV), (V), (VI), (VII), (VIII), and (IX), X is —N—; $R^1$ is Cl; $R^2$ is Cl; and $R^4$ is H.

In another embodiment, in each of Formulas (I), (II), (III), (IV), (V), (VI), (VII), (VIII), and (IX), L is a bond; $R^3$ is H; X is CH; $R^2$ is —S(O)2CH3; $R^1$ is H; and $R^2$ is H.

The following alternative embodiments of L and $R^3$ apply to each of Formulas (I), (II), (III), (IV), (V), (VI), (VII), (VIII), and (IX), and also to each of the embodiments and alternative embodiments of described hereinabove.

In another embodiment, in each of Formulas (I), (II), (III), (IV), (V), (VI), (VII), (VIII), and (IX):
L is a bond and $R^3$ is selected from the group consisting of —(C$_1$-C$_6$)alkyl and —(C$_1$-C$_6$)alkyl-OH;

In another embodiment, in each of Formulas (I), (II), (III), (IV), (V), (VI), (VII), (VIII), and (IX):
L is a divalent moiety selected from the group consisting of —C(O)— and —S(O)$_2$—; and
$R^3$ is —N(R$^{N1}$)(R$^{N2}$), wherein R$^{N1}$ and R$^{N2}$ are each independently selected from the group consisting of H and —(C$_1$-C$_6$)alkyl.

In another embodiment, in each of Formulas (I), (II), (III), (IV), (V), (VI), (VII), (VIII), and (IX):
L is —C(O)—; and
$R^3$ is —N(R$^{N1}$)(R$^{N2}$), wherein R$^{N1}$ and R$^{N2}$ are each independently selected from the group consisting of H and —(C$_1$-C$_6$)alkyl.

In another embodiment, in each of Formulas (I), (II), (III), (IV), (V), (VI), (VII), (VIII), and (IX): L is —C(O)—; and $R^3$ is —N(CH$_3$)$_2$.

In another embodiment, in each of Formulas (I), (II), (III), (IV), (V), (VI), (VII), (VIII), and (IX):
L is —S(O)$_2$—; and
$R^3$ is —N(R$^{N1}$)(R$^{N2}$), wherein R$^{N1}$ and R$^{N2}$ are each independently selected from the group consisting of H and —(C$_1$-C$_6$)alkyl.

In another embodiment, in each of Formulas (I), (II), (III), (IV), (V), (VI), (VII), (VIII), and (IX):
L is —C(O)—; and $R^3$ is —N(R$^{N1}$)(R$^{N2}$), wherein:
R$^{N1}$ is selected from the group consisting of H and —(C$_1$-C$_6$)alkyl; and
R$^{N2}$ is —(C$_1$-C$_6$)alkyl which is optionally substituted with 1 or 2 groups independently selected from:
  optionally substituted phenyl, (wherein said optional substituents on said phenyl are 1 to 3 groups independently selected from OH, CN, —(C$_1$-C$_4$)alkyl, —(C$_1$-C$_4$)alkoxyl),
  optionally substituted heteroaryl, (wherein said optional substituents on said heteroaryl are 1 to 3 groups independently selected from —(C$_1$-C$_6$)alkyl, —(C$_1$-C$_4$) alkoxyl, and cyclopropyl),
  optionally substituted cyclopropyl (wherein said optional substituents on said cyclopropyl are 1 to 3 groups independently selected from —(C$_1$-C$_6$)alkyl),
  optionally substituted heterocycloalkyl (wherein said optional substitutents on said heterocycloalkyl are 1 to 3 groups independently selected from halogen, —OH, oxo, CN, and —(C$_1$-C$_6$)alkyl, and
  O—(C$_1$-C$_6$)alkyl, —OH, F, Cl, and —CN.

In each of the above embodiments, non-limiting examples of said optionally substituted heteroaryl include: pyridyl, pyrazinyl, furanyl, thienyl, pyrimidinyl, isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, oxindolyl, indolyl, azaindolyl, imidazolyl, thienopyridyl, imidazopyridyl, isoquinolinyl, benzoazaindolyl, and triazinyl. In one embodiment, said optionally substituted heteroaryl is isoxazolyl, oxadiazolyl, or thiazolyl.

In each of the above embodiments, non-limiting examples of said optionally substituted heterocycloalkyl include: tetrahydrofuranyl and morpholinyl.

In each of the above embodiments, non-limiting examples of said optionally substituted cycloalkyl include cyclopropyl, cyclobutyl, cyclopentyl and cyclohexyl.

In another embodiment, in each of Formulas (I), (II), (III), (IV), (V), (VI), (VII), (VIII), and (IX):
L is —C(O)—; and $R^3$ is —N(R$^{N1}$)(R$^{N2}$), wherein:
R$^{N1}$ and R$^{N2}$ are taken together with the nitrogen atom to which they are shown attached to form a 4-, 5-, or 6-membered fully saturated heterocyclic ring comprising (including said nitrogen atom) 1, 2, or 3 ring heteroatoms selected from the group consisting of N, N-oxide, O, S, and S-oxide, wherein said heterocyclic ring is unsubstituted or substituted with 1, 2, or 3 substituents independently selected from the group consisting of halogen, —OH, oxo, CN, —(C$_1$-C$_6$)alkyl, amino-substituted —(C$_1$-C$_6$)alkyl (wherein said amino is 1, 2, or 3 groups independently selected from the group consisting of —NH$_2$, —N(C$_1$-C$_4$alkyl)$_2$, and —NH(C$_1$-C$_4$alkyl)), —O—(C$_1$-C$_6$)alkyl, —(C$_1$-C$_6$)haloalkyl, —C(O)O—(C$_1$-C$_6$)alkyl, cyclopropyl, spirocyclopropyl, —NHC(O)O—(C$_1$-C$_6$)alkyl, —CH$_2$—NHC(O)O—(C$_1$-C$_6$)alkyl, —CH$_2$—N(CH$_3$)C(O)O—(C$_1$-C$_6$)alkyl, phenyl, benzyl, —NHC(O)-phenyl, heteroaryl, and —(C$_1$-C$_4$)alkylheteroaryl, heterocycloalkyl.

In the immediately preceding embodiment, non-limiting examples of said unsubstituted or substituted heterocyclic ring include azetidinyl, pyrrolidinyl, piperidinyl, and morpholinyl.

In another embodiment, in each of Formulas (I), (II), (III), (IV), (V), (VI), (VII), (VIII), and (IX), L is a bond; R$^3$ is H or —(C$_1$-C$_6$)alkyl which is optionally substituted with OH; X is CH; R$^2$ is —S(O)2CH3; R$^1$ is H; and R$^2$ is H.

In an alternative of the immediately preceding embodiment, R$^3$ is

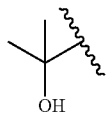

In another embodiment, in Formula (I), L is a —C(O)—; and R$^3$ is —O—(C$_1$-C$_6$)alkyl.

The following alternative embodiments of Q and R$^5$ apply to each of Formulas (I), (II), (III), (IV), (V), (VI), (VII), (VIII), and (IX), and also to each of the embodiments and alternative embodiments of described hereinabove.

In one embodiment, in each of Formulas (I), (II), (III), (IV), (V), (VI), (VII), (VIII), and (IX):

Q is a bond or a divalent moiety selected from the group consisting of —C(O)—, —S(O)$_2$—, and —C(O)O—; and R$^5$ is —C(R$^{5A}$)(R$^{5B}$)(R$^{5C}$), wherein each of R$^{5A}$, R$^{5B}$ and R$^{5C}$ is independently selected from the group consisting of: H, F, Cl, OH, NH$_2$, —(C$_1$-C$_6$)alkyl, —(C$_1$-C$_6$)haloalkyl, —(C$_1$-C$_6$)alkenyl, —(C$_1$-C$_6$)alkynyl, —(C$_3$-C$_6$)cycloalkyl, —(C$_3$-C$_6$)cycloalkyl substituted with —(C$_1$-C$_6$)alkyl, —(C$_1$-C$_6$)alkenyl, —(C$_1$-C$_6$)alkynyl, phenyl, phenyl substituted with from 1 to 3 groups independently selected from halogen, CN, methyl, CF$_3$, —OCF$_3$, —C(O)O—(C$_1$-C$_6$)alkyl, and —N(CH$_3$)$_2$.

In another alternative of the immediately preceding embodiment, Q is —C(O)—;
R$^{5A}$ is OH or NH$_2$;
R$^{5B}$ is —(C$_1$-C$_3$)fluoroalkyl; and
R$^{5C}$ is selected from the group consisting of:
—(C$_1$-C$_6$)alkyl, —(C$_1$-C$_4$)fluoroalkyl, phenyl optionally substituted with 1 to 3 groups, —C(O)phenyl optionally substituted with 1 to 3 groups, cyclopropyl optionally substituted with 1 to 2 groups, cyclobutyl optionally substituted with 1 to 2 groups, thienyl optionally substituted with 1 to 2 groups, pyridyl optionally substituted with 1 to 2 groups, naphthyl optionally substituted with 1 to 3 groups, cyclopentylphenyl optionally substituted with 1 to 3 groups, and benzthiazolyl optionally substituted with 1 to 3 groups,
wherein each said optional substituent is independently selected from halogen —(C$_1$-C$_6$)alkyl, —(C$_1$-C$_6$)alkenyl, and —O(C$_1$-C$_6$)alkyl, and —(C$_1$-C$_6$)haloalkyl. Non-limiting examples of such optional substituents are as shown in the example compounds below.

In one embodiment, in each of Formulas (I), (II), (III), (IV), (V), (VI), (VII), (VIII), and (IX):
Q is a bond or a divalent moiety selected from the group consisting of —C(O)—, —S(O)$_2$—, and —C(O)O—; and R$^5$ is selected from the group consisting of

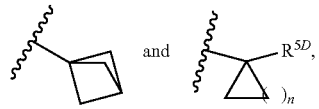

wherein n is an integer from 1 to 4; and R$^{5D}$ is selected from the group consisting of H, —(C$_1$-C$_6$)alkyl, —(C$_1$-C$_6$)haloalkyl, phenyl, and phenyl substituted with from 1 to 3 groups independently selected from the group consisting of OH, F, Cl, —(C$_1$-C$_6$)alkyl, and —O—(C$_1$-C$_6$)alkyl.

In an alternative of the immediately preceding embodiment, Q is —C(O)—.

In one embodiment, in each of Formulas (I), (II), (III), (IV), (V), (VI), (VII), (VIII), and (IX):
Q is a bond or a divalent moiety selected from the group consisting of —C(O)—, —S(O)$_2$—, and —C(O)O—; and R$^5$ is phenyl, benzyl, or thienyl, wherein:
said phenyl and said benzyl are unsubstituted or substituted with 1, 2, or 3 groups, and wherein said thienyl is unsubstituted or substituted with 1 or 2 groups, independently selected from the group consisting of F, Cl, CN, —(C$_1$-C$_6$)alkyl, —O—(C$_1$-C$_6$)alkyl, —(C$_1$-C$_6$)haloalkyl, and —O—(C$_1$-C$_6$)haloalkyl.

In an alternative of the immediately preceding embodiment, Q is a bond. In another alternative of the immediately preceding embodiment, Q is —C(O)—. In another alternative of the immediately preceding embodiment, Q is —S(O)$_2$—. In another alternative of the immediately preceding embodiment, Q is —C(O)—.

Specific non-limiting examples of compounds of the invention are shown in the examples below.

In another embodiment, 1 to 3 carbon atoms of the compounds of the invention may be replaced with 1 to 3 silicon atoms so long as all valence requirements are satisfied.

In another embodiment, there is provided a composition comprising a compound of the invention and a pharmaceutically acceptable carrier or diluent.

In one embodiment, the invention is directed to methods of treating a patient (preferably a human) for inflammatory diseases and diseases characterized by defects in cholesterol or lipid metabolism, by administering to the patient a compound of the invention or a pharmaceutically acceptable salt thereof.

The invention is also directed to the use of a compound of the invention for treating inflammatory diseases and diseases characterized by defects in cholesterol or lipid metabolism, by administering to a patient (preferably a human) a compound of the invention or a pharmaceutically acceptable salt thereof.

The invention is also directed to medicaments or pharmaceutical compositions for treating inflammatory diseases and diseases characterized by defects in cholesterol or lipid metabolism, by administering to a patient (preferably a human) a compound of the invention, or a pharmaceutically acceptable salt thereof, and a pharmaceutically acceptable carrier.

The invention is further directed to a the manufacture of a medicament or a composition for inflammatory diseases and diseases characterized by defects in cholesterol or lipid metabolism, by administering to a patient (preferably a human) a compound of the invention or a pharmaceutically acceptable salt thereof, with one or more pharmaceutically acceptable carriers.

Exemplary inflammatory diseases and diseases characterized by defects in cholesterol or lipid metabolism for which the compounds of the invention are useful include neurodegenerative and neurological diseases, such as Alzheimer's Disease, Neimann-Pick disease type C1, Parkinson's Disease, amyotrophic lateral sclerosis, stroke, age-related macular degeneration, psychiatric disorders such as schizophrenia and depression, and metabolic disorders such as cardiovascular disease, obesity and diabetes.

The present invention is directed to the use of the compounds of the invention as LXRβ agonists in a patient or subject such as a mammal in need of such activity, comprising the administration of an effective amount of the compound. In addition to humans, a variety of other mammals can be treated according to the method of the present invention.

The compounds of the invention may have utility in treating or ameliorating Alzheimer's disease. The compounds may also be useful in treating or ameliorating other inflammatory diseases and diseases characterized by defects in cholesterol and lipid metabolism, such as Neimann-Pick disease type C1, Parkinson's Disease, amyotrophic lateral sclerosis, stroke, age-related macular degeneration, psychiatric disorders such as schizophrenia and depression, and metabolic disorders such as cardiovascular disease, obesity and diabetes.

For example, the compounds of the invention may be useful for the prevention of dementia of the Alzheimer's type, as well as for the treatment of early stage, intermediate stage or late stage dementia of the Alzheimer's type.

Potential cardiovascular conditions or disorders for which the compounds of the invention may be useful include atherosclerosis, hypertension, hyperlipidemia, coronary heart disease, peripheral vascular disease, dyslipidemia, hyperbetalipoproteinemia, hypoalphalipoproteinemia, hypercholesterolemia, hypertriglyceridemia, familial-hypercholesterolemia, angina, ischemia, cardiac ischemia, stroke, myocardial infarction, reperfusion injury, angioplastic restenosis, vascular complications of diabetes, obesity (including abdominal obesity) and endotoxemia.

The compounds of the invention may also be useful in the treatment of the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome have an increased risk of developing the macrovascular and microvascular complications that are listed above, including atherosclerosis and coronary heart disease.

The compounds of the invention may also be useful for the treatment of Type 2 diabetes, and conditions and disorders related to Type 2 diabetes, such as (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component.

The compounds of the invention may also have utility in treating certain kinds of cancers which are affected by the LXR mechanism. Such cancers include, but are not limited to, prostate, breast, ovarian, melanoma, pancreas, lung, colon and hematological malignancy. (Lin, C—Y and Gustafsson, J-A, (2015) Nature Reviews Cancer 15, 216-224).

The compounds of the invention may be used in combination with one or more other drugs in the treatment of diseases or conditions for which the compounds of the invention have utility, where the combination of the drugs together are safer or more effective than either drug alone. Additionally, the compounds of the invention may be used in combination with one or more other drugs that treat, prevent, control, ameliorate, or reduce the risk of side effects or toxicity of the compounds of the invention. Such other drugs may be administered, by a route and in an amount commonly used contemporaneously or sequentially with the compounds of the invention. Accordingly, the pharmaceutical compositions of the present invention include those that contain one or more other active ingredients, in addition to the compounds of the invention. The combinations may be administered as part of a unit dosage form combination product, or as a kit or treatment protocol wherein one or more additional drugs are administered in separate dosage forms as part of a treatment regimen.

Examples of combinations of the compounds of the invention include combinations with anti-Alzheimer's Disease agents, for example: other LXRβ agonists; beta-secretase inhibitors including verubecestat (N-[3-[(5R)-3-amino-2,5-dimethyl-1,1-dioxo-6H-1,2,4-thiadiazin-5-yl]-4-fluorophenyl]-5-fluoropyridine-2-carboxamide); alpha 7 nicotinic agonists; ADAM 10 ligands or activators; gamma-secretase inhibitors, such as LY450139 and TAK 070; gamma secretase modulators; tau phosphorylation inhibitors; glycine transport inhibitors; ApoE4 conformational modulators; NR2B antagonists; androgen receptor modulators; blockers of Aβ 18 cortico formation; 5-HT4 agonists, such as PRX-03140; 5-HT6 antagonists, such as xaliproden; 5-HT1a antagonists, such as lecozotan; p25/CDK5 inhibitors; NK1/NK3 receptor antagonists; COX-2 inhibitors; HMG-CoA reductase inhibitors; NSAIDs including ibuprofen; vitamin E; anti-amyloid antibodies (including anti-amyloid humanized monoclonal antibodies), such as bapineuzumab; anti-inflammatory compounds such as I-flurbiprofen, nitroflurbiprofen; PPAR gamma agonists, such as pioglitazone and rosiglitazone; CB-1 receptor antagonists or CB-1 receptor inverse agonists; antibiotics such as doxycycline and rifampin; N-methyl-D-aspartate (NMDA) receptor antagonists, such as memantine, neramexane and EVT101; cholinesterase inhibitors such as galantamine, rivastigmine, donepezil, tacrine, phenserine and ladostigil; growth hormone secretagogues such as ibutamoren, ibutamoren mesylate, and capromorelin; histamine H3 receptor antagonists; AMPA agonists or AMPA modulators; PDE IV inhibitors; GABAA inverse agonists; GSK3β inhibitors; neuronal nicotinic agonists; selective M1 agonists; HDAC inhibitors; and microtubule affinity regulating kinase (MARK) ligands; dimebon; or other drugs that affect receptors or enzymes that either increase the efficacy, safety, convenience, or reduce unwanted side effects or toxicity of the compounds of the invention.

Other examples of combinations of the compounds of the invention include combinations with anti-obesity agents such as apolipoprotein-B secretion/microsomal triglyceride transfer protein (apo-B/MTP) inhibitors, 11β-hydroxy steroid dehydrogenase-1 (11 β-HSD type 1) inhibitors, peptide $YY_{3-36}$ or analogs thereof, MCR-4 agonists, cholecystokinin-A (CCK-A) agonists, monoamine reuptake inhibitors (such as sibutramine), sympathomimetic agents, $β_3$ adrenergic receptor agonists, dopamine agonists (such as bromocriptine), melanocyte-stimulating hormone receptor analogs, 5HT2c agonists, melanin concentrating hormone antagonists, leptin (the OB protein), leptin analogs, leptin receptor agonists, galanin antagonists, lipase inhibitors (such as tetrahydrolipstatin, i.e. orlistat), anorectic agents (such as a bombesin agonist), neuropeptide-Y antagonists (e.g., NPY Y5 receptor antagonists) thyromimetic agents, dehydroepiandrosterone or an analog thereof, glucocorticoid receptor agonists or antagonists, orexin receptor antagonists, glucagon-like peptide-1 receptor agonists, ciliary neurotrophic factors (such as Axokine™, available from Regeneron Pharmaceuticals, Inc., Tarrytown, N.Y. and Procter & Gamble Company, Cincinnati, Ohio), human agouti-related proteins (AGRP), ghrelin receptor antagonists, histamine 3 receptor antagonists or inverse agonists, neuromedin U receptor agonists and the like.

Other examples of combinations of the compounds of the invention include combinations with antihypertensive agents; anti-inflammatory agents (e.g., COX-2 inhibitors); antidepressants (e.g., fluoxetine hydrochloride (Prozac™)); cognitive improvement agents (e.g., donepezil hydrochloride (Aricept™) and other acetylcholinesterase inhibitors); neuroprotective agents (e.g., memantine); antipsychotic medications (e.g., ziprasidone (Geodon™), risperidone and olanzapine); insulin and insulin analogs (e.g., LysPro insulin); GLP-1 (7-37) (insulinotropin) and GLP-1 (7-36)-$NH_2$; sulfonylureas and analogs thereof: chlorpropamide, glibenclamide, tolbutamide, tolazamide, acetohexamide, Glypizide™, glimepiride, repaglinide, meglitinide; biguanides: metformin, phenformin, buformin; alpha2-antagonists and imidazolines: midaglizole, isaglidole, deriglidole, idazoxan, efaroxan, fluparoxan; other insulin secretagogues: linogliride, A-4166; glitazones: ciglitazone, pioglitazone, englitazone, troglitazone, darglitazone, Avandia™; fatty acid oxidation inhibitors: clomoxir, etomoxir; alpha-glucosidase inhibitors: acarbose, miglitol, emiglitate, voglibose, MDL-25,637, camiglibose, MDL-73,945; β-agonists: BRL 35135, BRL 37344, RO 16-8714, ICI D7114, CL 316,243; phosphodiesterase inhibitors: L-386,398; lipid-lowering agents: benfluorex: fenfluramine; vanadate and vanadium complexes (e.g., Naglivan™) and peroxovanadium complexes; amylin antagonists; glucagon antagonists; gluconeogenesis inhibitors; somatostatin analogs; antilipolytic agents: nicotinic acid, acipimox, WAG 994, pramlintide (Symlin™), AC 2993, nateglinide, aldose reductase inhibitors (e.g., zopolrestat), glycogen phosphorylase inhibitors, sorbitol dehydrogenase inhibitors, sodium-hydrogen exchanger type 1 (NHE-1) inhibitors and/or cholesterol biosynthesis inhibitors or cholesterol absorption inhibitors, especially a HMG-CoA reductase inhibitor, or a HMG-CoA synthase inhibitor, or a HMG-CoA reductase or synthase gene expression inhibitor, a CETP inhibitor, a bile acid sequesterant, a fibrate, an ACAT inhibitor, a squalene synthetase inhibitor, an anti-oxidant or niacin. Non-limiting examples of HMG-CoA reductase inhibitors include statins in their lactonized or dihydroxy open acid forms and pharmaceutically acceptable salts and esters thereof, including but not limited to lovastatin; simvastatin; dihydroxy open-acid simvastatin, particularly the ammonium or calcium salts thereof; pravastatin, particularly the sodium salt thereof; fluvastatin, particularly the sodium salt thereof; atorvastatin, particularly the calcium salt thereof; cerivastatin, particularly the sodium salt thereof, and nisvastatin.

The compounds of the invention may also be administered in combination with a naturally occurring compound that acts to lower plasma cholesterol levels. Such naturally occurring compounds are commonly called nutraceuticals and include, for example, garlic extract, Hoodia plant extracts, and niacin.

Other examples of combinations of the compounds of the invention include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, corticotrophi, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be used in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the compounds of the invention may be used in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Other examples of combinations of the compounds of the invention include combinations with agents for the treatment of stroke or stroke recovery. Examples of such second agents for treatment of stroke include, but are not limited to, aspirin, intercellular adhesion molecule (ICAM)-I and LFA-I antagonists including antibodies such as enlimomab (an anti-ICAM-1 monoclonal antibody), and anti-CD18 and anti-CD 1Ia antibodies, human anti-leukocytic antibodies such as Hu23F2G, glycoprotein Iib Ilia antagonists such as eptifibatide (INTEGRELIN™), direct thrombin inhibitors, external or local ultrasound, mechanical clot retrieval or inaceration, fibrinolytic agents, neuronal wound healing agents such as basic fibroblast growth factor (e.g., FIBLAST™), neuroprotective agents such as citicoline, magnesium, nalmefene, dizocilpine, nimodipine, lamotrigine, sipatrigine, lubeluzole, mexiletine, clomethiazole, calcium and sodium channel blocking agents, beta-amino-3-hydroxy-5-methylisoxazole-4-proprionic acid antagonist, a serotonin agonist, a transmembrane potassium channel modulator, agents that inhibit astrocyte activation (e.g., ONO 2506), antioxidants (e.g., MCI-186), anti-adhesion monoclonal antibodies and antagonists and antibodies inhibiting platelet aggregation such as argatroban and abciximab (REOPRO™), phenytoin, nitrogen oxides, CNS-protective therapies, free-radical scavengers such as tirilazad, reactive oxygen metabolites, and antioxidants, and other thrombolytic agents than tenecteplase, as defined below, such as, for example, acylated plasminogen-streptokinase activator complex (APSAC), single-chain urokinase-plasminogen activator (scu-PA), thrombin-like enzymes from snake venoms such as ancrod, streptokinase (e.g., SAKSTAR™), urokinase, anistreplase, alteplase, saruplase, reteplase, lanoteplase (SUN-9216; Genetics Institute Inc.), plasmin, a truncated form of plasmin (microplasmin; ThromboGenics Ltd), a direct-acting thrombolytic with non-thrombolytic—related neuroprotective activities, recombinant *desmodus rotundus* salivary plasminogen activator (rDSPA) alpha-1 (Schering/Teijin Pharmaceuticals), a mutant fibrin-activated human plasminogen (BB 101 53; British Biotech Inc.), staphylokinase, fibrolase, prourokinase (intra-arterial administration directly into M1 or M2 arterial thrombus), monteplase (modified rtPA), pamiteplase, tisokinase, and vampire bat plasminogen activator, a spin-trap agent such as NXY-059 (cerovive), clopidogrel, n-methyl-dextro-aspartic acid receptor blocking agent, an anticonvulsive agent, a caspase 3 inhibitor, ((tert butylimino)methyl) 1,3 (benzenedisulfonate disodium n oxide), ebselen, glutathione peroxidase, norphenazone, rovelizumab, lactacystin beta-lactone, tsukubaenolide, 4 phosphonomethylpipecolic acid, eliprodil, antibodies to ganglioside GM1; and thrombolytic agents, including streptokinase, acylated plasminogen-streptokinase activator complex (APSAC), urokinase, single-chain urokinase-plasminogen activator (scu-PA), thrombin-like enzymes from snake venoms such as ancrod (Bell, W. "Defibrinogenating enzymes" In Colman et al (eds), *Hemostasis and Thrombosis* Lippincott, Philadelphia (1987) p. 886), tPA, and biologically active variants of each of the above.

Other examples of combinations of the compounds of the invention include combinations with agents for the treatment of depression or anxiety, such as norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), alpha-adrenoreceptor antagonists, atypical anti-depressants, benzodiazepines, 5-$HT_{1A}$ agonists or antagonists, especially 5-$HT_{1A}$ partial agonists, 23orticotrophin releasing factor (CRF) antagonists, and pharmaceutically acceptable salts thereof.

Other examples of combinations of the compounds of the invention include combinations with agents for the treatment of diabetes or diabetes conditions, including dipeptidyl peptidase IV (DPP-IV) inhibitors (including isoleucine thiazolidide vildagliptin, stigaliptin, and saxagliptin); insulin sensitizers, including (i) PPARγ agonists, such as the glitazones (e.g. troglitazone, pioglitazone, englitazone, MCC-555, rosiglitazone, balaglitazone, and the like) and other PPAR ligands, including PPARα/γ dual agonists, such as KRP-297, muraglitazar, naveglitazar, tesaglitazar, TAK-559, PPARα agonists, such as fenofibric acid derivatives (gemfibrozil, clofibrate, fenofibrate and bezafibrate), and selective PPAR gamma modulators (SPPARγM's); (ii) biguanides such as metformin and phenformin, and (iii) protein tyrosine phosphatase-1B (PTP-1B) inhibitors; insulin or insulin mimetics; sulfonylureas and other insulin secretagogues, such as tolbutamide, glyburide, glipizide, glimepiride, and meglitinides, such as nateglinide and repaglinide; α-glucosidase inhibitors (such as acarbose and miglitol); glucagon receptor antagonists; GLP-1, GLP-1 analogues or mimetics, and GLP-1 receptor agonists, such as exendin-4 (exenatide), liraglutide; GIP and GIP mimetics and GIP receptor agonists; PACAP, PACAP mimetics, and PACAP receptor agonists; cholesterol lowering agents; PPAR delta agonists; antiobesity agents; ileal bile acid transporter inhibitors; agents intended for use in inflammatory conditions such as aspirin, non-steroidal anti-inflammatory drugs (NSAIDs), glucocorticoids, azulfidine, and selective cyclooxygenase-2 (COX-2) inhibitors; antihypertensive agents, such as ACE inhibitors (enalapril, lisinopril, captopril, quinapril, tandolapril), A-II receptor blockers (losartan, candesartan, irbesartan, valsartan, telmisartan, and eprosartan), beta blockers and calcium channel blockers; glucokinase activators (GKAs); inhibitors of 11-β-hydroxysteroid dehydrogenase type 1; inhibitors of cholesteryl ester transfer protein (CETP), such as torcetrapib; and inhibitors of fructose 1,6-bisphosphatase.

The subject or patient to whom the compounds of the invention is administered is generally a human being, male or female, in whom LXRβ agonism is desired, but may also encompass other mammals, such as dogs, cats, mice, rats, cattle, horses, sheep, rabbits, monkeys, chimpanzees or other apes or primates, for which treatment of the above noted disorders is desired.

Definitions

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" protion of "hydroxyalkyl", "haloalkyl", arylalkyl-, alkylaryl-, "alkoxy" etc.

It shall be understood that, in the various embodiments of the invention described herein, any variable not explicitly defined in the context of the embodiment is as defined in Formula (I). All valences not explicitly filled are assumed to be filled by hydrogen.

"Patient" includes both human and non-human animals. Non-human animals include those research animals and companion animals such as mice, primates, monkeys, great apes, canine (e.g., dogs), and feline (e.g., house cats).

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, and they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

"Halogen" (or "halo") means fluorine, chlorine, bromine, or iodine. Preferred are fluorine, chlorine and bromine.

"Alkyl" means an aliphatic hydrocarbon group, which may be straight or branched, comprising 1 to about 10 carbon atoms. "Lower alkyl" means a straight or branched alkyl group comprising 1 to about 4 carbon atoms. Branched means that one or more lower alkyl groups such as methyl, ethyl or propyl, are attached to a linear alkyl chain or to the same methyl group. Non-limiting examples of suitable alkyl groups include methyl, ethyl, n-propyl, isopropyl, n-butyl, i-butyl, and t-butyl.

"Haloalkyl" means an alkyl as defined above wherein one or more hydrogen atoms on the alkyl is replaced by a halo group defined above.

"Alkenyl" means an aliphatic hydrocarbon group containing at least one carbon-carbon double bond and which may be straight or branched and comprising about 2 to about 10 carbon atoms in the straight or branched chain. Branched means that one or more lower alkyl groups such as methyl, ethyl propyl, ethenyl or propenyl are attached to a linear or branched alkenyl chain. "Lower alkenyl" means about 2 to about 4 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 10 carbon atoms in the chain. Branched means that one or more lower alkyl groups such as methyl, ethyl or propyl, or lower alkenyl or lower alkynyl groups, are attached to a linear alkynyl chain. "Lower alkynyl" means about 2 to about 4 carbon atoms in the chain which may be straight or branched. Non-limiting examples of suitable alkynyl groups include ethynyl, propynyl, 2-butynyl and 3-methylbutynyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more substituents, which may be the same or different, as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from the group consisting of N, O, and S, and oxides thereof. The point of attachment to the parent moiety is to any available ring carbon or ring heteroatom. Non-limiting examples of monocyclic heteroaryl moieties include pyridyl, pyrazinyl, furanyl, thienyl, pyrimidinyl, pyridazinyl, pyridoneyl, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof.

"Cycloalkyl" means a non-aromatic monocyclic or multicyclic ring system comprising about 3 to about 10 carbon atoms, preferably about 3 to about 6 carbon atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl and the like. Non-limiting examples of multicyclic cycloalkyls include [1.1.1]-bicyclopentane, 1-decalinyl, norbornyl, adamantyl and the like.

"Heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

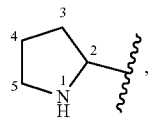

As used herein, the term "monocyclic heterocycloalkyl" refers monocyclic versions of the heterocycloalkyl moities decribed herein and include a 4- to 7-membered monocyclic heterocycloalkyl groups comprising from 1 to 4 ring heteroatoms, said ring heteroatoms being independently selected from the group consisting of N, N-oxide, O, S, S-oxide, S(O), and S(O)$_2$. The point of attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. Non-limiting examples of lower alkyl-substituted oxetanyl include the moiety:

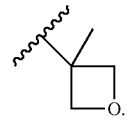

It should be noted that in hetero-atom containing ring systems of this invention, there are no hydroxyl groups on carbon atoms adjacent to a N, O or S, as well as there are no N or S groups on carbon adjacent to another heteroatom.

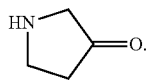

there is no —OH attached directly to carbons marked 2 and 5.

"Alkoxy" means an —O-alkyl group in which the alkyl group is as previously described. Non-limiting examples of alkoxy groups include methoxy, ethoxy, n-propoxy, isopropoxy and n-butoxy. The bond to the parent moiety is through the oxygen.

Any of the foregoing functional groups may be unsubstituted or substituted as described herein. The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl-moiety or the like includes substitution on any ring portion and/or on the alkyl portion of the group.

When a variable appears more than once in a group, e.g., R$^6$ in —N(R$^6$)$_2$, or a variable appears more than once in a structure presented herein, the variables can be the same or different.

The line —, as a bond generally indicates a mixture of, or either of, the possible isomers, e.g., containing (R)- and (S)-stereochemistry. For example:

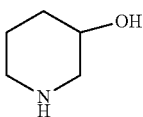

means containing both

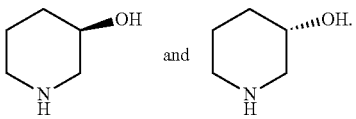

The wavy line ⌇⌇⌇, as used herein, indicates a point of attachment to the rest of the compound. Lines drawn into the ring systems, such as, for example:

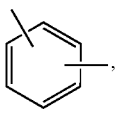

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g.,

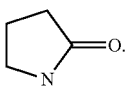

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

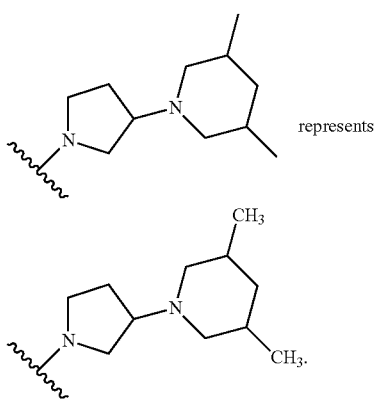

In another embodiment, the compounds of the invention, and/or compositions comprising them, are present in isolated and/or purified form. The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer thereof, or pharmaceutically acceptable salt of said compound or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

Those skilled in the art will recognize those instances in which the compounds of the invention may be converted to prodrugs and/or solvates, another embodiment of the present invention. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms where they exist. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "salt(s)", as employed herein, denotes any of the following: acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also potentially useful. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplary acid addition salts which may be useful include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered as potentially useful alternatives to the free forms of the corresponding compounds for purposes of the invention.

Another embodiment which may be useful includes pharmaceutically acceptable esters of the compounds of the invention. Such esters may include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

As mentioned herein, under certain conditions the compounds of the invention may form tautomers. Such tautomers, when present, comprise another embodiment of the invention. It shall be understood that all tautomeric forms of such compounds are within the scope of the compounds of the invention. For example, all keto-enol and imine-enamine forms of the compounds, when present, are included in the invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Where various stereoisomers of the compounds of the invention are possible, another embodiment provides for diastereomeric mixtures and individual enantiomers of the compounds of the invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

All stereoisomers (for example, geometric isomers, optical isomers and the like) of the compounds of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated as embodiments within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Another embodiment which may be useful include isotopically-labelled compounds of the invention. Such compounds are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^{1}H$) and deuterium ($^{2}H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Polymorphic forms of the compounds of the invention, and of the salts, solvates, esters and prodrugs of the compounds of the invention, are intended to be included in the present invention.

Another embodiment provides suitable dosages and dosage forms of the compounds of the invention. Suitable doses for administering compounds of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from about 0.001 to 500 mg/kg of body weight/day of the compound of the invention. In one embodiment, the dosage is from about 0.01 to about 25 mg/kg of body weight/day of a compound of the invention, or a pharmaceutically acceptable salt or solvate of said compound. In another embodiment, the quantity of active compound in a unit dose of preparation may be varied or adjusted from about 1 mg to about 100 mg, preferably from about 1 mg to about 50 mg, more preferably from about 1 mg to about 25 mg, according to the particular application. In another embodiment, a typical recommended daily dosage regimen for oral administration can range from about 1 mg/day to about 500 mg/day, preferably 1 mg/day to 200 mg/day, in two to four divided doses.

When used in combination with one or more additional therapeutic agents, the compounds of this invention may be administered together or sequentially. When administered sequentially, compounds of the invention may be administered before or after the one or more additional therapeutic agents, as determined by those skilled in the art or patient preference.

If formulated as a fixed dose, such combination products employ the compounds of this invention within the dosage range described herein and the other pharmaceutically active agent or treatment within its dosage range.

Accordingly, another embodiment provides combinations comprising an amount of at least one compound of the invention, or a pharmaceutically acceptable salt, solvate, ester or prodrug thereof, and an effective amount of one or more additional agents described above.

Another embodiment provides for pharmaceutically acceptable compositions comprising a compound of the invention, either as the neat chemical or optionally further comprising additional ingredients. For preparing pharmaceutical compositions from the compounds of the invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18$^{th}$ Edition, (1990), Mack Publishing Co., Easton, Pa.

Liquid form preparations include solutions, suspensions and emulsions. Non-limiting examples which may be useful include water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

Another embodiment which may be useful includes compositions comprising a compound of the invention formulated for transdermal delivery. The transdermal compositions can take the form of creams, lotions, aerosols and/or emulsions and can be included in a transdermal patch of the matrix or reservoir type as are conventional in the art for this purpose.

Other embodiment which may be useful includes compositions comprising a compound of the invention formulated for subcutaneous delivery or for oral delivery. In some embodiments, it may be advantageous for the pharmaceutical preparation comprising one or more compounds of the invention be prepared in a unit dosage form. In such forms, the preparation may be subdivided into suitably sized unit doses containing appropriate quantities of the active component, e.g., an effective amount to achieve the desired purpose. Each of the foregoing alternatives, together with their corresponding methods of use, are considered as included in the various embodiments of the invention.

General Schemes

Several methods for preparing the compounds of this invention are illustrated in the Schemes and Examples herein. Starting materials are made according to procedures known in the art or as illustrated herein. The following examples are provided so that the invention might be more fully understood. These examples are illustrative only and should not be construed as limiting the invention in any way. In the schemes below, each variable is as defined in Formula (I) unless otherwise indicated.

General Reaction Scheme I illustrates the preparation of the compounds of the invention, starting with aryl halide I-1. This material can be converted to I-3 via Pd-catalyzed Buchwald-Hartwig amination reactions when X is Br or I, or displacement reactions when X is F or Cl. After deprotection by either TFA treatment when the protecting group is Boc, or hydrogenation when the protecting group is Cbz, the amine I-4 is coupled with acid or sulfonyl chloride to give I-5 or I-5'.

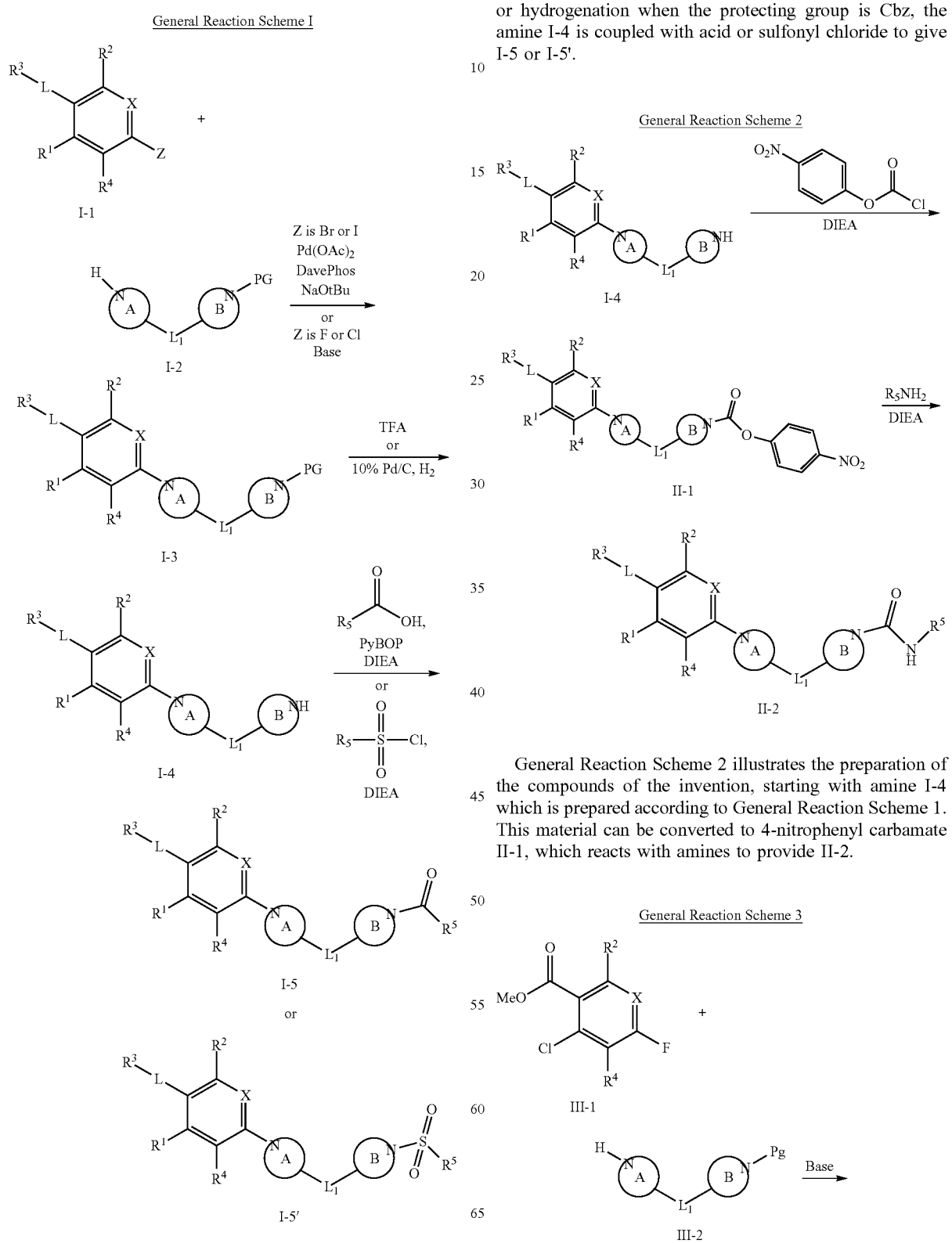

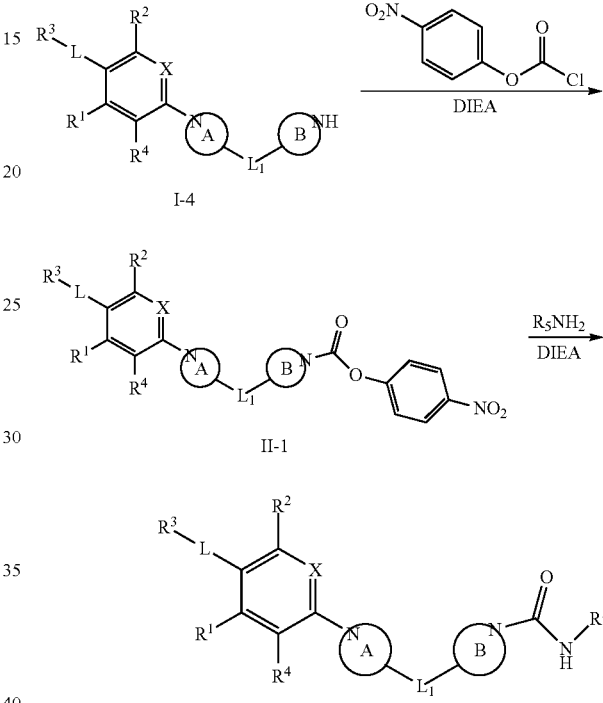

General Reaction Scheme 2 illustrates the preparation of the compounds of the invention, starting with amine I-4 which is prepared according to General Reaction Scheme 1. This material can be converted to 4-nitrophenyl carbamate II-1, which reacts with amines to provide II-2.

31
-continued

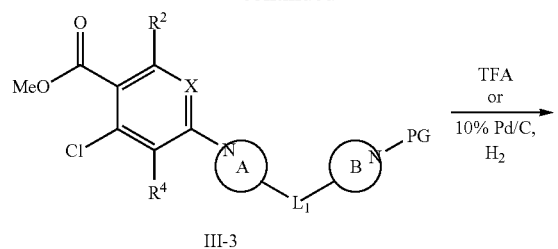

III-3

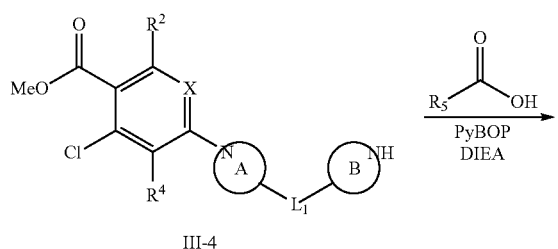

III-4

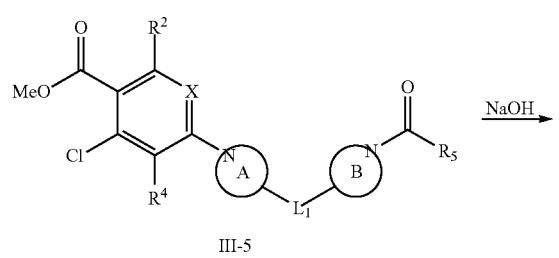

III-5

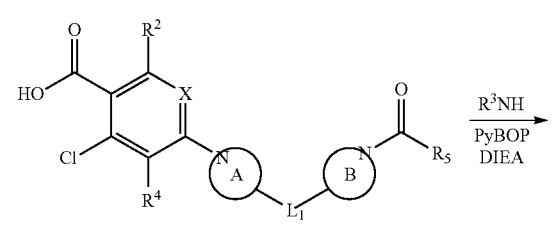

III-6

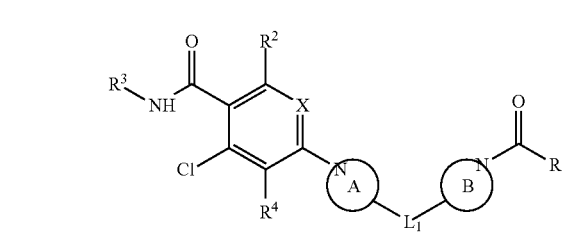

III-7

General Reaction Scheme 3 illustrates the preparation of the compounds of the invention, starting with ester III-1. This material can be converted to amide III-5 via a three-step sequence, displacement, de-protection and amide coupling. III-5 is hydrolyzed to give acid III-6, which is reacted with amines to provide III-7.

32

General Reaction Scheme 4

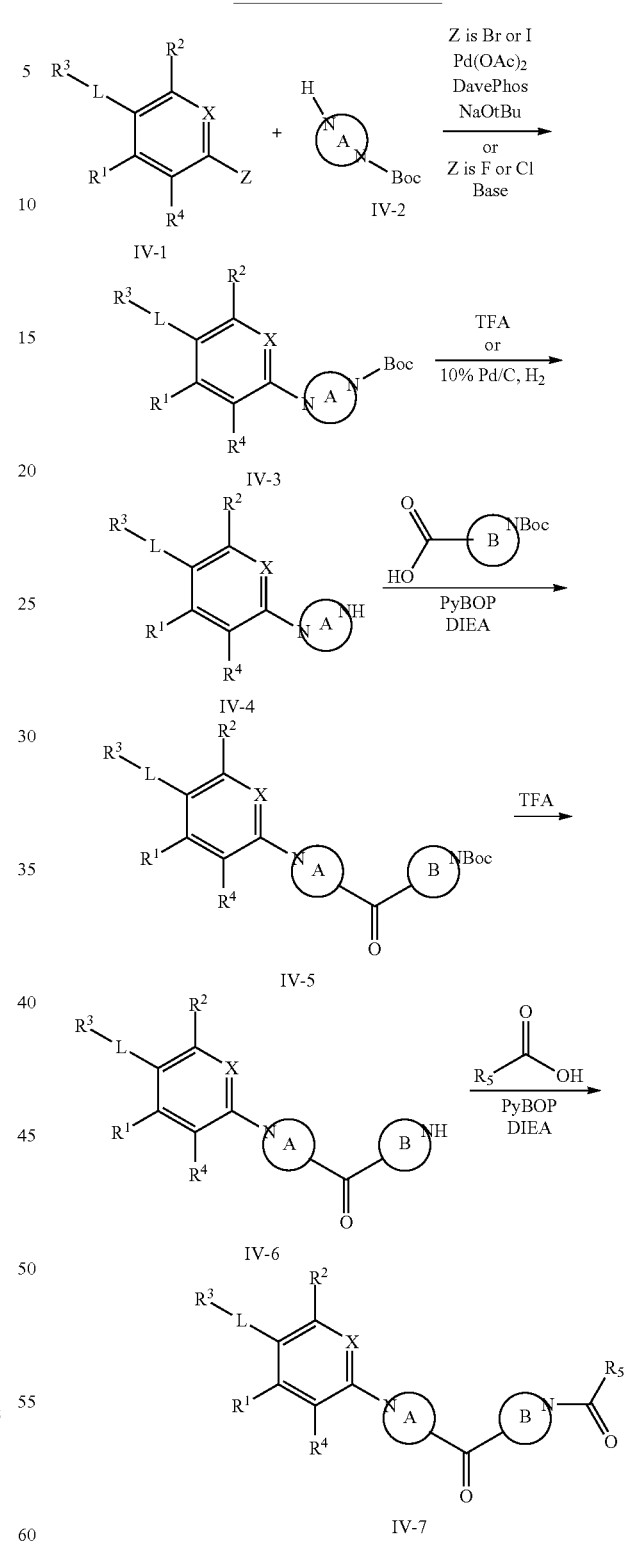

Reaction Scheme 4 illustrates the preparation of the compounds of the invention, starting with aryl halide IV-1. This material can be converted to IV-3 via Pd-catalyzed Buchwald-Hartwig amination reactions when X is Br or I, or displacement reactions when X is F or Cl. IV-3 is converted to IV-5 after removing the protecting group and then coupling with acids. IV-7 is prepared from IV-5 through a two-step sequence, deprotection and amide coupling.

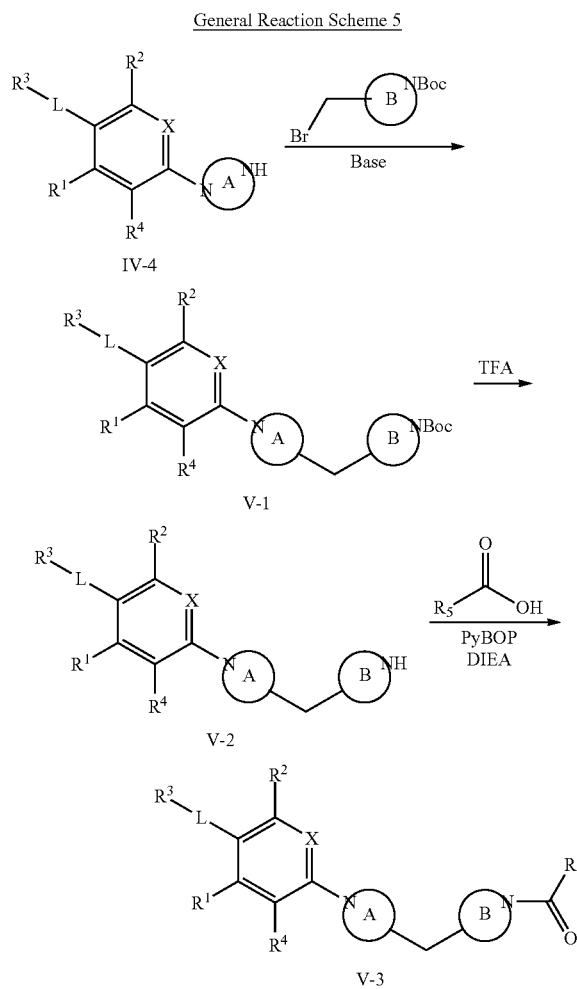

General Reaction Scheme 5

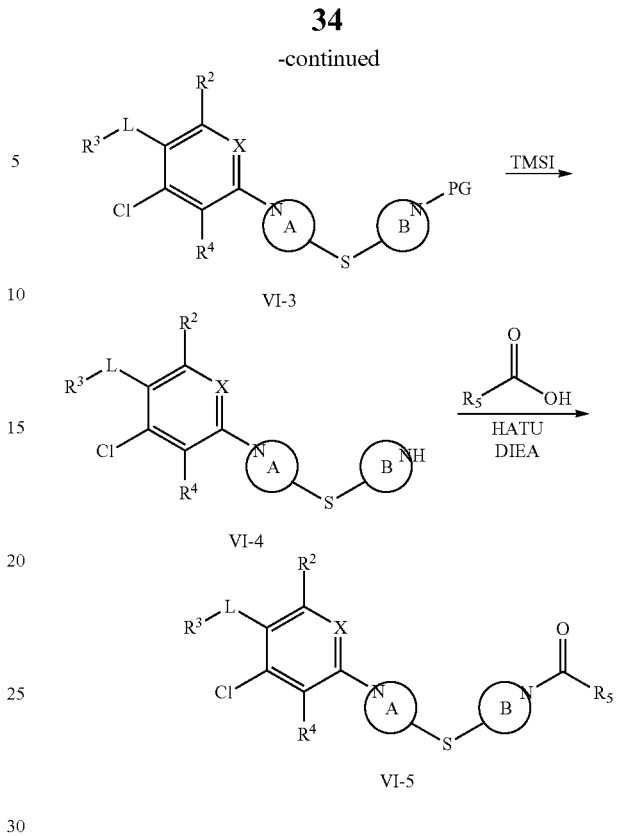

Reaction Scheme 5 illustrates the preparation of the compounds of the invention, starting with amine IV-4 which is prepared according to General Reaction Scheme 4. This material can be converted to V-3 via a two-step sequence, deprotection and amide coupling.

General Reaction Scheme 6

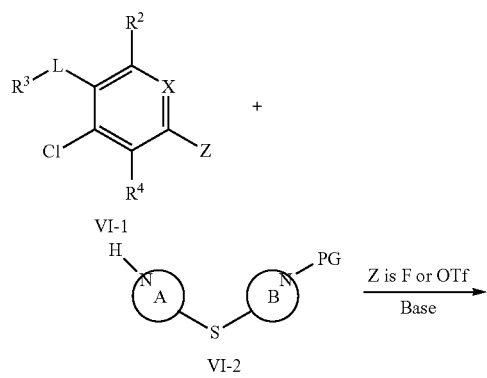

Reaction Scheme 6 illustrates the preparation of the compounds of the invention, starting with aryl halide VI-1. This material can be converted to VI-3 by displacement reactions. VI-5 is prepared from VI-3 through a two-step sequence, TMSI-mediated deprotection and amide coupling.

The following abbreviations are used herein:
BOP (benzotriazol-1-yloxy)tris(dimethylamino)phosphonium hexafluorophosphate
$Br_2BH$-$SMe_2$ dibromoborane-methylsulfide complex
CDI N,N'-carbonyldiimidazole
$Cs_2CO_3$ cesium carbonate
DCC N,N'-dicyclohexylcarbodiimide
DCE dichloroethane
DCM dichloromethane
DIAD diisopropyl azodicarboxylate
DIBAL-H diisobutylaluminum hydride
DIEA diisopropylethylamine
DMF dimethylformamide
DMSO dimethyl sulfoxide
Dppf diphenylphosphinoferrocene
EDC N-(3-dimethylaminopropyl)-N'-ethylcarbodiimide
$Et_2O$ diethyl ether
$Et_3N$ triethylamine
EtOAc ethyl acetate
EtOH ethanol
HATU O-(7-azabenzotriazol-1-yl)-N,N,N',N'-tetramethyluronium hexafluorophosphate
HBTU N,N,N',N'-Tetramethyl-O-(1H-benzotriazol-1-yl)uronium hexafluorophosphate, O-(Benzotriazol-1-yl)-N,N,N',N'-tetramethyluronium hexafluorophosphate
HCl hydrochloric acid
$(HF)_3$-$Et_3N$ triethylamine trihydrofluoride
IPA isopropanol
$K_2CO_3$ potassium carbonate
$KHSO_4$ potassium bisulfate
KOAc potassium acetate
LiOH lithium hydroxide MeCN acetonitrile
MeOH methanol
MgSO$_4$ magnesium sulfate
MIDA N-methyliminodiacetic acid
Na$_2$SO$_4$ sodium sulfate
NaHCO$_3$ sodium bicarbonate
NaH sodium hydride
NaOH sodium hydroxide
n-BuLi n-butyl lithium
NIS N-iodosuccinimide
Pd(Ph$_3$P)$_4$ tetrakis(triphenylphosphine) palladium (0)
Pd/C palladium on carbon
PdCl$_2$(dppf)-CH$_2$Cl$_2$ adduct dichloro[1,1'-bis(diphenylphosphino)ferrocene]palladium (II) dichloromethane adduct
PdCl$_2$(PPh$_3$)$_2$ palladium dichloride bis-triphenylphosphine
PE Petroleum ether
POCl$_3$ phosphorous oxychloride
PPh$_3$ triphenylphosphine
RT, r.t., rt room temperature
TBTU O-benzotriazol-1-yl-N,N,N',N'-tetramethyluronium tetrafluoroborate
Tf$_2$O triflic anhydride
TFA trifluoroacetatic acid
TfOH trifluoromethanesulfonic acid
THF tetrahydofuran
Xphos 2-Dicyclohexylphosphino-2',4',6'-triisopropylbiphenyl Synthesis of Intermediate A Intermediate A1:
4-Bromo-2-chloro-N,N-dimethylbenzamide

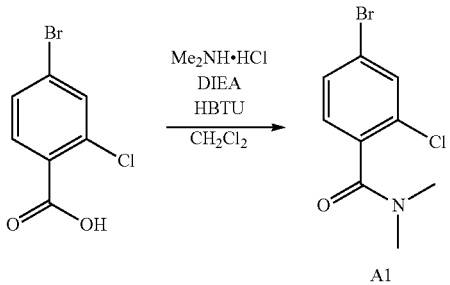

To a mixture of 4-bromo-2-chlorobenzoic acid (2.40 g, 10.2 mmol) and dimethylamine hydrochloride (0.91 g, 11.2 mmol) in CH$_2$Cl$_2$ (20 mL) was added HBTU (4.06 g, 10.7 mmol) and then DIEA (5.51 mL, 31.6 mmol). The reaction was stiired at room temperature overnight. The reaction mixture was purified by ISCO column chromatography (silica gel ISCO 120 g prepacked column, eluting with 0-100% EtOAc/Hexane) to give the title compound (2.56 g). LCMS m/z (M+H): Calc'd 262.0, found 262.1.

Intermediate A2:
5-bromo-N,N,3-trimethylpicolinamide

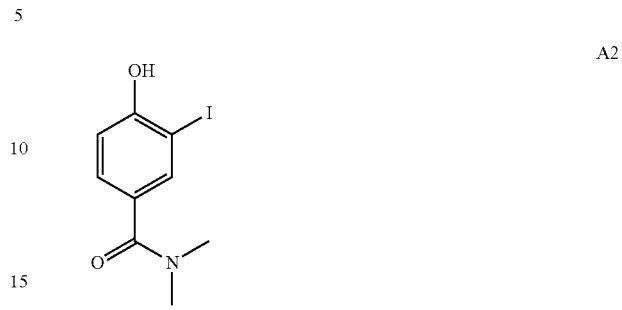

The title compound was made in a similar manner to 4-bromo-2-chloro-N,N-dimethylbenzamide (intermediate A1). LCMS m/z (M+H): Calc'd 243.0, found 243.1.

Intermediate A3:
5-bromo-3-chloro-N,N-dimethylpicolinamide

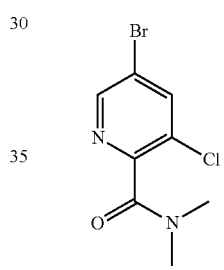

The title compound was made in a similar manner to 4-bromo-2-chloro-N,N-dimethylbenzamide (intermediate A1). LCMS m/z (M+H): Calc'd 263.0, found 263.1.

Intermediate A4: 4-iodo-N,N-dimethylbenzamide

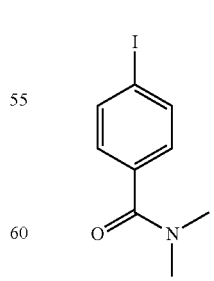

The title compound was made in a similar manner to 4-bromo-2-chloro-N,N-dimethylbenzamide (intermediate A1). LCMS m/z (M+H): Calc'd 276.0, found 275.9.

Intermediate A5:
6-chloro-2-methoxy-N,N-dimethylnicotinamide

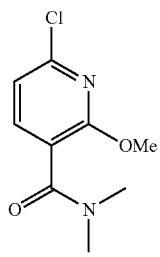

The title compound was made in a similar manner to 4-bromo-2-chloro-N,N-dimethylbenzamide (intermediate A1). LCMS m/z (M+H): Calc'd 215.0, found 215.1.

Intermediate A6:
6-chloro-2-cyclopropyl-N,N-dimethylnicotinamide

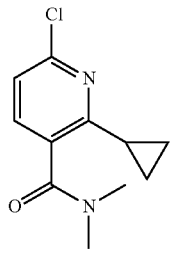

The title compound was made in a similar manner to 4-bromo-2-chloro-N,N-dimethylbenzamide (intermediate A1). LCMS m/z (M+H): Calc'd 225.0, found 225.1.

Intermediate A7:
6-fluoro-N,N,2-trimethylnicotinamide

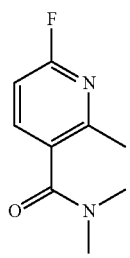

The title compound was made in a similar manner to 4-bromo-2-chloro-N,N-dimethylbenzamide (intermediate A1). LCMS m/z (M+H): Calc'd 183.1, found 183.3.

Intermediate A8
4,6-dichloro-N,N-dimethylnicotinamide

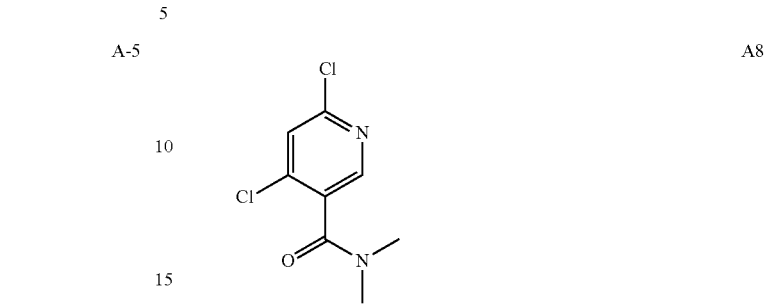

The title compound was made in a similar manner to 4-bromo-2-chloro-N,N-dimethylbenzamide (intermediate A1). LCMS m/z (M+H): Calc'd 219.0, found 219.1.

Intermediate A9:
6-fluoro-N,N,4-trimethylnicotinamide

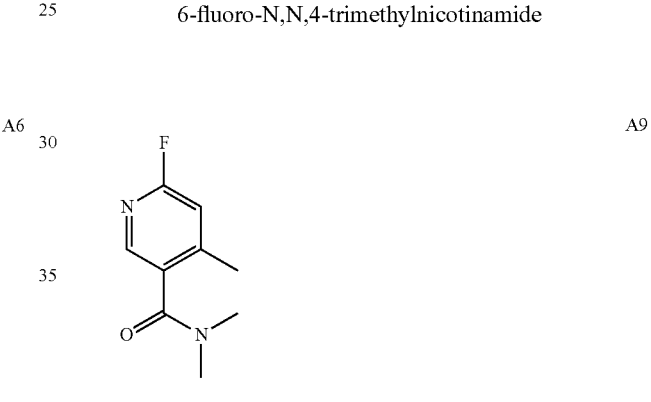

The title compound was made in a similar manner to 4-bromo-2-chloro-N,N-dimethylbenzamide (intermediate A1). LCMS m/z (M+H): Calc'd 183.1, found 183.3.

Intermediate A10:
6-fluoro-N,N-dimethylnicotinamide

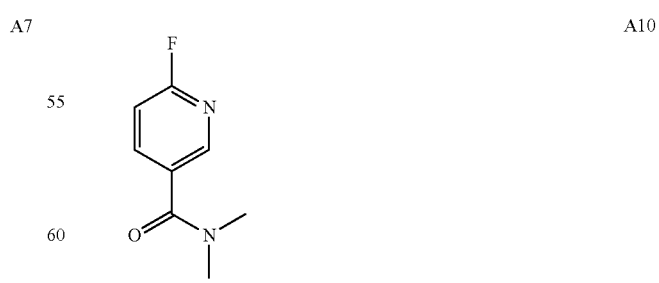

The title compound was made in a similar manner to 4-bromo-2-chloro-N,N-dimethylbenzamide (intermediate A1). LCMS m/z (M+H): Calc'd 169.1, found 169.1.

Intermediate A11:
2-chloro-4-fluoro-N-methylbenzamide

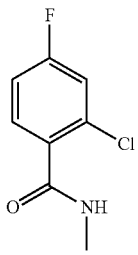

The title compound was made in a similar manner to 4-bromo-2-chloro-N,N-dimethylbenzamide (intermediate A1) by using methanamine hydrochloride instead of dimethylamine hydrochloride. LCMS m/z (M+H): Calc'd 187.0, found 187.0.

Intermediate A12:
6-chloro-5-(dimethylcarbamoyl)pyridin-2-yl trifluoromethanesulfonate

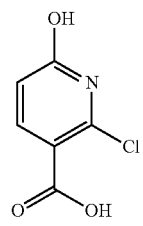
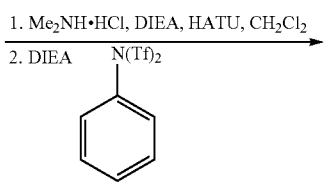
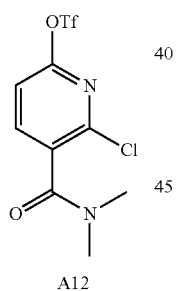

Dimethylamine hydrochloride (1.97 g, 24.2 mmol) and then DIEA (9.60 mL, 69.1 mmol) were added to a mixture of 2-chloro-6-hydroxynicotinic acid (3.00 g, 17.3 mmol) and HATU (7.89 g, 20.7 mmol) in CH$_2$Cl$_2$ (86 mL). After the reaction was stirred at room temperature for 30 mins, more DIEA (4.8 mL, 34.6 mmol) and 1,1,1-trifluoro-N-phenyl-N-((trifluoromethyl)sulfonyl)methanesulfonamide (6.18 g, 17.3 mmol) were added. The reaction was stiired at room temperature for two more hours to complete the conversion. The mixture was diluted with H$_2$O, and the aq. layer was extracted with CH$_2$Cl$_2$ (3×). The combined organic fractions were dried over Na$_2$SO$_4$, filtered and the solvent was evaporated under reduced pressure. The reaction mixture was purified by ISCO column chromatography (silica gel ISCO 120 g prepacked column, eluting with 0-100% EtOAc/Hexane) to give the title compound (3.81 g). LCMS m/z (M+H): Calc'd 333.0, found 333.1.

Intermediate A13:
6-chloro-5-(dimethylcarbamoyl)pyridin-2-yl trifluoromethanesulfonate

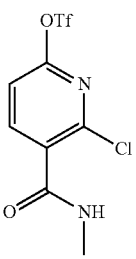

The title compound was made in a similar manner to 6-chloro-5-(dimethylcarbamoyl)pyridin-2-yl trifluoromethanesulfonate (intermediate A12) by using methanamine hydrochloride instead of dimethylamine hydrochloride. LCMS m/z (M+H): Calc'd 319.0, found 319.1.

Synthesis of Intermediate B

Intermediate B1: tert-butyl 3-(piperidin-4-ylmethyl)azetidine-1-carboxylate

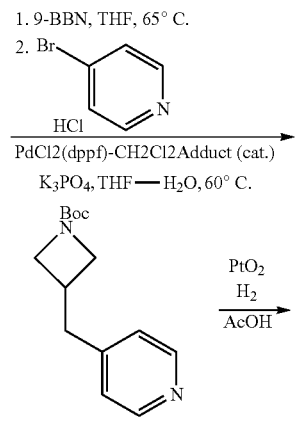

Step 1: tert-butyl 3-(pyridin-4-ylmethyl)azetidine-1-carboxylate

At room temperature, 9-BBN (0.5 M in THF, 3.9 mL, 1.95 mmol) was added to tert-butyl 3-methyleneazetidine-1-carboxylate (331 mg, 1.95 mmol) in THF (1 mL) and the mixture was heated at 65° C. for 1 h. After cooling to room temperature, PdCl$_2$(dppf)-CH$_2$Cl$_2$Adduct (80 mg, 0098 mmol), K$_3$PO$_4$ (1240 mg, 5.86 mmol) and 4-bromopyridine hydrochloride (380 mg, 1.95 mmol), THF (5 mL) and H$_2$O (0.6 mL) were added. After heated at 60° C. for 60 min under microwave condition, the mixture was filtered and then concentrated to dryness. The residue was purified by ISCO column chromatography (silica gel 40 g, 0-100% EtOAc/Hexane) to give the title compound (319 mg). LCMS m/z (M+H): Calc'd 249.1, found 249.2.

Step 2: tert-butyl 3-(piperidin-4-ylmethyl)azetidine-1-carboxylate

The mixture of tert-butyl 3-(pyridin-4-ylmethyl)azetidine-1-carboxylate (319 mg, 1.28 mmol) and PtO$_2$ (29.2 mg, 0.13 mmol) in acetic acid (6.4 mL) was degassed (3×pump/N$_2$) then placed under an atmosphere of H$_2$ (1×pump/balloon H$_2$) and stirred rapidly at room temperature overnight. After purged with N$_2$, the mixture was filtered, washed with small amount of acetic acid, and concentrated to dryness to give the crude title compound which was used without further purification. LCMS m/z (M+H): Calc'd 255.2, found 255.3.

Intermediate B2: tert-butyl 3-(piperidin-4-ylmethyl)pyrrolidine-1-carboxylate

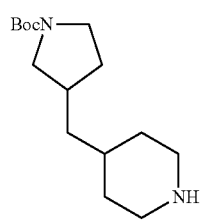

B2

The title compound was made in a similar manner to tert-butyl 3-(piperidin-4-ylmethyl)azetidine-1-carboxylate (intermediate B1). LCMS m/z (M+H): Calc'd 269.2, found 269.3.

Intermediate B3: tert-butyl 4-(piperidin-4-ylmethyl)azepane-1-carboxylate

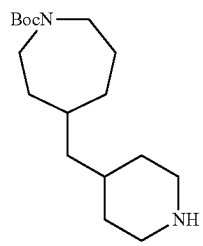

B3

The title compound was made in a similar manner to tert-butyl 3-(piperidin-4-ylmethyl)azetidine-1-carboxylate (intermediate B1). LCMS m/z (M+H): Calc'd 297.2, found 297.3.

Intermediate B4: tert-butyl 4-methyl-4-(piperidin-4-ylmethyl)piperidine-1-carboxylate

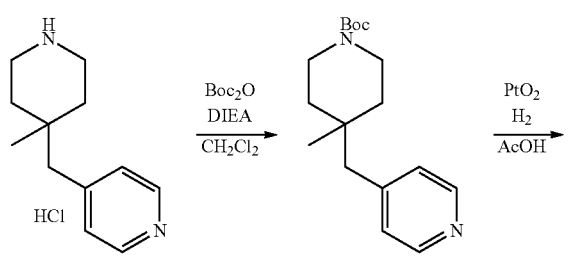

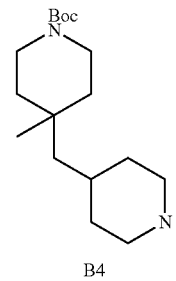

B4

Step 1: tert-butyl 4-methyl-4-(pyridin-4-ylmethyl)piperidine-1-carboxylate

At 0° C., DIEA (3.47 ml, 19.85 mmol) and then Boc$_2$O (2.21 g, 10.14 mmol) were added to 4-((4-methylpiperidin-4-yl)methyl)pyridine hydrochloride (2.00 g, 8.82 mmol) in DCM (29.4 mL). The reaction mixture was slowly warmed up to room temperature and stirred at the same temperature for 4 h. The mixture was purified by ISCO column chromatography (silica gel 80 g, 0-100% EtOAc/Hexane) to give the title compound (2.39 g). LCMS m/z (M+H): Calc'd 291.2, found 291.2.

Step 2: tert-butyl 4-methyl-4-(piperidin-4-ylmethyl)piperidine-1-carboxylate The title compound was made in a similar manner to step 2 of the synthesis of tert-butyl 3-(piperidin-4-ylmethyl)azetidine-1-carboxylate (intermediate B1). LCMS m/z (M+H): Calc'd 297.2, found 297.4.

Intermediate B5: benzyl 4-(azetidin-3-ylmethyl)piperidine-1-carboxylate

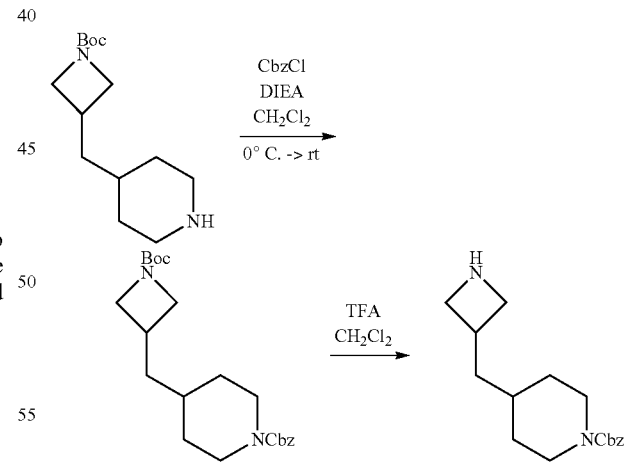

B5

Step 1: benzyl 4-((1-(tert-butoxycarbonyl)azetidin-3-yl)methyl)piperidine-1-carboxylate At 0° C., DIEA (206 uL, 1.18 mmol) and then Cbz-Cl (221 mg, 1.30 mmol) were added to a solution of tert-butyl 3-(piperidin-4-ylmethyl)azetidine-1-carboxylate (300 mg, 1.18 mmol) in DCM (12 mL). After stirring at room temperature for 3 h, the reaction mixture was loaded and purified by ISCO column chromatography (silica gel ISCO, 40 g prepacked, eluting with 0-100% EtOAc/Hexane) to give the title compound (409 mg). LCMS m/z (M+H): Calc'd 389.2, found 389.2.

Step 2: benzyl 4-(azetidin-3-ylmethyl)piperidine-1-carboxylate

Benzyl 4-((1-(tert-butoxycarbonyl)azetidin-3-yl)methyl)piperidine-1-carboxylate (409 mg, 1.05 mmol) was treated with a mixture of TFA:DCM (1:5, 10 mL) at room temperature for 0.5 h. The mixture was concentrated to dryness to give the crude title compound which was used without further purification. LCMS m/z (M+H): Calc'd 289.2, found 289.2.

Intermediate B6: benzyl 4-((4-methylpiperidin-4-yl)methyl)piperidine-1-carboxylate

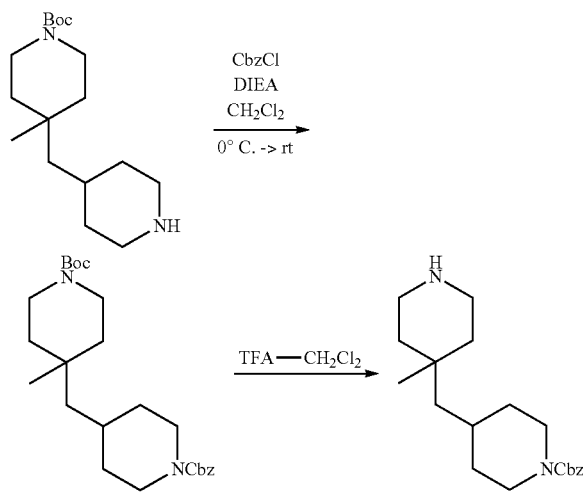

The title compound was made in a similar manner to benzyl 4-(azetidin-3-ylmethyl)piperidine-1-carboxylate. LCMS m/z (M+H): Calc'd 331.2, found 331.3.

Intermediate B7: benzyl 4-(piperidin-4-ylmethyl)piperazine-1-carboxylate

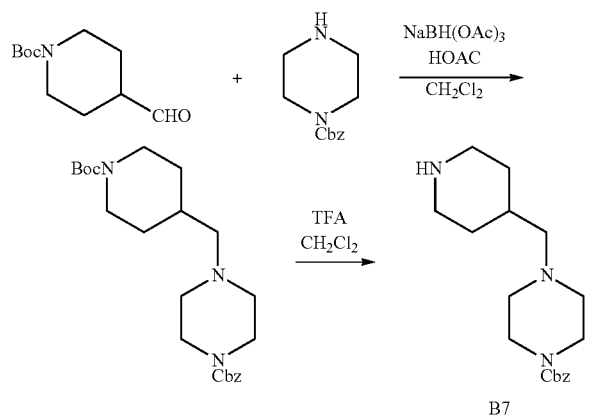

Step 1: benzyl 4-((1-(tert-butoxycarbonyl)piperidin-4-yl)methyl)piperazine-1-carboxylate Sodium triacetoxyborohydride (1732 mg, 8.17 mmol) was added to a mixture of benzyl piperazine-1-carboxylate (600 mg, 2.72 mmol), tert-butyl 4-formylpiperidine-1-carboxylate (697 mg, 3.27 mmol) and acetic acid (156 uL, 2.72 mmol) in DCM (14 mL) at room temperature. After stirring at room temperature overnight, the mixture was quenched with sat. NaHCO$_3$, the aq. layer was CH$_2$Cl$_2$ extraction (2×20 mL). The combined org. fractions were dried over Na$_2$SO$_4$ and concentrated to dryness. The residue was purified by ISCO column chromatography (silica gel ISCO 24 g prepacked, eluting with 0-100% EtOAc/Hexane) to give the title compound (693 mg). LCMS m/z (M+H): Calc'd 418.2, found 418.4.

Step 2: benzyl 4-(piperidin-4-ylmethyl)piperazine-1-carboxylate

The title compound was made in a similar manner to the step 2 of the synthesis of benzyl 4-(azetidin-3-ylmethyl)piperidine-1-carboxylate (intermediate B5). LCMS m/z (M+H): Calc'd 318.2, found 318.3.

Intermediate B8: benzyl 4-(piperidin-4-ylthio)piperidine-1-carboxylate 2,2,2-trifluoroacetic Acid Salt

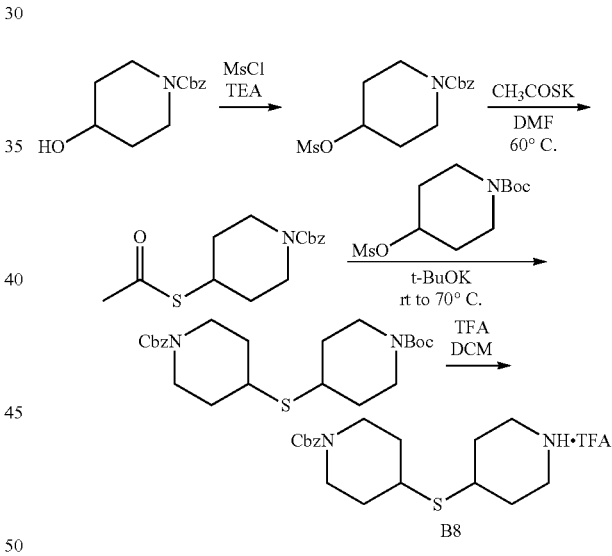

Step 1: benzyl 4-(methylsulfonyloxy)piperidine-1-carboxylate

To a solution of benzyl 4-hydroxypiperidine-1-carboxylate (2 g, 8.5 mmol, 1.0 eq) and triethylamine (3.4 g, 34 mmol, 4.0 eq) in dichloromethane (20 mL) was added a solution of methanesulfonyl chloride (2.9 g, 25.5 mmol, 3 eq) in dichloromethane (10 mL). The resulting mixture was stirred at room temperature overnight and diluted with dichloromethane (200 mL). The organic phase was washed with water (100 mL×3), brine (10 mL×3) and dried over anhydrous Na$_2$SO$_4$. The organic layer was concentrated in vacuo to afford the crude product. The curde product was purified by column chromatography (silica gel: 300-400 mesh, PE/EtOAc=3/1 to 1/1) to give the title compound (1.62 g, 61%) as a colorless oil. LRMS m/z (M+H): Calc'd 314.1, found 314.0.

Step 2: benzyl 4-(acetylthio)piperidine-1-carboxylate

To a solution of benzyl 4-(methylsulfonyloxy)piperidine-1-carboxylate (1 g, 3.2 mmol, 1.0 eq) in DMF (10 mL) was added potassium ethanethiolate (0.55 g, 4.8 mmol, 1.5 eq) at room temperature. After stirring at 60° C. overnight, the reaction was diluted with EtOAc (100 mL). The organic phase was washed with water (20 mL×3), brine (10 mL×3) and dried over anhydrous $Na_2SO_4$. The organic phase was concentrated and the residue was purified by column chromatography (silica gel: 300-400 mesh, PE/EtOAc=20/1 to 5/1) to afford the title compound (0.8 g, 85%) as a colorless oil. LRMS m/z (M+H): Calc'd 294.1, found 294.1.

Step 3: tert-butyl 4-(1-(benzyloxycarbonyl)piperidin-4-ylthio)piperidine-1-carboxylate A mixture of benzyl 4-(acetylthio)piperidine-1-carboxylate (0.95 g, 3.2 mmol, 1 eq) and t-BuOK (537 mg, 4.8 mmol, 1.5 eq) in t-BuOH (30 mL) was stirred at 40° C. for 1 h. Then tert-butyl 4-(methylsulfonyloxy)piperidine-1-carboxylate (1.07 g, 3.84 mmol) was added to the mixture. The resulting mixture was heated to 70° C. overnight. The reaction was quenched by the addition of saturated ammonium chloride (10 mL), then extracted with EtOAc (150 mL). The organic phase was washed with water (20 mL×3), brine (10 mL×3) and dried over anhydrous $Na_2SO_4$. The organic phase was concentrated and the residue was purified by column chromatography (silica gel: 300-400 mesh, PE/EtOAc=8/1 to 3/1) to give the title compound as a colorless oil (1.0 g, 71%). LRMS m/z (M-Boc+H): Calc'd 335.2, found 335.2.

Step 4: Benzyl 4-(piperidin-4-ylthio)piperidine-1-carboxylate 2,2,2-trifluoroacetic Acid Salt To a solution of tert-butyl 4-(1-(benzyloxycarbonyl)piperidin-4-ylthio)piperidine-1-carboxylate (1.0 g, 2.3 mmol) in DCM (20 mL) was added 2,2,2-trifluoroacetic acid (2 mL) at room temperature. The mixture was concentrated in vacuo to afford the crude title compund (1 g, 100%). LRMS m/z (M+H): Calc'd 335.2, found 335.2.

Example 1-1: tert-butyl 4-((1-(3-chloro-4-(dimethylcarbamoyl)phenyl)piperidin-4-yl)methyl)piperidine-1-carboxylate

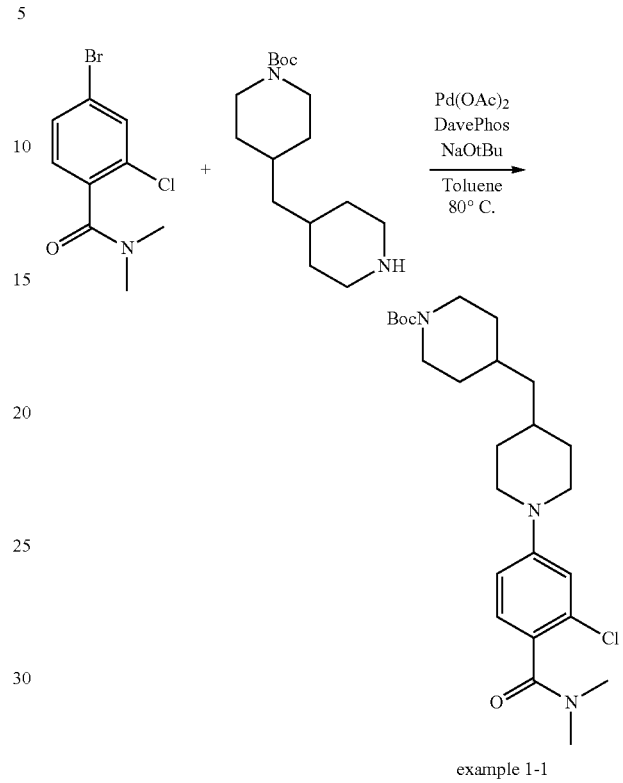

example 1-1

A mixture of tert-butyl 4-(piperidin-4-ylmethyl)piperidine-1-carboxylate (504 mg, 1.78 mmol), 4-bromo-2-chloro-N,N-dimethylbenzamide (intermediate A1, 426 mg, 1.62 mmol), 2-dicyclohexylphoshino-2'-(N,N-dimethylamino)biphenyl (96 mg, 0.24 mmol), palladium (II) acetate (18.2 mg, 0.081 mmol), and sodium tert-butoxide (187 mg, 1.95 mmol) in Toluene (8.1 ml) was degassed by bubbling with $N_2$ and heated at 80° C. overnight. The reaction mixture was filtered and then concentrated to dry. The residue was purified by ISCO column chromatography (ISCO 40 g prepacked, eluting with 0-100% EtOAc/Hexane) to give the title compound (467 mg). LCMS m/z (M+H): Calc'd 464.3, found 464.4.

The following compounds were prepared according to the procedure for Example 1-1 using the appropriate intermediate A.

| Example | Structure | IUPAC Name | Exact Mass [M + H]+ |
|---|---|---|---|
| Example 1-2 | 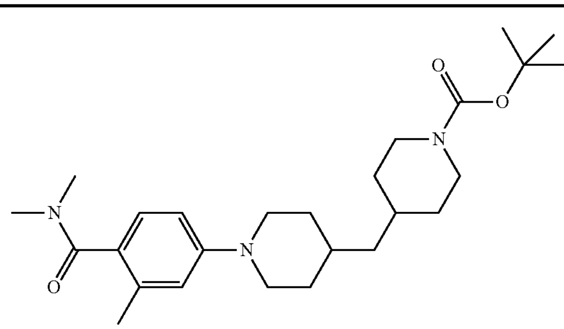 | tert-butyl 4-({1-[4-(dimethylcarbamoyl)-3-methylphenyl]piperidin-4-yl}methyl)piperidine-1-carboxylate | Calc'd 444.3, found 444.4 |

Example 2-1: 2-chloro-N,N-dimethyl-4-(4-((1-(2-methyl-2-phenylpropanoyl)piperidin-4-yl)methyl)piperidin-1-yl)benzamide

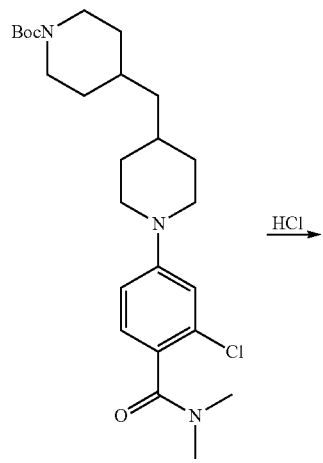

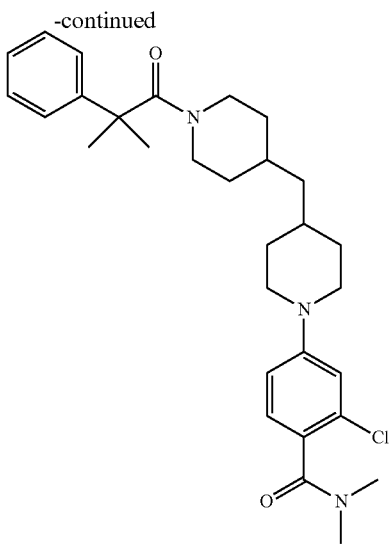

example 2-1

Step 1: 2-chloro-N,N-dimethyl-4-(4-(piperidin-4-ylmethyl)piperidin-1-yl)benzamide A solution of tert-butyl 4-((1-(3-chloro-4-(dimethylcarbamoyl)phenyl)piperidin-4-yl)methyl)piperidine-1-carboxylate (example 1-1, 1101 mg, 2.37 mmol) in DCM (10 ml) was treated with TFA (2 mL) at room temperature for 1 h. The mixture was concentrated to dryness to give the crude title compound which was used without further purification. LCMS m/z (M+H): Calc'd 364.2, found 364.4.

Step 2: 2-chloro-N,N-dimethyl-4-(4-((1-(2-methyl-2-phenylpropanoyl)piperidin-4-yl)methyl)piperidin-1-yl)benzamide

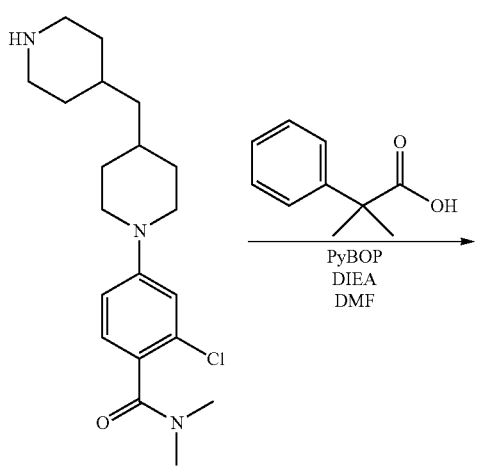

A mixture of 2-methyl-2-phenylpropanoic acid (18.2 mg, 0.11 mmol) and PYBOP (42.1 mg, 0.11 mmol) in DMF (100 ul) was first stirred at room temperature for 10 min, followed by the addition of a solution of 2-chloro-N,N-dimethyl-4-(4-(piperidin-4-ylmethyl)piperidin-1-yl)benzamide (32 mg, 0.074 mmol) and DIEA (38.2 mg, 0.29 mmol) in DMF (400 ul). After stirring at room temperature overnight, the crude sample was purified by mass-directed HPLC purification (2 cm×5 cm C18, acetonitrile-water gradient, 0.05% TFA added) to give the title compound (30 mg). LCMS m/z (M+H): Calc'd 510.3, found 510.5.

The following compounds were prepared according to the procedure for Example 2-1 using the appropriate intermediate A, B or available protected diamine, and acid.

| example | Structure | IUPAC Name | Exact Mass [M + H]+ |
|---|---|---|---|
| Example 2-2 | 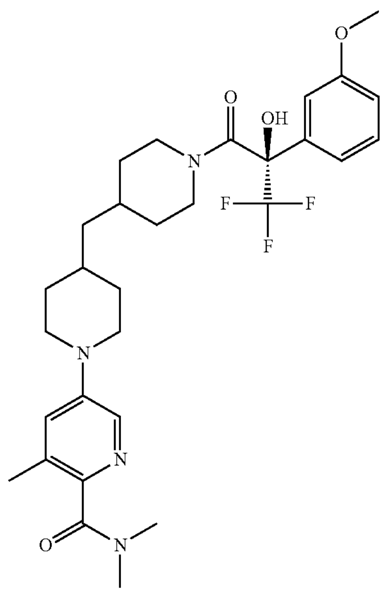 | N,N,3-trimethyl-5-[4-({1-[(2R)-3,3,3-trifluoro-2-hydroxy-2-(3-methoxyphenyl)propanoyl]piperidin-4-yl}methyl)piperidin-1-yl]pyridine-2-carboxamide | Calc'd 577.3, found 577.3 |
| Example 2-3 | 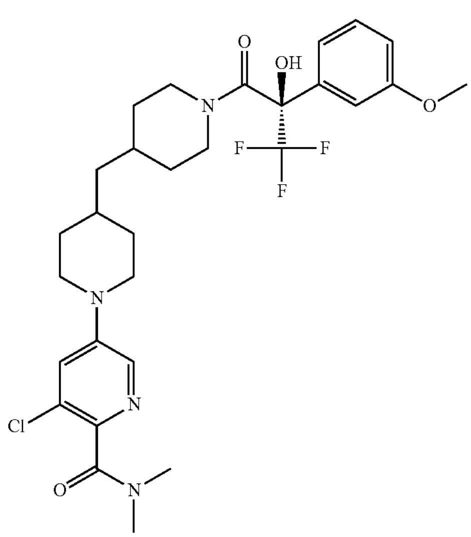 | 3-chloro-N,N-dimethyl-5-[4-({1-[(2R)-3,3,3-trifluoro-2-hydroxy-2-(3-methoxyphenyl)propanoyl]piperidin-4-yl}methyl)piperidin-1-yl]pyridine-2-carboxamide | Calc'd 597.2, found 597.2 |

-continued

| example | Structure | IUPAC Name | Exact Mass [M + H]+ |
| --- | --- | --- | --- |
| Example 2-4 | 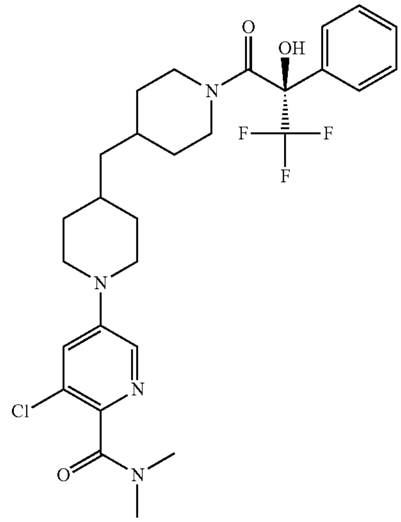 | 3-chloro-N,N-dimethyl-5-[4-({1-[(2R)-3,3,3-trifluoro-2-hydroxy-2-phenylpropanoyl]piperidin-4-yl}methyl)piperidin-1-yl]pyridine-2-carboxamide | Calc'd 567.2, found 567.2 |
| Example 2-5 | 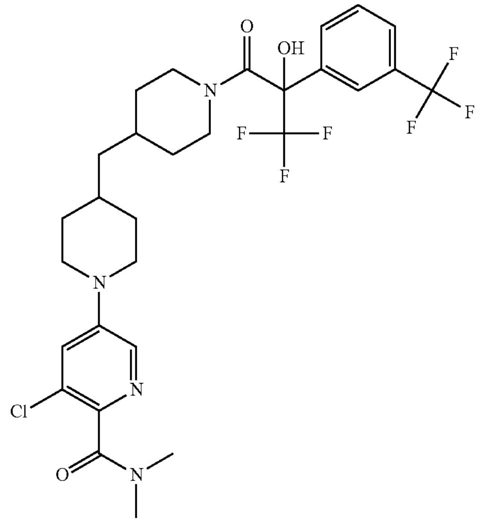 [SMILES: CN(C)C(=O)c1ncc(N2CCC(CC3CCN(C(=O)C(O)(c4cccc(C(F)(F)F)c4)C(F)(F)F)CC3)CC2)cc1Cl] | 3-chloro-N,N-dimethyl-5-{4-[(1-{3,3,3-trifluoro-2-hydroxy-2-[3-(trifluoromethyl)phenyl]propanoyl}piperidin-4-yl)methyl]piperidin-1-yl}pyridine-2-carboxamide | Calc'd 635.2, found 635.2 |
| Example 2-6 | 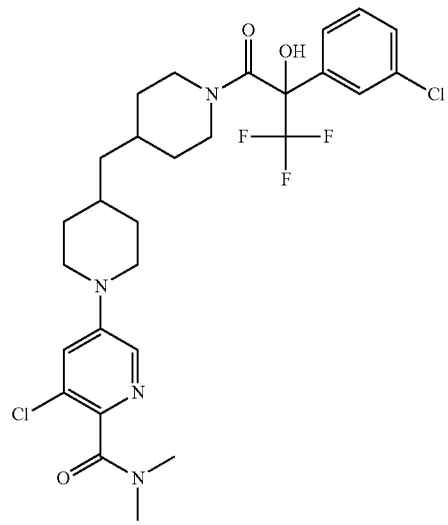 [SMILES: CN(C)C(=O)c1ncc(N2CCC(CC3CCN(C(=O)C(O)(c4cccc(Cl)c4)C(F)(F)F)CC3)CC2)cc1Cl] | 3-chloro-5-[4-({1-[2-(3-chlorophenyl)-3,3,3-trifluoro-2-hydroxypropanoyl]piperidin-4-yl}methyl)piperidin-1-yl]-N,N-dimethylpyridine-2-carboxamide | Calc'd 601.2, found 601.2 |

-continued

| example | Structure | IUPAC Name | Exact Mass [M + H]+ |
| --- | --- | --- | --- |
| Example 2-7 | 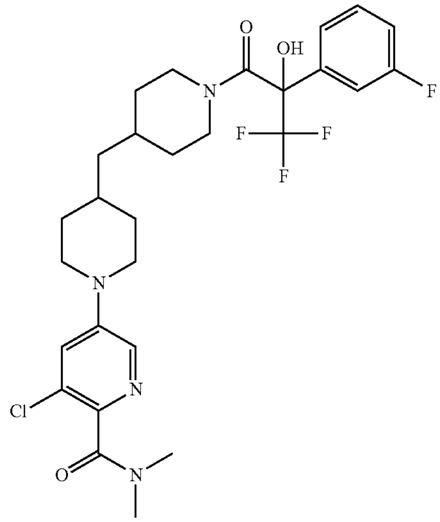 [SMILES: CN(C)C(=O)c1ncc(N2CCC(CC3CCN(C(=O)C(O)(c4cccc(F)c4)C(F)(F)F)CC3)CC2)cc1Cl] | 3-chloro-N,N-dimethyl-5-[4-({1-[3,3,3-trifluoro-2-(3-fluorophenyl)-2-hydroxy-propanoyl]piperidin-4-yl}methyl)piperidin-1-yl]pyridine-2-carboxamide | Calc'd 585.2, found 585.2 |
| Example 2-8 | 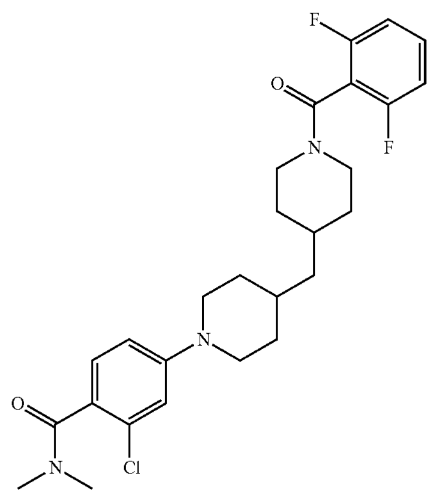 [SMILES: CN(C)C(=O)c1ccc(N2CCC(CC3CCN(C(=O)c4c(F)cccc4F)CC3)CC2)cc1Cl] | 2-chloro-4-[4-({1-[(2,6-difluorophenyl)carbonyl]piperidin-4-yl}methyl)piperidin-1-yl]-N,N-dimethyl-benzamide | Calc'd 504.2, found 504.2 |
| Example 2-9 | 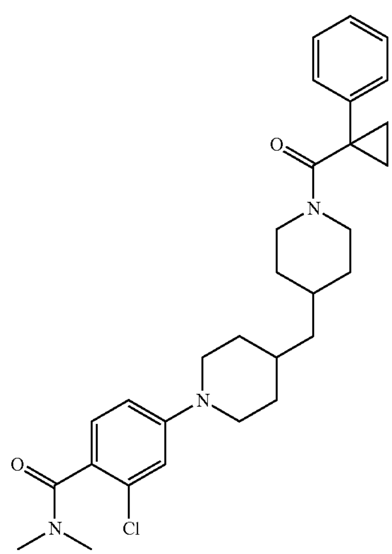 [SMILES: CN(C)C(=O)c1ccc(N2CCC(CC3CCN(C(=O)C4(c5ccccc5)CC4)CC3)CC2)cc1Cl] | 2-chloro-N,N-dimethyl-4-[4-({1-[(1-phenyl-cyclopropyl)carbonyl]piperidin-4-yl}methyl)piperidin-1-yl]benzamide | Calc'd 508.3, found 508.3 |

| example | Structure | IUPAC Name | Exact Mass [M + H]+ |
|---|---|---|---|
| Example 2-10 | 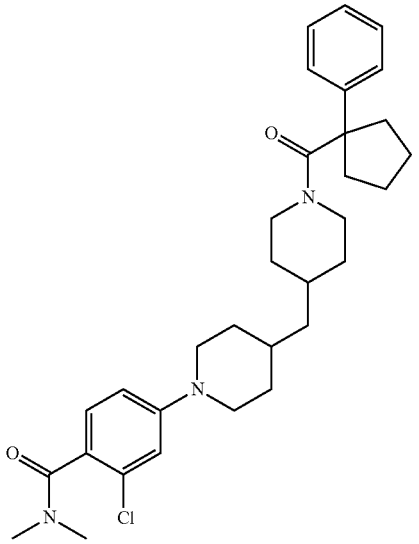 [SMILES: CN(C)C(=O)c1ccc(N2CCC(CC3CCN(C(=O)C4(c5ccccc5)CCCC4)CC3)CC2)cc1Cl] | 2-chloro-N,N-dimethyl-4-[4-({1-[(1-phenyl-cyclopentyl)carbonyl]piperidin-4-yl}methyl)piperidin-1-yl]benzamide | Calc'd 536.3, found 536.3 |
| Example 2-11 | 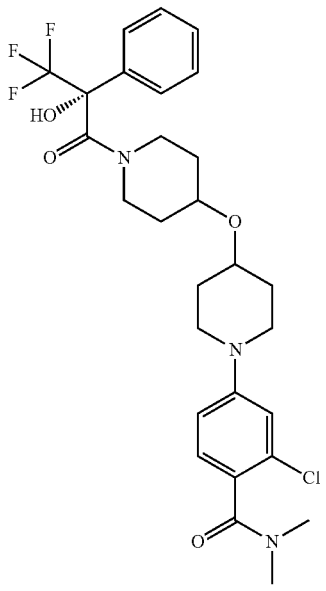 [SMILES: CN(C)C(=O)c1ccc(N2CCC(OC3CCN(C(=O)[C@](O)(c4ccccc4)C(F)(F)F)CC3)CC2)cc1Cl] | 2-chloro-N,N-dimethyl-4-[4-({1-[(2R)-3,3,3-trifluoro-2-hydroxy-2-phenylpropanoyl]piperidin-4-yl}oxy)piperidin-1-yl]benzamide | Calc'd 568.2, found 568.3 |

-continued

| example | Structure | IUPAC Name | Exact Mass [M + H]+ |
|---|---|---|---|
| Example 2-12 | 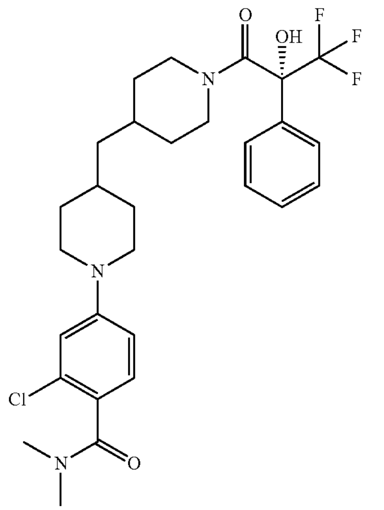 [SMILES: CN(C)C(=O)c1ccc(N2CCC(CC3CCN(C(=O)[C@](O)(c4ccccc4)C(F)(F)F)CC3)CC2)cc1Cl] | 2-chloro-N,N-dimethyl-4-[4-({1-[(2R)-3,3,3-trifluoro-2-hydroxy-2-phenylpropanoyl]piperidin-4-yl}methyl)piperidin-1-yl]benzamide | Calc'd 566.2, found 566.4 |
| Example 2-13 | 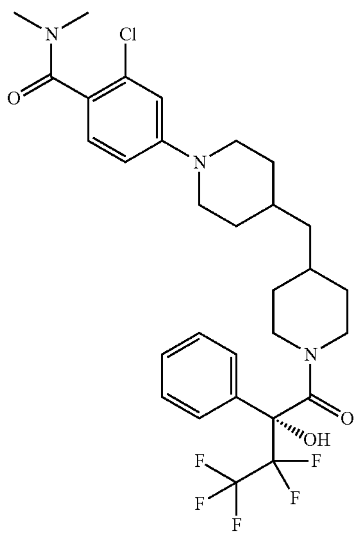 [SMILES: CN(C)C(=O)c1ccc(N2CCC(CC3CCN(C(=O)[C@](O)(c4ccccc4)C(F)(F)C(F)(F)F)CC3)CC2)cc1Cl] | 2-chloro-N,N-dimethyl-4-[4-({1-[(2R)-3,3,4,4,4-pentafluoro-2-hydroxy-2-phenylbutanoyl]piperidin-4-yl}methyl)piperidin-1-yl]benzamide | Calc'd 616.2, found 616.4 |
| Example 2-14 | 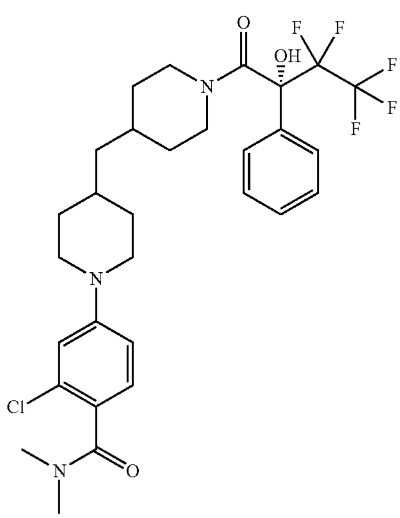 [SMILES: CN(C)C(=O)c1ccc(N2CCC(CC3CCN(C(=O)[C@](O)(c4ccccc4)C(F)(F)C(F)(F)F)CC3)CC2)cc1Cl] | 2-chloro-N,N-dimethyl-4-[4-({1-[(2R)-3,3,4,4,4-pentafluoro-2-hydroxy-2-phenylbutanoyl]piperidin-4-yl}methyl)piperidin-1-yl]benzamide | Calc'd 616.2, found 616.4 |

| example | Structure | IUPAC Name | Exact Mass [M + H]+ |
|---|---|---|---|
| Example 2-15 | 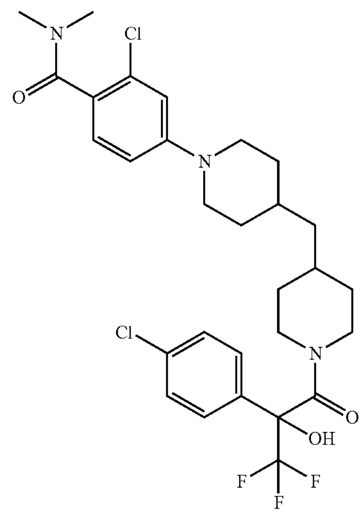 | 2-chloro-4-[4-({1-[2-(4-chlorophenyl)-3,3,3-trifluoro-2-hydroxy-propanoyl]piperidin-4-yl}methyl)piperidin-1-yl]-N,N-dimethyl-benzamide | Calc'd 600.2, found 600.4 |
| Example 2-16 | 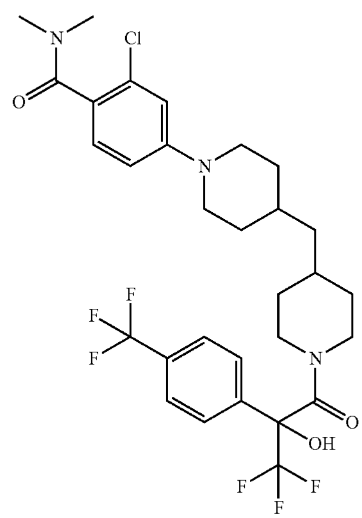 [SMILES: CN(C)C(=O)c1ccc(N2CCC(CC3CCN(C(=O)C(O)(c4ccc(C(F)(F)F)cc4)C(F)(F)F)CC3)CC2)cc1Cl] | 2-chloro-N,N-dimethyl-4-{4-[(1-{3,3,3-trifluoro-2-hydroxy-2-[4-(trifluoromethyl)phenyl]propanoyl}piperidin-4-yl)methyl]piperidin-1-yl}benzamide | Calc'd 634.2, found 634.4 |
| Example 2-17 | 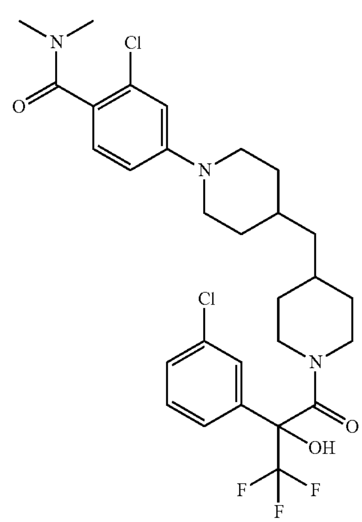 [SMILES: CN(C)C(=O)c1ccc(N2CCC(CC3CCN(C(=O)C(O)(c4cccc(Cl)c4)C(F)(F)F)CC3)CC2)cc1Cl] | 2-chloro-4-[4-({1-[2-(3-chlorophenyl)-3,3,3-trifluoro-2-hydroxy-propanoyl]piperidin-4-yl}methyl)piperidin-1-yl]-N,N-dimethyl-benzamide | Calc'd 600.2, found 600.4 |

-continued

| example | Structure | IUPAC Name | Exact Mass [M + H]+ |
|---|---|---|---|
| Example 2-18 | 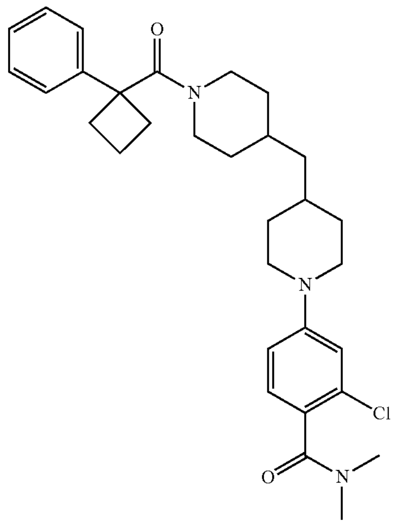 [SMILES: CN(C)C(=O)c1ccc(N2CCC(CC3CCN(C(=O)C4(c5ccccc5)CCC4)CC3)CC2)cc1Cl] | 2-chloro-N,N-dimethyl-4-[4-({1-[(1-phenylcyclobutyl)carbonyl]piperidin-4-yl}methyl)piperidin-1-yl]benzamide | Calc'd 522.3, found 522.5 |
| Example 2-19 | 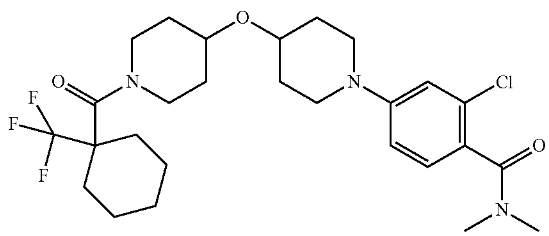 [SMILES: CN(C)C(=O)c1ccc(N2CCC(OC3CCN(C(=O)C4(C(F)(F)F)CCCCC4)CC3)CC2)cc1Cl] | 2-chloro-N,N-dimethyl-4-{4-[(1-{[1-(trifluoromethyl)cyclohexyl]carbonyl}piperidin-4-yl)oxy]piperidin-1-yl}benzamide | Calc'd 544.3, found 544.4 |
| Example 2-20 | 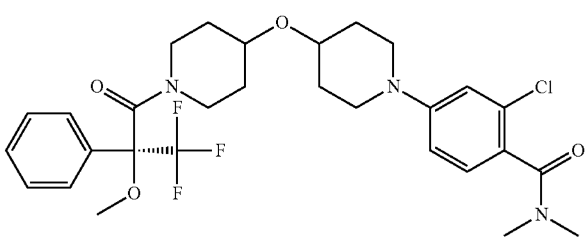 [SMILES: CO[C@](C(=O)N1CCC(OC2CCN(c3ccc(C(=O)N(C)C)c(Cl)c3)CC2)CC1)(c1ccccc1)C(F)(F)F] | 2-chloro-N,N-dimethyl-4-[4-({1-[(2S)-3,3,3-trifluoro-2-methoxy-2-phenylpropanoyl]piperidin-4-yl}oxy)piperidin-1-yl]benzamide | Calc'd 582.2, found 582.4 |
| Example 2-21 | 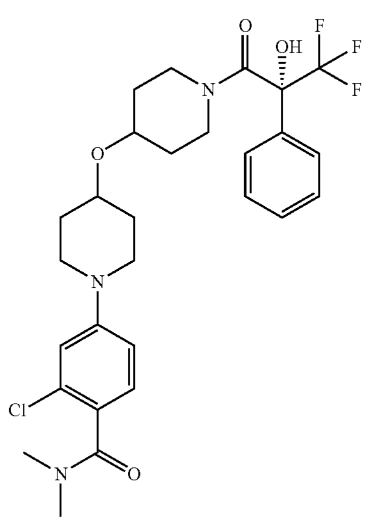 [SMILES: CN(C)C(=O)c1ccc(N2CCC(OC3CCN(C(=O)[C@](O)(c4ccccc4)C(F)(F)F)CC3)CC2)cc1Cl] | 2-chloro-N,N-dimethyl-4-[4-({1-[(2R)-3,3,3-trifluoro-2-hydroxy-2-phenylpropanoyl]piperidin-4-yl}oxy)piperidin-1-yl]benzamide | Calc'd 568.2, found 568.4 |

| example | Structure | IUPAC Name | Exact Mass [M + H]+ |
|---|---|---|---|
| Example 2-22 | 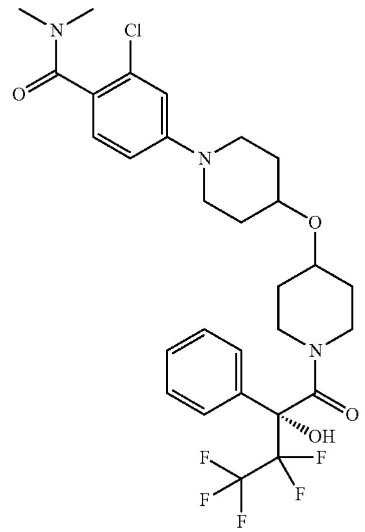 [SMILES: CN(C)C(=O)c1ccc(N2CCC(OC3CCN(C(=O)[C@](O)(c4ccccc4)C(F)(F)C(F)(F)F)CC3)CC2)cc1Cl] | 2-chloro-N,N-dimethyl-4-[4-({1-[(2R)-3,3,4,4,4-pentafluoro-2-hydroxy-2-phenylbutanoyl]piperidin-4-yl}oxy)piperidin-1-yl]benzamide | Calc'd 618.2, found 618.4 |
| Example 2-23 | 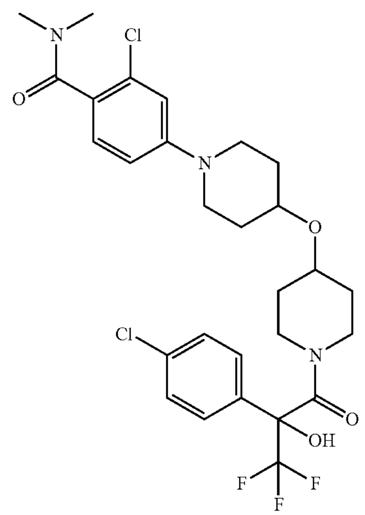 [SMILES: CN(C)C(=O)c1ccc(N2CCC(OC3CCN(C(=O)C(O)(c4ccc(Cl)cc4)C(F)(F)F)CC3)CC2)cc1Cl] | 2-chloro-4-[4-({1-[2-(4-chlorophenyl)-3,3,3-trifluoro-2-hydroxy-propanoyl]piperidin-4-yl}oxy)piperidin-1-yl]-N,N-dimethyl-benzamide | Calc'd 602.2, found 602.3 |
| Example 2-24 | 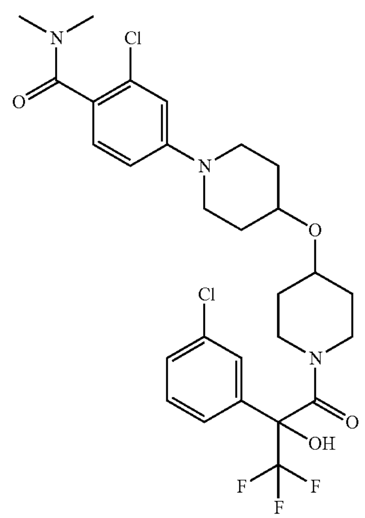 [SMILES: CN(C)C(=O)c1ccc(N2CCC(OC3CCN(C(=O)C(O)(c4cccc(Cl)c4)C(F)(F)F)CC3)CC2)cc1Cl] | 2-chloro-4-[4-({1-[2-(3-chlorophenyl)-3,3,3-trifluoro-2-hydroxy-propanoyl]piperidin-4-yl}oxy)piperidin-1-yl]-N,N-dimethyl-benzamide | Calc'd 602.2, found 602.4 |

| example | Structure | IUPAC Name | Exact Mass [M + H]+ |
|---|---|---|---|
| Example 2-25 | 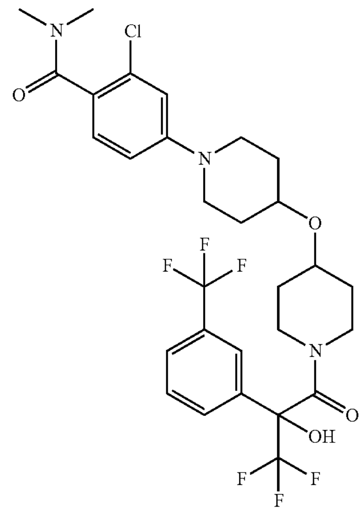 [SMILES: CN(C)C(=O)c1ccc(N2CCC(OC3CCN(C(=O)C(O)(c4cccc(C(F)(F)F)c4)C(F)(F)F)CC3)CC2)cc1Cl] | 2-chloro-N,N-dimethyl-4-{4-[(1-{3,3,3-trifluoro-2-hydroxy-2-[3-(trifluoromethyl)phenyl]propanoyl}piperidin-4-yl)oxy]piperidin-1-yl}benzamide | Calc'd 636.2, found 636.4 |
| Example 2-26 | 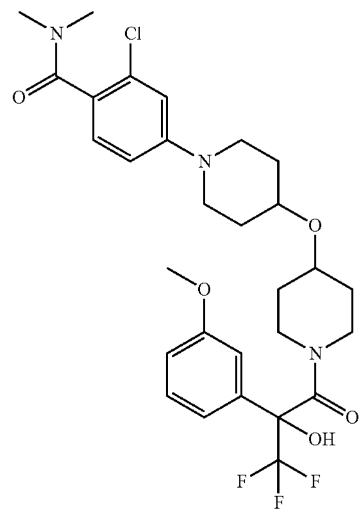 [SMILES: COc1cccc(C(O)(C(=O)N2CCC(OC3CCN(c4ccc(C(=O)N(C)C)c(Cl)c4)CC3)CC2)C(F)(F)F)c1] | 2-chloro-N,N-dimethyl-4-[4-({1-[3,3,3-trifluoro-2-hydroxy-2-(3-methoxyphenyl)propanoyl]piperidin-4-yl}oxy)piperidin-1-yl]benzamide | Calc'd 598.2, found 598.4 |
| Example 2-27 | 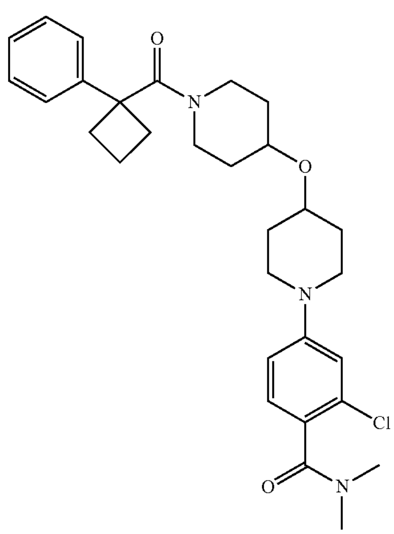 [SMILES: CN(C)C(=O)c1ccc(N2CCC(OC3CCN(C(=O)C4(c5ccccc5)CCC4)CC3)CC2)cc1Cl] | 2-chloro-N,N-dimethyl-4-[4-({1-[(1-phenylcyclobutyl)carbonyl]piperidin-4-yl}oxy)piperidin-1-yl]benzamide | Calc'd 524.3, found 524.4 |

-continued

| example | Structure | IUPAC Name | Exact Mass [M + H]+ |
|---|---|---|---|
| Example 2-28 | 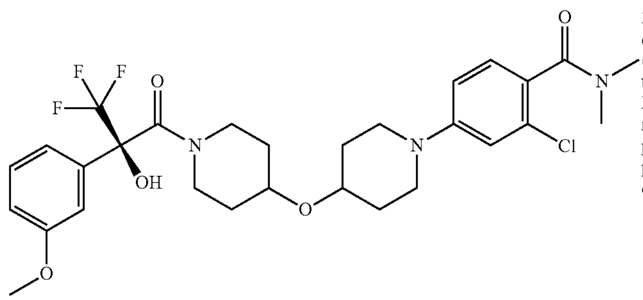 [SMILES: COc1cccc([C@@](O)(C(=O)N2CCC(OC3CCN(c4ccc(C(=O)N(C)C)c(Cl)c4)CC3)CC2)C(F)(F)F)c1] | 2-chloro-N,N-dimethyl-4-[4-({1-[(2R)-3,3,3-trifluoro-2-hydroxy-2-(3-methoxyphenyl)propanoyl]piperidin-4-yl}oxy)piperidin-1-yl]benzamide | Calc'd 598.2, found 598.4 |
| Example 2-29 | 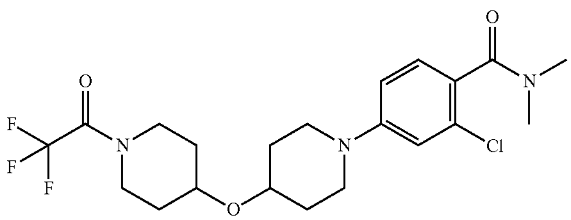 [SMILES: CN(C)C(=O)c1ccc(N2CCC(OC3CCN(C(=O)C(F)(F)F)CC3)CC2)cc1Cl] | 2-chloro-N,N-dimethyl-4-(4-{[1-(trifluoroacetyl)piperidin-4-yl]oxy}piperidin-1-yl)benzamide | Calc'd 462.2, found 462.3 |
| Example 2-30 | 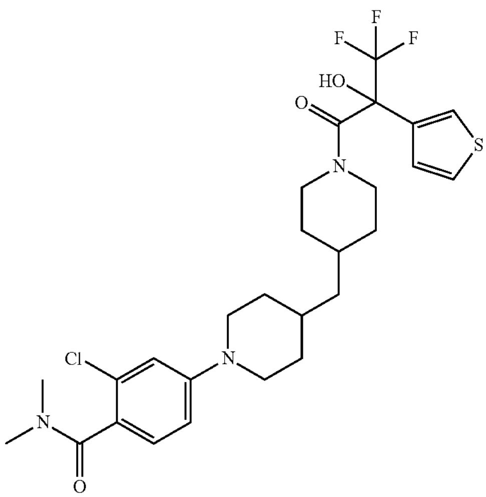 [SMILES: CN(C)C(=O)c1ccc(N2CCC(CC3CCN(C(=O)C(O)(c4ccsc4)C(F)(F)F)CC3)CC2)cc1Cl] | 2-chloro-N,N-dimethyl-4-(4-{[1-(3,3,3-trifluoro-2-hydroxy-2-thiophen-3-ylpropanoyl)piperidin-4-yl]methyl}piperidin-1-yl)benzamide | Calc'd 572.2, found 572.4 |
| Example 2-31 | 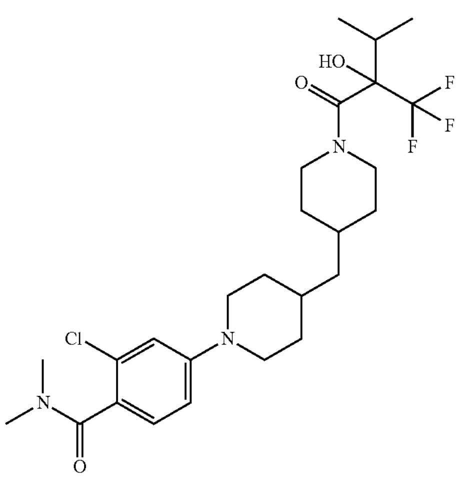 [SMILES: CC(C)C(O)(C(=O)N1CCC(CC2CCN(c3ccc(C(=O)N(C)C)c(Cl)c3)CC2)CC1)C(F)(F)F] | 2-chloro-4-[4-({1-[2-hydroxy-3-methyl-2-(trifluoromethyl)butanoyl]piperidin-4-yl}methyl)piperidin-1-yl]-N,N-dimethylbenzamide | Calc'd 532.3, found 532.4 |

-continued

| example | Structure | IUPAC Name | Exact Mass [M + H]+ |
|---|---|---|---|
| Example 2-32 | 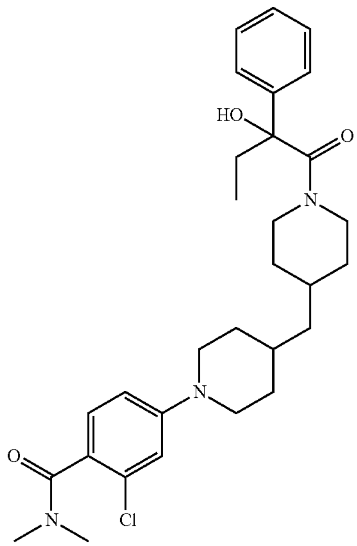 [SMILES: CCC(O)(C(=O)N1CCC(CC2CCN(c3ccc(C(=O)N(C)C)c(Cl)c3)CC2)CC1)c1ccccc1] | 2-chloro-4-(4-{[1-(2-hydroxy-2-phenyl-butanoyl)piperidin-4-yl]methyl}piperidin-1-yl)-N,N-dimethyl-benzamide | Calc'd 526.3, found 526.5 |
| Example 2-33 | 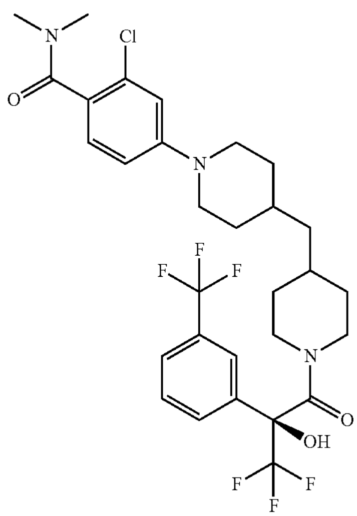 [SMILES: CN(C)C(=O)c1ccc(N2CCC(CC3CCN(C(=O)[C@@](O)(c4cccc(C(F)(F)F)c4)C(F)(F)F)CC3)CC2)cc1Cl] | 2-chloro-N,N-dimethyl-4-{4-[(1-{(2S)-3,3,3-trifluoro-2-hydroxy-2-[3-(trifluoromethyl)phenyl]propanoyl}piperidin-4-yl)methyl]piperidin-1-yl}benzamide | Calc'd 634.2, found 634.5 |
| Example 2-34 | 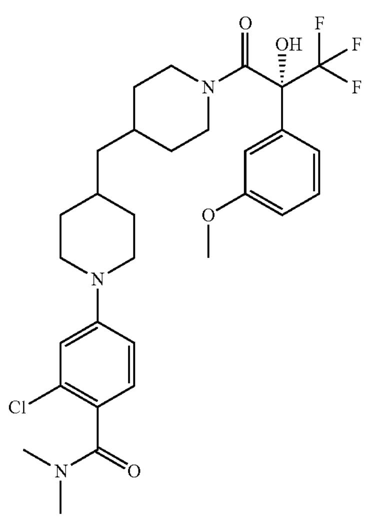 [SMILES: COc1cccc([C@@](O)(C(=O)N2CCC(CC3CCN(c4ccc(C(=O)N(C)C)c(Cl)c4)CC3)CC2)C(F)(F)F)c1] | 2-chloro-N,N-dimethyl-4-[4-({1-[(2S)-3,3,3-trifluoro-2-hydroxy-2-(3-methoxyphenyl)propanoyl]piperidin-4-yl}methyl)piperidin-1-yl]benzamide | Calc'd 596.2, found 596.5 |

| example | Structure | IUPAC Name | Exact Mass [M + H]+ |
|---|---|---|---|
| Example 2-35 | 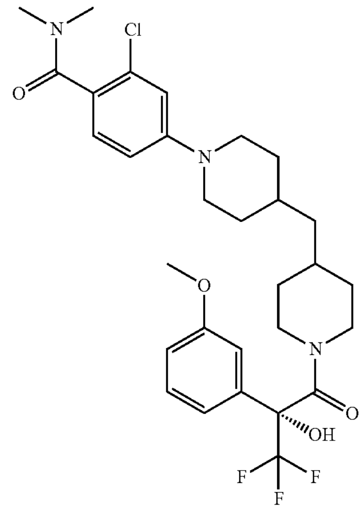 | 2-chloro-N,N-dimethyl-4-[4-({1-[(2R)-3,3,3-trifluoro-2-hydroxy-2-(3-methoxyphenyl)propanoyl]piperidin-4-yl}methyl)piperidin-1-yl]benzamide | Calc'd 596.2, found 596.5 |
| Example 2-36 | 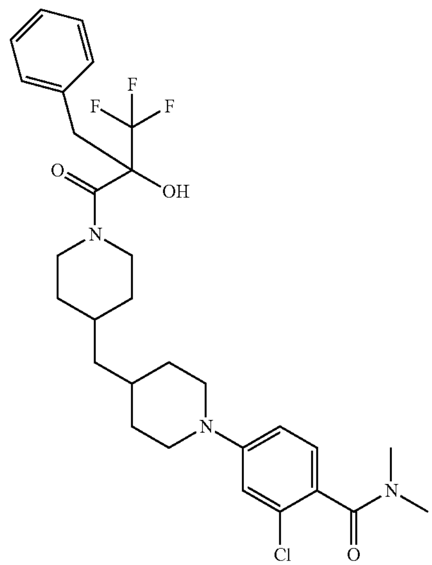 [SMILES: CN(C)C(=O)c1ccc(N2CCC(CC3CCN(C(=O)C(O)(Cc4ccccc4)C(F)(F)F)CC3)CC2)cc1Cl] | 4-(4-{[1-(2-benzyl-3,3,3-trifluoro-2-hydroxy-propanoyl)piperidin-4-yl]methyl}piperidin-1-yl)-2-chloro-N,N-dimethyl-benzamide | Calc'd 580.3, found 580.2 |
| Example 2-37 | 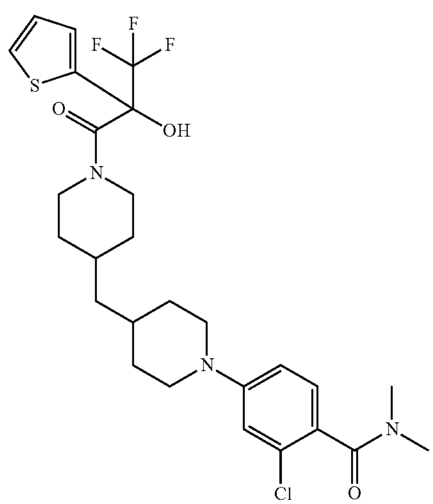 [SMILES: CN(C)C(=O)c1ccc(N2CCC(CC3CCN(C(=O)C(O)(c4cccs4)C(F)(F)F)CC3)CC2)cc1Cl] | 2-chloro-N,N-dimethyl-4-(4-{[1-(3,3,3-trifluoro-2-hydroxy-2-thiophen-2-ylpropanoyl)piperidin-4-yl]methyl}piperidin-1-yl)benzamide | Calc'd 572.2, found 572.2 |

| example | Structure | IUPAC Name | Exact Mass [M + H]+ |
|---------|-----------|------------|---------------------|
| Example 2-38 | 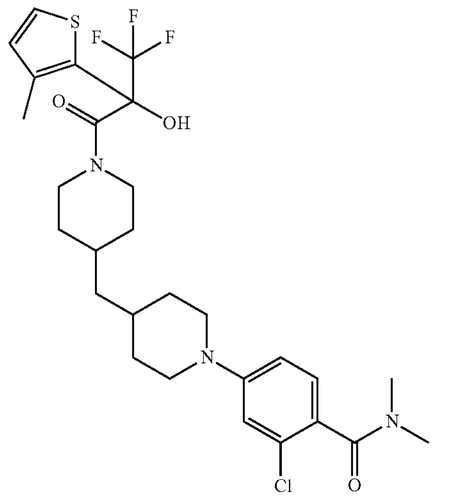 [SMILES: Cc1ccsc1C(O)(C(=O)N1CCC(CC2CCN(c3ccc(C(=O)N(C)C)c(Cl)c3)CC2)CC1)C(F)(F)F] | 2-chloro-N,N-dimethyl-4-[4-({1-[3,3,3-trifluoro-2-hydroxy-2-(3-methyl-thiophen-2-yl)propanoyl]piperidin-4-yl}methyl)piperidin-1-yl]benzamide | Calc'd 586.2, found 586.4 |
| Example 2-39 | 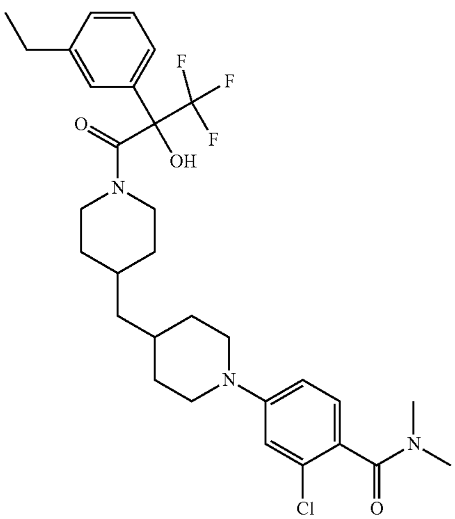 [SMILES: CCc1cccc(C(O)(C(=O)N2CCC(CC3CCN(c4ccc(C(=O)N(C)C)c(Cl)c4)CC3)CC2)C(F)(F)F)c1] | 2-chloro-4-[4-({1-[2-(3-ethylphenyl)-3,3,3-trifluoro-2-hydroxy-propanoyl]piperidin-4-yl}methyl)piperidin-1-yl]-N,N-dimethyl-benzamide | Calc'd 594.3, found 594.4 |
| Example 2-40 | 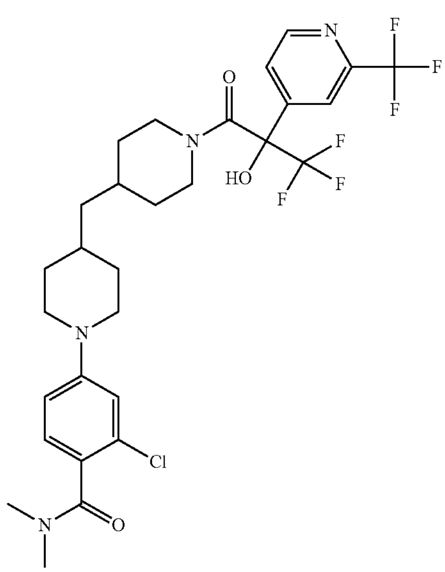 [SMILES: CN(C)C(=O)c1ccc(N2CCC(CC3CCN(C(=O)C(O)(c4ccnc(C(F)(F)F)c4)C(F)(F)F)CC3)CC2)cc1Cl] | 2-chloro-N,N-dimethyl-4-{4-[(1-{3,3,3-trifluoro-2-hydroxy-2-[2-(trifluoromethyl)pyridin-4-yl]propanoyl}piperidin-4-yl)methyl]piperidin-1-yl}benzamide | Calc'd 635.2, found 635.2 |

| example | Structure | IUPAC Name | Exact Mass [M + H]+ |
|---|---|---|---|
| Example 2-41 | 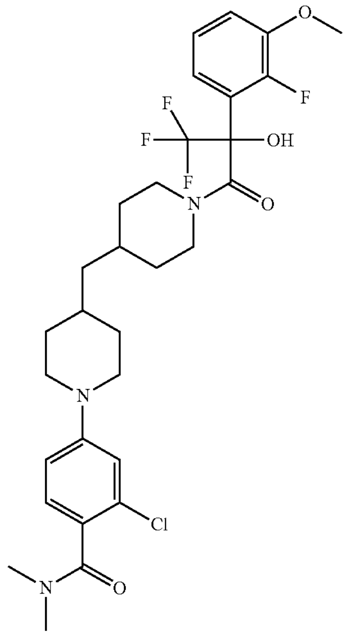 | 2-chloro-N,N-dimethyl-4-[4-({1-[3,3,3-trifluoro-2-(2-fluoro-3-methoxyphenyl)-2-hydroxy-propanoyl]piperidin-4-yl}methyl)piperidin-1-yl]benzamide | Calc'd 614.2, found 614.2 |
| Example 2-42 | 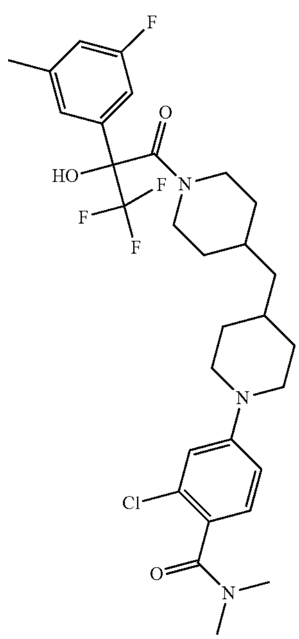 [SMILES: Cc1cc(F)cc(C(O)(C(=O)N2CCC(CC3CCN(c4ccc(C(=O)N(C)C)c(Cl)c4)CC3)CC2)C(F)(F)F)c1] | 2-chloro-N,N-dimethyl-4-[4-({1-[3,3,3-trifluoro-2-(3-fluoro-5-methylphenyl)-2-hydroxy-propanoyl]piperidin-4-yl}methyl)piperidin-1-yl]benzamide | Calc'd 598.2, found 598.2 |

-continued

| example | Structure | IUPAC Name | Exact Mass [M + H]+ |
|---|---|---|---|
| Example 2-43 | 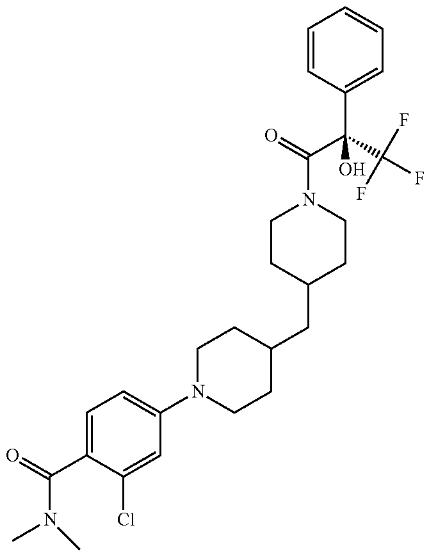 [SMILES: CN(C)C(=O)c1ccc(N2CCC(CC3CCN(C(=O)[C@](O)(c4ccccc4)C(F)(F)F)CC3)CC2)cc1Cl] | 2-chloro-N,N-dimethyl-4-[4-({1-[(2R)-3,3,3-trifluoro-2-hydroxy-2-phenyl-propanoyl]piperidin-4-yl}methyl)piperidin-1-yl]benzamide | Calc'd 566.2, found 566.3 |
| Example 2-44 | 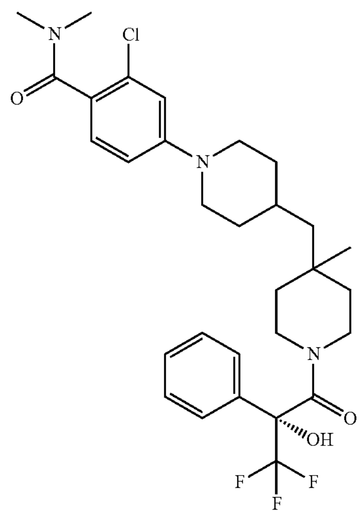 [SMILES: CN(C)C(=O)c1ccc(N2CCC(CC3(C)CCN(C(=O)[C@](O)(c4ccccc4)C(F)(F)F)CC3)CC2)cc1Cl] | 2-chloro-N,N-dimethyl-4-[4-({4-methyl-1-[(2R)-3,3,3-trifluoro-2-hydroxy-2-phenyl-propanoyl]piperidin-4-yl}methyl)piperidin-1-yl]benzamide | Calc'd 580.3, found 580.5 |
| Example 2-45 | 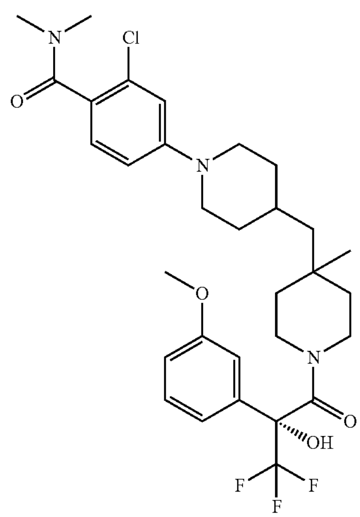 [SMILES: COc1cccc([C@@](O)(C(=O)N2CCC(C)(CC3CCN(c4ccc(C(=O)N(C)C)c(Cl)c4)CC3)CC2)C(F)(F)F)c1] | 2-chloro-N,N-dimethyl-4-[4-({4-methyl-1-[(2R)-3,3,3-trifluoro-2-hydroxy-2-(3-methoxyphenyl)propanoyl]piperidin-4-yl}methyl)piperidin-1-yl]benzamide | Calc'd 610.3, found 610.5 |

-continued

| example | Structure | IUPAC Name | Exact Mass [M + H]+ |
|---|---|---|---|
| Example 2-46 | 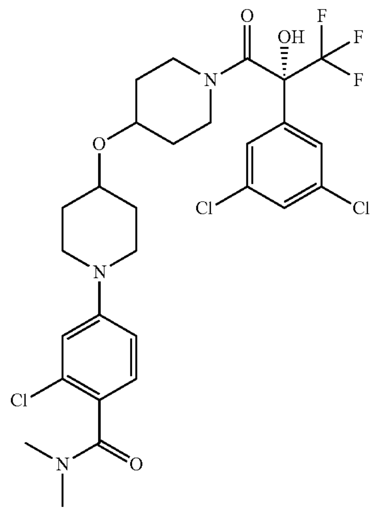 [SMILES: CN(C)C(=O)c1ccc(N2CCC(OC3CCN(C(=O)[C@](O)(c4cc(Cl)cc(Cl)c4)C(F)(F)F)CC3)CC2)cc1Cl] | 2-chloro-4-[4-({1-[(2R)-2-(3,5-dichlorophenyl)-3,3,3-trifluoro-2-hydroxypropanoyl]piperidin-4-yl}oxy)piperidin-1-yl]-N,N-dimethylbenzamide | Calc'd 636.1, found 636.3 |
| Example 2-47 | 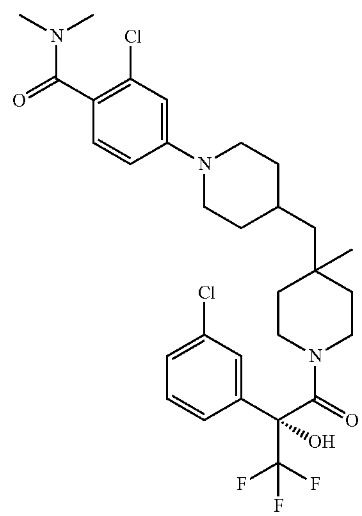 [SMILES: CN(C)C(=O)c1ccc(N2CCC(CC3(C)CCN(C(=O)[C@](O)(c4cccc(Cl)c4)C(F)(F)F)CC3)CC2)cc1Cl] | 2-chloro-4-[4-({1-[(2R)-2-(3-chlorophenyl)-3,3,3-trifluoro-2-hydroxypropanoyl]-4-methylpiperidin-4-yl}methyl)piperidin-1-yl]-N,N-dimethylbenzamide | Calc'd 614.2, found 614.4 |
| Example 2-48 | 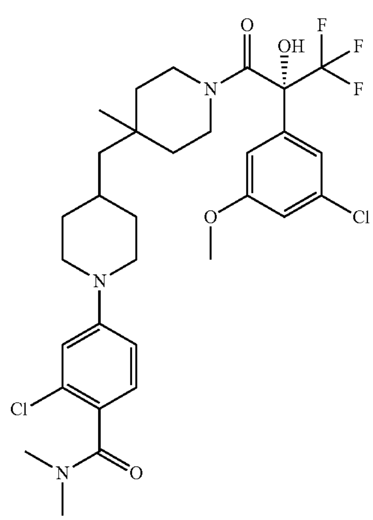 [SMILES: COc1cc(Cl)cc([C@@](O)(C(=O)N2CCC(C)(CC3CCN(c4ccc(C(=O)N(C)C)c(Cl)c4)CC3)CC2)C(F)(F)F)c1] | 2-chloro-4-[4-({1-[(2R)-2-(3-chloro-5-methoxyphenyl)-3,3,3-trifluoro-2-hydroxypropanoyl]-4-methylpiperidin-4-yl}methyl)piperidin-1-yl]-N,N-dimethylbenzamide | Calc'd 644.2, found 644.4 |

-continued

| example | Structure | IUPAC Name | Exact Mass [M + H]+ |
|---|---|---|---|
| Example 2-49 | 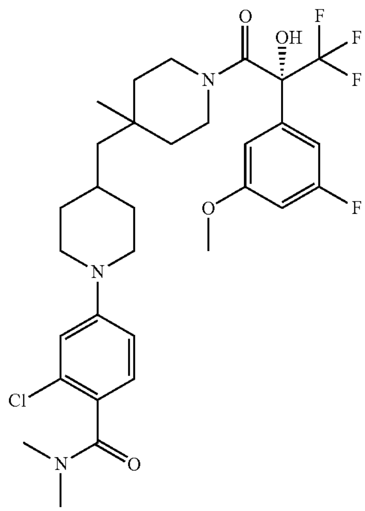 [SMILES: COc1cc(F)cc([C@@](O)(C(=O)N2CCC(C)(CC3CCN(c4ccc(C(=O)N(C)C)c(Cl)c4)CC3)CC2)C(F)(F)F)c1] | 2-chloro-N,N-dimethyl-4-[4-({4-methyl-1-[(2R)-3,3,3-trifluoro-2-(3-fluoro-5-methoxyphenyl)-2-hydroxy-propanoyl]piperidin-4-yl}methyl)piperidin-1-yl]benzamide | Calc'd 628.3, found 628.4 |
| Example 2-50 | 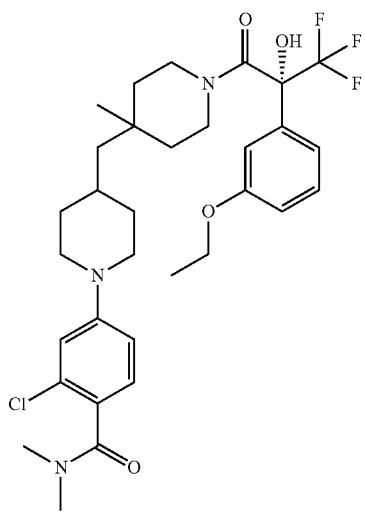 [SMILES: CCOc1cccc([C@@](O)(C(=O)N2CCC(C)(CC3CCN(c4ccc(C(=O)N(C)C)c(Cl)c4)CC3)CC2)C(F)(F)F)c1] | 2-chloro-4-[4-({1-[(2R)-2-(3-ethoxy-phenyl)-3,3,3-trifluoro-2-hydroxy-propanoyl]-4-methyl-piperidin-4-yl}methyl)piperidin-1-yl]-N,N-dimethyl-benzamide | Calc'd 624.3, found 624.4 |
| Example 2-51 | 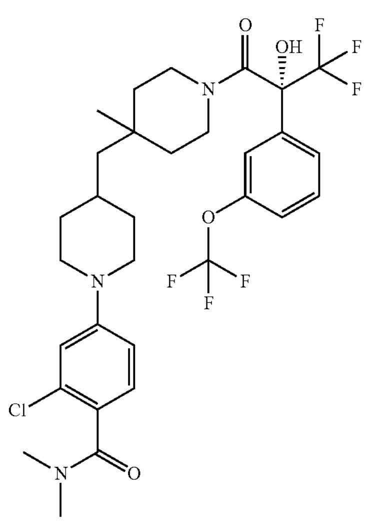 [SMILES: CN(C)C(=O)c1ccc(N2CCC(CC3(C)CCN(C(=O)[C@](O)(c4cccc(OC(F)(F)F)c4)C(F)(F)F)CC3)CC2)cc1Cl] | 2-chloro-N,N-dimethyl-4-{4-[(4-methyl-1-{(2R)-3,3,3-trifluoro-2-hydroxy-2-[3-(trifluoromethoxy)phenyl]propanoyl}piperidin-4-yl)methyl]piperidin-1-yl}benzamide | Calc'd 664.2, found 664.4 |

| example | Structure | IUPAC Name | Exact Mass [M + H]+ |
| --- | --- | --- | --- |
| Example 2-52 | 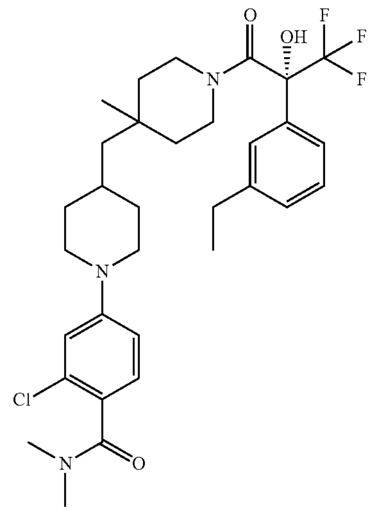 [SMILES: CCc1cccc([C@@](O)(C(=O)N2CCC(C)(CC3CCN(c4ccc(C(=O)N(C)C)c(Cl)c4)CC3)CC2)C(F)(F)F)c1] | 2-chloro-4-[4-({1-[(2R)-2-(3-ethyl-phenyl)-3,3,3-trifluoro-2-hydroxy-propanoyl]-4-methyl-piperidin-4-yl}methyl)piperidin-1-yl]-N,N-dimethyl-benzamide | Calc'd 608.3, found 608.4 |
| Example 2-53 | 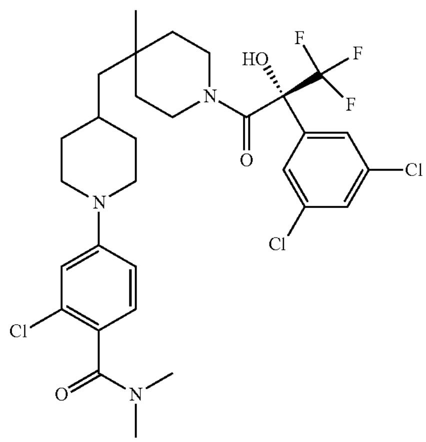 [SMILES: CN(C)C(=O)c1ccc(N2CCC(CC3(C)CCN(C(=O)[C@](O)(c4cc(Cl)cc(Cl)c4)C(F)(F)F)CC3)CC2)cc1Cl] | 2-chloro-4-[4-({1-[(2R)-2-(3,5-dichloro-phenyl)-3,3,3-trifluoro-2-hydroxy-propanoyl]-4-methylpiperidin-4-yl}methyl)piperidin-1-yl]-N,N-dimethyl-benzamide | Calc'd 648.2, found 648.4 |
| Example 2-54 | 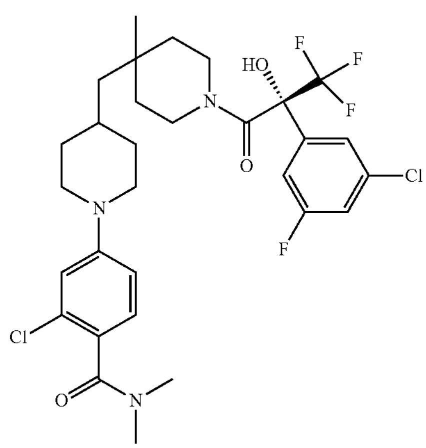 [SMILES: CN(C)C(=O)c1ccc(N2CCC(CC3(C)CCN(C(=O)[C@](O)(c4cc(F)cc(Cl)c4)C(F)(F)F)CC3)CC2)cc1Cl] | 2-chloro-4-[4-({1-[(2R)-2-(3-chloro-5-fluorophenyl)-3,3,3-trifluoro-2-hydroxy-propanoyl]-4-methylpiperidin-4-yl}methyl)piperidin-1-yl]-N,N-dimethyl-benzamide | Calc'd 632.2, found 632.4 |

| example | Structure | IUPAC Name | Exact Mass [M + H]+ |
|---|---|---|---|
| Example 2-55 | 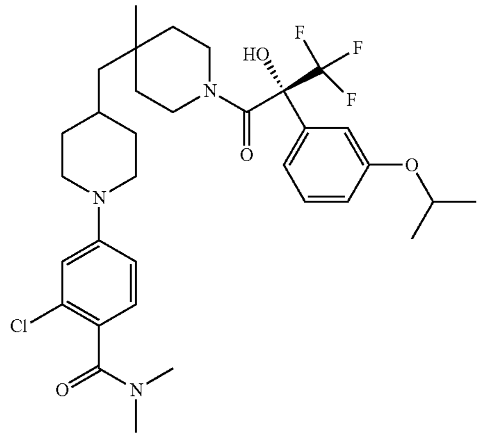 [SMILES: CC(C)Oc1cccc([C@@](O)(C(=O)N2CCC(C)(CC3CCN(c4ccc(C(=O)N(C)C)c(Cl)c4)CC3)CC2)C(F)(F)F)c1] | 2-chloro-N,N-dimethyl-4-{4-[(4-methyl-1-{(2R)-3,3,3-trifluoro-2-hydroxy-2-[3-(1-methyl-ethoxy)phenyl]propanoyl}piperidin-4-yl)methyl]piperidin-1-yl}benzamide | Calc'd 638.3, found 638.5 |
| Example 2-56 | 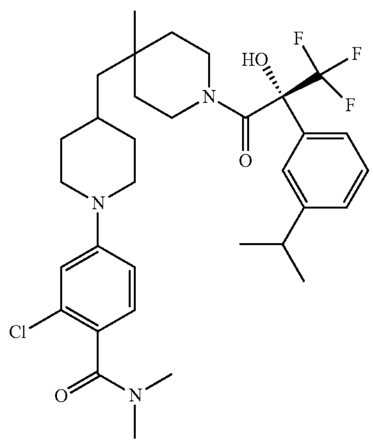 [SMILES: CC(C)c1cccc([C@@](O)(C(=O)N2CCC(C)(CC3CCN(c4ccc(C(=O)N(C)C)c(Cl)c4)CC3)CC2)C(F)(F)F)c1] | 2-chloro-N,N-dimethyl-4-{4-[(4-methyl-1-{(2R)-3,3,3-trifluoro-2-hydroxy-2-[3-(1-methylethyl)phenyl]propanoyl}piperidin-4-yl)methyl]piperidin-1-yl}benzamide | Calc'd 622.3, found 622.5 |
| Example 2-57 | 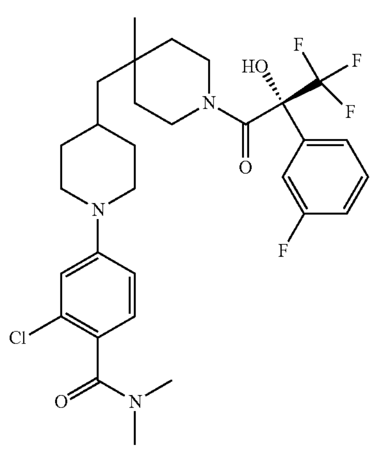 [SMILES: CN(C)C(=O)c1ccc(N2CCC(CC3(C)CCN(C(=O)[C@](O)(c4cccc(F)c4)C(F)(F)F)CC3)CC2)cc1Cl] | 2-chloro-N,N-dimethyl-4-[4-({4-methyl-1-[(2R)-3,3,3-trifluoro-2-(3-fluorophenyl)-2-hydroxypropanoyl]piperidin-4-yl}methyl)piperidin-1-yl]benzamide | Calc'd 598.2, found 598.5 |

| example | Structure | IUPAC Name | Exact Mass [M + H]+ |
|---|---|---|---|
| Example 2-58 | 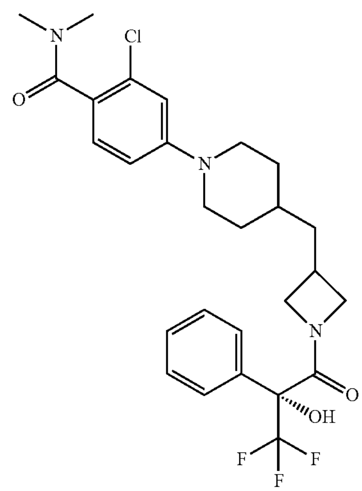 [SMILES: CN(C)C(=O)c1ccc(N2CCC(CC3CN(C(=O)[C@](O)(c4ccccc4)C(F)(F)F)C3)CC2)cc1Cl] | 2-chloro-N,N-dimethyl-4-[4-({1-[(2R)-3,3,3-trifluoro-2-hydroxy-2-phenylpropanoyl]azetidin-3-yl}methyl)piperidin-1-yl]benzamide | Calc'd 538.2, found 538.4 |
| Example 2-59 | 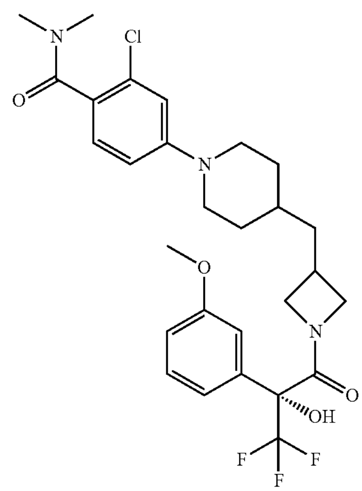 [SMILES: COc1cccc([C@@](O)(C(=O)N2CC(CC3CCN(c4ccc(C(=O)N(C)C)c(Cl)c4)CC3)C2)C(F)(F)F)c1] | 2-chloro-N,N-dimethyl-4-[4-({1-[(2R)-3,3,3-trifluoro-2-hydroxy-2-(3-methoxyphenyl)propanoyl]azetidin-3-yl}methyl)piperidin-1-yl]benzamide | Calc'd 568.2, found 568.5 |
| Example 2-60 | 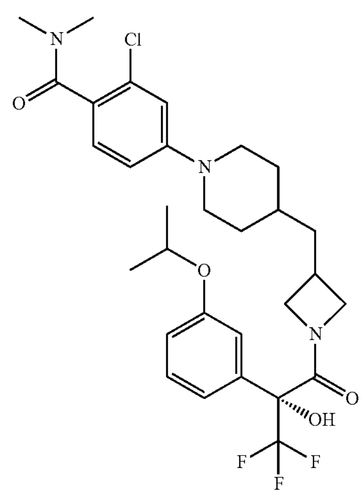 [SMILES: CC(C)Oc1cccc([C@@](O)(C(=O)N2CC(CC3CCN(c4ccc(C(=O)N(C)C)c(Cl)c4)CC3)C2)C(F)(F)F)c1] | 2-chloro-N,N-dimethyl-4-{4-[(1-{(2R)-3,3,3-trifluoro-2-hydroxy-2-[3-(1-methyl-ethoxy)phenyl]propanoyl}azetidin-3-yl)methyl]piperidin-1-yl}benzamide | Calc'd 596.2, found 596.5 |

-continued

| example | Structure | IUPAC Name | Exact Mass [M + H]+ |
|---|---|---|---|
| Example 2-61 | 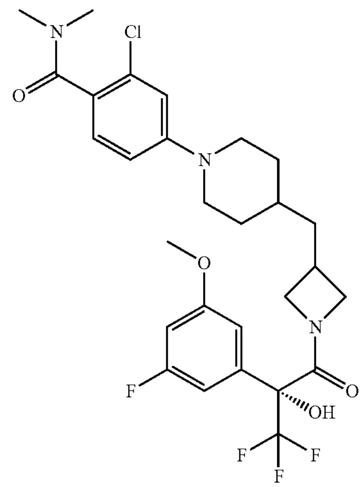 [SMILES: COc1cc(F)cc([C@@](O)(C(=O)N2CC(CC3CCN(c4ccc(C(=O)N(C)C)c(Cl)c4)CC3)C2)C(F)(F)F)c1] | 2-chloro-N,N-dimethyl-4-[4-({1-[(2R)-3,3,3-trifluoro-2-(3-fluoro-5-methoxyphenyl)-2-hydroxy-propanoyl]azetidin-3-yl}methyl)piperidin-1-yl]benzamide | Calc'd 586.2, found 586.4 |
| Example 2-62 | 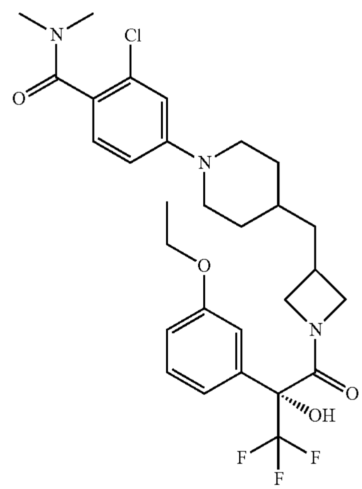 [SMILES: CCOc1cccc([C@@](O)(C(=O)N2CC(CC3CCN(c4ccc(C(=O)N(C)C)c(Cl)c4)CC3)C2)C(F)(F)F)c1] | 2-chloro-4-[4-({1-[(2R)-2-(3-ethoxy-phenyl)-3,3,3-trifluoro-2-hydroxy-propanoyl]azetidin-3-yl}methyl)piperidin-1-yl]-N,N-dimethyl-benzamide | Calc'd 582.2, found 582.4 |
| Example 2-63 | 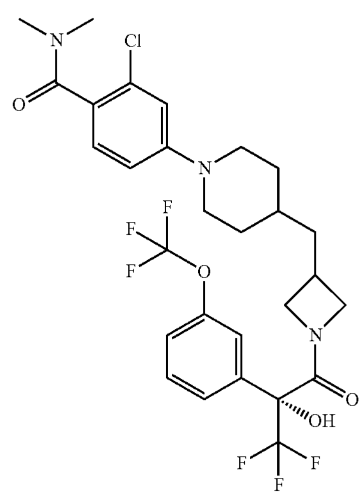 [SMILES: CN(C)C(=O)c1ccc(N2CCC(CC3CN(C(=O)[C@](O)(c4cccc(OC(F)(F)F)c4)C(F)(F)F)C3)CC2)cc1Cl] | 2-chloro-N,N-dimethyl-4-{4-[(1-{(2R)-3,3,3-trifluoro-2-hydroxy-2-[3-(trifluoro-methoxy)phenyl]propanoyl}azetidin-3-yl)methyl]piperidin-1-yl}benzamide | Calc'd 622.2, found 622.4 |

-continued

| example | Structure | IUPAC Name | Exact Mass [M + H]+ |
|---|---|---|---|
| Example 2-64 | 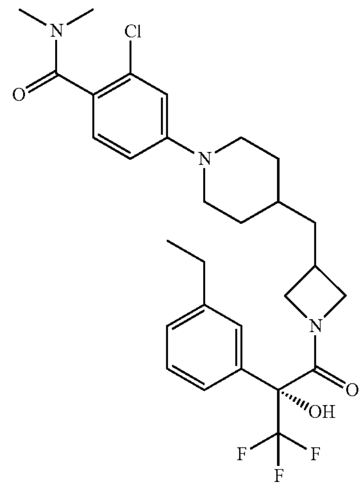 [SMILES: CCc1cccc([C@@](O)(C(=O)N2CC(CC3CCN(c4ccc(C(=O)N(C)C)c(Cl)c4)CC3)C2)C(F)(F)F)c1] | 2-chloro-4-[4-({1-[(2R)-2-(3-ethyl-phenyl)-3,3,3-trifluoro-2-hydroxy-propanoyl]azetidin-3-yl}methyl)piperidin-1-yl]-N,N-dimethyl-benzamide | Calc'd 566.2, found 566.4 |
| Example 2-65 | 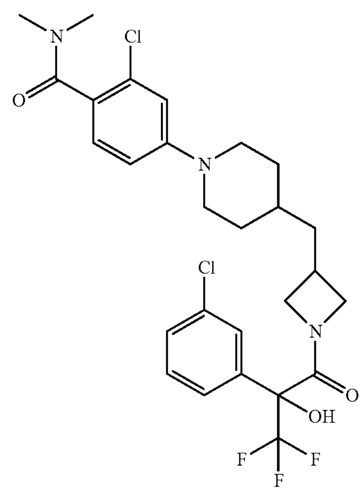 [SMILES: CN(C)C(=O)c1ccc(N2CCC(CC3CN(C(=O)C(O)(c4cccc(Cl)c4)C(F)(F)F)C3)CC2)cc1Cl] | 2-chloro-4-[4-({1-[2-(3-chlorophenyl)-3,3,3-trifluoro-2-hydroxy-propanoyl]azetidin-3-yl}methyl)piperidin-1-yl]-N,N-dimethyl-benzamide | Calc'd 572.2, found 572.4 |
| Example 2-66 | 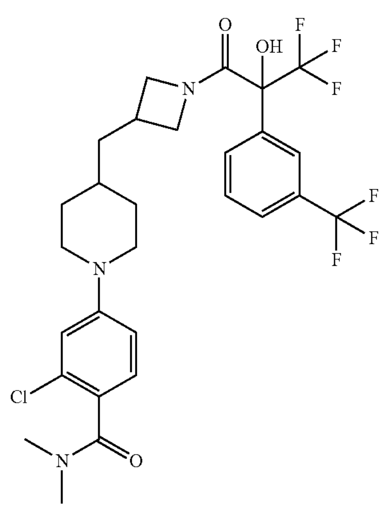 [SMILES: CN(C)C(=O)c1ccc(N2CCC(CC3CN(C(=O)C(O)(c4cccc(C(F)(F)F)c4)C(F)(F)F)C3)CC2)cc1Cl] | 2-chloro-N,N-dimethyl-4-{4-[(1-{3,3,3-trifluoro-2-hydroxy-2-[3-(trifluoromethyl)phenyl]propanoyl}azetidin-3-yl)methyl]piperidin-1-yl}benzamide | Calc'd 606.2, found 606.4 |

-continued

| example | Structure | IUPAC Name | Exact Mass [M + H]+ |
|---|---|---|---|
| Example 2-67 | 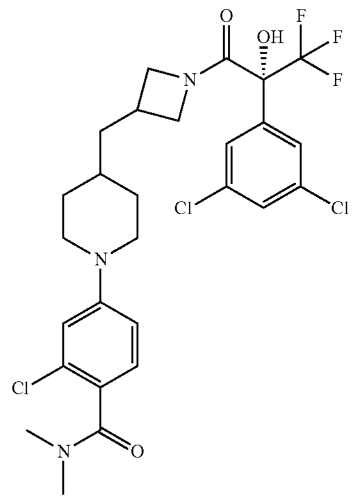 [SMILES: CN(C)C(=O)c1ccc(N2CCC(CC3CN(C(=O)[C@](O)(c4cc(Cl)cc(Cl)c4)C(F)(F)F)C3)CC2)cc1Cl] | 2-chloro-4-[4-({1-[(2R)-2-(3,5-dichloro-phenyl)-3,3,3-trifluoro-2-hydroxy-propanoyl]azetidin-3-yl}methyl)piperidin-1-yl]-N,N-dimethyl-benzamide | Calc'd 606.1, found 606.1 |
| Example 2-68 | 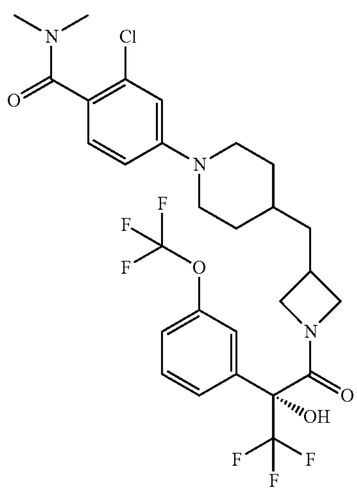 [SMILES: CN(C)C(=O)c1ccc(N2CCC(CC3CN(C(=O)[C@](O)(c4cccc(OC(F)(F)F)c4)C(F)(F)F)C3)CC2)cc1Cl] | 2-chloro-N,N-dimethyl-4-{4-[(1-{(2R)-3,3,3-trifluoro-2-hydroxy-2-[3-(trifluoro-methoxy)phenyl]propanoyl}azetidin-3-yl)methyl]piperidin-1-yl}benzamide | Calc'd 622.2, found 622.3 |
| Example 2-69 | 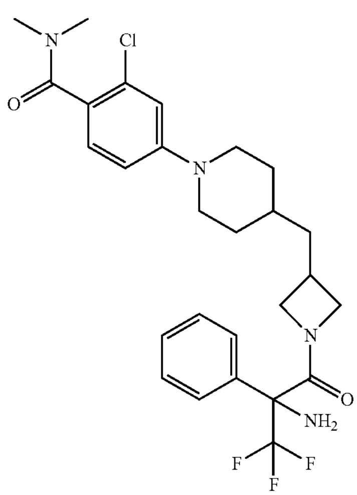 [SMILES: CN(C)C(=O)c1ccc(N2CCC(CC3CN(C(=O)C(N)(c4ccccc4)C(F)(F)F)C3)CC2)cc1Cl] | 4-(4-{[1-(2-amino-3,3,3-trifluoro-2-phenyl-propanoyl)azetidin-3-yl]methyl}piperidin-1-yl)-2-chloro-N,N-dimethyl-benzamide | Calc'd 537.2, found 537.3 |

-continued

| example | Structure | IUPAC Name | Exact Mass [M + H]+ |
|---|---|---|---|
| Example 2-70 | 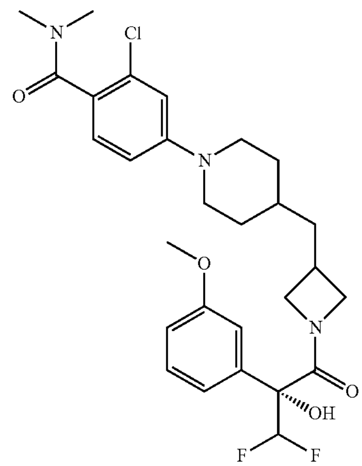 [SMILES: COc1cccc([C@@](O)(C(=O)N2CC(CC3CCN(c4ccc(C(=O)N(C)C)c(Cl)c4)CC3)C2)C(F)F)c1] | 2-chloro-4-[4-({1-[(2R)-3,3-difluoro-2-hydroxy-2-(3-methoxyphenyl)propanoyl]azetidin-3-yl}methyl)piperidin-1-yl]-N,N-dimethylbenzamide | Calc'd 550.2, found 550.3 |
| Example 2-71 | 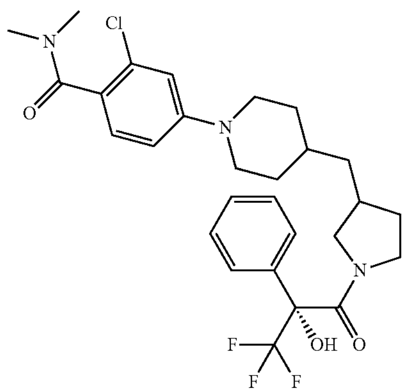 [SMILES: CN(C)C(=O)c1ccc(N2CCC(CC3CCN(C(=O)[C@](O)(c4ccccc4)C(F)(F)F)C3)CC2)cc1Cl] | 2-chloro-N,N-dimethyl-4-[4-({1-[(2R)-3,3,3-trifluoro-2-hydroxy-2-phenylpropanoyl]pyrrolidin-3-yl}methyl)piperidin-1-yl]benzamide | Calc'd 552.2, found 552.4 |
| Example 2-72 | 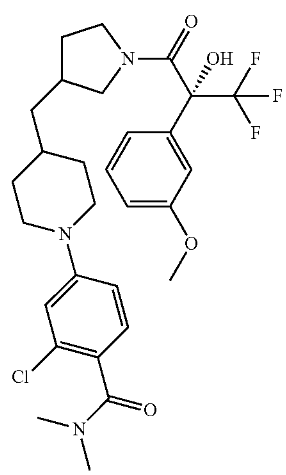 [SMILES: COc1cccc([C@@](O)(C(=O)N2CCC(CC3CCN(c4ccc(C(=O)N(C)C)c(Cl)c4)CC3)C2)C(F)(F)F)c1] | 2-chloro-N,N-dimethyl-4-[4-({1-[(2R)-3,3,3-trifluoro-2-hydroxy-2-(3-methoxyphenyl)propanoyl]pyrrolidin-3-yl}methyl)piperidin-1-yl]benzamide | Calc'd 582.2, found 582.5 |
| Example 2-73 | 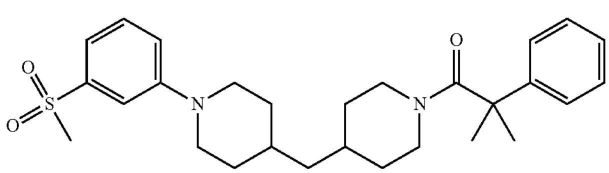 [SMILES: CC(C)(C(=O)N1CCC(CC2CCN(c3cccc(S(C)(=O)=O)c3)CC2)CC1)c1ccccc1] | 1-(2-methyl-2-phenylpropanoyl)-4-({1-[3-(methylsulfonyl)phenyl]piperidin-4-yl}methyl)piperidine | Calc'd 483.3, found 483.4 |

| example | Structure | IUPAC Name | Exact Mass [M + H]+ |
|---|---|---|---|
| Example 2-74 | 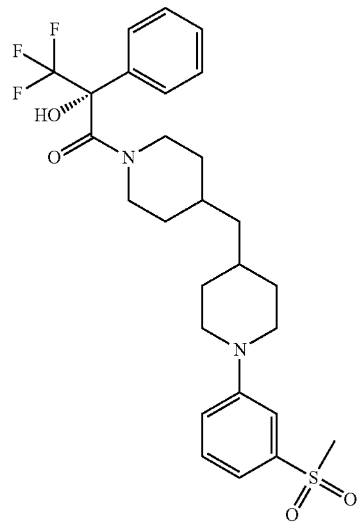 [SMILES: CS(=O)(=O)c1cccc(N2CCC(CC3CCN(C(=O)[C@](O)(c4ccccc4)C(F)(F)F)CC3)CC2)c1] | (2R)-1,1,1-trifluoro-3-[4-({1-[3-(methylsulfonyl)phenyl]piperidin-4-yl}methyl)piperidin-1-yl]-3-oxo-2-phenylpropan-2-ol | Calc'd 539.2, found 539.4 |
| Example 2-75 | 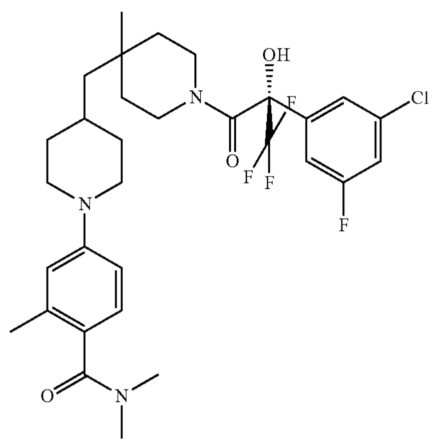 | 4-[4-({1-[(2R)-2-(3-chloro-5-fluorophenyl)-3,3,3-trifluoro-2-hydroxypropanoyl]-4-methylpiperidin-4-yl}methyl)piperidin-1-yl]-N,N,2-trimethylbenzamide | Calc'd 612.3, found 612.4 |
| Example 2-76 | 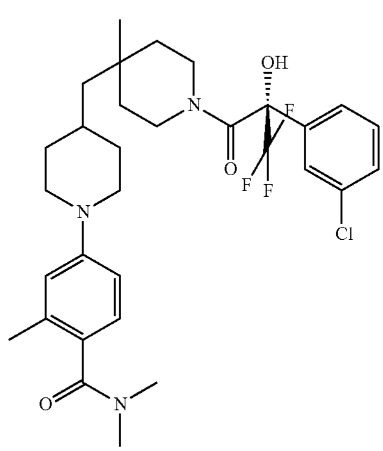 | 4-[4-({1-[(2R)-2-(3-chlorophenyl)-3,3,3-trifluoro-2-hydroxypropanoyl]-4-methylpiperidin-4-yl}methyl)piperidin-1-yl]-N,N,2-trimethylbenzamide | Calc'd 594.3, found 594.5 |

| example | Structure | IUPAC Name | Exact Mass [M + H]+ |
|---|---|---|---|
| Example 2-77 | 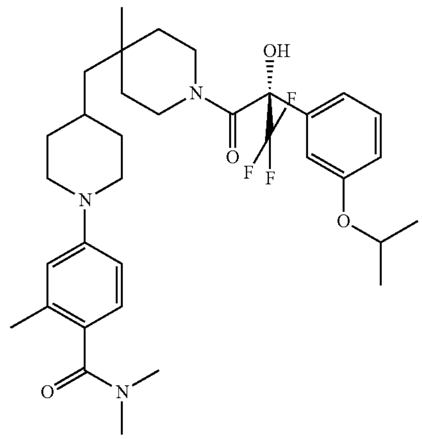 | N,N,2-trimethyl-4-{4-[(4-methyl-1-{(2R)-3,3,3-trifluoro-2-hydroxy-2-[3-(1-methylethoxy)phenyl]propanoyl}piperidin-4-yl)methyl]piperidin-1-yl}benzamide | Calc'd 618.4, found 618.5 |
| Example 2-78 | 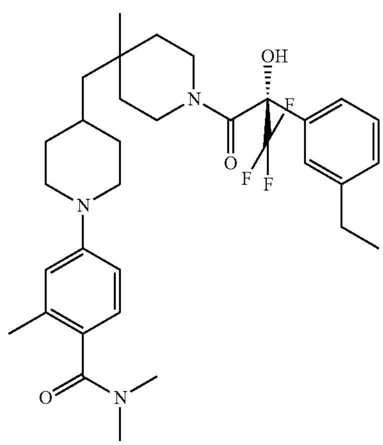 | 4-[4-({1-[(2R)-2-(3-ethylphenyl)-3,3,3-trifluoro-2-hydroxy-propanoyl]-4-methylpiperidin-4-yl}methyl)piperidin-1-yl]-N,N,2-trimethyl-benzamide | Calc'd 588.3, found 588.5 |
| Example 2-79 | 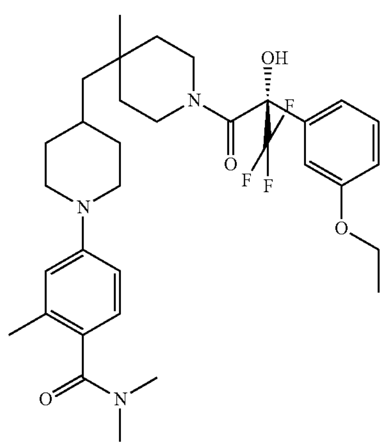 | 4-[4-({1-[(2R)-2-(3-ethoxy-phenyl)-3,3,3-trifluoro-2-hydroxy-propanoyl]-4-methylpiperidin-4-yl}methyl)piperidin-1-yl]-N,N,2-trimethyl-benzamide | Calc'd 604.3, found 604.5 |

| example | Structure | IUPAC Name | Exact Mass [M + H]+ |
|---|---|---|---|
| Example 2-80 | 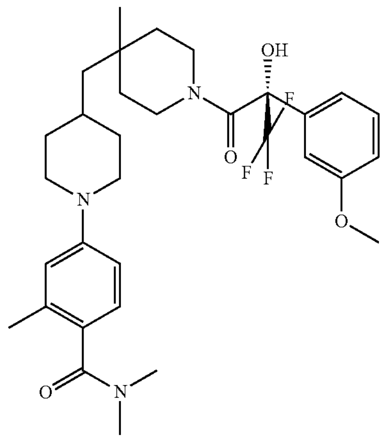 | N,N,2-trimethyl-4-[4-({4-methyl-1-[(2R)-3,3,3-trifluoro-2-hydroxy-2-(3-methoxyphenyl)propanoyl]piperidin-4-yl}methyl)piperidin-1-yl]benzamide | Calc'd 590.3, found 590.5 |
| Example 2-81 | 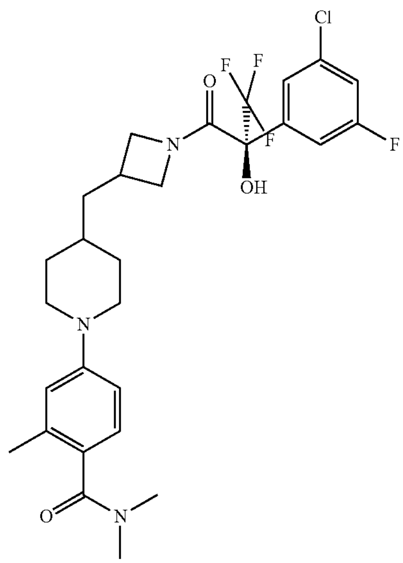 | 4-[4-({1-[(2R)-2-(3-chloro-5-fluorophenyl)-3,3,3-trifluoro-2-hydroxy-propanoyl]azetidin-3-yl}methyl)piperidin-1-yl]-N,N,2-trimethyl-benzamide | Calc'd 570.2, found 570.3 |
| Example 2-82 | 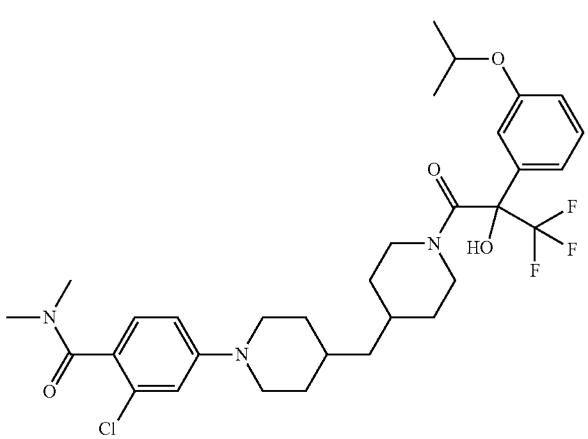 [SMILES: CC(C)Oc1cccc(C(O)(C(=O)N2CCC(CC3CCN(c4ccc(C(=O)N(C)C)c(Cl)c4)CC3)CC2)C(F)(F)F)c1] | 2-chloro-N,N-dimethyl-4-{4-[(1-{3,3,3-trifluoro-2-hydroxy-2-[3-(1-methyl-ethoxy)phenyl]propanoyl}piperidin-4-yl)methyl]piperidin-1-yl}benzamide | Calc'd 624.3, found 624.5 |

-continued

| example | Structure | IUPAC Name | Exact Mass [M + H]+ |
|---|---|---|---|
| Example 2-83 | 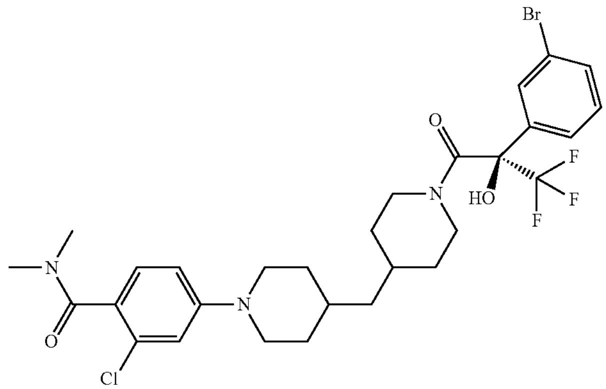 [SMILES: CN(C)C(=O)c1ccc(N2CCC(CC3CCN(C(=O)[C@](O)(c4cccc(Br)c4)C(F)(F)F)CC3)CC2)cc1Cl] | 4-[4-({1-[(2R)-2-(3-bromo-phenyl)-3,3,3-trifluoro-2-hydroxy-propanoyl]piperidin-4-yl}methyl)piperidin-1-yl]-2-chloro-N,N-dimethyl-benzamide | Calc'd 644.1, found 644.4 |
| Example 2-84 | 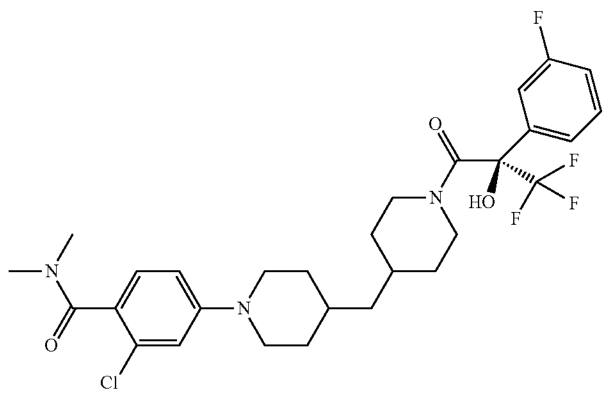 [SMILES: CN(C)C(=O)c1ccc(N2CCC(CC3CCN(C(=O)[C@](O)(c4cccc(F)c4)C(F)(F)F)CC3)CC2)cc1Cl] | 2-chloro-N,N-dimethyl-4-[4-({1-[(2R)-3,3,3-trifluoro-2-(3-fluoro-phenyl)-2-hydroxy-propanoyl]piperidin-4-yl}methyl)piperidin-1-yl]benzamide | Calc'd 584.2, found 584.0 |
| Example 2-85 | 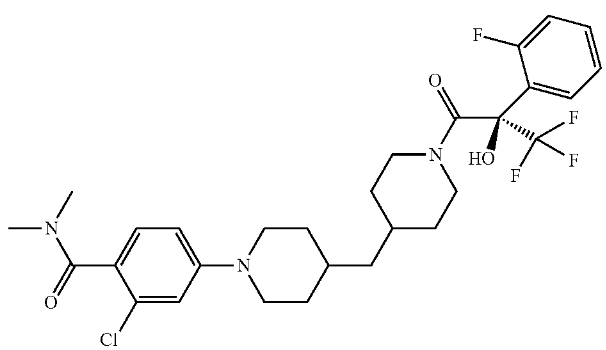 [SMILES: CN(C)C(=O)c1ccc(N2CCC(CC3CCN(C(=O)[C@](O)(c4ccccc4F)C(F)(F)F)CC3)CC2)cc1Cl] | 2-chloro-N,N-dimethyl-4-[4-({1-[(2R)-3,3,3-trifluoro-2-(2-fluorophenyl)-2-hydroxy-propanoyl]piperidin-4-yl}methyl)piperidin-1-yl]benzamide | Calc'd 584.2, found 584.0 |
| Example 2-86 | 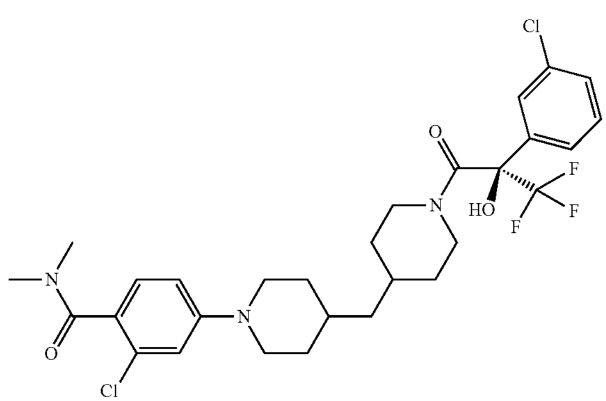 [SMILES: CN(C)C(=O)c1ccc(N2CCC(CC3CCN(C(=O)[C@](O)(c4cccc(Cl)c4)C(F)(F)F)CC3)CC2)cc1Cl] | 2-chloro-4-[4-({1-[(2R)-2-(3-chloro-phenyl)-3,3,3-trifluoro-2-hydroxy-propanoyl]piperidin-4-yl}methyl)piperidin-1-yl]-N,N-dimethyl-benzamide | Calc'd 600.2, found 600.0 |

| example | Structure | IUPAC Name | Exact Mass [M + H]+ |
|---|---|---|---|
| Example 2-87 | 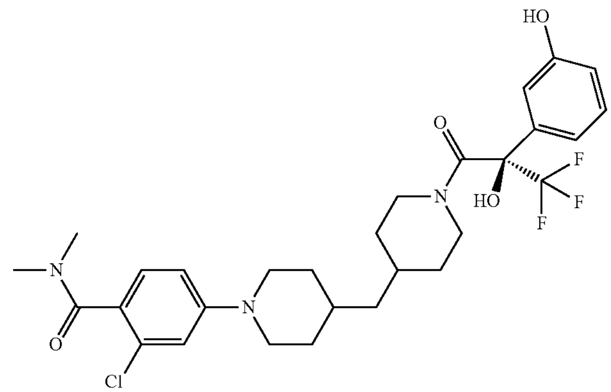 [SMILES: CN(C)C(=O)c1ccc(N2CCC(CC3CCN(C(=O)[C@](O)(c4cccc(O)c4)C(F)(F)F)CC3)CC2)cc1Cl] | 2-chloro-N,N-dimethyl-4-[4-({1-[(2R)-3,3,3-trifluoro-2-hydroxy-2-(3-hydroxyphenyl)propanoyl]piperidin-4-yl}methyl)piperidin-1-yl]benzamide | Calc'd 582.2, found 582.5 |
| Example 2-88 | 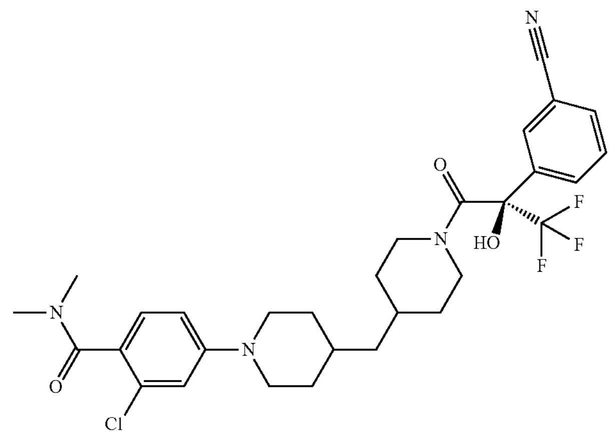 [SMILES: CN(C)C(=O)c1ccc(N2CCC(CC3CCN(C(=O)[C@](O)(c4cccc(C#N)c4)C(F)(F)F)CC3)CC2)cc1Cl] | 2-chloro-4-[4-({1-[(2R)-2-(3-cyanophenyl)-3,3,3-trifluoro-2-hydroxypropanoyl]piperidin-4-yl}methyl)piperidin-1-yl]-N,N-dimethylbenzamide | Calc'd 591.2, found 591.5 |
| Example 2-89 | 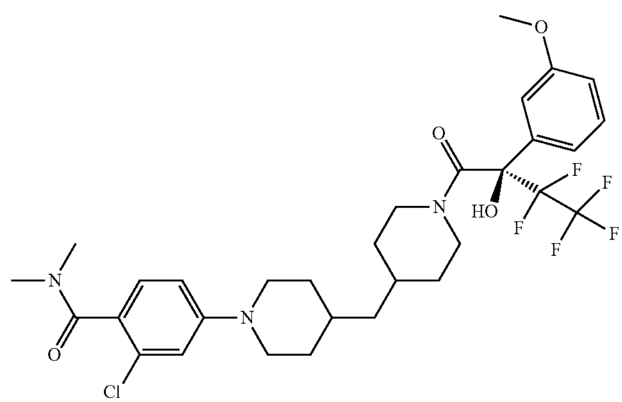 [SMILES: COc1cccc([C@@](O)(C(=O)N2CCC(CC3CCN(c4ccc(C(=O)N(C)C)c(Cl)c4)CC3)CC2)C(F)(F)C(F)(F)F)c1] | 2-chloro-N,N-dimethyl-4-[4-({1-[(2R)-3,3,4,4,4-pentafluoro-2-hydroxy-2-{3-methoxyphenyl)butanoyl]piperidin-4-yl}methyl)piperidin-1-yl]benzamide | Calc'd 646.2, found 646.2 |
| Example 2-90 | 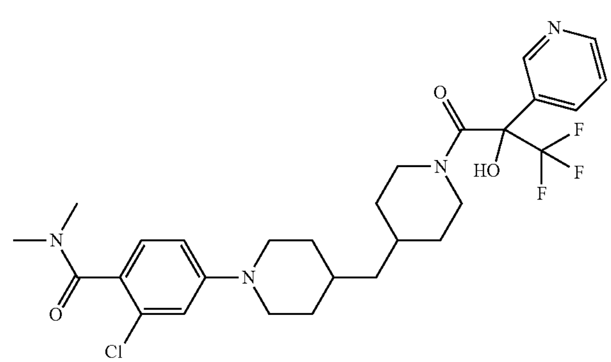 [SMILES: CN(C)C(=O)c1ccc(N2CCC(CC3CCN(C(=O)C(O)(c4cccnc4)C(F)(F)F)CC3)CC2)cc1Cl] | 2-chloro-N,N-dimethyl-4-(4-{[1-(3,3,3-trifluoro-2-hydroxy-2-pyridin-3-ylpropanoyl)piperidin-4-yl]methyl}piperidin-1-yl)benzamide | Calc'd 567.2, found 567.2 |

| example | Structure | IUPAC Name | Exact Mass [M + H]+ |
|---|---|---|---|
| Example 2-91 | 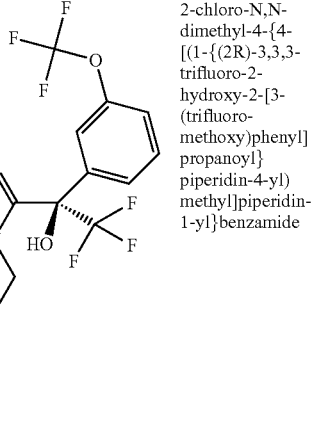 | 2-chloro-N,N-dimethyl-4-{4-[(1-{(2R)-3,3,3-trifluoro-2-hydroxy-2-[3-(trifluoromethoxy)phenyl]propanoyl}piperidin-4-yl)methyl]piperidin-1-yl}benzamide | Calc'd 650.2, found 650.2 |
| Example 2-92 | 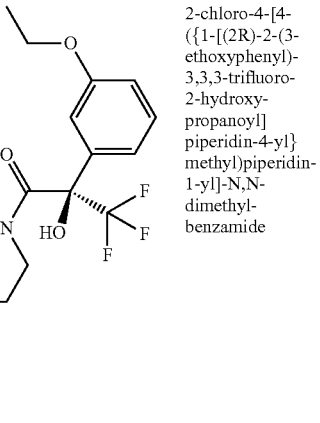 | 2-chloro-4-[4-({1-[(2R)-2-(3-ethoxyphenyl)-3,3,3-trifluoro-2-hydroxypropanoyl]piperidin-4-yl}methyl)piperidin-1-yl]-N,N-dimethylbenzamide | Calc'd 610.3, found 610.5 |
| Example 2-93 | 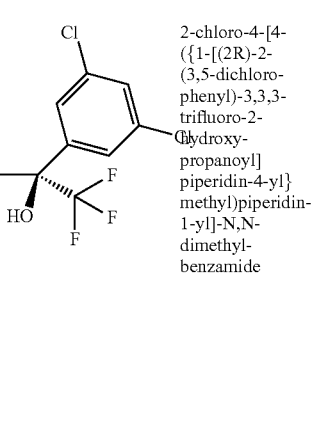 | 2-chloro-4-[4-({1-[(2R)-2-(3,5-dichlorophenyl)-3,3,3-trifluoro-2-hydroxypropanoyl]piperidin-4-yl}methyl)piperidin-1-yl]-N,N-dimethylbenzamide | Calc'd 634.2, found 634.4 |

-continued

| example | Structure | IUPAC Name | Exact Mass [M + H]+ |
|---|---|---|---|
| Example 2-94 | 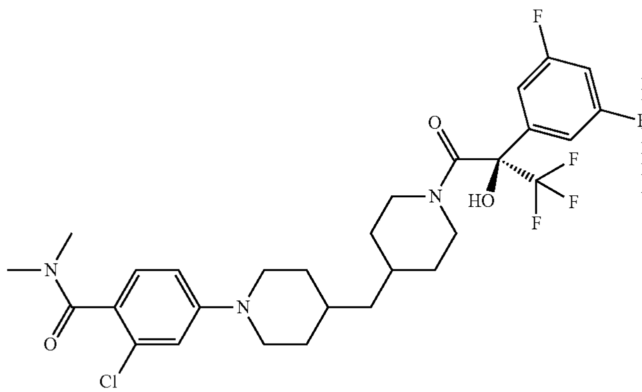 [SMILES: CN(C)C(=O)c1ccc(N2CCC(CC3CCN(C(=O)[C@](O)(c4cc(F)cc(F)c4)C(F)(F)F)CC3)CC2)cc1Cl] | 2-chloro-4-[4-({1-[(2R)-2-(3,5-difluoro-phenyl)-3,3,3-trifluoro-2-hydroxy-propanoyl]piperidin-4-yl}methyl)piperidin-1-yl]-N,N-dimethyl-benzamide | Calc'd 602.2, found 602.5 |
| Example 2-95 | 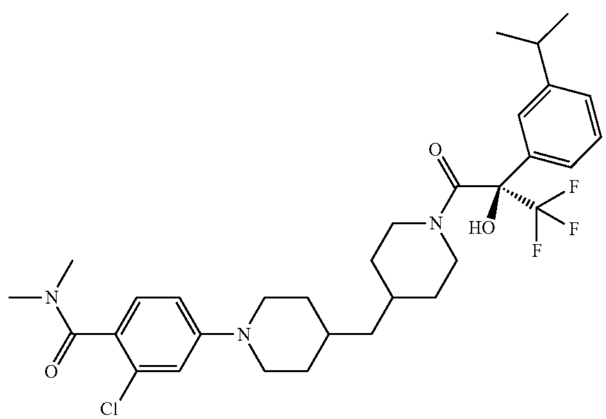 [SMILES: CC(C)c1cccc([C@@](O)(C(=O)N2CCC(CC3CCN(c4ccc(C(=O)N(C)C)c(Cl)c4)CC3)CC2)C(F)(F)F)c1] | 2-chloro-N,N-dimethyl-4-{4-[(1-{(2R)-3,3,3-trifluoro-2-hydroxy-2-[3-(1-methylethyl)phenyl]propanoyl}piperidin-4-yl)methyl]piperidin-1-yl}benzamide | Calc'd 608.3, found 608.5 |
| Example 2-96 | 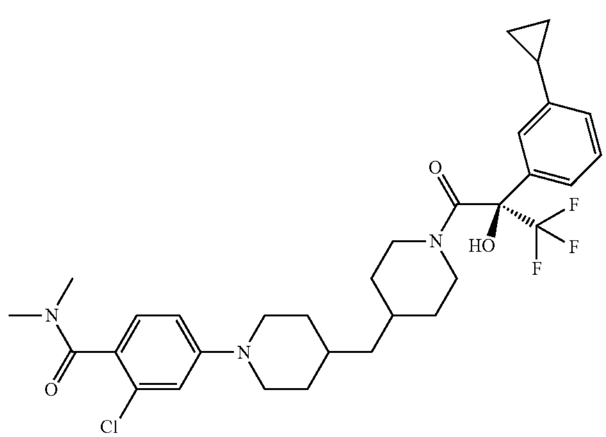 [SMILES: CN(C)C(=O)c1ccc(N2CCC(CC3CCN(C(=O)[C@](O)(c4cccc(C5CC5)c4)C(F)(F)F)CC3)CC2)cc1Cl] | 2-chloro-4-[4-({1-[(2R)-2-(3-cyclopropyl-phenyl)-3,3,3-trifluoro-2-hydroxy-propanoyl]piperidin-4-yl}methyl)piperidin-1-yl]-N,N-dimethyl-benzamide | Calc'd 606.3, found 606.5 |

-continued

| example | Structure | IUPAC Name | Exact Mass [M + H]+ |
|---|---|---|---|
| Example 2-97 | 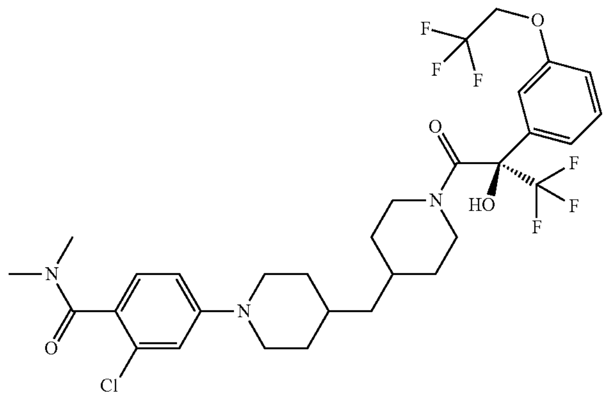 [SMILES: CN(C)C(=O)c1ccc(N2CCC(CC3CCN(C(=O)[C@](O)(c4cccc(OCC(F)(F)F)c4)C(F)(F)F)CC3)CC2)cc1Cl] | 2-chloro-N,N-dimethyl-4-{4-[(1-{(2R)-3,3,3-trifluoro-2-hydroxy-2-[3-(2,2,2-trifluoroethoxy)phenyl]propanoyl}piperidin-4-yl)methyl]piperidin-1-yl}benzamide | Calc'd 664.2, found 664.5 |
| Example 2-98 | 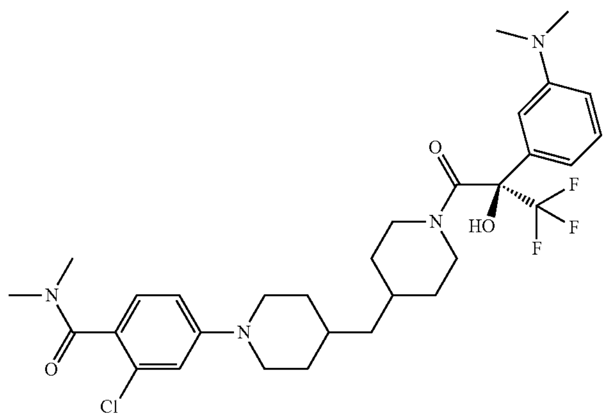 | 2-chloro-4-{4-[(2-{(2R)-2-[3-(dimethylamino)phenyl]-3,3,3-trifluoro-2-hydroxypropanoyl}piperidin-4-yl)methyl]piperidin-1-yl}-N,N-dimethylbenzamide | Calc'd 609.3, found 609.5 |
| Example 2-99 | 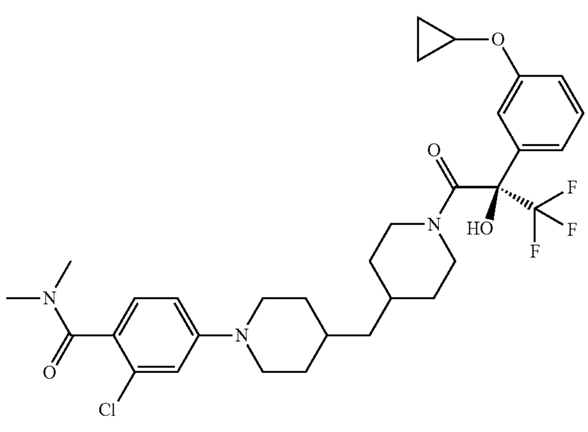 [SMILES: CN(C)C(=O)c1ccc(N2CCC(CC3CCN(C(=O)[C@](O)(c4cccc(OC5CC5)c4)C(F)(F)F)CC3)CC2)cc1Cl] | 2-chloro-4-{4-[(1-{(2R)-2-[3-(cyclopropyloxy)phenyl]-3,3,3-trifluoro-2-hydroxypropanoyl}piperidin-4-yl)methyl]piperidin-1-yl}-N,N-dimethylbenzamide | Calc'd 622.3, found 622.5 |

| example | IUPAC Name | Exact Mass [M + H]+ |
|---|---|---|
| Example 2-100 | 2-chloro-4-[4-({1-[(2R)-2-(3-chloro-5-methoxy-phenyl)-3,3,3-trifluoro-2-hydroxy-propanoyl]piperidin-4-yl}methyl)piperidin-1-yl]-N,N-dimethyl-benzamide | Calc'd 630.2, found 630.5 |
| Example 2-101 | 4-[4-({1-[2-amino-3,3,3-trifluoro-2-phenyl-propanoyl]piperidin-4-yl}methyl)piperidin-1-yl]-2-chloro-N,N-dimethyl-benzamide | Calc'd 565.3, found 565.4 |
| Example 2-102 | 2-chloro-4-[4-({1-[(2R)-2-(3-chloro-5-fluorophenyl)-3,3,3-trifluoro-2-hydroxy-propanoyl]piperidin-4-yl}methyl)piperidin-1-yl]-N,N-dimethyl-benzamide | Calc'd 618.2, found 618.4 |
| Example 2-103 | 4-[4-({1-[(2R)-2-amino-3,3,3-trifluoro-2-(3-methoxyphenyl)propanoyl]piperidin-4-yl}methyl)piperidin-1-yl]-2-chloro-N,N-dimethyl-benzamide | Calc'd 595.3, found 595.4 |

-continued

| example | Structure | IUPAC Name | Exact Mass [M + H]+ |
|---|---|---|---|
| Example 2-104 | 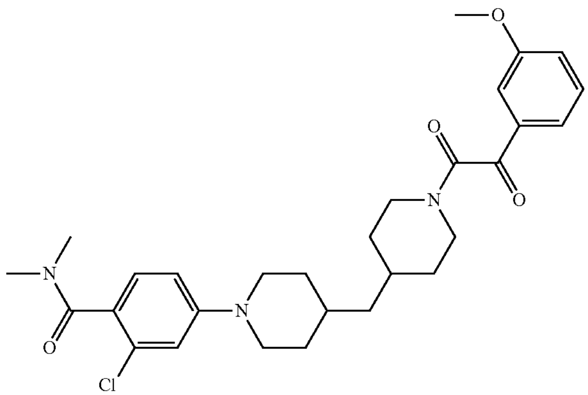 [SMILES: COc1cccc(C(=O)C(=O)N2CCC(CC3CCN(c4ccc(C(=O)N(C)C)c(Cl)c4)CC3)CC2)c1] | 2-chloro-4-[4-({1-[(3-methoxyphenyl)(oxo)acetyl]piperidin-4-yl}methyl)piperidin-1-yl]-N,N-dimethylbenzamide | Calc'd 526.2, found 526.4 |
| Example 2-105 | 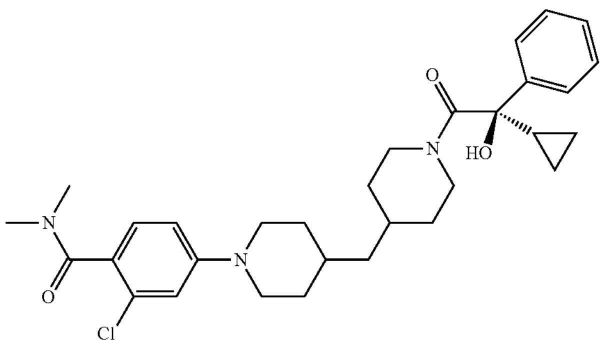 [SMILES: CN(C)C(=O)c1ccc(N2CCC(CC3CCN(C(=O)[C@](O)(c4ccccc4)C4CC4)CC3)CC2)cc1Cl] | 2-chloro-4-[4-({1-[(2R)-2-cyclopropyl-2-hydroxy-2-phenylacetyl]piperidin-4-yl}methyl)piperidin-1-yl]-N,N-dimethylbenzamide | Calc'd 538.3, found 538.4 |
| Example 2-106 | 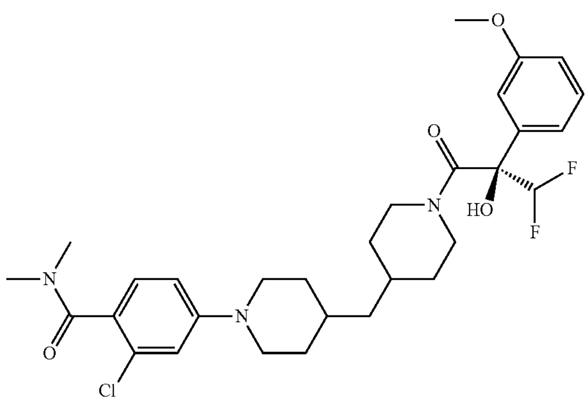 [SMILES: COc1cccc([C@@](O)(C(=O)N2CCC(CC3CCN(c4ccc(C(=O)N(C)C)c(Cl)c4)CC3)CC2)C(F)F)c1] | 2-chloro-4-[4-({1-[(2R)-3,3-difluoro-2-hydroxy-2-(3-methoxyphenyl)propanoyl]piperidin-4-yl}methyl)piperidin-1-yl]-N,N-dimethylbenzamide | Calc'd 578.3, found 578.4 |
| Example 2-107 | 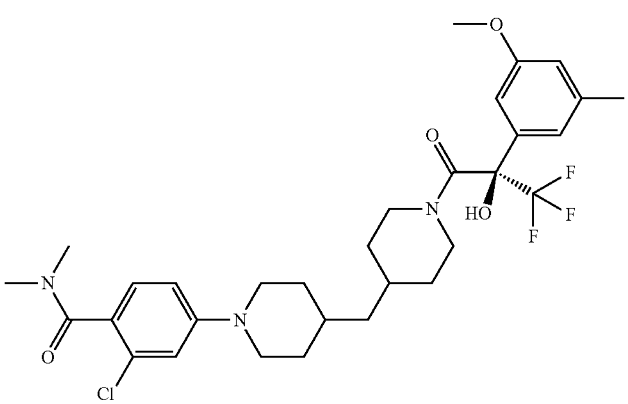 | 2-chloro-N,N-dimethyl-4-[4-({1-[(2R)-3,3,3-trifluoro-2-hydroxy-2-(3-methoxy-5-methylphenyl)propanoyl]piperidin-4-yl}methyl)piperidin-1-yl]benzamide | Calc'd 610.3, found 610.4 |

-continued

| example | Structure | IUPAC Name | Exact Mass [M + H]+ |
|---|---|---|---|
| Example 2-108 | 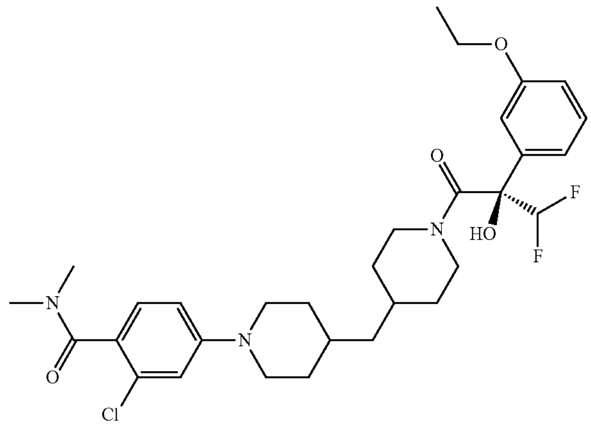 [SMILES: CCOc1cccc([C@@](O)(C(=O)N2CCC(CC3CCN(c4ccc(C(=O)N(C)C)c(Cl)c4)CC3)CC2)C(F)F)c1] | 2-chloro-4-[4-({1-[(2R)-2-(3-ethoxyphenyl)-3,3-difluoro-2-hydroxypropanoyl]piperidin-4-yl}methyl)piperidin-1-yl]-N,N-dimethylbenzamide | Calc'd 592.3, found 592.4 |
| Example 2-109 | 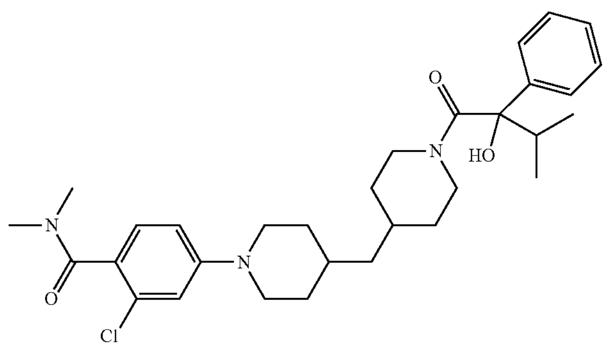 [SMILES: CC(C)C(O)(C(=O)N1CCC(CC2CCN(c3ccc(C(=O)N(C)C)c(Cl)c3)CC2)CC1)c1ccccc1] | 2-chloro-4-(4-{[1-(2-hydroxy-3-methyl-2-phenylbutanoyl)piperidin-4-yl]methyl}piperidin-1-yl)-N,N-dimethylbenzamide | Calc'd 540.3, found 540.5 |
| Example 2-110 | 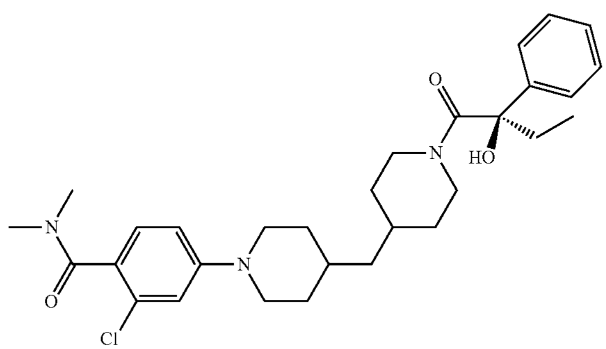 [SMILES: CC[C@](O)(C(=O)N1CCC(CC2CCN(c3ccc(C(=O)N(C)C)c(Cl)c3)CC2)CC1)c1ccccc1] | 2-chloro-4-[4-({1-[(2R)-2-hydroxy-2-phenylbutanoyl]piperidin-4-yl}methyl)piperidin-1-yl]-N,N-dimethylbenzamide | Calc'd 526.3, found 526.4 |
| Example 2-111 | 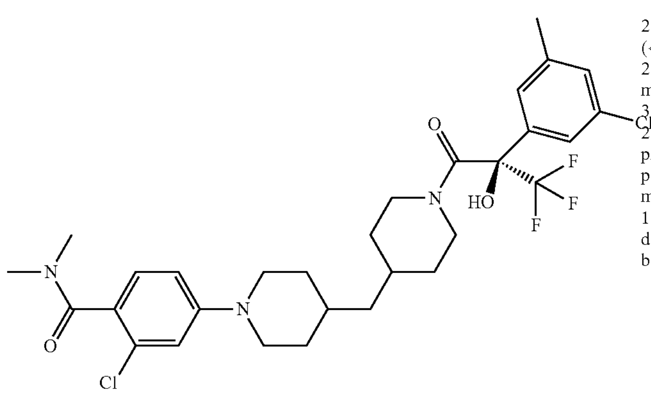 [SMILES: Cc1cc(Cl)cc([C@@](O)(C(=O)N2CCC(CC3CCN(c4ccc(C(=O)N(C)C)c(Cl)c4)CC3)CC2)C(F)(F)F)c1] | 2-chloro-4-[4-({1-[(2R)-2-(3-chloro-5-methylphenyl)-3,3,3-trifluoro-2-hydroxypropanoyl]piperidin-4-yl}methyl)piperidin-1-yl]-N,N-dimethylbenzamide | Calc'd 614.2, found 614.3 |

-continued

| example | Structure | IUPAC Name | Exact Mass [M + H]+ |
|---|---|---|---|
| Example 2-112 | 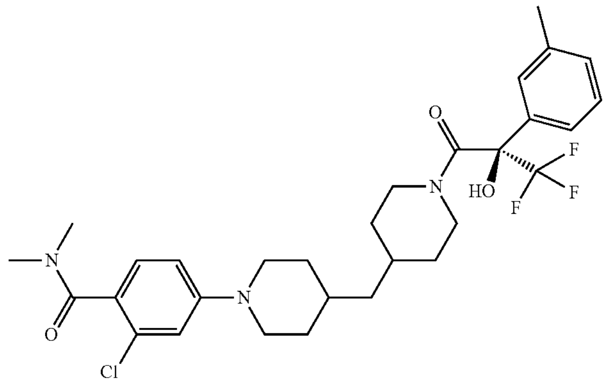 [SMILES: Cc1cccc([C@@](O)(C(=O)N2CCC(CC3CCN(c4ccc(C(=O)N(C)C)c(Cl)c4)CC3)CC2)C(F)(F)F)c1] | 2-chloro-N,N-dimethyl-4-[4-({1-[(2R)-3,3,3-trifluoro-2-hydroxy-2-(3-methylphenyl)propanoyl]piperidin-4-yl}methyl)piperidin-1-yl]benzamide | Calc'd 580.3, found 580.4 |
| Example 2-113 | 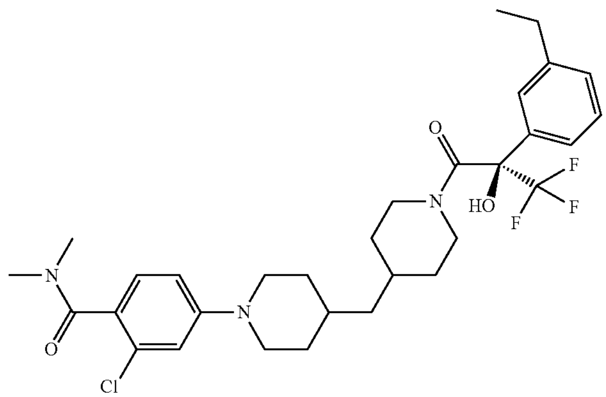 [SMILES: CCc1cccc([C@@](O)(C(=O)N2CCC(CC3CCN(c4ccc(C(=O)N(C)C)c(Cl)c4)CC3)CC2)C(F)(F)F)c1] | 2-chloro-4-[4-({1-[(2R)-2-(3-ethylphenyl)-3,3,3-trifluoro-2-hydroxypropanoyl]piperidin-4-yl}methyl)piperidin-1-yl]-N,N-dimethylbenzamide | Calc'd 594.3, found 594.4 |
| Example 2-114 | 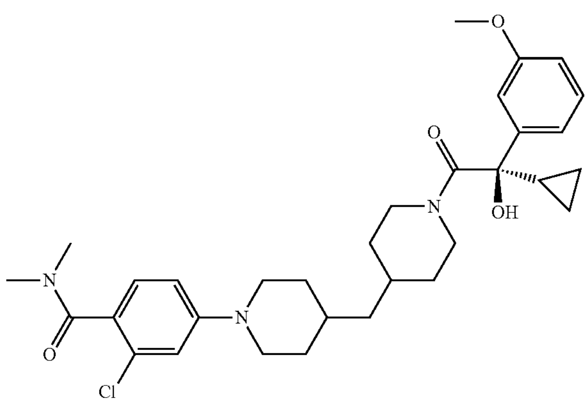 [SMILES: COc1cccc([C@@](O)(C(=O)N2CCC(CC3CCN(c4ccc(C(=O)N(C)C)c(Cl)c4)CC3)CC2)C2CC2)c1] | 2-chloro-4-[4-({1-[(2R)-2-cyclopropyl-2-hydroxy-2-(3-methoxyphenyl)acetyl]piperidin-4-yl}methyl)piperidin-1-yl]-N,N-dimethylbenzamide | Calc'd 568.3, found 568.4 |
| Example 2-115 | 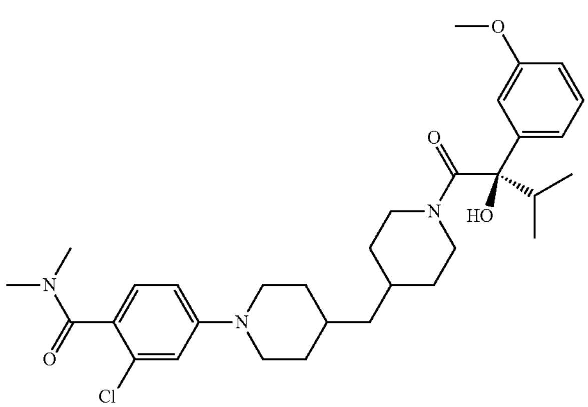 [SMILES: COc1cccc([C@@](O)(C(=O)N2CCC(CC3CCN(c4ccc(C(=O)N(C)C)c(Cl)c4)CC3)CC2)C(C)C)c1] | 2-chloro-4-[4-({1-[(2R)-2-hydroxy-2-(3-methoxyphenyl)-3-methylbutanoyl]piperidin-4-yl}methyl)piperidin-1-yl]-N,N-dimethylbenzamide | Calc'd 570.3, found 570.4 |

| example | Structure | IUPAC Name | Exact Mass [M + H]+ |
|---|---|---|---|
| Example 2-116 | 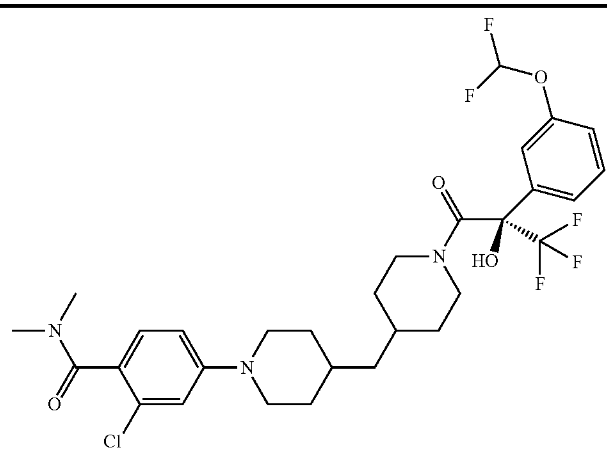 | 2-chloro-4-{4-[(1-{(2R)-2-[3-(difluoromethoxy)phenyl]-3,3,3-trifluoro-2-hydroxypropanoyl}piperidin-4-yl)methyl]piperidin-1-yl}-N,N-dimethylbenzamide | Calc'd 632.2, found 632.2 |
| Example 2-117 | 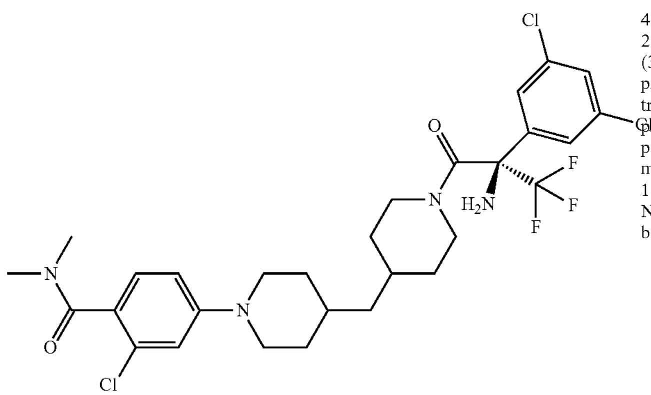 | 4-[4-({1-[(2R)-2-amino-2-(3,5-dichlorophenyl)-3,3,3-trifluoropropanoyl]piperidin-4-yl}methyl)piperidin-1-yl]-2-chloro-N,N-dimethylbenzamide | Calc'd 633.2, found 633.2 |
| Example 2-118 | 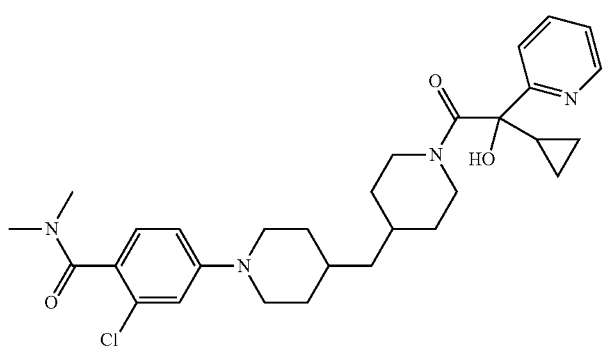 [SMILES: CN(C)C(=O)c1ccc(N2CCC(CC3CCN(C(=O)C(O)(c4ccccn4)C4CC4)CC3)CC2)cc1Cl] | 2-chloro-4-[4-({1-[cyclopropyl(hydroxy)pyridin-2-ylacetyl]piperidin-4-yl}methyl)piperidin-1-yl]-N,N-dimethylbenzamide | Calc'd 539.3, found 539.4 |
| Example 2-119 | 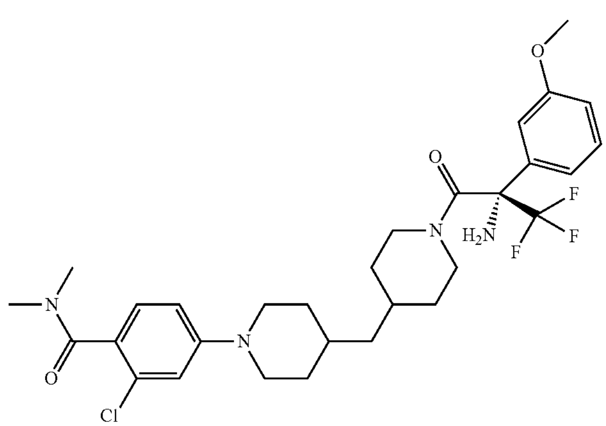 [SMILES: COc1cccc([C@](N)(C(=O)N2CCC(CC3CCN(c4ccc(C(=O)N(C)C)c(Cl)c4)CC3)CC2)C(F)(F)F)c1] | 4-[4-({1-[(2S)-2-amino-3,3,3-trifluoro-2-(3-methoxyphenyl)propanoyl]piperidin-4-yl}methyl)piperidin-1-yl]-2-chloro-N,N-dimethylbenzamide | Calc'd 595.3, found 595.3 |

| example | Structure | IUPAC Name | Exact Mass [M + H]+ |
|---|---|---|---|
| Example 2-120 | 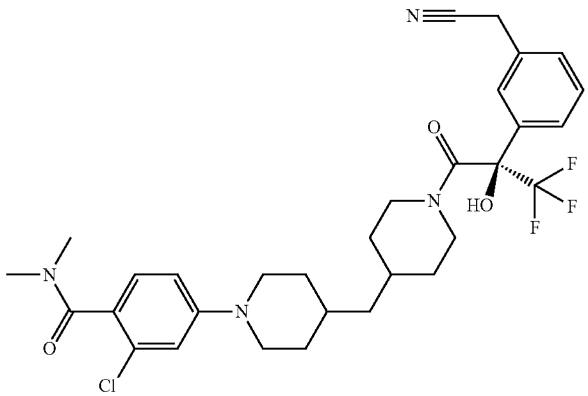 [SMILES: CN(C)C(=O)c1ccc(N2CCC(CC3CCN(C(=O)[C@](O)(c4cccc(CC#N)c4)C(F)(F)F)CC3)CC2)cc1Cl] | 2-chloro-4-{4-[(1-{(2R)-2-[3-(cyanomethyl)phenyl]-3,3,3-trifluoro-2-hydroxypropanoyl}piperidin-4-yl)methyl]piperidin-1-yl}-N,N-dimethylbenzamide | Calc'd 605.3, found 605.4 |
| Example 2-121 | 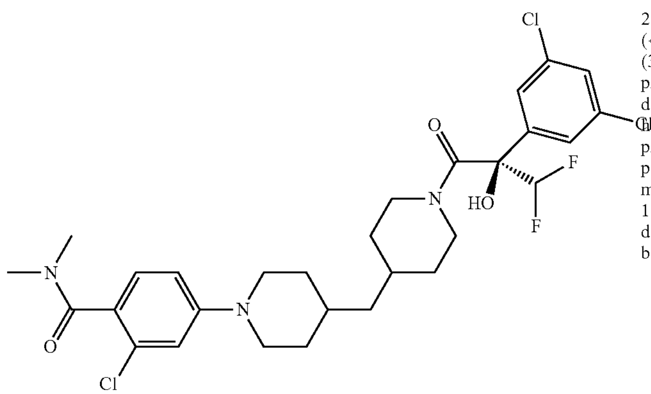 [SMILES: CN(C)C(=O)c1ccc(N2CCC(CC3CCN(C(=O)[C@](O)(c4cc(Cl)cc(Cl)c4)C(F)F)CC3)CC2)cc1Cl] | 2-chloro-4-[4-({1-[(2R)-2-(3,5-dichlorophenyl)-3,3-difluoro-2-hydroxypropanoyl]piperidin-4-yl}methyl)piperidin-1-yl]-N,N-dimethylbenzamide | Calc'd 616.2, found 616.3 |
| Example 2-122 | 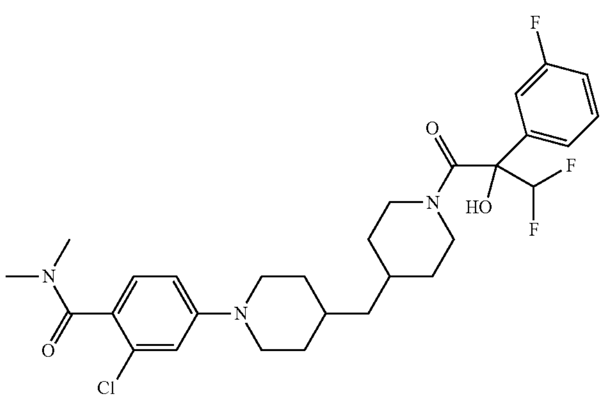 [SMILES: CN(C)C(=O)c1ccc(N2CCC(CC3CCN(C(=O)C(O)(c4cccc(F)c4)C(F)F)CC3)CC2)cc1Cl] | 2-chloro-4-[4-({1-[3,3-difluoro-2-(3-fluorophenyl)-2-hydroxypropanoyl]piperidin-4-yl}methyl)piperidin-1-yl]-N,N-dimethylbenzamide | Calc'd 566.2, found 566.3 |
| Example 2-123 | 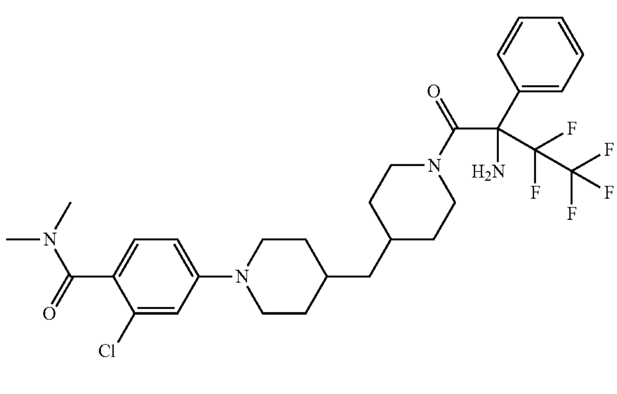 [SMILES: CN(C)C(=O)c1ccc(N2CCC(CC3CCN(C(=O)C(N)(c4ccccc4)C(F)(F)C(F)(F)F)CC3)CC2)cc1Cl] | 4-(4-{[1-(2-amino-3,3,4,4,4-pentafluoro-2-phenylbutanoyl)piperidin-4-yl]methyl}piperidin-1-yl)-2-chloro-N,N-dimethylbenzamide | Calc'd 615.3, found 615.3 |

| example | Structure | IUPAC Name | Exact Mass [M + H]+ |
|---|---|---|---|
| Example 2-124 | 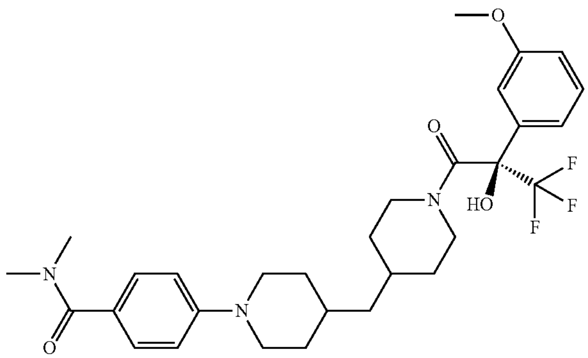 [SMILES: COc1cccc([C@@](O)(C(=O)N2CCC(CC3CCN(c4ccc(C(=O)N(C)C)cc4)CC3)CC2)C(F)(F)F)c1] | N,N-dimethyl-4-[4-({1-[(2R)-3,3,3-trifluoro-2-hydroxy-2-(3-methoxyphenyl)propanoyl]piperidin-4-yl}methyl)piperidin-1-yl]benzamide | Calc'd 562.3, found 562.4 |
| Example 2-125 | 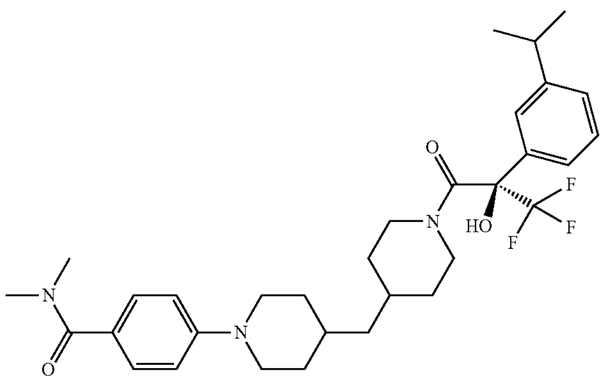 [SMILES: CC(C)c1cccc([C@@](O)(C(=O)N2CCC(CC3CCN(c4ccc(C(=O)N(C)C)cc4)CC3)CC2)C(F)(F)F)c1] | N,N-dimethyl-4-{4-[(1-{(2R)-3,3,3-trifluoro-2-hydroxy-2-[3-(1-methylethyl)phenyl]propanoyl}piperidin-4-yl)methyl]piperidin-1-yl}benzamide | Calc'd 574.3, found 574.4 |
| Example 2-126 | 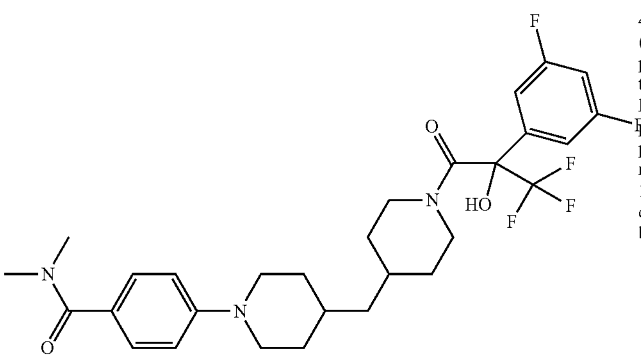 [SMILES: CN(C)C(=O)c1ccc(N2CCC(CC3CCN(C(=O)C(O)(c4cc(F)cc(F)c4)C(F)(F)F)CC3)CC2)cc1] | 4-[4-({1-[2-(3,5-difluorophenyl)-3,3,3-trifluoro-2-hydroxypropanoyl]piperidin-4-yl}methyl)piperidin-1-yl]-N,N-dimethylbenzamide | Calc'd 568.3, found 568.4 |
| Example 2-127 | 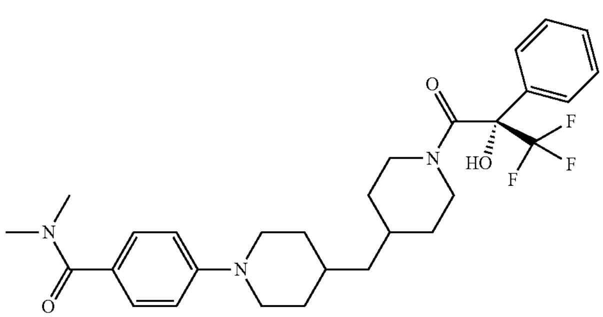 [SMILES: CN(C)C(=O)c1ccc(N2CCC(CC3CCN(C(=O)[C@@](O)(c4ccccc4)C(F)(F)F)CC3)CC2)cc1] | N,N-dimethyl-4-[4-({1-[(2S)-3,3,3-trifluoro-2-hydroxy-2-phenylpropanoyl]piperidin-4-yl}methyl)piperidin-1-yl]benzamide | Calc'd 532.3, found 532.4 |

| example | Structure | IUPAC Name | Exact Mass [M + H]+ |
|---|---|---|---|
| Example 2-128 | 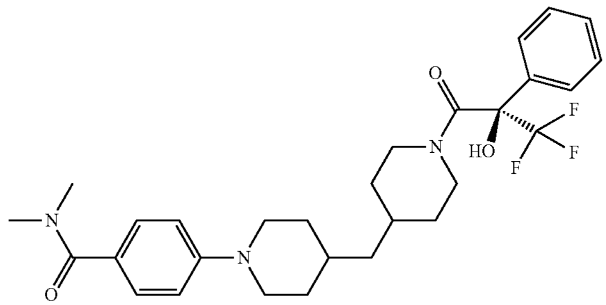 [SMILES: CN(C)C(=O)c1ccc(N2CCC(CC3CCN(C(=O)[C@](O)(c4ccccc4)C(F)(F)F)CC3)CC2)cc1] | N,N-dimethyl-4-[4-({1-[(2R)-3,3,3-trifluoro-2-hydroxy-2-phenyl-propanoyl]piperidin-4-yl}methyl)piperidin-1-yl]benzamide | Calc'd 532.3, found 532.4 |
| Example 2-129 | 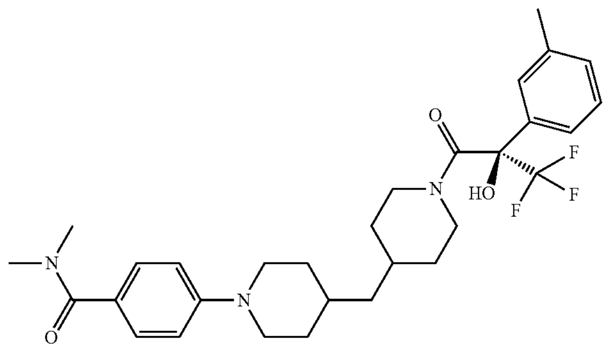 [SMILES: Cc1cccc([C@@](O)(C(=O)N2CCC(CC3CCN(c4ccc(C(=O)N(C)C)cc4)CC3)CC2)C(F)(F)F)c1] | N,N-dimethyl-4-[4-({1-[(2R)-3,3,3-trifluoro-2-hydroxy-2-(3-methylphenyl)propanoyl]piperidin-4-yl}methyl)piperidin-1-yl]benzamide | Calc'd 546.3, found 546.4 |
| Example 2-130 | 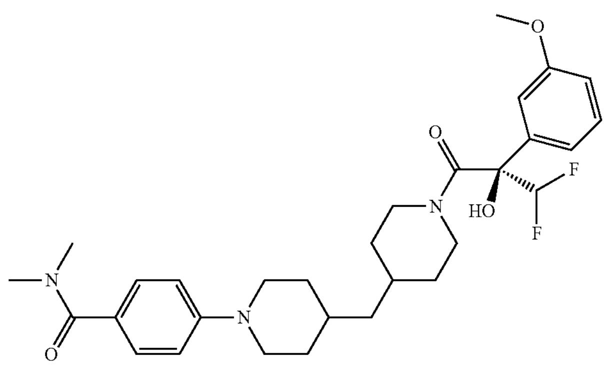 [SMILES: COc1cccc([C@@](O)(C(=O)N2CCC(CC3CCN(c4ccc(C(=O)N(C)C)cc4)CC3)CC2)C(F)F)c1] | 4-[4-({1-[(2R)-3,3-difluoro-2-hydroxy-2-(3-methoxyphenyl)propanoyl]piperidin-4-yl}methyl)piperidin-1-yl]-N,N-dimethylbenzamide | Calc'd 544.3, found 544.4 |
| Example 2-131 | 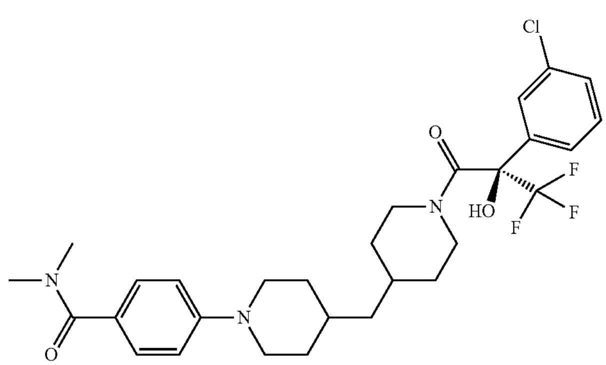 [SMILES: CN(C)C(=O)c1ccc(N2CCC(CC3CCN(C(=O)[C@](O)(c4cccc(Cl)c4)C(F)(F)F)CC3)CC2)cc1] | 4-[4-({1-[(2R)-2-(3-chlorophenyl)-3,3,3-trifluoro-2-hydroxypropanoyl]piperidin-4-yl}methyl)piperidin-1-yl]-N,N-dimethylbenzamide | Calc'd 566.2, found 566.4 |

| example | Structure | IUPAC Name | Exact Mass [M + H]+ |
|---|---|---|---|
| Example 2-132 | 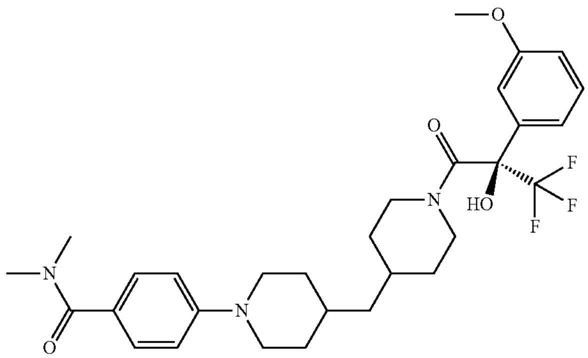 [SMILES: COc1cccc([C@@](O)(C(=O)N2CCC(CC3CCN(c4ccc(C(=O)N(C)C)cc4)CC3)CC2)C(F)(F)F)c1] | N,N-dimethyl-4-[4-({1-[(2R)-3,3,3-trifluoro-2-hydroxy-2-(3-methoxyphenyl)propanoyl]piperidin-4-yl}methyl)piperidin-1-yl]benzamide | Calc'd 562.3, found 562.4 |
| Example 2-133 | 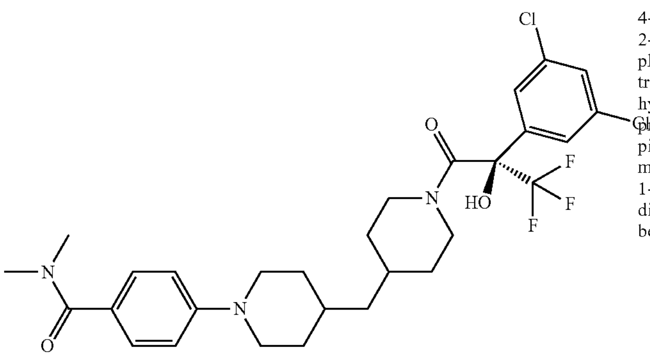 [SMILES: CN(C)C(=O)c1ccc(N2CCC(CC3CCN(C(=O)[C@](O)(c4cc(Cl)cc(Cl)c4)C(F)(F)F)CC3)CC2)cc1] | 4-[4-({1-[(2R)-2-(3,5-dichlorophenyl)-3,3,3-trifluoro-2-hydroxypropanoyl]piperidin-4-yl}methyl)piperidin-1-yl]-N,N-dimethylbenzamide | Calc'd 600.2, found 600.3 |
| Example 2-134 | 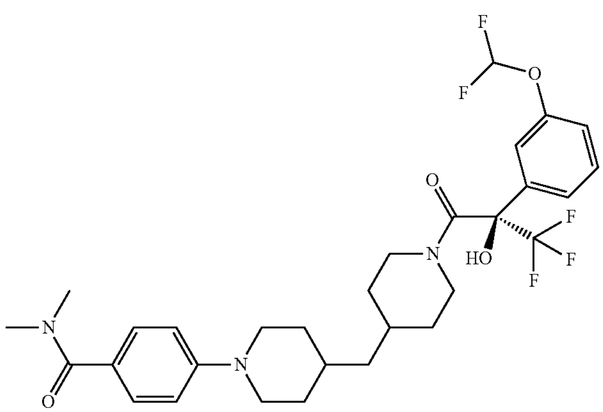 [SMILES: CN(C)C(=O)c1ccc(N2CCC(CC3CCN(C(=O)[C@](O)(c4cccc(OC(F)F)c4)C(F)(F)F)CC3)CC2)cc1] | 4-{4-[(1-{(2R)-2-[3-(difluoromethoxy)phenyl]-3,3,3-trifluoro-2-hydroxypropanoyl}piperidin-4-yl)methyl]piperidin-1-yl}-N,N-dimethylbenzamide | Calc'd 598.3, found 598.4 |
| Example 2-135 | 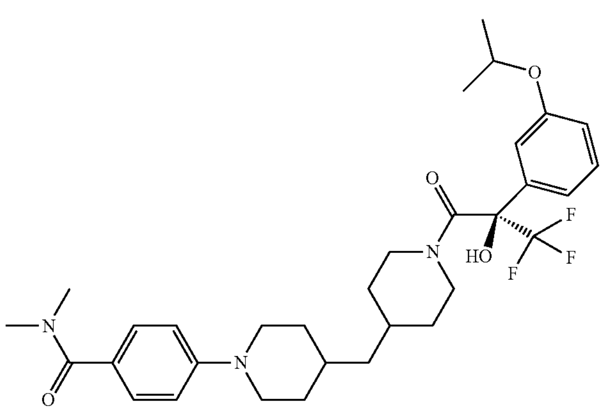 [SMILES: CC(C)Oc1cccc([C@@](O)(C(=O)N2CCC(CC3CCN(c4ccc(C(=O)N(C)C)cc4)CC3)CC2)C(F)(F)F)c1] | N,N-dimethyl-4-{4-[(1-{(2R)-3,3,3-trifluoro-2-hydroxy-2-[3-(1-methylethoxy)phenyl]propanoyl}piperidin-4-yl)methyl]piperidin-1-yl}benzamide | Calc'd 590.3, found 590.4 |

| example | Structure | IUPAC Name | Exact Mass [M + H]+ |
|---|---|---|---|
| Example 2-136 | 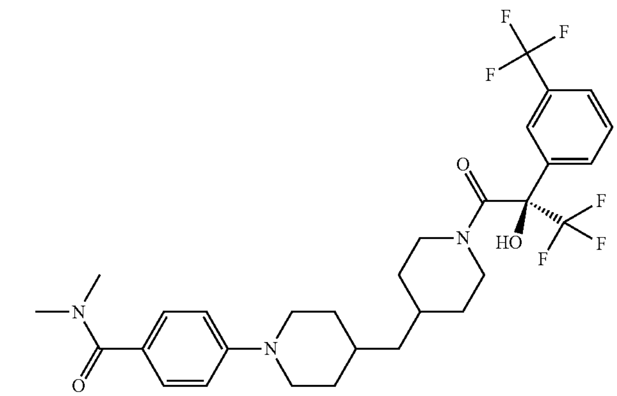 [SMILES: CN(C)C(=O)c1ccc(N2CCC(CC3CCN(C(=O)[C@](O)(c4cccc(C(F)(F)F)c4)C(F)(F)F)CC3)CC2)cc1] | N,N-dimethyl-4-{4-[(1-{(2R)-3,3,3-trifluoro-2-hydroxy-2-[3-(trifluoromethyl)phenyl]propanoyl}piperidin-4-yl)methyl]piperidin-1-yl}benzamide | Calc'd 600.3, found 600.4 |
| Example 2-137 | 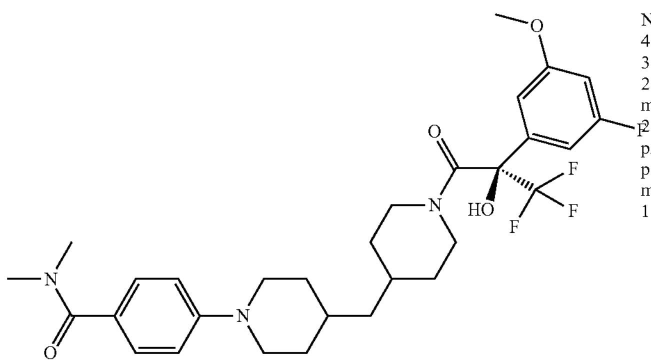 [SMILES: COc1cc(Cl)cc([C@@](O)(C(=O)N2CCC(CC3CCN(c4ccc(C(=O)N(C)C)cc4)CC3)CC2)C(F)(F)F)c1] | N,N-dimethyl-4-[4-({1-[(2R)-3,3,3-trifluoro-2-(3-fluoro-5-methoxyphenyl)-2-hydroxy-propanoyl]piperidin-4-yl}methyl)piperidin-1-yl]benzamide | Calc'd 580.3, found 580.4 |
| Example 2-138 | 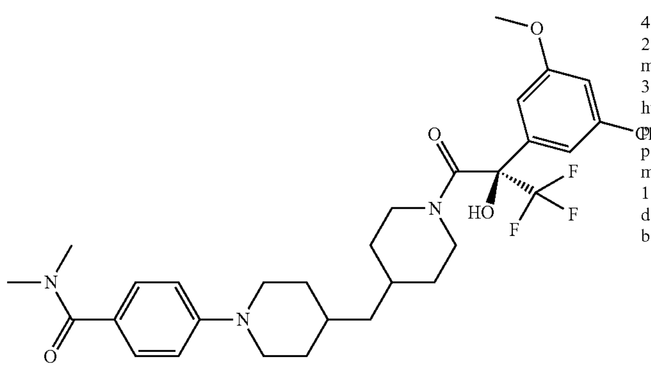 | 4-[4-({1-[(2R)-2-(3-chloro-5-methoxyphenyl)-3,3,3-trifluoro-2-hydroxy-propanoyl]piperidin-4-yl}methyl)piperidin-1-yl]-N,N-dimethyl-benzamide | Calc'd 596.2, found 596.4 |
| Example 2-139 | 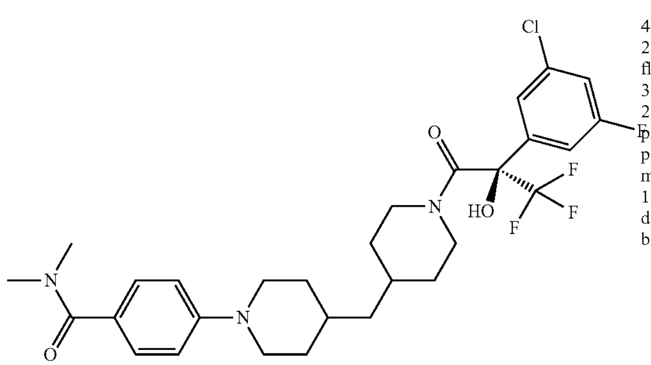 | 4-[4-({1-[(2R)-2-(3-chloro-5-fluorophenyl)-3,3,3-trifluoro-2-hydroxy-propanoyl]piperidin-4-yl}methyl)piperidin-1-yl]-N,N-dimethyl-benzamide | Calc'd 584.2, found 584.3 |

-continued

| example | Structure | IUPAC Name | Exact Mass [M + H]+ |
|---|---|---|---|
| Example 2-140 | 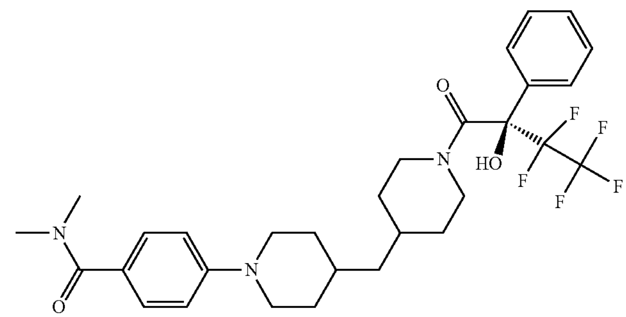 [SMILES: CN(C)C(=O)c1ccc(N2CCC(CC3CCN(C(=O)[C@](O)(c4ccccc4)C(F)(F)C(F)(F)F)CC3)CC2)cc1] | N,N-dimethyl-4-[4-({1-[(2R)-3,3,4,4,4-pentafluoro-2-hydroxy-2-phenylbutanoyl]piperidin-4-yl}methyl)piperidin-1-yl]benzamide | Calc'd 582.3, found 582.4 |
| Example 2-141 | 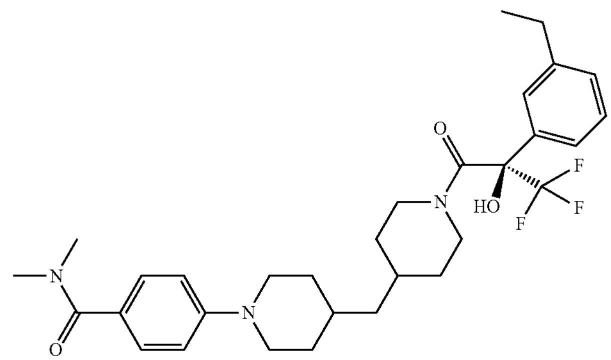 [SMILES: CCc1cccc([C@@](O)(C(=O)N2CCC(CC3CCN(c4ccc(C(=O)N(C)C)cc4)CC3)CC2)C(F)(F)F)c1] | 4-[4-({1-[(2R)-2-(3-ethyl-phenyl)-3,3,3-trifluoro-2-hydroxy-propanoyl]piperidin-4-yl}methyl)piperidin-1-yl]-N,N-dimethyl-benzamide | Calc'd 560.3, found 560.4 |
| Example 2-142 | 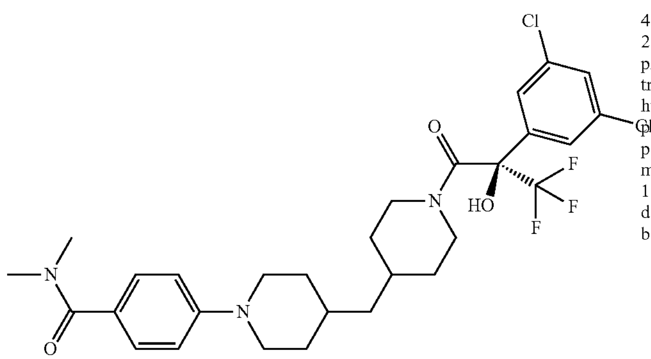 [SMILES: CN(C)C(=O)c1ccc(N2CCC(CC3CCN(C(=O)[C@](O)(c4cc(Cl)cc(Cl)c4)C(F)(F)F)CC3)CC2)cc1] | 4-[4-({1-[(2R)-2-(3,5-dichloro-phenyl)-3,3,3-trifluoro-2-hydroxy-propanoyl]piperidin-4-yl}methyl)piperidin-1-yl]-N,N-dimethyl-benzamide | Calc'd 600.2, found 600.3 |
| Example 2-143 | 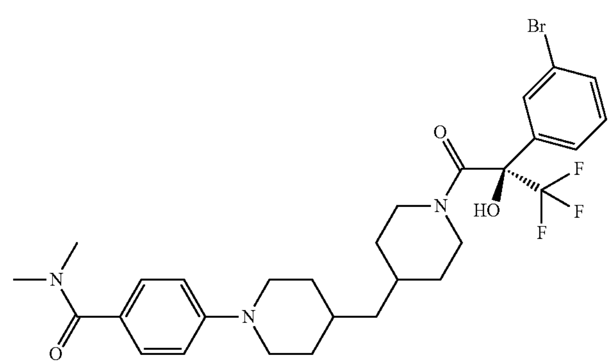 [SMILES: CN(C)C(=O)c1ccc(N2CCC(CC3CCN(C(=O)[C@](O)(c4cccc(Br)c4)C(F)(F)F)CC3)CC2)cc1] | 4-[4-({1-[(2R)-2-(3-bromo-phenyl)-3,3,3-trifluoro-2-hydroxy-propanoyl]piperidin-4-yl}methyl)piperidin-1-yl]-N,N-dimethyl-benzamide | Calc'd 610.2, found 610.3 |

| example | Structure | IUPAC Name | Exact Mass [M + H]+ |
|---|---|---|---|
| Example 2-144 | 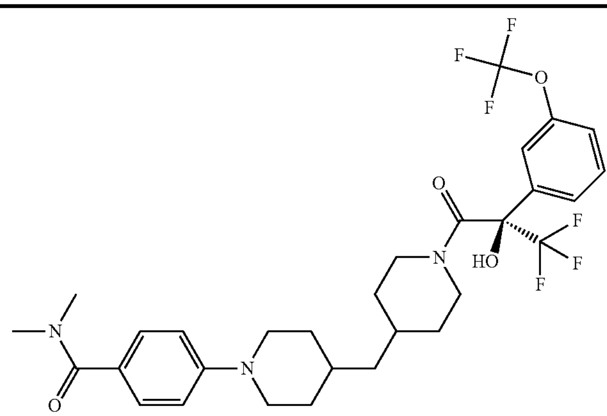 | N,N-dimethyl-4-{4-[(1-{(2R)-3,3,3-trifluoro-2-hydroxy-2-[3-(trifluoromethoxy)phenyl]propanoyl}piperidin-4-yl)methyl]piperidin-1-yl}benzamide | Calc'd 616.3, found 616.4 |
| Example 2-145 | 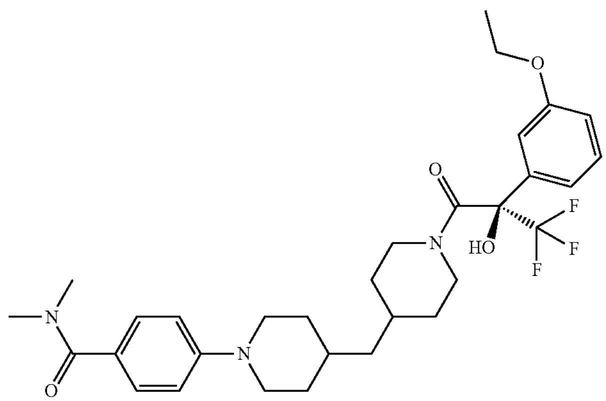 [SMILES: CCOc1cccc([C@@](O)(C(=O)N2CCC(CC3CCN(c4ccc(C(=O)N(C)C)cc4)CC3)CC2)C(F)(F)F)c1] | 4-[4-({1-[(2R)-2-(3-ethoxyphenyl)-3,3,3-trifluoro-2-hydroxypropanoyl]piperidin-4-yl}methyl)piperidin-1-yl]-N,N-dimethylbenzamide | Calc'd 576.3, found 576.5 |
| Example 2-146 | 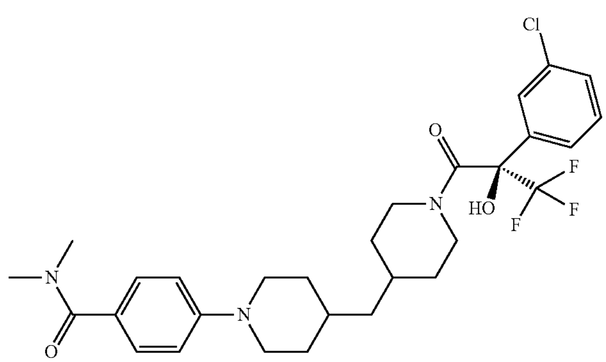 [SMILES: CN(C)C(=O)c1ccc(N2CCC(CC3CCN(C(=O)[C@](O)(c4cccc(Cl)c4)C(F)(F)F)CC3)CC2)cc1] | 4-[4-({1-[(2R)-2-(3-chlorophenyl)-3,3,3-trifluoro-2-hydroxypropanoyl]piperidin-4-yl}methyl)piperidin-1-yl]-N,N-dimethylbenzamide | Calc'd 566.2, found 566.4 |
| Example 2-147 | 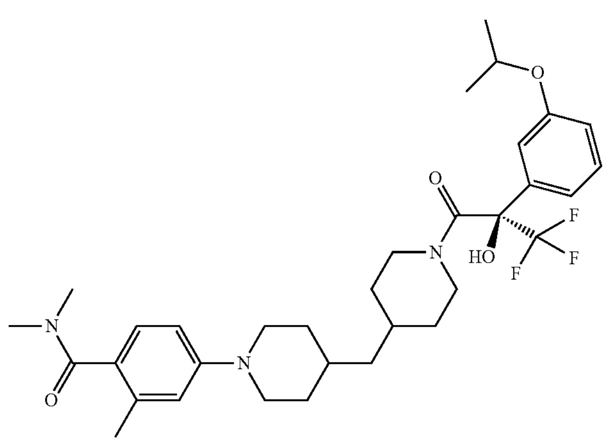 [SMILES: Cc1cc(N2CCC(CC3CCN(C(=O)[C@](O)(c4cccc(OC(C)C)c4)C(F)(F)F)CC3)CC2)ccc1C(=O)N(C)C] | N,N,2-trimethyl-4-{4-[(1-{(2R)-3,3,3-trifluoro-2-hydroxy-2-[3-(1-methylethoxy)phenyl]propanoyl}piperidin-4-yl)methyl]piperidin-1-yl}benzamide | Calc'd 604.3, found 604.5 |

-continued

| example | Structure | IUPAC Name | Exact Mass [M + H]+ |
|---|---|---|---|
| Example 2-148 | 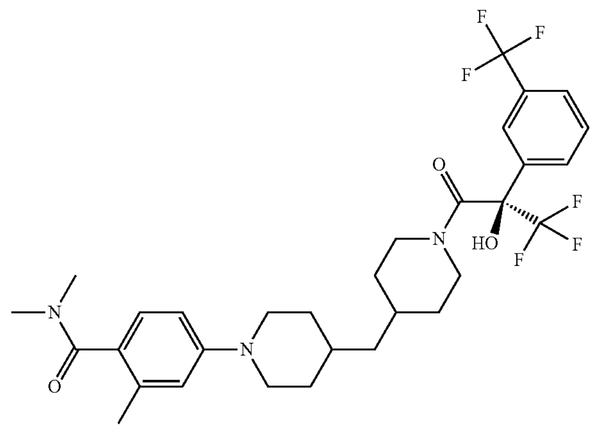 [SMILES: Cc1cc(N2CCC(CC3CCN(C(=O)[C@](O)(c4cccc(C(F)(F)F)c4)C(F)(F)F)CC3)CC2)ccc1C(=O)N(C)C] | N,N,2-trimethyl-4-{4-[(1-{(2R)-3,3,3-trifluoro-2-hydroxy-2-[3-(trifluoromethyl)phenyl]propanoyl}piperidin-4-yl)methyl]piperidin-1-yl}benzamide | Calc'd 614.3, found 614.5 |
| Example 2-149 | 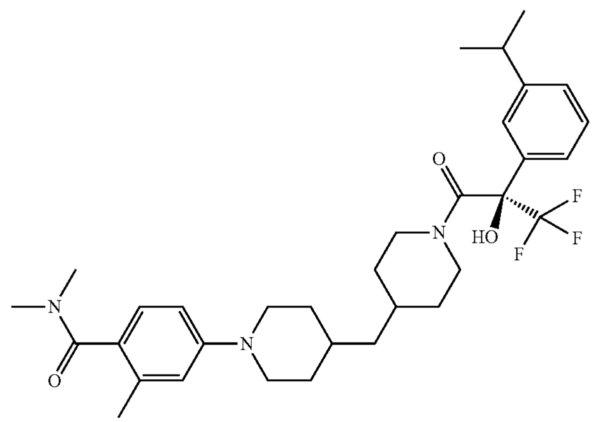 [SMILES: Cc1cc(N2CCC(CC3CCN(C(=O)[C@](O)(c4cccc(C(C)C)c4)C(F)(F)F)CC3)CC2)ccc1C(=O)N(C)C] | N,N,2-trimethyl-4-{4-[(1-{(2R)-3,3,3-trifluoro-2-hydroxy-2-[3-(1-methylethyl)phenyl]propanoyl}piperidin-4-yl)methyl]piperidin-1-yl}benzamide | Calc'd 588.3, found 588.5 |
| Example 2-150 | 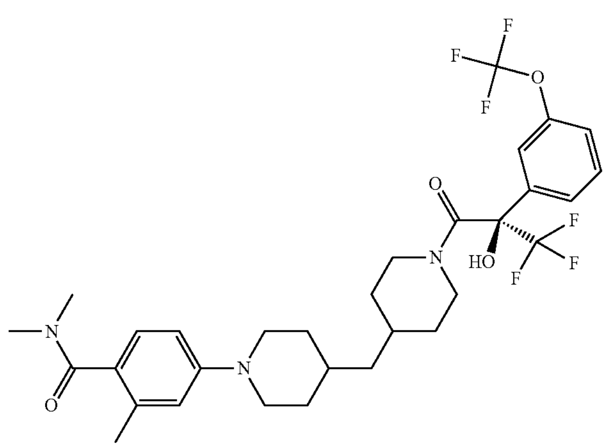 [SMILES: Cc1cc(N2CCC(CC3CCN(C(=O)[C@](O)(c4cccc(OC(F)(F)F)c4)C(F)(F)F)CC3)CC2)ccc1C(=O)N(C)C] | N,N,2-trimethyl-4-{4-[(1-{(2R)-3,3,3-trifluoro-2-hydroxy-2-[3-(trifluoromethoxy)phenyl]propanoyl}piperidin-4-yl)methyl]piperidin-1-yl}benzamide | Calc'd 630.3, found 630.4 |

-continued

| example | Structure | IUPAC Name | Exact Mass [M + H]+ |
|---|---|---|---|
| Example 2-151 | 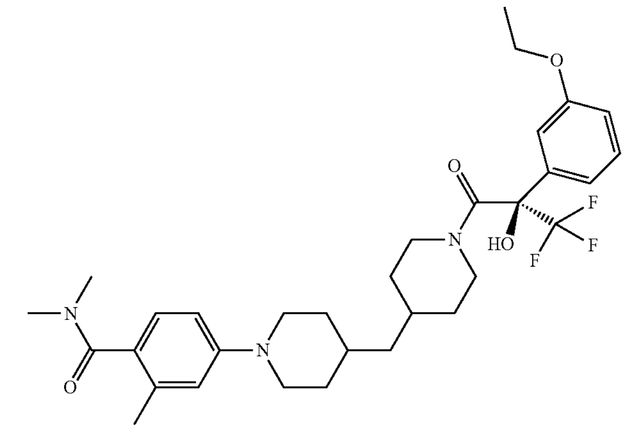 [SMILES: CCOc1cccc([C@@](O)(C(=O)N2CCC(CC3CCN(c4ccc(C(=O)N(C)C)c(C)c4)CC3)CC2)C(F)(F)F)c1] | 4-[4-({1-[(2R)-2-(3-ethoxyphenyl)-3,3,3-trifluoro-2-hydroxypropanoyl]piperidin-4-yl}methyl)piperidin-1-yl]-N,N,2-trimethylbenzamide | Calc'd 590.3, found 590.5 |
| Example 2-152 | 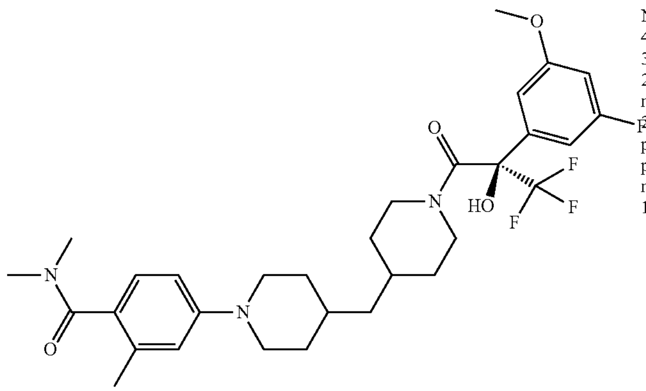 [SMILES: COc1cc(F)cc([C@@](O)(C(=O)N2CCC(CC3CCN(c4ccc(C(=O)N(C)C)c(C)c4)CC3)CC2)C(F)(F)F)c1] | N,N,2-trimethyl-4-[4-({1-[(2R)-3,3,3-trifluoro-2-(3-fluoro-5-methoxyphenyl)-2-hydroxypropanoyl]piperidin-4-yl}methyl)piperidin-1-yl]benzamide | Calc'd 594.3, found 594.4 |
| Example 2-153 | 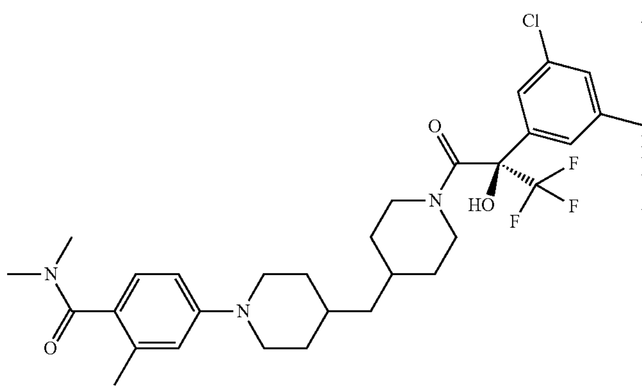 | 4-[4-({1-[(2R)-2-(3-chloro-5-fluorophenyl)-3,3,3-trifluoro-2-hydroxypropanoyl]piperidin-4-yl}methyl)piperidin-1-yl]-N,N,2-trimethylbenzamide | Calc'd 598.2, found 598.4 |
| Example 2-154 | 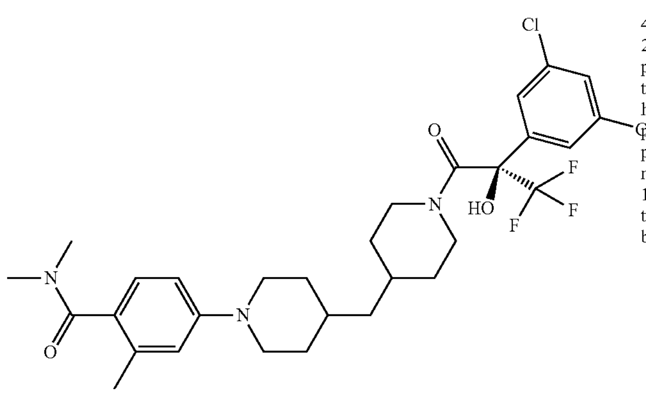 | 4-[4-({1-[(2R)-2-(3,5-dichlorophenyl)-3,3,3-trifluoro-2-hydroxypropanoyl]piperidin-4-yl}methyl)piperidin-1-yl]-N,N,2-trimethylbenzamide | Calc'd 614.2, found 614.4 |

| example | Structure | IUPAC Name | Exact Mass [M + H]+ |
|---|---|---|---|
| Example 2-155 | 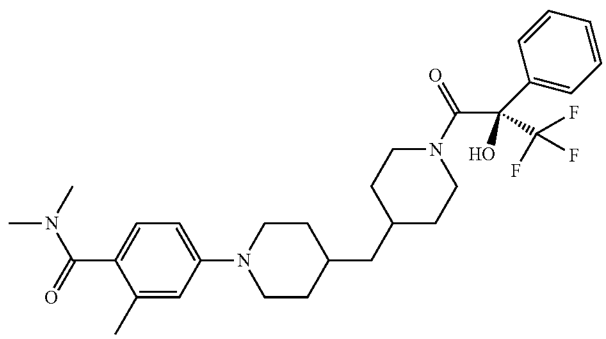 [SMILES: Cc1cc(N2CCC(CC3CCN(C(=O)[C@](O)(c4ccccc4)C(F)(F)F)CC3)CC2)ccc1C(=O)N(C)C] | N,N,2-trimethyl-4-[4-({1-[(2R)-3,3,3-trifluoro-2-hydroxy-2-phenyl-propanoyl] piperidin-4-yl} methyl)piperidin-1-yl]benzamide | Calc'd 546.3, found 546.4 |
| Example 2-156 | 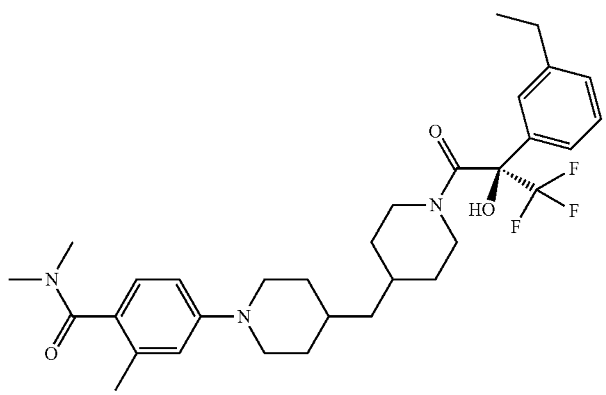 [SMILES: CCc1cccc([C@@](O)(C(=O)N2CCC(CC3CCN(c4ccc(C(=O)N(C)C)c(C)c4)CC3)CC2)C(F)(F)F)c1] | 4-[4-({1-[(2R)-2-(3-ethyl-phenyl)-3,3,3-trifluoro-2-hydroxy-propanoyl] piperidin-4-yl} methyl)piperidin-1-yl]-N,N,2-trimethyl-benzamide | Calc'd 574.3, found 574.5 |
| Example 2-157 | 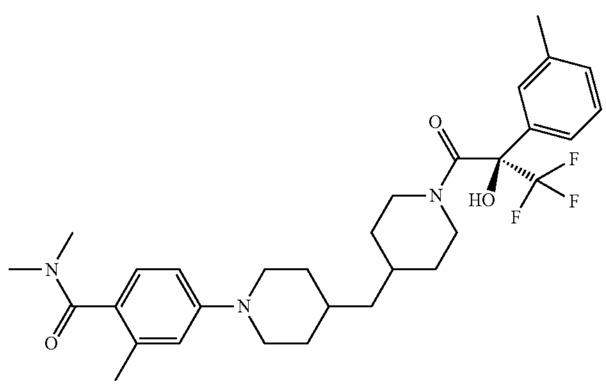 [SMILES: Cc1cccc([C@@](O)(C(=O)N2CCC(CC3CCN(c4ccc(C(=O)N(C)C)c(C)c4)CC3)CC2)C(F)(F)F)c1] | N,N,2-trimethyl-4-[4-({1-[(2R)-3,3,3-trifluoro-2-hydroxy-2-(3-methylphenyl) propanoyl] piperidin-4-yl} methyl)piperidin-1-yl]benzamide | Calc'd 560.3, found 560.4 |
| Example 2-158 | 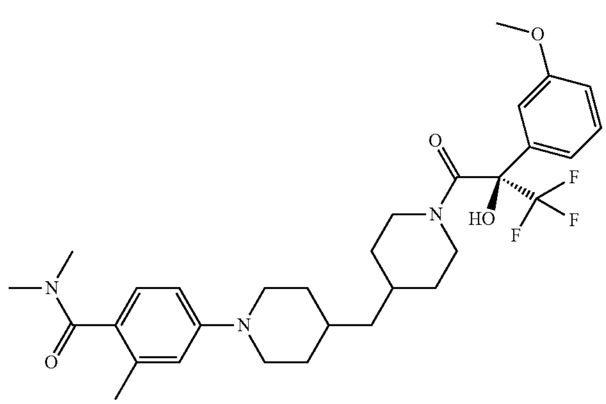 [SMILES: COc1cccc([C@@](O)(C(=O)N2CCC(CC3CCN(c4ccc(C(=O)N(C)C)c(C)c4)CC3)CC2)C(F)(F)F)c1] | N,N,2-trimethyl-4-[4-({1-[(2R)-3,3,3-trifluoro-2-hydroxy-2-(3-methoxyphenyl) propanoyl] piperidin-4-yl} methyl)piperidin-1-yl]benzamide | Calc'd 576.3, found 576.4 |

-continued

| example | Structure | IUPAC Name | Exact Mass [M + H]+ |
|---|---|---|---|
| Example 2-159 | 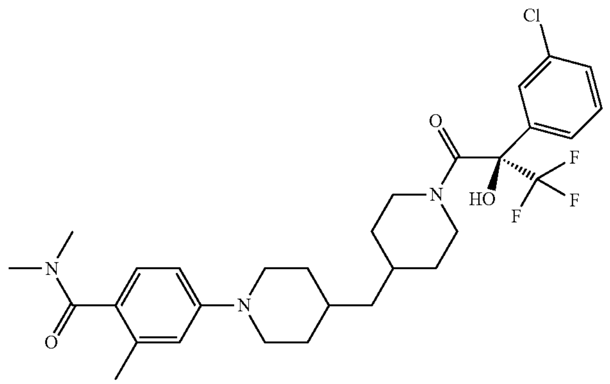 [SMILES: Cc1cc(N2CCC(CC3CCN(C(=O)[C@](O)(c4cccc(Cl)c4)C(F)(F)F)CC3)CC2)ccc1C(=O)N(C)C] | 4-[4-({1-[(2R)-2-(3-chloro-phenyl)-3,3,3-trifluoro-2-hydroxy-propanoyl]piperidin-4-yl}methyl)piperidin-1-yl]-N,N,2-trimethyl-benzamide | Calc'd 580.3, found 580.4 |
| Example 2-160 | 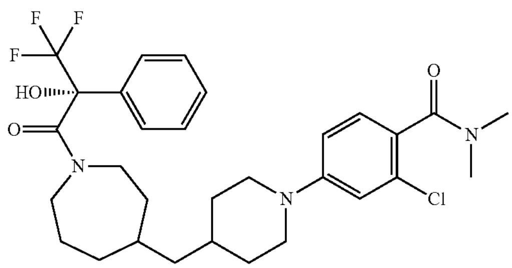 [SMILES: CN(C)C(=O)c1ccc(N2CCC(CC3CCCN(C(=O)[C@](O)(c4ccccc4)C(F)(F)F)CC3)CC2)cc1Cl] | 2-chloro-N,N-dimethyl-4-[4-({1-[(2R)-3,3,3-trifluoro-2-hydroxy-2-phenyl-propanoyl]azepan-4-yl}methyl)piperidin-1-yl]benzamide | Calc'd 580.3, found 580.4 |
| Example 2-161 | 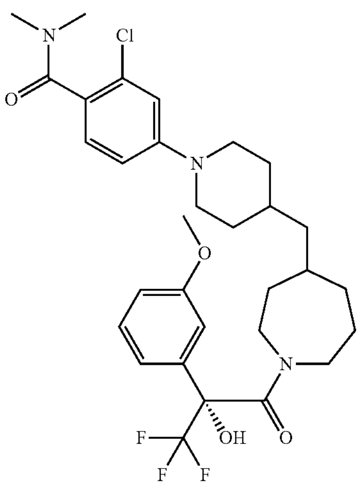 [SMILES: COc1cccc([C@@](O)(C(=O)N2CCCC(CC3CCN(c4ccc(C(=O)N(C)C)c(Cl)c4)CC3)CC2)C(F)(F)F)c1] | 2-chloro-N,N-dimethyl-4-[4-({1-[(2R)-3,3,3-trifluoro-2-hydroxy-2-(3-methoxy-phenyl)propanoyl]azepan-4-yl}methyl)piperidin-1-yl]benzamide | Calc'd 610.3, found 610.5 |
| Example 2-162 | 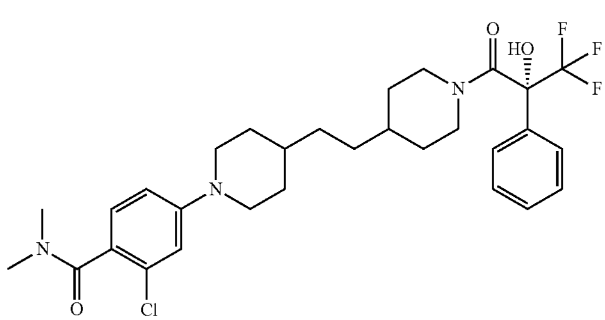 [SMILES: CN(C)C(=O)c1ccc(N2CCC(CCC3CCN(C(=O)[C@](O)(c4ccccc4)C(F)(F)F)CC3)CC2)cc1Cl] | 2-chloro-N,N-dimethyl-4-[4-(2-{1-[(2R)-3,3,3-trifluoro-2-hydroxy-2-phenyl-propanoyl]piperidin-4-yl}ethyl)piperidin-1-yl]benzamide | Calc'd 580.3, found 580.3 |

| example | Structure | IUPAC Name | Exact Mass [M + H]+ |
|---|---|---|---|
| Example 2-163 | 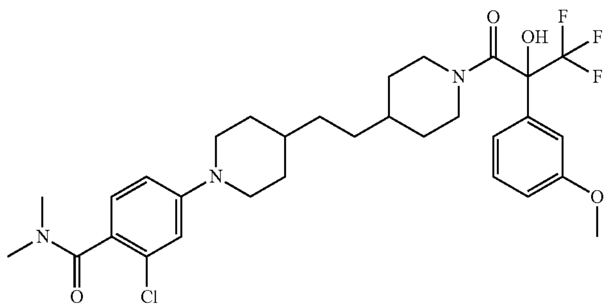 | 2-chloro-N,N-dimethyl-4-[4-(2-{1-[3,3,3-trifluoro-2-hydroxy-2-(3-methoxyphenyl)propanoyl]piperidin-4-yl}ethyl)piperidin-1-yl]benzamide | Calc'd 610.3, found 610.5 |
| Example 2-164 | 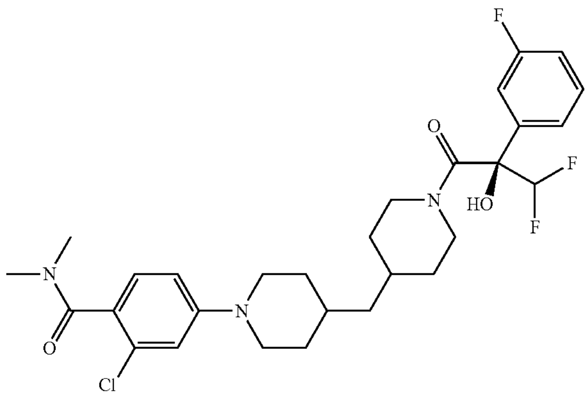 [SMILES: CN(C)C(=O)c1ccc(N2CCC(CC3CCN(C(=O)[C@](O)(c4cccc(F)c4)C(F)F)CC3)CC2)cc1Cl] | 2-chloro-4-[4-({1-[(2R)-3,3-difluoro-2-(3-fluorophenyl)-2-hydroxypropanoyl]piperidin-4-yl}methyl)piperidin-1-yl]-N,N-dimethylbenzamide | Calc'd 566.2, found 566.3 |
| Example 2-165 | 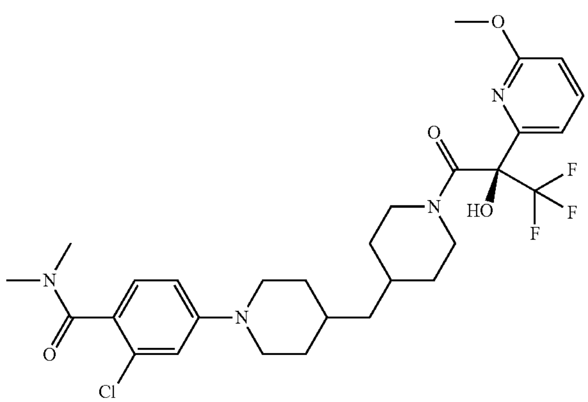 [SMILES: COc1cccc([C@@](O)(C(=O)N2CCC(CC3CCN(c4ccc(C(=O)N(C)C)c(Cl)c4)CC3)CC2)C(F)(F)F)n1] | 2-chloro-N,N-dimethyl-4-[4-({1-[3,3,3-trifluoro-2-hydroxy-2-(6-methoxypyridin-2-yl)propanoyl]piperidin-4-yl}methyl)piperidin-1-yl]benzamide | Calc'd 597.2, found 597.3 |
| Example 2-166 | 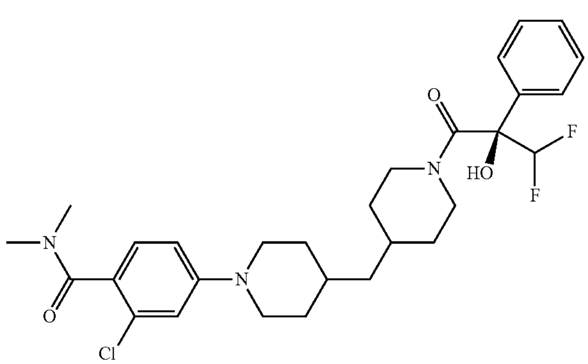 [SMILES: CN(C)C(=O)c1ccc(N2CCC(CC3CCN(C(=O)[C@](O)(c4ccccc4)C(F)F)CC3)CC2)cc1Cl] | 2-chloro-4-[4-({1-[(2R)-3,3-difluoro-2-hydroxy-2-phenylpropanoyl]piperidin-4-yl}methyl)piperidin-1-yl]-N,N-dimethylbenzamide | Calc'd 548.2, found 548.3 |

| example | Structure | IUPAC Name | Exact Mass [M + H]+ |
|---|---|---|---|
| Example 2-167 | 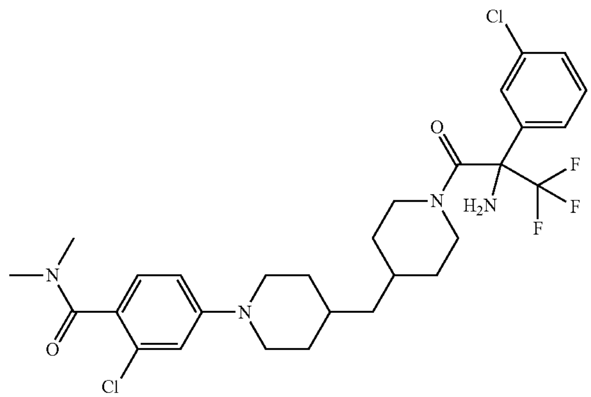 [SMILES: CN(C)C(=O)c1ccc(N2CCC(CC3CCN(C(=O)C(N)(c4cccc(Cl)c4)C(F)(F)F)CC3)CC2)cc1Cl] | 4-[4-({1-[2-amino-2-(3-chlorophenyl)-3,3,3-trifluoro-propanoyl]piperidin-4-yl}methyl)piperidin-1-yl]-2-chloro-N,N-dimethyl-benzamide | Calc'd 599.2, found 599.2 |
| Example 2-168 | 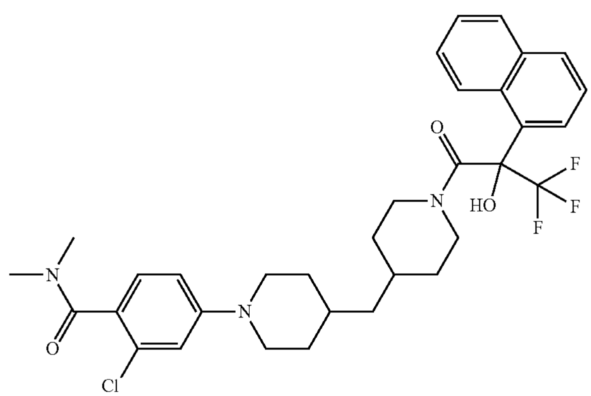 [SMILES: CN(C)C(=O)c1ccc(N2CCC(CC3CCN(C(=O)C(O)(c4cccc5ccccc45)C(F)(F)F)CC3)CC2)cc1Cl] | 2-chloro-N,N-dimethyl-4-(4-{[1-(3,3,3-trifluoro-2-hydroxy-2-naphthalen-1-ylpropanoyl)piperidin-4-yl]methyl}piperidin-1-yl)benzamide | Calc'd 616.3, found 616.4 |
| Example 2-169 | 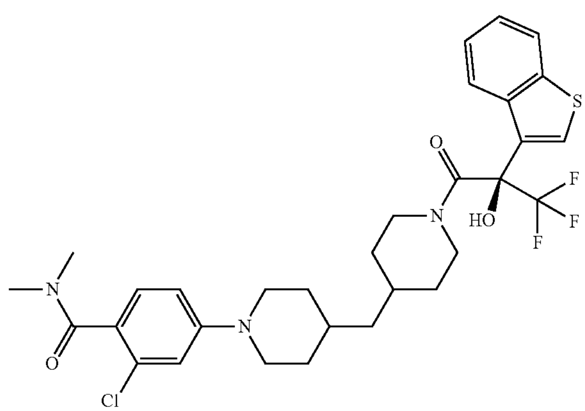 [SMILES: CN(C)C(=O)c1ccc(N2CCC(CC3CCN(C(=O)[C@](O)(c4csc5ccccc45)C(F)(F)F)CC3)CC2)cc1Cl] | 4-[4-({1-[2-(1-benzothiophen-3-yl)-3,3,3-trifluoro-2-hydroxy-propanoyl]piperidin-4-yl}methyl)piperidin-1-yl]-2-chloro-N,N-dimethyl-benzamide | Calc'd 622.2, found 622.3 |

US 10,752,587 B2
149                                                                                                     150
-continued
| example | Structure | IUPAC Name | Exact Mass [M + H]+ |
|---|---|---|---|
| Example 2-170 | 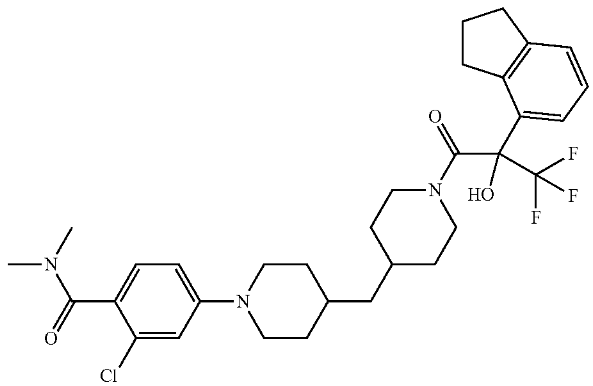 [SMILES: CN(C)C(=O)c1ccc(N2CCC(CC3CCN(C(=O)C(O)(c4cccc5c4CCC5)C(F)(F)F)CC3)CC2)cc1Cl] | 2-chloro-4-[4-({1-[2-(2,3-dihydro-1H-inden-4-yl)-3,3,3-trifluoro-2-hydroxy-propanoyl]piperidin-4-yl}methyl)piperidin-1-yl]-N,N-dimethyl-benzamide | Calc'd 606.3, found 606.4 |
Example 3-1: (R)-2-chloro-N,N-dimethyl-4-(4-methyl-4-((1-(3,3,3-trifluoro-2-hydroxy-2-(3-methoxyphenyl)propanoyl)piperidin-4-yl)methyl)piperidin-1-yl)benzamide
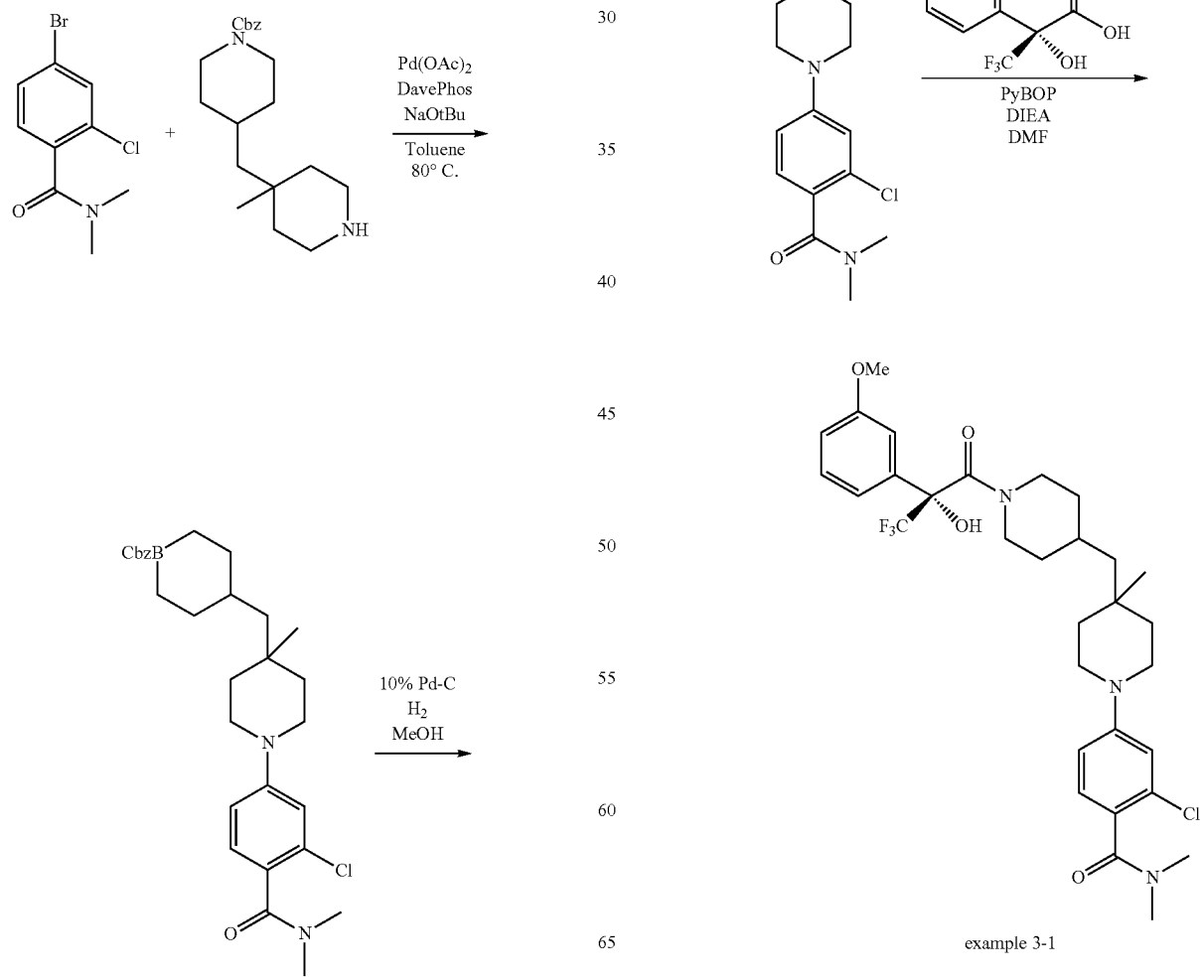
example 3-1

Step 1: benzyl 4-((1-(3-chloro-4-(dimethylcarbamoyl)phenyl)-4-methylpiperidin-4-yl)methyl)piperidine-1-carboxylate A mixture of benzyl 4-((4-methylpiperidin-4-yl)methyl)piperidine-1-carboxylate (40 mg, 0.09 mmol), 4-bromo-2-chloro-N,N-dimethylbenzamide (35 mg, 0.135 mmol), 2-dicyclohexylphosphino-2'-(N,N-dimethylamino)biphenyl (5.3 mg, 14 umol), palladium (II) acetate (1.0 mg, 4.5 umol), and sodium tert-butoxide (35 mg, 0.36 mmol) in Toluene (1 ml) was degassed by bubbling with $N_2$ and heated at 100° C. overnight. The mixture was cooled to room temperature, filtered, and concentrated to dryness. The residue was purified by ISCO column chromatography (silica gel 12 g, eluting with 0-100% EtOAc/Hexane) to give title compound (36 mg). LCMS m/z (M+H): Calc'd 512.3, found 512.4.

Step 2: 2-chloro-N,N-dimethyl-4-(4-methyl-4-(piperidin-4-ylmethyl)piperidin-1-yl)benzamide A mixture of benzyl 4-((1-(3-chloro-4-(dimethylcarbamoyl)phenyl)-4-methylpiperidin-4-yl)methyl)piperidine-1-carboxylate (0.036 g, 0.07 mmol) and 10% Pd/C (7.45 mg, 7.00 μmol) in MeOH was degassed (3×pump/$N_2$) then placed under an atmosphere of $H_2$ (1×pump/balloon $H_2$) and stirred rapidly at room temperature for 2 h. The mixture was filtered through celite, washing with ethyl acetate, and concentrated to dryness to give the crude title compound which was used without further purification.

Step 3: (R)-2-chloro-N,N-dimethyl-4-(4-methyl-4-((1-(3,3,3-trifluoro-2-hydroxy-2-(3-methoxyphenyl)propanoyl)piperidin-4-yl)methyl)piperidin-1-yl)benzamide A mixture of (R)-3,3,3-trifluoro-2-hydroxy-2-(3-methoxyphenyl)propanoic acid (26.3 mg, 0.11 mmol) and PYBOP (65.6 mg, 0.13 mmol) in DMF (100 uL) was stirred at room temperature for 10 min. A solution of 2-chloro-N,N-dimethyl-4-(4-methyl-4-(piperidin-4-ylmethyl)piperidin-1-yl)benzamide (26.5 mg, 0.07 mmol) and DIEA (73.4 ul, 0.42 mmol) in DMF (600 uL) was then added dropwise. The mixture was stirred at rt overnight. The residue was purified by preparative HPLC, Gilson GX-271, sunfire 19×150 column, 15 min run, eluting with 15%-85% CH3CN/H2O with 0.1% TFA to give the title compound (30.6 mg). LCMS m/z (M+H): Calc'd 610.1, found 610.3.

Example 4-1: (R)-1-(4-((1-(4-(azetidine-1-carbonyl)-3-chlorophenyl)piperidin-4-yl)methyl)piperidin-1-yl)-3,3,3-trifluoro-2-hydroxy-2-phenylpropan-1-one

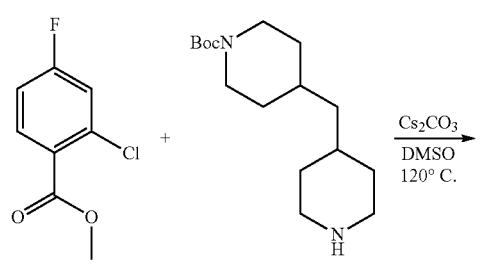

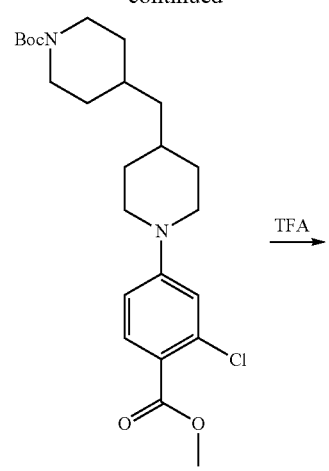

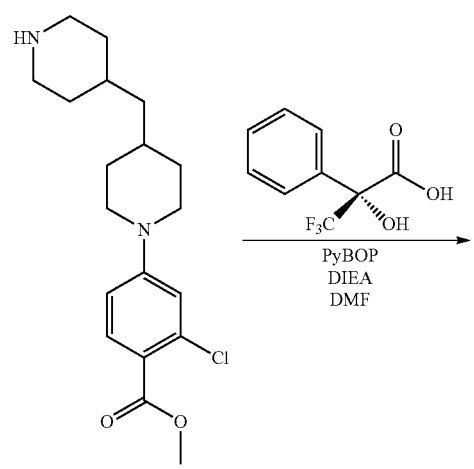

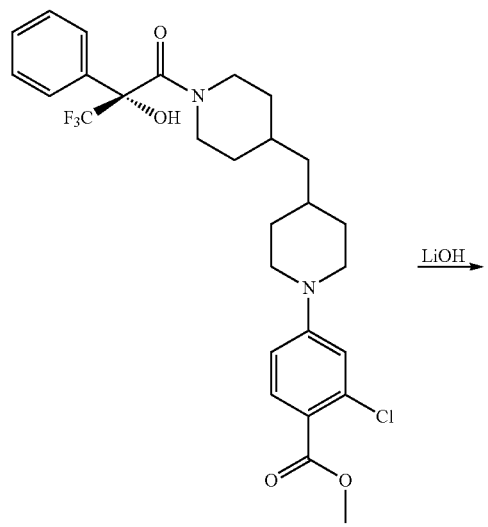

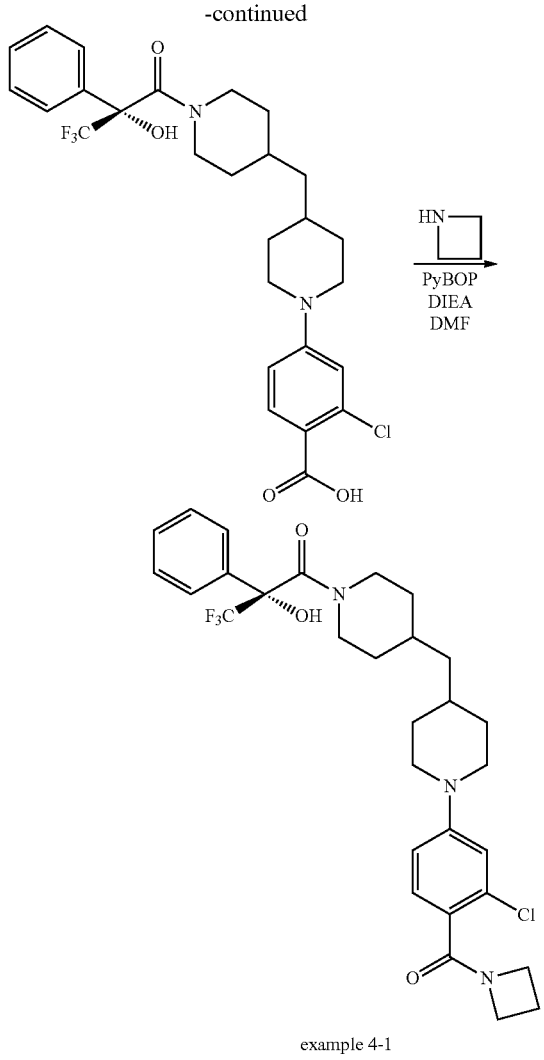

example 4-1

Step 1: tert-butyl 4-((1-(3-chloro-4-(methoxycarbonyl)phenyl)piperidin-4-yl)methyl)piperidine-1-carboxylate A mixture of methyl 2-chloro-4-fluorobenzoate (367 mg, 1.95 mmol), tert-butyl 4-(piperidin-4-ylmethyl)piperidine-1-carboxylate (500 mg, 1.77 mmol), and $Cs_2CO_3$ (1269 mg, 3.89 mmol) in DMSO (8.8 ml) was degassed by bubbling with $N_2$ and heated at 120° C. for 1 h under microwave condition. The mixture was diluted with EtOAc-$H_2O$, and the aq. layer was extracted with EtOAc (3×). The combined organic fractions were dried over $Na_2SO_4$, filtered and the solvent was evaporated under reduced pressure. The reaction mixture was purified by ISCO column chromatography (silica gel ISCO 40 g prepacked column, eluting with 0-100% EtOAc/Hexane) to give the title compound (578 mg). LCMS m/z (M+H): Calc'd 451.2, found 451.4.

Step 2: methyl 2-chloro-4-(4-(piperidin-4-ylmethyl)piperidin-1-yl)benzoate

A solution of tert-butyl 4-((1-(3-chloro-4-(methoxycarbonyl)phenyl)piperidin-4-yl)methyl)piperidine-1-carboxylate (578 mg, 1.28 mmol) in DCM (10 ml) was treated with TFA (2 ml) at room temperature for 1 h. The mixture was concentrated to dryness to give the crude title compound which was used without further purification. LCMS m/z (M+H): c Calc'd 364.2, found 364.4.

Step 3: (R)-methyl 2-chloro-4-(4-((1-(3,3,3-trifluoro-2-hydroxy-2-phenylpropanoyl)piperidin-4-yl)methyl)piperidin-1-yl)benzoate A mixture of (R)-3,3,3-trifluoro-2-hydroxy-2-phenylpropanoic acid (423 mg, 1.92 mmol) and PYBOP (1001 mg, 1.92 mmol) in DCM (6 ml) was first stirred at room temperature for 10 min, followed by the addition of a solution of methyl 2-chloro-4-(4-(piperidin-4-ylmethyl)piperidin-1-yl)benzoate (450 mg, 1.28 mmol) and DIEA (896 ul, 5.13 mmol) in DCM (7 ml). After stirring at room temperature for 3 h, the crude sample was purified by ISCO column chromatography (silica gel ISCO 40 g prepacked column, eluting with 0-100% EtOAc/Hexane) to give the title compound (688 mg). LCMS m/z (M+H): Calc'd 553.2, found 553.3.

Step 4: (R)-2-chloro-4-(4-((1-(3,3,3-trifluoro-2-hydroxy-2-phenylpropanoyl)piperidin-4-yl)methyl)piperidin-1-yl)benzoic acid At room temperature, aq. NaOH (1N NaOH, 3.73 ml) was added to a mixture of (R)-methyl 2-chloro-4-(4-((1-(3,3,3-trifluoro-2-hydroxy-2-phenylpropanoyl)piperidin-4-yl)methyl)piperidin-1-yl)benzoate in MeOH (12.4 ml). After heating at 65° C. for 4 h, the mixture was cooled to room temperature, concentrated to remove most of MeOH. The pH was adjusted to 2-3 by the addition of 1N HCl followed by CH2Cl2 extraction (3×). The combined organic fractions were dried over $Na_2SO_4$, filtered and concentrated to give the crude title compound which was used without further purification. LCMS m/z (M+H): Calc'd 539.2, found 539.3.

Step 5: (R)-1-(4-((1-(4-(azetidine-1-carbonyl)-3-chlorophenyl)piperidin-4-yl)methyl)piperidin-1-yl)-3,3,3-trifluoro-2-hydroxy-2-phenylpropan-1-one A mixture of (R)-2-chloro-4-(4-((1-(3,3,3-trifluoro-2-hydroxy-2-phenylpropanoyl)piperidin-4-yl)methyl)piperidin-1-yl)benzoic acid (20 mg, 0.037 mmol) and PYBOP (38.6 mg, 0.074 mmol) in DMF (100 ul) was first stirred at room temperature for 10 min, followed by the addition of a solution of azetidine (6.4 mg, 0.074 mmol) and DIEA (25.9 ul, 0.148 mmol) in DMF (640 ul). After stirring at room temperature overnight, the crude sample was purified by mass-directed HPLC purification (2 cm×5 cm C18, acetonitrile-water gradient, 0.05% TFA added) to give the title compound (16 mg). LCMS m/z (M+H): Calc'd 578.2, found 578.4.

The following compounds were prepared according to the procedure for Example 4-1 using the appropriate intermediate B or available monoprotected diamine, acid and amine.

| Example | Structure | IUPAC Name | Mass Exact [M + H]+ |
|---|---|---|---|
| Example 4-2 | 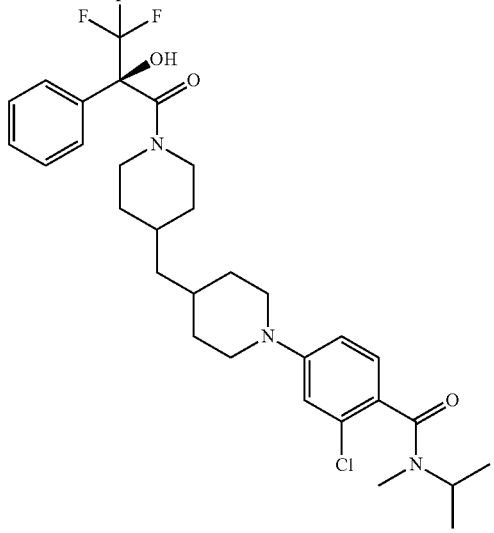 | 2-chloro-N-methyl-N-(1-methylethyl)-4-[4-({1-[(2R)-3,3,3-trifluoro-2-hydroxy-2-phenyl-propanoyl]piperidin-4-yl}methyl)piperidin-1-yl]benzamide | Calc'd 594.3, found 594.2 |
| Example 4-3 | 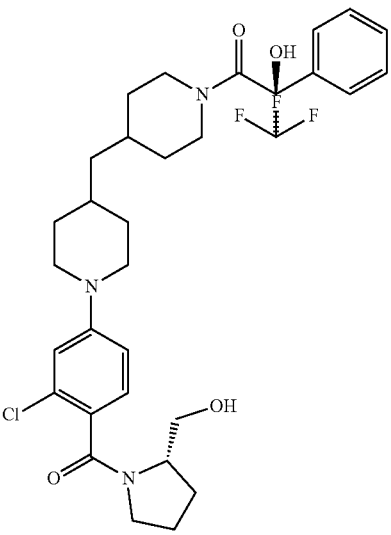 | (2R)-3-(4-{[1-(3-chloro-4-{[(2S)-2-(hydroxymethyl)pyrrolidin-1-yl]carbonyl}phenyl)piperidin-4-yl]methyl}piperidin-1-yl)-1,1,1-trifluoro-3-oxo-2-phenylpropan-2-ol | Calc'd 622.3, found 622.2 |

-continued

| Example | Structure | IUPAC Name | Mass Exact [M + H]+ |
|---|---|---|---|
| Example 4-4 | 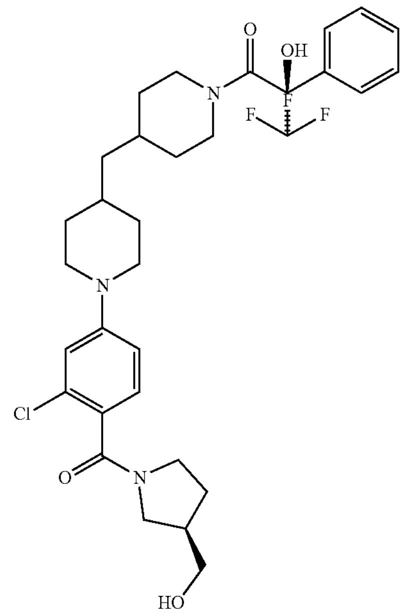 | (2R)-3-(4-{[1-(3-chloro-4-{[(3R)-3-(hydroxymethyl)pyrrolidin-1-yl]carbonyl}phenyl)piperidin-4-yl]methyl}piperidin-1-yl)-1,1,1-trifluoro-3-oxo-2-phenylpropan-2-ol | Calc'd 622.3, found 622.2 |
| Example 4-5 | 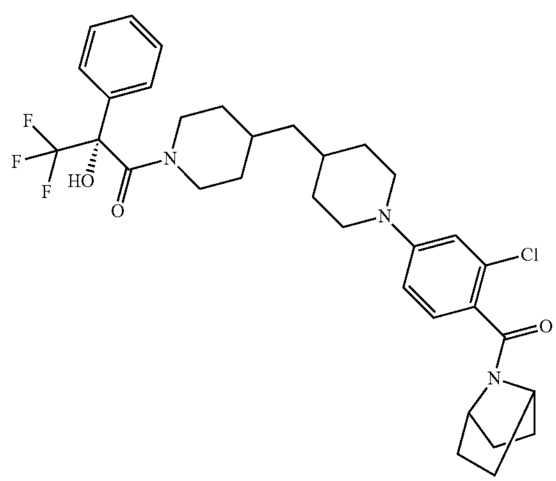 [SMILES: O=C(c1ccc(N2CCC(CC3CCN(C(=O)[C@](O)(c4ccccc4)C(F)(F)F)CC3)CC2)cc1Cl)N1C2CCC1CC2] | (2R)-3-[4-({1-[4-(7-azabicyclo[2.2.1]hept-7-ylcarbonyl)-3-chlorophenyl]piperidin-4-yl}methyl)piperidin-1-yl]-1,1,1-trifluoro-3-oxo-2-phenylpropan-2-ol | Calc'd 618.3, found 618.2 |
| Example 4-6 | 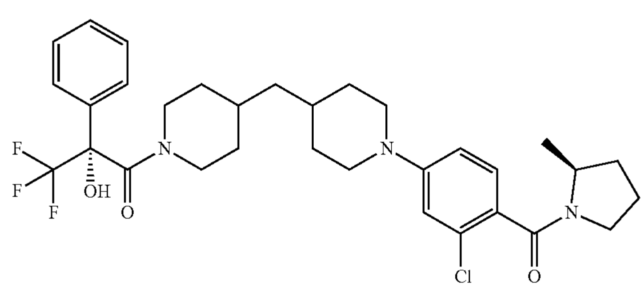 [SMILES: C[C@H]1CCCN1C(=O)c1ccc(N2CCC(CC3CCN(C(=O)[C@](O)(c4ccccc4)C(F)(F)F)CC3)CC2)cc1Cl] | (2R)-3-(4-{[1-(3-chloro-4-{[(2S)-2-methylpyrrolidin-1-yl]carbonyl}phenyl)piperidin-4-yl]methyl}piperidin-1-yl)-1,1,1-trifluoro-3-trifluoro-3-oxo-2-phenylpropan-2-ol | Calc'd 606.3, found 606.2 |

-continued
| Example | Structure | IUPAC Name | Mass Exact [M + H]+ |
|---|---|---|---|
| Example 4-7 | 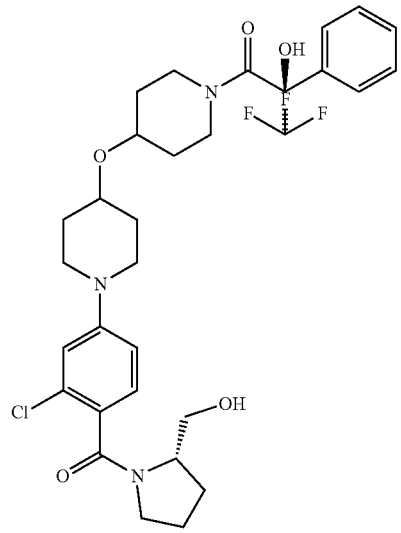 | (2R)-3-(4-{[1-(3-chloro-4-{[(2S)-2-(hydroxymethyl)pyrrolidin-1-yl]carbonyl}phenyl)piperidin-4-yl]oxy}piperidin-1-yl)-1,1,1-trifluoro-3-oxo-2-phenylpropan-2-ol | Calc'd 624.2, found 624.2 |
| Example 4-8 | 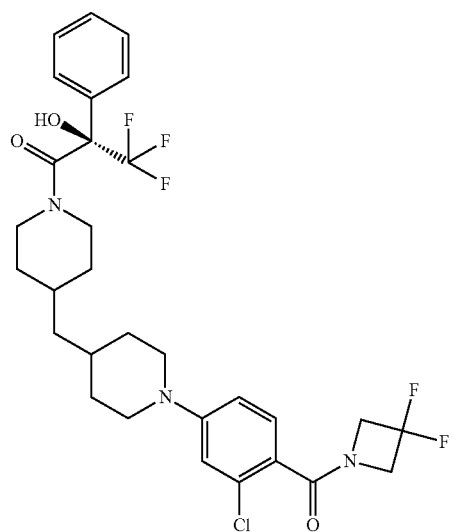 | (2R)-3-{4-[(1-{3-chloro-4-[(3,3-difluoroazetidin-1-yl)carbonyl]phenyl}piperidin-4-yl)methyl]piperidin-1-yl}-1,1,1-trifluoro-3-oxo-2-phenylpropan-2-ol | Calc'd 614.2, found 614.3 |

| Example | Structure | IUPAC Name | Mass Exact [M+H]+ |
|---|---|---|---|
| Example 4-9 | 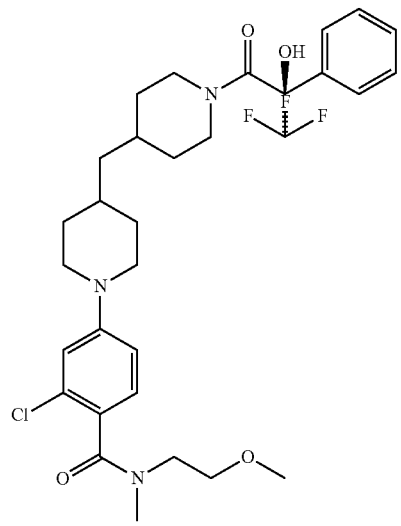 | 2-chloro-N-(2-methoxyethyl)-N-methyl-4-[4-({1-[(2R)-3,3,3-trifluoro-2-hydroxy-2-phenylpropanoyl]piperidin-1-yl]benzamide | Calc'd 610.3, found 610.2 |
| Example 4-10 | 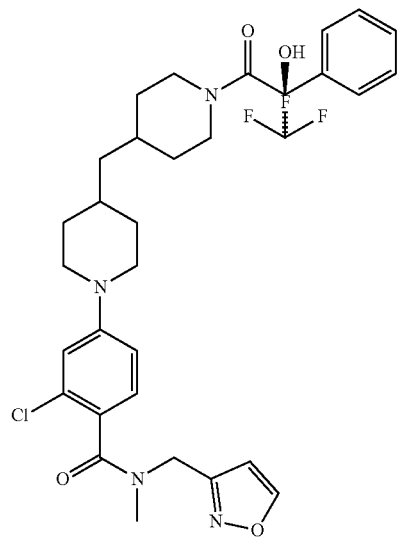 | 2-chloro-N-(isoxazol-3-ylmethyl)-N-methyl-4-[4-({1-[(2R)-3,3,3-trifluoro-2-hydroxy-2-phenylpropanoyl]piperidin-4-yl}methyl)piperidin-1-yl]benzamide | Calc'd 633.2, found 633.2 |

-continued
| Example | Structure | IUPAC Name | Mass Exact [M + H]+ |
|---|---|---|---|
| Example 4-11 | 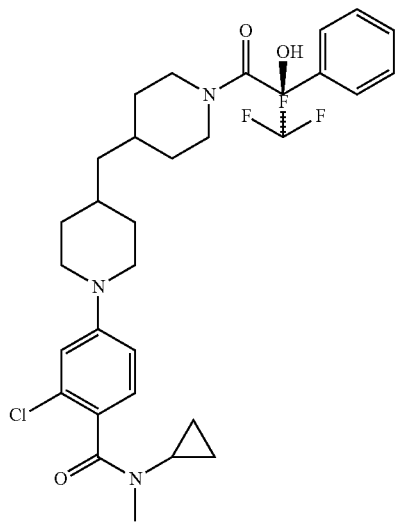 | 2-chloro-N-cyclopropyl-N-methyl-4-[4-({1-[(2R)-3,3,3-trifluoro-2-hydroxy-2-phenylpropanoyl]piperidin-4-yl}methyl)piperidin-1-yl]benzamide | Calc'd 592.3, found 592.2 |
| Example 4-12 | 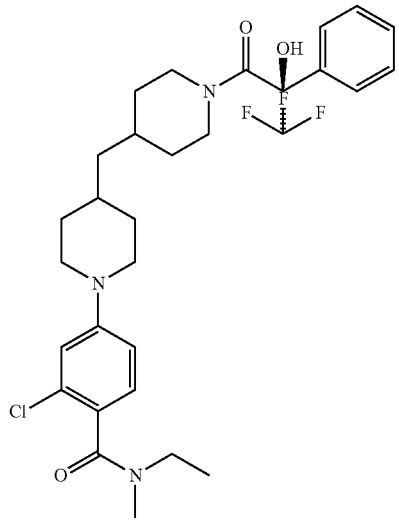 | 2-chloro-N-ethyl-N-methyl-4-[4-({1-[(2R)-3,3,3-trifluoro-2-hydroxy-2-phenylpropanoyl]piperidin-4-yl}methyl)piperidin-1-yl]benzamide | Calc'd 580.3, found 580.2 |

| Example | Structure | IUPAC Name | Mass Exact [M+H]+ |
|---|---|---|---|
| Example 4-13 | 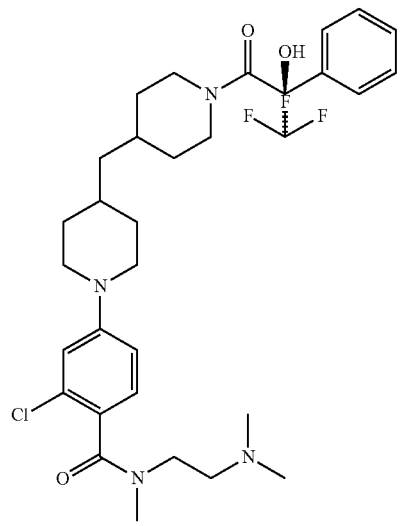 | 2-chloro-N-[2-(dimethylamino)ethyl]-N-methyl-4-[4-({1-[(2R)-3,3,3-trifluoro-2-hydroxy-2-phenylpropanoyl]piperidin-4-yl}methyl)piperidin-1-yl]benzamide | Calc'd 623.3, found 623.2 |
| Example 4-14 | 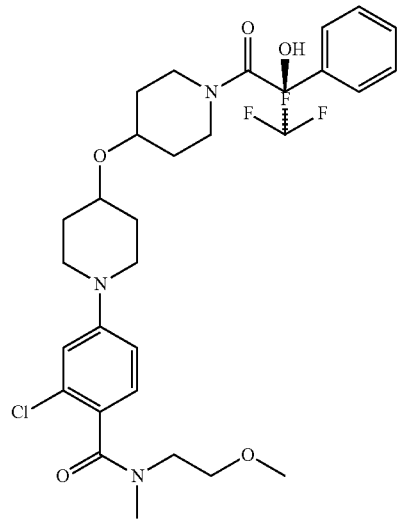 | 2-chloro-N-(2-methoxyethyl)-N-methyl-4-[4-({1-[(2R)-3,3,3-trifluoro-2-hydroxy-2-phenylpropanoyl]piperidin-4-yl}oxy)piperidin-1-yl]benzamide | Calc'd 612.2, found 612.4 |

| Example | Structure | IUPAC Name | Mass Exact [M + H]+ |
|---|---|---|---|
| Example 4-15 | 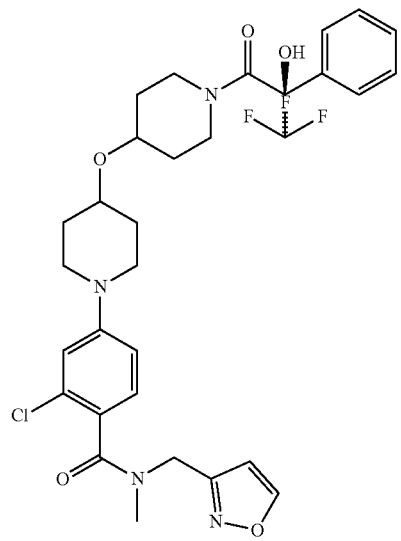 | 2-chloro-N-(isoxazol-3-yl-methyl)-N-methyl-4-[4-({1-[(2R)-3,3,3-trifluoro-2-hydroxy-2-phenylpropanoyl]piperidin-4-yl}oxy)piperidin-1-yl]benzamide | Calc'd 635.2, found 635.4 |
| Example 4-16 | 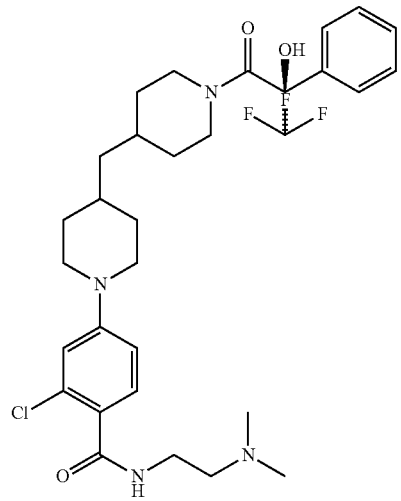 | 2-chloro-N-[2-(dimethylamino)ethyl]-4-[4-({1-[(2R)-3,3,3-trifluoro-2-hydroxy-2-phenylpropanoyl]piperidin-4-yl}methyl)piperidin-1-yl]benzamide | Calc'd 609.3, found 609.4 |

| Example | Structure | IUPAC Name | Mass Exact [M + H]+ |
|---|---|---|---|
| Example 4-17 | 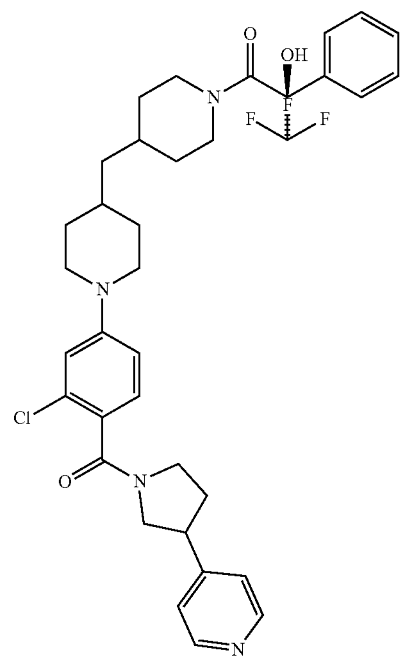 | (2R)-3-{4-[(1-{3-chloro-4-[(3-pyridin-4-ylpyrrolidin-1-yl)carbonyl]phenyl}piperidin-4-yl)methyl]piperidin-1-yl}-1,1,1-trifluoro-3-oxo-2-phenylpropan-2-ol | Calc'd 669.3, found 669.3 |
| Example 4-18 | 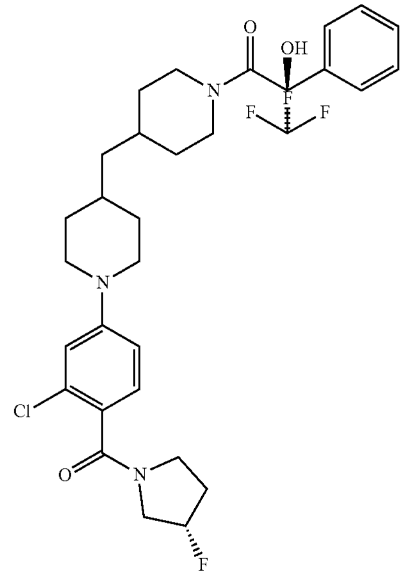 | (2R)-3-(4-{[1-(3-chloro-4-{[(3S)-3-fluoropyridin-1-yl]carbonyl}phenyl)piperidin-4-yl]methyl}piperidin-1-yl)-1,1,1-trifluoro-3-oxo-2-phenylpropan-2-ol | Calc'd 610.2, found 610.2 |

| Example | Structure | IUPAC Name | Mass Exact [M + H]+ |
|---|---|---|---|
| Example 4-19 | 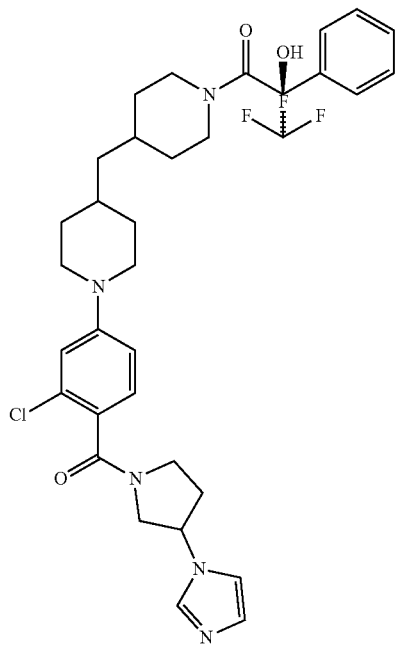 | (2R)-3-(4-{[1-(3-chloro-4-{[3-(1H-imidazol-1-yl)pyrrolidin-1-yl]carbonyl}phenyl)piperidin-4-yl]methyl}piperidin-1-yl)-1,1,1-trifluoro-3-oxo-2-phenylpropan-2-ol | Calc'd 658.3, found 658.2 |
| Example 4-20 | 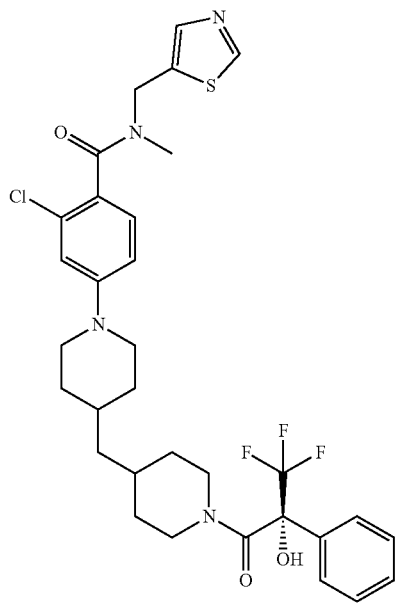 | 2-chloro-N-methyl-N-(1,3-thiazol-5-ylmethyl)-4-[4-({1-[(2R)-3,3,3-trifluoro-2-hydroxy-2-phenylpropanoyl]piperidin-4-yl}methyl)piperidin-1-yl]benzamide | Calc'd 649.2, found 649.2 |

-continued

| Example | Structure | IUPAC Name | Mass Exact [M + H]+ |
|---|---|---|---|
| Example 4-21 | 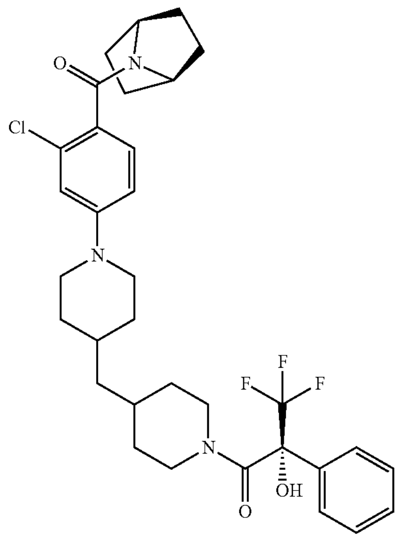 | (2R)-3-{4-[(1-{4-[(1s,4s)-7-aza-bicyclo[2.2.1]hept-7-ylcarbonyl]-3-chlorophenyl} piperidin-4-yl)methyl]piperidin-1-yl}-1,1,1-trifluoro-3-oxo-2-phenylpropan-2-ol | Calc'd 618.3, found 618.2 |
| Example 4-22 | 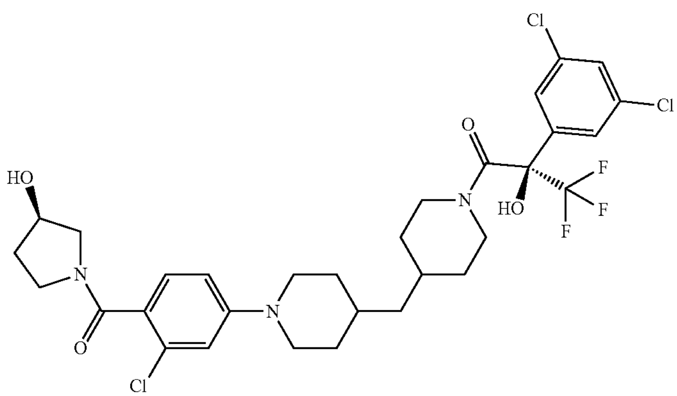 [SMILES: O=C(c1ccc(N2CCC(CC3CCN(C(=O)[C@](O)(c4cc(Cl)cc(Cl)c4)C(F)(F)F)CC3)CC2)cc1Cl)N1CC[C@@H](O)C1] | (3R)-1-({2-chloro-4-[4-({1-[(2R)-2-(3,5-dichloro-phenyl)-3,3,3-trifluoro-2-hydroxypropanoyl] piperidin-4-yl}methyl) piperidin-1-yl] phenyl}carbonyl) pyrrolidin-3-ol | Calc'd 676.2, found |
| Example 4-23 | 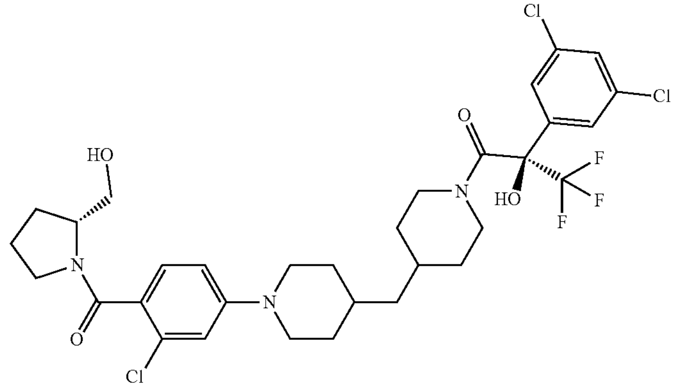 [SMILES: O=C(c1ccc(N2CCC(CC3CCN(C(=O)[C@](O)(c4cc(Cl)cc(Cl)c4)C(F)(F)F)CC3)CC2)cc1Cl)N1CCC[C@@H]1CO] | (2R)-3-(4-{[1-(3-chloro-4-{[(2R)-2-(hydroxymethyl) pyrrolidin-1-yl]carbonyl}phenyl) piperidin-4-yl]methyl}piperidin-1-yl)-2-(3,5-dichlorophenyl)-1,1,1-trifluoro-3-oxopropan-2-ol | Calc'd 690.2, found |

| Example | Structure | IUPAC Name | Mass Exact [M + H]+ |
|---|---|---|---|
| Example 4-24 | 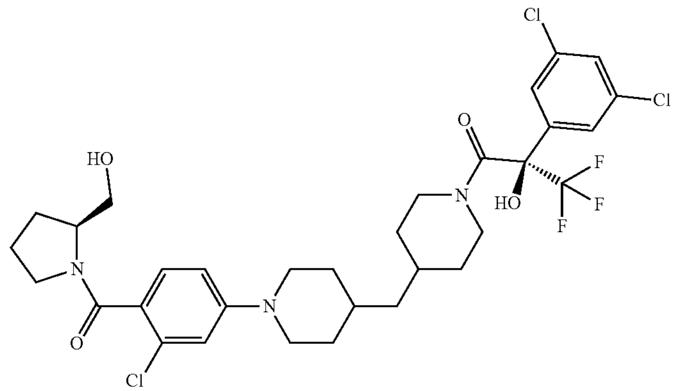 [SMILES: O=C(c1ccc(N2CCC(CC3CCN(C(=O)[C@](O)(c4cc(Cl)cc(Cl)c4)C(F)(F)F)CC3)CC2)cc1Cl)N1CCC[C@H]1CO] | (2R)-3-(4-{[1-(3-chloro-4-{[(2S)-2-(hydroxymethyl)pyrrolidin-1-yl]carbonyl}phenyl)piperidin-4-yl]methyl}piperidin-1-yl)-2-(3,5-dichlorophenyl)-1,1,1-trifluoro-3-oxopropan-2-ol | Calc'd 690.2, found |
| Example 4-25 | 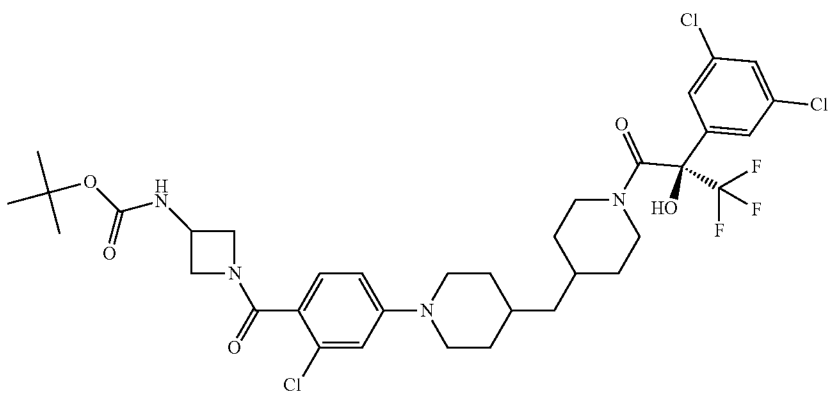 [SMILES: CC(C)(C)OC(=O)NC1CN(C(=O)c2ccc(N3CCC(CC4CCN(C(=O)[C@](O)(c5cc(Cl)cc(Cl)c5)C(F)(F)F)CC4)CC3)cc2Cl)C1] | tert-butyl [1-({2-chloro-4-[4-({1-[(2R)-2-(3,5-dichlorophenyl)-3,3,3-trifluoro-2-hydroxypropanoyl]piperidin-4-yl}methyl)piperidin-1-yl]phenyl}carbonyl)azetidin-3-yl]carbamate | Calc'd 761.2, found |
| Example 4-26 | 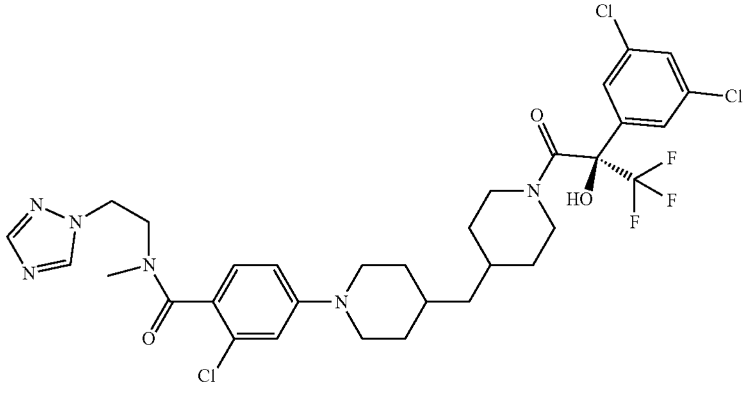 [SMILES: CN(CCn1cncn1)C(=O)c1ccc(N2CCC(CC3CCN(C(=O)[C@](O)(c4cc(Cl)cc(Cl)c4)C(F)(F)F)CC3)CC2)cc1Cl] | 2-chloro-4-[4-({1-[(2R)-2-(3,5-dichlorophenyl)-3,3,3-trifluoro-2-hydroxypropanoyl]piperidin-4-yl}methyl)piperidin-1-yl]-N-methyl-N-[2-(1H-1,2,4-triazol-1-yl)ethyl]benzamide | Calc'd 715.2, found |

Example 5-1: (R)-2-chloro-N,N-dimethyl-4-(4-(1-(3,3,3-trifluoro-2-hydroxy-2-(3-methoxyphenyl)propanoyl)piperidine-4-carbonyl)piperazin-1-yl)benzamide

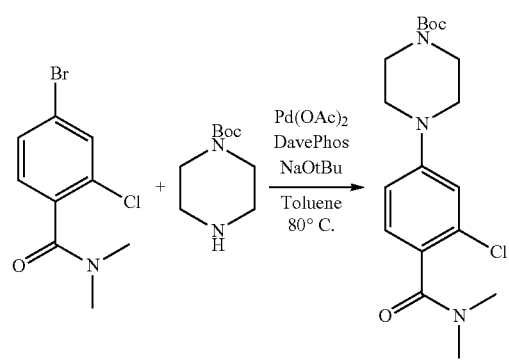

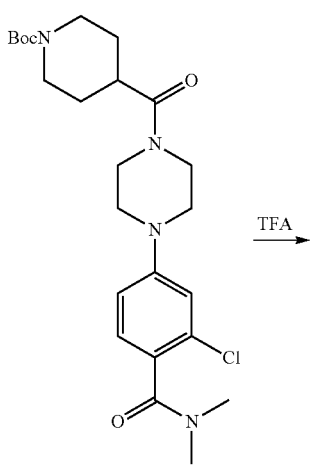

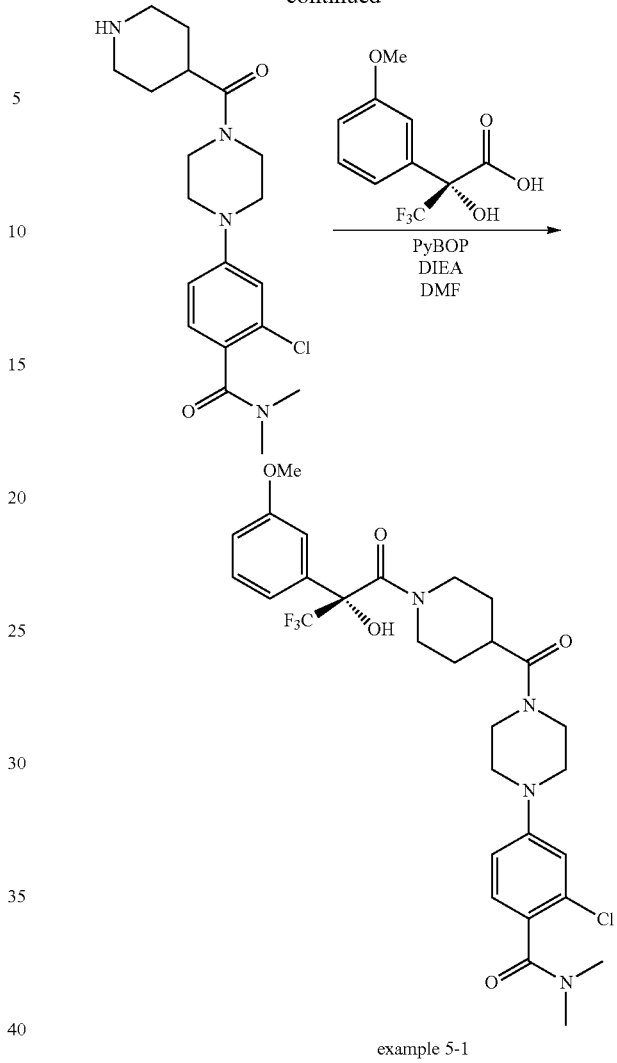

example 5-1

Step 1: tert-butyl 4-(3-chloro-4-(dimethylcarbamoyl)phenyl)piperazine-1-carboxylate A mixture of tert-butyl piperazine-1-carboxylate (426 mg, 2.29 mmol), 4-bromo-2-chloro-N,N-dimethylbenzamide (600 mg, 2.29 mmol), 2-dicyclohexylphosphino-2'-(N,N-dimethylamino)biphenyl (135 mg, 0.34 mmol), palladium (II) acetate (25.7 mg, 0.11 mmol), and sodium tert-butoxide (264 mg, 2.74 mmol) in Toluene (11.5 ml) was degassed by bubbling with N$_2$ and heated at 80° C. overnight. The reaction mixture was filtered and then concentrated to dry. The residue was purified by ISCO column chromatography (ISCO 40 g prepacked, eluting with 0-100% EtOAc/Hexane) to give the title compound (782 mg). LCMS m/z (M+H): Calc'd, 368.1, found 368.2.

Step 2: 2-chloro-N,N-dimethyl-4-(piperazin-1-yl)benzamide

Tert-butyl 4-(3-chloro-4-(dimethylcarbamoyl)phenyl)piperazine-1-carboxylate (782 mg, 2.13 mmol) was treated with TFA:DCM (1:1, 21 ml) at room temperature for 1 h. The mixture was concentrated to dryness to give the crude title compound which was used without further purification. LCMS m/z (M+H): calculated, 268.1, observed, 268.2.

Step 3: tert-butyl 4-(4-(3-chloro-4-(dimethylcarbamoyl)phenyl)piperazine-1-carbonyl)piperidine-1-carboxylate DIEA (235 ul, 1.35 mmol) was added to a mixture of 2-chloro-N,N-dimethyl-4-(piperazin-1-yl)benzamide (60 mg, 0.22 mmol), 1-(tert-butoxycarbonyl)piperidine-4-carboxylic acid (103 mg, 0.44 mmol), and PYBOP (233 mg, 0.44 mmol) in DCM (3 ml) at room temperature. After stirring at room temperature overnight, the reaction mixture was purified by ISCO column chromatography (silica gel ISCO, 12 g prepacked, 12 min run, eluting with 0-100% EtOAc/Hexane) to give the title compound (105 mg). LCMS m/z (M+H): Calc'd, 479.2, found, 479.4.

Step 4: 2-chloro-N,N-dimethyl-4-(4-(piperidine-4-carbonyl)piperazin-1-yl)benzamide Tert-butyl 4-(4-(3-chloro-4-(dimethylcarbamoyl)phenyl) piperazine-1-carbonyl)piperidine-1-carboxylate (105 mg, 0.22 mol) was dissolve in MeOH (0.81 ml) and treated with 4N HCl in dixoane (0.27 ml) for 1.5 h. The reaction mixture was concentrated and the residue was used without further purification. LCMS m/z (M+H): Calc'd, 379.2, found, 379.3.

Step 5: (R)-2-chloro-N,N-dimethyl-4-(4-(1-(3,3,3-trifluoro-2-hydroxy-2-(3-methoxyphenyl)propanoyl) piperidine-4-carbonyl)piperazin-1-yl)benzamide A mixture of (R)-3,3,3-trifluoro-2-hydroxy-2-(3-methoxyphenyl)propanoic acid (19 mg, 0.077 mmol) and PYBOP (44 mg, 0.085 mmol) in DMF (100 ul) was first stirred at room temperature for 10 min, followed by the addition of a solution of 2-chloro-N,N-dimethyl-4-(4-(piperidine-4-carbonyl)piperazin-1-yl)benzamide (19 mg, 0.039 mmol) and DIEA (40 ul, 0.23 mmol) in DMF (450 ul). After stirring at room temperature overnight, the crude sample was purified by mass-directed HPLC purification (2 cm×5 cm C18, acetonitrile-water gradient, 0.05% TFA added) to give the title compound (11.4 mg). LCMS m/z (M+H): Calc'd, 611.2, found, 611.4.

Example 6-1: 2-chloro-N,N-dimethyl-4-[4-({1-[(2R)-3,3,3-trifluoro-2-hydroxy-2-phenylpropanoyl] piperidin-4-yl}methyl)piperazin-1-yl]benzamide

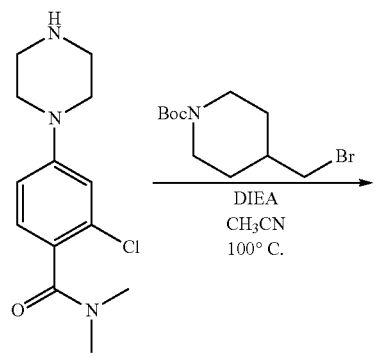

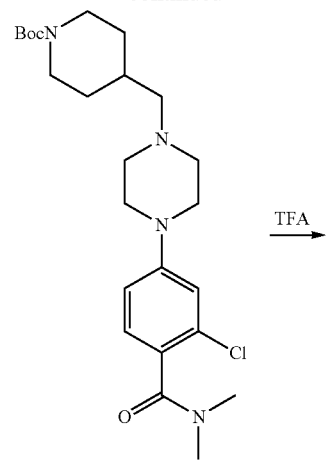

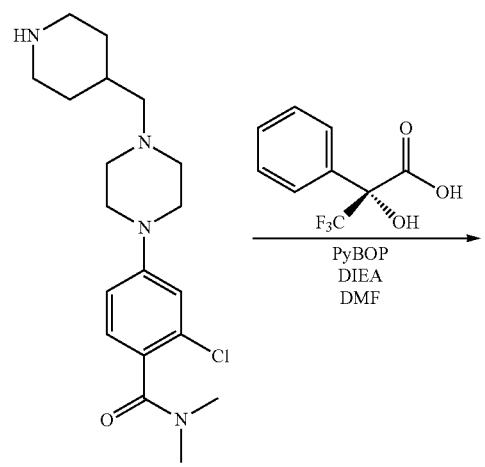

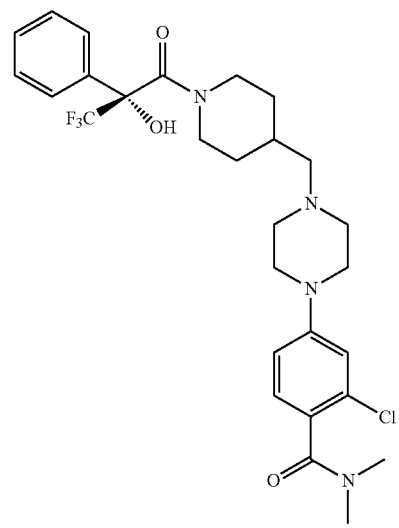

Example 6-1

Step 1: tert-butyl 4-((4-(3-chloro-4-(dimethylcarbamoyl)phenyl)piperazin-1-yl)methyl)piperidine-1-carboxylate After degassing, a mixture of 2-chloro-N,N-dimethyl-4-(piperazin-1-yl)benzamide (example 5-1, step 2, 113 mg, 0.41 mmol) tert-butyl 4-(bromomethyl)piperidine-1-carboxylate (138 mg, 0.41 mmol) and DIEA (283 ul, 1.62 mmol) was heated at 100° C. for 1 h under microwave condition. The reaction mixture was concentrated and purified by ISCO column chromatography (ISCO 24 g pre-packed, eluting with 0-20% MeOH/CH$_2$Cl$_2$) to give the title compound (123 mg). LCMS m/z (M+H): Calc'd 465.3, found 465.4.

Step 2: 2-chloro-N,N-dimethyl-4-(4-(piperidin-4-ylmethyl)piperazin-1-yl)benzamide A solution of tert-butyl 4-((1-(3-chloro-4-(dimethylcarbamoyl)phenyl)piperidin-4-yl)methyl)piperidine-1-carboxylate (123 mg, 0.26 mmol) in DCM (10 ml) was treated with TFA (2 mL) at room temperature for 1 h. The mixture was concentrated to dryness to give the crude title compound which was used without further purification. LCMS m/z (M+H): Calc'd 365.2, found 365.3.

Step 3: 2-chloro-N,N-dimethyl-4-[4-({1-[(2R)-3,3,3-trifluoro-2-hydroxy-2-phenylpropanoyl]piperidin-4-yl}methyl)piperazin-1-yl]benzamide A mixture of (R)-3,3,3-trifluoro-2-hydroxy-2-phenylpropanoic acid (30.8 mg, 0.14 mmol) and PYBOP (72.9 mg, 0.14 mmol) in DMF (100 ul) was first stirred at room temperature for 10 min, followed by the addition of a solution of 2-chloro-N,N-dimethyl-4-(4-(piperidin-4-ylmethyl)piperazin-1-yl)benzamide (25.5 mg, 0.07 mmol) and DIEA (61.1 ul, 0.35 mmol) in DMF (900 ul). After stirring at room temperature overnight, the crude sample was purified by mass-directed HPLC purification (2 cm×5 cm C18, acetonitrile-water gradient, 0.05% TFA added) to give the title compound (6.2 mg). LCMS m/z (M+H): Calc'd 567.2, found 567.4.

Example 6-3: 2-chloro-N,N-dimethyl-4-[(1R,5S)-3-({1-[(2R)-3,3,3-trifluoro-2-hydroxy-2-phenylpropanoyl]piperidin-4-yl}methyl)-3,8-diazabicyclo[3.2.1]oct-8-yl]benzamide

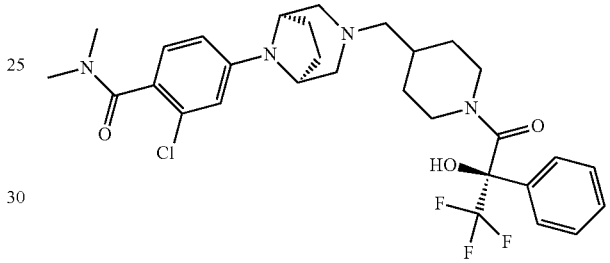

The title compound was prepared according to example 6-1 starting with 4-((1R,5S)-3,8-diazabicyclo[3.2.1]octan-8-yl)-2-chloro-N,N-dimethylbenzamide in step 1 which was prepared from tert-butyl (1R,5S)-3,8-diazabicyclo[3.2.1]octane-3-carboxylate according to the procedure in example 5-1. LCMS m/z (M+H): Calc'd 593.3, found 593.2.

The following compounds were prepared according to the procedure for Example 6-1 using the appropriate intermediate B or available protected diamine and acid.

| Example | Structure | IUPAC Name | Exact Mass [M + H]+ |
|---|---|---|---|
| Example 6-2 | 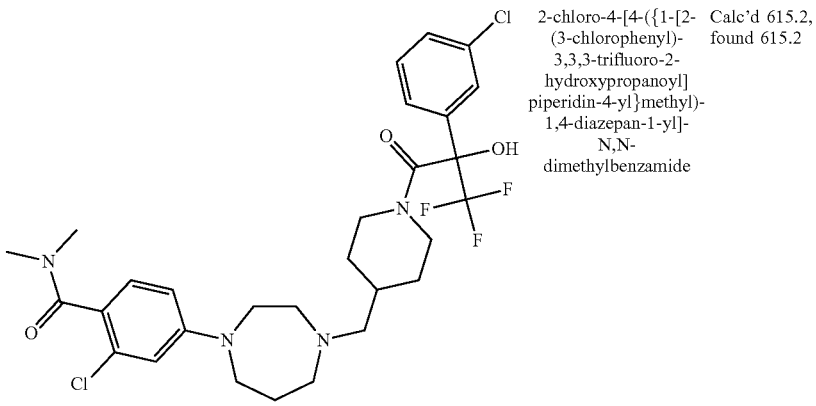 | 2-chloro-4-[4-({1-[2-(3-chlorophenyl)-3,3,3-trifluoro-2-hydroxypropanoyl]piperidin-4-yl}methyl)-1,4-diazepan-1-yl]-N,N-dimethylbenzamide | Calc'd 615.2, found 615.2 |

-continued

| Example | Structure | IUPAC Name | Exact Mass [M + H]+ |
|---|---|---|---|
| Example 6-3 | 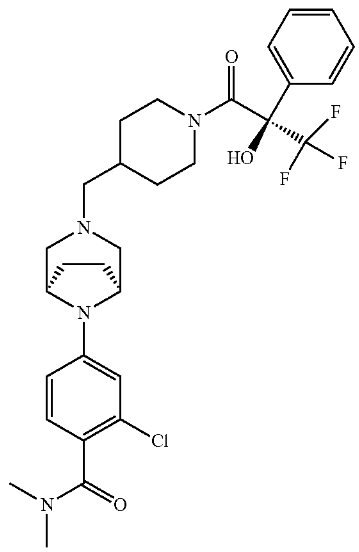 [SMILES: CN(C)C(=O)c1ccc(N2[C@@H]3CC[C@H]2CN(CC2CCN(C(=O)[C@](O)(c4ccccc4)C(F)(F)F)CC2)C3)cc1Cl] | 2-chloro-N,N-dimethyl-4-[(1R,5S)-3-({1-[(2R)-3,3,3-trifluoro-2-hydroxy-2-phenylpropanoyl]piperidin-4-yl}methyl)-3,8-diazabicyclo[3.2.1]oct-8-yl]benzamide | Calc'd 595.3, found 593.2 |
| Example 6-4 | 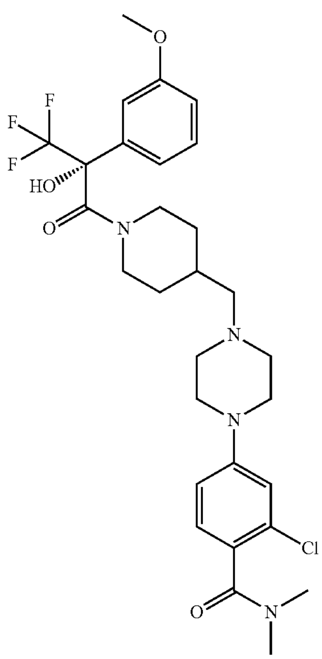 [SMILES: COc1cccc([C@@](O)(C(=O)N2CCC(CN3CCN(c4ccc(C(=O)N(C)C)c(Cl)c4)CC3)CC2)C(F)(F)F)c1] | 2-chloro-N,N-dimethyl-4-[4-({1-[(2R)-3,3,3-trifluoro-2-hydroxy-2-(3-methoxyphenyl)propanoyl]piperidin-4-yl}methyl)piperazin-1-yl]benzamide | Calc'd 597.2, found 597.4 |

185

Example 7-1: (R)—N,N,2-trimethyl-6-(4-((1-(3,3,3-trifluoro-2-hydroxy-2-phenylpropanoyl)piperidin-4-yl)methyl)piperidin-1-yl)nicotinamide

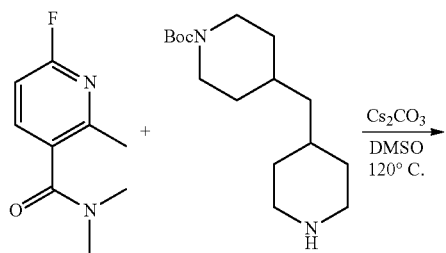

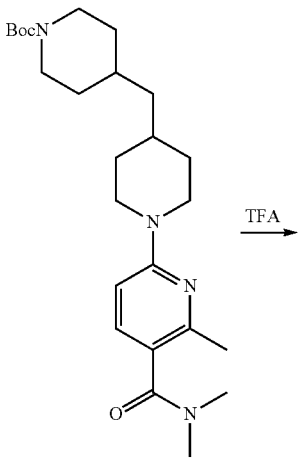

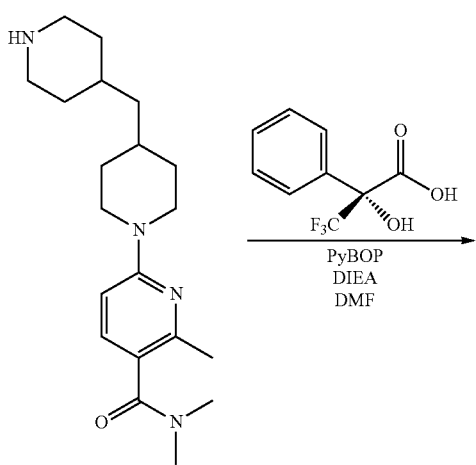

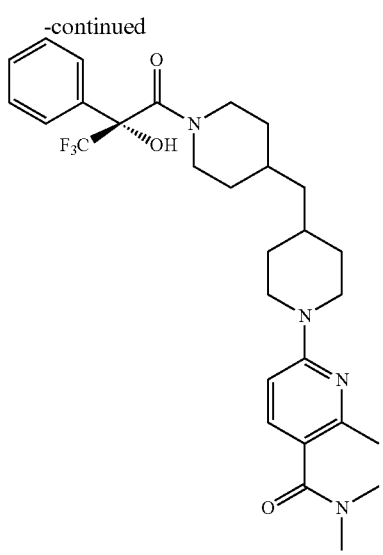

example 7-1

Step 1: tert-butyl 4-((1-(5-(dimethylcarbamoyl)-6-methylpyridin-2-yl)piperidin-4-yl)methyl)piperidine-1-carboxylate A mixture of 6-fluoro-N,N,2-trimethylnicotinamide (102 mg, 0.56 mmol), tert-butyl 4-(piperidin-4-ylmethyl)piperidine-1-carboxylate (158 mg, 0.56 mmol), and $Cs_2CO_3$ (182 mg, 0.56 mmol) in DMSO (1.9 ml) was degassed by bubbling with N2 and heated at 120° C. for 1 h under microwave condition. The mixture was diluted with EtOAc-$H_2O$, and the aq. layer was extracted with EtOAc (3×). The combined organic fractions were dried over $Na_2SO_4$, filtered and the solvent was evaporated under reduced pressure. The reaction mixture was purified by ISCO column chromatography (silica gel ISCO 40 g prepacked column, eluting with 0-100% EtOAc/Hexane) to give the title compound (179 mg). LCMS m/z (M+H): Calc'd 445.3, found 445.5.

Step 2: N,N,2-trimethyl-6-(4-(piperidin-4-ylmethyl)piperidin-1-yl)nicotinamide

A solution of tert-butyl 4-((1-(5-(dimethylcarbamoyl)-6-methylpyridin-2-yl)piperidin-4-yl)methyl)piperidine-1-carboxylate (67.5 mg, 0.15 mmol) in DCM (2.5 ml) was treated with TFA (0.5 mL) at room temperature for 1 h. The mixture was concentrated to dryness to give the crude title compound which was used without further purification. LCMS m/z (M+H): Calc'd 345.3, found 345.4.

Step 3: (R)—N,N,2-trimethyl-6-(4-((1-(3,3,3-trifluoro-2-hydroxy-2-phenylpropanoyl)piperidin-4-yl)methyl)piperidin-1-yl)nicotinamide A mixture of (R)-3,3,3-trifluoro-2-hydroxy-2-phenylpropanoic acid (13 mg, 0.06 mmol) and PYBOP (31 mg, 0.06 mmol) in DMF (100 ul) was first stirred at room temperature for 10 min, followed by the addition of a solution of N,N,2-trimethyl-6-(4-(piperidin-4-ylmethyl)piperidin-1-yl)nicotinamide (10.3 mg, 0.03 mmol) and DIEA (21 ul, 0.12 mmol) in DMF (900 ul). After stirring at room temperature overnight, the crude sample was purified by mass-directed HPLC purification (2 cm×5 cm C18, acetonitrile-water gradient, 0.05% TFA added) to give the title compound (12 mg). LCMS m/z (M+H): Calc'd 547.3, found 547.4.

The following compounds were prepared according to the procedure for Example 7-1 using the appropriate intermediate A, B or available protected diamine, and acid.

| Example | Structure | IUPAC Name | Exact Mass [M + H]+ |
|---|---|---|---|
| Example 7-2 | 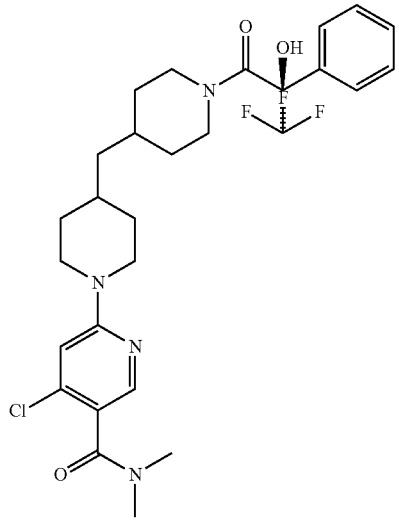 | 4-chloro-N,N-dimethyl-6-[4-({1-[(2R)-3,3,3-trifluoro-2-hydroxy-2-phenylpropanoyl]piperidin-4-yl}methyl)piperidin-1-yl]pyridine-3-carboxamide | Calc'd 567.2, found 567.2 |
| Example 7-3 | 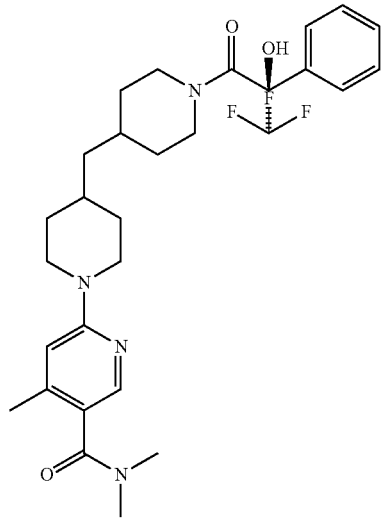 | N,N,4-trimethyl-6-[4-({1-[(2R)-3,3,3-trifluoro-2-hydroxy-2-phenylpropanoyl]piperidin-4-yl}methyl)piperidin-1-yl]pyridine-3-carboxamide | Calc'd 547.3, found 547.2 |

-continued

| Example | Structure | IUPAC Name | Exact Mass [M + H]+ |
|---|---|---|---|
| Example 7-4 | 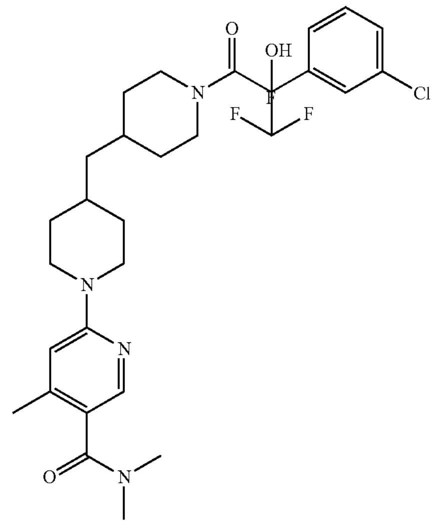 | 6-[4-({1-[2-(3-chlorophenyl)-3,3,3-trifluoro-2-hydroxypropanoyl]piperidin-4-yl}methyl)piperidin-1-yl]-N,N,4-trimethylpyridine-3-carboxamide | Calc'd 581.3, found 581.2 |
| Example 7-5 | 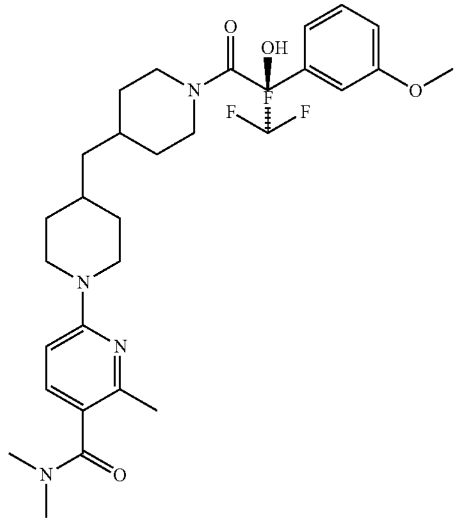 | N,N,2-trimethyl-6-[4-({1-[(2R)-3,3,3-trifluoro-2-hydroxy-2-(3-methoxyphenyl)propanoyl]piperidin-4-yl}methyl)piperidin-1-yl]pyridine-3-carboxamide | Calc'd 577.3, found 577.4 |
| Example 7-6 | 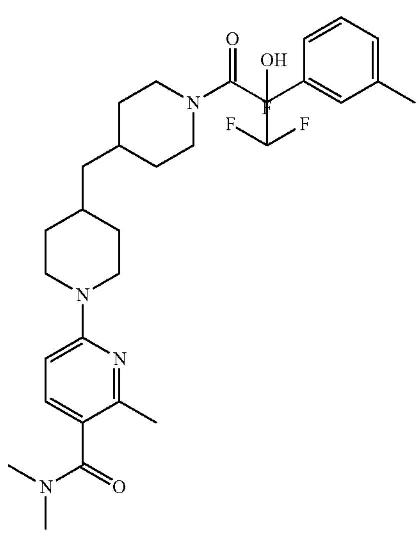 | N,N,2-trimethyl-6-[4-({1-[3,3,3-trifluoro-2-hydroxy-2-(3-methylphenyl)propanoyl]piperidin-4-yl}methyl)piperidin-1-yl]pyridine-3-carboxamide | Calc'd 561.3, found 561.2 |

-continued

| Example | Structure | IUPAC Name | Exact Mass [M + H]+ |
|---|---|---|---|
| Example 7-7 | 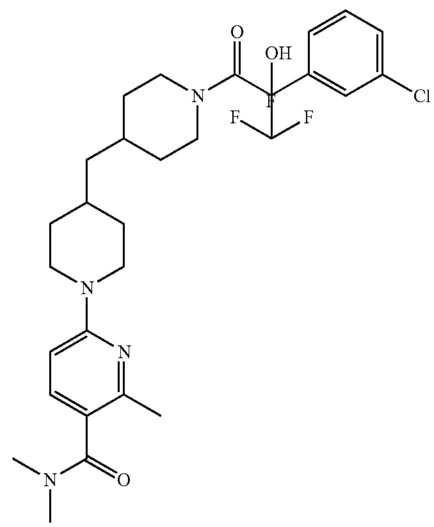 | 6-[4-({1-[2-(3-chlorophenyl)-3,3,3-trifluoro-2-hydroxypropanoyl]piperidin-4-yl}methyl)piperidin-1-yl]-N,N,2-trimethylpyridine-3-carboxamide | Calc'd 581.3, found 581.2 |
| Example 7-8 | 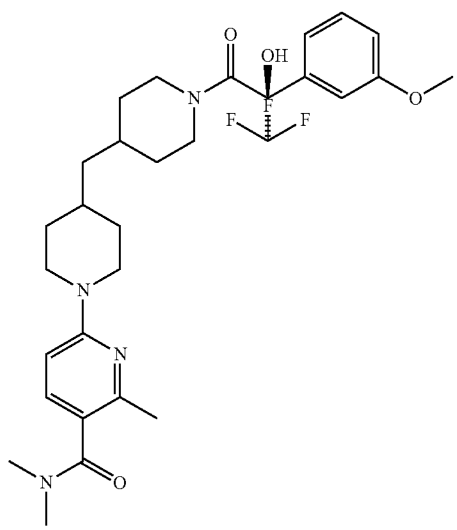 | N,N,2-trimethhyl-6-[4-({1-[(2R)-3,3,3-trifluoro-2-hydroxy-2-(3-methoxyphenyl)propanoyl]piperidin-4-yl}methyl)piperidin-1-yl]pyridine-3-carboxamide | Calc'd 577.3, found 577.4 |
| Example 7-9 | 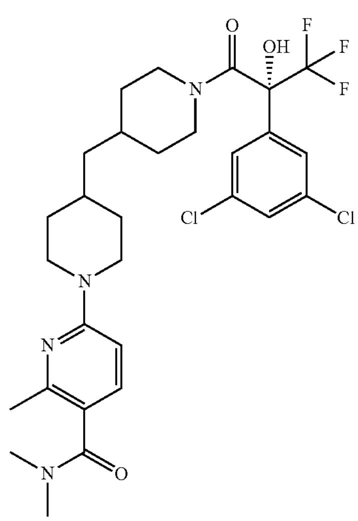 [SMILES: Cc1nc(N2CCC(CC3CCN(C(=O)[C@](O)(c4cc(Cl)cc(Cl)c4)C(F)(F)F)CC3)CC2)ccc1C(=O)N(C)C] | 6-[4-({1-[(2R)-2-(3,5-dichlorophenyl)-3,3,3-trifluoro-2-hydroxypropanoyl]piperidin-4-yl}methyl)piperidin-1-yl]-N,N,2-trimethylpyridine-3-carboxamide | Calc'd 615.2, found 615.4 |

-continued

| Example | Structure | IUPAC Name | Exact Mass [M + H]+ |
|---|---|---|---|
| Example 7-10 | 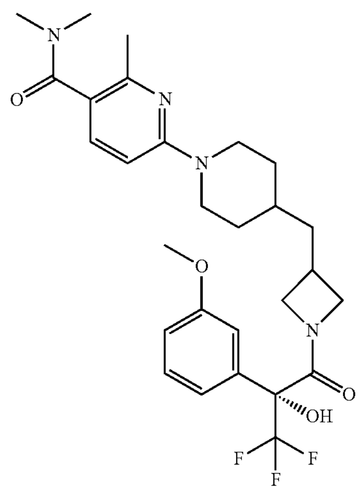 [SMILES: COc1cccc([C@@](O)(C(=O)N2CC(CC3CCN(c4ccc(C(=O)N(C)C)c(C)n4)CC3)C2)C(F)(F)F)c1] | N,N,2-trimethyl-6-[4-({1-[(2R)-3,3,3-trifluoro-2-hydroxy-2-(3-methoxyphenyl)propanoyl]azetidin-3-yl}methyl)piperidin-1-yl]pyridine-3-carboxamide | Calc'd 549.3, found 549.4 |
| Example 7-11 | 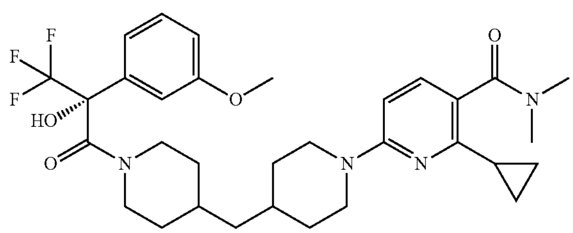 [SMILES: COc1cccc([C@@](O)(C(=O)N2CCC(CC3CCN(c4ccc(C(=O)N(C)C)c(C5CC5)n4)CC3)CC2)C(F)(F)F)c1] | 2-cyclopropyl-N,N-dimethyl-6-[4-({1-[(2R)-3,3,3-trifluoro-2-hydroxy-2-(3-methoxyphenyl)propanoyl]piperidin-4-yl}methyl)piperidin-1-yl]pyridine-3-carboxamide | Calc'd 603.3, found 603.5 |
| Example 7-12 | 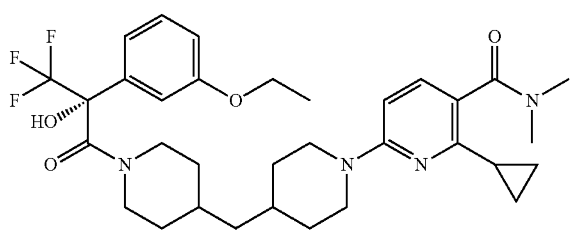 [SMILES: CCOc1cccc([C@@](O)(C(=O)N2CCC(CC3CCN(c4ccc(C(=O)N(C)C)c(C5CC5)n4)CC3)CC2)C(F)(F)F)c1] | 2-cyclopropyl-6-[4-({1-[(2R)-2-(3-ethoxyphenyl)-3,3,3-trifluoro-2-hydroxypropanoyl]piperidin-4-yl}methyl)piperidin-1-yl]-N,N-dimethylpyridine-3-carboxamide | Calc'd 617.3, found 617.5 |
| Example 7-13 | 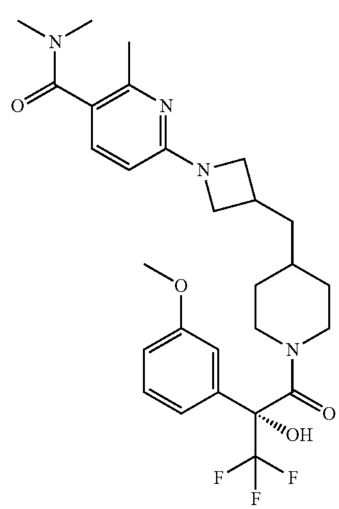 [SMILES: COc1cccc([C@@](O)(C(=O)N2CCC(CC3CN(c4ccc(C(=O)N(C)C)c(C)n4)C3)CC2)C(F)(F)F)c1] | N,N,2-trimethyl-6-[3-({1-[(2R)-3,3,3-trifluoro-2-hydroxy-2-(3-methoxyphenyl)propanoyl]piperidin-4-yl}methyl)azetidin-1-yl]pyridine-3-carboxamide | Calc'd 549.3, found 549.4 |

| Example | Structure | IUPAC Name | Exact Mass [M + H]+ |
|---|---|---|---|
| Example 7-14 | 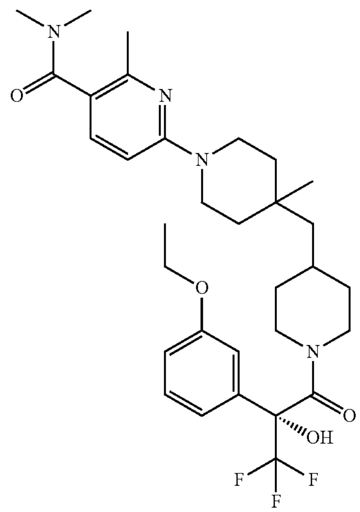 [SMILES: CCOc1cccc([C@@](O)(C(=O)N2CCC(CC3(C)CCN(c4ccc(C(=O)N(C)C)c(C)n4)CC3)CC2)C(F)(F)F)c1] | 6-[4-({1-[(2R)-2-(3-ethoxyphenyl)-3,3,3-trifluoro-2-hydroxypropanoyl]piperidin-4-yl}methyl)-4-methylpiperidin-1-yl]-N,N,2-trimethylpyridine-3-carboxamide | Calc'd 605.3, found 605.4 |
| Example 7-15 | 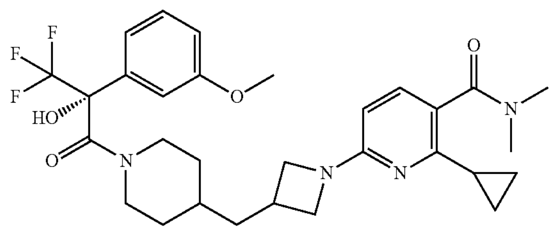 [SMILES: COc1cccc([C@@](O)(C(=O)N2CCC(CC3CN(c4ccc(C(=O)N(C)C)c(C5CC5)n4)C3)CC2)C(F)(F)F)c1] | 2-cyclopropyl-N,N-dimethyl-6-[3-({1-[(2R)-3,3,3-trifluoro-2-hydroxy-2-(3-methoxyphenyl)propanoyl]piperidin-4-yl}methyl)azetidin-1-yl]pyridine-3-carboxamide | Calc'd 575.3, found 575.4 |
| Example 7-16 | 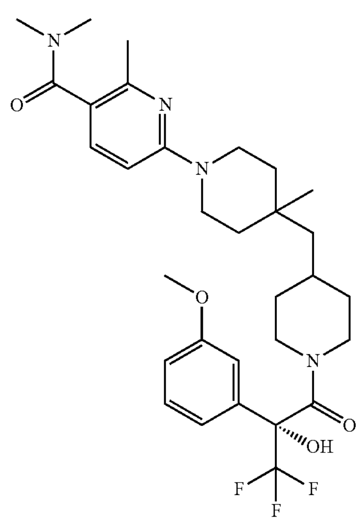 [SMILES: COc1cccc([C@@](O)(C(=O)N2CCC(CC3(C)CCN(c4ccc(C(=O)N(C)C)c(C)n4)CC3)CC2)C(F)(F)F)c1] | N,N,2-trimethyl-6-[4-methyl-4-({1-[(2R)-3,3,3-trifluoro-2-hydroxy-2-(3-methoxyphenyl)propanoyl]piperidin-4-yl}methyl)piperidin-1-yl]pyridine-3-carboxamide | Calc'd 591.3, found 591.4 |

| Example | Structure | IUPAC Name | Exact Mass [M + H]+ |
|---|---|---|---|
| Example 7-17 | 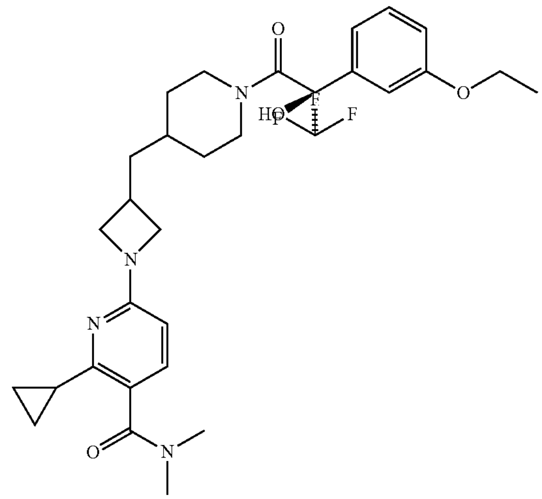 | 2-cyclopropyl-6-[3-({1-[(2R)-2-(3-ethoxyphenyl)-3,3,3-trifluoro-2-hydroxypropanoyl]piperidin-4-yl}methyl)azetidin-1-yl]-N,N-dimethylpyridine-3-carboxamide | Calc'd 589.3, found 589.4 |
| Example 7-18 | 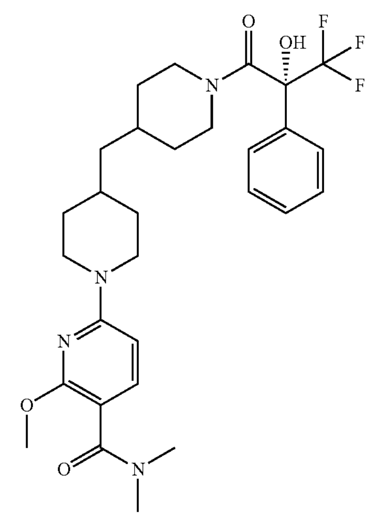 [SMILES: COc1nc(N2CCC(CC3CCN(C(=O)[C@](O)(c4ccccc4)C(F)(F)F)CC3)CC2)ccc1C(=O)N(C)C] | 2-methoxy-N,N-dimethyl-6-[4-({1-[(2R)-3,3,3-trifluoro-2-hydroxy-2-phenylpropanoyl]piperidin-4-yl}methyl)piperidin-1-yl]pyridine-3-carboxamide | Calc'd 563.3, found 563.4 |
| Example 7-19 | 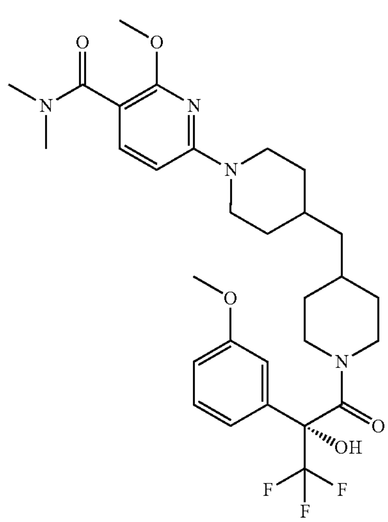 [SMILES: COc1cccc([C@@](O)(C(=O)N2CCC(CC3CCN(c4ccc(C(=O)N(C)C)c(OC)n4)CC3)CC2)C(F)(F)F)c1] | 2-methoxy-N,N-dimethyl-6-[4-({1-[(2R)-3,3,3-trifluoro-2-hydroxy-2-(3-methoxyphenyl)propanoyl]piperidin-4-yl}methyl)piperidin-1-yl]pyridine-3-carboxamide | Calc'd 593.3, found 593.4 |

| Example | Structure | IUPAC Name | Exact Mass [M + H]+ |
|---|---|---|---|
| Example 7-20 | 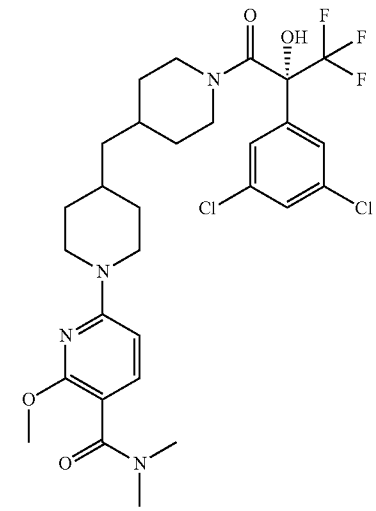 [SMILES: COc1nc(N2CCC(CC3CCN(C(=O)[C@](O)(c4cc(Cl)cc(Cl)c4)C(F)(F)F)CC3)CC2)ccc1C(=O)N(C)C] | 6-[4-({1-[(2R)-2-(3,5-dichlorophenyl)-3,3,3-trifluoro-2-hydroxypropanoyl]piperidin-4-yl}methyl)piperidin-1-yl]-2-methoxy-N,N-dimethylpyridine-3-carboxamide | Calc'd 631.2, found 631.4 |
| Example 7-21 | 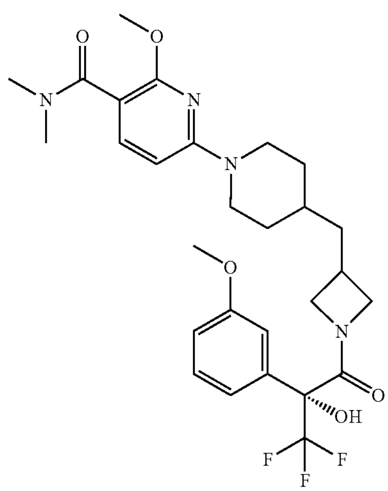 [SMILES: COc1cccc([C@@](O)(C(=O)N2CC(CC3CCN(c4ccc(C(=O)N(C)C)c(OC)n4)CC3)C2)C(F)(F)F)c1] | 2-methoxy-N,N-dimethyl-6-[4-[{1-[(2R)-3,3,3-trifluoro-2-hydroxy-2-(3-methoxyphenyl)propanoyl]azetidin-3-yl}methyl)piperidin-1-yl]pyridine-3-carboxamide | Calc'd 565.3, found 565.4 |
| Example 7-22 | 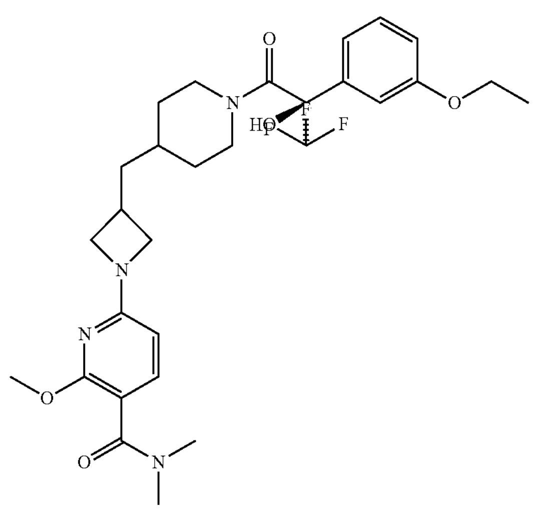 | 6-[3-({1-[(2R)-2-(3-ethoxyphenyl)-3,3,3-trifluoro-2-hydroxypropanoyl]piperidin-4-yl}methyl)azetidin-1-yl]-2-methoxy-N,N-dimethylpyridine-3-carboxamide | Calc'd 579.3, found 579.4 |

-continued

| Example | Structure | IUPAC Name | Exact Mass [M + H]+ |
|---|---|---|---|
| Example 7-23 | 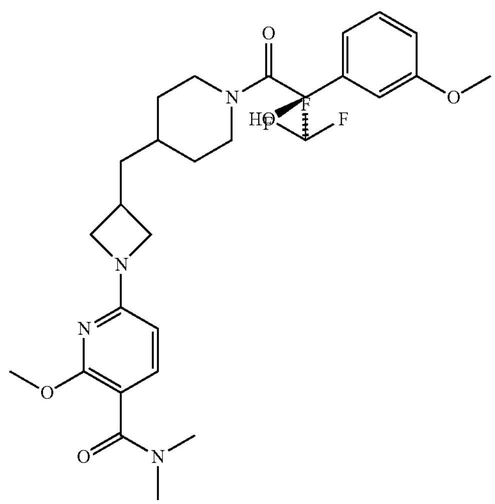 | 2-methoxy-N,N-dimethyl-6-[3-({1-[(2R)-3,3,3-trifluoro-2-hydroxy-2-(3-methoxyphenyl)propanoyl]piperidin-4-yl}methyl)azetidin-1-yl]pyridine-3-carboxamide | Calc'd 565.3, found 565.5 |
| Example 7-24 | 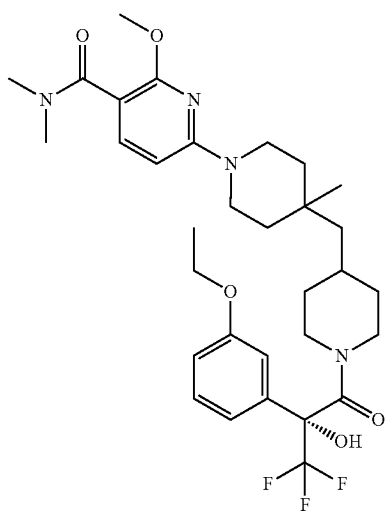 [SMILES: CCOc1cccc([C@@](O)(C(=O)N2CCC(CC3(C)CCN(c4ccc(C(=O)N(C)C)c(OC)n4)CC3)CC2)C(F)(F)F)c1] | 6-[4-({1-[(2R)-2-(3-ethoxyphenyl)-3,3,3-trifluoro-2-hydroxypropanoyl]piperidin-4-yl}methyl)-4-methylpiperidin-1-yl]-2-hydroxy-N,N-dimethylpyridine-3-carboxamide | Calc'd 621.3, found 621.4 |
| Example 7-25 | 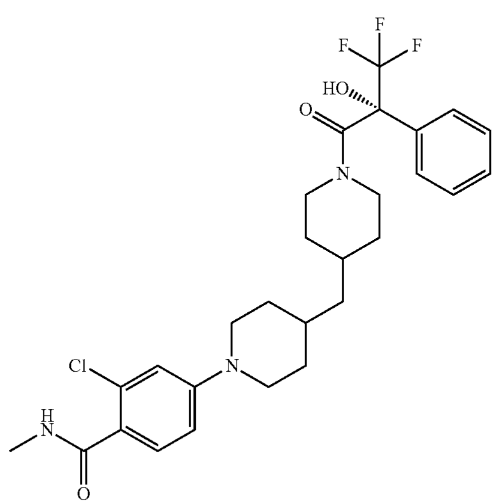 [SMILES: CNC(=O)c1ccc(N2CCC(CC3CCN(C(=O)[C@](O)(c4ccccc4)C(F)(F)F)CC3)CC2)cc1Cl] | 2-chloro-N-methyl-4-[4-({1-[(2R)-3,3,3-trifluoro-2-hydroxy-2-phenylpropanoyl]piperidin-4-yl}methyl)piperidin-1-yl]benzamide | Calc'd 552.2, found 552.2 |

| Example | Structure | IUPAC Name | Exact Mass [M + H]+ |
|---|---|---|---|
| Example 7-26 | 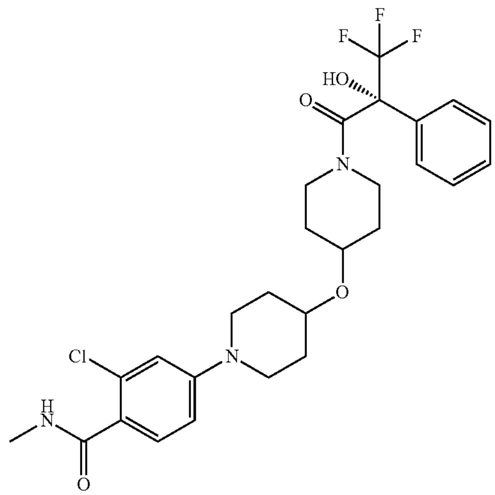 | 2-chloro-N-methyl-4-[4-({1-[(2R)-3,3,3-trifluoro-2-hydroxy-2-phenylpropanoyl]piperidin-4-yl}oxy)piperidin-1-yl]benzamide | Calc'd 554.2, found 554.2 |
| Example 7-27 | 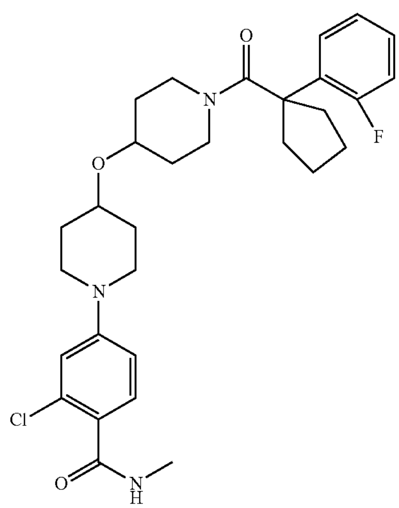 [SMILES: CNC(=O)c1ccc(N2CCC(OC3CCN(C(=O)C4(c5ccccc5F)CCCC4)CC3)CC2)cc1Cl] | 2-chloro-4-{4-[(1-{[1-(2-fluorophenyl)cyclopentyl]carbonyl}piperidin-4-yl)oxy]piperidin-1-yl}-N-methylbenzamide | Calc'd 542.3, found 542.2 |
| Example 7-28 | 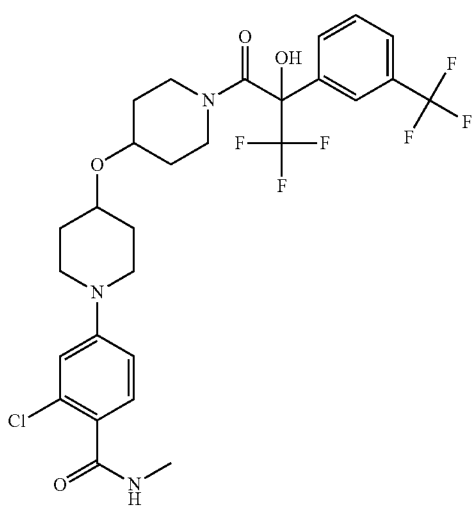 [SMILES: CNC(=O)c1ccc(N2CCC(OC3CCN(C(=O)C(O)(c4cccc(C(F)(F)F)c4)C(F)(F)F)CC3)CC2)cc1Cl] | 2-chloro-N-methyl-4-{4-[(1-{3,3,3-trifluoro-2-hydroxy-2-[3-(trifluoromethyl)phenyl]propanoyl}piperidin-4-yl)oxy]piperidin-1-yl}benzamide | Calc'd 622.2, found 622.1 |

-continued

| Example | Structure | IUPAC Name | Exact Mass [M + H]+ |
|---|---|---|---|
| Example 7-29 | 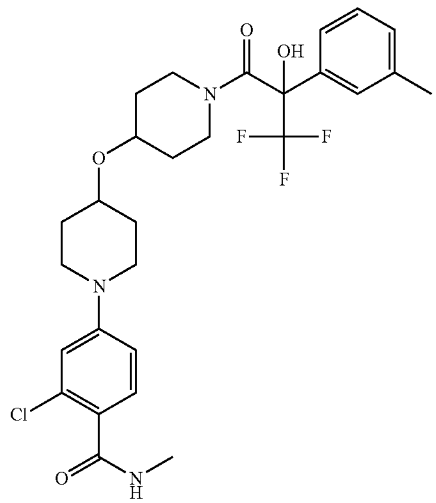 [SMILES: CNC(=O)c1ccc(N2CCC(OC3CCN(C(=O)C(O)(c4cccc(C)c4)C(F)(F)F)CC3)CC2)cc1Cl] | 2-chloro-N-methyl-4-[4-({1-[3,3,3-trifluoro-2-hydroxy-2-(3-methylphenyl)propanoyl]piperidin-4-yl}oxy)piperidin-1-yl]benzamide | Calc'd 568.2, found 568.2 |
| Example 7-30 | 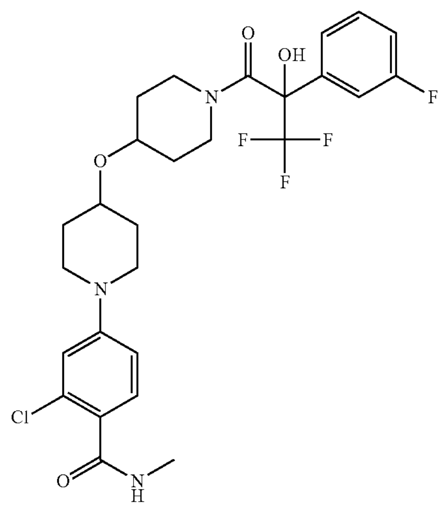 [SMILES: CNC(=O)c1ccc(N2CCC(OC3CCN(C(=O)C(O)(c4cccc(F)c4)C(F)(F)F)CC3)CC2)cc1Cl] | 2-chloro-N-methyl-4-[4-({1-[3,3,3-trifluoro-2-(3-fluorophenyl)-2-hydroxypropanoyl]piperidin-4-yl}oxy)piperidin-1-yl]benzamide | Calc'd 572.2, found 572.2 |
| Example 7-31 | 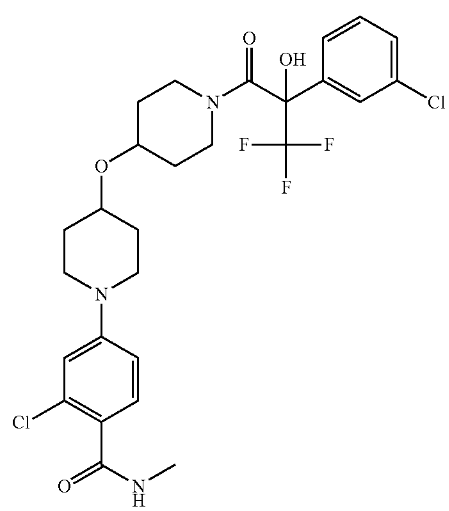 [SMILES: CNC(=O)c1ccc(N2CCC(OC3CCN(C(=O)C(O)(c4cccc(Cl)c4)C(F)(F)F)CC3)CC2)cc1Cl] | 2-chloro-4-[4-({1-[2-(3-chlorophenyl)-3,3,3-trifluoro-2-hydroxypropanoyl]piperidin-4-yl}oxy)piperidin-1-yl]-N-methylbenzamide | Calc'd 588.2, found 588.1 |

-continued

| Example | Structure | IUPAC Name | Exact Mass [M + H]+ |
|---|---|---|---|
| Example 7-32 | 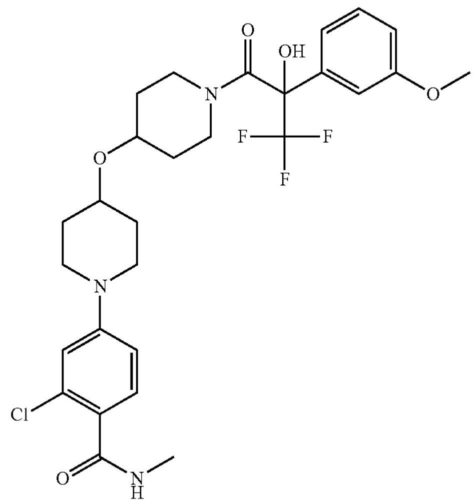 [SMILES: CNC(=O)c1ccc(N2CCC(OC3CCN(C(=O)C(O)(c4cccc(OC)c4)C(F)(F)F)CC3)CC2)cc1Cl] | 2-chloro-N-methyl-4-[4-({1-[3,3,3-trifluoro-2-hydroxy-2-(3-methoxyphenyl)propanoyl]piperidin-4-yl}oxy)piperidin-1-yl]benzamide | Calc'd 584.2, found 584.2 |
| Example 7-33 | 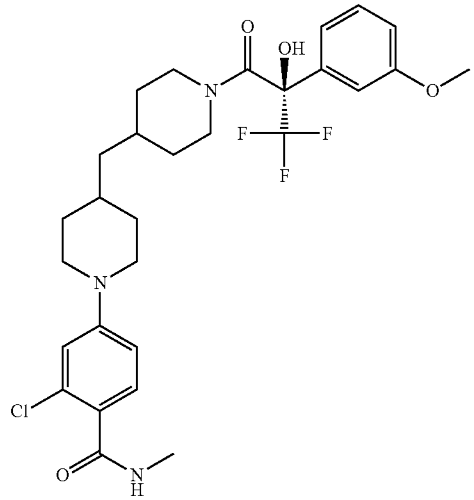 | 2-chloro-N-methyl-4-[4-({1-[(2R)-3,3,3-trifluoro-2-hydroxy-2-(3-methoxyphenyl)propanoyl]piperidin-4-yl}methyl)piperidin-1-yl]benzamide | Calc'd 582.2, found 582.2 |
| Example 7-34 | 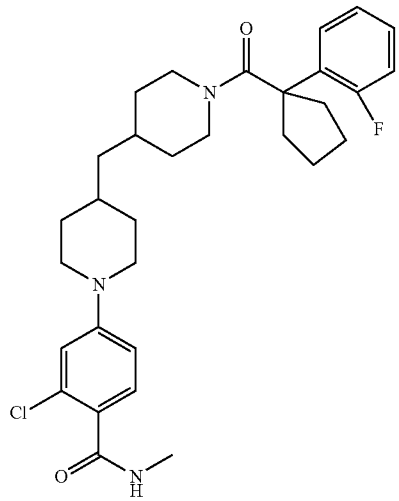 [SMILES: CNC(=O)c1ccc(N2CCC(CC3CCN(C(=O)C4(c5ccccc5F)CCCC4)CC3)CC2)cc1Cl] | 2-chloro-4-{4-[(1-{[1-(2-fluorophenyl)cyclopentyl]carbonyl}piperidin-4-yl)methyl]piperidin-1-yl}-N-methylbenzamide | Calc'd 540.3, found 540.2 |

| Example | Structure | IUPAC Name | Exact Mass [M + H]+ |
|---|---|---|---|
| Example 7-35 | 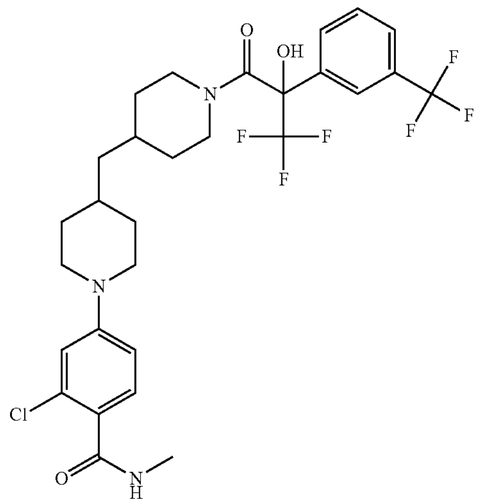 [SMILES: CNC(=O)c1ccc(N2CCC(CC3CCN(C(=O)C(O)(c4cccc(C(F)(F)F)c4)C(F)(F)F)CC3)CC2)cc1Cl] | 2-chloro-N-methyl-4-{4-[(1-{3,3,3-trifluoro-2-hydroxy-2-[3-(trifluoromethyl)phenyl]propanoyl}piperidin-4-yl)methyl]piperidin-1-yl}benzamide | Calc'd 620.2, found 620.2 |
| Example 7-36 | 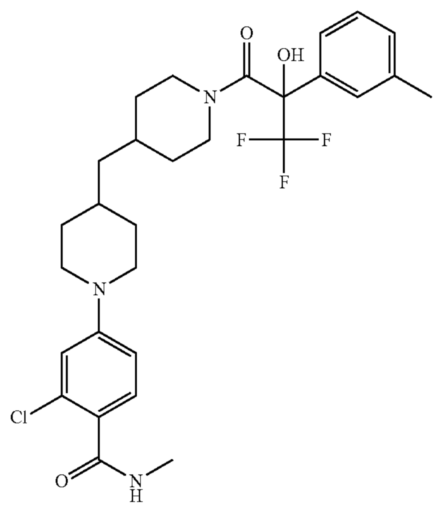 [SMILES: CNC(=O)c1ccc(N2CCC(CC3CCN(C(=O)C(O)(c4cccc(C)c4)C(F)(F)F)CC3)CC2)cc1Cl] | 2-chloro-N-methyl-4-[4-({1-[3,3,3-trifluoro-2-hydroxy-2-(3-methylphenyl)propanoyl]piperidin-4-yl}methyl)piperidin-1-yl]benzamide | Calc'd 566.2, found 566.2 |
| Example 7-37 | 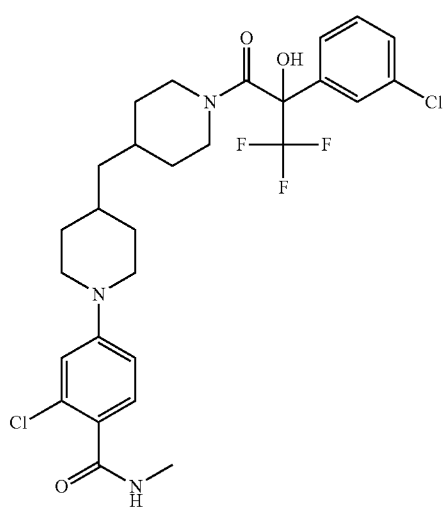 [SMILES: CNC(=O)c1ccc(N2CCC(CC3CCN(C(=O)C(O)(c4cccc(Cl)c4)C(F)(F)F)CC3)CC2)cc1Cl] | 2-chloro-4-[4-({1-[2-(3-chlorophenyl)-3,3,3-trifluoro-2-hydroxypropanoyl]piperidin-4-yl}methyl)piperidin-1-yl]-N-methylbenzamide | Calc'd 586.2, found 586.1 |

| Example | Structure | IUPAC Name | Exact Mass [M + H]+ |
|---|---|---|---|
| Example 7-38 | 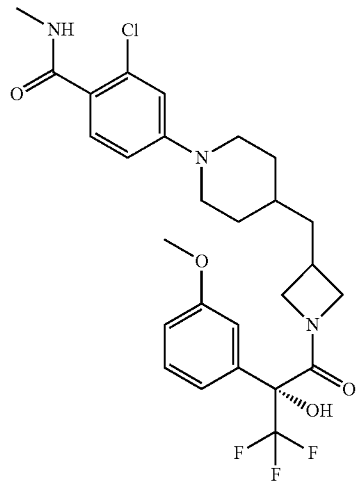 [SMILES: CNC(=O)c1ccc(N2CCC(CC3CN(C(=O)[C@](O)(c4cccc(OC)c4)C(F)(F)F)C3)CC2)cc1Cl] | 2-chloro-N-methyl-4-[4-({1-[(2R)-3,3,3-trifluoro-2-hydroxy-2-(3-methoxyphenyl)propanoyl]azetidin-3-yl}methyl)piperidin-1-yl]benzamide | Calc'd 554.2, found 554.4 |
| Example 7-39 | 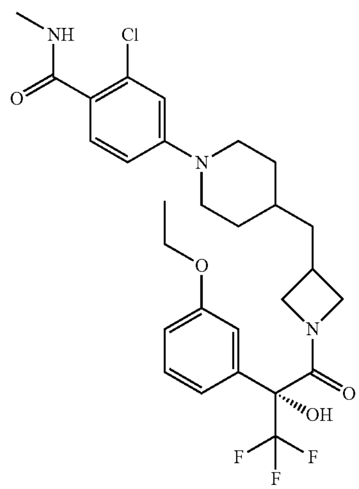 [SMILES: CCOc1cccc([C@@](O)(C(=O)N2CC(CC3CCN(c4ccc(C(=O)NC)c(Cl)c4)CC3)C2)C(F)(F)F)c1] | 2-chloro-4-[4-({1-[(2R)-2-(3-ethoxyphenyl)-3,3,3-trifluoro-2-hydroxypropanoyl]azetidin-3-yl}methyl)piperidin-1-yl]-N-methylbenzamide | Calc'd 568.2, found 568.4 |
| Example 7-40 | 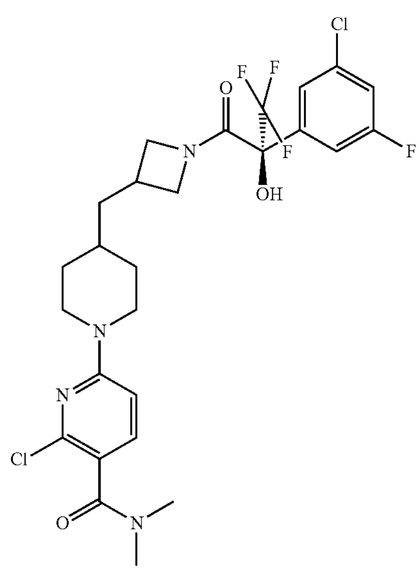 | 2-chloro-6-[4-({1-[(2R)-2-(3-chloro-5-fluorophenyl)-3,3,3-trifluoro-2-hydroxypropanoyl]azetidin-3-yl}methyl)piperidin-1-yl]-N,N-dimethylpyridine-3-carboxamide | Calc'd 591.2, found 591.3 |

-continued

| Example | Structure | IUPAC Name | Exact Mass [M + H]+ |
|---|---|---|---|
| Example 7-41 | 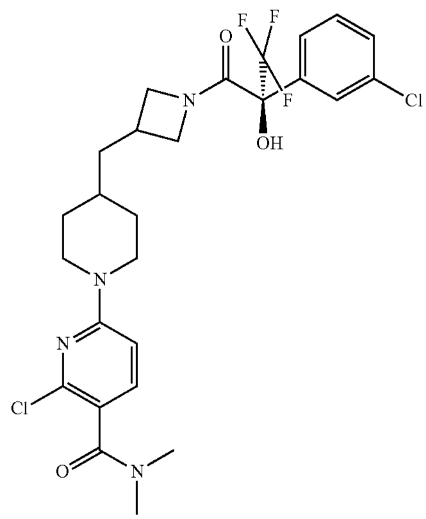 | 2-chloro-6-[4-({1-[(2R)-2-(3-chlorophenyl)-3,3,3-trifluoro-2-hydroxypropanoyl]azetidin-3-yl}methyl)piperidin-1-yl]-N,N-dimethylpyridine-3-carboxamide | Calc'd 573.2, found 573.3 |
| Example 7-42 | 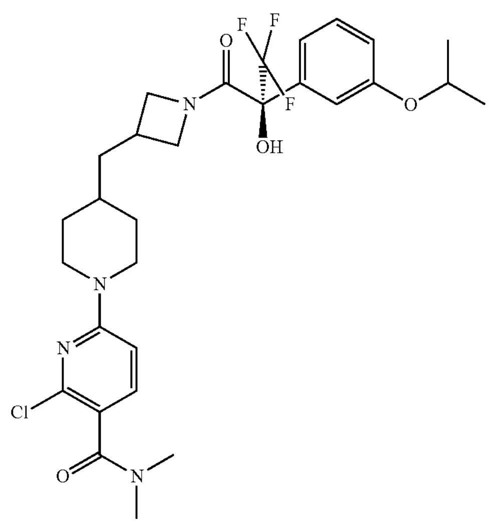 | 2-chloro-N,N-dimethyl-6-{4-[(1-{(2R)-3,3,3-trifluoro-2-hydroxy-2-[3-(1-methylethoxy)phenyl]propanoyl}azetidin-3-yl)methyl]piperidin-1-yl}pyridine-3-carboxamide | Calc'd 597.2, found 597.4 |
| Example 7-43 | 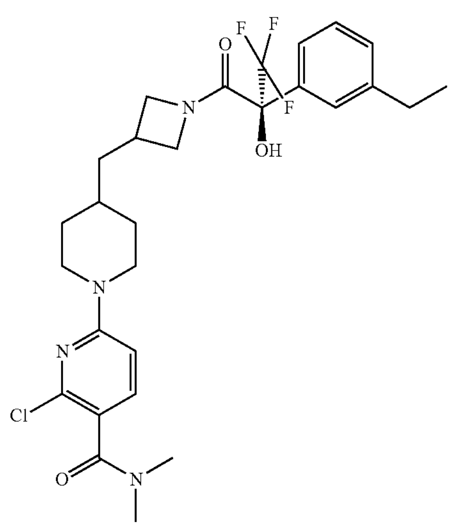 | 2-chloro-6-[4-({1-[(2R)-2-(3-ethylphenyl)-3,3,3-trifluoro-2-hydroxypropanoyl]azetidin-3-yl}methyl)piperidin-1-yl]-N,N-dimethylpyridine-3-carboxamide | Calc'd 567.2, found 567.4 |

-continued

| Example | Structure | IUPAC Name | Exact Mass [M + H]+ |
|---|---|---|---|
| Example 7-44 | 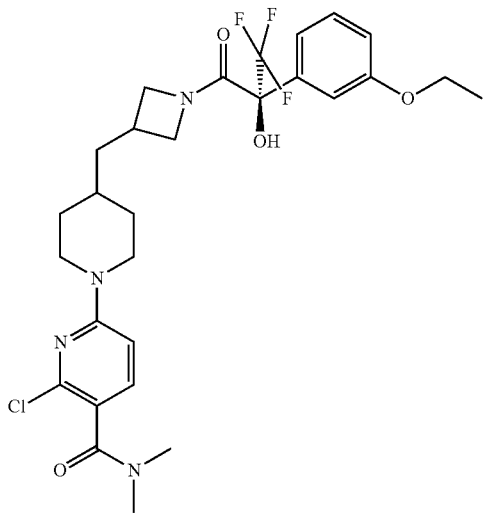 | 2-chloro-6-[4-({1-[(2R)-2-(3-ethoxyphenyl)-3,3,3-trifluoro-2-hydroxypropanoyl]azetidin-3-yl}methyl)piperidin-1-yl]-N,N-dimethylpyridine-3-carboxamide | Calc'd 583.2, found 583.4 |
| Example 7-45 | 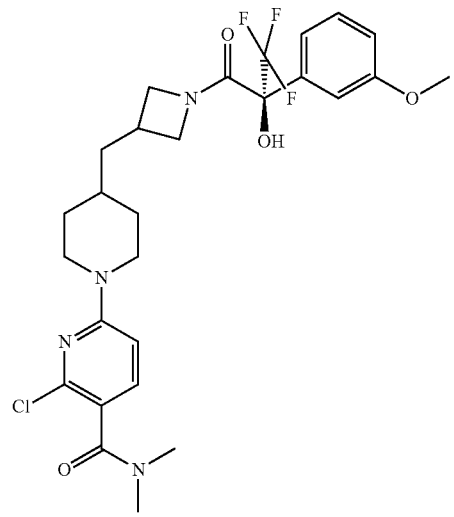 | 2-chloro-N,N-dimethyl-6-[4-({1-[(2R)-3,3,3-trifluoro-2-hydroxy-2-(3-methoxyphenyl)propanoyl]azetidin-3-yl}methyl)piperidin-1-yl]pyridine-3-carboxamide | Calc'd 569.2, found 569.4 |
| Example 7-46 | 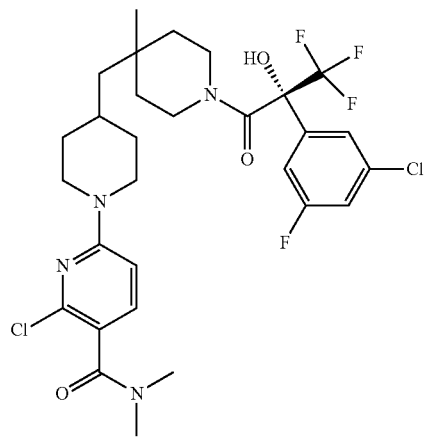 [SMILES: CN(C)C(=O)c1ccc(N2CCC(CC3(C)CCN(C(=O)[C@](O)(c4cc(F)cc(Cl)c4)C(F)(F)F)CC3)CC2)nc1Cl] | 2-chloro-6-[4-({1-[(2R)-2-(3-chloro-5-fluorophenyl)-3,3,3-trifluoro-2-hydroxypropanoyl]-4-methylpiperidin-4-yl}methyl)piperidin-1-yl]-N,N-dimethylpyridine-3-carboxamide | Calc'd 633.2, found 633.3 |

| Example | Structure | IUPAC Name | Exact Mass [M + H]+ |
|---|---|---|---|
| Example 7-47 | 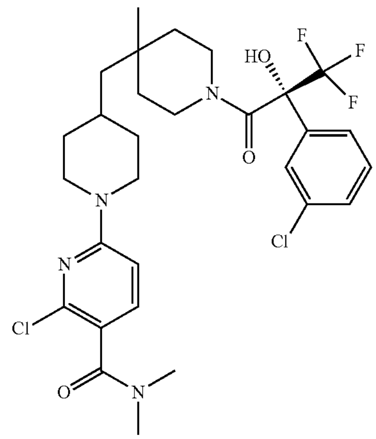 [SMILES: CN(C)C(=O)c1ccc(N2CCC(CC3(C)CCN(C(=O)[C@](O)(c4cccc(Cl)c4)C(F)(F)F)CC3)CC2)nc1Cl] | 2-chloro-6-[4-({1-[(2R)-2-(3-chlorophenyl)-3,3,3-trifluoro-2-hydroxypropanoyl]-4-methylpiperidin-4-yl}methyl)piperidin-1-yl]-N,N-dimethylpyridine-3-carboxamide | Calc'd 615.2, found 615.3 |
| Example 7-48 | 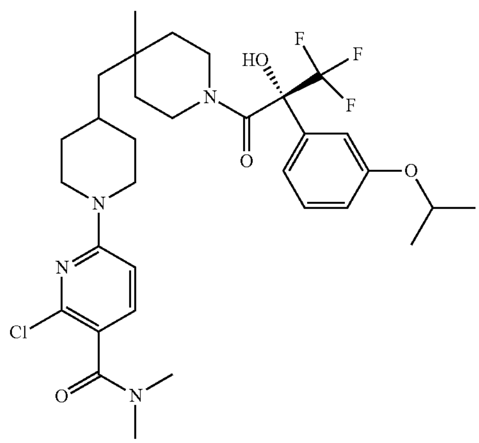 | 2-chloro-N,N-dimethyl-6-{4-[(4-methyl-1-{(2R)-3,3,3-trifluoro-2-hydroxy-2-[3-(1-methylethoxy)phenyl]propanoyl}piperidin-4-yl)methyl]piperidin-1-yl}pyridine-3-carboxamide | Calc'd 639.3, found 639.4 |
| Example 7-49 | 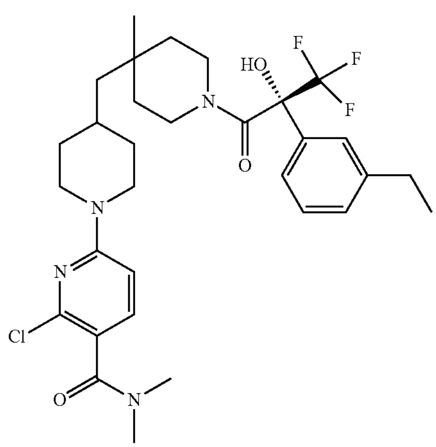 [SMILES: CCc1cccc([C@@](O)(C(=O)N2CCC(C)(CC3CCN(c4ccc(C(=O)N(C)C)c(Cl)n4)CC3)CC2)C(F)(F)F)c1] | 2-chloro-6-[4-({1-[(2R)-2-(3-ethylphenyl)-3,3,3-trifluoro-2-hydroxypropanoyl]-4-methylpiperidin-4-yl}methyl)piperidin-1-yl]-N,N-dimethylpyridine-3-carboxamide | Calc'd 609.3, found 609.4 |

-continued

| Example | Structure | IUPAC Name | Exact Mass [M + H]+ |
|---|---|---|---|
| Example 7-50 | 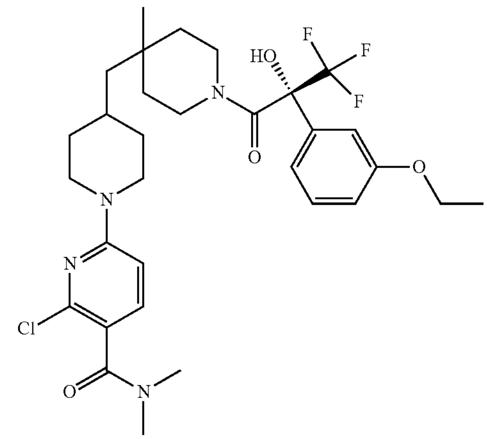 [SMILES: CCOc1cccc([C@@](O)(C(=O)N2CCC(C)(CC3CCN(c4ccc(C(=O)N(C)C)c(Cl)n4)CC3)CC2)C(F)(F)F)c1] | 2-chloro-6-[4-({1-[(2R)-2-(3-ethoxyphenyl)-3,3,3-trifluoro-2-hydroxypropanoyl]-4-methylpiperidin-4-yl}methyl)piperidin-1-yl]-N,N-dimethylpyridine-3-carboxamide | Calc'd 625.3, found 625.4 |
| Example 7-51 | 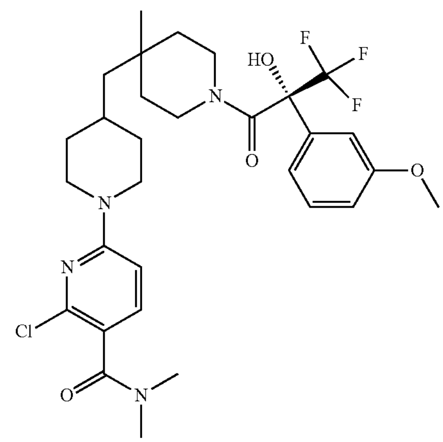 [SMILES: COc1cccc([C@@](O)(C(=O)N2CCC(C)(CC3CCN(c4ccc(C(=O)N(C)C)c(Cl)n4)CC3)CC2)C(F)(F)F)c1] | 2-chloro-N,N-dimethyl-6-[4-({4-methyl-1[(2R)-3,3,3-trifluoro-2-hydroxy-2-(3-methoxyphenyl)propanoyl]piperidin-4-yl}methyl)piperidin-1-yl]pyridine-3-carboxamide | Calc'd 611.3, found 611.4 |
| Example 7-52 | 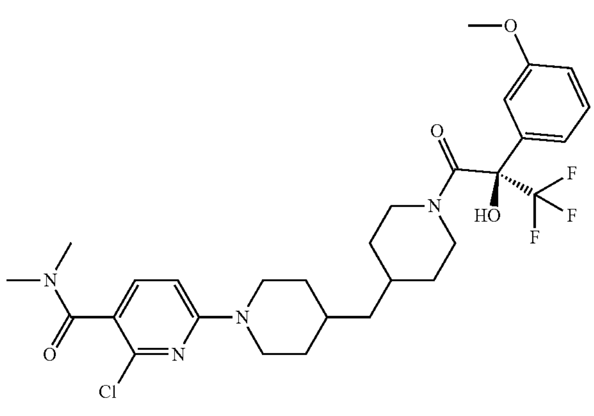 [SMILES: COc1cccc([C@@](O)(C(=O)N2CCC(CC3CCN(c4ccc(C(=O)N(C)C)c(Cl)n4)CC3)CC2)C(F)(F)F)c1] | 2-chloro-N,N-dimethyl-6-[4-({1-[(2R)-3,3,3-trifluoro-2-hydroxy-2-(3-methoxyphenyl)propanoyl]piperidin-4-yl}methyl)piperidin-1-yl]pyridine-3-carboxamide | Calc'd 597.2, found 597.2 |

| Example | IUPAC Name | Exact Mass [M + H]+ |
|---|---|---|
| Example 7-53 | 2-chloro-6-{4-[(1-{[1-(2-chlorophenyl)cyclopropyl]carbonyl}piperidin-4-yl)methyl]piperidin-1-yl}-N,N-dimethylpyridine-3-carboxamide | Calc'd 543.2, found 543.2 |
| Example 7-54 | 2-chloro-N,N-dimethyl-6-{4-[(1-{3,3,3-trifluoro-2-hydroxy-2-[3-(trifluoromethyl)phenyl]propanoyl}piperidin-4-yl)methyl]piperidin-1-yl}pyridine-3-carboxamide | Calc'd 635.2, found 635.2 |
| Example 7-55 | 2-chloro-N,N-dimethyl-6-[4-({1-[3,3,3-trifluoro-2-hydroxy-2-(3-methylphenyl)propanoyl]piperidin-4-yl}methyl)piperidin-1-yl]pyridine-3-carboxamide | Calc'd 581.3, found 581.2 |
| Example 7-56 | 2-chloro-N,N-dimethyl-6-{4-[(1-{[1-(2-methylphenyl)cyclobutyl]carbonyl}piperidin-4-yl)methyl]piperidin-1-yl}pyridine-3-carboxamide | Calc'd 537.3, found 537.3 |

-continued

| Example | Structure | IUPAC Name | Exact Mass [M + H]+ |
|---|---|---|---|
| Example 7-57 | 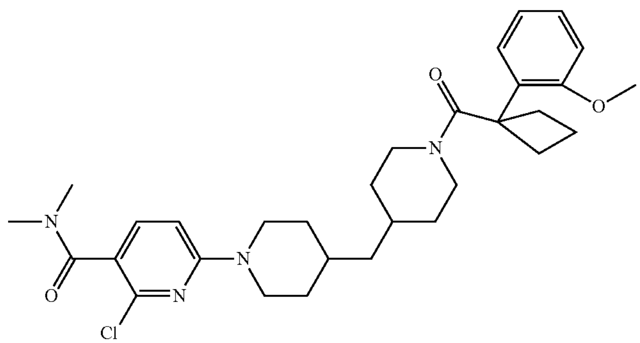 | 2-chloro-6-{4-[(1-{[1-(2-methoxyphenyl)cyclobutyl]carbonyl}piperidin-4-yl)methyl]piperidin-1-yl}-N,N-dimethylpyridine-3-carboxamide | Calc'd 553.3, found 553.3 |
| Example 7-58 | 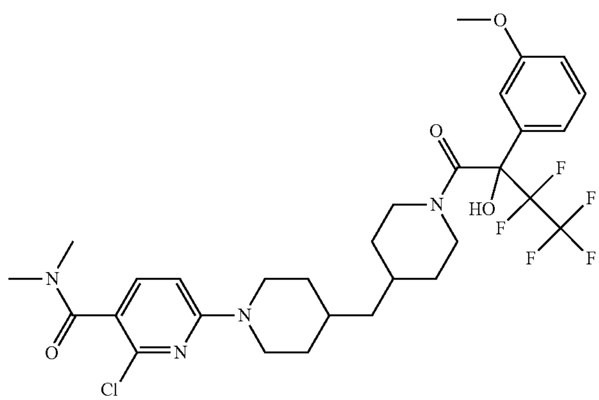 [SMILES: COc1cccc(C(O)(C(=O)N2CCC(CC3CCN(c4ccc(C(=O)N(C)C)c(Cl)n4)CC3)CC2)C(F)(F)C(F)(F)F)c1] | 2-chloro-N,N-dimethyl-6-[4-({1-[3,3,4,4,4-pentafluoro-2-hydroxy-2-(3-methoxyphenyl)butanoyl]piperidin-4-yl}methyl)piperidin-1-yl]pyridine-3-carboxamide | Calc'd 647.2, found 647.2 |
| Example 7-59 | 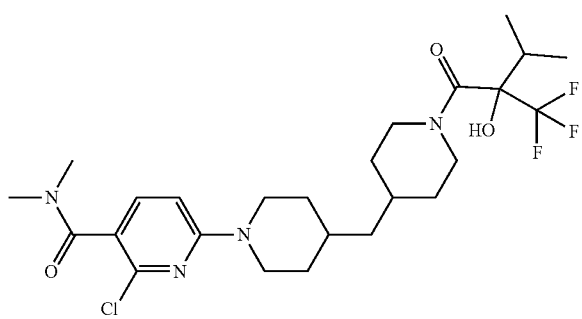 [SMILES: CC(C)C(O)(C(=O)N1CCC(CC2CCN(c3ccc(C(=O)N(C)C)c(Cl)n3)CC2)CC1)C(F)(F)F] | 2-chloro-6-[4-({1-[2-hydroxy-3-methyl-2-(trifluoromethyl)butanoyl]piperidin-4-yl}methyl)piperidin-1-yl]-N,N-dimethylpyridine-3-carboxamide | Calc'd 533.3, found 533.5 |
| Example 7-60 | 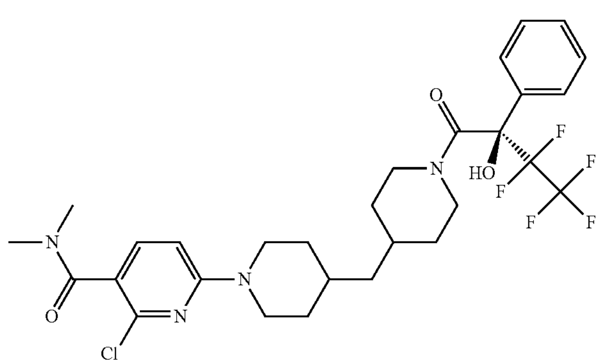 [SMILES: CN(C)C(=O)c1ccc(N2CCC(CC3CCN(C(=O)[C@](O)(c4ccccc4)C(F)(F)C(F)(F)F)CC3)CC2)nc1Cl] | 2-chloro-N,N-dimethyl-6-[4-({1-[(2R)-3,3,4,4,4-pentafluoro-2-hydroxy-2-phenylbutanoyl]piperidin-4-yl}methyl)piperidin-1-yl]pyridine-3-carboxamide | Calc'd 617.2, found 617.2 |

-continued

| Example | Structure | IUPAC Name | Exact Mass [M + H]+ |
|---|---|---|---|
| Example 7-61 | 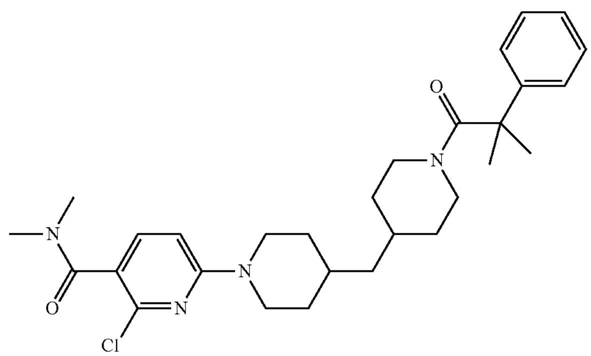 [SMILES: CN(C)C(=O)c1ccc(N2CCC(CC3CCN(C(=O)C(C)(C)c4ccccc4)CC3)CC2)nc1Cl] | 2-chloro-N,N-dimethyl-6-(4-{[1-(2-methyl-2-phenylpropanoyl)piperidin-4-yl]methyl}piperidin-1-yl)pyridine-3-carboxamide | Calc'd 511.3, found 511.2 |
| Example 7-62 | 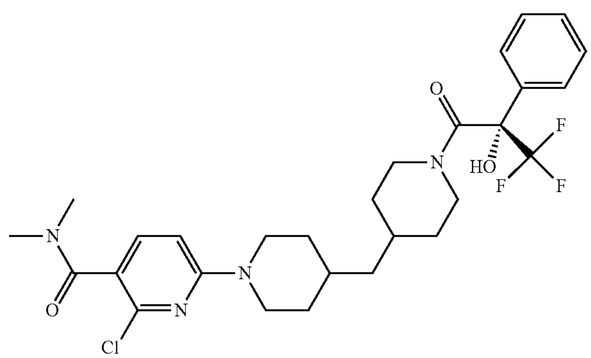 [SMILES: CN(C)C(=O)c1ccc(N2CCC(CC3CCN(C(=O)[C@@](O)(c4ccccc4)C(F)(F)F)CC3)CC2)nc1Cl] | 2-chloro-N,N-dimethyl-6-[4-({1-[(2S)-3,3,3-trifluoro-2-hydroxy-2-phenylpropanoyl]piperidin-4-yl}methyl)piperidin-1-yl]pyridine-3-carboxamide | Calc'd 567.2, found 567.2 |
| Example 7-63 | 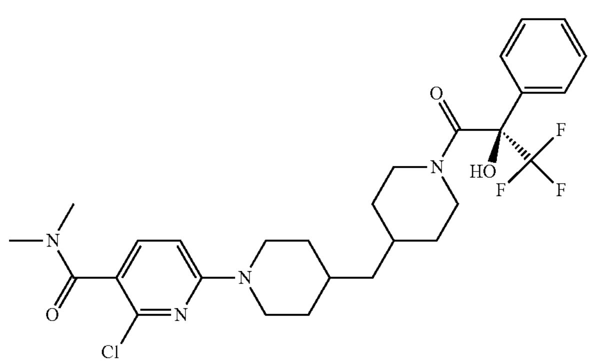 [SMILES: CN(C)C(=O)c1ccc(N2CCC(CC3CCN(C(=O)[C@](O)(c4ccccc4)C(F)(F)F)CC3)CC2)nc1Cl] | 2-chloro-N,N-dimethyl-6-[4-({1-[(2R)-3,3,3-trifluoro-2-hydroxy-2-phenylpropanoyl]piperidin-4-yl}methyl)piperidin-1-yl]pyridine-3-carboxamide | Calc'd 567.2, found 567.2 |
| Example 7-64 | 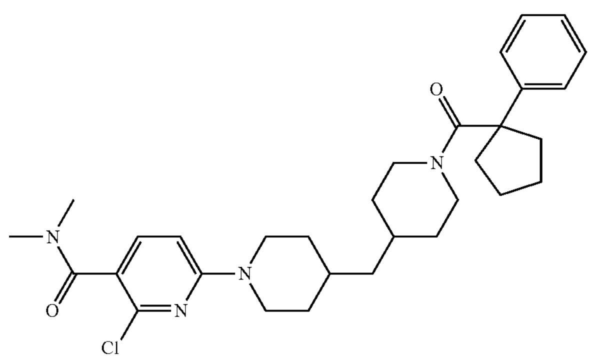 [SMILES: CN(C)C(=O)c1ccc(N2CCC(CC3CCN(C(=O)C4(c5ccccc5)CCCC4)CC3)CC2)nc1Cl] | 2-chloro-N,N-dimethyl-6-[4-({1-[(1-phenylcyclopentyl)carbonyl]piperidin-4-yl}methyl)piperidin-1-yl]pyridine-3-carboxamide | Calc'd 537.3, found 537.3 |

-continued

| Example | Structure | IUPAC Name | Exact Mass [M + H]+ |
|---|---|---|---|
| Example 7-65 | 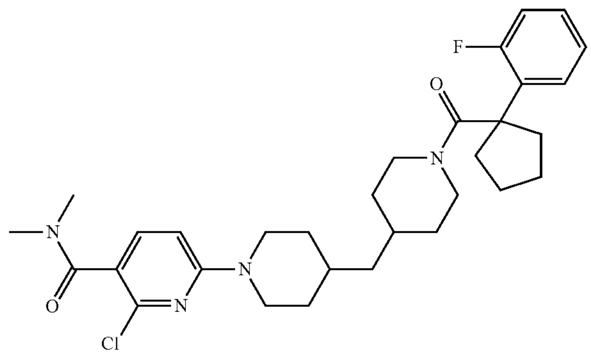 [SMILES: CN(C)C(=O)c1ccc(N2CCC(CC3CCN(C(=O)C4(c5ccccc5F)CCCC4)CC3)CC2)nc1Cl] | 2-chloro-6-{4-[(1-{[1-(2-fluorophenyl)cyclopentyl]carbonyl}piperidin-4-yl)methyl]piperidin-1-yl}-N,N-dimethylpyridine-3-carboxamide | Calc'd 555.3, found 555.2 |
| Example 7-66 | 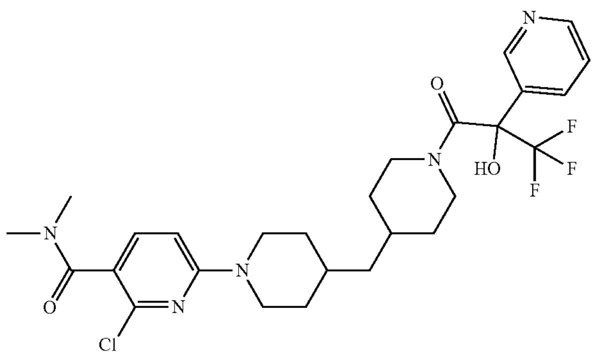 [SMILES: CN(C)C(=O)c1ccc(N2CCC(CC3CCN(C(=O)C(O)(c4cccnc4)C(F)(F)F)CC3)CC2)nc1Cl] | 2-chloro-N,N-dimethyl-6-(4-{[1-(3,3,3-trifluoro-2-hydroxy-2-pyridin-3-ylpropanoyl)piperidin-4-yl]methyl}piperidin-1-yl)pyridine-3-carboxamide | Calc'd 568.2, found 568.2 |
| Example 7-67 | 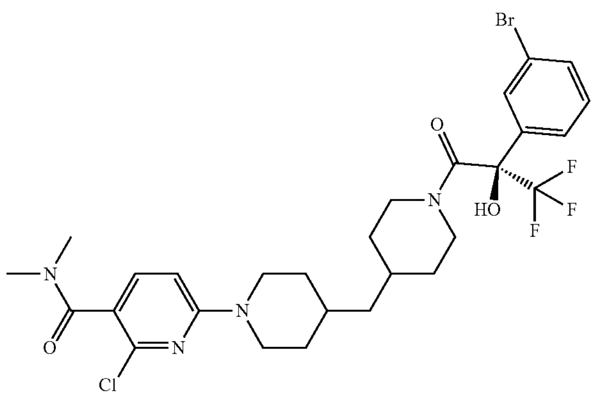 [SMILES: CN(C)C(=O)c1ccc(N2CCC(CC3CCN(C(=O)[C@](O)(c4cccc(Cl)c4)C(F)(F)F)CC3)CC2)nc1Cl] | 6-[4-({1-[(2R)-2-(3-bromophenyl)-3,3,3-trifluoro-2-hydroxypropanoyl]piperidin-4-yl}methyl)piperidin-1-yl]-2-chloro-N,N-dimethylpyridine-3-carboxamide | Calc'd 645.1, found 645.3 |
| Example 7-68 | 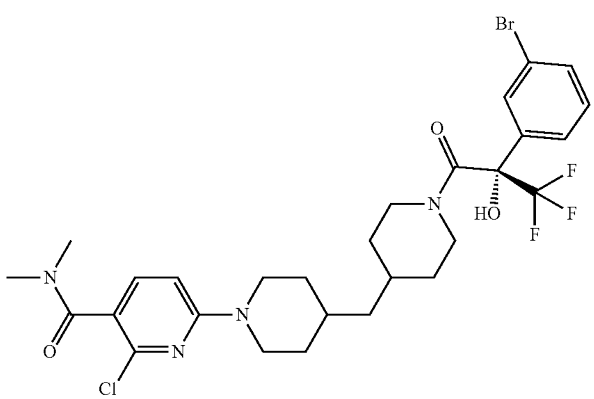 [SMILES: CN(C)C(=O)c1ccc(N2CCC(CC3CCN(C(=O)[C@@](O)(c4cccc(Cl)c4)C(F)(F)F)CC3)CC2)nc1Cl] | 6-[4-({1-[(2S)-2-(3-bromophenyl)-3,3,3-trifluoro-2-hydroxypropanoyl]piperidin-4-yl}methyl)piperidin-1-yl]-2-chloro-N,N-dimethylpyridine-3-carboxamide | Calc'd 645.1, found 645.3 |

| Example | Structure | IUPAC Name | Exact Mass [M + H]+ |
|---|---|---|---|
| Example 7-69 | 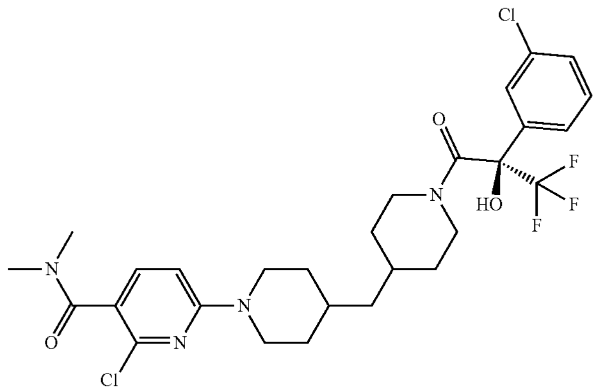 | 2-chloro-6-[4-({1-[(2R)-2-(3-chlorophenyl)-3,3,3-trifluoro-2-hydroxypropanoyl]piperidin-4-yl}methyl)piperidin-1-yl]-N,N-dimethylpyridine-3-carboxamide | Calc'd 601.2, found 601.2 |
| Example 7-70 | 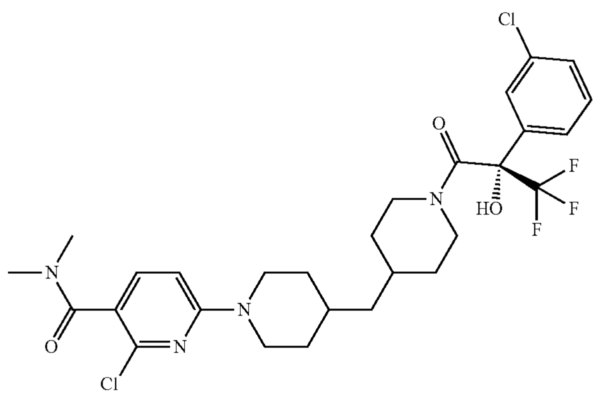 | 2-chloro-6-[4-({1-[(2S)-2-(3-chlorophenyl)-3,3,3-trifluoro-2-hydroxypropanoyl]piperidin-4-yl}methyl)piperidin-1-yl]-N,N-dimethyl-pyridine-3-carboxamide | Calc'd 601.2, found 601.2 |
| Example 7-71 | 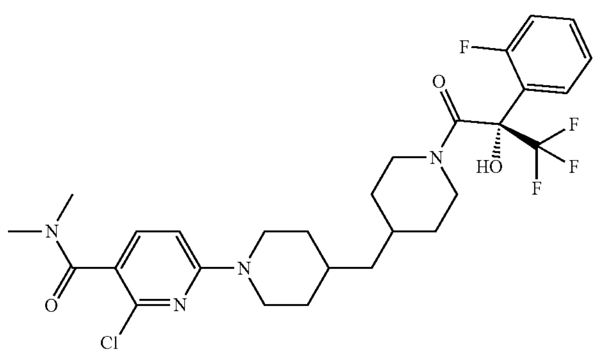 [SMILES: CN(C)C(=O)c1ccc(N2CCC(CC3CCN(C(=O)[C@@](O)(c4ccccc4F)C(F)(F)F)CC3)CC2)nc1Cl] | 2-chloro-N,N-dimethyl-6-[4-({1-[(2S)-3,3,3-trifluoro-2-(2-fluorophenyl)-2-hydroxypropanoyl]piperidin-4-yl}methyl)piperidin-1-yl]pyridine-3-carboxamide | Calc'd 585.2, found 585.2 |
| Example 7-72 | 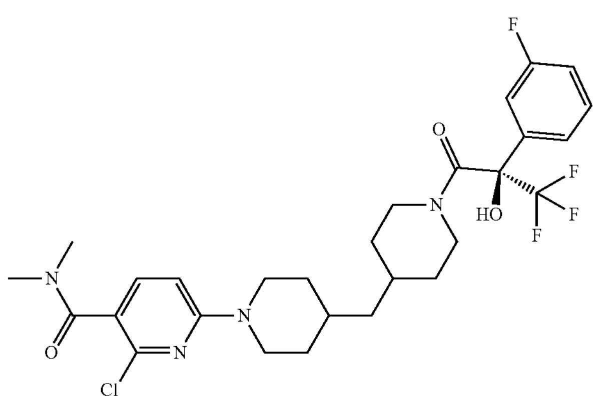 [SMILES: CN(C)C(=O)c1ccc(N2CCC(CC3CCN(C(=O)[C@](O)(c4cccc(F)c4)C(F)(F)F)CC3)CC2)nc1Cl] | 2-chloro-N,N-dimethyl-6-[4-({1-[(2R)-3,3,3-trifluoro-2-(3-fluorophenyl)-2-hydroxypropanoyl]piperidin-4-yl}methyl)piperidin-1-yl]pyridine-3-carboxamide | Calc'd 585.2, found 585.2 |

-continued

| Example | Structure | IUPAC Name | Exact Mass [M + H]+ |
|---|---|---|---|
| Example 7-73 | 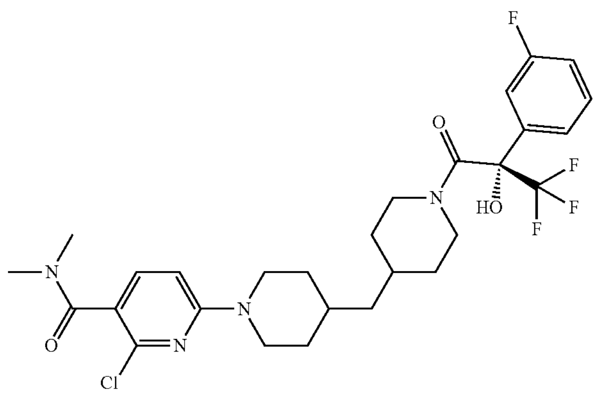 [SMILES: CN(C)C(=O)c1ccc(N2CCC(CC3CCN(C(=O)[C@@](O)(c4cccc(F)c4)C(F)(F)F)CC3)CC2)nc1Cl] | 2-chloro-N,N-dimethyl-6-[4-({1-[(2S)-3,3,3-trifluoro-2-(3-fluorophenyl)-2-hydroxypropanoyl]piperidin-4-yl}methyl)piperidin-1-yl]pyridine-3-carboxamide | Calc'd 585.2, found 585.2 |
| Example 7-74 | 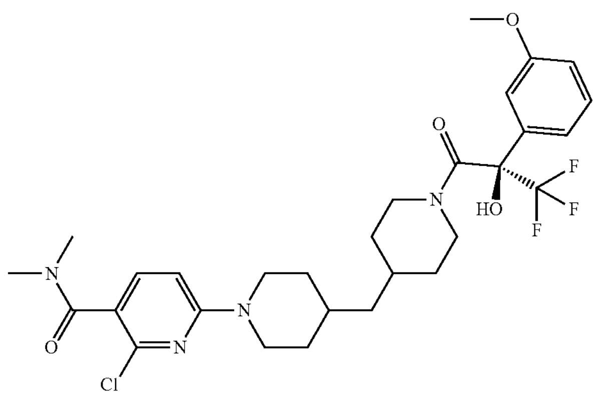 [SMILES: COc1cccc([C@@](O)(C(=O)N2CCC(CC3CCN(c4ccc(C(=O)N(C)C)c(Cl)n4)CC3)CC2)C(F)(F)F)c1] | 2-chloro-N,N-dimethyl-6-[4-({1-[(2R)-3,3,3-trifluoro-2-hydroxy-2-(3-methoxyphenyl)propanoyl]piperidin-4-yl}methyl)piperidin-1-yl]pyridine-3-carboxamide | Calc'd 597.2, found 597.5 |
| Example 7-75 | 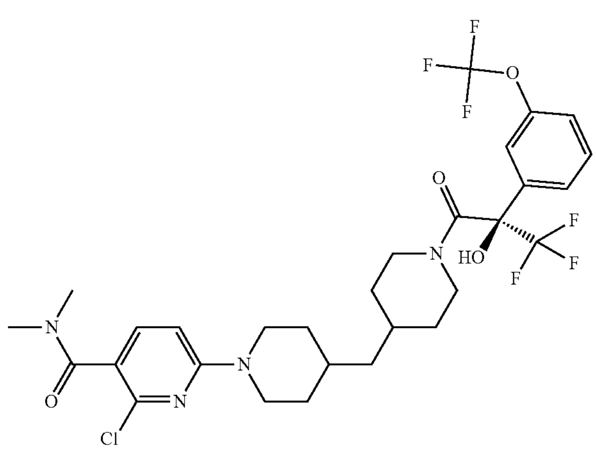 [SMILES: CN(C)C(=O)c1ccc(N2CCC(CC3CCN(C(=O)[C@](O)(c4cccc(OC(F)(F)F)c4)C(F)(F)F)CC3)CC2)nc1Cl] | 2-chloro-N,N-dimethyl-6-{4-[(1-{(2R)-3,3,3-trifluoro-2-hydroxy-2-[3-(trifluoromethoxy)phenyl]propanoyl}piperidin-4-yl)methyl]piperidin-1-yl}pyridine-3-carboxamide | Calc'd 651.2, found 651.2 |

-continued

| Example | Structure | IUPAC Name | Exact Mass [M + H]+ |
|---|---|---|---|
| Example 7-76 | 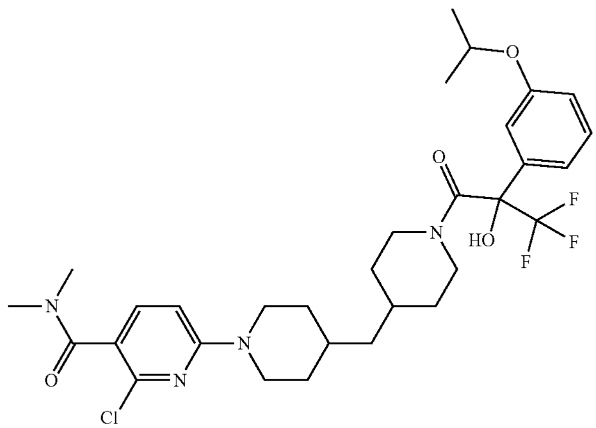 [SMILES: CC(C)Oc1cccc(C(O)(C(=O)N2CCC(CC3CCN(c4ccc(C(=O)N(C)C)c(Cl)n4)CC3)CC2)C(F)(F)F)c1] | 2-chloro-N,N-dimethyl-6-{4-[(1-{3,3,3-trifluoro-2-hydroxy-2-[3-(1-methylethoxy)phenyl]propanoyl}piperidin-4-yl)methyl]piperidin-1-yl}pyridine-3-carboxamide | Calc'd 625.3, found 625.2 |
| Example 7-77 | 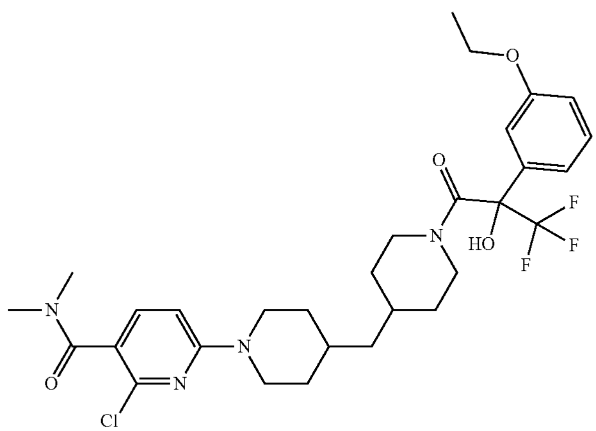 [SMILES: CCOc1cccc(C(O)(C(=O)N2CCC(CC3CCN(c4ccc(C(=O)N(C)C)c(Cl)n4)CC3)CC2)C(F)(F)F)c1] | 2-chloro-6-[4-({1-[2-(3-ethoxyphenyl)-3,3,3-trifluoro-2-hydroxypropanoyl]piperidin-4-yl}methyl)piperidin-1-yl]-N,N-dimethylpyridine-3-carboxamide | Calc'd 611.3, found 611.2 |
| Example 7-78 | 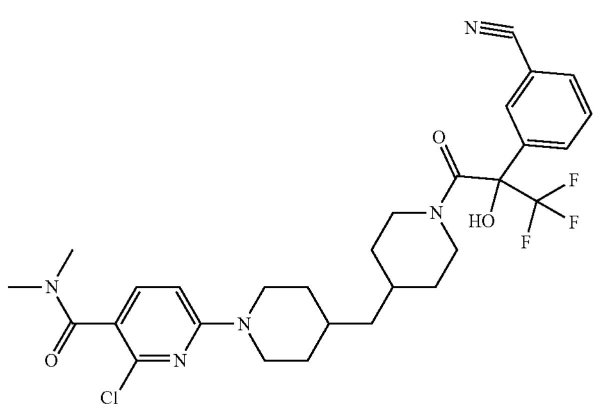 [SMILES: CN(C)C(=O)c1ccc(N2CCC(CC3CCN(C(=O)C(O)(c4cccc(C#N)c4)C(F)(F)F)CC3)CC2)nc1Cl] | 2-chloro-6-[4-({1-[2-(3-cyanophenyl)-3,3,3-trifluoro-2-hydroxypropanoyl]piperidin-4-yl}methyl)piperidin-1-yl]-N,N-dimethylpyridine-3-carboxamide | Calc'd 592.2, found 592.2 |

-continued

| Example | Structure | IUPAC Name | Exact Mass [M + H]+ |
|---|---|---|---|
| Example 7-79 | 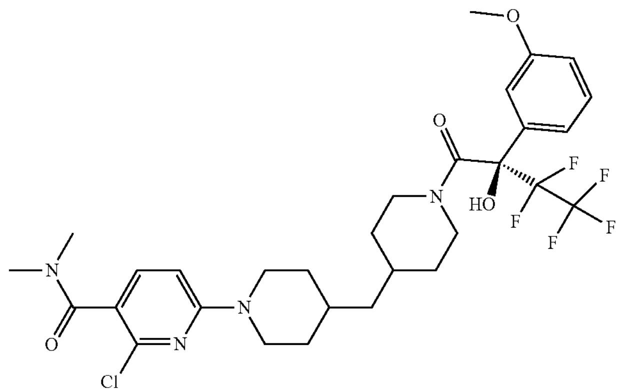 [SMILES: COc1cccc([C@@](O)(C(=O)N2CCC(CC3CCN(c4ccc(C(=O)N(C)C)c(Cl)n4)CC3)CC2)C(F)(F)C(F)(F)F)c1] | 2-chloro-N,N-dimethyl-6-[4-({1-[(2R)-3,3,4,4,4-pentafluoro-2-hydroxy-2-(3-methoxyphenyl)butanoyl]piperidin-4-yl}methyl)piperidin-1-yl]pyridine-3-carboxamide | Calc'd 647.2, found 647.2 |
| Example 7-80 | 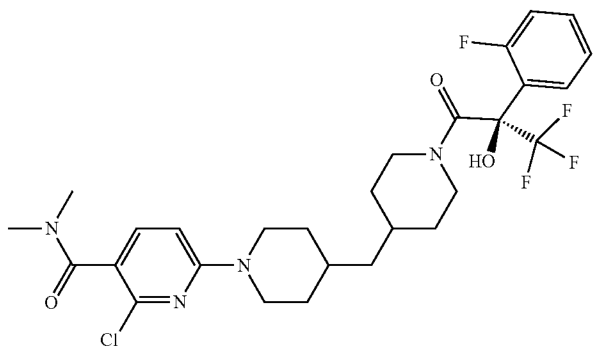 [SMILES: CN(C)C(=O)c1ccc(N2CCC(CC3CCN(C(=O)[C@](O)(c4ccccc4F)C(F)(F)F)CC3)CC2)nc1Cl] | 2-chloro-N,N-dimethyl-6-[4-({1-[(2R)-3,3,3-trifluoro-2-(2-fluorophenyl)-2-hydroxypropanoyl]piperidin-4-yl}methyl)piperidin-1-yl]pyridine-3-carboxamide | Calc'd 585.2, found 585.2 |
| Example 7-81 | 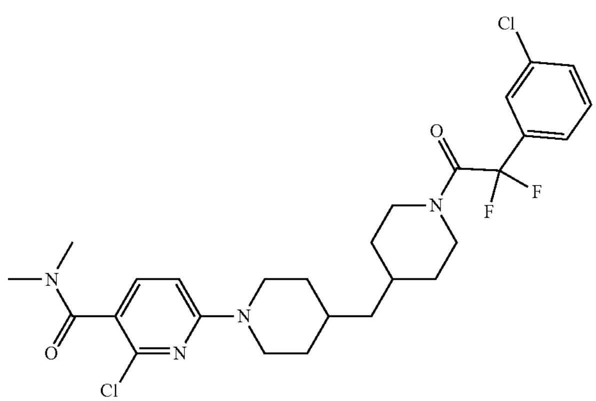 [SMILES: CN(C)C(=O)c1ccc(N2CCC(CC3CCN(C(=O)C(F)(F)c4cccc(Cl)c4)CC3)CC2)nc1Cl] | 2-chloro-6-[4-({1-[(3-chlorophenyl)(difluoro)acetyl]piperidin-4-yl}methyl)piperidin-1-yl]-N,N-dimethylpyridine-3-carboxamide | Calc'd 553.2, found 553.4 |
| Example 7-82 | 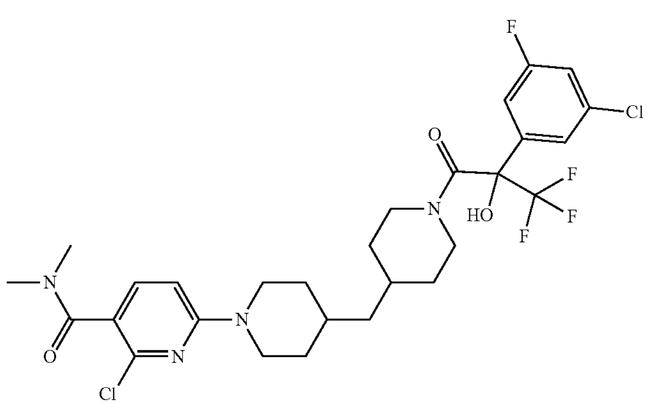 [SMILES: CN(C)C(=O)c1ccc(N2CCC(CC3CCN(C(=O)C(O)(c4cc(F)cc(Cl)c4)C(F)(F)F)CC3)CC2)nc1Cl] | 2-chloro-6-[4-({1-[2-(3,5-difluorophenyl)-3,3,3-trifluoro-2-hydroxypropanoyl]piperidin-4-yl}methyl)piperidin-1-yl]-N,N-dimethylpyridine-3-carboxamide | Calc'd 603.2, found 603.5 |

| Example | Structure | IUPAC Name | Exact Mass [M + H]+ |
|---|---|---|---|
| Example 7-83 | 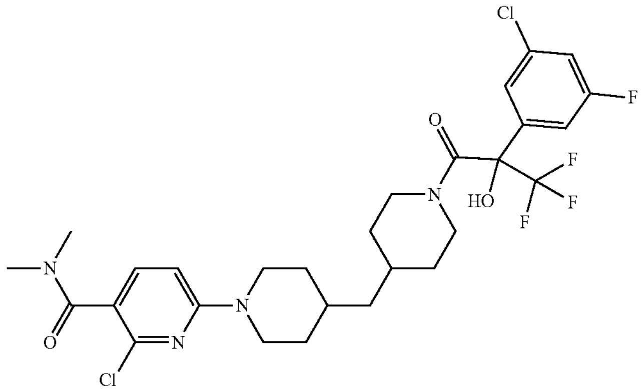 [SMILES: CN(C)C(=O)c1ccc(N2CCC(CC3CCN(C(=O)C(O)(c4cc(F)cc(Cl)c4)C(F)(F)F)CC3)CC2)nc1Cl] | 2-chloro-6-[4-({1-[2-(3,5-dichlorophenyl)-3,3,3-trifluoro-2-hydroxypropanoyl]piperidin-4-yl}methyl)piperidin-1-yl]-N,N-dimethylpyridine-3-carboxamide | Calc'd 635.2, found 635.4 |
| Example 7-84 | 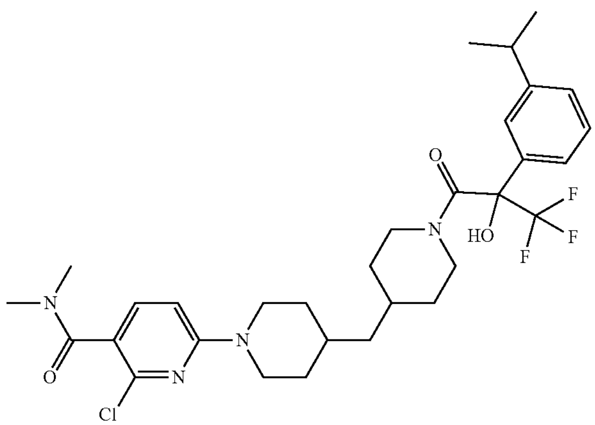 [SMILES: CC(C)c1cccc(C(O)(C(=O)N2CCC(CC3CCN(c4ccc(C(=O)N(C)C)c(Cl)n4)CC3)CC2)C(F)(F)F)c1] | 2-chloro-N,N-dimethyl-6-{4-[(1-{3,3,3-trifluoro-2-hydroxy-2-[3-(1-methylethyl)phenyl]propanoyl}piperidin-4-yl)methyl]piperidin-1-yl}pyridine-3-carboxamide | Calc'd 609.3, found 609.5 |
| Example 7-85 | 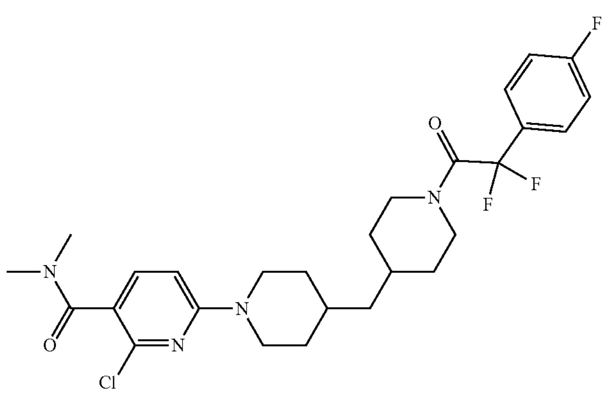 [SMILES: CN(C)C(=O)c1ccc(N2CCC(CC3CCN(C(=O)C(F)(F)c4ccc(F)cc4)CC3)CC2)nc1Cl] | 2-chloro-6-[4-({1-[difluoro(4-fluorophenyl)acetyl]piperidin-4-yl}methyl)piperidin-1-yl]-N,N-dimethylpyridine-3-carboxamide | Calc'd 537.2, found 537.5 |
| Example 7-86 | 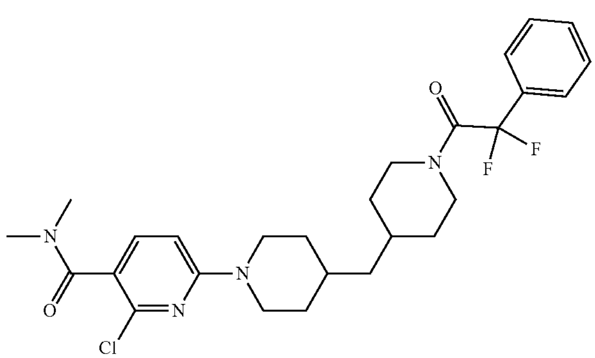 [SMILES: CN(C)C(=O)c1ccc(N2CCC(CC3CCN(C(=O)C(F)(F)c4ccccc4)CC3)CC2)nc1Cl] | 2-chloro-6-[4-({1-[difluoro(phenyl)acetyl]piperidin-4-yl}methyl)piperidin-1-yl]-N,N-dimethylpyridine-3-carboxamide | Calc'd 519.2, found 519.5 |

| Example | Structure | IUPAC Name | Exact Mass [M + H]+ |
|---|---|---|---|
| Example 7-87 | 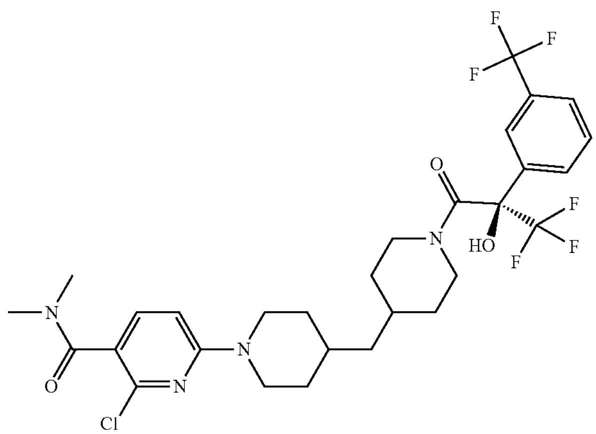 [SMILES: CN(C)C(=O)c1ccc(N2CCC(CC3CCN(C(=O)[C@](O)(c4cccc(C(F)(F)F)c4)C(F)(F)F)CC3)CC2)nc1Cl] | 2-chloro-N,N-dimethyl-6-{4-[(1-{(2R)-3,3,3-trifluoro-2-hydroxy-2-[3-(trifluoromethyl)phenyl]propanoyl}piperidin-4-yl)methyl]piperidin-1-yl}pyridine-3-carboxamide | Calc'd 635.2, found 635.5 |
| Example 7-88 | 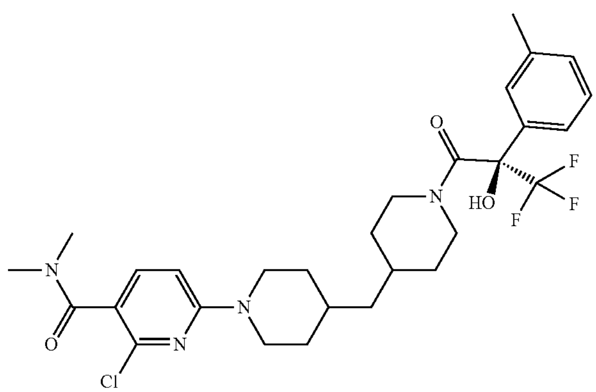 [SMILES: Cc1cccc([C@@](O)(C(=O)N2CCC(CC3CCN(c4ccc(C(=O)N(C)C)c(Cl)n4)CC3)CC2)C(F)(F)F)c1] | 2-chloro-N,N-dimethyl-6-[4-({1-[(2R)-3,3,3-trifluoro-2-hydroxy-2-(3-methylphenyl)propanoyl]piperidin-4-yl}methyl)piperidin-1-yl]pyridine-3-carboxamide | Calc'd 581.3, found 581.5 |
| Example 7-89 | 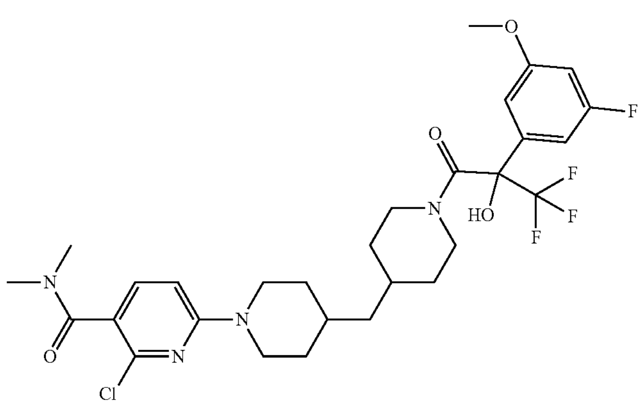 [SMILES: COc1cc(F)cc(C(O)(C(=O)N2CCC(CC3CCN(c4ccc(C(=O)N(C)C)c(Cl)n4)CC3)CC2)C(F)(F)F)c1] | 2-chloro-N,N-dimethyl-6-[4-({1-[3,3,3-trifluoro-2-(3-fluoro-5-methoxyphenyl)-2-hydroxypropanoyl]piperidin-4-yl}methyl)piperidin-1-yl]pyridine-3-carboxamide | Calc'd 615.2, found 615.5 |

| Example | Structure | IUPAC Name | Exact Mass [M + H]+ |
|---|---|---|---|
| Example 7-90 | 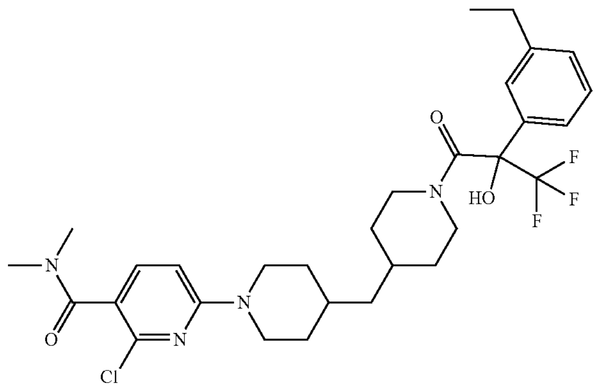 [SMILES: CCc1cccc(C(O)(C(=O)N2CCC(CC3CCN(c4ccc(C(=O)N(C)C)c(Cl)n4)CC3)CC2)C(F)(F)F)c1] | 2-chloro-6-[4-({1-[2-(3-ethylphenyl)-3,3,3-trifluoro-2-hydroxypropanoyl]piperidin-4-yl}methyl)piperidin-1-yl]-N,N-dimethylpyridine-3-carboxamide | Calc'd 595.3, found 595.5 |
| Example 7-91 | 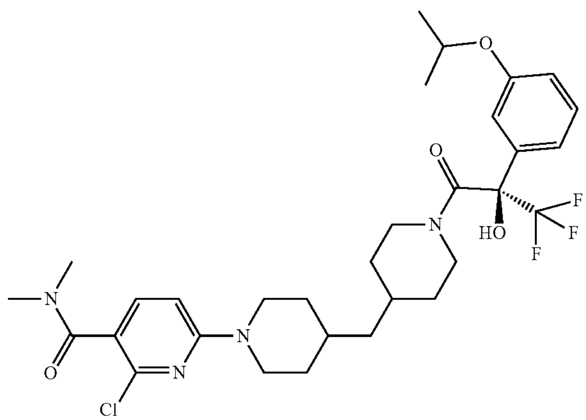 [SMILES: CC(C)Oc1cccc([C@@](O)(C(=O)N2CCC(CC3CCN(c4ccc(C(=O)N(C)C)c(Cl)n4)CC3)CC2)C(F)(F)F)c1] | 2-chloro-N,N-dimethyl-6-{4-[(1-{(2R)-3,3,3-trifluoro-2-hydroxy-2-[3-(1-methylethoxy)phenyl]propanoyl}piperidin-4-yl)methyl]piperidin-1-yl}pyridine-3-carboxamide | Calc'd 625.3, found 625.5 |
| Example 7-92 | 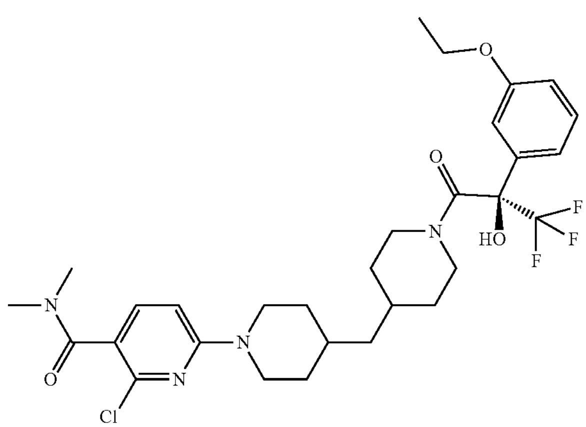 [SMILES: CCOc1cccc([C@@](O)(C(=O)N2CCC(CC3CCN(c4ccc(C(=O)N(C)C)c(Cl)n4)CC3)CC2)C(F)(F)F)c1] | 2-chloro-6-[4-({1-[(2R)-2-(3-ethoxyphenyl)-3,3,3-trifluoro-2-hydroxypropanoyl]piperidin-4-yl}methyl)piperidin-1-yl]-N,N-dimethylpyridine-3-carboxamide | Calc'd 611.3, found 611.5 |

-continued

| Example | Structure | IUPAC Name | Exact Mass [M + H]+ |
|---|---|---|---|
| Example 7-93 | 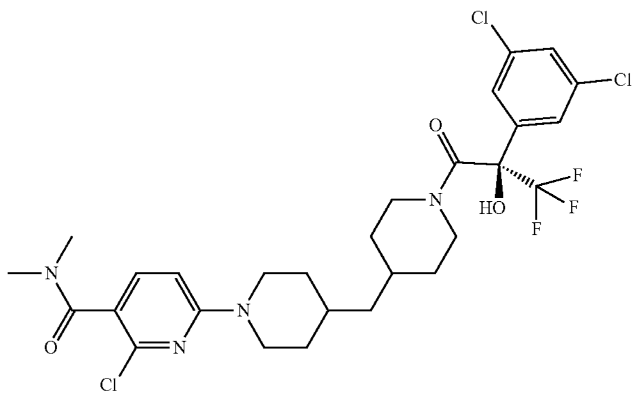 [SMILES: CN(C)C(=O)c1ccc(N2CCC(CC3CCN(C(=O)[C@](O)(c4cc(Cl)cc(Cl)c4)C(F)(F)F)CC3)CC2)nc1Cl] | 2-chloro-6-[4-({1-[(2R)-2-(3,5-dichlorophenyl)-3,3,3-trifluoro-2-hydroxypropanoyl]piperidin-4-yl}methyl)piperidin-1-yl]-N,N-dimethylpyridine-3-carboxamide | Calc'd 635.2, found 635.4 |
| Example 7-94 | 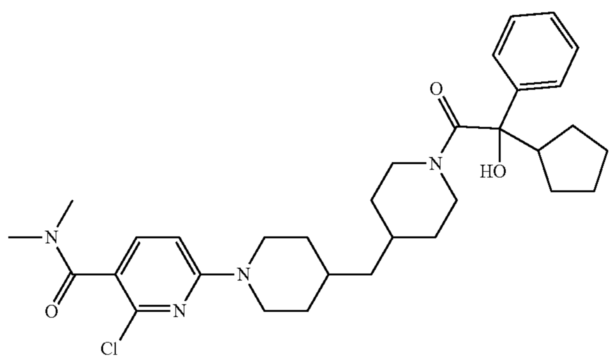 [SMILES: CN(C)C(=O)c1ccc(N2CCC(CC3CCN(C(=O)C(O)(c4ccccc4)C4CCCC4)CC3)CC2)nc1Cl] | 2-chloro-6-[4-({1-[cyclopentyl(hydroxy)phenylacetyl]piperidin-4-yl}methyl)piperidin-1-yl]-N,N-dimethylpyridine-3-carboxamide | Calc'd 567.3, found 567.5 |
| Example 7-95 | 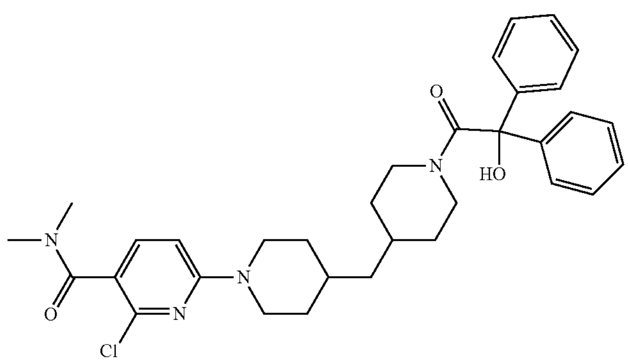 [SMILES: CN(C)C(=O)c1ccc(N2CCC(CC3CCN(C(=O)C(O)(c4ccccc4)c4ccccc4)CC3)CC2)nc1Cl] | 2-chloro-6-[4-({1-[hydroxy(diphenyl)acetyl]piperidin-4-yl}methyl)piperidin-1-yl]-N,N-dimethylpyridine-3-carboxamide | Calc'd 575.3, found 575.5 |
| Example 7-96 | 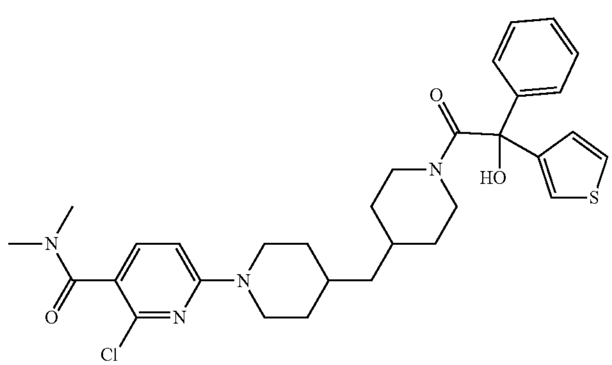 [SMILES: CN(C)C(=O)c1ccc(N2CCC(CC3CCN(C(=O)C(O)(c4ccccc4)c4ccsc4)CC3)CC2)nc1Cl] | 2-chloro-6-[4-({1-[hydroxy(phenyl)thiophen-3-ylacetyl]piperidin-4-yl}methyl)piperidin-1-yl]-N,N-dimethylpyridine-3-carboxamide | Calc'd 581.2, found 581.5 |

-continued

| Example | Structure | IUPAC Name | Exact Mass [M + H]+ |
|---|---|---|---|
| Example 7-97 | 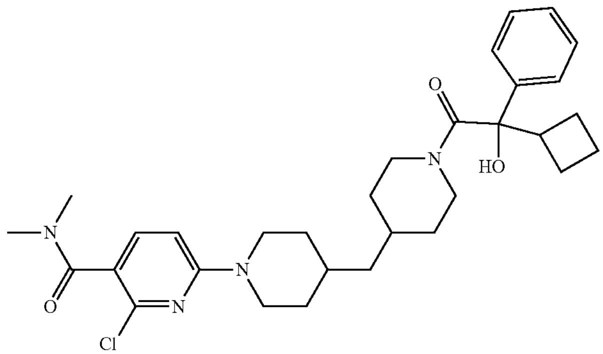 [SMILES: CN(C)C(=O)c1ccc(N2CCC(CC3CCN(C(=O)C(O)(c4ccccc4)C4CCC4)CC3)CC2)nc1Cl] | 2-chloro-6-[4-({1-[cyclobutyl(hydroxy)phenylacetyl]piperidin-4-yl}methyl)piperidin-1-yl]-N,N-dimethylpyridine-3-carboxamide | Calc'd 553.3, found 553.5 |
| Example 7-98 | 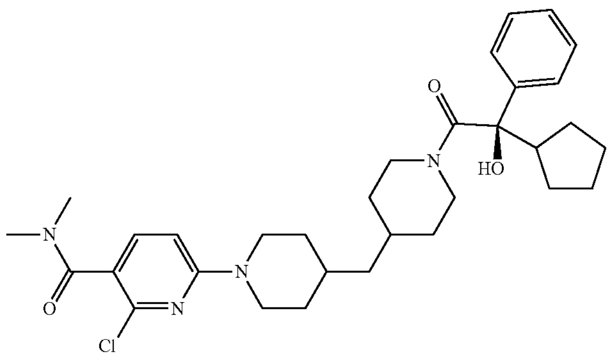 [SMILES: CN(C)C(=O)c1ccc(N2CCC(CC3CCN(C(=O)[C@](O)(c4ccccc4)C4CCCC4)CC3)CC2)nc1Cl] | 2-chloro-6-[4-({1-[(2R)-2-cyclopentyl-2-hydroxy-2-phenylacetyl]piperidin-4-yl}methyl)piperidin-1-yl]-N,N-dimethylpyridine-3-carboxamide | Calc'd 567.3, found 567.5 |
| Example 7-99 | 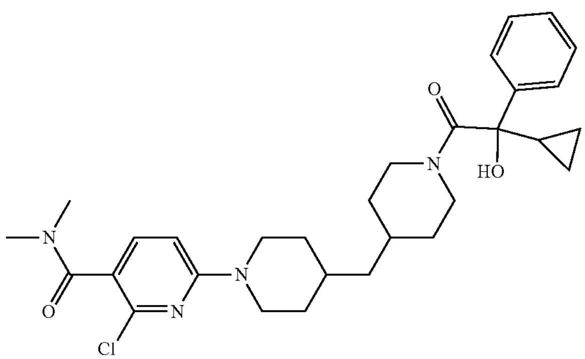 [SMILES: CN(C)C(=O)c1ccc(N2CCC(CC3CCN(C(=O)C(O)(c4ccccc4)C4CC4)CC3)CC2)nc1Cl] | 2-chloro-6-[4-({1-[cyclopropyl(hydroxy)phenylacetyl]piperidin-4-yl}methyl)piperidin-1-yl]-N,N-dimethylpyridine-3-carboxamide | Calc'd 539.3, found 539.5 |
| Example 7-100 | 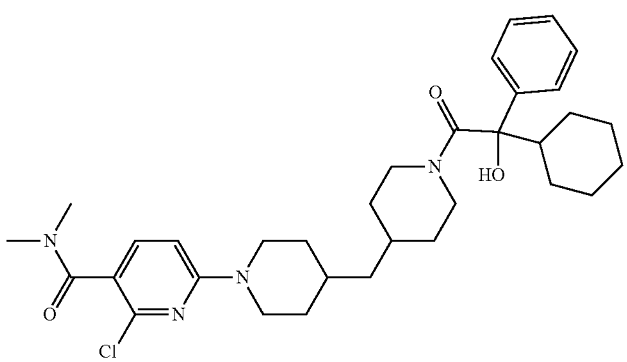 [SMILES: CN(C)C(=O)c1ccc(N2CCC(CC3CCN(C(=O)C(O)(c4ccccc4)C4CCCCC4)CC3)CC2)nc1Cl] | 2-chloro-6-[4-({1-[cyclohexyl(hydroxy)phenylacetyl]piperidin-4-yl}methyl)piperidin-1-yl]-N,N-dimethylpyridine-3-carboxamide | Calc'd 581.3, found 581.6 |

| Example | Structure | IUPAC Name | Exact Mass [M + H]+ |
|---|---|---|---|
| Example 7-101 | 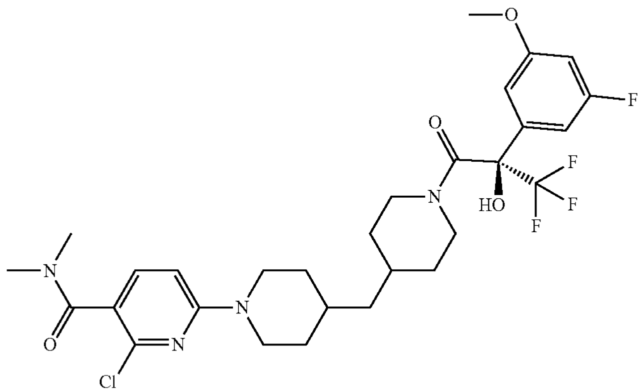 [SMILES: COc1cc(F)cc([C@@](O)(C(=O)N2CCC(CC3CCN(c4ccc(C(=O)N(C)C)c(Cl)n4)CC3)CC2)C(F)(F)F)c1] | 2-chloro-N,N-dimethyl-6-[4-({1-[(2R)-3,3,3-trifluoro-2-(3-fluoro-5-methoxyphenyl)-2-hydroxypropanoyl]piperidin-4-yl}methyl)piperidin-1-yl]pyridine-3-carboxamide | Cal'd 615.2, found 615.4 |
| Example 7-102 | 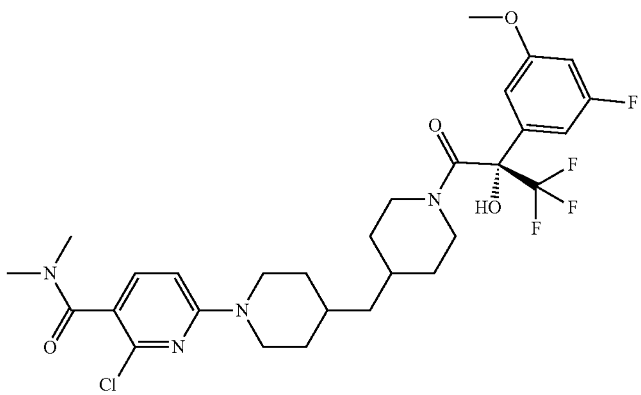 [SMILES: COc1cc(F)cc([C@](O)(C(=O)N2CCC(CC3CCN(c4ccc(C(=O)N(C)C)c(Cl)n4)CC3)CC2)C(F)(F)F)c1] | 2-chloro-N,N-dimethyl-6-[4-({1-[(2S)-3,3,3-trifluoro-2-(3-fluoro-5-methoxyphenyl)-2-hydroxypropanoyl]piperidin-4-yl}methyl)piperidin-1-yl]pyridine-3-carboxamide | Calc'd 615.2, found 615.4 |
| Example 7-103 | 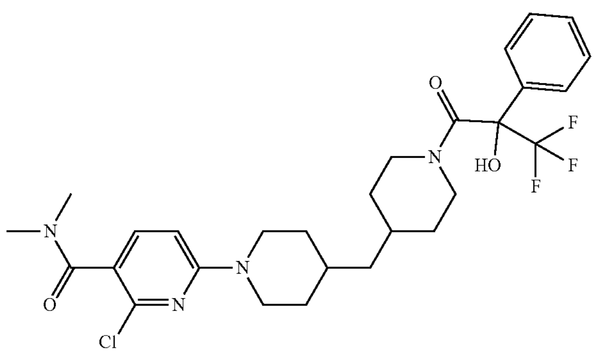 [SMILES: CN(C)C(=O)c1ccc(N2CCC(CC3CCN(C(=O)C(O)(c4ccccc4)C(F)(F)F)CC3)CC2)nc1Cl] | 6-(4-{[1-(2-amino-3,3,3-trifluoro-2-phenylpropanoyl)piperidin-4-yl]methyl}piperidin-1-yl)-2-chloro-N,N-dimethylpyridine-3-carboxamide | Calc'd 566.3, found 566.4 |
| Example 7-104 | 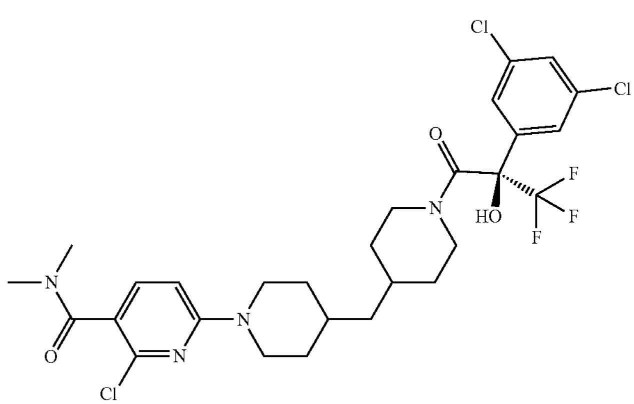 [SMILES: CN(C)C(=O)c1ccc(N2CCC(CC3CCN(C(=O)[C@](O)(c4cc(Cl)cc(Cl)c4)C(F)(F)F)CC3)CC2)nc1Cl] | 2-chloro-6-[4-({1-[(2R)-2-(3,5-dichlorophenyl)-3,3,3-trifluoro-2-hydroxypropanoyl]piperidin-4-yl}methyl)piperidin-1-yl]-N,N-dimethylpyridine-3-carboxamide | Calc'd 635.2, found 635.4 |

| Example | Structure | IUPAC Name | Exact Mass [M + H]+ |
|---|---|---|---|
| Example 7-105 | 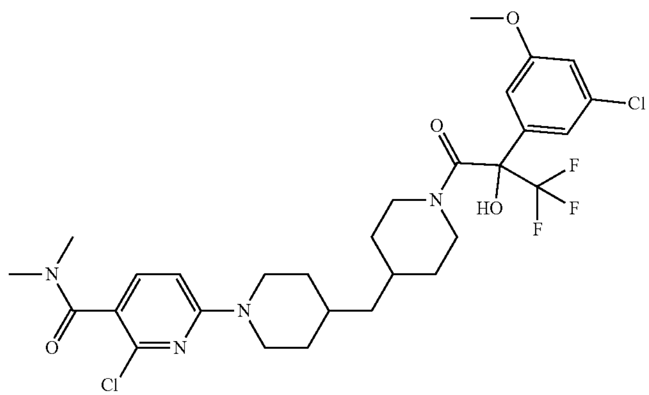 [SMILES: COc1cc(Cl)cc(C(O)(C(=O)N2CCC(CC3CCN(c4ccc(C(=O)N(C)C)c(Cl)n4)CC3)CC2)C(F)(F)F)c1] | 2-chloro-6-[4-({1-[2-(3-chloro-5-methoxyphenyl)-3,3,3-trifluoro-2-hydroxypropanoyl]piperidin-4-yl}methyl)piperidin-1-yl]-N,N-dimethylpyridine-3-carboxamide | Calc'd 631.2, found 631.4 |
| Example 7-106 | 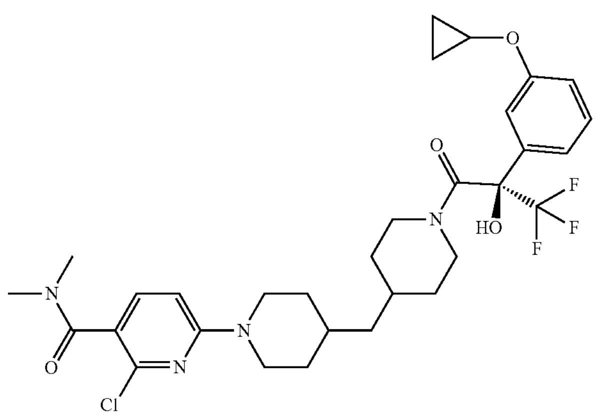 [SMILES: CN(C)C(=O)c1ccc(N2CCC(CC3CCN(C(=O)[C@](O)(c4cccc(OC5CC5)c4)C(F)(F)F)CC3)CC2)nc1Cl] | 2-chloro-6-{4-[(1-{(2R)-2-[3-(cyclopropyloxy)phenyl]-3,3,3-trifluoro-2-hydroxypropanoyl}piperidin-4-yl)methyl]piperidin-1-yl}-N,N-dimethylpyridine-3-carboxamide | Calc'd 623.3, found 623.5 |
| Example 7-107 | 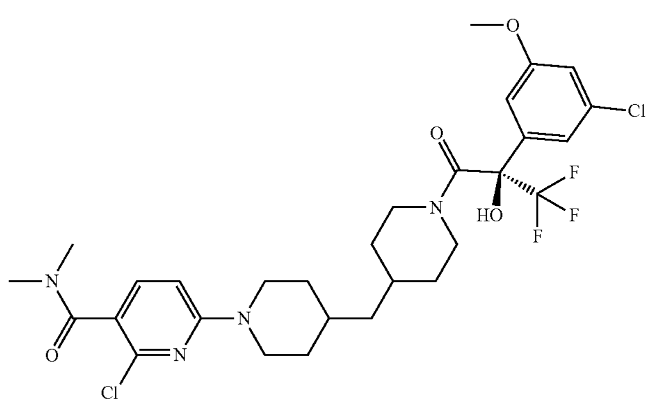 [SMILES: COc1cc(Cl)cc([C@@](O)(C(=O)N2CCC(CC3CCN(c4ccc(C(=O)N(C)C)c(Cl)n4)CC3)CC2)C(F)(F)F)c1] | 2-chloro-6-[4-({1-[(2R)-2-(3-chloro-5-methoxyphenyl)-3,3,3-trifluoro-2-hydroxypropanoyl]piperidin-4-yl}methyl)piperidin-1-yl]-N,N-dimethylpyridine-3-carboxamide | Calc'd 631.2, found 631.5 |

-continued

| Example | Structure | IUPAC Name | Exact Mass [M + H]+ |
|---|---|---|---|
| Example 7-108 | 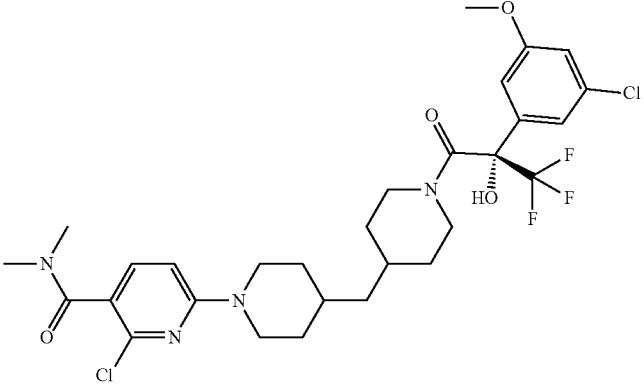 [SMILES: COc1cc(Cl)cc([C@](O)(C(=O)N2CCC(CC3CCN(c4ccc(C(=O)N(C)C)c(Cl)n4)CC3)CC2)C(F)(F)F)c1] | 2-chloro-6-[4-({1-[(2S)-2-(3-chloro-5-methoxyphenyl)-3,3,3-trifluoro-2-hydroxypropanoyl]piperidin-4-yl}methyl)piperidin-1-yl]-N,N-dimethylpyridine-3-carboxamide | Calc'd 631.2, found 631.4 |
| Example 7-109 | 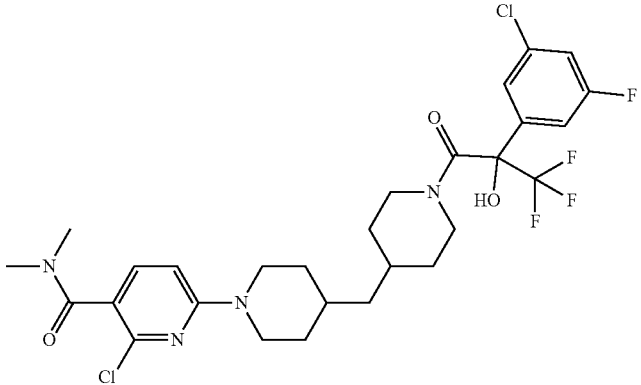 [SMILES: CN(C)C(=O)c1ccc(N2CCC(CC3CCN(C(=O)C(O)(c4cc(F)cc(Cl)c4)C(F)(F)F)CC3)CC2)nc1Cl] | 2-chloro-6-[4-({1-[2-(3-chloro-5-fluorophenyl)-3,3,3-trifluoro-2-hydroxypropanoyl]piperidin-4-yl}methyl)piperidin-1-yl]-N,N-dimethyl-pyridine-3-carboxamide | Calc'd 619.2, found 619.3 |
| Example 7-110 | 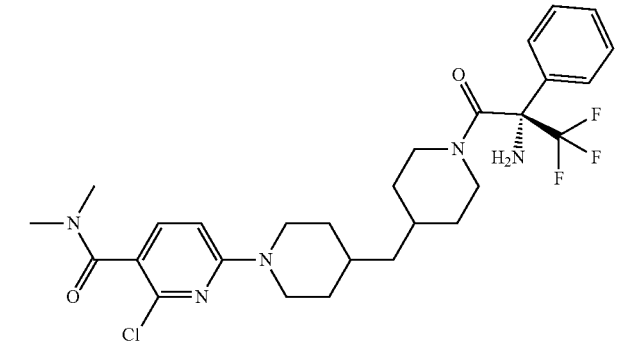 [SMILES: CN(C)C(=O)c1ccc(N2CCC(CC3CCN(C(=O)[C@@](N)(c4ccccc4)C(F)(F)F)CC3)CC2)nc1Cl] | 6-[4-({1-[(2S)-2-amino-3,3,3-trifluoro-2-phenylpropanoyl]piperidin-4-yl}methyl)piperidin-1-yl]-2-chloro-N,N-dimethylpyridine-3-carboxamide | Calc'd 566.3, found 566.4 |
| Example 7-111 | 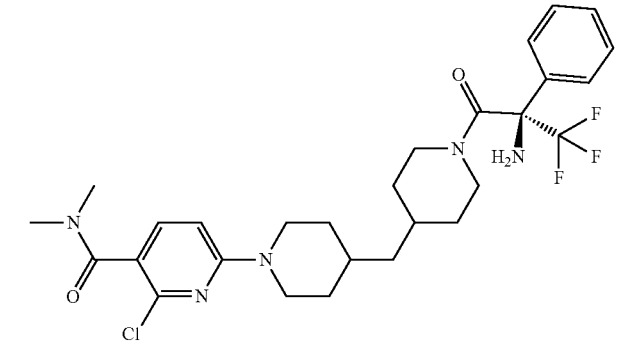 [SMILES: CN(C)C(=O)c1ccc(N2CCC(CC3CCN(C(=O)[C@](N)(c4ccccc4)C(F)(F)F)CC3)CC2)nc1Cl] | 6-[4-({1-[(2R)-2-amino-3,3,3-trifluoro-2-phenylpropanoyl]piperidin-4-yl}methyl)piperidin-1-yl]-2-chloro-N,N-dimethylpyridine-3-carboxamide | Calc'd 566.3, found 566.4 |

-continued

| Example | Structure | IUPAC Name | Exact Mass [M + H]+ |
|---|---|---|---|
| Example 7-112 | 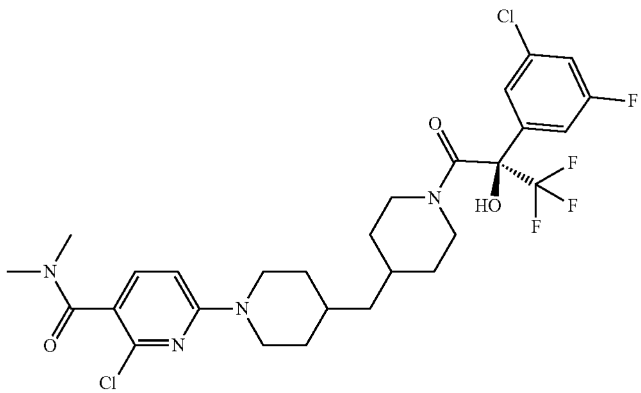 [SMILES: CN(C)C(=O)c1ccc(N2CCC(CC3CCN(C(=O)[C@](O)(c4cc(F)cc(Cl)c4)C(F)(F)F)CC3)CC2)nc1Cl] | 2-chloro-6-[4-({1-[(2R)-2-(3-chloro-5-fluorophenyl)-3,3,3-trifluoro-2-hydroxypropanoyl]piperidin-4-yl}methyl)piperidin-1-yl]-N,N-dimethylpyridine-3-carboxamide | Calc'd 619.2, found 619.3 |
| Example 7-113 | 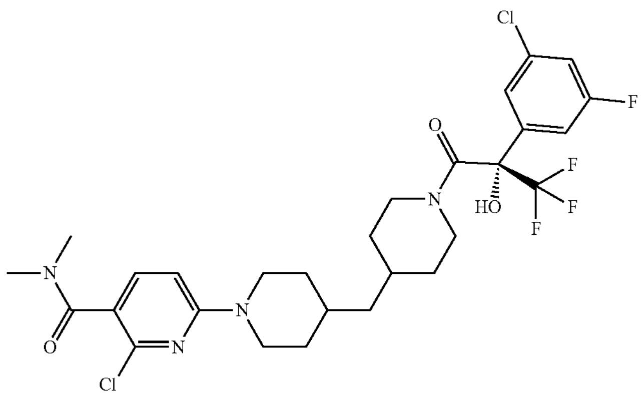 [SMILES: CN(C)C(=O)c1ccc(N2CCC(CC3CCN(C(=O)[C@@](O)(c4cc(F)cc(Cl)c4)C(F)(F)F)CC3)CC2)nc1Cl] | 2-chloro-6-[4-({1-[(2S)-2-(3-chloro-5-fluorophenyl)-3,3,3-trifluoro-2-hydroxypropanoyl]piperidin-4-yl}methyl)piperidin-1-yl]-N,N-dimethylpyridine-3-carboxamide | Calc'd 619.2, found 619.4 |
| Example 7-114 | 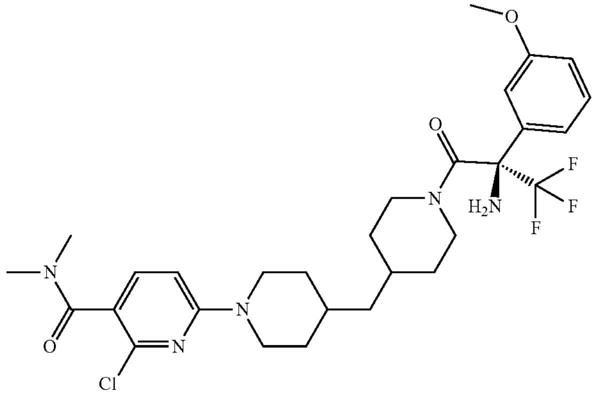 [SMILES: COc1cccc([C@@](N)(C(=O)N2CCC(CC3CCN(c4ccc(C(=O)N(C)C)c(Cl)n4)CC3)CC2)C(F)(F)F)c1] | 6-[4-({1-[(2R)-2-amino-3,3,3-trifluoro-2-(3-methoxyphenyl)propanoyl]piperidin-4-yl}methyl)piperidin-1-yl]-2-chloro-N,N-dimethylpyridine-3-carboxamide | Calc'd 596.3, found 596.4 |

-continued

| Example | Structure | IUPAC Name | Exact Mass [M + H]+ |
|---|---|---|---|
| Example 7-115 | 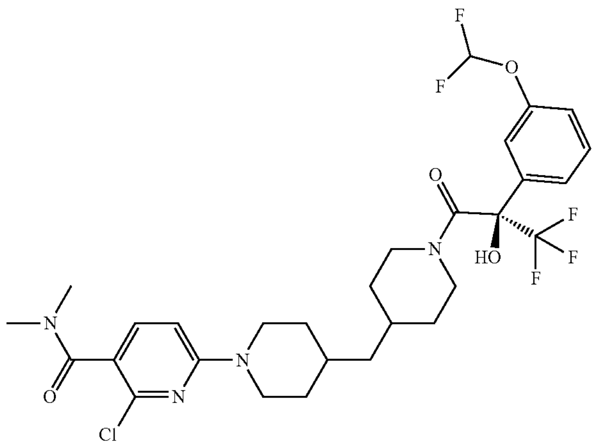 [SMILES: CN(C)C(=O)c1ccc(N2CCC(CC3CCN(C(=O)[C@](O)(c4cccc(OC(F)F)c4)C(F)(F)F)CC3)CC2)nc1Cl] | 2-chloro-6-{4-[(1-{(2R)-2-[3-(difluoromethoxy)phenyl]-3,3,3-trifluoro-2-hydroxypropanoyl}piperidin-4-yl)methyl]piperidin-1-yl}-N,N-dimethylpyridine-3-carboxamide | Calc'd 633.2 found 633.4 |
| Example 7-116 | 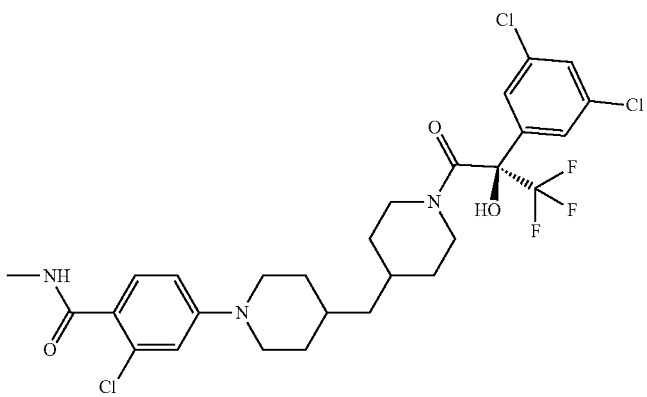 [SMILES: CNC(=O)c1ccc(N2CCC(CC3CCN(C(=O)[C@](O)(c4cc(Cl)cc(Cl)c4)C(F)(F)F)CC3)CC2)cc1Cl] | 2-chloro-4-[4-({1-[(2R)-2-(3,5-dichlorophenyl)-3,3,3-trifluoro-2-hydroxypropanoyl]piperidin-4-yl}methyl)piperidin-1-yl]-N-methylbenzamide | Calc'd 620.1, found 620.3 |
| Example 7-117 | 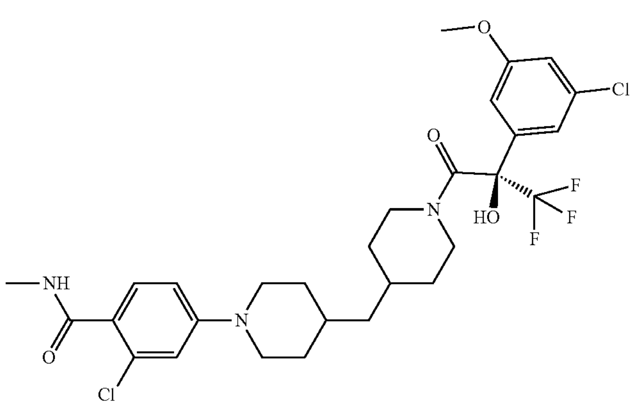 [SMILES: CNC(=O)c1ccc(N2CCC(CC3CCN(C(=O)[C@](O)(c4cc(Cl)cc(OC)c4)C(F)(F)F)CC3)CC2)cc1Cl] | 2-chloro-4-[4-({1-[(2R)-2-(3-chloro-5-methoxyphenyl)-3,3,3-trifluoro-2-hydroxypropanoyl]piperidin-4-yl}methyl)piperidin-1-yl]-N-methylbenzamide | Calc'd 616.2, found 616.4 |

| Example | Structure | IUPAC Name | Exact Mass [M + H]+ |
|---|---|---|---|
| Example 7-118 | 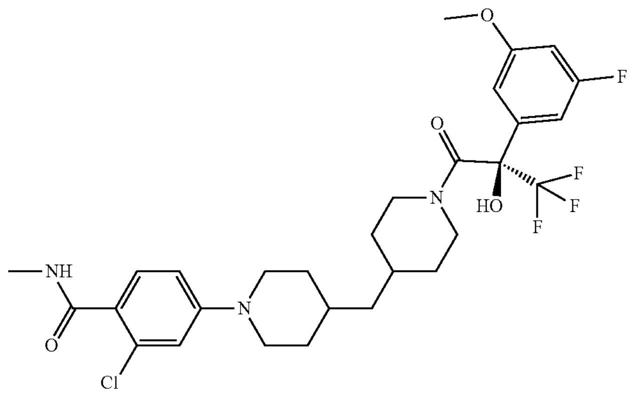 [SMILES: CNC(=O)c1ccc(N2CCC(CC3CCN(C(=O)[C@](O)(c4cc(F)cc(OC)c4)C(F)(F)F)CC3)CC2)cc1Cl] | 2-chloro-N-methyl-4-[4-({1-[(2R)-3,3,3-trifluoro-2-(3-fluoro-5-methoxyphenyl)-2-hydroxypropanoyl]piperidin-4-yl}methyl)piperidin-1-yl]benzamide | Calc'd 600.2, found 600.4 |
| Example 7-119 | 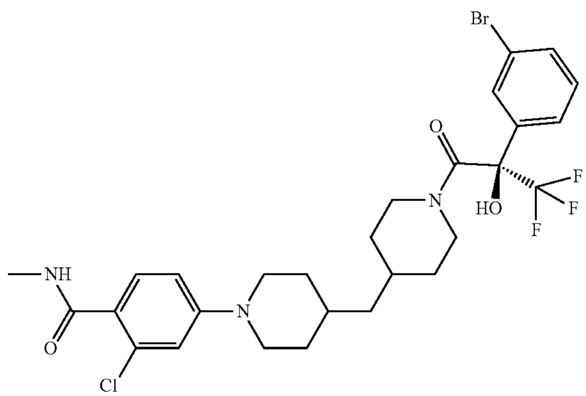 [SMILES: CNC(=O)c1ccc(N2CCC(CC3CCN(C(=O)[C@](O)(c4cccc(Br)c4)C(F)(F)F)CC3)CC2)cc1Cl] | 4-[4-({1-[(2R)-2-(3-bromophenyl)-3,3,3-trifluoro-2-hydroxypropanoyl]piperidin-4-yl}methyl)piperidin-1-yl]-2-chloro-N-methyl-benzamide | Calc'd 630.1, found 630.3 |
| Example 7-120 | 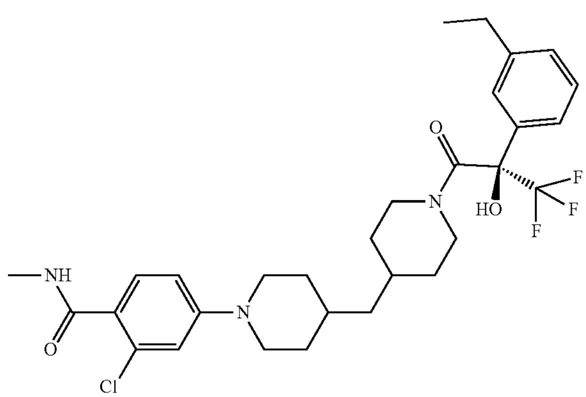 [SMILES: CCc1cccc([C@@](O)(C(=O)N2CCC(CC3CCN(c4ccc(C(=O)NC)c(Cl)c4)CC3)CC2)C(F)(F)F)c1] | 2-chloro-4-[4-({1-[(2R)-2-(3-ethylphenyl)-3,3,3-trifluoro-2-hydroxypropanoyl]piperidin-4-yl}methyl)piperidin-1-yl]-N-methylbenzamide | Calc'd 580.3, found 580.4 |

| Example | Structure | IUPAC Name | Exact Mass [M + H]+ |
|---|---|---|---|
| Example 7-121 | 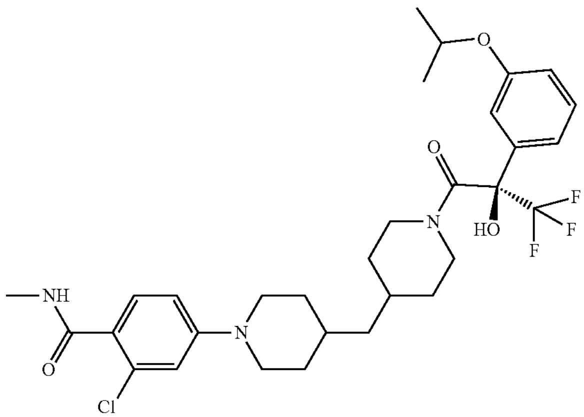 [SMILES: CNC(=O)c1ccc(N2CCC(CC3CCN(C(=O)[C@](O)(c4cccc(OC(C)C)c4)C(F)(F)F)CC3)CC2)cc1Cl] | 2-chloro-N-methyl-4-{4-[(1-{(2R)-3,3,3-trifluoro-2-hydroxy-2-[3-(1-methylethoxy)phenyl]propanoyl}piperidin-4-yl)methyl]piperidin-1-yl}benzamide | Calc'd 610.3, found 610.5 |
| Example 7-122 | 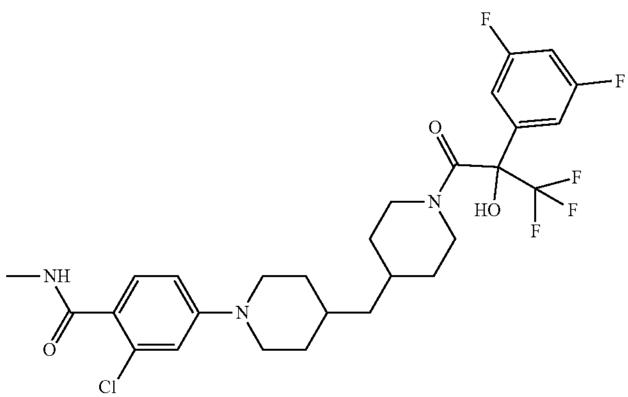 [SMILES: CNC(=O)c1ccc(N2CCC(CC3CCN(C(=O)C(O)(c4cc(F)cc(F)c4)C(F)(F)F)CC3)CC2)cc1Cl] | 2-chloro-4-[4-({1-[2-(3,5-difluorophenyl)-3,3,3-trifluoro-2-hydroxypropanoyl]piperidin-4-yl}methyl)piperidin-1-yl]-N-methylbenzamide | Calc'd 588.2, found 588.4 |
| Example 7-123 | 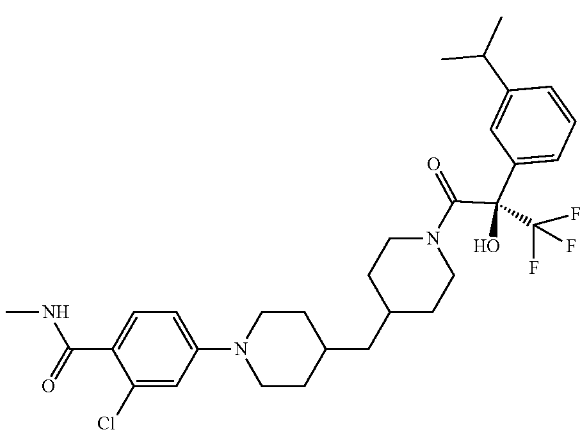 [SMILES: CNC(=O)c1ccc(N2CCC(CC3CCN(C(=O)[C@](O)(c4cccc(C(C)C)c4)C(F)(F)F)CC3)CC2)cc1Cl] | 2-chloro-N-methyl-4-{4-[(1-{(2R)-3,3,3-trifluoro-2-hydroxy-2-[3-(1-methylethyl)phenyl]propanoyl}piperidin-4-yl)methyl]piperidin-1-yl}benzamide | Calc'd 594.3 found 594.5 |

| Example | Structure | IUPAC Name | Exact Mass [M + H]+ |
|---|---|---|---|
| Example 7-124 | 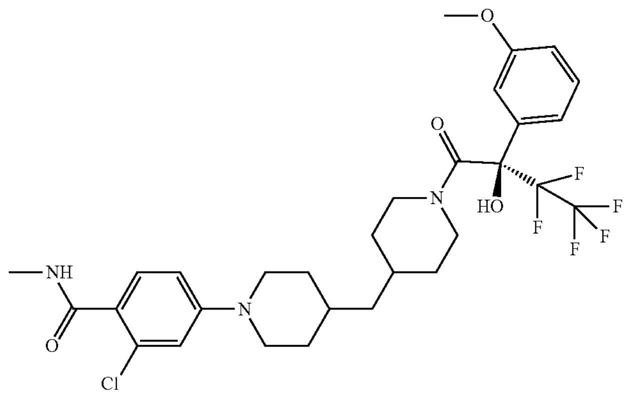 [SMILES: CNC(=O)c1ccc(N2CCC(CC3CCN(C(=O)[C@](O)(c4cccc(OC)c4)C(F)(F)C(F)(F)F)CC3)CC2)cc1Cl] | 2-chloro-N-methyl-4-[4-({1-[(2R)-3,3,4,4,4-pentafluoro-2-hydroxy-2-(3-methoxyphenyl)butanoyl]piperidin-4-yl}methyl)piperidin-1-yl]benzamide | Calc'd 632.2, found 632.4 |
| Example 7-125 | 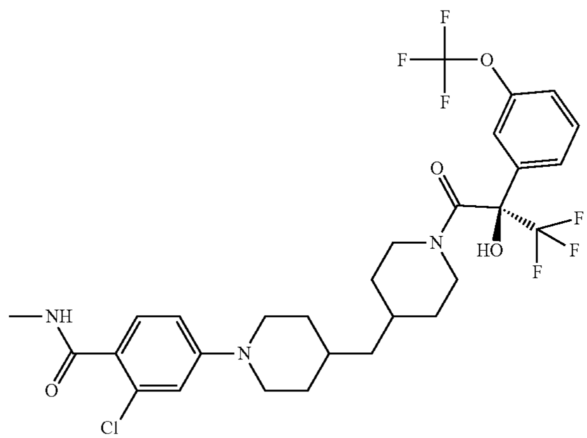 [SMILES: CNC(=O)c1ccc(N2CCC(CC3CCN(C(=O)[C@](O)(c4cccc(OC(F)(F)F)c4)C(F)(F)F)CC3)CC2)cc1Cl] | 2-chloro-N-methyl-4-{4-[(1-{(2R)-3,3,3-trifluoro-2-hydroxy-2-[3-(trifluoromethoxy)phenyl]propanoyl}piperidin-4-yl)methyl]piperidin-1-yl}benzamide | Calc'd 636.2, found 636.4 |
| Example 7-126 | 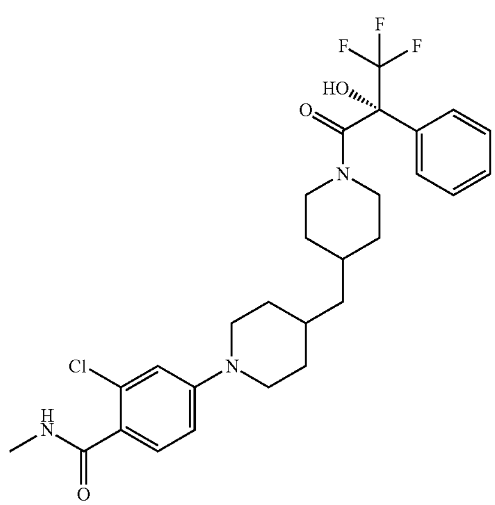 [SMILES: CNC(=O)c1ccc(N2CCC(CC3CCN(C(=O)[C@](O)(c4ccccc4)C(F)(F)F)CC3)CC2)cc1Cl] | 2-chloro-N-methyl-4-[4-({1-[(2R)-3,3,3-trifluoro-2-hydroxy-2-phenylpropanoyl]piperidin-4-yl}methyl)piperidin-1-yl]benzamide | Calc'd 552.2, found 552.4 |

| Example | Structure | IUPAC Name | Exact Mass [M + H]+ |
|---|---|---|---|
| Example 7-127 | 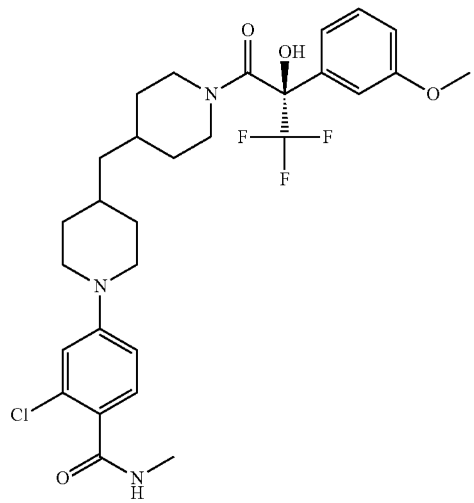 | 2-chloro-N-methyl-4-[4-({1-[(2R)-3,3,3-trifluoro-2-hydroxy-2-(3-methoxyphenyl)propanoyl]piperidin-4-yl}methyl)piperidin-1-yl]benzamide | Calc'd 582.2, found 582.4 |
| Example 7-128 | 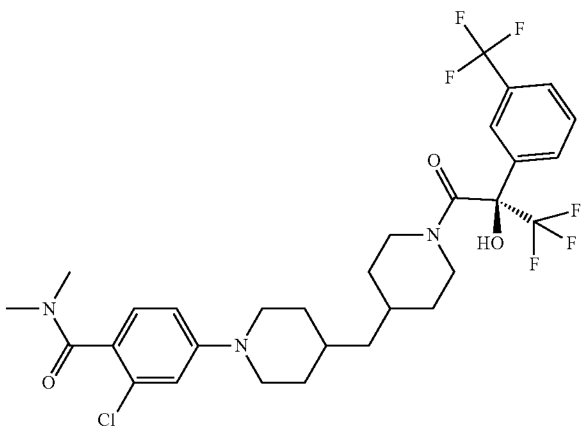 [SMILES: CN(C)C(=O)c1ccc(N2CCC(CC3CCN(C(=O)[C@](O)(c4cccc(C(F)(F)F)c4)C(F)(F)F)CC3)CC2)cc1Cl] | 2-chloro-N-methyl-4-{4-[(1-{(2R)-3,3,3-trifluoro-2-hydroxy-2-[3-(trifluoromethyl)phenyl]propanoyl}piperidin-4-yl)methyl]piperidin-1-yl}benzamide | Calc'd 620.2, found 620.4 |
| Example 7-129 | 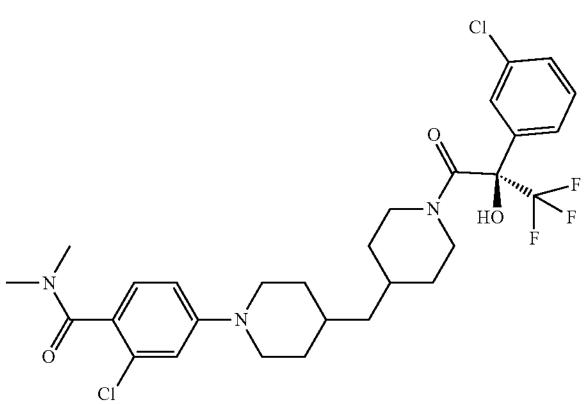 [SMILES: CN(C)C(=O)c1ccc(N2CCC(CC3CCN(C(=O)[C@](O)(c4cccc(Cl)c4)C(F)(F)F)CC3)CC2)cc1Cl] | 2-chloro-4-[4-({1-[2-(3-chlorophenyl)-3,3,3-trifluoro-2-hydroxypropanoyl]piperidin-4-yl}methyl)piperidin-1-yl]-N-methylbenzamide | Calc'd 586.2, found 586.4 |

| Example | Structure | IUPAC Name | Exact Mass [M + H]+ |
|---|---|---|---|
| Example 7-130 | 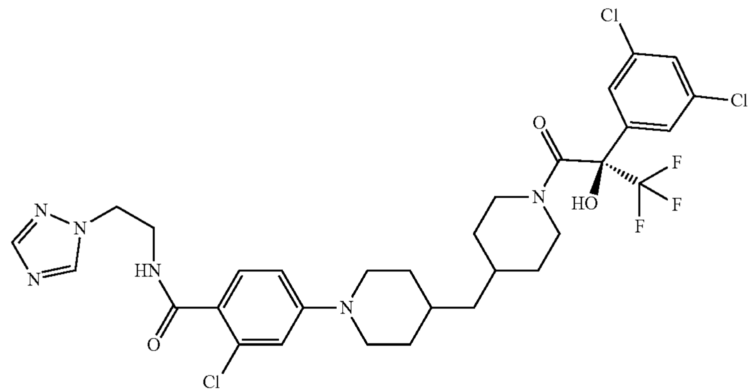 [SMILES: O=C(NCCn1cncn1)c1ccc(N2CCC(CC3CCN(C(=O)[C@](O)(c4cc(Cl)cc(Cl)c4)C(F)(F)F)CC3)CC2)cc1Cl] | 2-chloro-4-[4-({1-[(2R)-2-(3,5-dichlorophenyl)-3,3,3-trifluoro-2-hydroxypropanoyl]piperidin-4-yl}methyl)piperidin-1-yl]-N-[2-(1H-1,2,4-triazol-1-yl)ethyl]benzamide | Calc'd 701.2, found 701.4 |
| Example 7-131 | 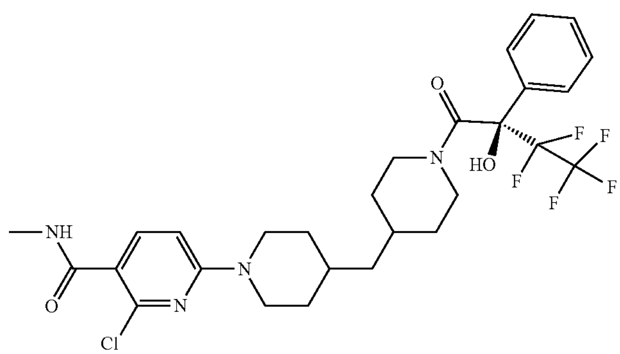 [SMILES: CNC(=O)c1ccc(N2CCC(CC3CCN(C(=O)[C@](O)(c4ccccc4)C(F)(F)C(F)(F)F)CC3)CC2)nc1Cl] | 2-chloro-N-methyl-6-[4-({1-[(2R)-3,3,4,4,4-pentafluoro-2-hydroxy-2-phenylbutanoyl]piperidin-4-yl}methyl)piperidin-1-yl]pyridine-3-carboxamide | Calc'd 603.2, found 603.5 |
| Example 7-132 | 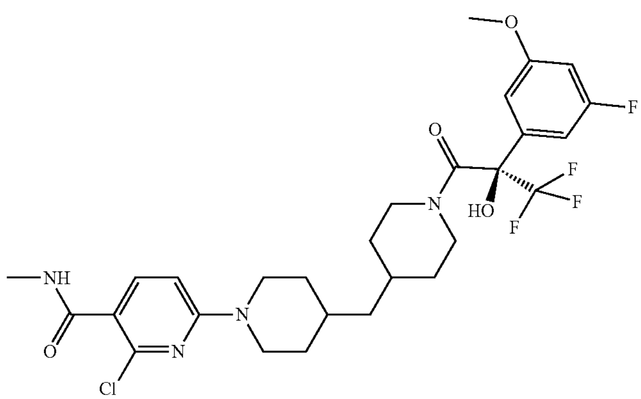 [SMILES: CNC(=O)c1ccc(N2CCC(CC3CCN(C(=O)[C@](O)(c4cc(F)cc(OC)c4)C(F)(F)F)CC3)CC2)nc1Cl] | 2-chloro-N-methyl-6-[4-({1-[(2R)-3,3,3-trifluoro-2-(3-fluoro-5-methoxyphenyl)-2-hydroxypropanoyl]piperidin-4-yl}methyl)piperidin-1-yl]pyridine-3-carboxamide | Calc'd 601.2, found 601.5 |
| Example 7-133 | 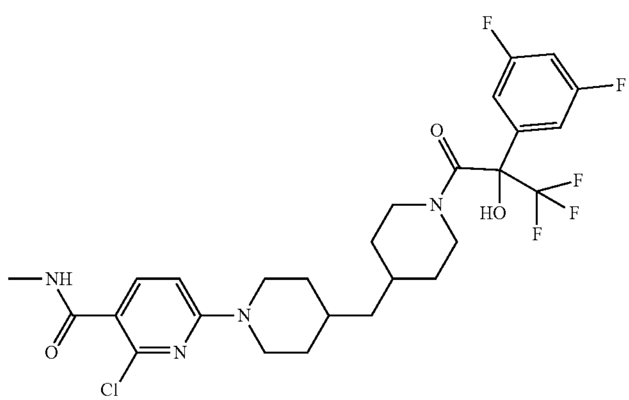 [SMILES: CNC(=O)c1ccc(N2CCC(CC3CCN(C(=O)C(O)(c4cc(F)cc(F)c4)C(F)(F)F)CC3)CC2)nc1Cl] | 2-chloro-6-[4-({1-[2-(3,5-difluorophenyl)-3,3,3-trifluoro-2-hydroxypropanoyl]piperidin-4-yl}methyl)piperidin-1-yl]-N-methylpyridine-3-carboxamide | Calc'd 589.2, found 589.4 |

-continued

| Example | Structure | IUPAC Name | Exact Mass [M + H]+ |
|---|---|---|---|
| Example 7-134 | 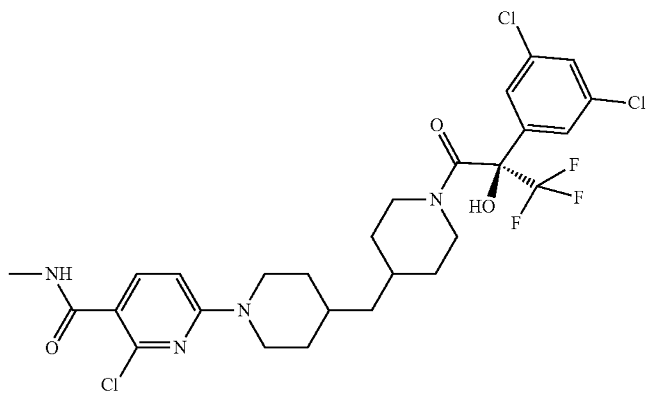 [SMILES: CNC(=O)c1ccc(N2CCC(CC3CCN(C(=O)[C@](O)(c4cc(Cl)cc(Cl)c4)C(F)(F)F)CC3)CC2)nc1Cl] | 2-chloro-6-[4-({1-[(2R)-2-(3,5-dichlorophenyl)-3,3,3-trifluoro-2-hydroxypropanoyl]piperidin-4-yl}methyl)piperidin-1-yl]-N-methylpyridine-3-carboxamide | Calc'd 621.1, found 621.4 |
| Example 7-135 | 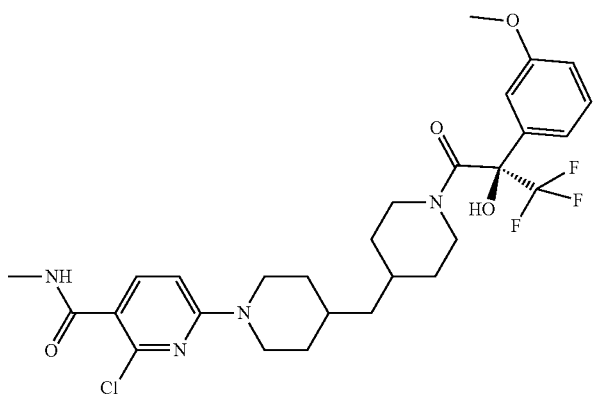 [SMILES: CNC(=O)c1ccc(N2CCC(CC3CCN(C(=O)[C@](O)(c4cccc(OC)c4)C(F)(F)F)CC3)CC2)nc1Cl] | 2-chloro-N-methyl-6-[4-({1-[(2R)-3,3,3-trifluoro-2-hydroxy-2-(3-methoxyphenyl)propanoyl]piperidin-4-yl}methyl)piperidin-1-yl]pyridine-3-carboxamide | Calc'd 583.2, found 583.5 |
| Example 7-136 | 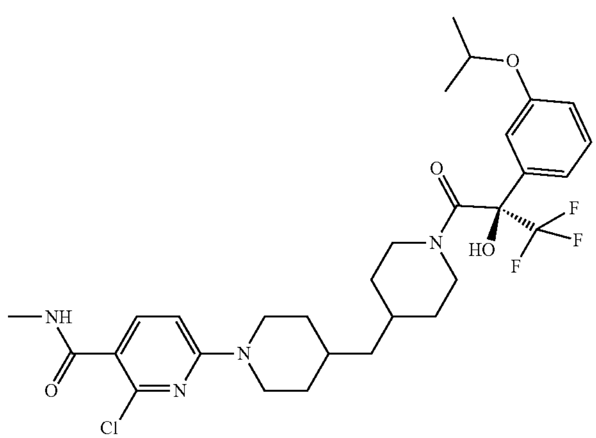 [SMILES: CNC(=O)c1ccc(N2CCC(CC3CCN(C(=O)[C@](O)(c4cccc(OC(C)C)c4)C(F)(F)F)CC3)CC2)nc1Cl] | 2-chloro-N-methyl-6-{4-[(1-{(2R)-3,3,3-trifluoro-2-hydroxy-2-[3-(1-methylethoxy)phenyl]propanoyl}piperidin-4-yl)methyl]piperidin-1-yl}pyridine-3-carboxamide | Calc'd 611.3, found 611.5 |

| Example | Structure | IUPAC Name | Exact Mass [M + H]+ |
|---|---|---|---|
| Example 7-137 | 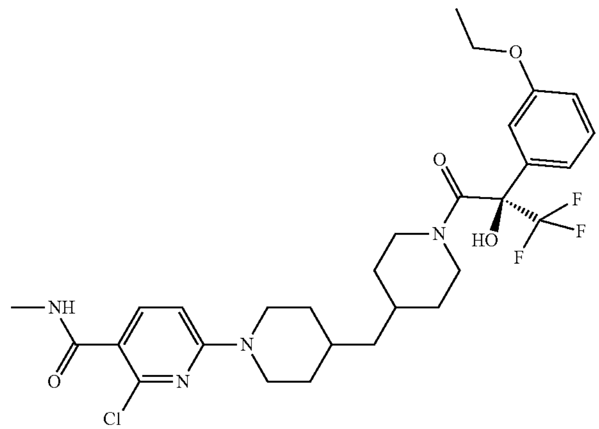 [SMILES: CCOc1cccc([C@@](O)(C(=O)N2CCC(CC3CCN(c4ccc(C(=O)NC)c(Cl)n4)CC3)CC2)C(F)(F)F)c1] | 2-chloro-6-[4-({1-[(2R)-2-(3-ethoxyphenyl)-3,3,3-trifluoro-2-hydroxypropanoyl]piperidin-4-yl}methyl)piperidin-1-yl]-N-methylpyridine-3-carboxamide | Calc'd 597.2, found 597.5 |
| Example 7-138 | 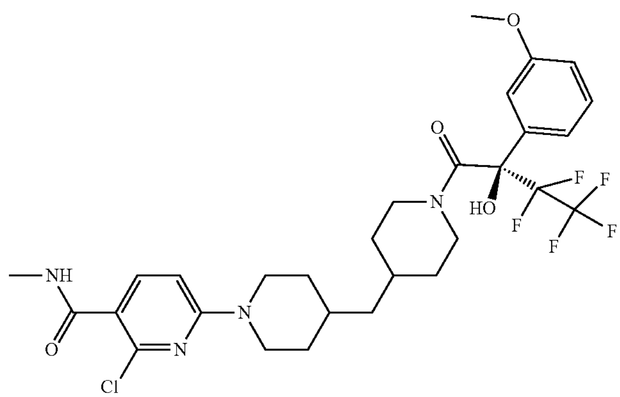 [SMILES: CNC(=O)c1ccc(N2CCC(CC3CCN(C(=O)[C@](O)(c4cccc(OC)c4)C(F)(F)C(F)(F)F)CC3)CC2)nc1Cl] | 2-chloro-N-methyl-6-[4-({1-[(2R)-3,3,4,4,4-pentafluoro-2-hydroxy-2-(3-methoxyphenyl)butanoyl]piperidin-4-yl}methyl)piperidin-1-yl]pyridine-3-carboxamide | Calc'd 633.2, found 633.5 |
| Example 7-139 | 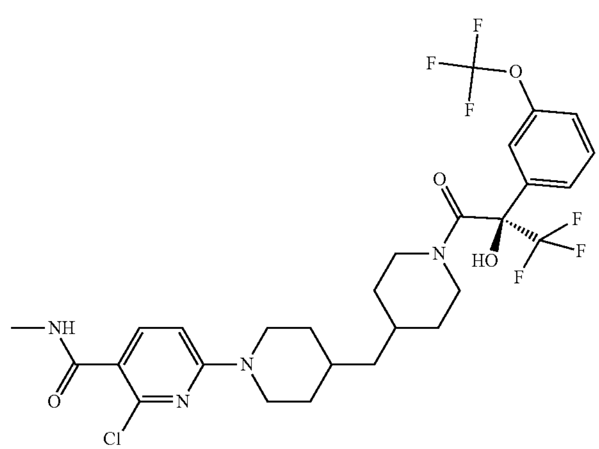 [SMILES: CNC(=O)c1ccc(N2CCC(CC3CCN(C(=O)[C@](O)(c4cccc(OC(F)(F)F)c4)C(F)(F)F)CC3)CC2)nc1Cl] | 2-chloro-N-methyl-6-{4-[(1-{(2R)-3,3,3-trifluoro-2-hydroxy-2-[3-(trifluoromethoxy)phenyl]propanoyl}piperidin-4-yl)methyl]piperidin-1-yl}pyridine-3-carboxamide | Calc'd 637.2, found 637.5 |

| Example | Structure | IUPAC Name | Exact Mass [M + H]+ |
|---|---|---|---|
| Example 7-140 | 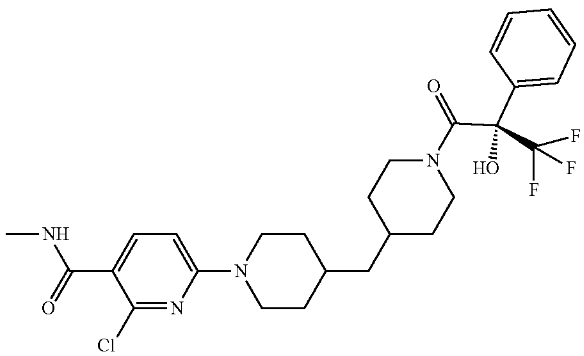 [SMILES: CNC(=O)c1ccc(N2CCC(CC3CCN(C(=O)[C@@](O)(c4ccccc4)C(F)(F)F)CC3)CC2)nc1Cl] | 2-chloro-N-methyl-6-[4-({1-[(2S)-3,3,3-trifluoro-2-hydroxy-2-phenylpropanoyl]piperidin-4-yl}methyl)piperidin-1-yl]pyridine-3-carboxamide | Calc'd 553.2, found 553.4 |
| Example 7-141 | 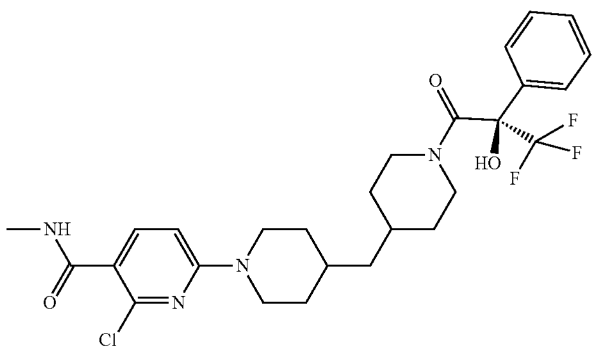 [SMILES: CNC(=O)c1ccc(N2CCC(CC3CCN(C(=O)[C@](O)(c4ccccc4)C(F)(F)F)CC3)CC2)nc1Cl] | 2-chloro-N-methyl-6-[4-({1-[(2R)-3,3,3-trifluoro-2-hydroxy-2-phenylpropanoyl]piperidin-4-yl}methyl)piperidin-1-yl]pyridine-3-carboxamide | Calc'd 553.2, found 553.4 |
| Example 7-142 | 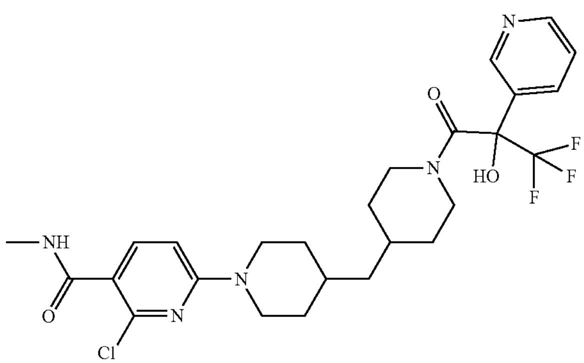 [SMILES: CNC(=O)c1ccc(N2CCC(CC3CCN(C(=O)C(O)(c4cccnc4)C(F)(F)F)CC3)CC2)nc1Cl] | 2-chloro-N-methyl-6-(4-{[1-(3,3,3-trifluoro-2-hydroxy-2-pyridin-3-ylpropanoyl)piperidin-4-yl]methyl}piperidin-1-yl)pyridine-3-carboxamide | Calc'd 554.2, found 554.4 |
| Example 7-143 | 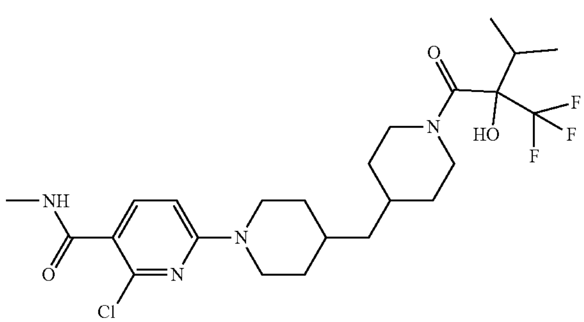 [SMILES: CNC(=O)c1ccc(N2CCC(CC3CCN(C(=O)C(O)(C(C)C)C(F)(F)F)CC3)CC2)nc1Cl] | 2-chloro-6-[4-({1-[2-hydroxy-3-methyl-2-(trifluoromethyl)butanoyl]piperidin-4-yl}methyl)piperidin-1-yl]-N-methylpyridine-3-carboxamide | Calc'd 519.2, found 519.4 |

-continued

| Example | Structure | IUPAC Name | Exact Mass [M + H]+ |
|---|---|---|---|
| Example 7-144 | 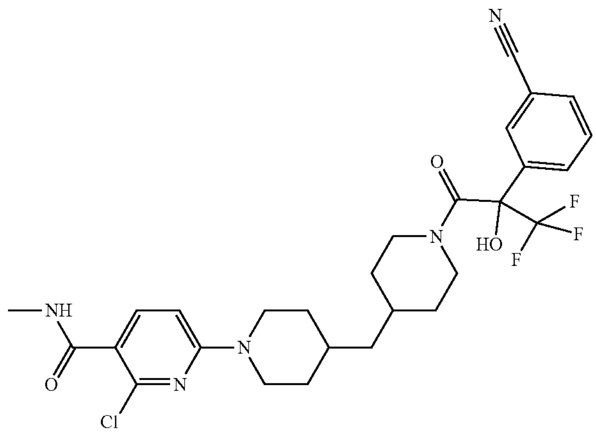 [SMILES: CNC(=O)c1ccc(N2CCC(CC3CCN(C(=O)C(O)(c4cccc(C#N)c4)C(F)(F)F)CC3)CC2)nc1Cl] | 2-chloro-6-[4-({1-[2-(3-cyanophenyl)-3,3,3-trifluoro-2-hydroxypropanoyl]piperidin-4-yl}methyl)piperidin-1-yl]-N-methylpyridine-3-carboxamide | Calc'd 578.2, found 578.4 |
| Example 7-145 | 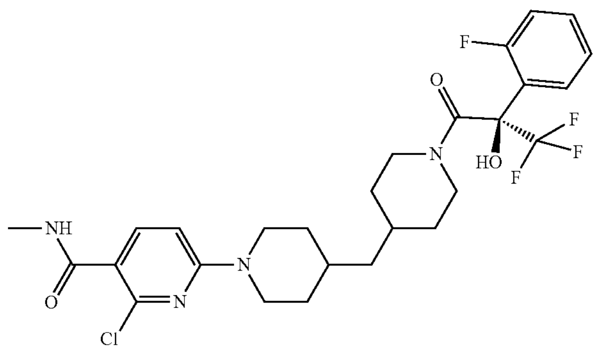 [SMILES: CNC(=O)c1ccc(N2CCC(CC3CCN(C(=O)[C@](O)(c4ccccc4F)C(F)(F)F)CC3)CC2)nc1Cl] | 2-chloro-N-methyl-6-[4-({1-[(2R)-3,3,3-trifluoro-2-(2-fluorophenyl)-2-hydroxypropanoyl]piperidin-4-yl}methyl)piperidin-1-yl]pyridine-3-carboxamide | Calc'd 571.2, found 571.4 |
| Example 7-146 | 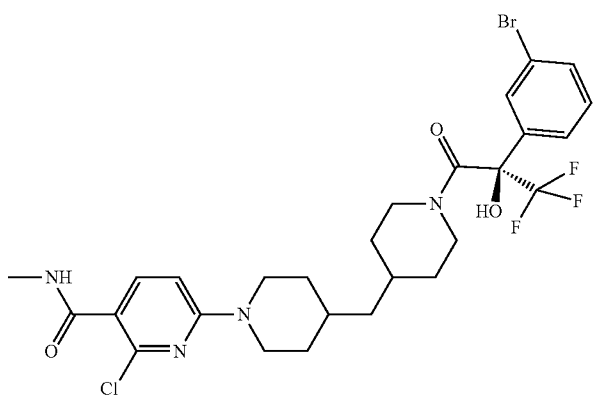 | 6-[4-({1-[(2R)-2-(3-bromophenyl)-3,3,3-trifluoro-2-hydroxypropanoyl]piperidin-4-yl}methyl)piperidin-1-yl]-2-chloro-N-methylpyridine-3-carboxamide | Calc'd 631.1, found 631.3 |
| Example 7-147 | 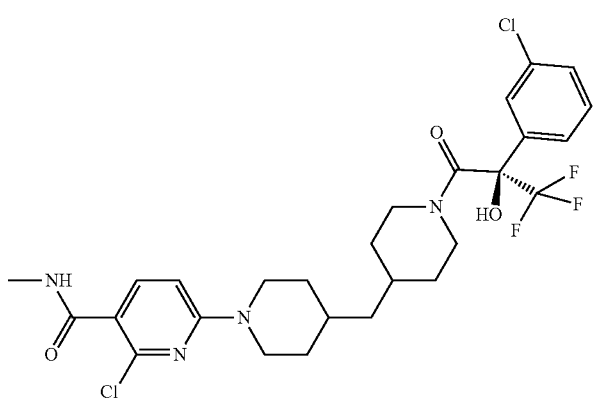 [SMILES: CNC(=O)c1ccc(N2CCC(CC3CCN(C(=O)[C@](O)(c4cccc(Cl)c4)C(F)(F)F)CC3)CC2)nc1Cl] | 2-chloro-6-[4-({1-[(2R)-2-(3-chlorophenyl)-3,3,3-trifluoro-2-hydroxypropanoyl]piperidin-4-yl}methyl)piperidin-1-yl]-N-methylpyridine-3-carboxamide | Calc'd 587.2, found 587.4 |

-continued

| Example | Structure | IUPAC Name | Exact Mass [M + H]+ |
|---|---|---|---|
| Example 7-148 | 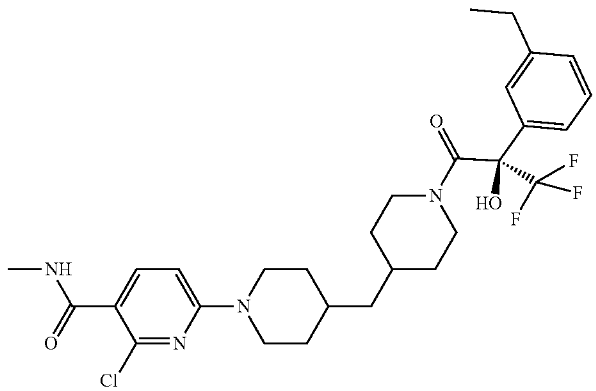 [SMILES: CCc1cccc([C@@](O)(C(=O)N2CCC(CC3CCN(c4ccc(C(=O)NC)c(Cl)n4)CC3)CC2)C(F)(F)F)c1] | 2-chloro-6-[4-({1-[(2R)-2-(3-ethylphenyl)-3,3,3-trifluoro-2-hydroxypropanoyl]piperidin-4-yl}methyl)piperidin-1-yl]-N-methylpyridine-3-carboxamide | Calc'd 581.3, found 581.5 |
| Example 7-149 | 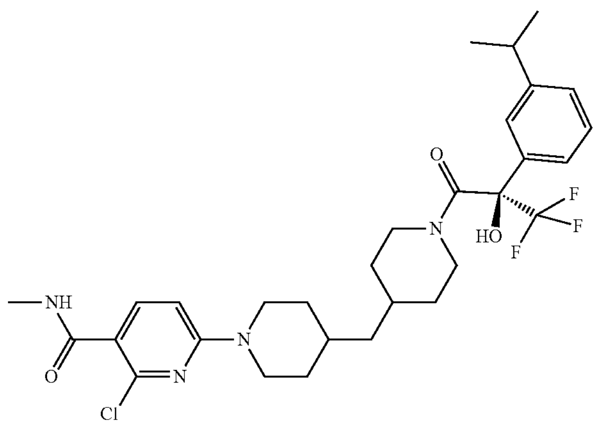 [SMILES: CNC(=O)c1ccc(N2CCC(CC3CCN(C(=O)[C@](O)(c4cccc(C(C)C)c4)C(F)(F)F)CC3)CC2)nc1Cl] | 2-chloro-N-methyl-6-{4-[(1-{(2R)-3,3,3-trifluoro-2-hydroxy-2-[3-(1-methylethyl)phenyl]propanoyl}piperidin-4-yl)methyl]piperidin-1-yl}pyridine-3-carboxamide | Calc'd 595.3, found 595.5 |
| Example 7-150 | 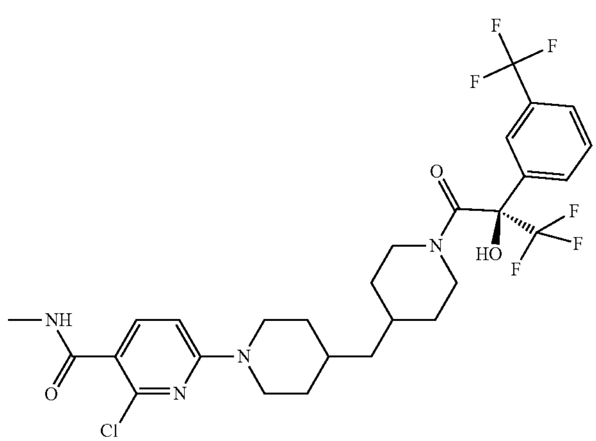 [SMILES: CNC(=O)c1ccc(N2CCC(CC3CCN(C(=O)[C@](O)(c4cccc(C(F)(F)F)c4)C(F)(F)F)CC3)CC2)nc1Cl] | 2-chloro-N-methyl-6-{4-[(1-{(2R)-3,3,3-trifluoro-2-hydroxy-2-[3-(trifluoromethyl)phenyl]propanoyl}piperidin-4-yl)methyl]piperidin-1-yl}pyridine-3-carboxamide | Calc'd 621.2, found 621.4 |

| Example | Structure | IUPAC Name | Exact Mass [M + H]+ |
|---|---|---|---|
| Example 7-151 | 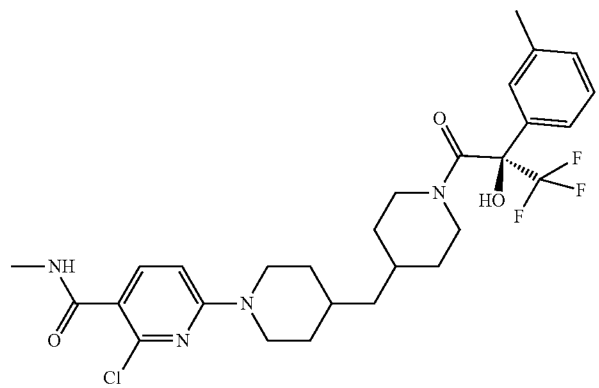 [SMILES: CNC(=O)c1ccc(N2CCC(CC3CCN(C(=O)[C@](O)(c4cccc(C)c4)C(F)(F)F)CC3)CC2)nc1Cl] | 2-chloro-N-methyl-6-[4-({1-[(2R)-3,3,3-trifluoro-2-hydroxy-2-(3-methylphenyl)propanoyl]piperidin-4-yl}methyl)piperidin-1-yl]pyridine-3-carboxamide | Calc'd 567.2, found 567.4 |
| Example 7-152 | 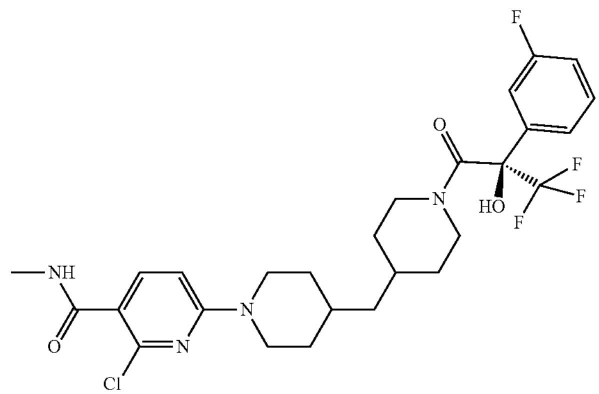 [SMILES: CNC(=O)c1ccc(N2CCC(CC3CCN(C(=O)[C@](O)(c4cccc(F)c4)C(F)(F)F)CC3)CC2)nc1Cl] | 2-chloro-N-methyl-6-[4-({1-[(2R)-3,3,3-trifluoro-2-(3-fluorophenyl)-2-hydroxypropanoyl]piperidin-4-yl}methyl)piperidin-1-yl]pyridine-3-carboxamide | Calc'd 571.2, found 571.4 |
| Example 7-153 | 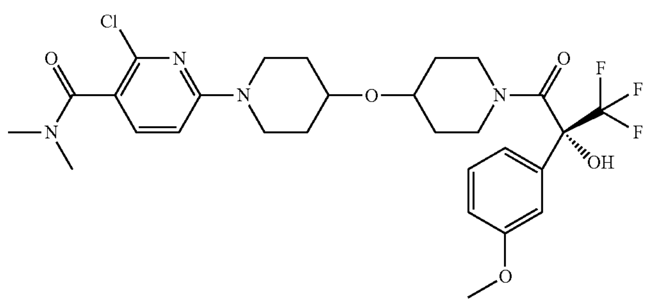 [SMILES: COc1cccc([C@@](O)(C(=O)N2CCC(OC3CCN(c4ccc(C(=O)N(C)C)c(Cl)n4)CC3)CC2)C(F)(F)F)c1] | 2-chloro-N,N-dimethyl-6-[4-({1-[(2R)-3,3,3-trifluoro-2-hydroxy-2-(3-methoxyphenyl)propanoyl]piperidin-4-yl}oxy)piperidin-1-yl]pyridine-3-carboxamide | Calc'd 599.2, found 599.2 |
| Example 7-154 | 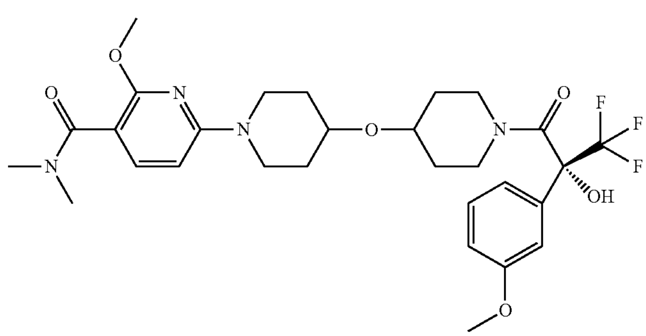 [SMILES: COc1cccc([C@@](O)(C(=O)N2CCC(OC3CCN(c4ccc(C(=O)N(C)C)c(OC)n4)CC3)CC2)C(F)(F)F)c1] | 2-methoxy-N,N-dimethyl-6-[4-({1-[(2R)-3,3,3-trifluoro-2-hydroxy-2-(3-methoxyphenyl)propanoyl]piperidin-4-yl}oxy)piperidin-1-yl]pyridine-3-carboxamide | Calc'd 595.3, found 595.3 |

Example 8-1 2-chloro-4-(4-((1-(3-hydroxy-3-(trifluoromethyl)azetidine-1-carbonyl)piperidin-4-yl)oxy)piperidin-1-yl)-N,N-dimethylbenzamide

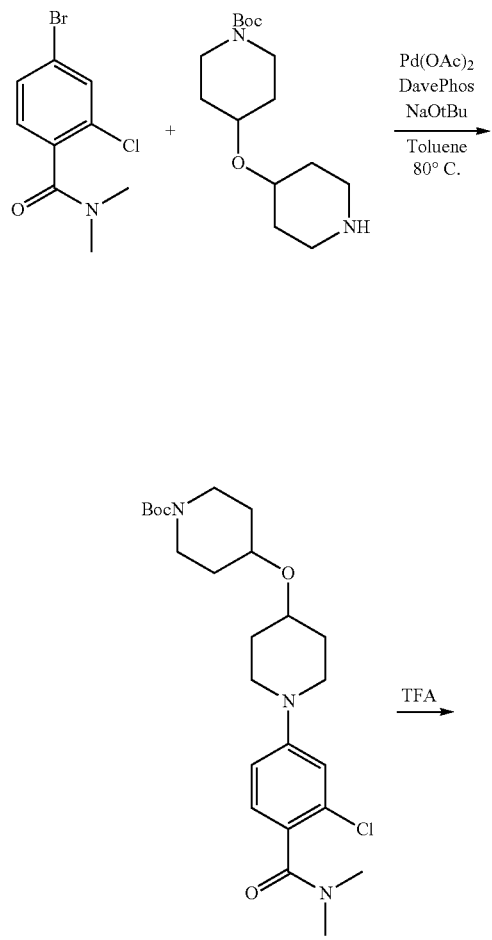

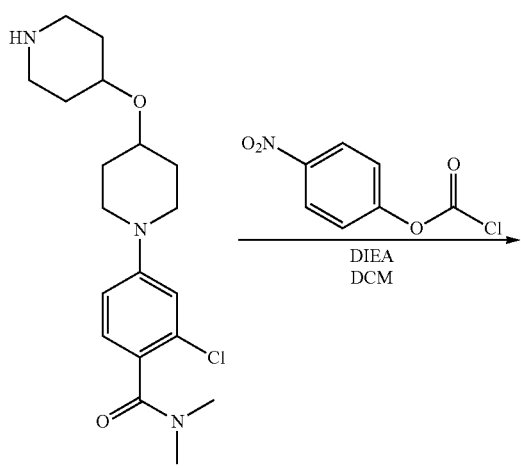

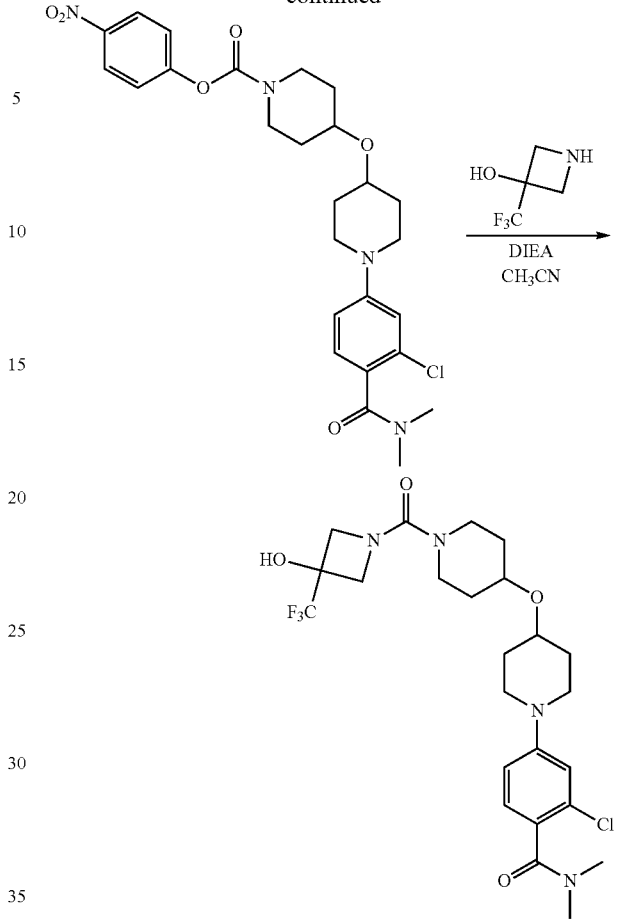

example 8-1

Step 1: tert-butyl 4-((1-(3-chloro-4-(dimethylcarbamoyl)phenyl)piperidin-4-yl)oxy)piperidine-1-carboxylate A mixture of tert-butyl 4-(piperidin-4-yloxy)piperidine-1-carboxylate (611.2 mg, 2.15 mmol), 4-bromo-2-chloro-N,N-dimethylbenzamide (564 mg, 2.15 mmol), 2-dicyclohexylphosphino-2'-(N,N-dimethylamino)biphenyl (127 mg, 0.32 mmol), palladium (II) acetate (24.1 mg, 0.11 mmol), and sodium tert-butoxide (310 mg, 3.22 mmol) in Toluene (10.7 ml) was degassed by bubbling with $N_2$ and heated at 100° C. overnight. The reaction mixture was cooled to room temperature, filtered and then concentrated to dryness. The residue was purified by ISCO column chromatography (ISCO 80 g prepacked, eluting with 0-100% EtOAc/Hexane) to give the title compound (790 mg). LCMS m/z (M+H): Calc'd 466.2, found 466.4.

Step 2: 2-chloro-N,N-dimethyl-4-(4-(piperidin-4-yloxy)piperidin-1-yl)benzamide

Tert-butyl 4-((1-(3-chloro-4-(dimethylcarbamoyl)phenyl)piperidin-4-yl)oxy)piperidine-1-carboxylate (96.5 mg, 0.21 mmol) was treated with TFA:DCM (1:1, 2 ml) for 1 h at room temperature. The mixture was concentrated to dryness to give the crude title compound which was used without further purification.

Step 3: 4-nitrophenyl 4-((1-(3-chloro-4-(dimethylcarbamoyl)phenyl)piperidin-4-yl)oxy)piperidine-1-carboxylate At 0° C., 2-chloro-N,N-dimethyl-4-(4-(piperidin-4-yloxy)piperidin-1-yl)benzamide (76 mg, 0.21 mmol), DIEA (217 ul, 1.24 mmol) and then 4-nitrophenyl carbonochloridate (83 mg, 0.41 mmol) was added to a mixture of crude N-dimethyl-4-(4-(piperidin-4-yloxy)piperidin-1-yl)benzamide from step 2 in DCM (5 ml). After stirring at room temperature overnight, the residue was purified by ISCO column chromatography (ISCO 24 g prepacked, eluting with 0-100% EtOAc/Hexane) to give the title compound (87 mg). LCMS m/z (M+H): Calc'd 531.2, found 531.4.

Step 4: 2-chloro-4-(4-((1-(3-hydroxy-3-(trifluoromethyl)azetidine-1-carbonyl)piperidin-4-yl)oxy)piperidin-1-yl)-N,N-dimethylbenzamide A mixture of 4-nitrophenyl 4-((1-(3-chloro-4-(dimethylcarbamoyl)phenyl)piperidin-4-yl)oxy)piperidine-1-carboxylate (53 mg, 0.10 mmol), 3-(trifluoromethyl)azetidin-3-ol (41.8 mg, 0.24 mmol) and DIEA (99 ul, 0.56 mmol) in CH₃CN (1 ml) was degassed, and then heated at 120° C. for 1 h under microwave condition. The reaction mixture was concentrated, dissolved in DMSO (1 ml) and purified by mass-directed HPLC purification (2 cm×5 cm C18, acetonitrile-water gradient, 0.05% TFA added) to give the title compound (49 mg). LCMS m/z (M+H): Calc'd 533.2, found 533.4.

Example 9-1: (R)-2-chloro-N,N-dimethyl-6-(4-(1-(3,3,3-trifluoro-2-hydroxy-2-(3-(trifluoromethoxy)phenyl)propanoyl)piperidin-4-ylthio)piperidin-1-yl)nicotinamide

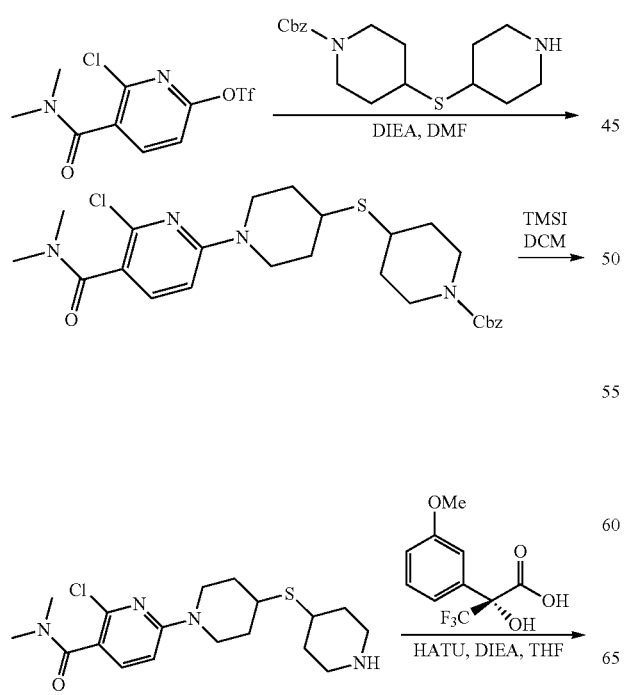

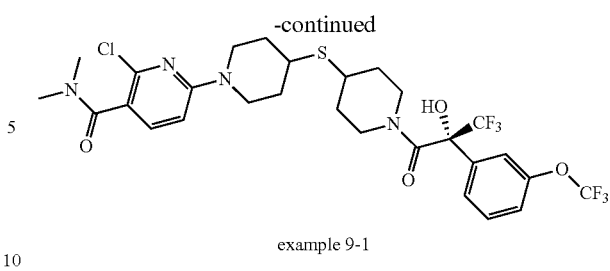

example 9-1

Step 1: benzyl 4-(1-(6-chloro-5-(dimethylcarbamoyl)pyridin-2-yl)piperidin-4-ylthio)piperidine-1-carboxylate To a solution of benzyl 4-(piperidin-4-ylthio)piperidine-1-carboxylate 2,2,2-trifluoroacetic acid (intermediate B8, 345 mg, 0.77 mmol) in DMF (8 mL) was added DIEA (300 mg, 2.3 mmol) and 6-chloro-5-(dimethylcarbamoyl)pyridin-2-yl trifluoromethanesulfonate (intermediate A12, 268 mg, 0.81 mmol). After stirring at 80° C. for 3 h, the reaction was diluted with EtOAc (80 mL). The organic phase was washed with water (10 mL×3), brine (10 mL×3) and dried over anhydrous Na₂SO₄. The organic phase was concentrated and the residue was purified by Prep-TLC (silica gel, PE/EtOAc=1/3) to afford the title compound (356 mg). LRMS m/z (M+H): Calc'd 517.2; found 517.2.

Step 2: 2-chloro-N,N-dimethyl-6-(4-(piperidin-4-ylthio)piperidin-1-yl)nicotinamide To a solution of benzyl 4-(1-(6-chloro-5-(dimethylcarbamoyl)pyridin-2-yl)piperidin-4-ylthio)piperidine-1-carboxylate (150 mg, 0.29 mmol) in DCM (5 mL) was added iodotrimethylsilane (0.3 mL) at room temperature. The mixture was stirred at the same temperature for 3 h and the solvent was removed under reduced pressure. The residue was purified by Combi-Flash (mobile phase: methanol/water (10 mM NH₄HCO₃)) to afford the title compound (60 mg). LRMS m/z (M+H): Calc'd 383.2; found 383.2.

Step 3: (R)-2-chloro-N,N-dimethyl-6-(4-(1-(3,3,3-trifluoro-2-hydroxy-2-(3-(trifluoromethoxy)phenyl)propanoyl)piperidin-4-ylthio)piperidin-1-yl)nicotinamide A mixture of 2-chloro-N,N-dimethyl-6-(4-(piperidin-4-ylthio)piperidin-1-yl)nicotinamide (15 mg, 0.04 mmol), (R)-3,3,3-trifluoro-2-hydroxy-2-(3-(trifluoromethoxy)phenyl)propanoic acid (15 mg, 0.049 mmol), HATU (23 mg, 0.06 mmol) and DIEA (10 mg, 0.08 mmol) in THF (1 mL) was stirred at room temperature overnight. The mixture was directly purified by Combi-Flash (mobile phase: methanol/water (10 mM NH₄HCO₃)) to afford the title compound (20 mg) as a white solid. ¹H NMR (400 MHz, MeOD): δ 7.60-7.39 (m, 5H), 6.75 (d, J=8.8 Hz, 1H), 4.42-3.83 (m, 4H), 3.09-2.74 (m, 12H), 2.01-1.94 (m, 3H), 1.55-1.30 (m, 5H). LRMS m/z (M+H): Calc'd 669.2; found 669.2.

The following compounds were prepared according to the procedure for Example 9-1 using the appropriate acid.

| Example | Structure | IUPAC Name | Exact Mass [M + H]+ |
|---|---|---|---|
| Example 9-2 | 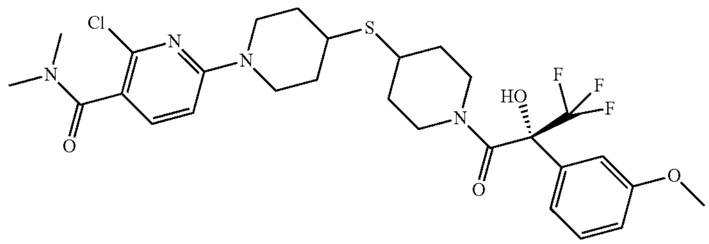 | 2-chloro-N,N-dimethyl-6-[4-({1-[(2R)-3,3,3-trifluoro-2-hydroxy-2-(3-methoxyphenyl)-propanoyl]piperidin-4-yl}sulfanyl)-piperidin-1-yl]-pyridine-3-carboxamide | Calc'd 615.2, found 615.2 |
| Example 9-3 | 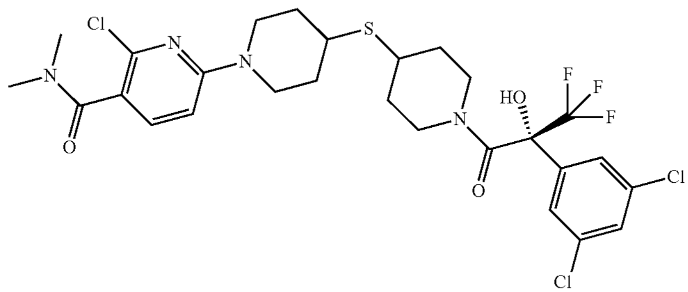 [SMILES: CN(C)C(=O)c1ccc(N2CCC(SC3CCN(C(=O)[C@](O)(c4cc(Cl)cc(Cl)c4)C(F)(F)F)CC3)CC2)nc1Cl] | 2-chloro-6-[4-({1-[(2R)-2-(3,5-dichlorophenyl)-3,3,3-trifluoro-2-hydroxypropanoyl]-piperidin-4-yl}-sulfanyl)piperidin-1-yl]-N,N-dimethyl-pyridine-3-carboxamide | Calc'd 653.1, found 653.0 |

Example 10-1: (R)-2-chloro-N,N-dimethyl-4-(4-(1-(3,3,3-trifluoro-2-hydroxy-2-(3-methoxyphenyl)propanoyl)piperidin-4-ylthio)piperidin-1-yl)benzamide

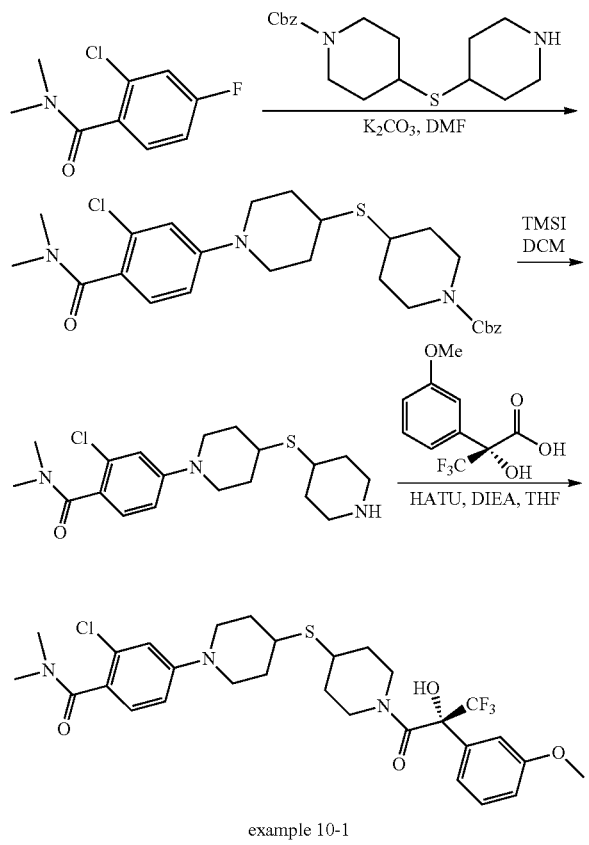

example 10-1

Step 1: benzyl 4-(1-(3-chloro-4-(dimethylcarbamoyl)phenyl)piperidin-4-ylthio)piperidine-1-carboxylate To a solution of benzyl 4-(piperidin-4-ylthio)piperidine-1-carboxylate 2,2,2-trifluoroacetic acid (150 mg, 0.33 mmol) and chloro-4-fluoro-N,N-dimethylbenzamide (100 mg, 0.5 mmol) in DMF (2 mL) was added K₂CO₃ (91 mg, 0.66 mmol) at room temperature. The resulting mixture was heat to 80° C. for 2 h and quenched with aq NH₄Cl (5 mL). The mixture was extracted with EtOAc (10 mL×3), and the combined organic layer was washed with brine (5 mL×2) and dried over anhydrous Na₂SO₄. The organic phase was concentrated and the residue was purified by Prep-TLC (silica gel, PE/EtOAc=1/1) to afford the title compound (68 mg). LRMS m/z (M+H): Calc'd 516.1, found 516.2.

Step 2: 2-chloro-N,N-dimethyl-4-(4-(piperidin-4-ylthio)piperidin-1-yl)benzamide

To a solution of benzyl 4-(1-(3-chloro-4-(dimethylcarbamoyl)phenyl)piperidin-4-ylthio)piperidine-1-carboxylate (68 mg, 0.13 mmol) in DCM (2 mL) was added iodotrimethylsilane (0.1 mL, 0.7 mmol) at room temperature. The mixture was stirred at room temperature for 3 h and the solvent was removed under reduced pressure. The residue was purified by Combi-Flash (mobile phase: methanol/water (10 mM NH₄HCO₃)) to afford the title compound (30 mg). LRMS m/z (M+H): Calc'd 382.3, found 382.2.

Step 3: (R)-2-chloro-N,N-dimethyl-4-(4-(1-(3,3,3-trifluoro-2-hydroxy-2-(3-methoxyphenyl)propanoyl)piperidin-4-ylthio)piperidin-1-yl)benzamide A mixture of 2-chloro-N,N-dimethyl-4-(4-(piperidin-4-ylthio)piperidin-1-yl)benzamide (2-7) (14 mg, 0.036 mmol), (R)-3,3,3-trifluoro-2-hydroxy-2-(3-methoxyphenyl)propanoic acid (10 mg, 0.04 mmol), HATU (42 mg, 0.11 mmol) and DIEA (14 mg, 0.11 mmol) in THF (2 mL) was stirred at room temperature overnight. The mixture was directly purified by Combi-Flash (mobile phase: methanol/water (10 mM NH₄HCO₃)) to afford the title compound (16 mg) as a white solid. ¹H NMR (400 MHz, CDCl₃): δ 7.34 (t, J=8.0 Hz, 1H), 7.16 (d, J=8.8 Hz, 1H), 7.01-6.81 (m, 5H), 5.58 (br, 1H), 4.33-4.30 (m, 1H), 3.81 (s, 3H), 3.62-3.58 (m, 3H), 3.22-2.75 (m, 12H), 2.05 (m, 2H), 1.69-1.56 (m, 6H). LRMS m/z (M+H): Calc'd 614.0, found 614.2.

Example 11-1: (R)-2-chloro-N-methyl-6-(4-(1-(3,3,3-trifluoro-2-hydroxy-2-(3-methoxyphenyl)propanoyl)piperidin-4-ylthio)piperidin-1-yl)nicotinamide

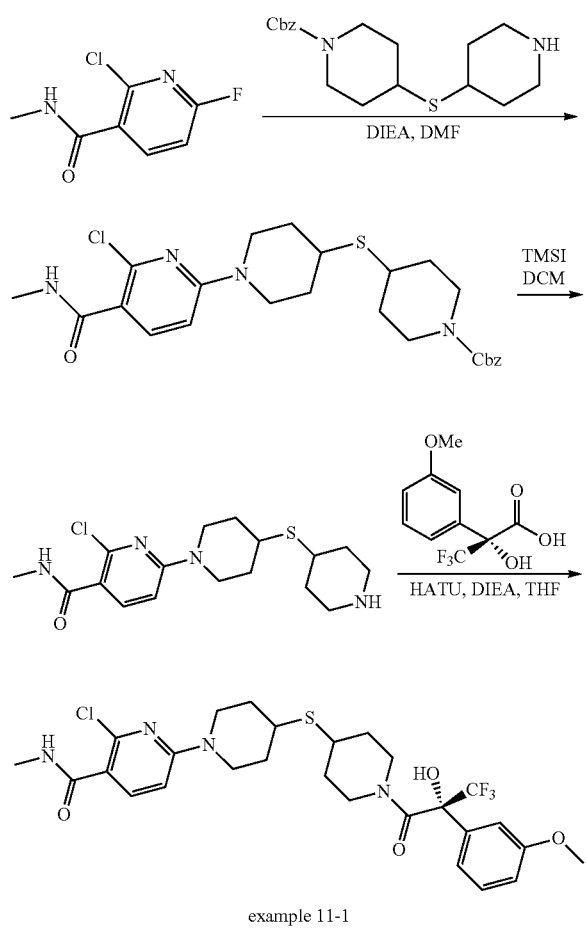

example 11-1

Step 1: benzyl 4-(1-(6-chloro-5-(methylcarbamoyl)pyridin-2-yl)piperidin-4-ylthio)piperidine-1-carboxylate To a solution of benzyl 4-(piperidin-4-ylthio)piperidine-1-carboxylate 2,2,2-trifluoroacetic acid (200 mg, 0.45 mmol) in DMF (5 mL) was added DIEA (170 mg, 1.32 mmol) and 6-chloro-5-(methylcarbamoyOpyridin-2-yl trifluoromethanesulfonate (157 mg, 0.49 mmol). After stirring at 80°° C. for 1 h, the reaction was diluted with EtOAc (80 mL). The organic phase was washed with water (10 mL×3), brine (10 mL×3) and dried over anhydrous Na₂SO₄. The organic phase was concentrated and the residue was purified by Prep-TLC (silica gel, PE/EtOAc=1/2) to afford the title compound (116 mg). LRMS m/z (M+H): Calc'd 503.2; found 503.2.

Step 2: 2-chloro-N-methyl-6-(4-(piperidin-4-ylthio)piperidin-1-yl)nicotinamide

To a solution of benzyl 4-(1-(6-chloro-5-(methylcarbamoyl)pyridin-2-yl)piperidin-4-ylthio)piperidine-1-carboxylate (3-6) (116 mg, 0.23 mmol) in DCM (5 mL) was added iodotrimethylsilane (1 mL) at rt. The mixture was stirred at rt overnight and the solvent was removed under reduced pressure. The residue was purified by Combi-Flash (mobile phase: methanol/water (10 mM NH₄HCO₃)) to afford the title compound (80 mg). LRMS m/z (M+H): Calc'd 369.2; found 369.2.

Step 3: (R)-2-chloro-N-methyl-6-(4-(1-(3,3,3-trifluoro-2-hydroxy-2-(3-methoxyphenyl)propanoyl)piperidin-4-ylthio)piperidin-1-yl)nicotinamide A mixture of 2-chloro-N-methyl-6-(4-(piperidin-4-ylthio)piperidin-1-yl)nicotinamide (3-7) (20 mg, 0.054 mmol), (R)-3,3,3-trifluoro-2-hydroxy-2-(3-methoxyphenyl)propanoic acid (18 mg, 0.072 mmol), HATU (31 mg, 0.081 mmol) and DIEA (20 mg, 0.016 mmol) in THF (2 mL) was stirred at room temperature overnight. The mixture was directly purified by Combi-Flash (mobile phase: methanol/water (10 mM NH₄HCO₃)) to afford the tile compound (25 mg) as a white solid. LRMS m/z (M+H): Calc'd 601.2; found 601.2.

The following compounds were prepared according to the procedure for Example 11-1 using the appropriate acid.

| Example | Structure | IUPAC Name | Exact Mass [M + H]+ |
|---|---|---|---|
| Example 11-2 | 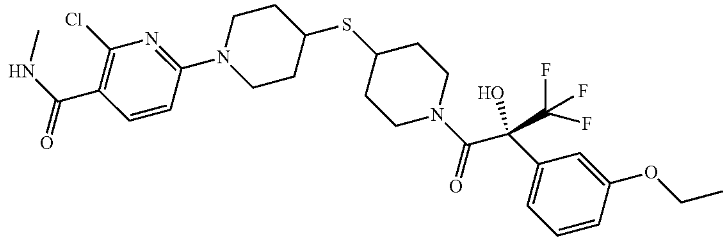 [SMILES: CCOc1cccc([C@@](O)(C(=O)N2CCC(SC3CCN(c4ccc(C(=O)NC)c(Cl)n4)CC3)CC2)C(F)(F)F)c1] | 2-chloro-6-[4-({1-[(2R)-2-(3-ethoxyphenyl)-3,3,3-trifluoro-2-hydroxypropanoyl]-piperidin-4-yl}-sulfanyl)piperidin-1-yl]-N-methyl-pyridine-3-carboxamide | Calc'd 615.2, found 615.1 |

Example 12-1: 2-chloro-4-[4-({1-[(2R)-2-(3,5-di-chlorophenyl)-3,3,3-trifluoro-2-hydroxypropanoyl]piperidin-4-yl}methyl)piperidin-1-yl]benzamide

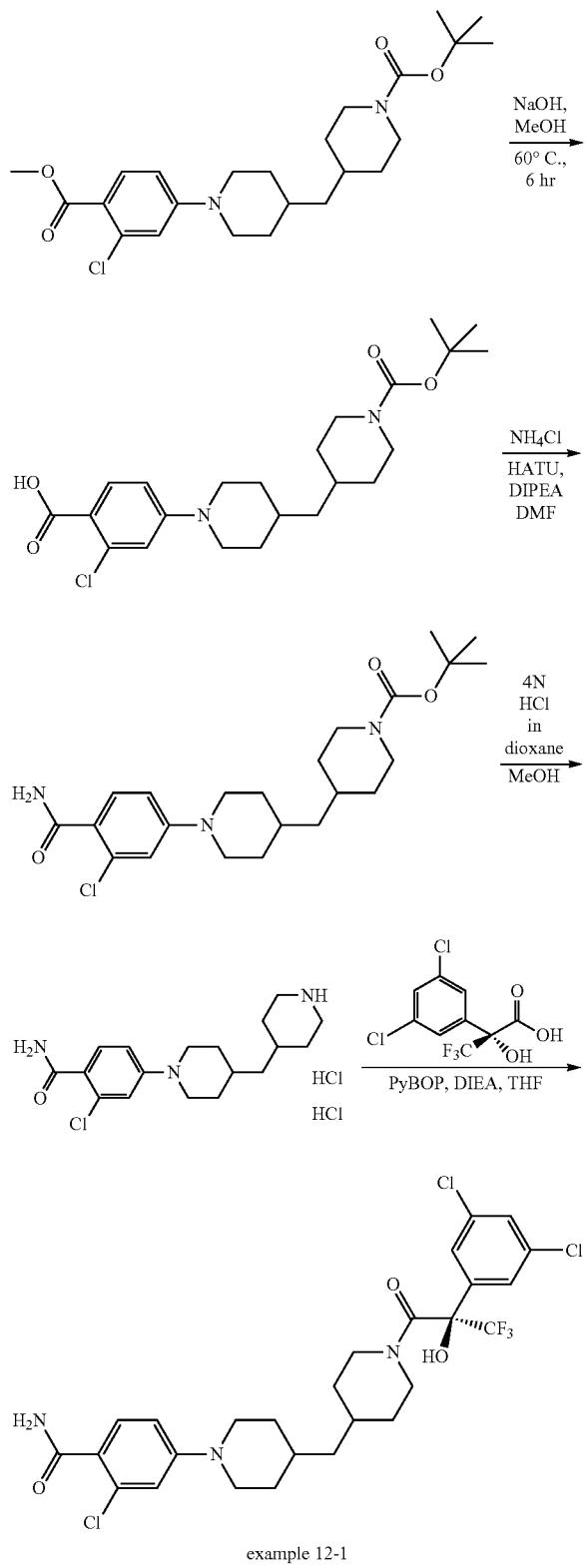

example 12-1

Step 1: 4-(4-((1-(tert-butoxycarbonyl)piperidin-4-yl)methyl)piperidin-1-yl)-2-chlorobenzoic Acid To a solution of tert-butyl 4-((1-(3-chloro-4-methoxycarbonyl)phenyl)piperidin-4-yl)methyl)piperidine-1-carboxylate (example 4-1, step 1, 1.3 g, 2.88 mmol, 1 eq) in MeOH (29 mL), aqueous NaOH (4 N, 3.4 mL, 6 eq) was added. The solution was stirred at 60° C. for 6 hours, and was then concentrated to remove most of the MeOH. The resulting solution was diluted with EtOAc (100 mL) and pH was adjusted to 4 using HCl (1N). Some desired product crashed out as a white solid. The solid was filtered, and washed with water (10 mL). The resulting filtrate was partitioned with more EtOAc (30 mL×2). The combined EtOAc extract was washed with water (10 mL) and brine (20 mL), dried over anhy. MgSO4, and concentrated to give a white solid. Both solids were combined and dried on high vacuum to yield 4-(4-((1-(tert-butoxycarbonyl)piperidin-4-yl)methyl)piperidin-1-yl)-2-chlorobenzoic acid (1.23 g, 93%). LRMS m/z (M+H): Calc'd 381.2 (fragment loss of t-Butyl), found 381.3 (fragment loss of t-Butyl).

Step 2: tert-butyl 4-((1-(4-carbamoyl-3-chlorophenyl)piperidin-4-yl)methyl)piperidine-1-carboxylate Solid ammonium chloride (90 mg, 1.6 eq), 4-(4-((1-(tert-butoxycarbonyl)piperidin-4-yl)methyl)piperidin-1-yl)-2-chlorobenzoic acid (1-2) (460 mg, 1.05 mmol) and HATU (520 mg, 1.3 eq) were stirred in anhy. DMF (5.3 mL) for 15 mins. DIPEA (0.74 mL, 4 eq) was added and continued to stir for 1 hr. The reaction mixture was partitioned between EtOAc (100 mL) and aq. NaHCO$_3$ (2 M, 20 mL). The EtOAc extract was washed with brine, dried over anhy. Na2SO4, concentrated, and purified by silica gel flash chromatography using a step gradient of 0% to 100% EtOAc in hexanes to give the title compound (450 mg, 95%) as a white solid. LRMS m/z (M+H): Calc'd 436.2, found 436.4.

Step 3: 2-chloro-4-(4-(piperidin-4-ylmethyl)piperidin-1-yl)benzamide dihydrochloride To a solution of tert-butyl 4-((1-(4-carbamoyl-3-chlorophenyl)piperidin-4-yl)methyl)piperidine-1-carboxylate (450 mg, 1.03 mmol) in MeOH (20 mL) was added a solution of HCl in dioxane (4 N, 13 mL) and stirred at rt for 4 hours. The solution was concentrated and dried on high vacuum to give the title compound (442 mg, 105%) as a sticky light yellow solid. It was used in the next step without further purification. LRMS m/z (M+H): Calc'd 336.3, found 336.3.

Step 4: 2-chloro-4-[4-({1-[(2R)-2-(3,5-dichlorophenyl)-3,3,3-trifluoro-2-hydroxypropanoyl]piperidin-4-yl}methyl)piperidin-1-yl]benzamide The title compound was made in a similar manner to 2-chloro-N,N-dimethyl-4-(4-((1-(2-methyl-2-phenylpropanoyl)piperidin-4-yl)methyl)piperidin-1-yl)benzamide (example 2-1, step 2). LRMS m/z (M+H): Calc'd 606.1, found 606.3.

The following compounds were prepared according to the procedure for Example 12-1 using the appropriate acid.

| Example | Structure | IUPAC Name | Exact Mass [M + H]+ |
|---|---|---|---|
| Example 12-2 | 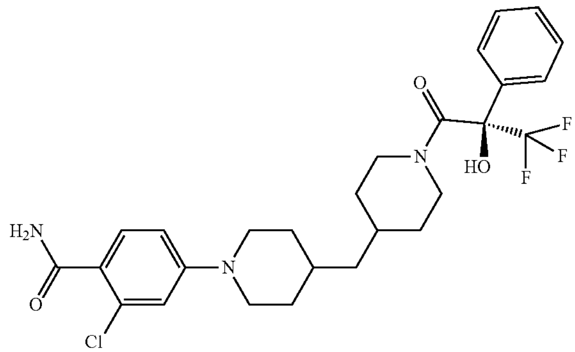 [SMILES: NC(=O)c1ccc(N2CCC(CC3CCN(C(=O)[C@](O)(c4ccccc4)C(F)(F)F)CC3)CC2)cc1Cl] | 2-chloro-4-[4-({1-[(2R)-3,3,3-trifluoro-2-hydroxy-2-phenyl-propanoyl]piperidin-4-yl}methyl)piperidin-1-yl]benzamide | Calc'd 538.2, found 538.4 |
| Example 12-3 | 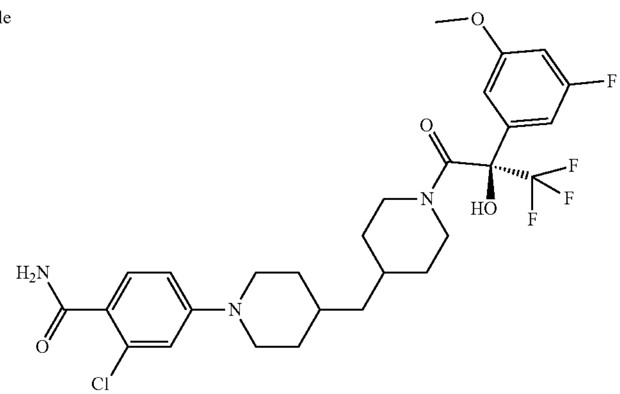 | 2-chloro-4-[4-({1-[(2R)-3,3,3-trifluoro-2-(3-fluoro-5-methoxy-phenyl)-2-hydroxy-propanoyl]piperidin-4-yl}methyl)-piperidin-1-yl]-benzamide | Calc'd 586.2, found 586.4 |
| Example 12-4 | 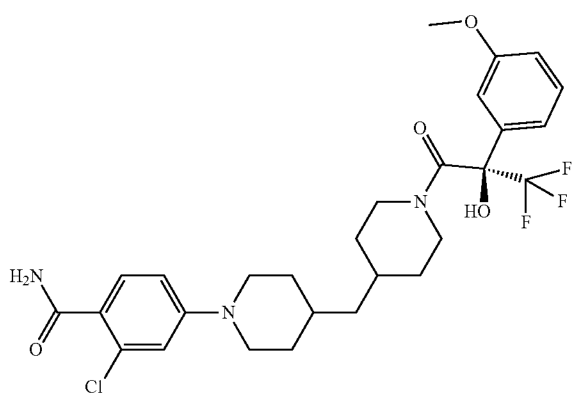 [SMILES: COc1cccc([C@@](O)(C(=O)N2CCC(CC3CCN(c4ccc(C(N)=O)c(Cl)c4)CC3)CC2)C(F)(F)F)c1] | 2-chloro-4-[4-({1-[(2R)-3,3,3-trifluoro-2-hydroxy-2-(3-methoxyphenyl)-propanoyl]piperidin-4-yl}methyl)piperidin-1-yl]benzamide | Calc'd 568.2, found 568.4 |
| Example 12-5 | 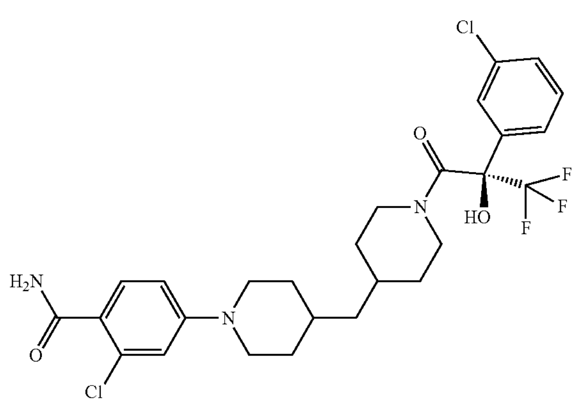 [SMILES: NC(=O)c1ccc(N2CCC(CC3CCN(C(=O)[C@](O)(c4cccc(Cl)c4)C(F)(F)F)CC3)CC2)cc1Cl] | 2-chloro-4-[4-({1-[(2R)-2-(3-chlorophenyl)-3,3,3-trifluoro-2-hydroxypropanoyl]-piperidin-4-yl}-methyl)piperidin-1-yl]benzamide | Calc'd 572.2, found 572.4 |

-continued

| Example | Structure | IUPAC Name | Exact Mass [M + H]+ |
|---|---|---|---|
| Example 12-6 | 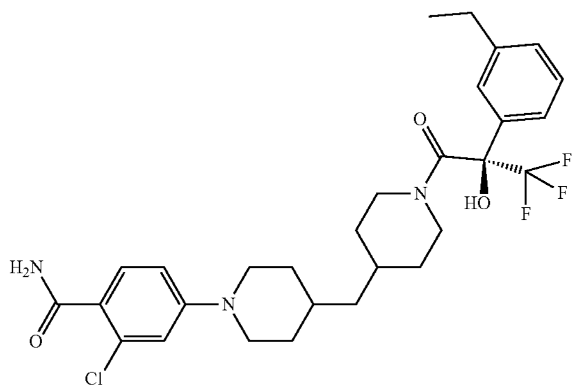 [SMILES: CCc1cccc([C@@](O)(C(=O)N2CCC(CC3CCN(c4ccc(C(N)=O)c(Cl)c4)CC3)CC2)C(F)(F)F)c1] | 2-chloro-4-[4-({1-[(2R)-2-(3-ethylphenyl)-3,3,3-trifluoro-2-hydroxy-propanoyl]piperidin-4-yl}methyl)piperidin-1-yl]benzamide | Calc'd 566.2, found 566.4 |
| Example 12-7 | 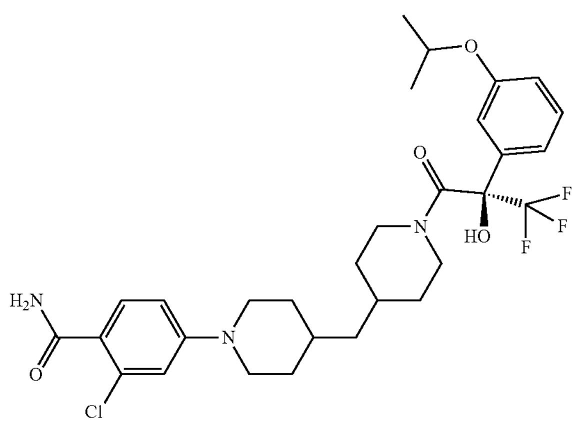 [SMILES: CC(C)Oc1cccc([C@@](O)(C(=O)N2CCC(CC3CCN(c4ccc(C(N)=O)c(Cl)c4)CC3)CC2)C(F)(F)F)c1] | 2-chloro-4-{4-[(1-{(2R)-3,3,3-trifluoro-2-hydroxy-2-[3-(1-methylethoxy)phenyl)-propanoyl}piperidin-4-yl)methyl]piperidin-1-yl}benzamide | Calc'd 596.2, found 596.5 |
| Example 12-8 | 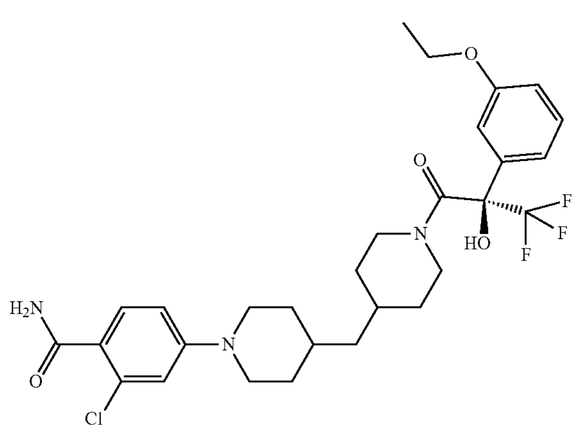 [SMILES: CCOc1cccc([C@@](O)(C(=O)N2CCC(CC3CCN(c4ccc(C(N)=O)c(Cl)c4)CC3)CC2)C(F)(F)F)c1] | 2-chloro-4-[4-({1-[(2R)-2-(3-ethoxyphenyl)-3,3,3-trifluoro-2-hydroxypropanoyl]-piperidin-4-yl}methyl)-piperidin-1-yl]-benzamide | Calc'd 582.2, found 582.4 |

| Example | Structure | IUPAC Name | Exact Mass [M + H]+ |
|---|---|---|---|
| Example 12-9 | 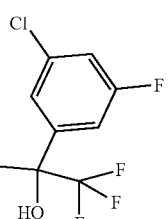 | 2-chloro-4-[4-({1-[2-(3-chloro-5-fluorophenyl)-3,3,3-trifluoro-2-hydroxy-propanoyl]piperidin-4-yl}methyl)piperidin-1-yl]benzamide | Calc'd 590.2, found 590.3 |
| Example 12-10 | 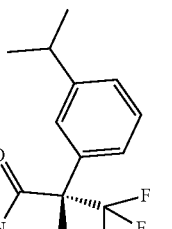 | 2-chloro-4-{4-[(1-{(2R)-3,3,3-trifluoro-2-hydroxy-2-[3-(1-methylethyl)phenyl]-propanoyl}piperidin-4-yl)methyl]piperidin-1-yl}benzamide | Calc'd 580.3, found 580.5 |

Example 13-1: 2-chloro-N,N-dimethyl-4-(4-((1-(2-methyl-2-phenylpropanoyl)piperidin-4-yl)methyl)piperidin-1-yl)benzamide

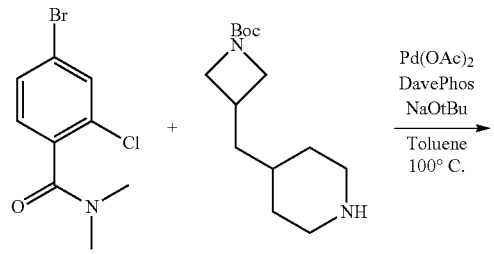

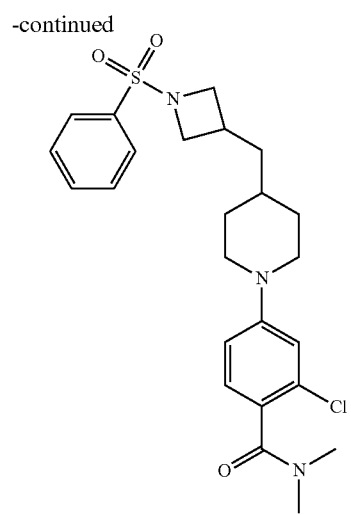

example 13-1

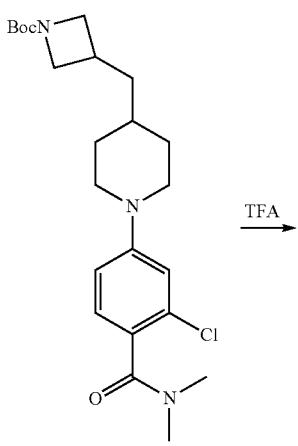

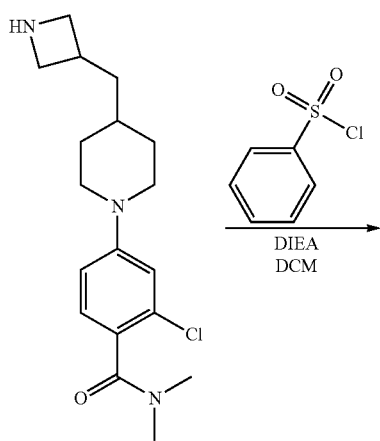

Step 1: tert-butyl 3-((1-(3-chloro-4-(dimethylcarbamoyl)phenyl)piperidin-4-yl)methyl)azetidine-1-carboxylate A mixture of tert-butyl 3-(piperidin-4-ylmethyl)azetidine-1-carboxylate (484 mg, 1.91 mmol), 4-bromo-2-chloro-N,N-dimethylbenzamide (500 mg, 1.91 mmol), 2-2-dicyclohexylphosphino-2'-(N,N-dimethylamino)biphenyl (112 mg, 0.29 mmol), palladium (II) acetate (21.4 mg, 0.095 mmol), and sodium tert-butoxide (549 mg, 5.71 mmol) in Toluene (9.5 ml) was degassed by bubbling with $N_2$ and heated at 100° C. for 3 h. The reaction mixture was filtered and then concentrated to dry. The residue was purified by ISCO column chromatography (ISCO 40 g prepacked, eluting with 0-100% EtOAc/Hexane) to give the title compound (565 mg). LCMS m/z (M+H): Calc'd 436.2, found 436.3.

Step 2: 4-(4-(azetidin-3-ylmethyl)piperidin-1-yl)-2-chloro-N,N-dimethylbenzamide Tert-butyl 3-((1-(3-chloro-4-(dimethylcarbamoyl)phenyl)piperidin-4-yl)methyl)azetidine-1-carboxylate (565 mg, 1.29 mmol) was treated with TFA:DCM (1:4, 13 ml) at rt for 0.5 h. The mixture was concentrated to dryness to give the crude title compound which was used without further purification. LCMS m/z (M+H): Calc'd 336.2, found 336.3.

Step 3: 2-chloro-N,N-dimethyl-4-(4-((1-(phenylsulfonyl)azetidin-3-yl)methyl)piperidin-1-yl)benzamide At 0° C., benzenesulfonyl chloride (26.3 mg, 0.15 mmol) was added to a mixture of 4-(4-(azetidin-3-ylmethyl)piperidin-1-yl)-2-chloro-N,N-dimethylbenzamide (50 mg, 0.15 mmol) and DIEA (130 uL, 0.75 mmol) in DCM (750 uL). After stirring at room temperature overnight, the mxiture was concentrated to dryness and purified by mass-directed HPLC purification (2 cm×5 cm C18, acetonitrile-water gradient, 0.05% TFA added) to give the title compound (26 mg). LCMS m/z (M+H): Calc'd 476.2, found 476.3.

The following compounds were prepared according to the procedure for Example 13-1 using the appropriate intermediates B or available protected diamine, and sulfonyl chlorides.

| Example | Structure | IUPAC Name | Exact Mass [M + H]+ |
|---|---|---|---|
| Example 13-2 | 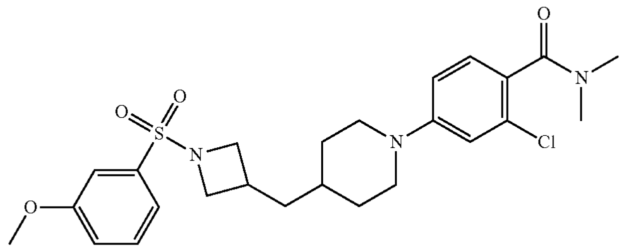 | 2-chloro-4-[4-({1-[(3-methoxyphenyl)-sulfonyl]azetidin-3-yl}methyl)piperidin-1-yl]-N,N-dimethyl-benzamide | Calc'd 506.2, found 506.3 |
| Example 13-3 | 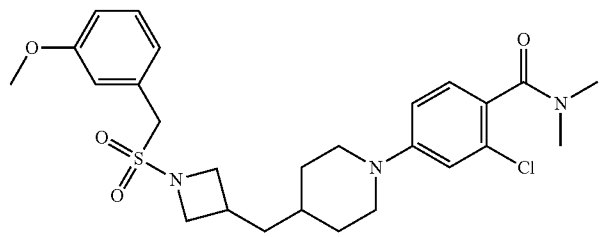 | 2-chloro-4-[4-({1-[(3-methoxybenzyl)-sulfonyl]azetidin-3-yl}methyl)piperidin-1-yl]-N,N-dimethyl-benzamide | Calc'd 520.2, found 520.3 |
| Example 13-4 | 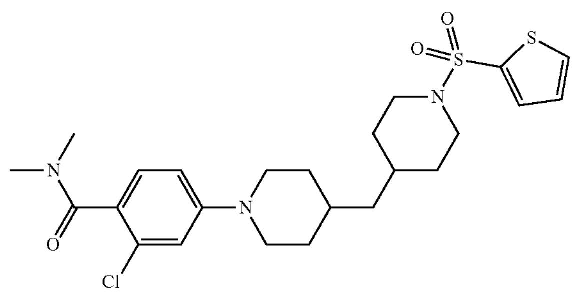 [SMILES: CN(C)C(=O)c1ccc(N2CCC(CC3CCN(S(=O)(=O)c4cccs4)CC3)CC2)cc1Cl] | 2-chloro-N,N-dimethyl-4-(4-{[1-(thiopen-2-ylsulfonyl)piperidin-4-yl]methyl}piperidin-1-yl)benzamide | Calc'd 510.2, found 510.2 |
| Example 13-5 | 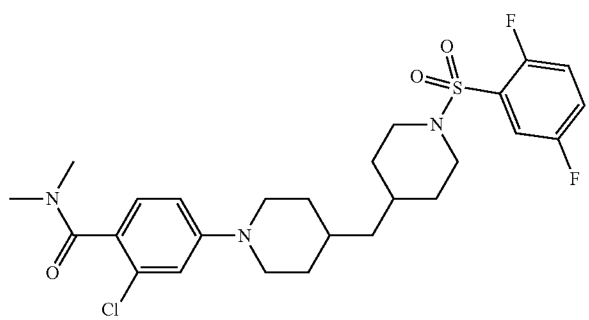 [SMILES: CN(C)C(=O)c1ccc(N2CCC(CC3CCN(S(=O)(=O)c4cc(F)ccc4F)CC3)CC2)cc1Cl] | 2-chloro-4-[4-({1-[(2,5-difluorophenyl)-sulfonyl]piperidin-4-yl}methyl)piperidin-1-yl]-N,N-dimethylbenzamide | Calc'd 540.2, found 540.3 |
| Example 13-6 | 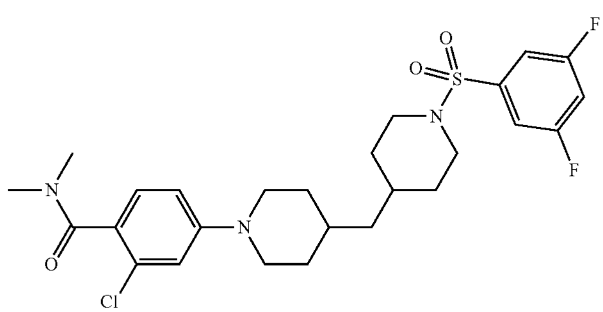 [SMILES: CN(C)C(=O)c1ccc(N2CCC(CC3CCN(S(=O)(=O)c4cc(F)cc(F)c4)CC3)CC2)cc1Cl] | 2-chloro-4-[4-({1-[(3,5-difluorophenyl)-sulfonyl]piperidin-4-yl}methyl)piperidin-1-yl]-N,N-dimethylbenzamide | Calc'd 540.2, found 540.3 |

| Example | Structure | IUPAC Name | Exact Mass [M + H]+ |
|---|---|---|---|
| Example 13-7 | 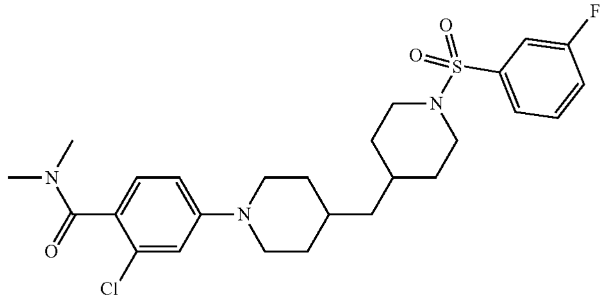 [SMILES: CN(C)C(=O)c1ccc(N2CCC(CC3CCN(S(=O)(=O)c4cccc(F)c4)CC3)CC2)cc1Cl] | 2-chloro-4-[4-({1-[(3-fluorophenyl)sulfonyl]-piperidin-4-yl}methyl)-piperidin-1-yl]-N,N-dimethylbenzamide | Calc'd 522.2, found 522.3 |
| Example 13-8 | 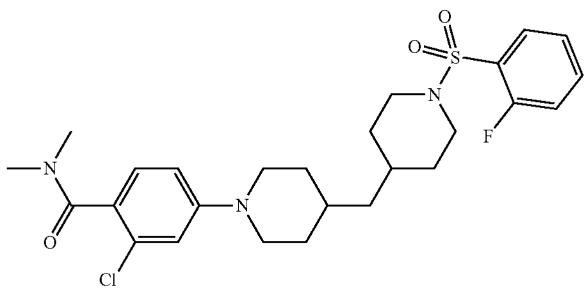 [SMILES: CN(C)C(=O)c1ccc(N2CCC(CC3CCN(S(=O)(=O)c4ccccc4F)CC3)CC2)cc1Cl] | 2-chloro-4-[4-({1-[(2-fluorophenyl)sulfonyl]-piperidin-4-yl}methyl)-piperidin-1-yl]-N,N-dimethylbenzamide | Calc'd 522.2, found 522.3 |
| Example 13-9 | 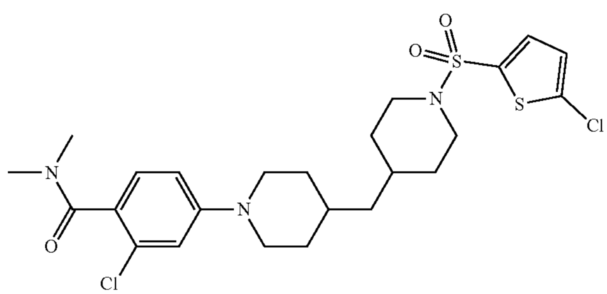 [SMILES: CN(C)C(=O)c1ccc(N2CCC(CC3CCN(S(=O)(=O)c4ccc(Cl)s4)CC3)CC2)cc1Cl] | 2-chloro-4-[4-({1-[(5-chlorothiophen-2-yl)-sulfonyl]piperidin-4-yl}methyl)piperidin-1-yl]-N,N-dimethylbenzamide | Calc'd 544.1, found 544.2 |
| Example 13-10 | 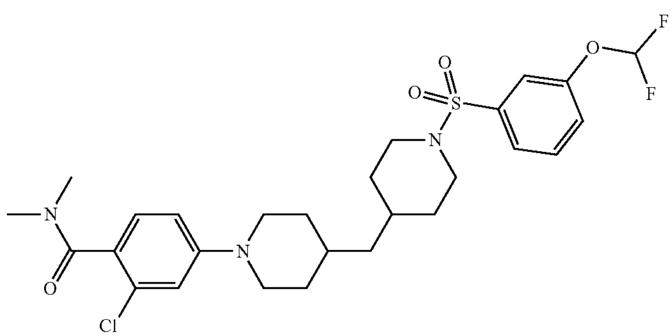 [SMILES: CN(C)C(=O)c1ccc(N2CCC(CC3CCN(S(=O)(=O)c4cccc(OC(F)F)c4)CC3)CC2)cc1Cl] | 2-chloro-4-{4[(1-{[3-(difluoromethoxy)-phenyl]sulfonyl}-piperidin-4-yl)methyl]-piperidin-1-yl}-N,N-dimethylbenzamide | Calc'd 570.2, found 570.3 |
| Example 13-11 | 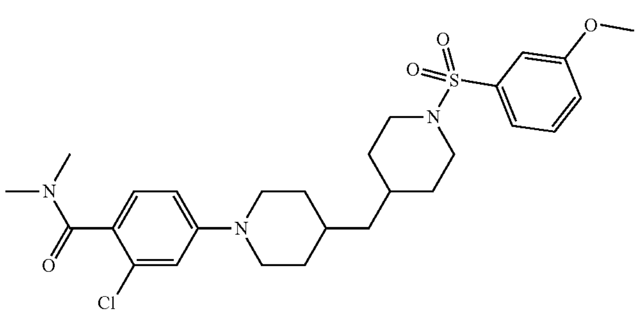 | 2-chloro-4-[4({1-[(3-methoxyphenyl)-sulfonyl]piperidin-4-yl}methyl)piperidin-1-yl]-N,N-dimethyl-benzamide | Calc'd 534.2, found 534.3 |

| Example | Structure | IUPAC Name | Exact Mass [M + H]+ |
|---|---|---|---|
| Example 13-12 | 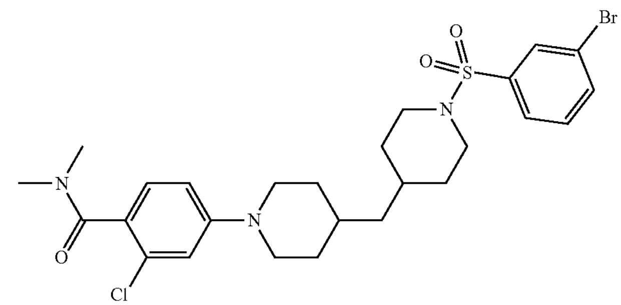 [SMILES: CN(C)C(=O)c1ccc(N2CCC(CC3CCN(S(=O)(=O)c4cccc(Br)c4)CC3)CC2)cc1Cl] | 4-[4-({1-[(3-bromo-phenyl)sulfonyl]-piperidin-4-yl}methyl)-piperidin-1-yl]-2-chloro-N,N-dimethyl-benzamide | Calc'd 582.1, found 582.2 |
| Example 13-13 | 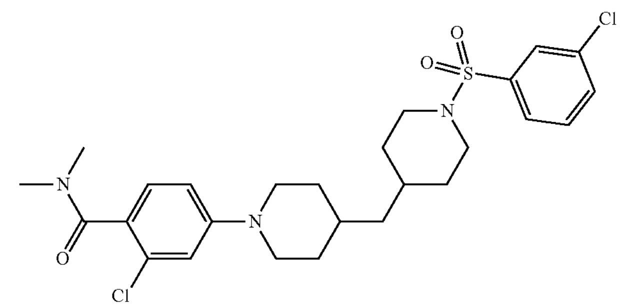 [SMILES: CN(C)C(=O)c1ccc(N2CCC(CC3CCN(S(=O)(=O)c4cccc(Cl)c4)CC3)CC2)cc1Cl] | 2-chloro-4-[4-({1-[(3-chlorophenyl)sulfonyl]-piperidin-4-yl}methyl)-piperidin-1-yl]-N,N-dimethylbenzamide | Calc'd 538.2, found 538.3 |
| Example 13-14 | 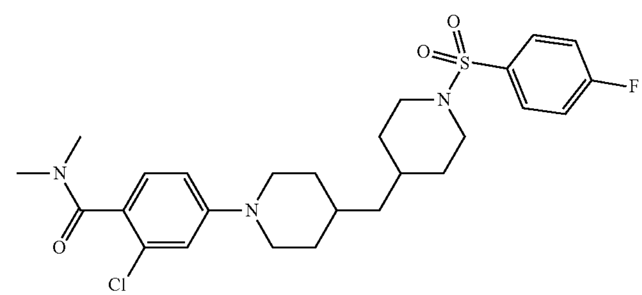 [SMILES: CN(C)C(=O)c1ccc(N2CCC(CC3CCN(S(=O)(=O)c4ccc(F)cc4)CC3)CC2)cc1Cl] | 2-chloro-4-[4-({1-[(4-fluorophenyl)sulfonyl]-piperidin-4-yl}methyl)-piperidin-1-yl]-N,N-dimethylbenzamide | Calc'd 522.2, found 522.3 |
| Example 13-15 | 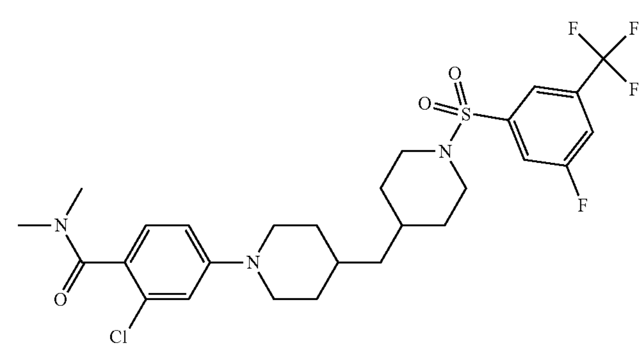 [SMILES: CN(C)C(=O)c1ccc(N2CCC(CC3CCN(S(=O)(=O)c4cc(F)cc(C(F)(F)F)c4)CC3)CC2)cc1Cl] | 2-chloro-4-{4-[(1-{[3-fluoro-5-(trifluoro-methyl)phenyl]-sulfonyl}piperidin-4-yl)methyl]piperidin-1-yl}-N,N-dimethylbenzamide | Calc'd 590.2, found 590.3 |

| Example | Structure | IUPAC Name | Exact Mass [M + H]+ |
|---|---|---|---|
| Example 13-16 | 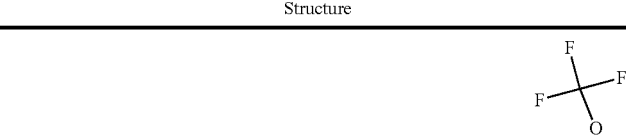 | 2-chloro-N,N-dimethyl-4-{4-[1-{[3-(trifluoromethoxy)phenyl]sulfonyl}piperidin-4-yl)methyl]piperidin-1-yl}benzamide | Calc'd 588.2, found 588.3 |

Example 14-1: (R)—N,N,2-trimethyl-6-(4-((1-(3,3,3-trifluoro-2-hydroxy-2-phenylpropanoyl)piperidin-4-yl)methyl)piperidin-1-yl)nicotinamide

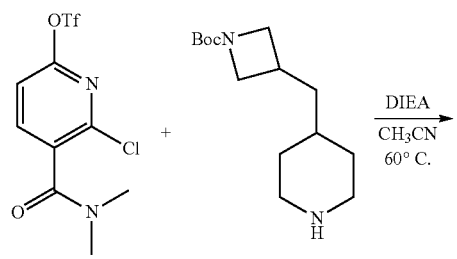

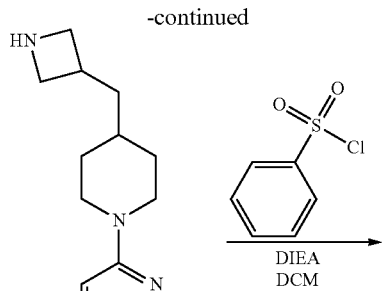

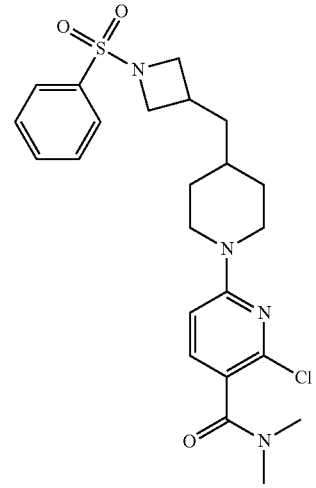

example 14-1

Step 1: tert-butyl 3-((1-(6-chloro-5-(dimethylcarbamoyl)pyridin-2-yl)piperidin-4-yl)methyl)azetidine-1-carboxylate A mixture of 6-chloro-5-(dimethylcarbamoyl)pyridin-2-yl trifluoromethanesulfonate (600 mg, 1.80 mmol), tert-butyl 3-(piperidin-4-ylmethyl)azetidine-1-carboxylate (459 mg, 1.80 mmol), and DIEA (945 uL, 5.41 mmol) in CH₃CN (9.0 mL) was degassed by bubbling with N₂ and heated at 60° C. for 3 h under microwave condition. The reaction mixture was concentrated and purified by ISCO column chromatography (silica gel ISCO 40 g prepacked column, eluting with 0-10% MeOH/CH₂Cl₂) to give the title compound (515 mg). LCMS m/z (M+H): Calc'd 437.2, found 437.3.

Step 2: 6-(4-(azetidin-3-ylmethyl)piperidin-1-yl)-2-chloro-N,N-dimethylnicotinamide Tert-butyl 4-((1-(4-(dimethylcarbamoyl)-3-isopropylphenyl)piperidin-4-yl)methyl)piperidine-1-carboxylate (515 mg, 1.18 mmol) was treated with TFA:DCM (1:4, 12 mL) at room temperature for 0.5 h. The mixture was concentrated to dryness to give the crude title compound which was used without further purification. LCMS m/z (M+H): Calc'd 337.2, found 337.3.

Step 3: 2-chloro-N,N-dimethyl-6-(4-((1-(phenylsulfonyl)azetidin-3-yl)methyl)piperidin-1-yl)nicotinamide At 0° C., benzenesulfonyl chloride (26.2 mg, 0.148 mmol) was added to a mixture of 6-(4-(azetidin-3-ylmethyl) piperidin-1-yl)-2-chloro-N,N-dimethylnicotinamide (50 mg, 0.148 mmol) and DIEA (130 uL, 0.75 mmol) in DCM (750 uL). After stirring at room temperature overnight, the mxiture was concentrated to dryness and purified by mass-directed HPLC purification (2 cm×5 cm C18, acetonitrile-water gradient, 0.05% TFA added) to give the title compound (19 mg). LCMS m/z (M+H): Calc'd 477.2, found 477.3.

The following compounds were prepared according to the procedure for Example 14-1 using the appropriate sulfonyl chlorides.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

Biological Assays

Potency (Inflection Point, IP) and efficacy (Emax) are evaluated via compound-induced co-activator recruitment to glutathione-S-transferase (GST) tagged LXRbeta and LXRalpha LBD (ligand binding domain) proteins in relation to reference dual agonist compound T0901317 (N-(2,2,2-Trifluoroethyl)-N-[4-[2,2,2-trifluoro-1-hydroxy-1-(trifluoromethyl)ethyl] phenyl] benzenesulfonamide) using the LanthaScreen™ TR-FRET Liver X Receptor Coactivator Assays according to manufacturer's instructions (Invitrogen catalog number pv4658.pps and pv4655). While running the LanthaScreen™ TR-FRET Liver X Receptor Coactivator Assay, LXR alpha-LBD or LXR beta-LBD was added to ligand test compounds followed by addition of a mixture of a fluorescein-labelled coactivator peptide and terbium-conjugated anti-GST antibody. After an incubation period at room temperature, TR-FRET (time-resolved fluorescence resonance energy transfer) was measured using a filter-based instrument capable of TR-FRET, e.g. PerkinElmer Envision. When the terbium label on the anti-GST antibody was excited at 340 nm, energy was transferred to the fluorescein label on the coactivator peptide and detected as emission at 520 nm, providing an indication of ligand binding that enables ligand-dependent recruitment of coactivator peptide, and the ratio of 520 nm:495 nm is calculated and is used to determine the ligands potencies and efficacies from appropriate dose response curves of the compound. IP and % Emax values for compounds of the invention were measured in accordance with the above and are provided in the Table below.

| Example | Structure | IUPAC Name | Exact Mass [M + H]+ |
|---|---|---|---|
| Example 14-2 | 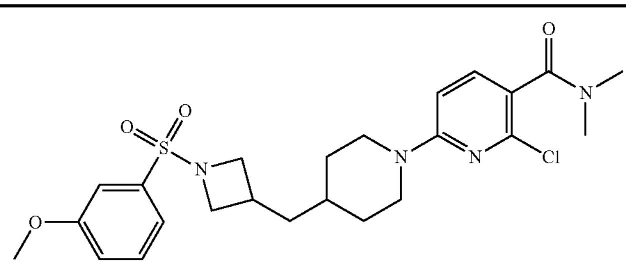 | 2-chloro-6-[4-({1-[(3-methoxyphenyl)-sulfonyl]azetidin-3-yl}methyl)piperidin-1-yl}-N,N-dimethyl-pyridine-3-carboxamide | Calc'd 507.2, found 507.3 |
| Example 14-3 | 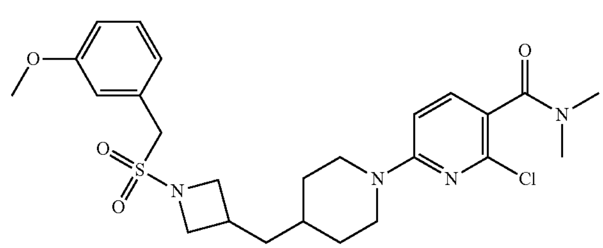 | 2-chloro-6-[4({1-[(3-methoxybenzyl)-sulfonyl]azetidin-3-yl}methyl)piperidin-1-yl]-N,N-dimethyl-pyridine-3-carboxamide | Calc'd 521.2, found 521.3 |

| Example | LXR beta IP (nM) | LXR beta Activity @ max dose (%) | LXR alpha IP (nM) | LXR alpha Activity @ max dose (%) |
| --- | --- | --- | --- | --- |
| Example 1-1 | 136 | 63 | 844 | 22 |
| Example 1-2 | 240 | 58 | NO IP | 13 |
| Example 2-1 | 157 | 59 | NO IP | 5 |
| Example 2-2 | 155 | 43 | NO IP | 5 |
| Example 2-3 | 26 | 50 | NO IP | 6 |
| Example 2-4 | 19 | 80 | 461 | 24 |
| Example 2-5 | 29 | 57 | 752 | 19 |
| Example 2-6 | 22 | 60 | 875 | 26 |
| Example 2-7 | 17 | 80 | 464 | 30 |
| Example 2-8 | 352 | 40 | NO IP | 0 |
| Example 2-9 | 97 | 48 | NO IP | 0 |
| Example 2-10 | 50 | 60 | NO IP | 0 |
| Example 2-11 | 33 | 83 | 1108 | 33 |
| Example 2-12 | 157 | 79 | 531 | 25 |
| Example 2-13 | 8 | 119 | 177 | 56 |
| Example 2-14 | 422 | 89 | NO IP | 14 |
| Example 2-15 | 298 | 26 | NO IP | 0 |
| Example 2-16 | 598 | 15 | NO IP | 0 |
| Example 2-17 | 11 | 63 | 140 | 24 |
| Example 2-18 | 151 | 46 | NO IP | 6 |
| Example 2-19 | 206 | 75 | 1813 | 23 |
| Example 2-20 | 335 | 81 | NO IP | 4 |
| Example 2-21 | 145 | 65 | NO IP | 0 |
| Example 2-22 | 21 | 131 | 900 | 51 |
| Example 2-23 | 513 | 51 | NO IP | 0 |
| Example 2-24 | 14 | 99 | 465 | 37 |
| Example 2-25 | 28 | 89 | 695 | 26 |
| Example 2-26 | 23 | 68 | NO IP | 0 |
| Example 2-27 | 371 | 82 | 4622 | 19 |
| Example 2-28 | 25 | 87 | 1736 | 28 |
| Example 2-29 | 3792 | 65 | NO IP | 25 |
| Example 2-30 | 36 | 64 | 821 | 25 |
| Example 2-31 | 784 | 74 | 4449 | 24 |
| Example 2-32 | 72 | 55 | 1424 | 19 |
| Example 2-33 | 722 | 75 | NO IP | 5 |
| Example 2-34 | 494 | 69 | NO IP | 1 |
| Example 2-35 | 8 | 44 | NO IP | 6 |
| Example 2-36 | 110 | 126 | 1061 | 43 |
| Example 2-37 | 29 | 73 | 620 | 33 |
| Example 2-38 | 49 | 67 | 575 | 15 |
| Example 2-39 | 36 | 30 | 1775 | 2 |
| Example 2-40 | 72 | 34 | NO IP | 9 |
| Example 2-41 | 14 | 63 | NO IP | 10 |
| Example 2-42 | 12 | 76 | 162 | 25 |
| Example 2-43 | 11 | 75 | 147 | 16 |
| Example 2-44 | 1 | 37 | 32 | 20 |
| Example 2-45 | 7 | 18 | NO IP | 0 |
| Example 2-46 | 9 | 102 | 216 | 31 |
| Example 2-47 | 4 | 49 | NO IP | 7 |
| Example 2-48 | 27 | 30 | NO IP | 0 |
| Example 2-49 | 6 | 59 | NO IP | 5 |
| Example 2-50 | 8 | 29 | NO IP | 0 |
| Example 2-51 | 32 | 57 | NO IP | 11 |
| Example 2-52 | 15 | 20 | NO IP | 0 |
| Example 2-53 | 5 | 50 | NO IP | 0 |
| Example 2-54 | 4 | 79 | 38 | 23 |
| Example 2-55 | 8 | 44 | NO IP | 0 |
| Example 2-56 | 18 | 37 | NO IP | 2 |
| Example 2-57 | 5 | 67 | 37 | 27 |
| Example 2-58 | 16 | 88 | 951 | 38 |
| Example 2-59 | 18 | 62 | NO IP | 3 |
| Example 2-60 | 26 | 66 | NO IP | 2 |
| Example 2-61 | 7 | 74 | 277 | 21 |
| Example 2-62 | 20 | 71 | NO IP | 0 |
| Example 2-63 | 21 | 79 | 1509 | 22 |
| Example 2-64 | 30 | 75 | 1074 | 18 |
| Example 2-65 | 17 | 89 | 694 | 35 |
| Example 2-66 | 50 | 69 | NO IP | 14 |
| Example 2-67 | 19 | 77 | NO IP | 9 |
| Example 2-68 | 22 | 63 | NO IP | 16 |
| Example 2-69 | 1113 | 112 | NO IP | 16 |
| Example 2-70 | 92 | 48 | NO IP | 2 |
| Example 2-71 | 84 | 64 | NO IP | 9 |
| Example 2-72 | 74 | 39 | NO IP | 0 |
| Example 2-73 | 223 | 77 | 5366 | 35 |
| Example 2-74 | 39 | 87 | 444 | 38 |
| Example 2-75 | 12 | 80 | 167 | 31 |
| Example 2-76 | 14 | 46 | NO IP | 4 |
| Example 2-77 | 45 | 44 | NO IP | 2 |
| Example 2-78 | 32 | 20 | NO IP | 1 |
| Example 2-79 | 40 | 30 | NO IP | 0 |
| Example 2-80 | 19 | 19 | NO IP | 0 |
| Example 2-81 | 39 | 103 | 798 | 40 |
| Example 2-82 | 12 | 50 | NO IP | 13 |
| Example 2-83 | 4 | 68 | 83 | 26 |
| Example 2-84 | 7 | 83 | 140 | 38 |
| Example 2-85 | 17 | 68 | 554 | 21 |
| Example 2-86 | 6 | 68 | 98 | 22 |
| Example 2-87 | 19 | 74 | NO IP | 14 |
| Example 2-88 | 11 | 79 | 137 | 29 |
| Example 2-89 | 21 | 83 | 304 | 23 |
| Example 2-90 | 78 | 99 | 3549 | 46 |
| Example 2-91 | 23 | 58 | 199 | 20 |
| Example 2-92 | 12 | 56 | NO IP | 3 |
| Example 2-93 | 5 | 59 | NO IP | 7 |
| Example 2-94 | 4 | 89 | 50 | 48 |
| Example 2-95 | 6 | 50 | 341 | 15 |
| Example 2-96 | 4 | 63 | 66 | 20 |
| Example 2-97 | 40 | 20 | NO IP | 0 |
| Example 2-98 | 8 | 20 | NO IP | 0 |
| Example 2-99 | 8 | 37 | NO IP | 0 |
| Example 2-100 | 6 | 24 | NO IP | 0 |
| Example 2-101 | 114 | 106 | 1771 | 21 |
| Example 2-102 | 2 | 81 | 29 | 36 |
| Example 2-103 | 181 | 16 | NO IP | 0 |
| Example 2-104 | 409 | 31 | NO IP | 3 |
| Example 2-105 | 21 | 48 | NO IP | 12 |
| Example 2-106 | 10 | 19 | NO IP | 0 |
| Example 2-107 | 238 | 14 | 309 | 4 |
| Example 2-108 | 33 | 10 | NO IP | 0 |
| Example 2-109 | 72 | 75 | 982 | 26 |
| Example 2-110 | 54 | 50 | NO IP | 17 |
| Example 2-111 | 7 | 28 | NO IP | 0 |
| Example 2-112 | 8 | 44 | NO IP | 10 |
| Example 2-113 | 15 | 36 | NO IP | 4 |
| Example 2-114 | 266 | 19 | NO IP | 6 |
| Example 2-115 | 53 | 30 | NO IP | 0 |
| Example 2-116 | 7 | 58 | 227 | 20 |
| Example 2-117 | 22 | 125 | 1007 | 29 |
| Example 2-118 | 219 | 68 | NO IP | 11 |
| Example 2-119 | 208 | 99 | NO IP | 11 |
| Example 2-120 | 16 | 46 | NO IP | 6 |
| Example 2-121 | 7 | 51 | NO IP | 0 |
| Example 2-122 | 27 | 69 | 543 | 29 |
| Example 2-123 | 335 | 106 | 1473 | 21 |
| Example 2-124 | 43 | 55 | NO IP | 4 |
| Example 2-125 | 52 | 64 | 459 | 15 |
| Example 2-126 | 38 | 118 | 126 | 33 |
| Example 2-127 | 877 | 68 | NO IP | 9 |
| Example 2-128 | 58 | 73 | 1037 | 34 |
| Example 2-129 | 51 | 51 | NO IP | 5 |
| Example 2-130 | 191 | 31 | NO IP | 0 |
| Example 2-131 | 53 | 59 | NO IP | 10 |
| Example 2-132 | 51 | 49 | NO IP | 7 |
| Example 2-133 | 36 | 54 | NO IP | 6 |
| Example 2-134 | 120 | 67 | 1984 | 18 |
| Example 2-135 | 44 | 63 | NO IP | 3 |
| Example 2-136 | 69 | 64 | 714 | 20 |
| Example 2-137 | 30 | 78 | NO IP | 15 |
| Example 2-138 | 74 | 35 | NO IP | 0 |
| Example 2-139 | 14 | 95 | 266 | 36 |
| Example 2-140 | 84 | 118 | 836 | 43 |
| Example 2-141 | 74 | 51 | NO IP | 12 |
| Example 2-142 | 60 | 60 | NO IP | 4 |
| Example 2-143 | 46 | 69 | 413 | 23 |
| Example 2-144 | 78 | 55 | NO IP | 14 |
| Example 2-145 | 73 | 54 | NO IP | 4 |
| Example 2-146 | 33 | 64 | NO IP | 10 |

| Example | LXR beta IP (nM) | LXR beta Activity @ max dose (%) | LXR alpha IP (nM) | LXR alpha Activity @ max dose (%) | Example | LXR beta IP (nM) | LXR beta Activity @ max dose (%) | LXR alpha IP (nM) | LXR alpha Activity @ max dose (%) |
|---|---|---|---|---|---|---|---|---|---|
| Example 2-147 | 19 | 52 | NO IP | 7 | Example 7-18 | 6 | 80 | 442 | 34 |
| Example 2-148 | 24 | 62 | 400 | 22 | Example 7-19 | 7 | 61 | NO IP | 3 |
| Example 2-149 | 20 | 54 | NO IP | 14 | Example 7-20 | 6 | 79 | NO IP | 29 |
| Example 2-150 | 23 | 56 | NO IP | 15 | Example 7-21 | 169 | 70 | NO IP | 2 |
| Example 2-151 | 9 | 45 | NO IP | 4 | Example 7-22 | 1270 | 45 | NO IP | 0 |
| Example 2-152 | 11 | 74 | NO IP | 18 | Example 7-23 | 1226 | 54 | NO IP | 0 |
| Example 2-153 | 8 | 95 | 123 | 41 | Example 7-24 | 92 | 106 | NO IP | 7 |
| Example 2-154 | 23 | 54 | NO IP | 6 | Example 7-25 | 20 | 77 | 343 | 44 |
| Example 2-155 | 25 | 69 | 386 | 33 | Example 7-26 | 125 | 115 | 2259 | 35 |
| Example 2-156 | 21 | 42 | NO IP | 12 | Example Ϊ-Y1 | 446 | 113 | 4391 | 27 |
| Example 2-157 | 16 | 43 | NO IP | 9 | Example 7-28 | 243 | 105 | 2016 | 28 |
| Example 2-158 | 20 | 44 | NO IP | 6 | Example 7-29 | 176 | 102 | 3244 | 25 |
| Example 2-159 | 21 | 65 | 156 | 22 | Example 7-30 | 91 | 120 | 3786 | 50 |
| Example 2-160 | 26 | 33 | NO IP | 12 | Example 7-31 | 52 | 112 | 1583 | 40 |
| Example 2-161 | 13 | 28 | NO IP | 0 | Example 7-32 | 184 | 92 | 4239 | 18 |
| Example 2-162 | 502 | 38 | NO IP | 12 | Example 7-33 | 10 | 60 | NO IP | 12 |
| Example 2-163 | 728 | 39 | NO IP | 0 | Example 7-34 | 169 | 82 | 2194 | 19 |
| Example 2-164 | 12 | 70 | 294 | 29 | Example 7-35 | 96 | 78 | 784 | 25 |
| Example 2-165 | 2.5 | 108 | NO IP | 18 | Example 7-36 | 28 | 65 | 762 | 19 |
| Example 2-166 | 14 | 46 | 296 | 20 | Example 7-37 | 16 | 90 | 340 | 27 |
| Example 2-167 | 37 | 75 | NO IP | 18 | Example 7-38 | 136 | 67 | NO IP | 1 |
| Example 2-168 | 58 | 21 | NO IP | 0 | Example 7-39 | 91 | 59 | NO IP | 0 |
| Example 2-169 | 11 | 71 | NO IP | 17 | Example 7-40 | 4 | 113 | 291 | 49 |
| Example 2-170 | 27 | 19 | NO IP | 0 | Example 7-41 | 11 | 110 | 525 | 35 |
| Example 3-1 | 35 | 63 | NO IP | 5 | Example 7-42 | 30 | 83 | NO IP | 9 |
| Example 4-1 | 53 | 72 | 555 | 31 | Example 7-43 | 33 | 80 | NO IP | 16 |
| Example 4-2 | 29 | 73 | 270 | 30 | Example 7-44 | 34 | 75 | NO IP | 8 |
| Example 4-3 | 5 | 63 | 50 | 30 | Example 7-45 | 22 | 92 | NO IP | 14 |
| Example 4-4 | 179 | 56 | 459 | 24 | Example 7-46 | 2 | 109 | 40 | 46 |
| Example 4-5 | 59 | 53 | 401 | 29 | Example 7-47 | 3 | 66 | 60 | 22 |
| Example 4-6 | 38 | 78 | 331 | 39 | Example 7-48 | 10 | 64 | NO IP | 16 |
| Example 4-7 | 31 | 76 | 516 | 50 | Example 7-49 | 6 | 40 | NO IP | 8 |
| Example 4-8 | 172 | 93 | 984 | 37 | Example 7-50 | 10 | 47 | NO IP | 6 |
| Example 4-9 | 17 | 69 | 195 | 31 | Example 7-51 | 5 | 35 | NO IP | 4 |
| Example 4-10 | 8 | 62 | 246 | 30 | Example 7-52 | 5 | 69 | 120 | 14 |
| Example 4-11 | 43 | 74 | 402 | 38 | Example 7-53 | 31 | 118 | 571 | 45 |
| Example 4-12 | 14 | 83 | 166 | 34 | Example 7-54 | 10 | 77 | 356 | 21 |
| Example 4-13 | 21 | 62 | 678 | 30 | Example 7-55 | 5 | 59 | 141 | 9 |
| Example 4-14 | 117 | 88 | 2171 | 42 | Example 7-56 | 20 | 114 | 429 | 37 |
| Example 4-15 | 38 | 87 | 1302 | 40 | Example 7-57 | 16 | 123 | 438 | 39 |
| Example 4-16 | 183 | 64 | 688 | 28 | Example 7-58 | 11 | 80 | 274 | 19 |
| Example 4-17 | 270 | 45 | 1018 | 27 | Example 7-59 | 293 | 107 | 2681 | 39 |
| Example 4-18 | 59 | 67 | 485 | 39 | Example 7-60 | 7 | 153 | 148 | 60 |
| Example 4-19 | 141 | 43 | 765 | 25 | Example 7-61 | 45 | 68 | 817 | 21 |
| Example 4-20 | 95 | 63 | 541 | 34 | Example 7-62 | 82 | 119 | 1353 | 31 |
| Example 4-21 | 74 | 63 | 457 | 25 | Example 7-63 | 6 | 102 | 158 | 39 |
| Example 4-22 | 35 | 38 | NO IP | 0 | Example 7-64 | 57 | 80 | 663 | 19 |
| Example 4-23 | 51 | 30 | NO IP | 4 | Example 7-65 | 48 | 95 | 658 | 29 |
| Example 4-24 | 7 | 28 | NO IP | 0 | Example 7-66 | 83 | 108 | 1592 | 48 |
| Example 4-25 | 3 | 40 | NO IP | 0 | Example 7-67 | 4 | 73 | 109 | 0 |
| Example 4-26 | 4 | 67 | NO IP | 3 | Example 7-68 | 64 | 118 | 1020 | 12 |
| Example 5-1 | 12350 | 31 | NO IP | 5 | Example 7-69 | 3 | 82 | 70 | 30 |
| Example 6-1 | 84 | 60 | 9032 | 29 | Example 7-70 | 25 | 110 | 1252 | 34 |
| Example 6-2 | 533 | 98 | NO IP | 14 | Example 7-71 | 55 | 122 | 2055 | 45 |
| Example 6-3 | 2546 | 37 | NO IP | 18 | Example 7-72 | 3 | 91 | 88 | 50 |
| Example 6-4 | 192 | 34 | NO IP | 4 | Example 7-73 | 47 | 128 | 922 | 47 |
| Example 7-1 | 19 | 80 | 895 | 35 | Example 7-74 | 7 | 61 | NO IP | 9 |
| Example 7-2 | 4671 | 32 | NO IP | 36 | Example 7-75 | 10 | 67 | NO IP | 13 |
| Example 7-3 | 153 | 71 | 2182 | 23 | Example 7-76 | 10 | 56 | NO IP | 10 |
| Example 7-4 | 52 | 63 | 1327 | 19 | Example 7-77 | 10 | 53 | NO IP | 6 |
| Example 7-5 | 25 | 69 | NO IP | 8 | Example 7-78 | 6 | 95 | 298 | 31 |
| Example 7-6 | 46 | 70 | NO IP | 11 | Example 7-79 | 9 | 86 | 429 | 22 |
| Example 7-7 | 36 | 95 | 508 | 24 | Example 7-80 | 12 | 85 | 425 | 27 |
| Example 7-8 | 12 | 53 | NO IP | 6 | Example 7-81 | 206 | 51 | NO IP | 19 |
| Example 7-9 | 12 | 70 | NO IP | 3 | Example 7-82 | 7 | 111 | 106 | 53 |
| Example 7-10 | 136 | 77 | 20 | 28 | Example 7-83 | 8 | 53 | NO IP | 13 |
| Example 7-11 | 19 | 73 | NO IP | 8 | Example 7-84 | 13 | 54 | NO IP | 11 |
| Example 7-12 | 24 | 71 | NO IP | 6 | Example 7-85 | 236 | 29 | NO IP | 7 |
| Example 7-13 | 1149 | 72 | NO IP | 4 | Example 7-86 | 165 | 75 | NO IP | 32 |
| Example 7-14 | 105 | 100 | NO IP | 0 | Example 7-87 | 7 | 69 | 252 | 23 |
| Example 7-15 | 1427 | 91 | NO IP | 0 | Example 7-88 | 4 | 52 | NO IP | 15 |
| Example 7-16 | 66 | 65 | NO IP | 8 | Example 7-89 | 6 | 86 | 112 | 19 |
| Example 7-17 | 1294 | 36 | NO IP | 0 | Example 7-90 | 6 | 41 | NO IP | 10 |

| Example | LXR beta IP (nM) | LXR beta Activity @ max dose (%) | LXR alpha IP (nM) | LXR alpha Activity @ max dose (%) |
|---|---|---|---|---|
| Example 7-91 | 8 | 58 | NO IP | 14 |
| Example 7-92 | 6 | 51 | NO IP | 8 |
| Example 7-93 | 6 | 55 | NO IP | 1 |
| Example 7-94 | 72 | 62 | NO IP | 10 |
| Example 7-95 | 98 | 21 | NO IP | 1 |
| Example 7-96 | 89 | 23 | NO IP | 5 |
| Example 7-97 | 40 | 98 | 1183 | 38 |
| Example 7-98 | 74 | 76 | 1086 | 19 |
| Example 7-99 | 48 | 74 | 2795 | 20 |
| Example 7-100 | 200 | 37 | NO IP | 4 |
| Example 7-101 | 4 | 84 | 41 | 22 |
| Example 7-102 | 78 | 114 | NO IP | 16 |
| Example 7-103 | 31 | 122 | 1685 | 47 |
| Example 7-104 | 3 | 51 | NO IP | 0 |
| Example 7-105 | 76 | 30 | NO IP | 0 |
| Example 7-106 | 5 | 41 | NO IP | 0 |
| Example 7-107 | 3 | 26 | NO IP | 0 |
| Example 7-108 | 47 | 101 | NO IP | 10 |
| Example 7-109 | 4 | 107 | 51 | 52 |
| Example 7-110 | 118 | 54 | NO IP | 10 |
| Example 7-111 | 49 | 151 | 1748 | 49 |
| Example 7-112 | 3 | 96 | 65 | 45 |
| Example 7-113 | 34 | 125 | 1607 | 31 |
| Example 7-114 | 236 | 21 | NO IP | 0 |
| Example 7-115 | 5 | 60 | 251 | 17 |
| Example 7-116 | 13 | 76 | NO IP | 9 |
| Example 7-117 | 25 | 35 | NO IP | 0 |
| Example 7-118 | 7 | 98 | 243 | 20 |
| Example 7-119 | 12 | 82 | 182 | 32 |
| Example 7-120 | 22 | 60 | NO IP | 12 |
| Example 7-121 | 21 | 69 | NO IP | 11 |
| Example 7-122 | 9 | 104 | 94 | 54 |
| Example 7-123 | 17 | 73 | 307 | 21 |
| Example 7-124 | 28 | 96 | 482 | 36 |
| Example 7-125 | 37 | 79 | 740 | 24 |
| Example 7-126 | 19 | 91 | 455 | 46 |
| Example 7-127 | 19 | 60 | NO IP | 7 |
| Example 7-128 | 51 | 78 | 1177 | 30 |
| Example 7-129 | 16 | 90 | NO IP | |
| Example 7-130 | 73 | 54 | NO IP | 7 |
| Example 7-131 | 27 | 145 | 373 | 74 |
| Example 7-132 | 5 | 124 | 75 | 22 |
| Example 7-133 | 6 | 123 | 83 | 66 |
| Example 7-134 | 9 | 78 | NO IP | 14 |
| Example 7-135 | 13 | 81 | NO IP | 14 |
| Example 7-136 | 14 | 86 | NO IP | 6 |
| Example 7-137 | 23 | 82 | NO IP | 9 |
| Example 7-138 | 30 | 102 | 424 | 39 |
| Example 7-139 | 26 | 91 | 223 | 26 |
| Example 7-140 | 158 | 122 | 1131 | 44 |
| Example 7-141 | 13 | 102 | 173 | 47 |
| Example 7-142 | 99 | 133 | 2552 | 81 |
| Example 7-143 | 327 | 104 | 1312 | 58 |
| Example 7-144 | 20 | 107 | 215 | 61 |
| Example 7-145 | 23 | 115 | 791 | 47 |
| Example 7-146 | 9 | 113 | 127 | 51 |
| Example 7-147 | 4 | 100 | 51 | 63 |
| Example 7-148 | 12 | 65 | 120 | 24 |
| Example 7-149 | 17 | 91 | 163 | 32 |
| Example 7-150 | 24 | 84 | 256 | 42 |
| Example 7-151 | 7 | 81 | 121 | 34 |
| Example 7-152 | 6 | 127 | 69 | 58 |
| Example 7-153 | 25 | 100 | 890 | 29 |
| Example 7-154 | 47 | 93 | 2945 | 34 |
| Example 8-1 | 30000 | 18 | NO IP | 2 |
| Example 9-1 | 13 | 60 | 546 | 21 |
| Example 9-2 | 14 | 70 | NO IP | 7 |
| Example 9-3 | 14 | 63 | NO IP | 10 |
| Example 10-1 | 22 | 56 | NO IP | 8 |
| Example 11-1 | 17 | 93 | NO IP | 17 |
| Example 11-2 | 22 | 95 | NO IP | 10 |
| Example 12-1 | 3 | 37 | NO IP | 9 |
| Example 12-2 | 9 | 74 | 58 | 52 |
| Example 12-3 | 5 | 79 | 49 | 20 |
| Example 12-4 | 5 | 55 | NO IP | 13 |
| Example 12-5 | 4 | 76 | 32 | 38 |
| Example 12-6 | 7 | 40 | 30 | 23 |
| Example 12-7 | 6 | 33 | NO IP | 12 |
| Example 12-8 | 4 | 46 | NO IP | 12 |
| Example 12-9 | 8 | 98 | 47 | 52 |
| Example 12-10 | 8 | 51 | 85 | 26 |
| Example 13-1 | 61 | 73 | 2476 | 37 |
| Example 13-2 | 96 | 70 | 3392 | 26 |
| Example 13-3 | 604 | 26 | NO IP | 0 |
| Example 13-4 | 26 | 67 | 264 | 43 |
| Example 13-5 | 52 | 63 | 590 | 33 |
| Example 13-6 | 75 | 41 | NO IP | 12 |
| Example 13-7 | 60 | 67 | 1188 | 25 |
| Example 13-8 | 43 | 95 | 935 | 46 |
| Example 13-9 | 230 | 20 | NO IP | 0 |
| Example 13-10 | 104 | 52 | NO IP | 5 |
| Example 13-11 | 98 | 64 | 733 | 23 |
| Example 13-12 | 83 | 54 | NO IP | 16 |
| Example 13-13 | 74 | 49 | NO IP | 15 |
| Example 13-14 | 497 | 58 | 2729 | 24 |
| Example 13-15 | 171 | 32 | NO IP | 0 |
| Example 13-16 | 135 | 35 | NO IP | 0 |
| Example 14-1 | 44 | 111 | 3431 | 55 |
| Example 14-2 | 50 | 93 | 10330 | 45 |
| Example 14-3 | 1509 | 48 | NO IP | 5 |

We claim:

1. A compound having the structural Formula (I):

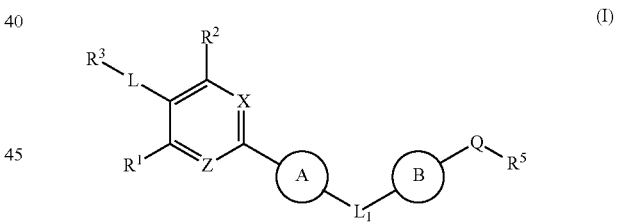

or a pharmaceutically acceptable salt thereof, wherein:

ring A is

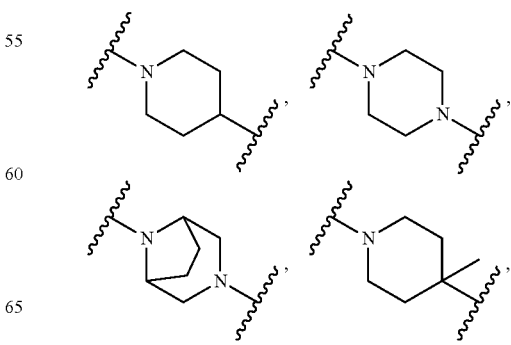

-continued

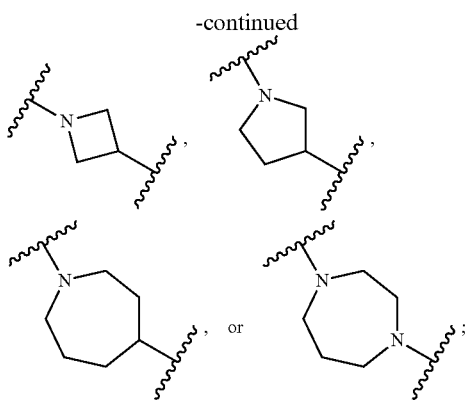

ring B is

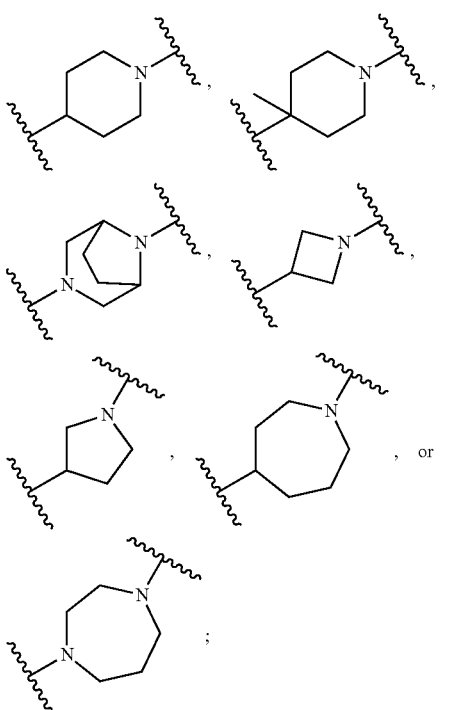

L₁- is —CH₂—, —CH₂CH₂—, —C(O)—, —O—, or —S—;

R¹ is selected from the group consisting of H, methyl, and halogen;

R² is selected from the group consisting of H, —S(O)₂(C₁-C₆alkyl), and halogen;

X is selected from the group consisting of —N— and —CH—;

Z is selected from the group consisting of N and C(R⁴);

R⁴ is selected from the group consisting of H and methyl;

L is a bond and R³ is selected from the group consisting of H, —(C₁-C₆)alkyl and —(C₁-C₆)alkyl-OH;

or, alternatively, L is a divalent moiety selected from the group consisting of —C(O)— and —S(O)₂—;

and R³ is —N(R$^{N1}$)(R$^{N2}$), wherein:

R$^{N1}$ is selected from the group consisting of H and —(C₁-C₆)alkyl; and

R$^{N2}$ is selected from the group consisting of: H, —(C₁-C₆)alkyl, —O—(C₁-C₆)alkyl, —OH, halogen, —CN, and —(C₁-C₆)alkyl which is substituted with 1 or 2 groups independently selected from the group consisting of:
—OH, halogen, —CN,
—NH₂, —NH(C₁-C₆)alkyl, —N((C₁-C₆)alkyl)₂,
optionally substituted phenyl, (wherein said optional substitutents on said phenyl are 1 to 3 groups independently selected from OH, CN, —(C₁-C₄)alkyl, —(C₁-C₄)alkoxyl),
optionally substituted heteroaryl, (wherein said optional substituents on said heteroaryl are 1 to 3 groups independently selected from —(C₁-C₆)alkyl, —(C₁-C₄)alkoxyl, and cyclopropyl),
optionally substituted cyclopropyl (wherein said optional substituents on said cyclopropyl are 1 to 3 groups independently selected from —(C₁-C₆)alkyl), and
optionally substituted heterocycloalkyl (wherein said optional substitutents on said heterocycloalkyl are 1 to 3 groups independently selected from halogen, —OH, oxo, CN, and —(C₁-C₆)alkyl,
or, alternatively, R$^{N1}$ and R$^{N2}$ are taken together with the nitrogen atom to which they are shown attached to form a 4-, 5-, or 6-membered fully saturated heterocyclic ring comprising (including said nitrogen atom) 1, 2, or 3 ring heteroatoms selected from the group consisting of N, N-oxide, O, S, and S-oxide,
wherein said heterocyclic ring is unsubstituted or substituted with 1, 2, or 3 substituents independently selected from the group consisting of halogen, —OH, oxo, CN, —(C₁-C₆)alkyl, amino-substituted —(C₁-C₆)alkyl (wherein said amino is 1, 2, or 3 groups independently selected from the group consisting of —NH₂, —N(C₁-C₄alkyl)₂, and —NH(C₁-C₄alkyl)), —O—(C₁-C₆)alkyl, —(C₁-C₆)alkyl-OH, —(C₁-C₆)haloalkyl, —C(O)O—(C₁-C₆)alkyl, cyclopropyl, spirocyclopropyl, —NHC(O)O—(C₁-C₆)alkyl, —CH₂—NHC(O)O—(C₁-C₆)alkyl, —CH₂—N(CH₃)C(O)O—(C₁-C₆)alkyl, phenyl, benzyl, —NHC(O)-phenyl, heteroaryl, and —(C₁-C₄)alkylheteroaryl, heterocycloalkyl;

Q is a bond or a divalent moiety selected from the group consisting of —C(O)—, —S(O)₂—, and —C(O)O—; and R⁵ is selected from the group consisting of:
—C(R$^{5A}$)(R$^{5B}$)(R$^{5C}$), wherein:
each of R$^{5A}$ and R$^{5B}$ and R$^{5C}$ is independently selected from the group consisting of: H, halogen, OH, NH₂, —(C₁-C₆)alkyl, —(C₁-C₆)haloalkyl, —(C₁-C₆)alkenyl, —(C₁-C₆)alkynyl, —(C₃-C₆)cycloalkyl, —(C₃-C₆)cycloalkyl substituted with —(C₁-C₆)alkyl, —(C₁-C₆)alkenyl, —(C₁-C₆)alkynyl, phenyl, —C(O)phenyl, heteroaryl, heterocycloalkyl, and aryl,
wherein said phenyl, said —C(O)phenyl, said heteroaryl, said heterocycloalkyl, and said aryl are unsubstituted or substituted with from 1, 2, or 3 groups independently selected from halogen, CN, —(C₁-C₆)alkyl, —(C₁-C₆)haloalkyl, —O—(C₁-C₆)alkyl, —O—(C₁-C₆)haloalkyl, —C(O)O—(C₁-C₆)alkyl, and —N(C₁-C₆alkyl)₂,

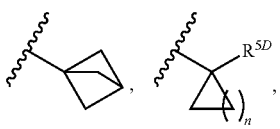

wherein:
n is an integer from 1 to 4; and $R^{5D}$ is selected from the group consisting of H, —$(C_1-C_6)$alkyl, —$(C_1-C_6)$haloalkyl, phenyl, and phenyl substituted with from 1 to 3 groups independently selected from the group consisting of OH, halogen, —$(C_1-C_6)$alkyl, and —O—$(C_1-C_6)$alkyl, and benzyl or thienyl, wherein:
said benzyl is unsubstituted or substituted with 1, 2, or 3 groups, and wherein said thienyl is unsubstituted or substituted with 1 or 2 groups, independently selected from the group consisting of halogen, CN, —$(C_1-C_6)$alkyl, —O—$(C_1-C_6)$alkyl, —$(C_1-C_6)$haloalkyl, and —O—$(C_1-C_6)$haloalkyl.

2. The compound of claim 1, or a pharmaceutically acceptable salt thereof wherein:
Q is a bond or a divalent moiety selected from the group consisting of —C(O)—, —S(O)$_2$—, and —C(O)O—; and
$R^5$ is —C($R^{5A}$)($R^{5B}$)($R^{5C}$),
each of $R^{5A}$ and $R^{5B}$ and $R^{5C}$ is independently selected from the group consisting of: H, halogen, OH, NH$_2$, —$(C_1-C_6)$alkyl, —$(C_1-C_6)$haloalkyl, —$(C_1-C_6)$alkenyl, —$(C_1-C_6)$alkynyl, —$(C_3-C_6)$cycloalkyl, —$(C_3-C_6)$cycloalkyl substituted with —$(C_1-C_6)$alkyl, —$(C_1-C_6)$alkenyl, —$(C_1-C_6)$alkynyl, phenyl, —C(O)phenyl, heteroaryl, heterocycloalkyl, and aryl,
wherein said phenyl, said —C(O)phenyl, said heteroaryl, said heterocycloalkyl, and said aryl are unsubstituted or substituted with from 1, 2, or 3 groups independently selected from halogen, CN, —$(C_1-C_6)$alkyl, —$(C_1-C_6)$haloalkyl, —O—$(C_1-C_6)$alkyl, —O—$(C_1-C_6)$haloalkyl, —C(O)O—$(C_1-C_6)$alkyl, and —N($C_1-C_6$alkyl)$_2$.

3. The compound of claim 1, or a pharmaceutically acceptable salt thereof, wherein:
Q is —C(O)—;
$R^{5A}$ is OH or NH$_2$;
$R^{5B}$ is —$(C_1-C_3)$fluoroalkyl; and
$R^{5C}$ is selected from the group consisting of:
—$(C_1-C_6)$alkyl, —$(C_1-C_4)$fluoroalkyl, phenyl optionally substituted with 1 to 3 groups, —C(O)phenyl optionally substituted with 1 to 3 groups, cyclopropyl optionally substituted with 1 to 2 groups, cyclobutyl optionally substituted with 1 to 2 groups, thienyl optionally substituted with 1 to 2 groups, pyridyl optionally substituted with 1 to 2 groups, naphthyl optionally substituted with 1 to 3 groups, cyclopentylphenyl optionally substituted with 1 to 3 groups, and benzthiazolyl optionally substituted with 1 to 3 groups,
wherein each said optional substituent is independently selected from halogen —$(C_1-C_6)$alkyl, —$(C_1-C_6)$alkenyl, and —O$(C_1-C_6)$alkyl, and —$(C_1-C_6)$haloalkyl.

4. The compound of claim 1, or a pharmaceutically acceptable salt thereof, wherein:
Q is a bond or a divalent moiety selected from the group consisting of —C(O)—, —S(O)$_2$—, and —C(O)O—; and $R^5$ is selected from the group consisting of

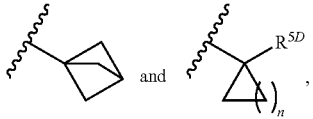

wherein n is an integer from 1 to 4; and $R^{5D}$ is selected from the group consisting of H, —$(C_1-C_6)$alkyl, —$(C_1-C_6)$haloalkyl, phenyl, and phenyl substituted with from 1 to 3 groups independently selected from the group consisting of OH, F, Cl, —$(C_1-C_6)$alkyl, and —O—$(C_1-C_6)$alkyl.

5. The compound according to claim 1, or a pharmaceutically acceptable salt thereof wherein:
L is —C(O)—; and $R^3$ is —N($R^{N1}$)($R^{N2}$), wherein:
$R^{N1}$ is selected from the group consisting of H and —$(C_1-C_6)$alkyl; and
$R^{N2}$ is selected from the group consisting of: H, —$(C_1-C_6)$alkyl, —O—$(C_1-C_6)$alkyl, —OH, halogen, —CN, and —$(C_1-C_6)$alkyl which is substituted with 1 or 2 groups independently selected from the group consisting of:
—OH, halogen, —CN,
—NH$_2$, —NH$(C_1-C_6)$alkyl, —N$((C_1-C_6)$alkyl$)_2$,
optionally substituted phenyl, (wherein said optional substitutents on said phenyl are 1 to 3 groups independently selected from OH, CN, —$(C_1-C_4)$alkyl, —$(C_1-C_4)$alkoxyl),
optionally substituted heteroaryl, (wherein said optional substituents on said heteroaryl are 1 to 3 groups independently selected from —$(C_1-C6)$alkyl, —$(C_1-C_4)$alkoxyl, and cyclopropyl),
optionally substituted cyclopropyl (wherein said optional substituents on said cyclopropyl are 1 to 3 groups independently selected from —$(C_1-C_6)$alkyl), and
optionally substituted heterocycloalkyl (wherein said optional substitutents on said heterocycloalkyl are 1 to 3 groups independently selected from halogen, —OH, oxo, CN, and —$(C_1-C_6)$alkyl.

6. The compound according to claim 1, or a pharmaceutically acceptable salt thereof, wherein:
L is selected from the group consisting of —C(O)— and —S(O)$_2$—; and
$R^3$ is —N($R^{N1}$)($R^{N2}$), wherein $R^{N1}$ and $R^{N2}$ are each independently selected from the group consisting of H and —$(C_1-C_6)$alkyl.

7. The compound according to claim 1, or a pharmaceutically acceptable salt thereof, wherein:
L is —C(O)—; and $R^3$ is —N($R^{N1}$)($R^{N2}$), wherein:
$R^{N1}$ and $R^{N2}$ are taken together with the nitrogen atom to which they are shown attached to form a 4-, 5-, or 6-membered fully saturated heterocyclic ring comprising (including said nitrogen atom) 1, 2, or 3 ring heteroatoms selected from the group consisting of N, N-oxide, O, S, and S-oxide,
wherein said heterocyclic ring is unsubstituted or substituted with 1, 2, or 3 substituents independently selected from the group consisting of halogen, —OH, oxo, CN, —$(C_1-C_6)$alkyl, amino-substituted —$(C_1-C_6)$alkyl (wherein said amino is 1, 2, or 3 groups independently selected from the group consisting of —NH$_2$, —N$(C_1-C_4$alkyl$)_2$, and —NH$(C_1-C_4$alkyl)), —O—$(C_1-C_6)$alkyl, —$(C_1-C_6)$alkyl-OH, —$(C_1-C_6)$haloalkyl, —C(O)O—$(C_1-C_6)$alkyl, cyclopropyl, spirocyclopropyl, —NHC(O)O—$(C_1$-

C$_6$)alkyl, —CH$_2$—NHC(O)O—(C$_1$-C$_6$)alkyl, —CH$_2$—N(CH$_3$)C(O)O—(C$_1$-C$_6$)alkyl, phenyl, benzyl, —NHC(O)-phenyl, heteroaryl, and —(C$_1$-C$_4$)alkylheteroaryl, heterocycloalkyl.

8. The compound according to claim 1, or a pharmaceutically acceptable salt thereof, wherein:

L is a bond; R$^3$ is H or —(C$_1$-C$_6$)alkyl which is optionally substituted with OH; X is CH; R$^2$ is —S(O)$_2$CH$_3$; R$^1$ is H; and R$^2$ is H.

9. A compound or a pharmaceutically acceptable salt thereof, said compound selected from the group consisting of:

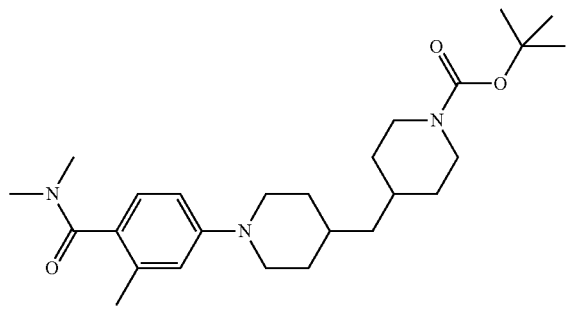

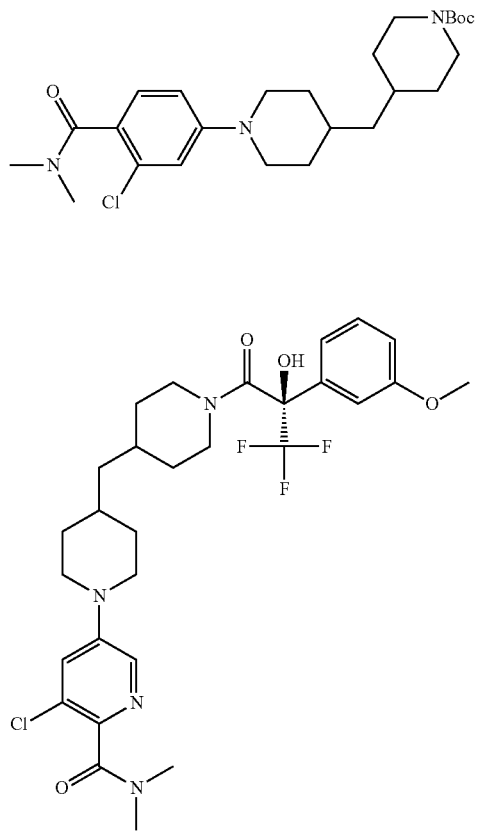

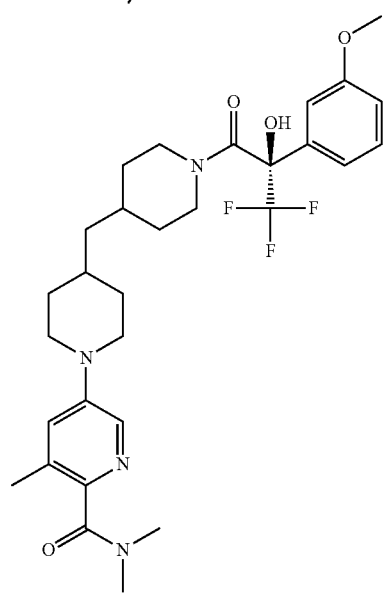

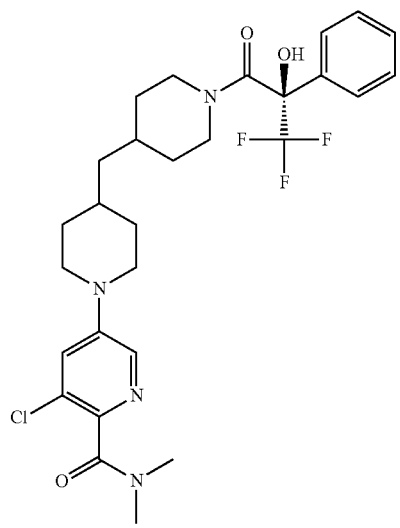

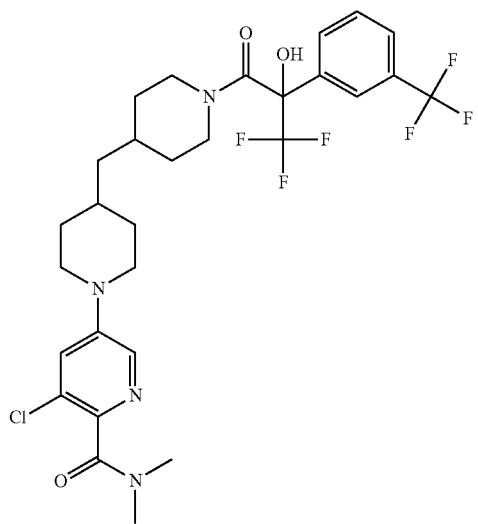

319
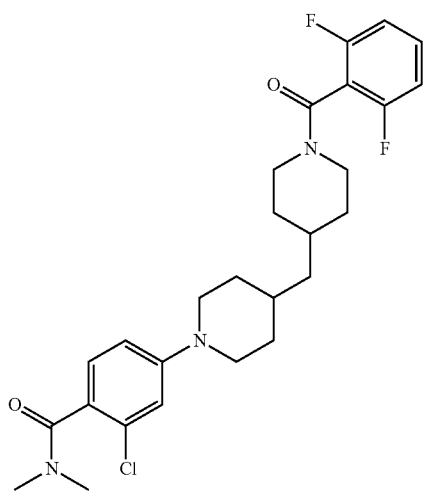
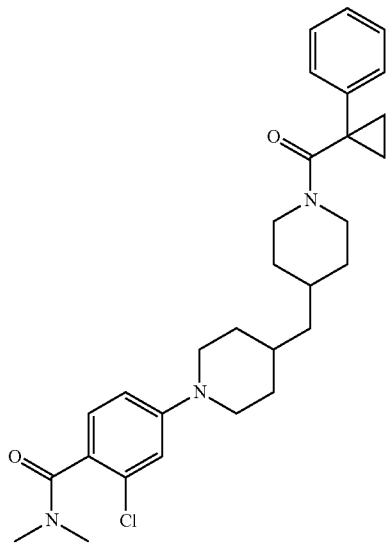
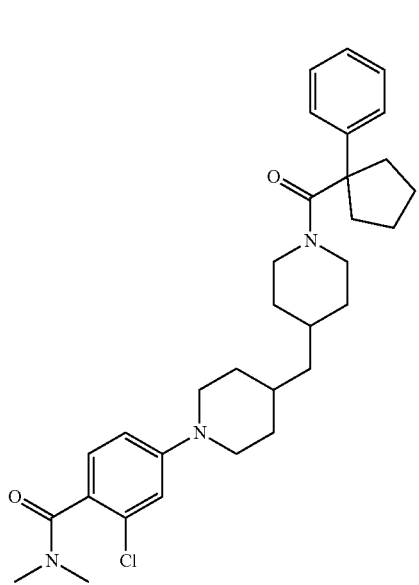
-continued
320
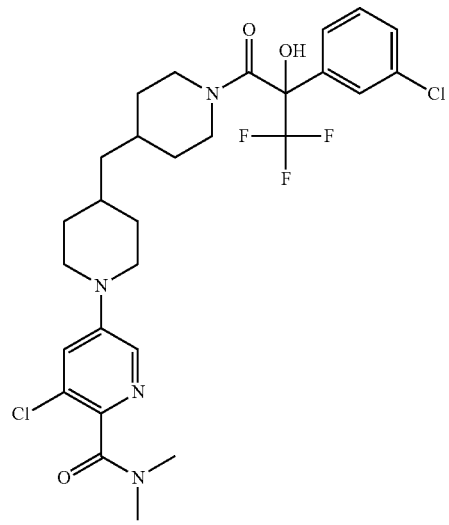
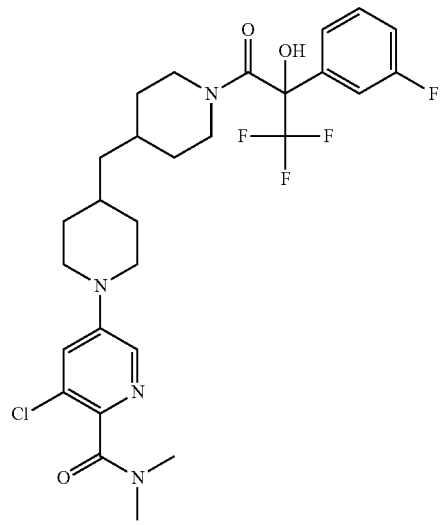
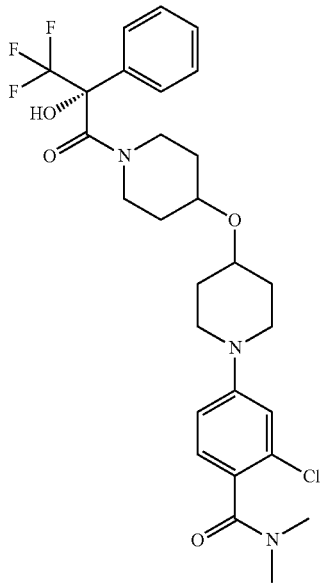

321
322
-continued
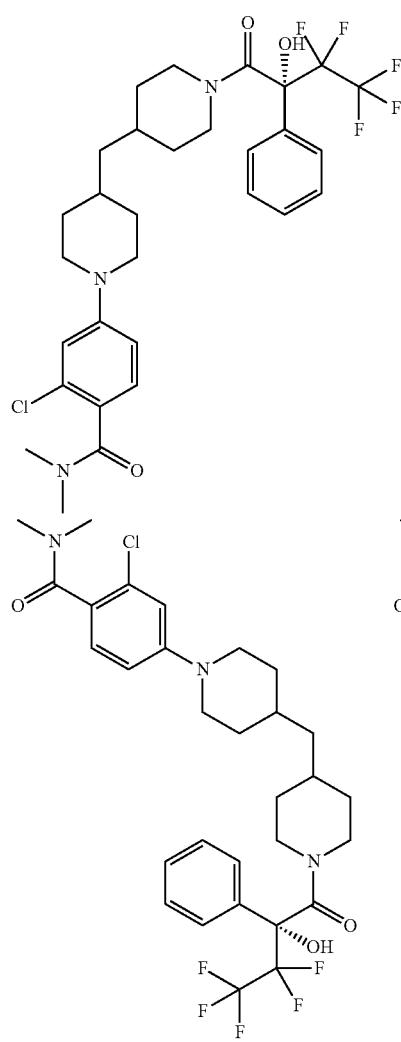
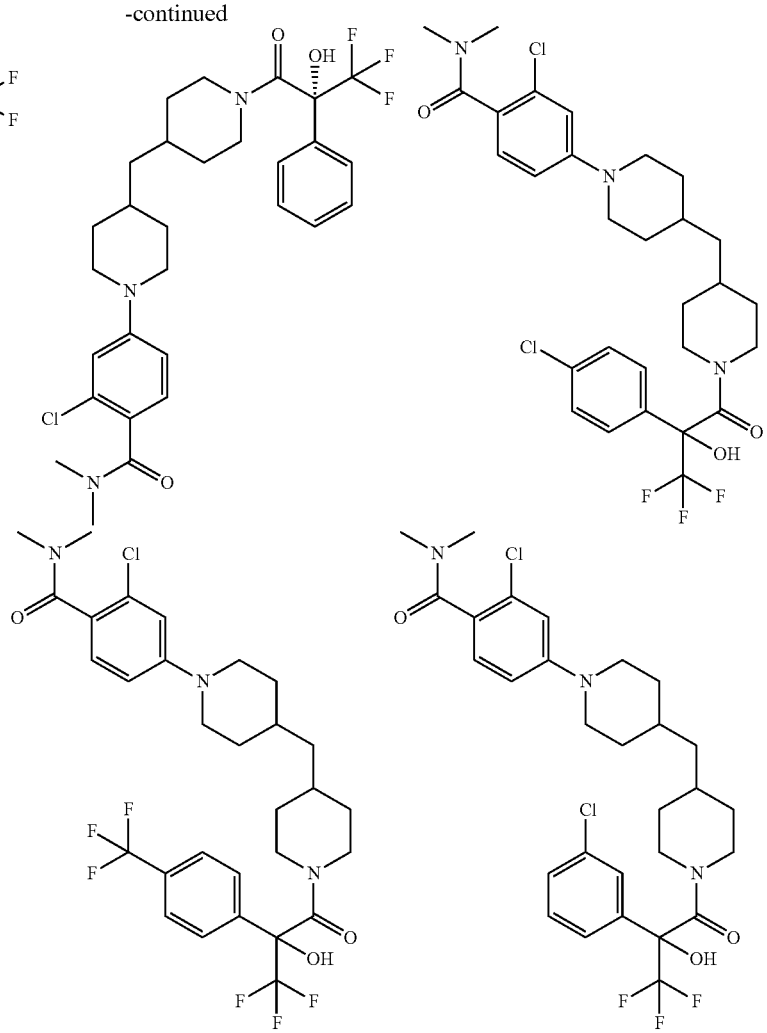
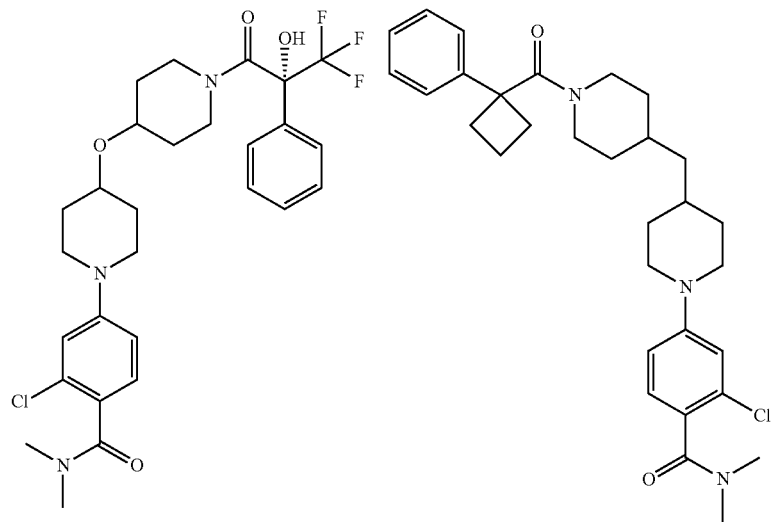
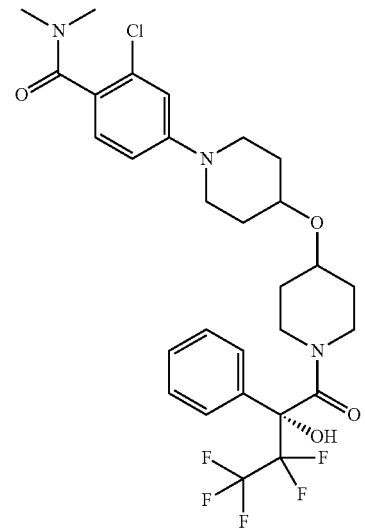

323 324
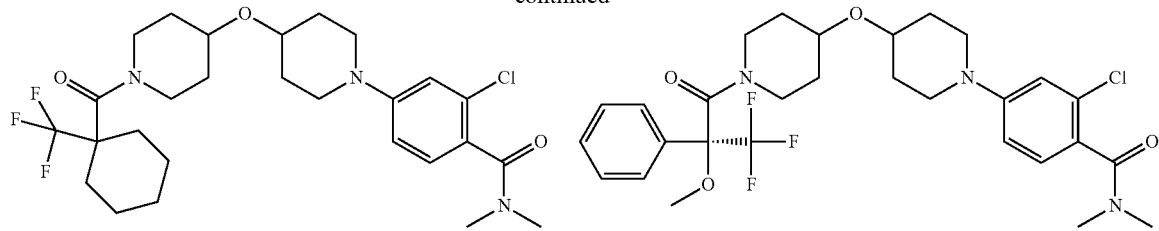
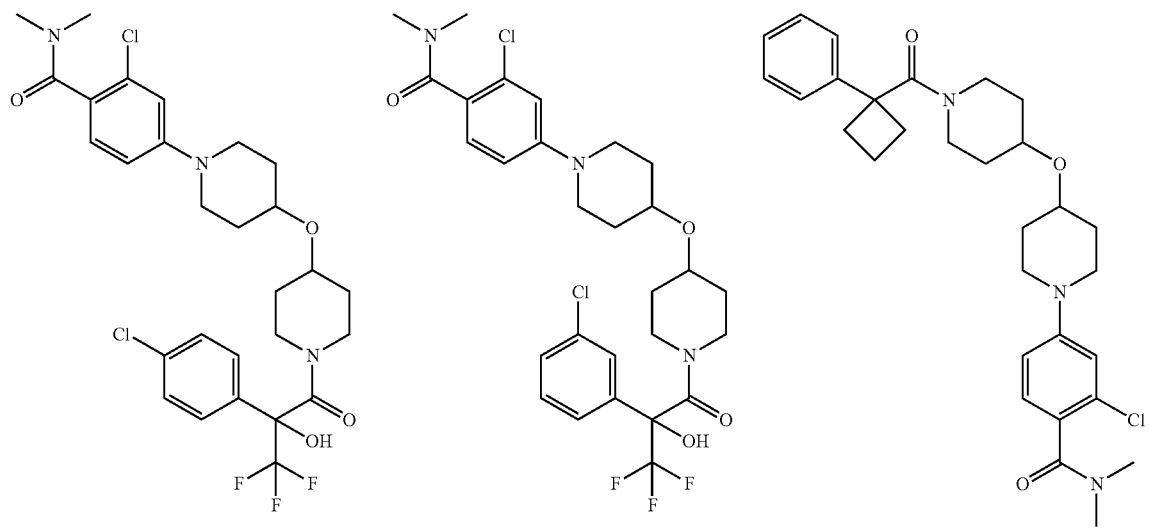 [SMILES: CN(C)C(=O)c1ccc(N2CCC(OC3CCN(C(=O)C(O)(c4ccc(Cl)cc4)C(F)(F)F)CC3)CC2)cc1Cl ; CN(C)C(=O)c1ccc(N2CCC(OC3CCN(C(=O)C(O)(c4cccc(Cl)c4)C(F)(F)F)CC3)CC2)cc1Cl ; CN(C)C(=O)c1ccc(N2CCC(OC3CCN(C(=O)C4(c5ccccc5)CCC4)CC3)CC2)cc1Cl]
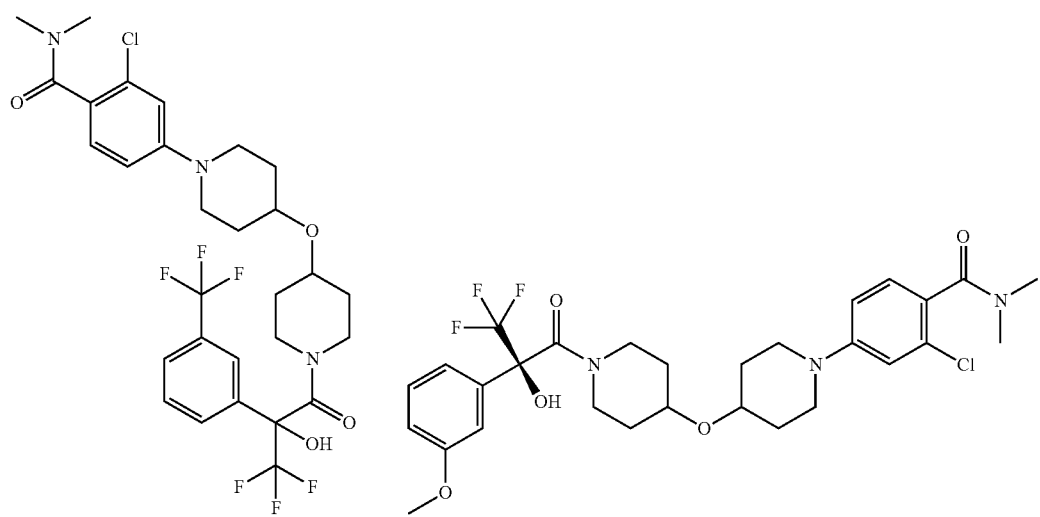

325
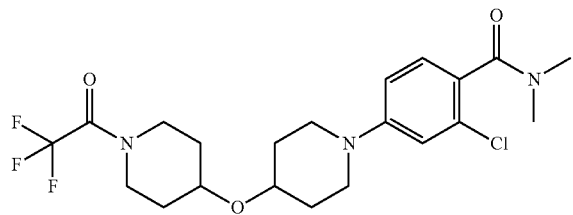
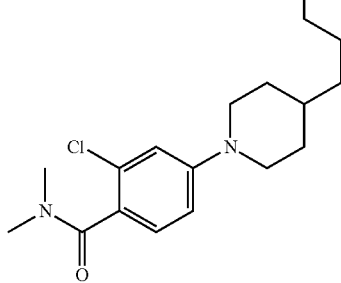
326
-continued
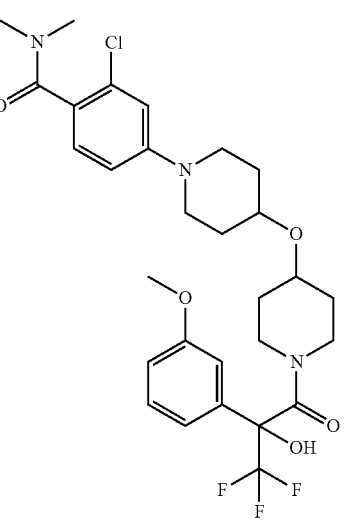
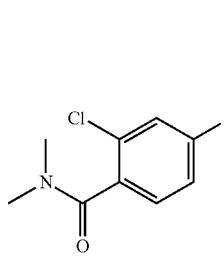
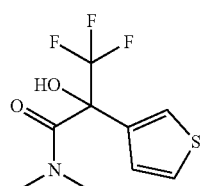
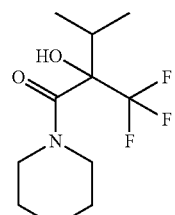
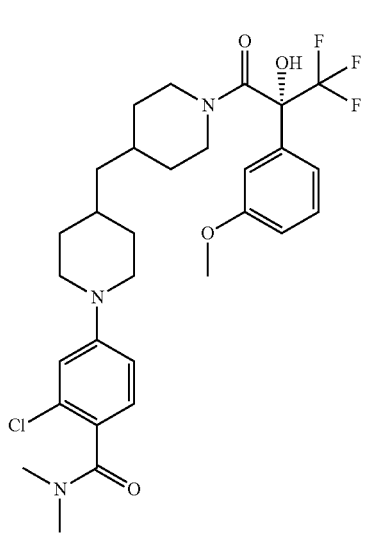
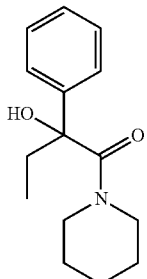
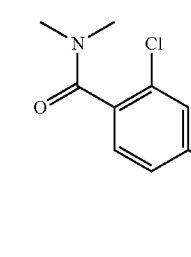
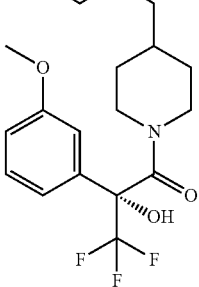

-continued
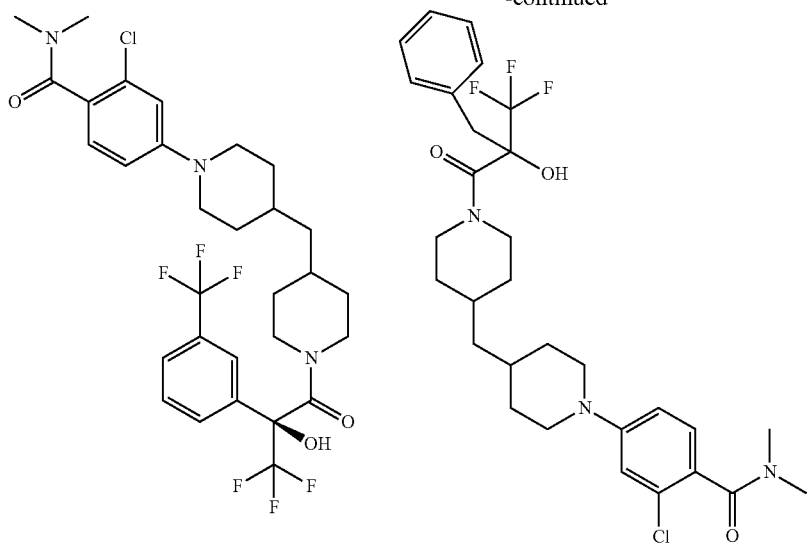
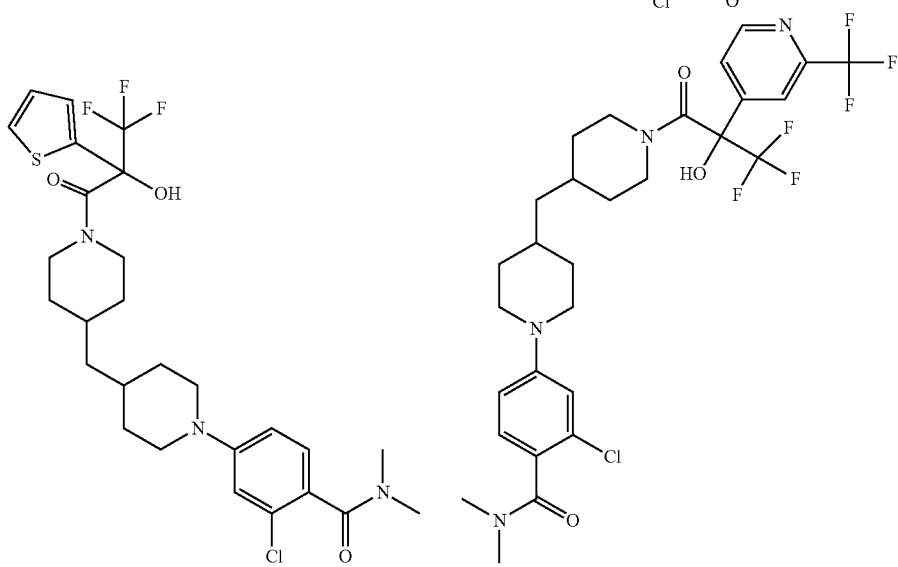
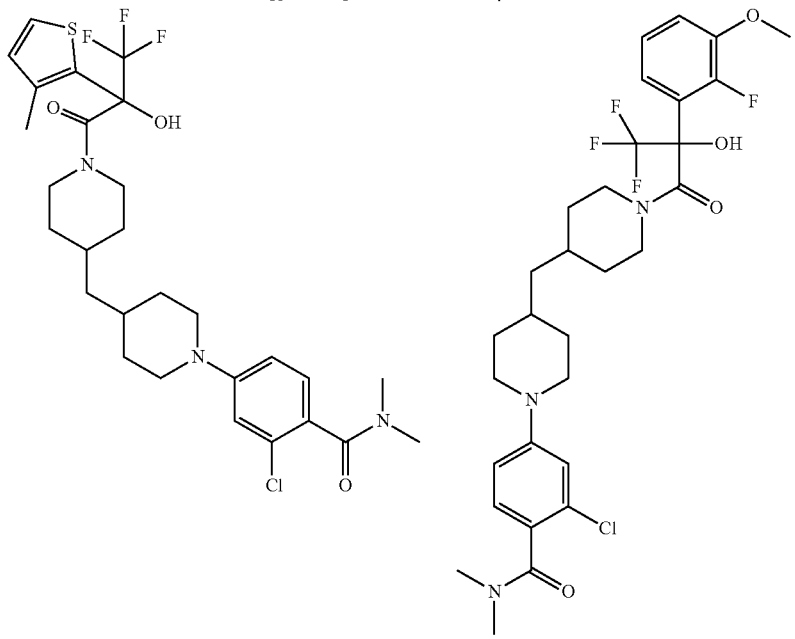

329
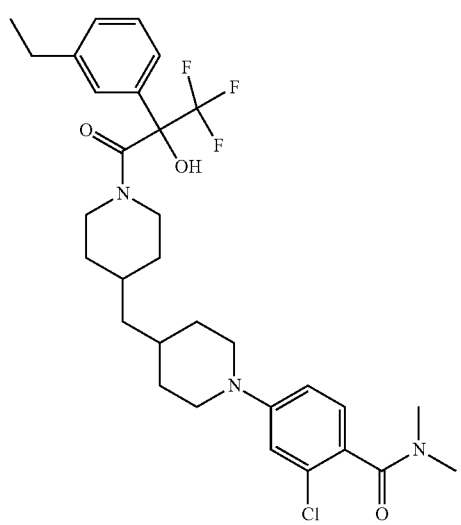
330
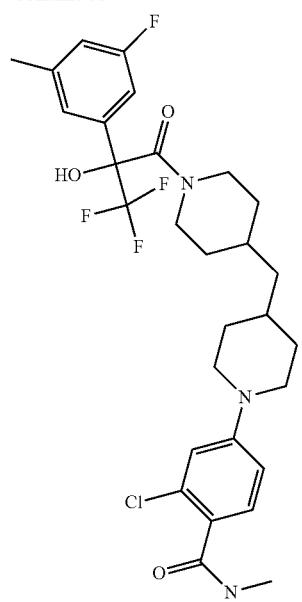
-continued
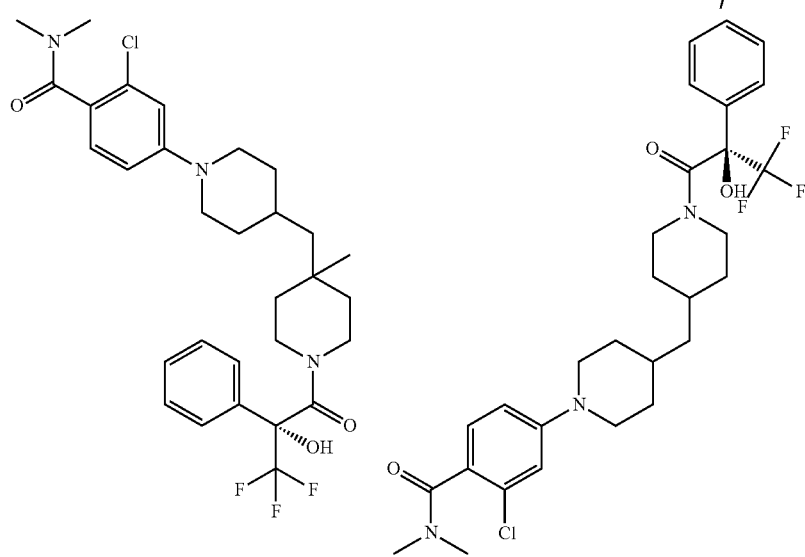
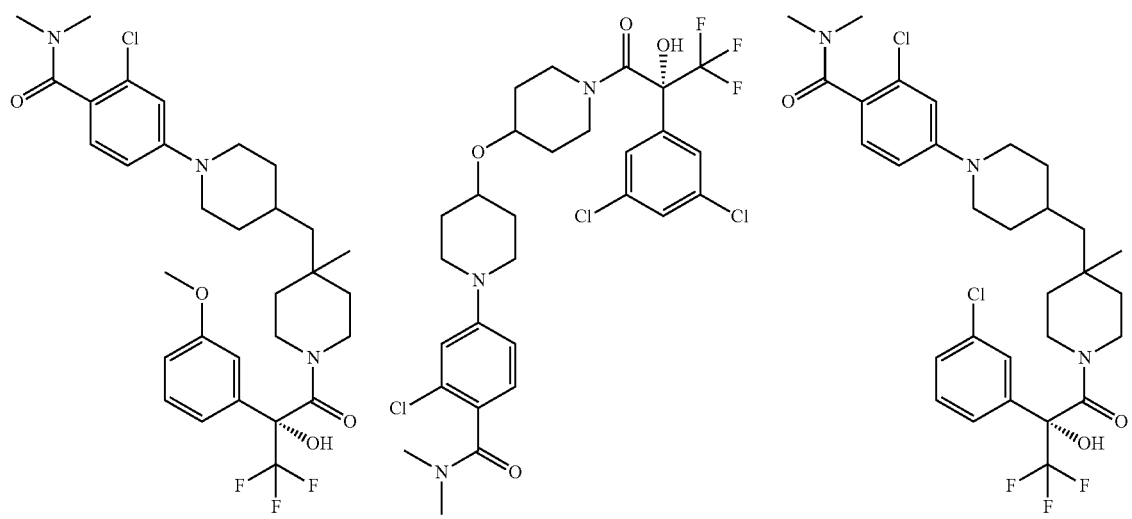

331
-continued
332
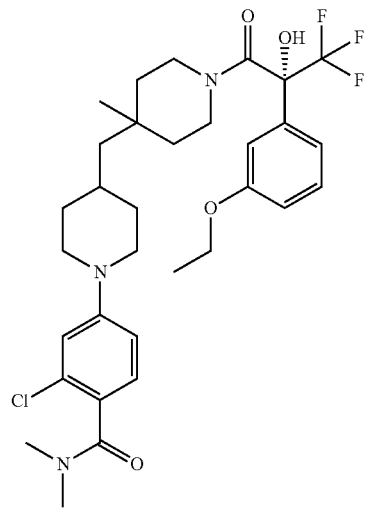
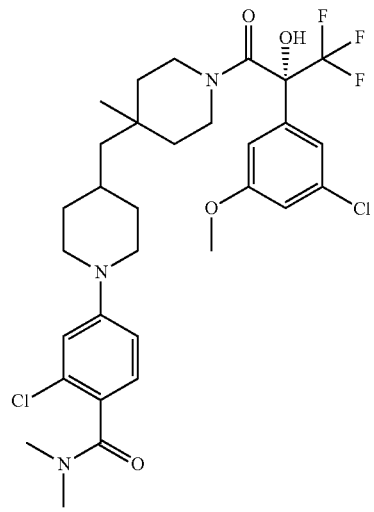
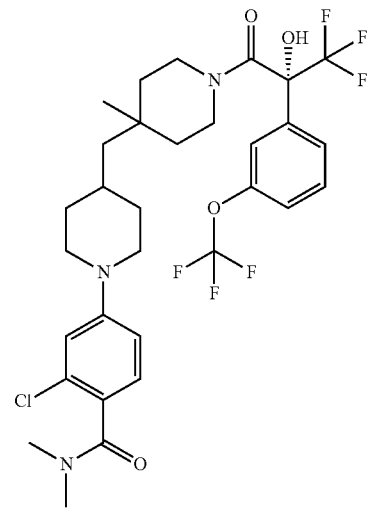
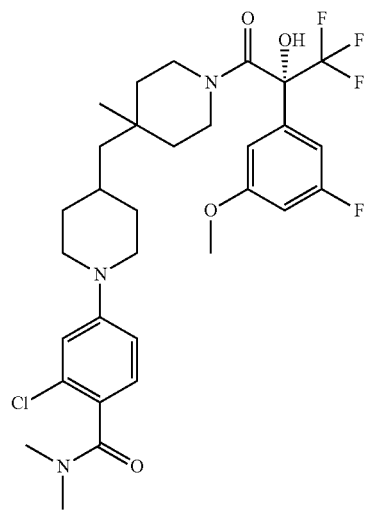
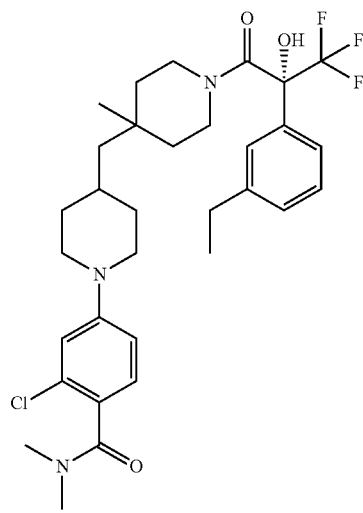
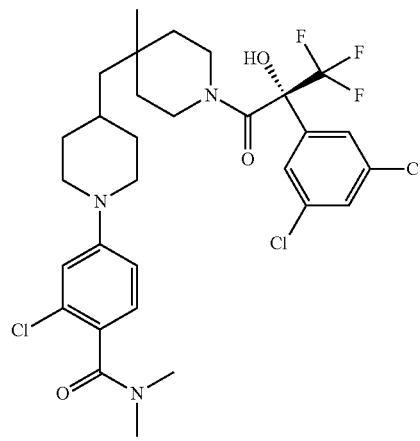
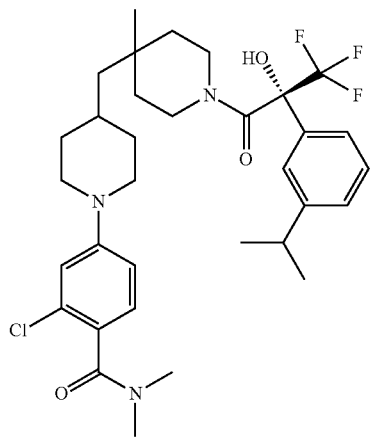

333
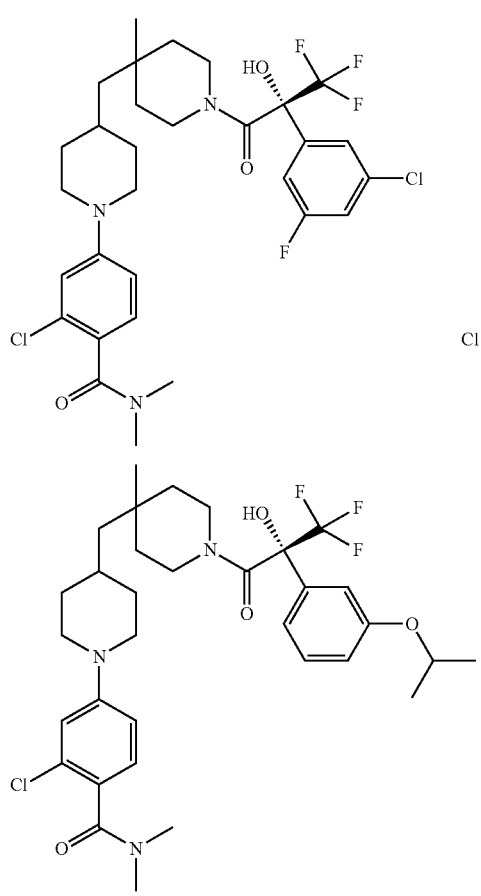
334
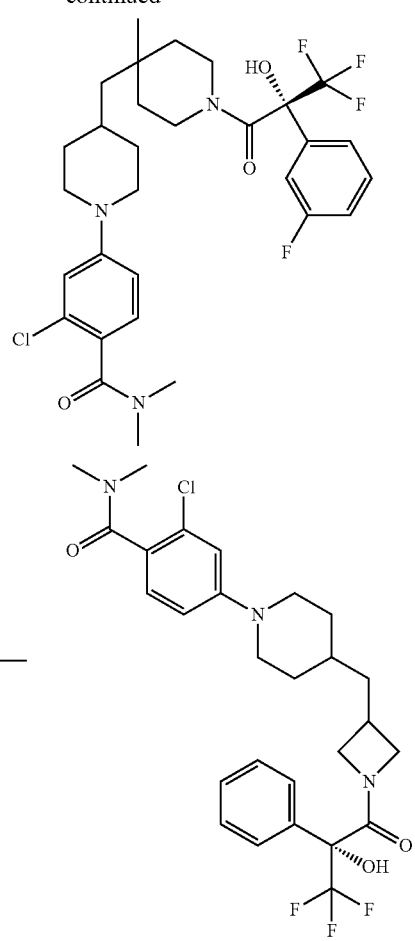
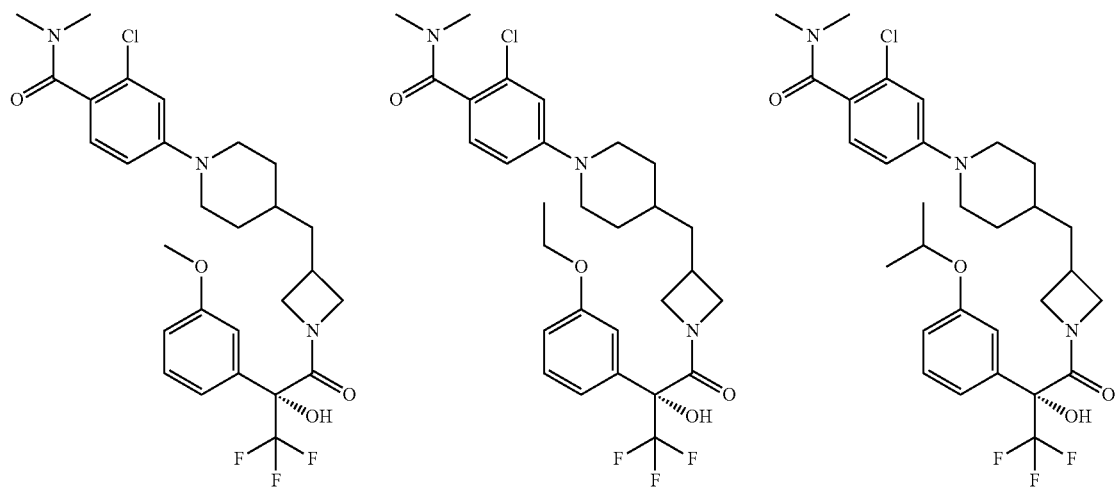 [SMILES: COc1cccc([C@@](O)(C(=O)N2CC(CC3CCN(c4ccc(C(=O)N(C)C)c(Cl)c4)CC3)C2)C(F)(F)F)c1 ; CCOc1cccc([C@@](O)(C(=O)N2CC(CC3CCN(c4ccc(C(=O)N(C)C)c(Cl)c4)CC3)C2)C(F)(F)F)c1 ; CC(C)Oc1cccc([C@@](O)(C(=O)N2CC(CC3CCN(c4ccc(C(=O)N(C)C)c(Cl)c4)CC3)C2)C(F)(F)F)c1]

335
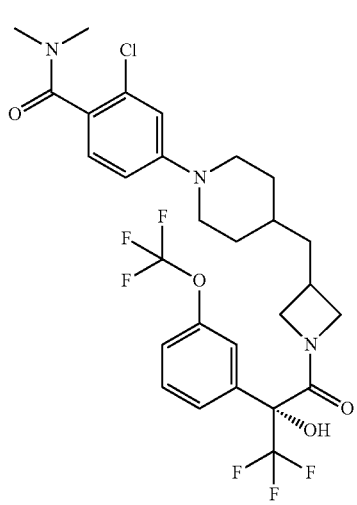
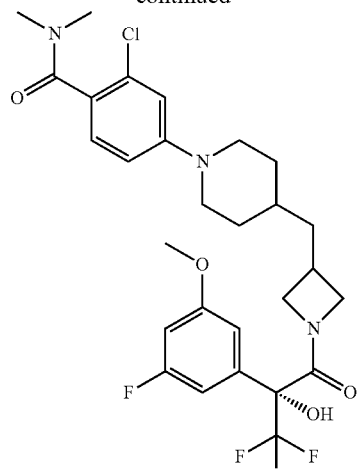
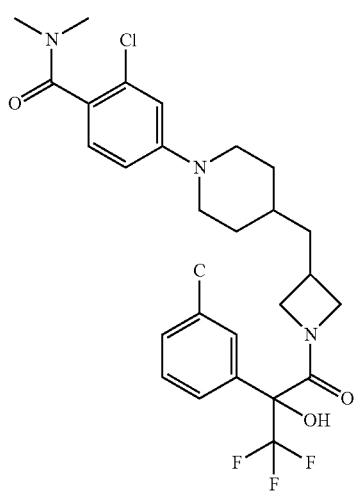
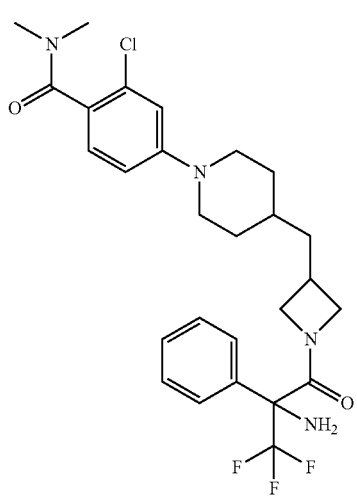
-continued
336
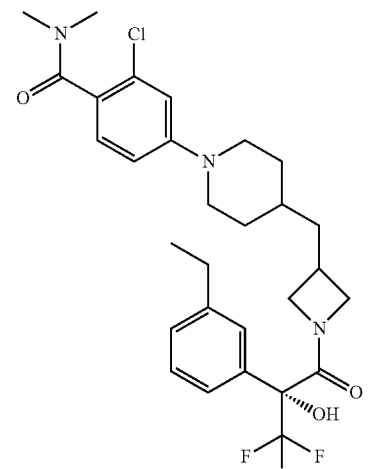
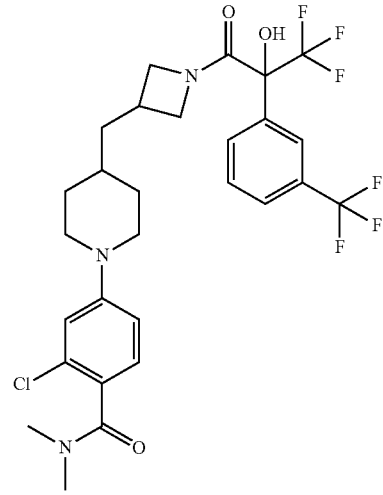
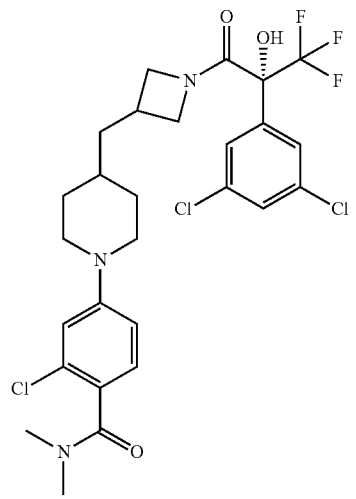
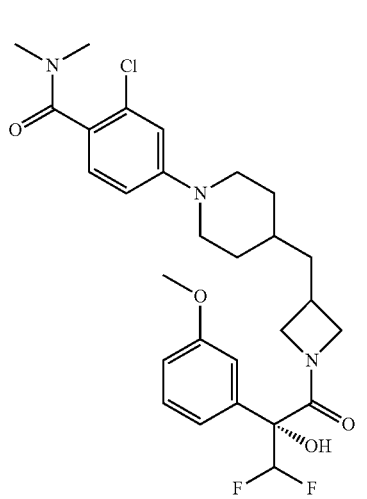

-continued
337
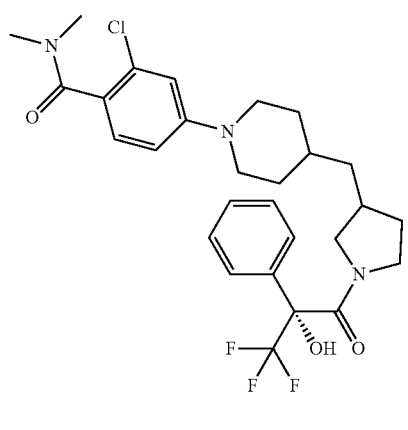
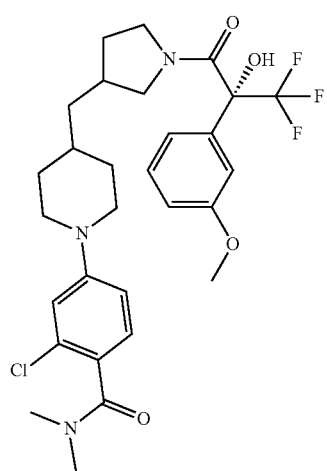
338
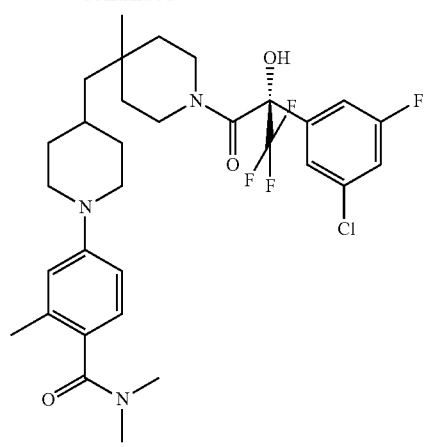
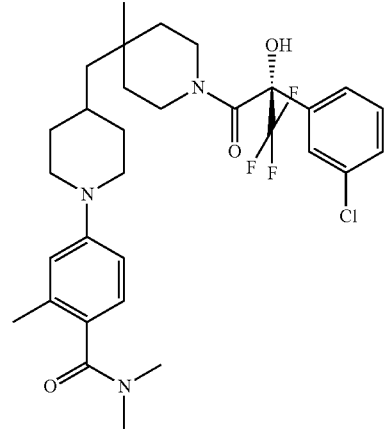
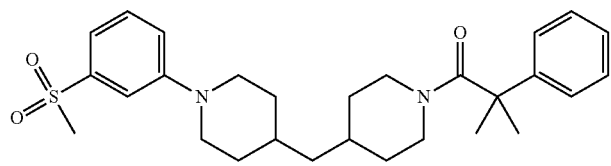
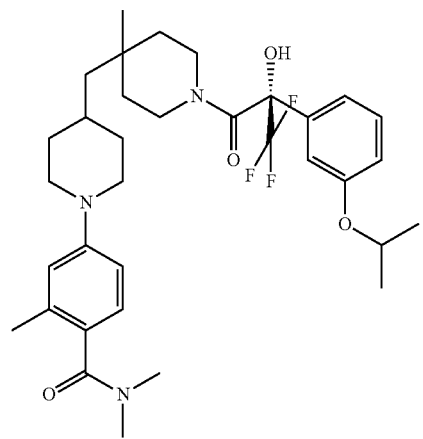

-continued
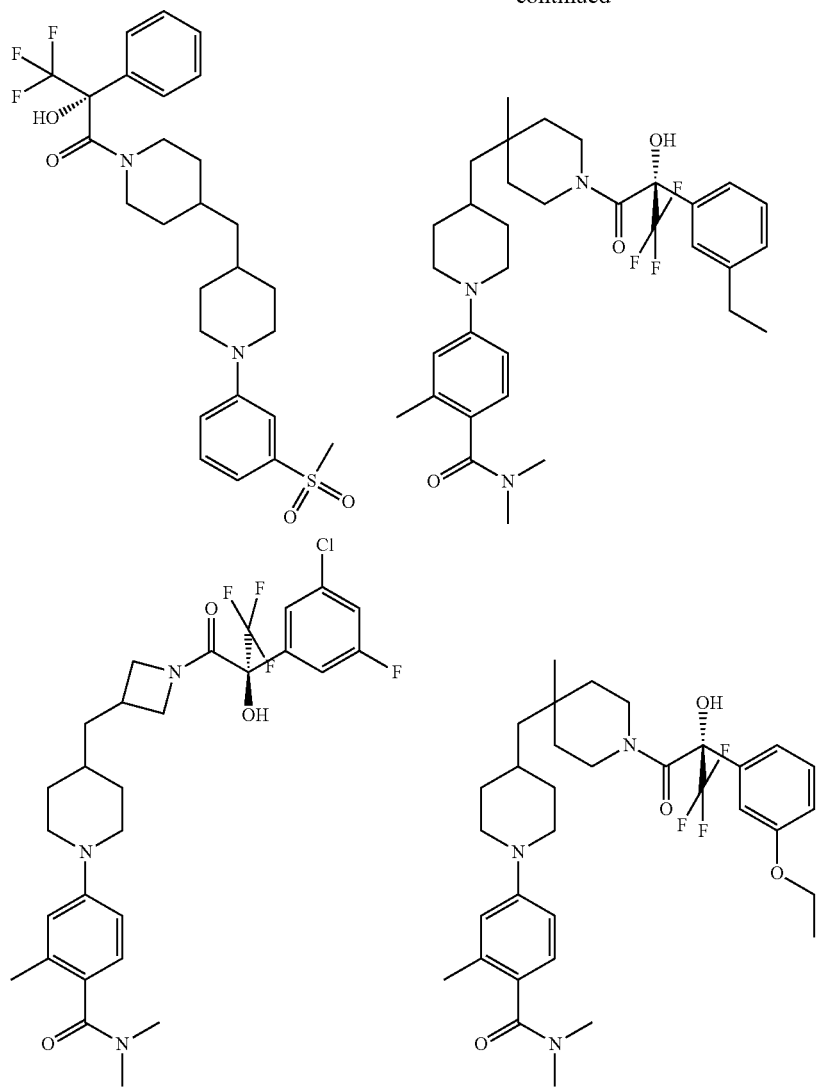
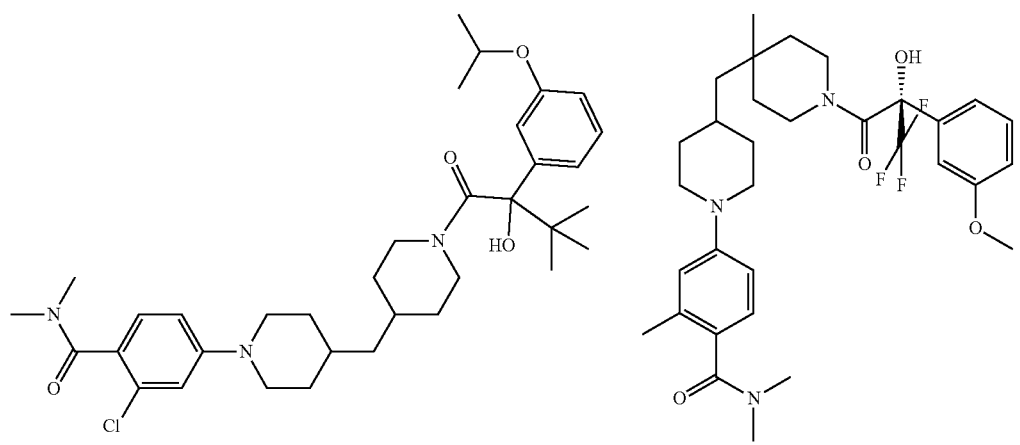

-continued
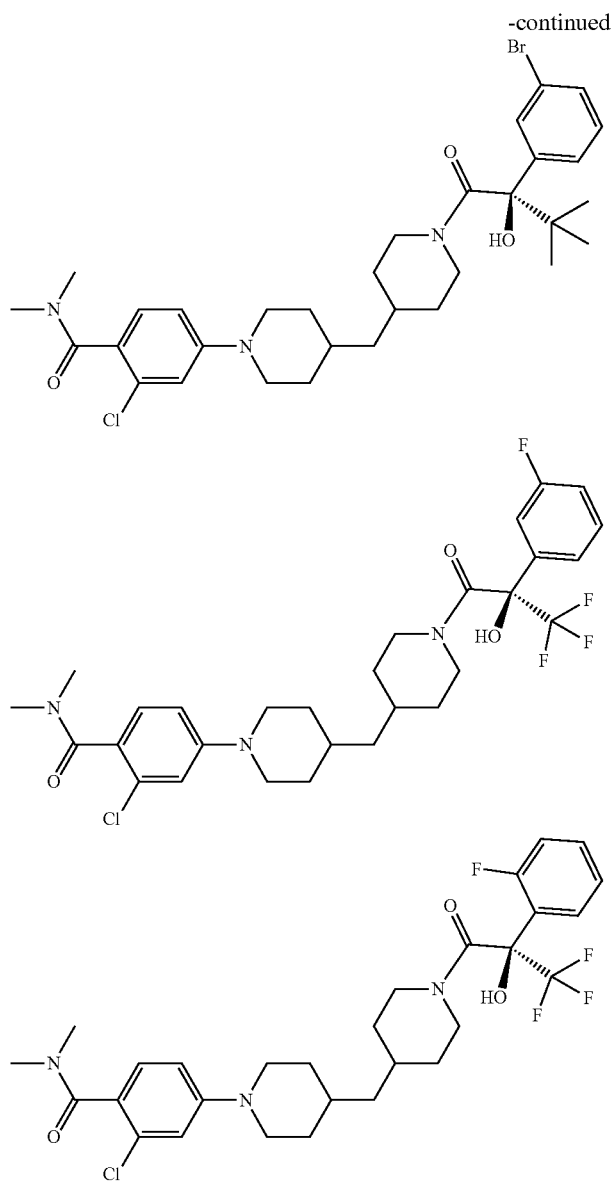
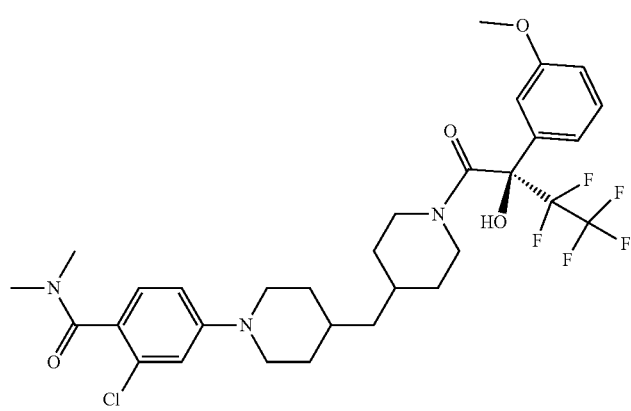

-continued
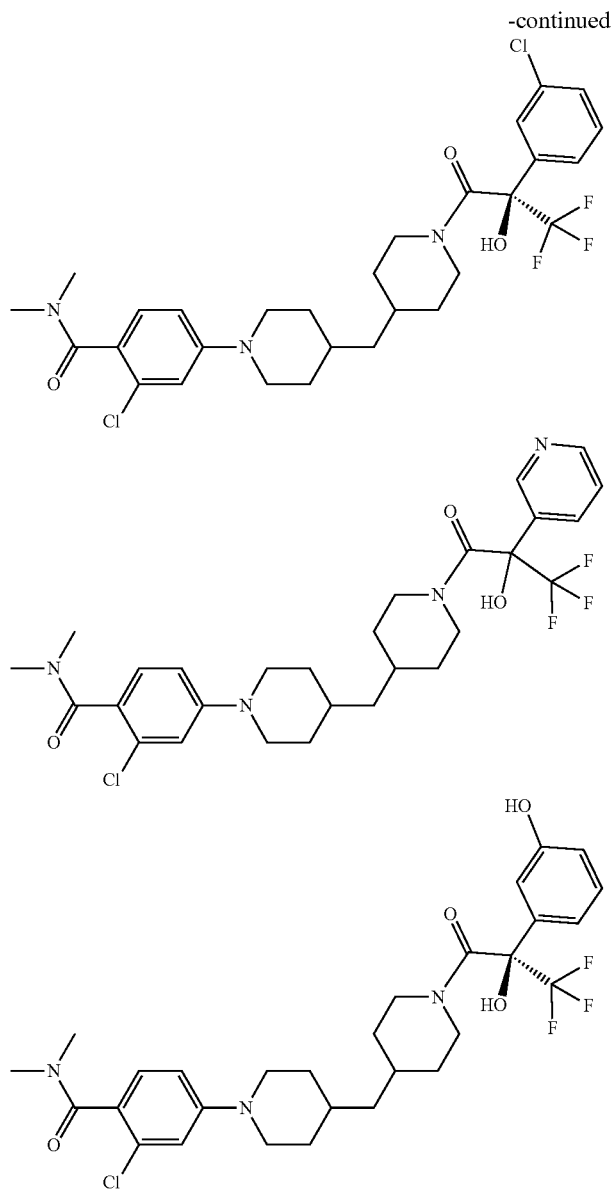
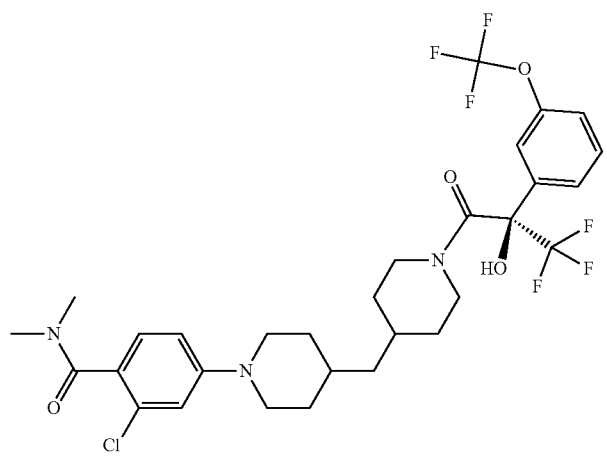

-continued
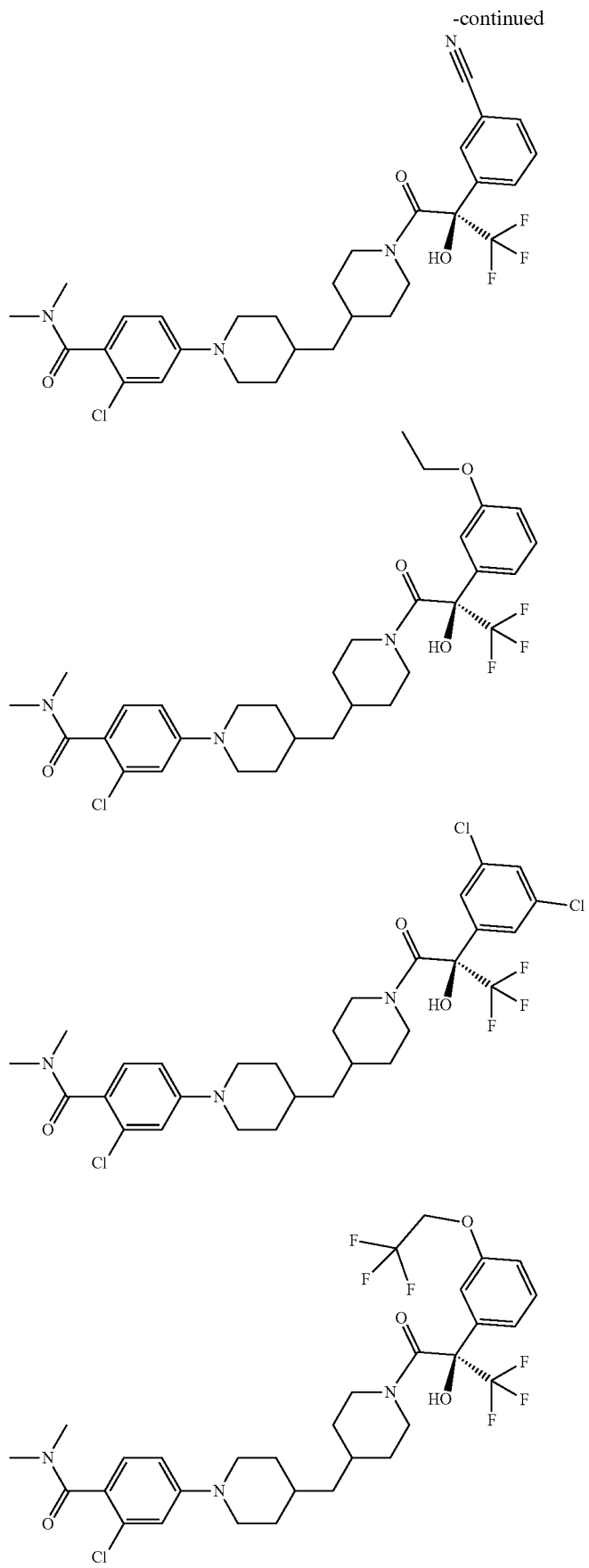

-continued
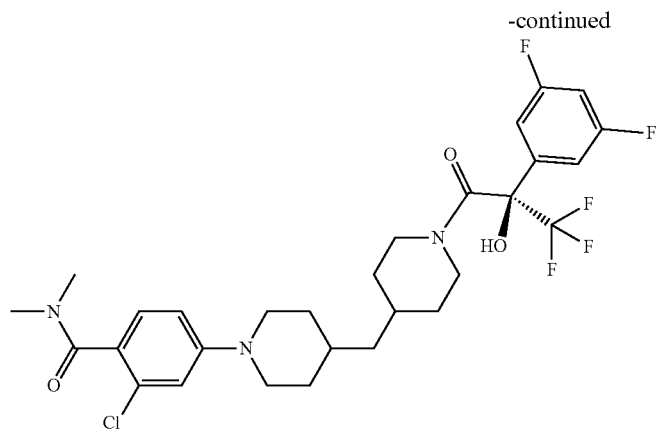
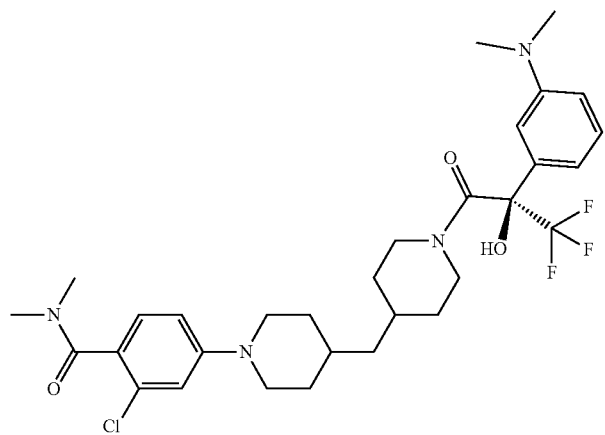
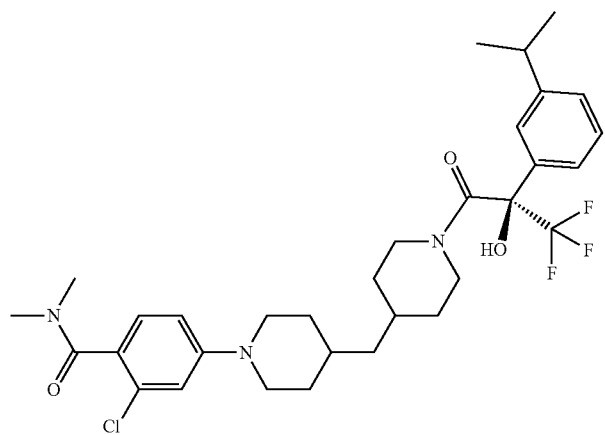
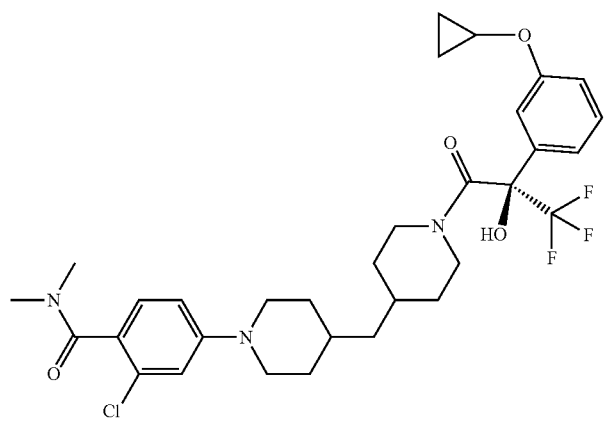

-continued
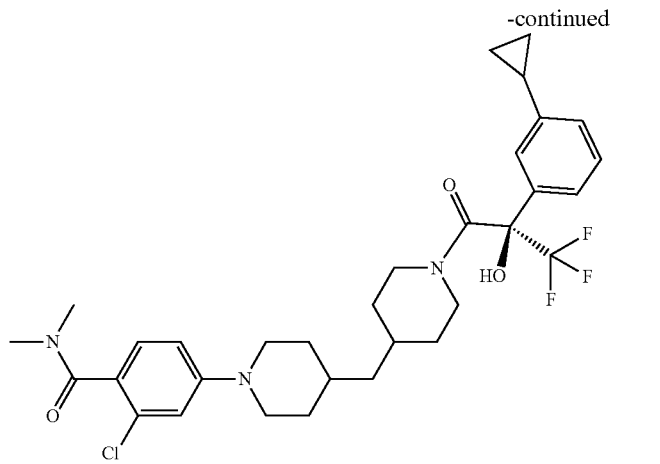
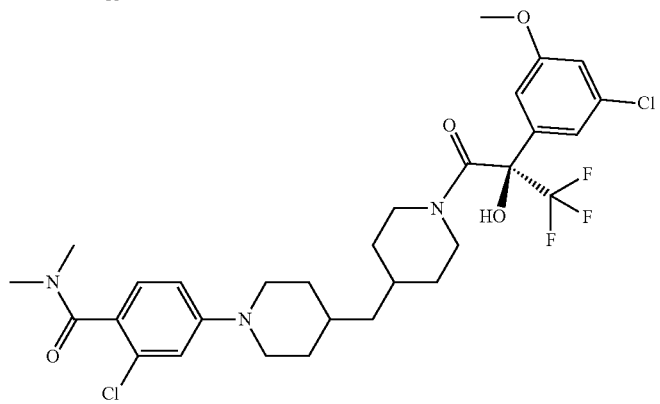
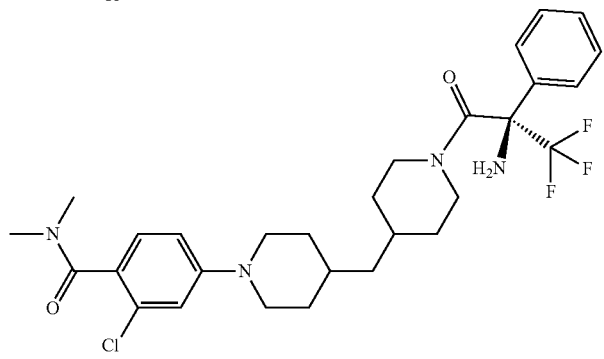
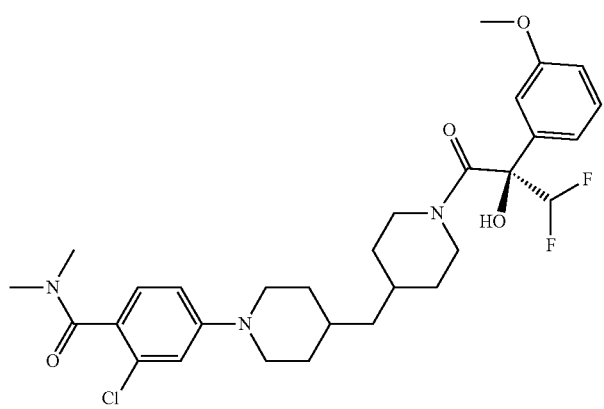

-continued
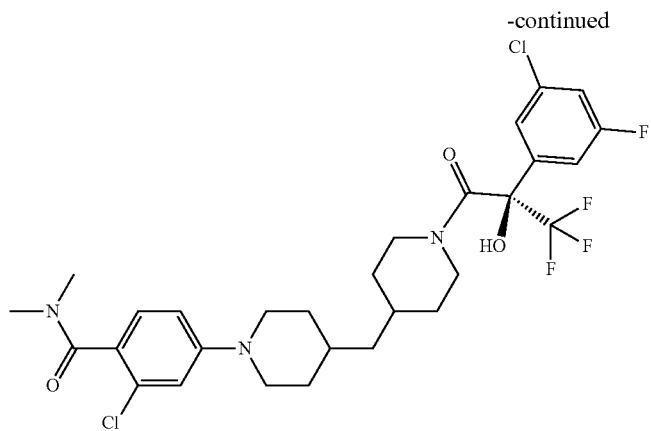
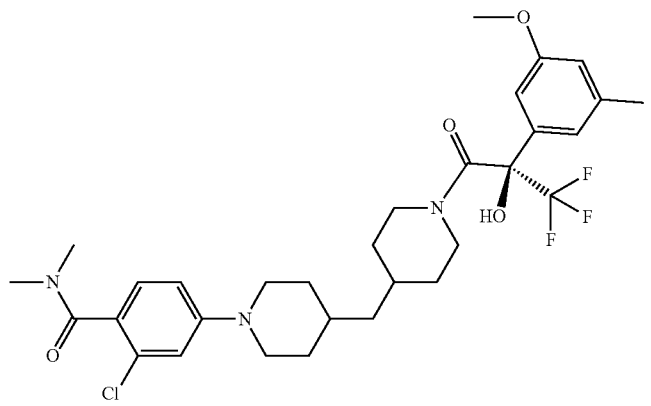
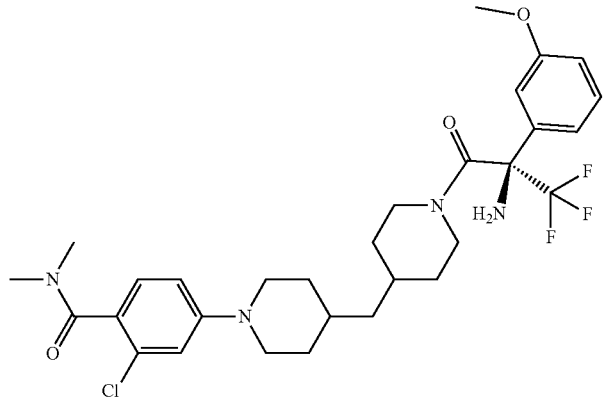
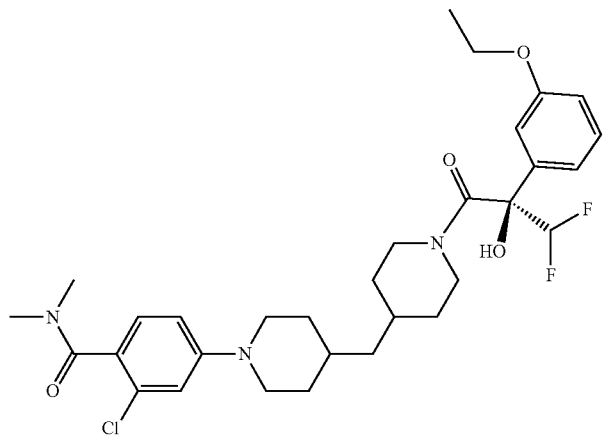

-continued
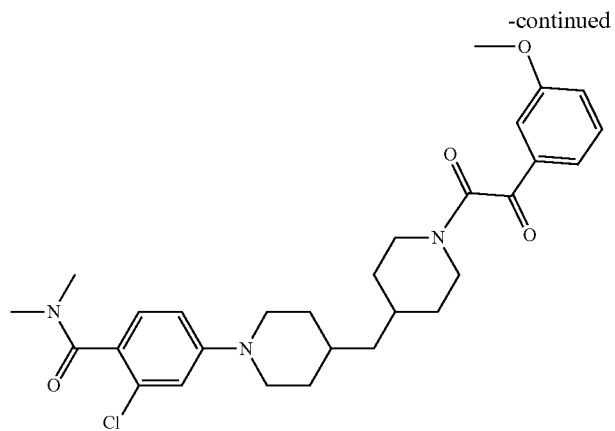
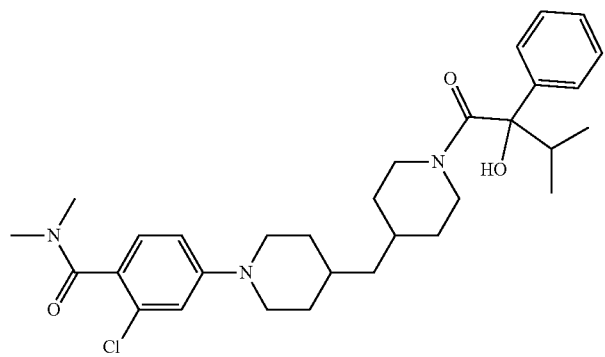
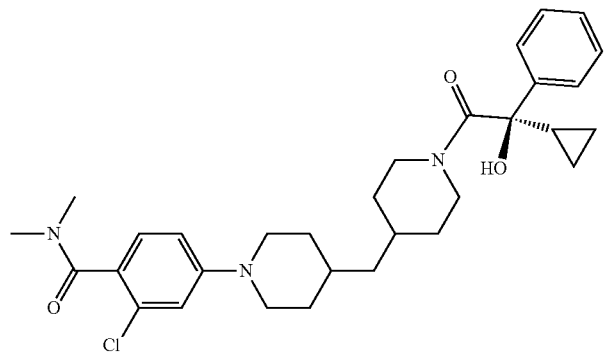
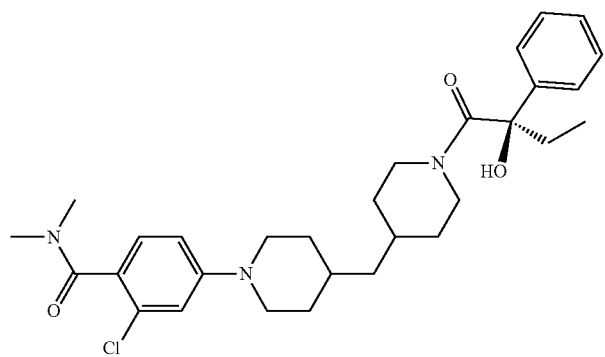

-continued
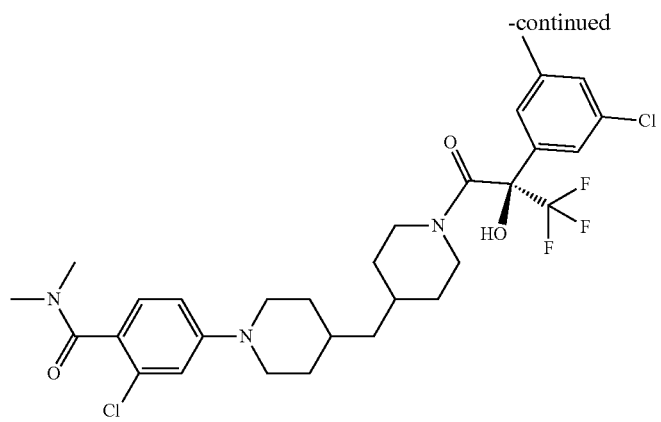
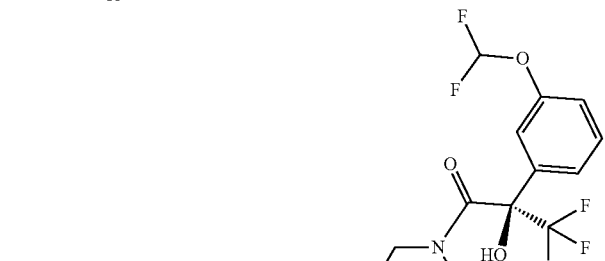
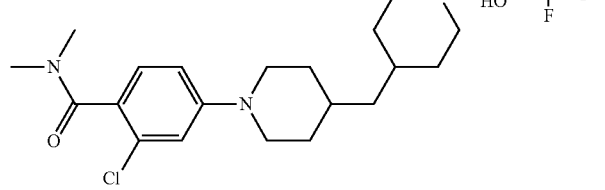
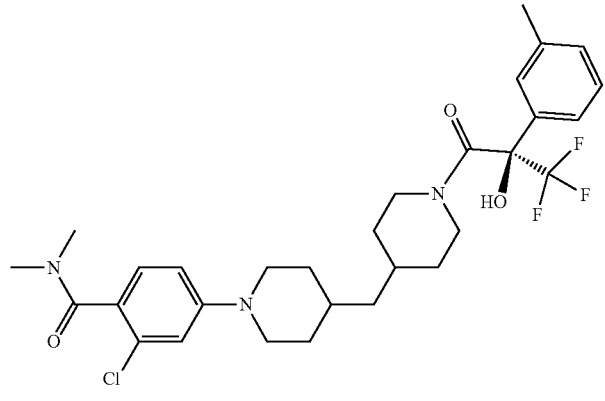

-continued
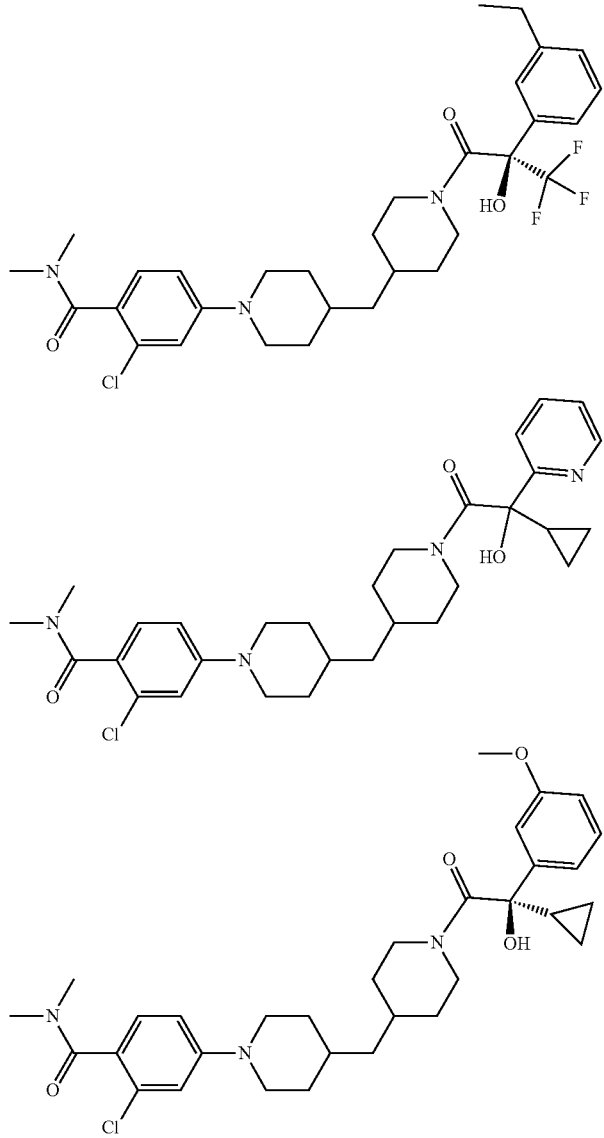
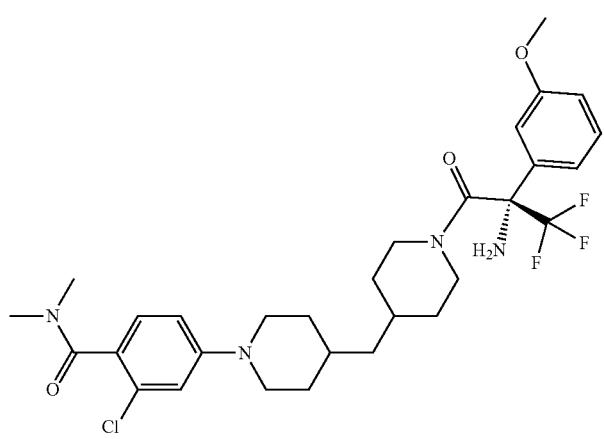

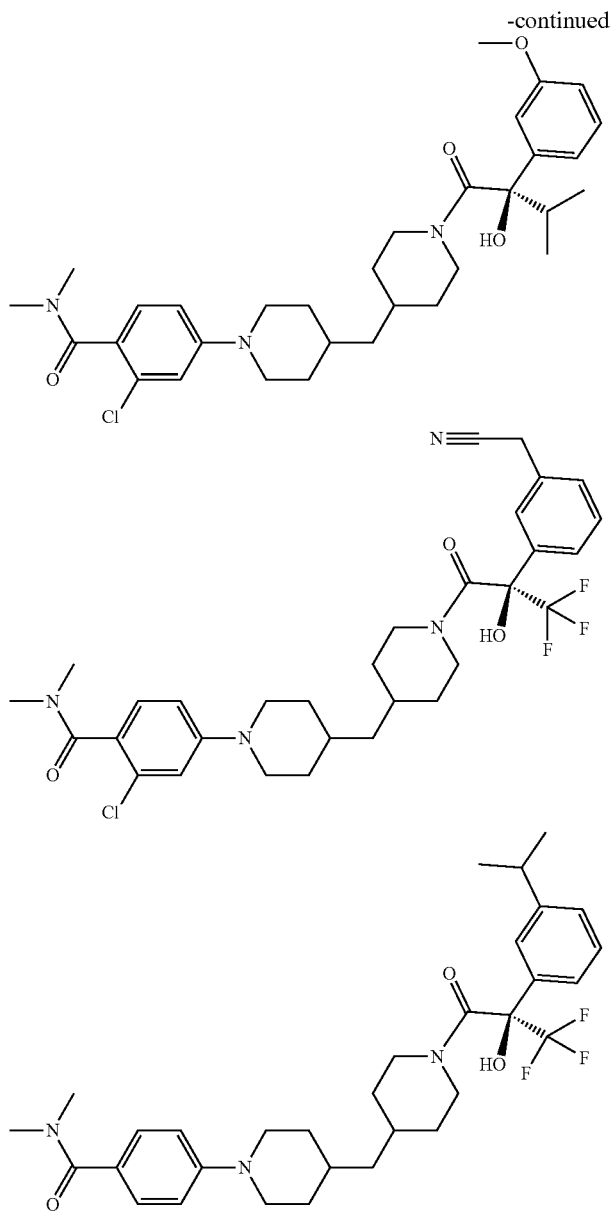
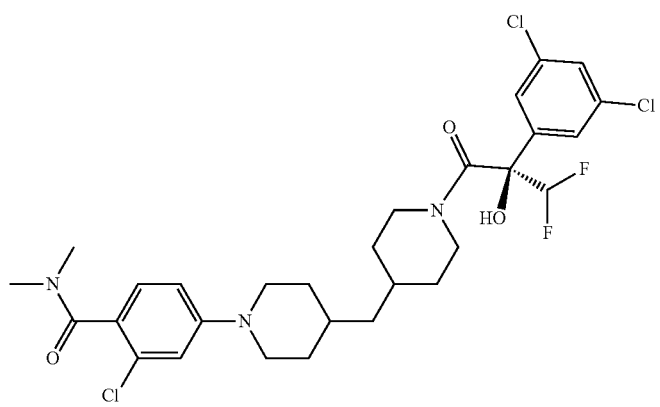

-continued
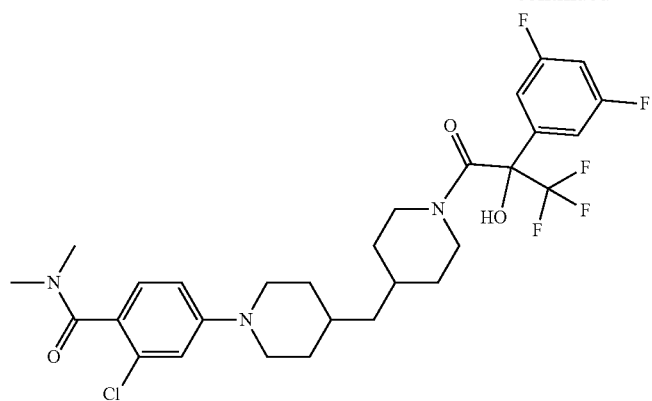
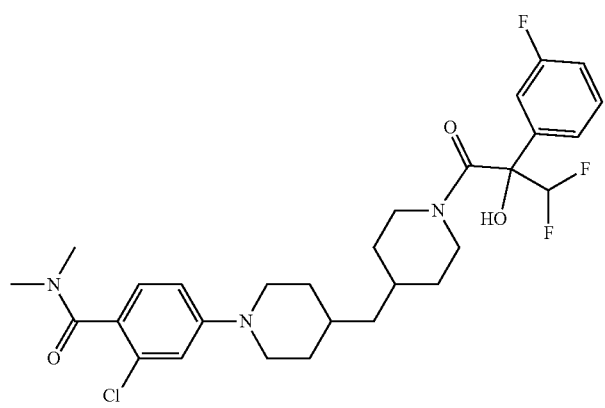
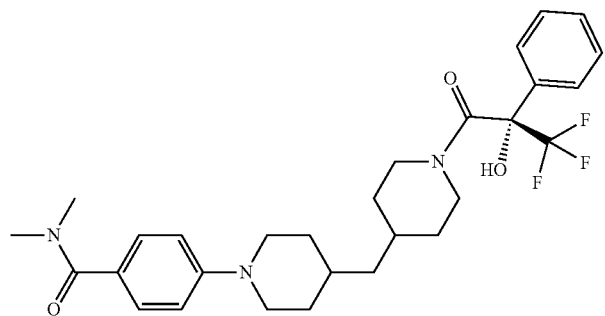
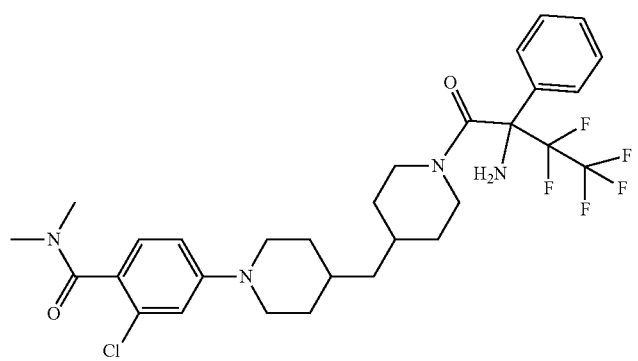

-continued
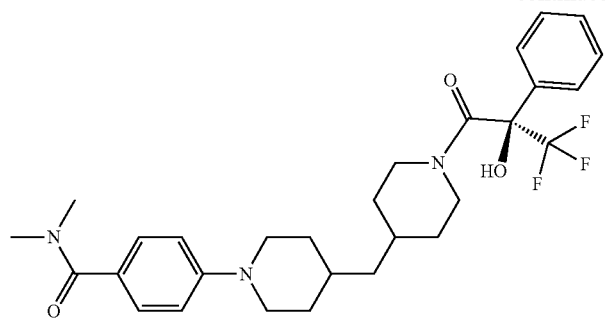
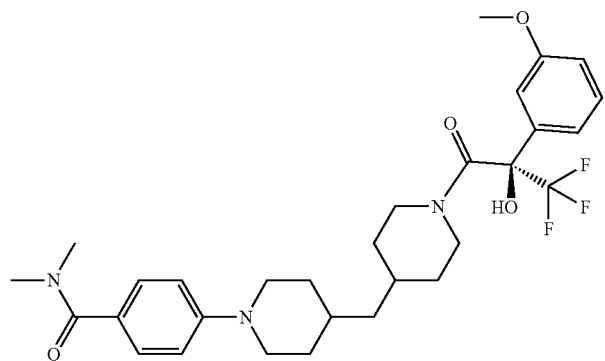
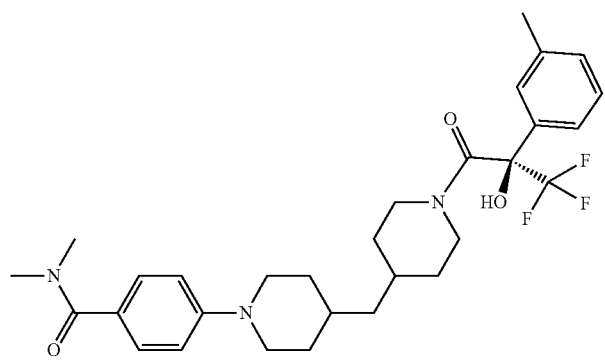
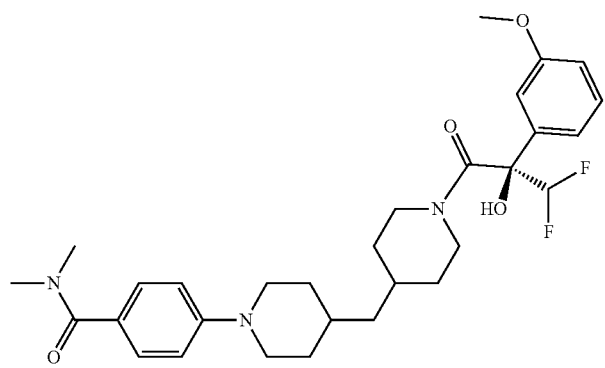

-continued
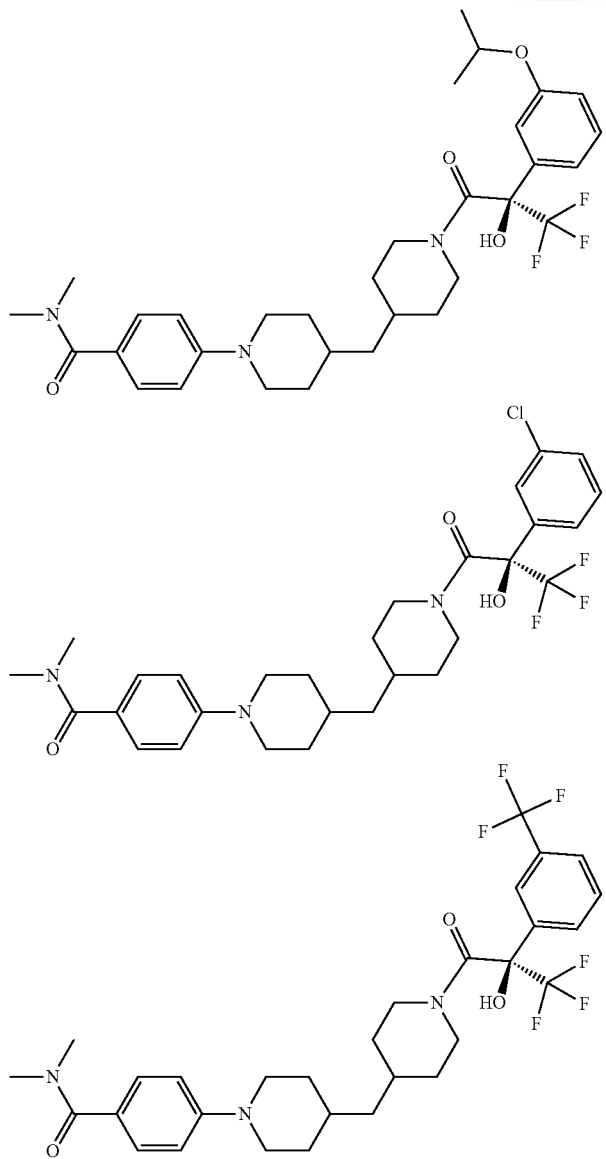
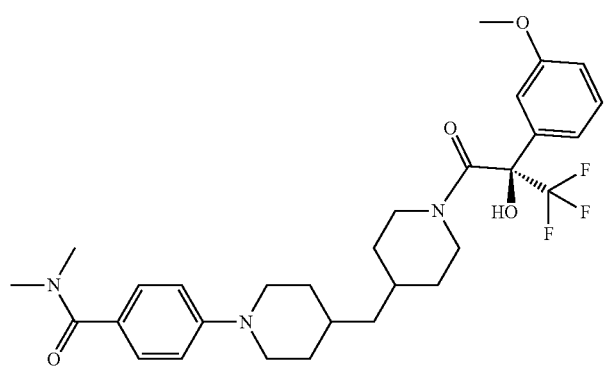

-continued
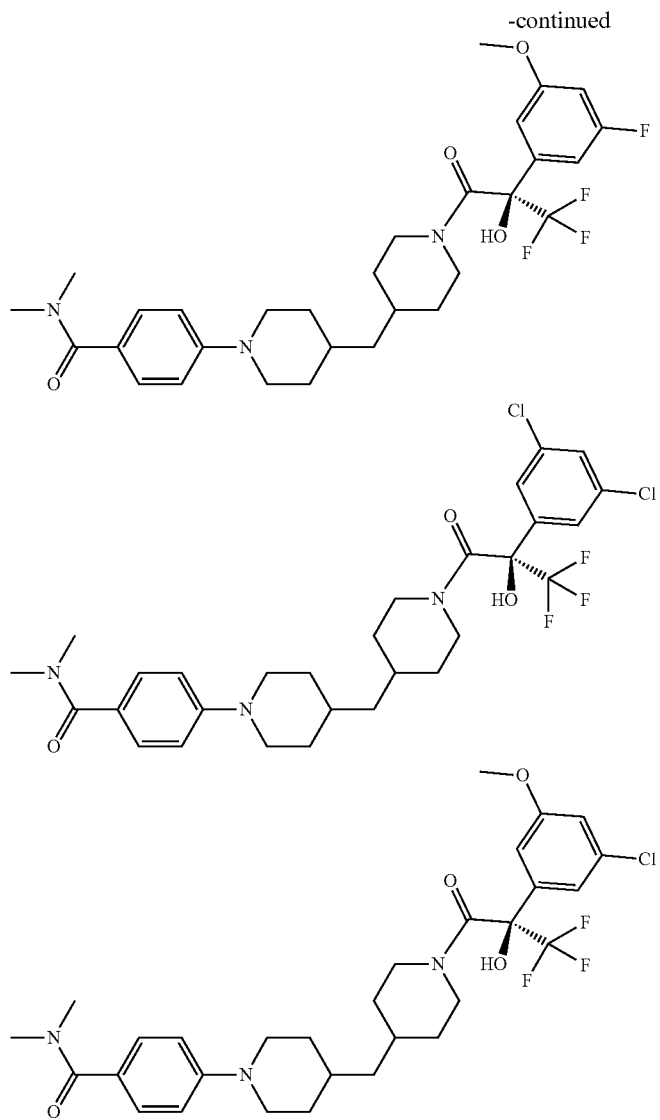
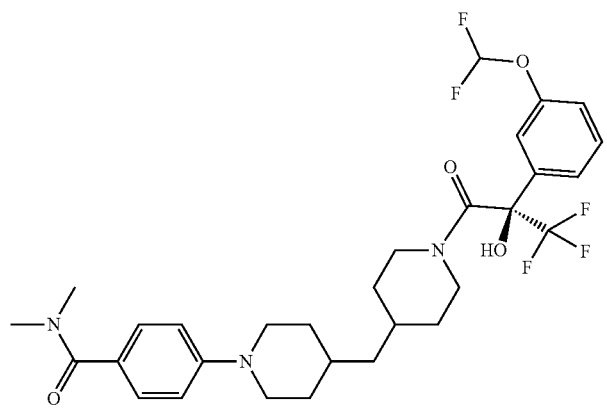

-continued
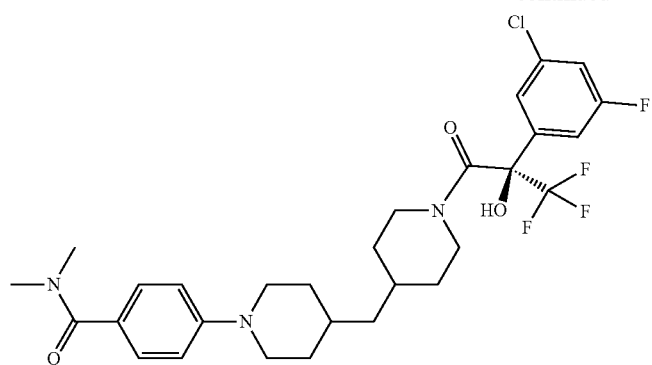
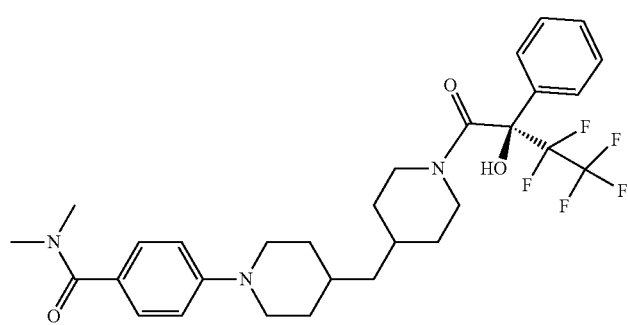
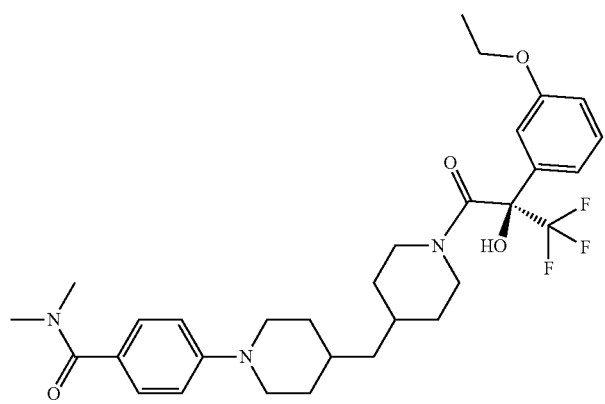
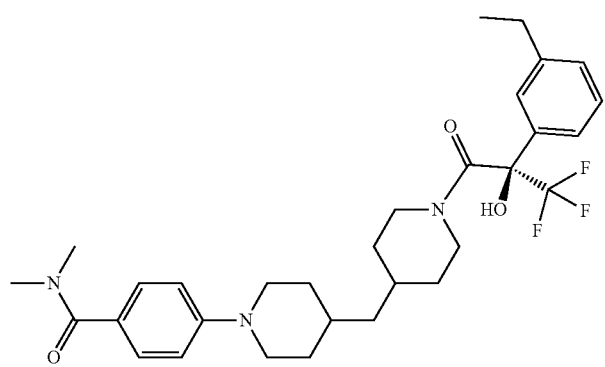

-continued
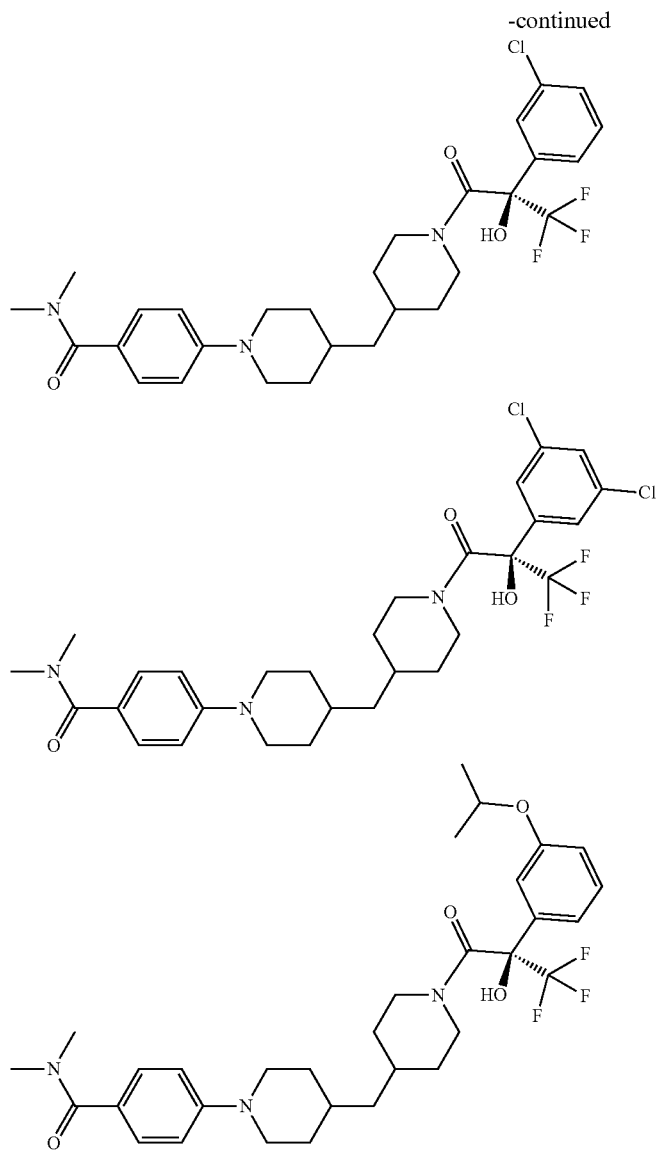
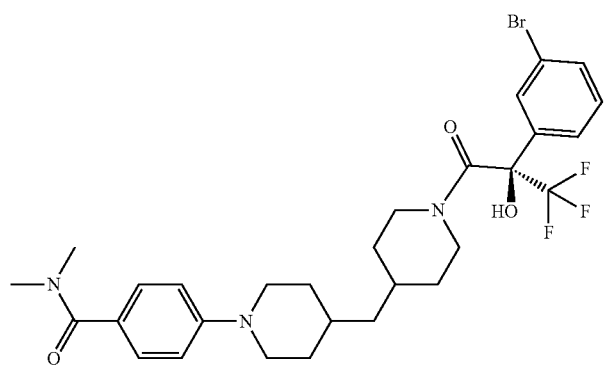

-continued
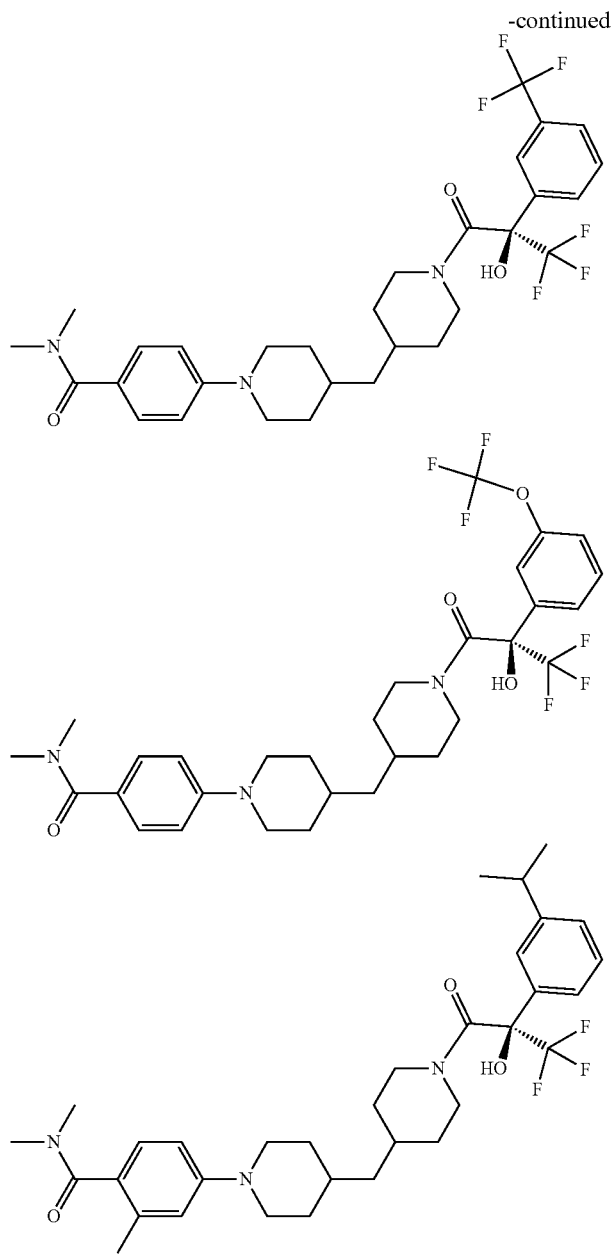
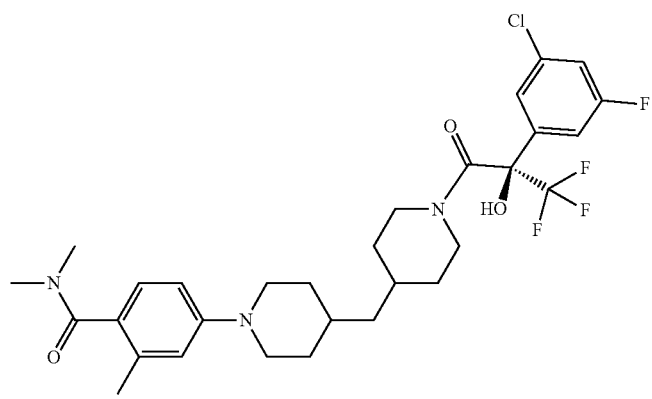

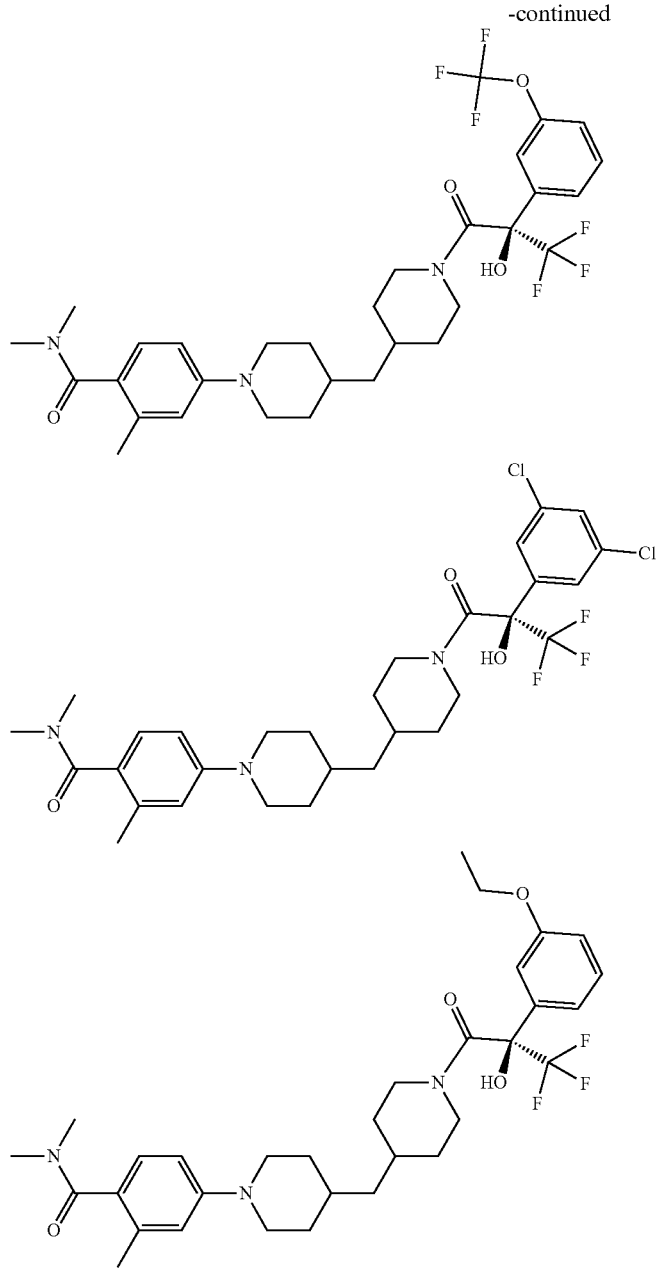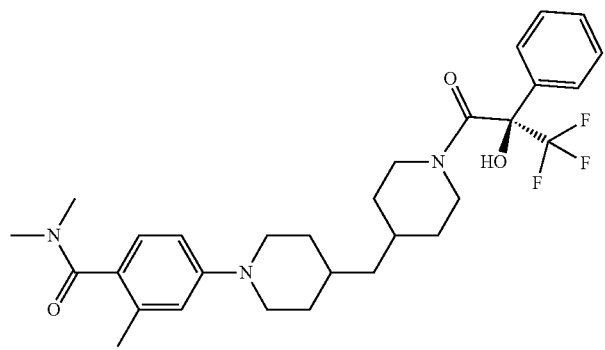

-continued
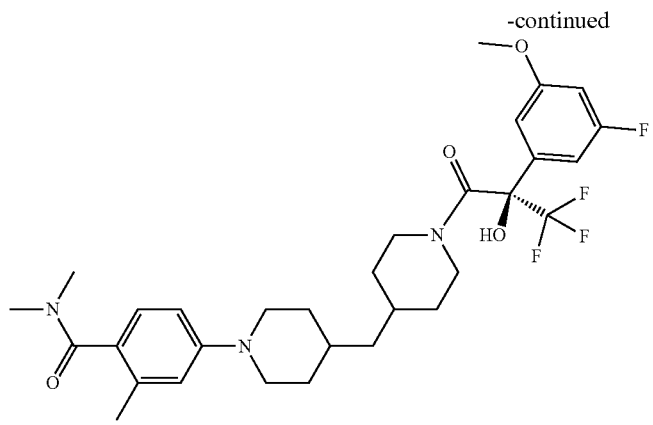
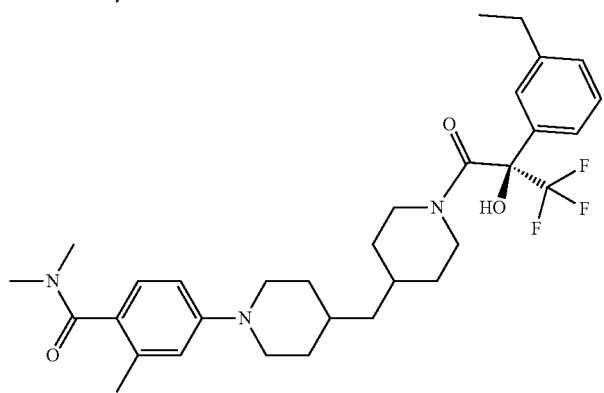
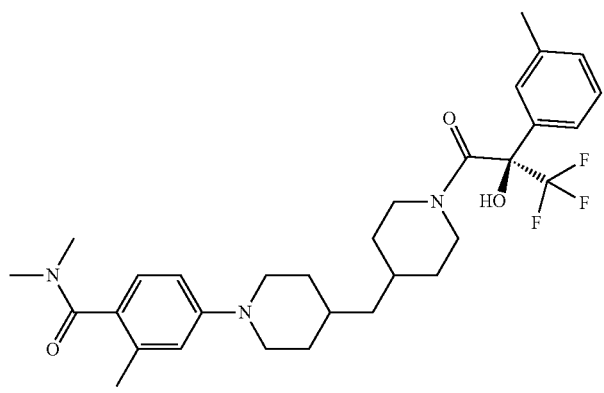
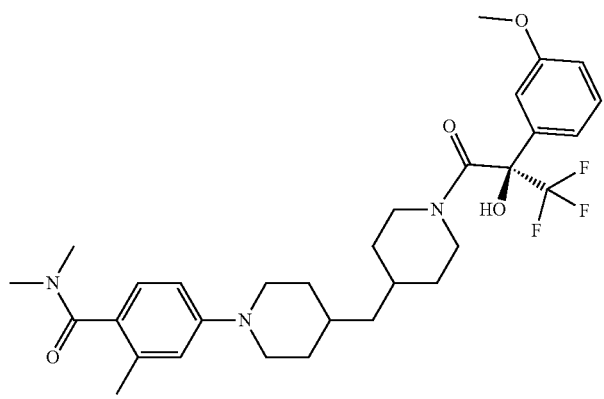

-continued
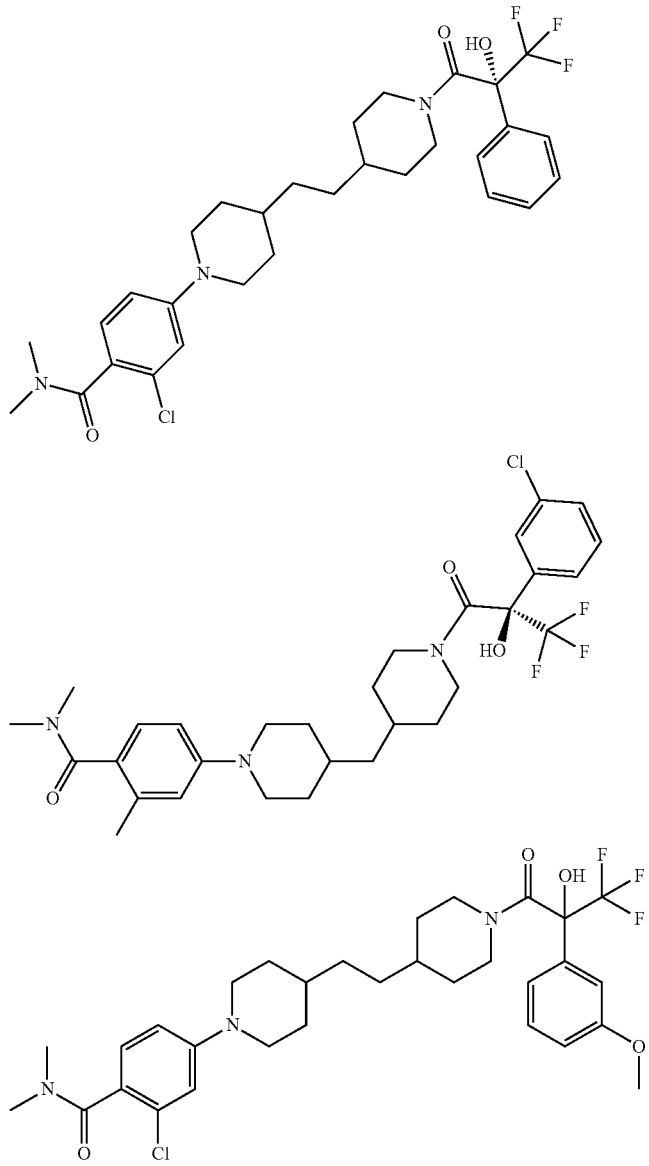
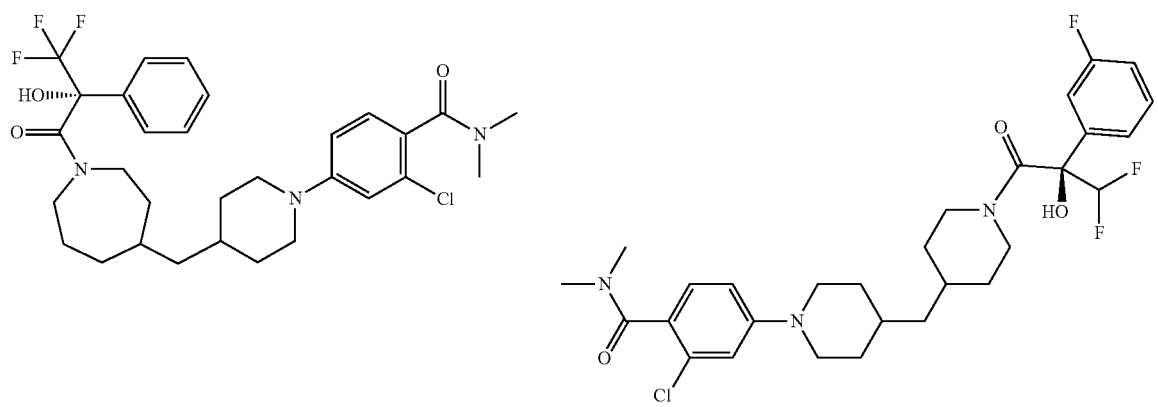

381
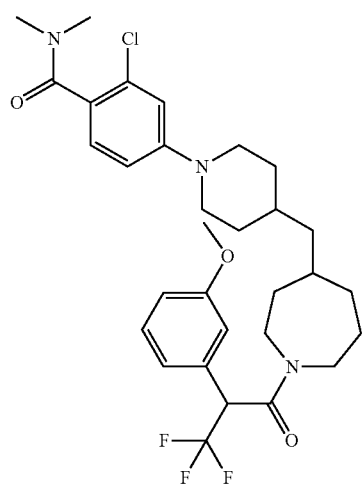
382
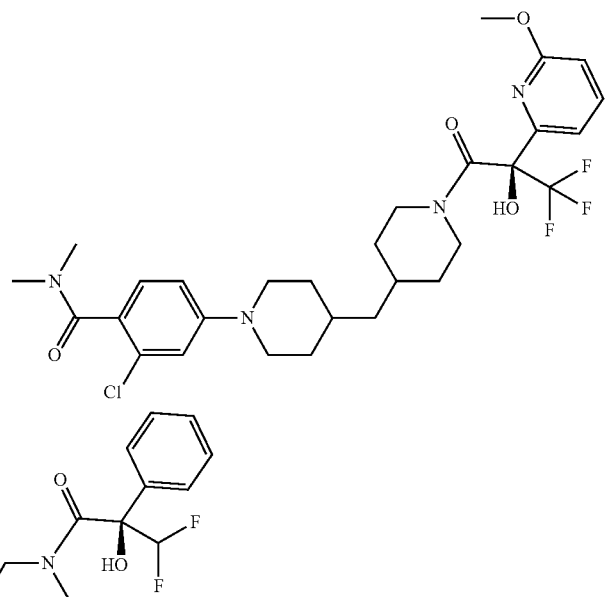
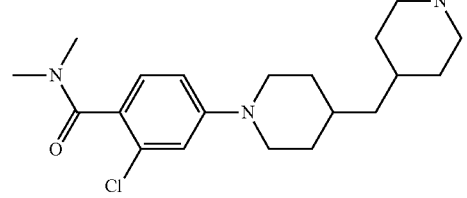
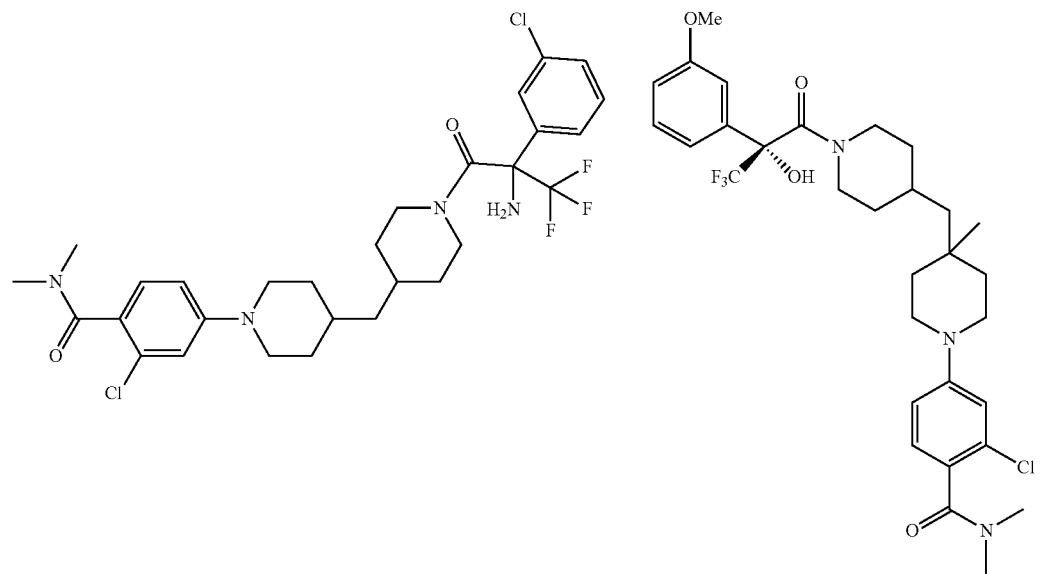

383
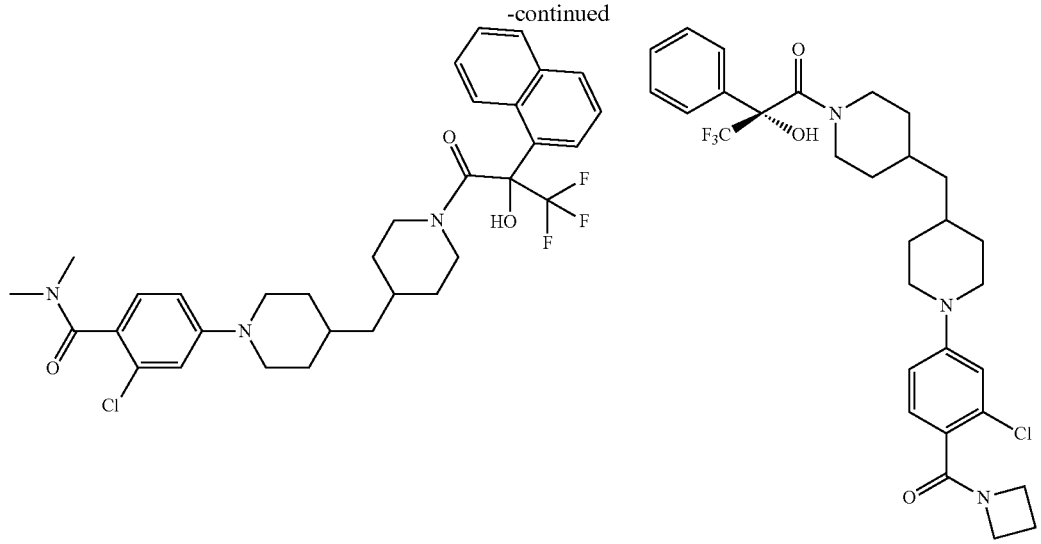
-continued
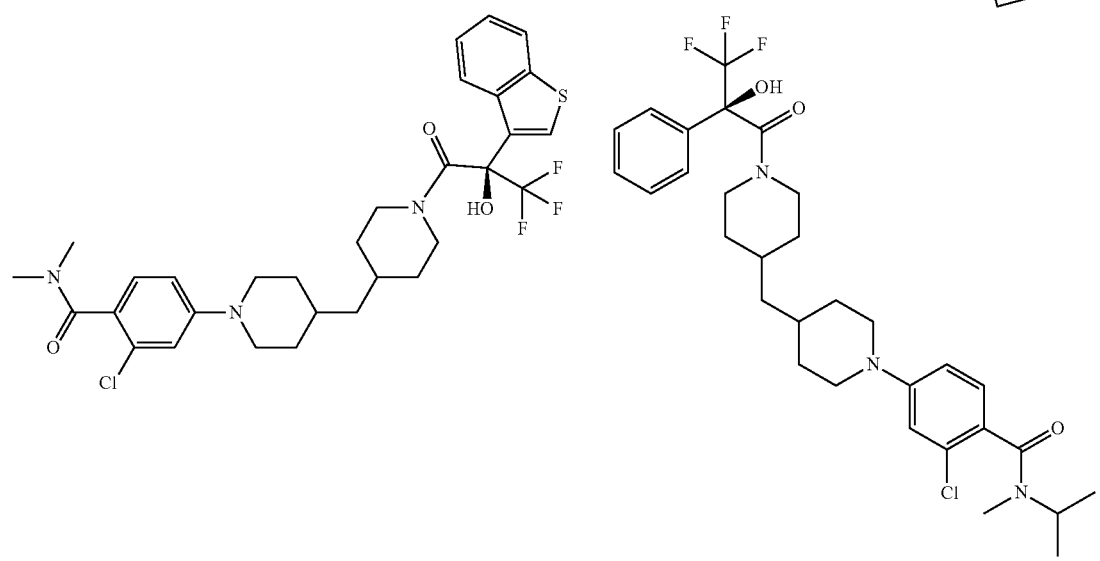
384
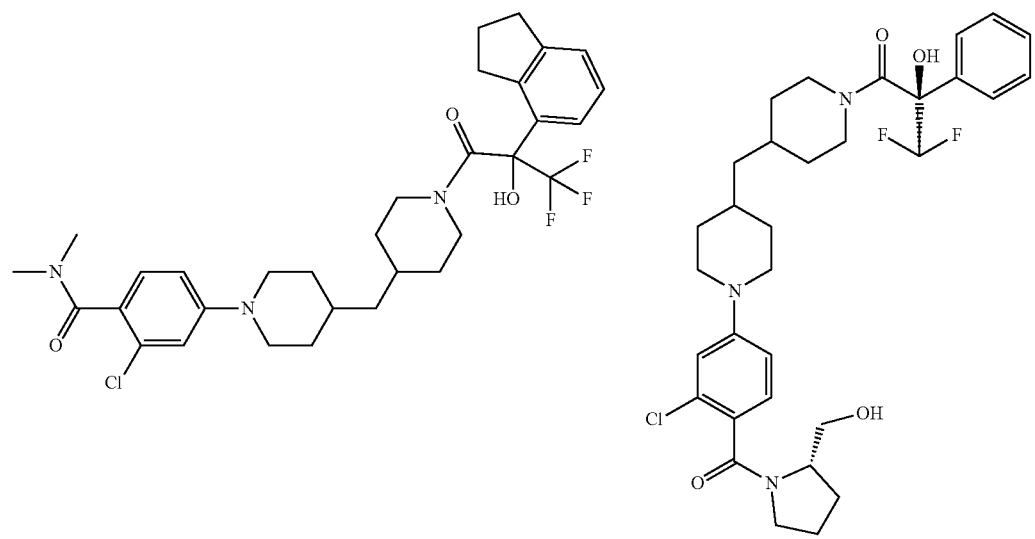

385
-continued
386
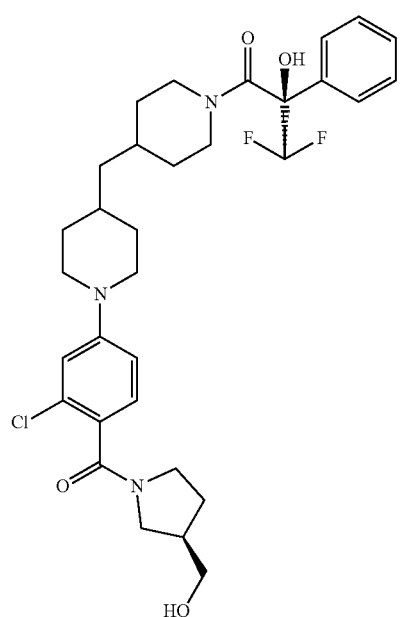
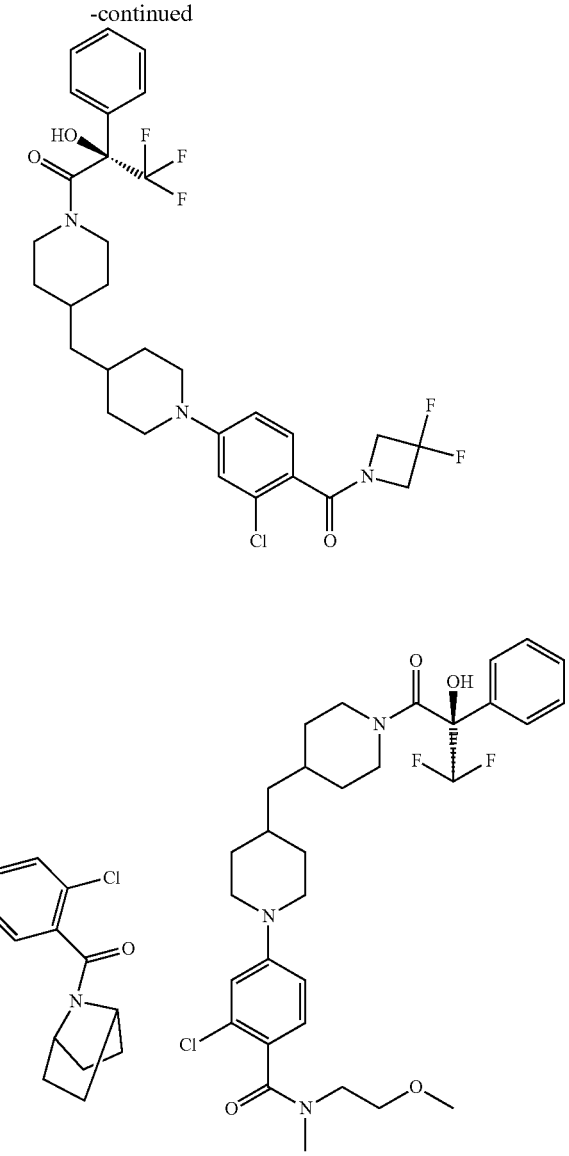
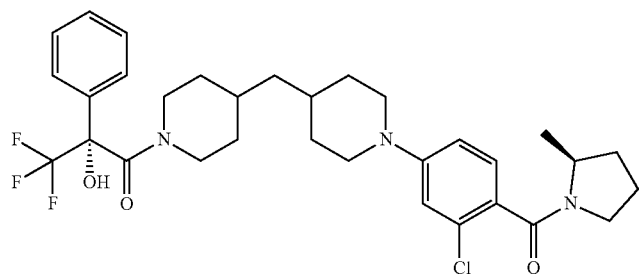
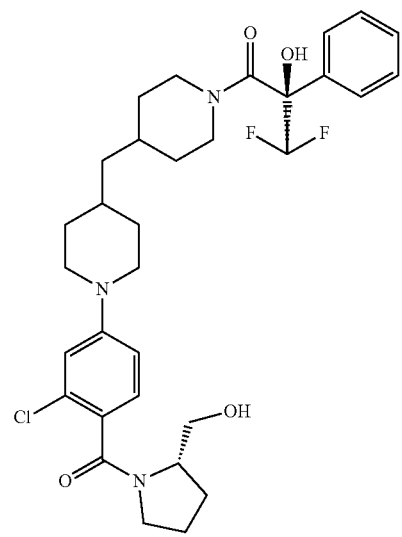

387
388
-continued
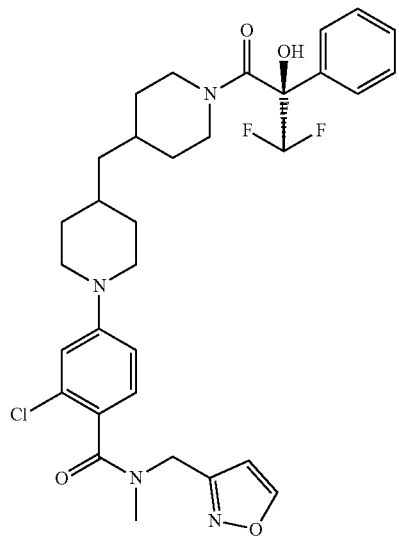
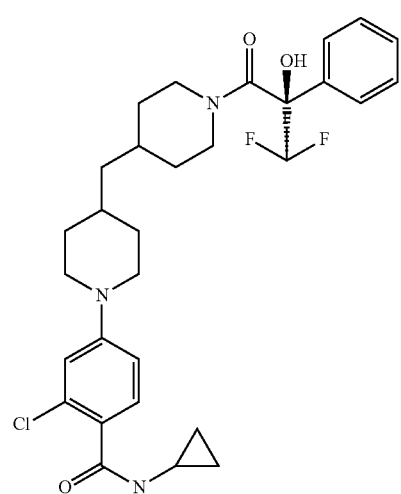
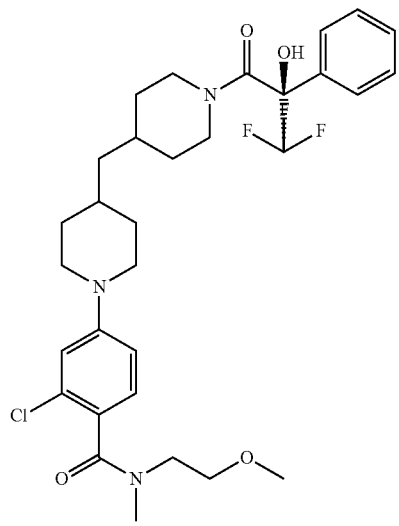
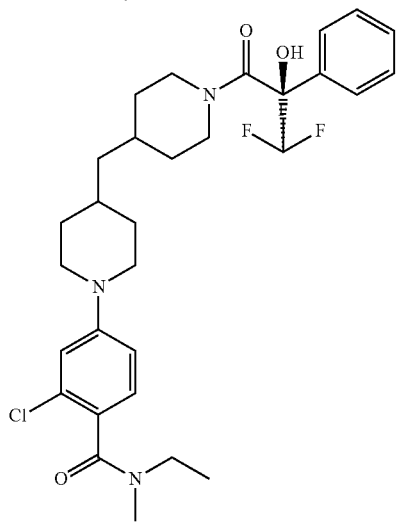
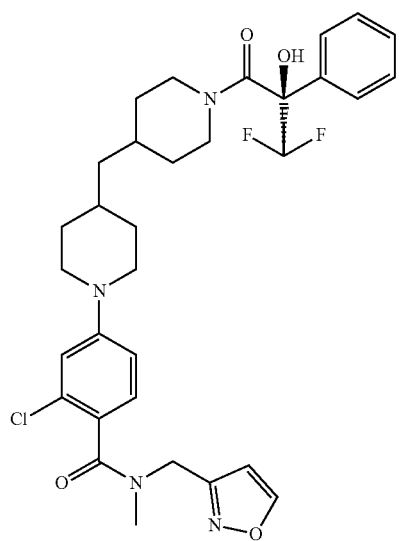
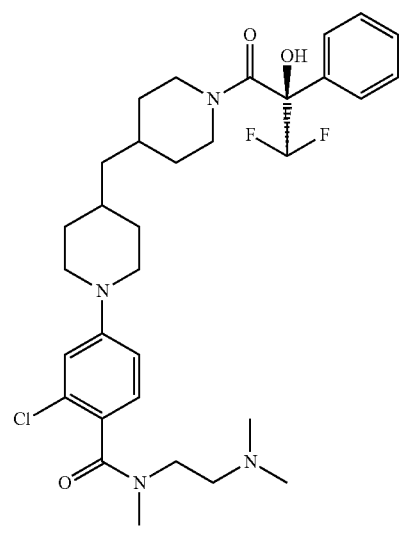

-continued
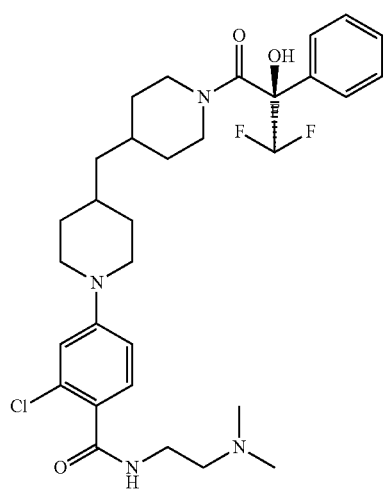
389
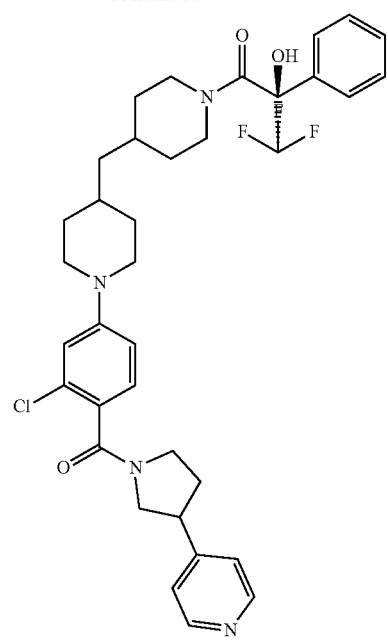
390
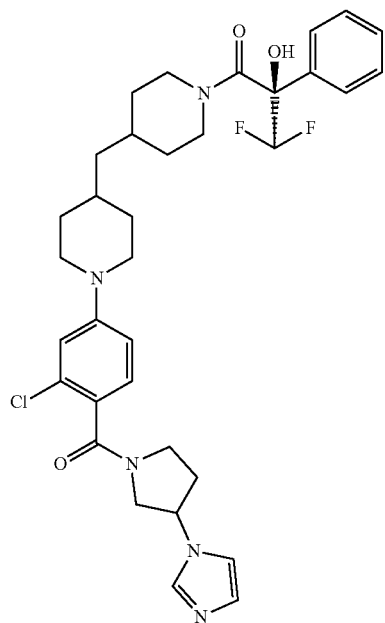
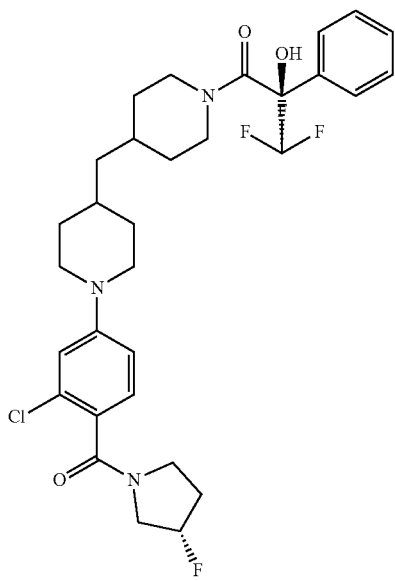

391
392
-continued
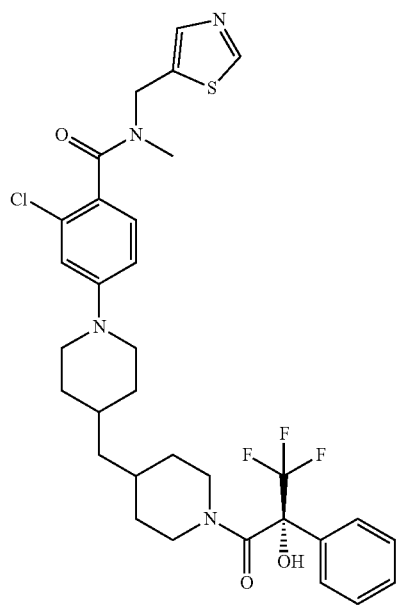
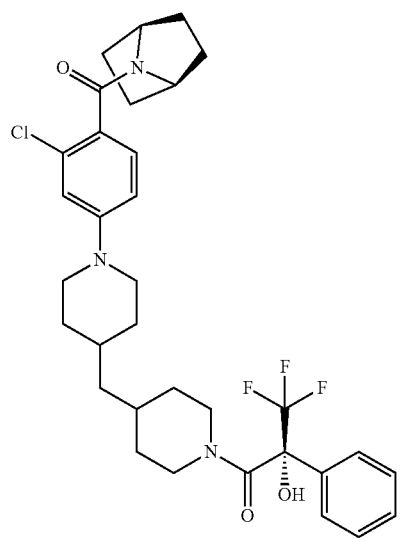
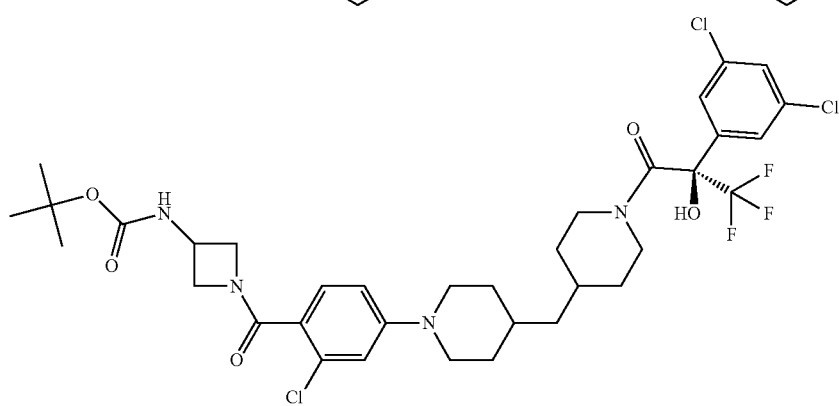
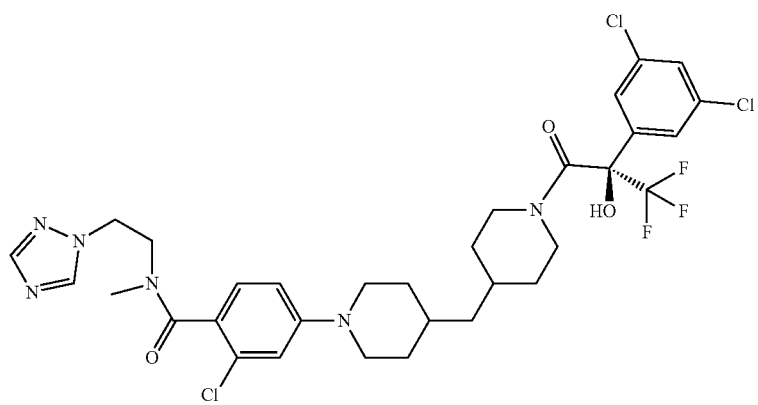

393
394
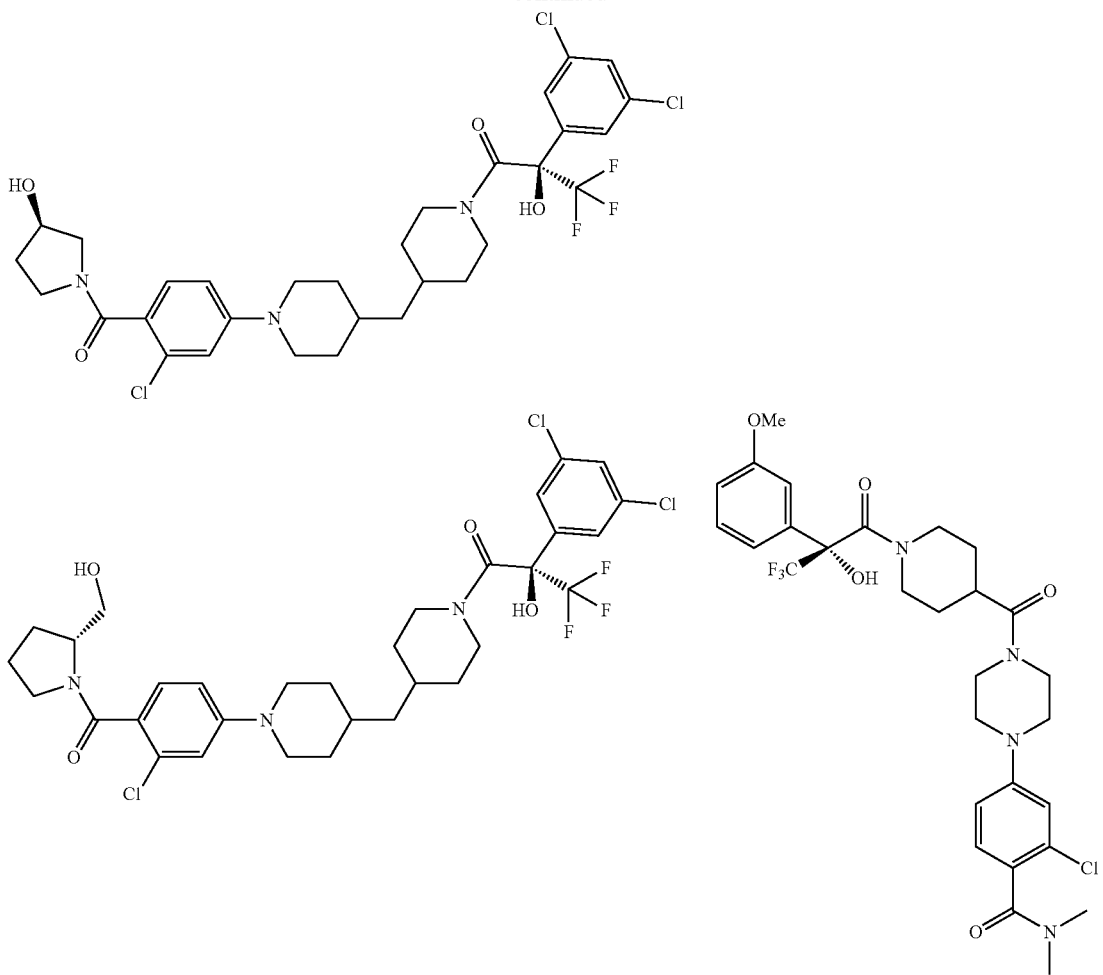
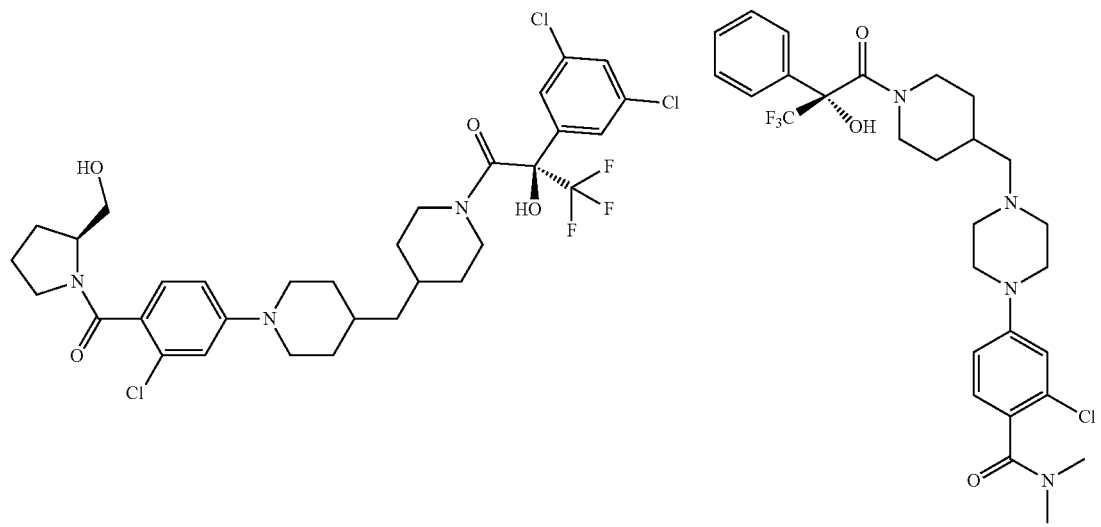

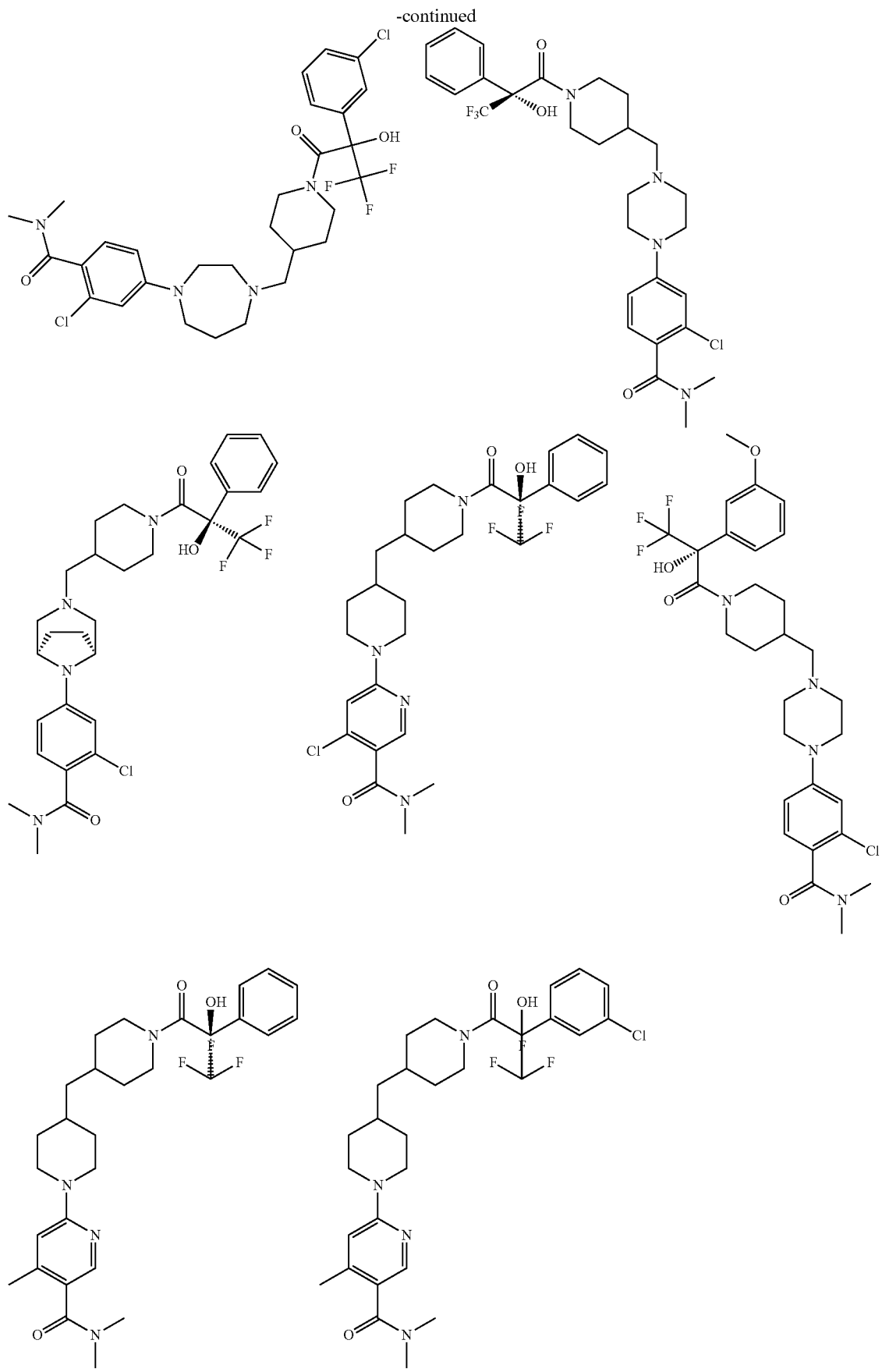

-continued
397
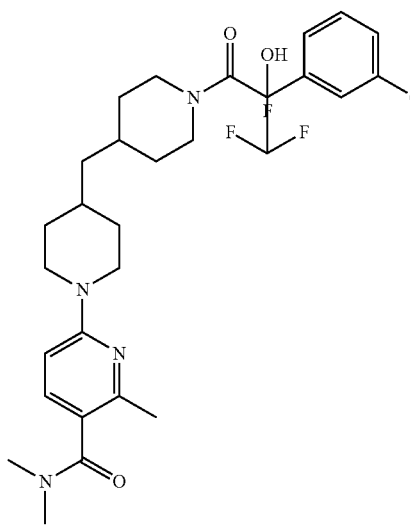
398
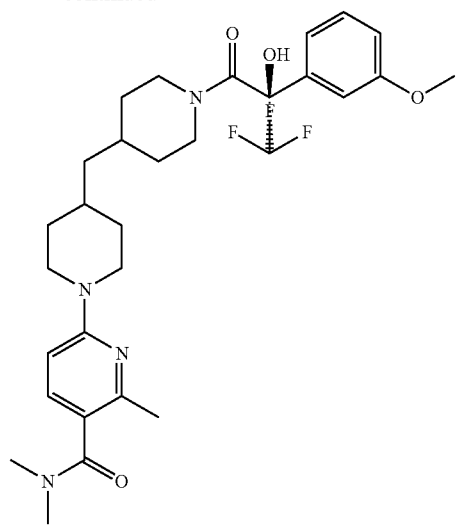
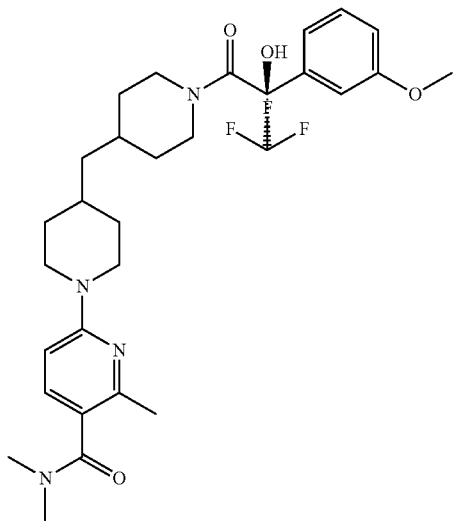
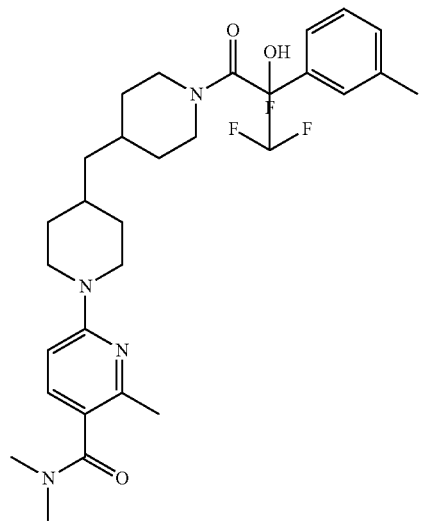
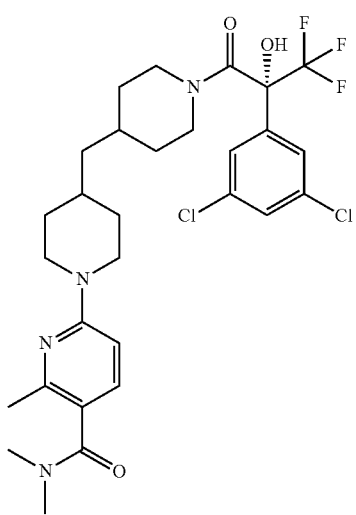
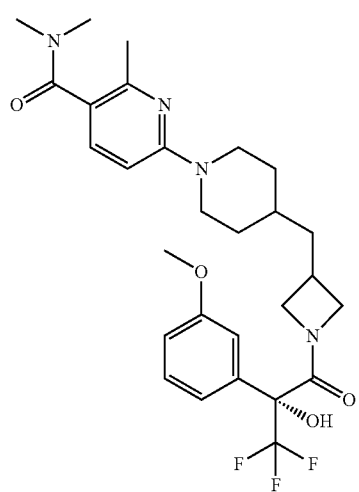

399
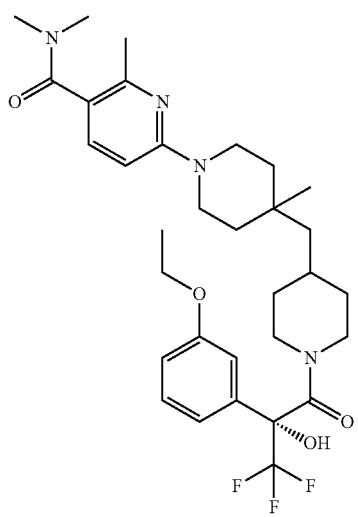
-continued
400
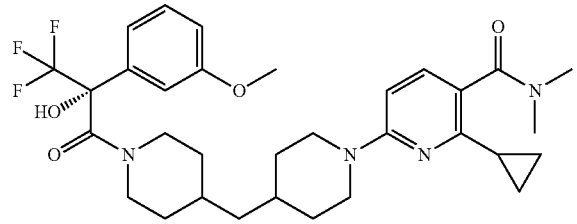
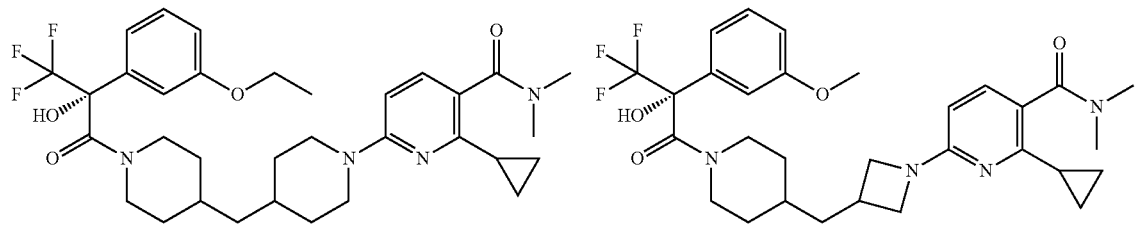
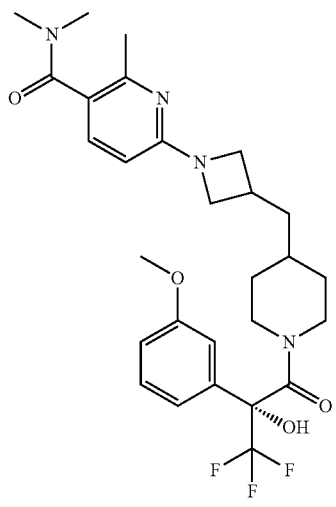
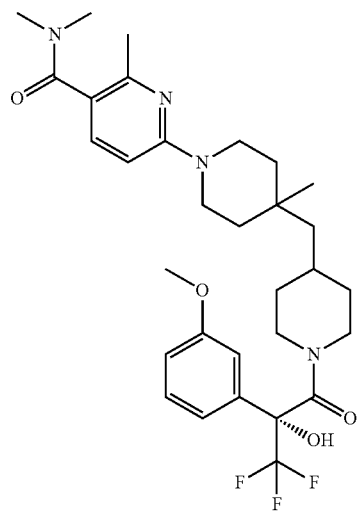

-continued
401
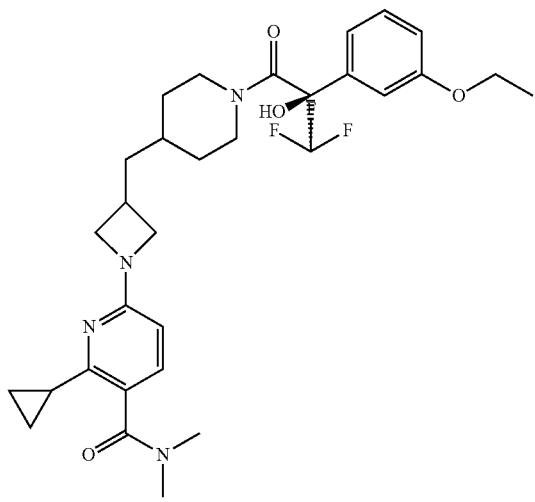
402
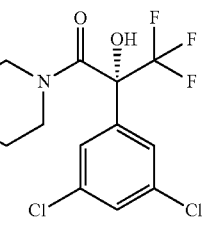
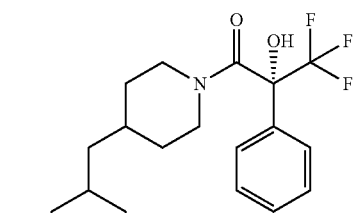
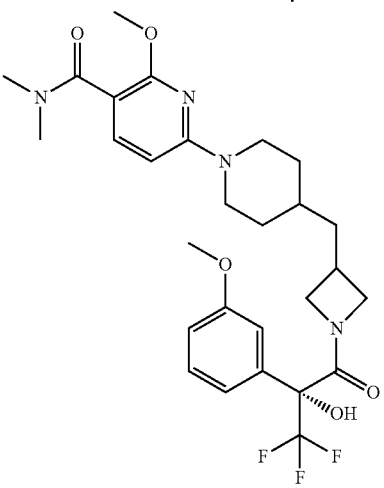
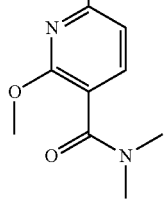
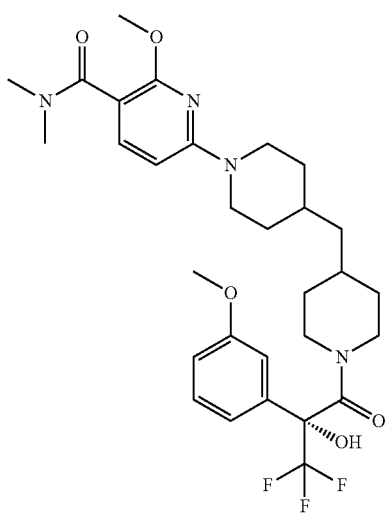
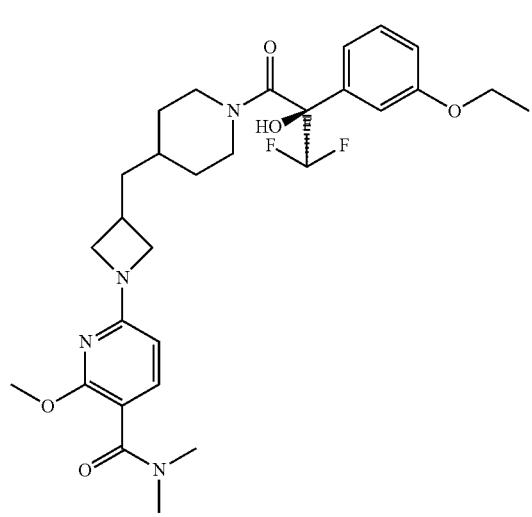

-continued
403
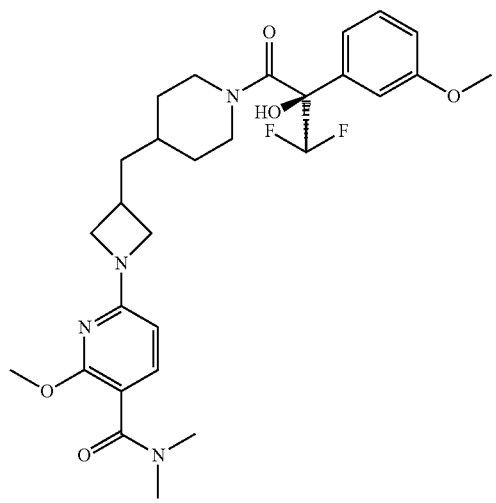
404
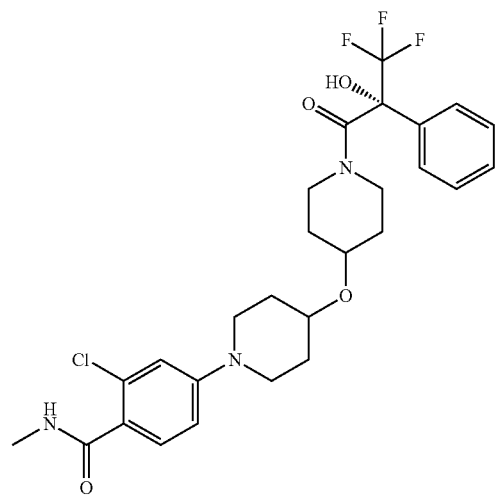
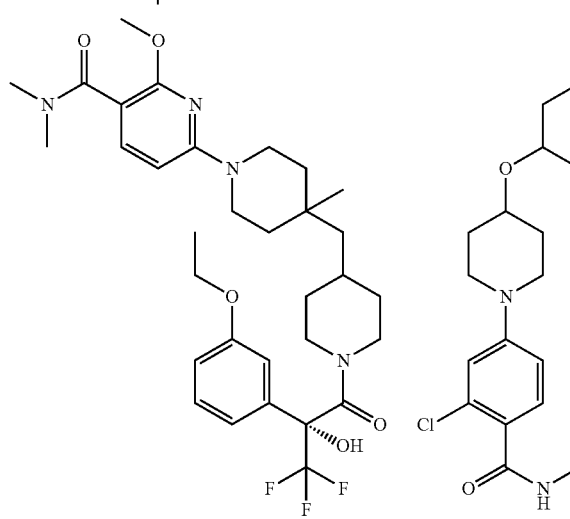
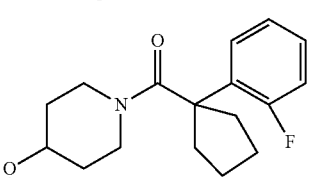
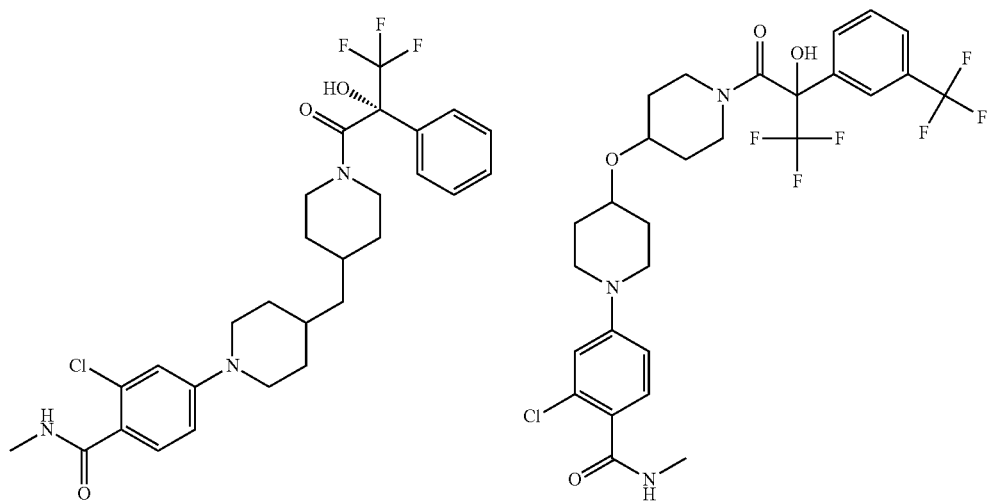

-continued
| 405 | 406 |
|---|---|
| 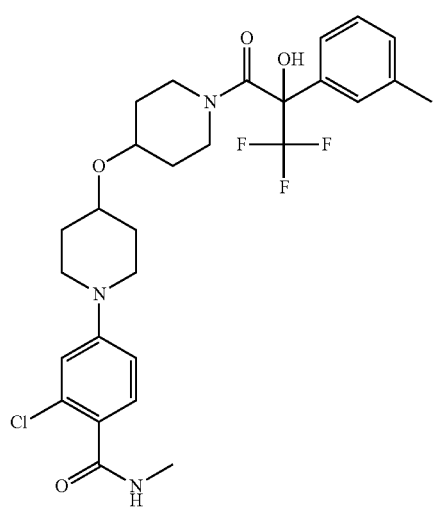 | 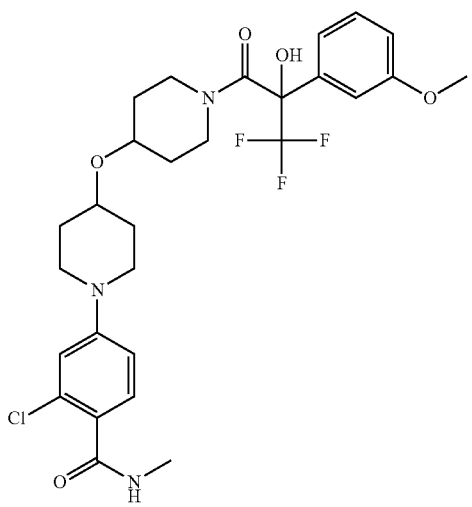 |
| 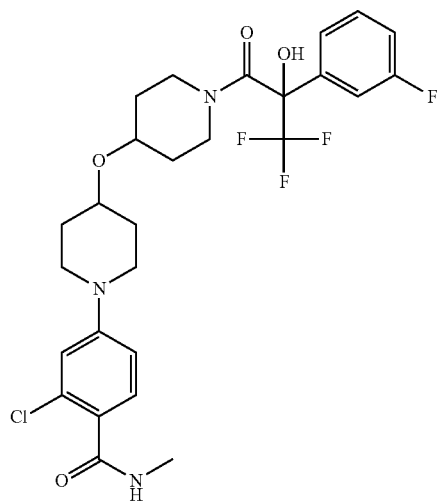 | 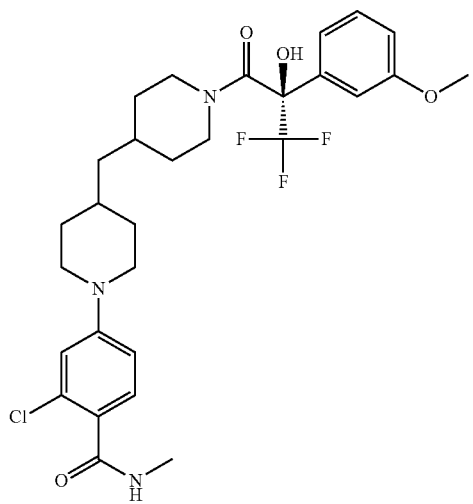 |
| 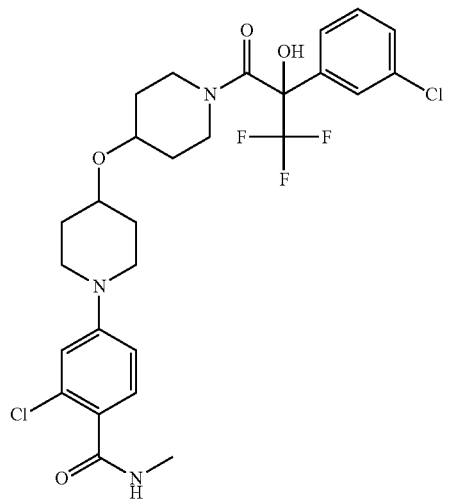 | 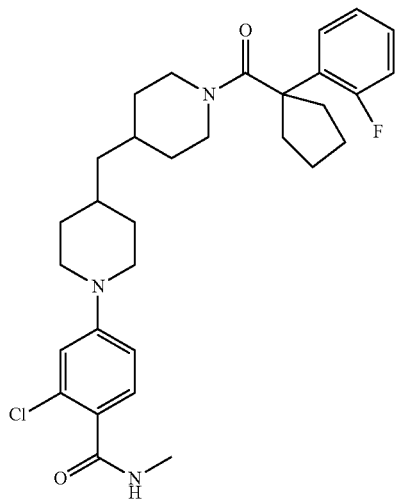 |

407
408
-continued
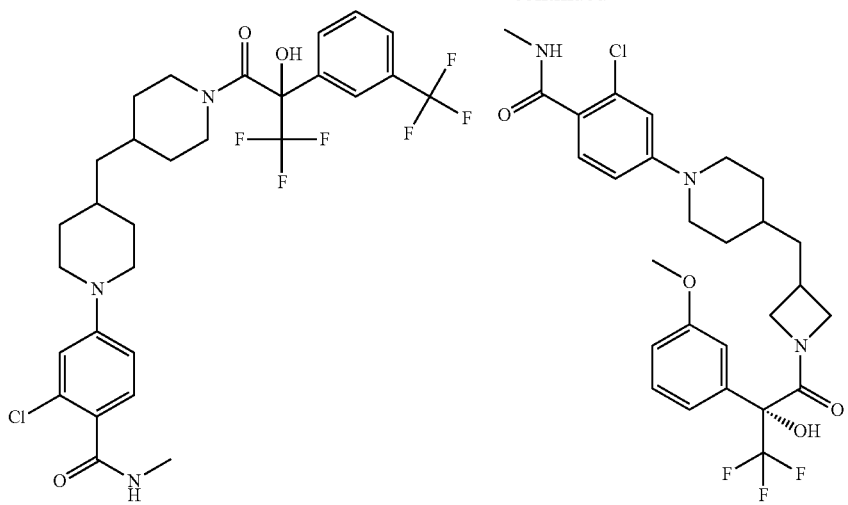
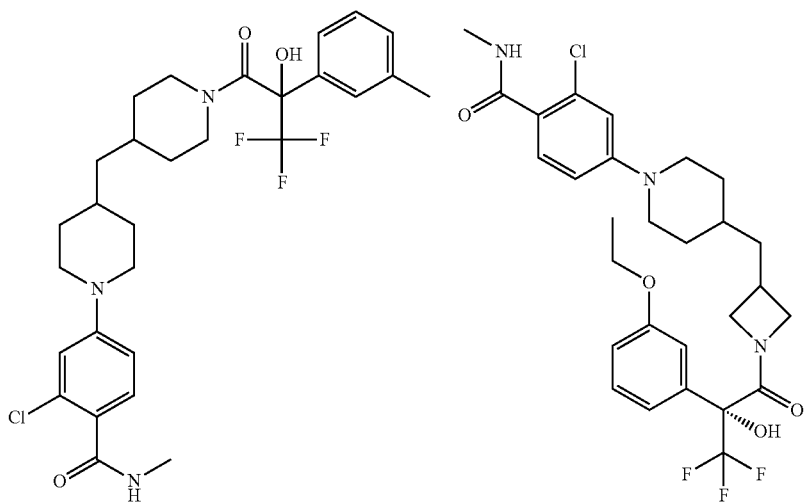
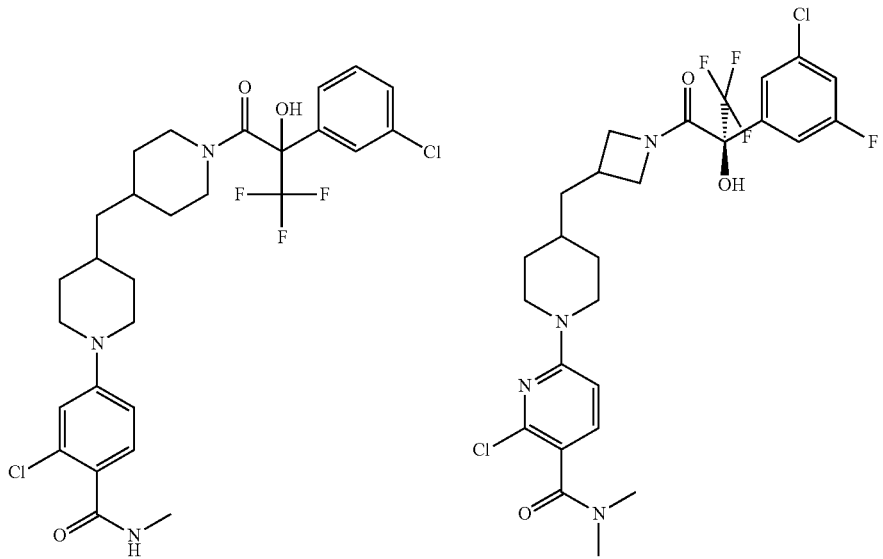

409
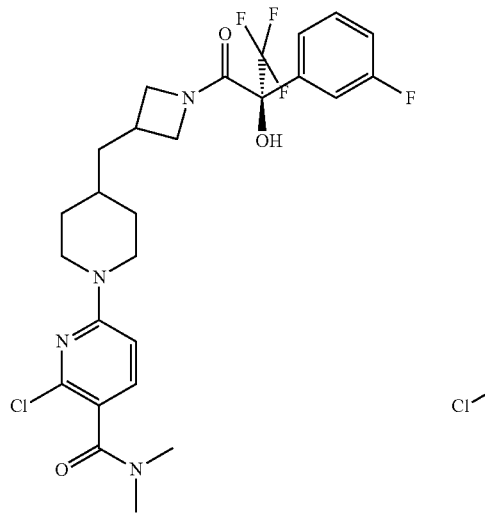
-continued
410
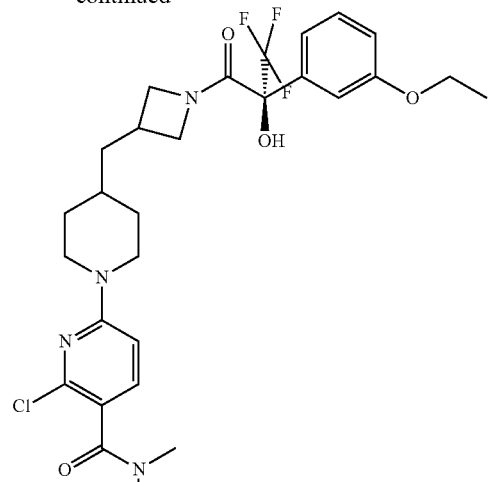
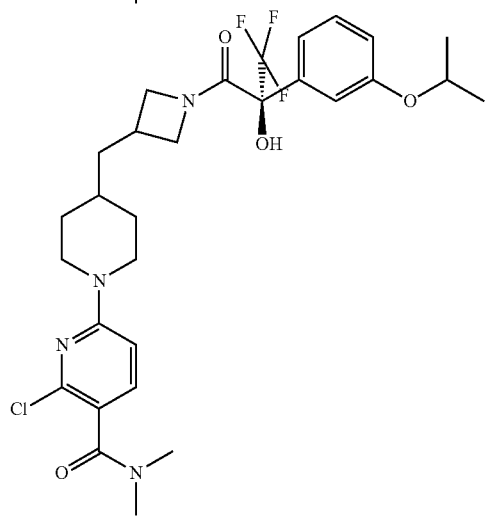
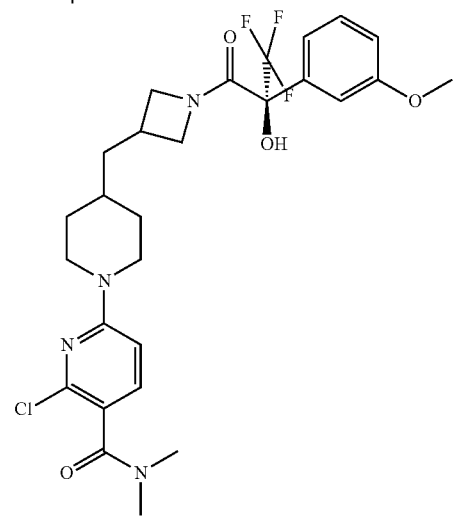
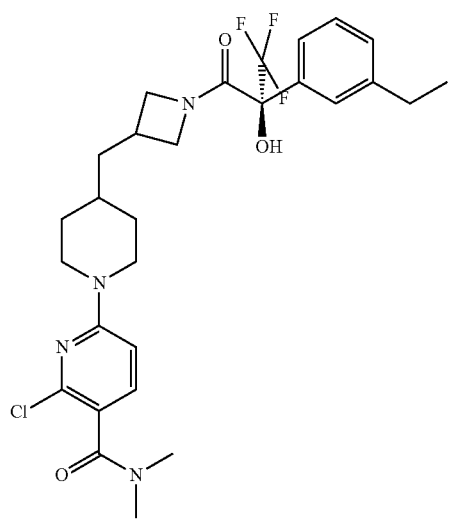
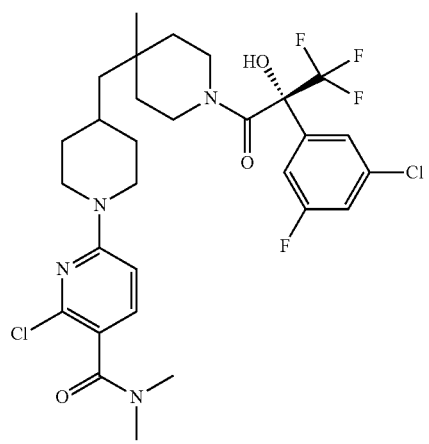

411
412
-continued
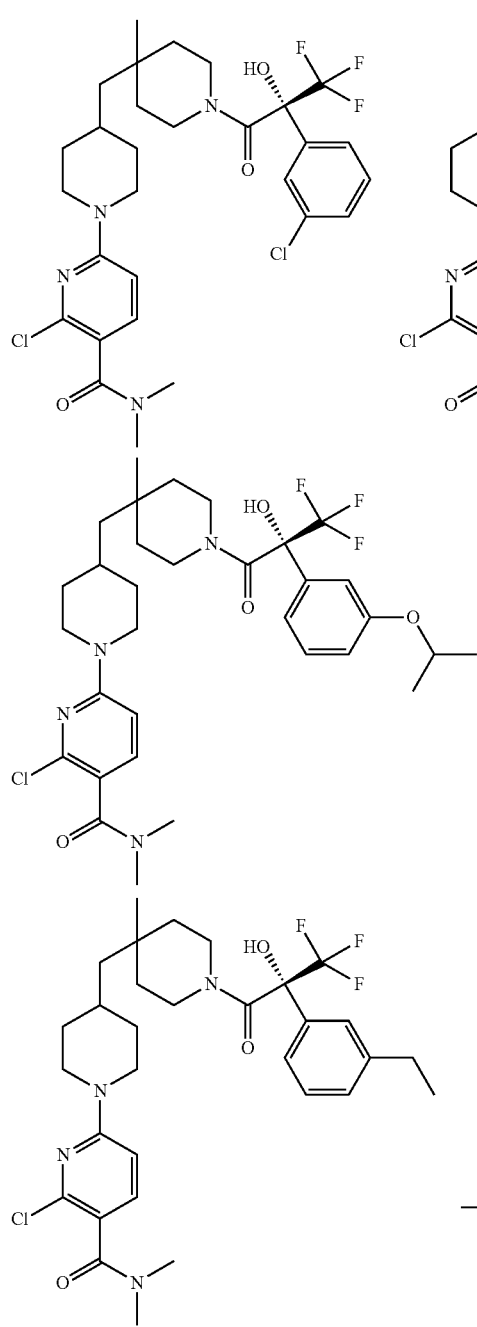
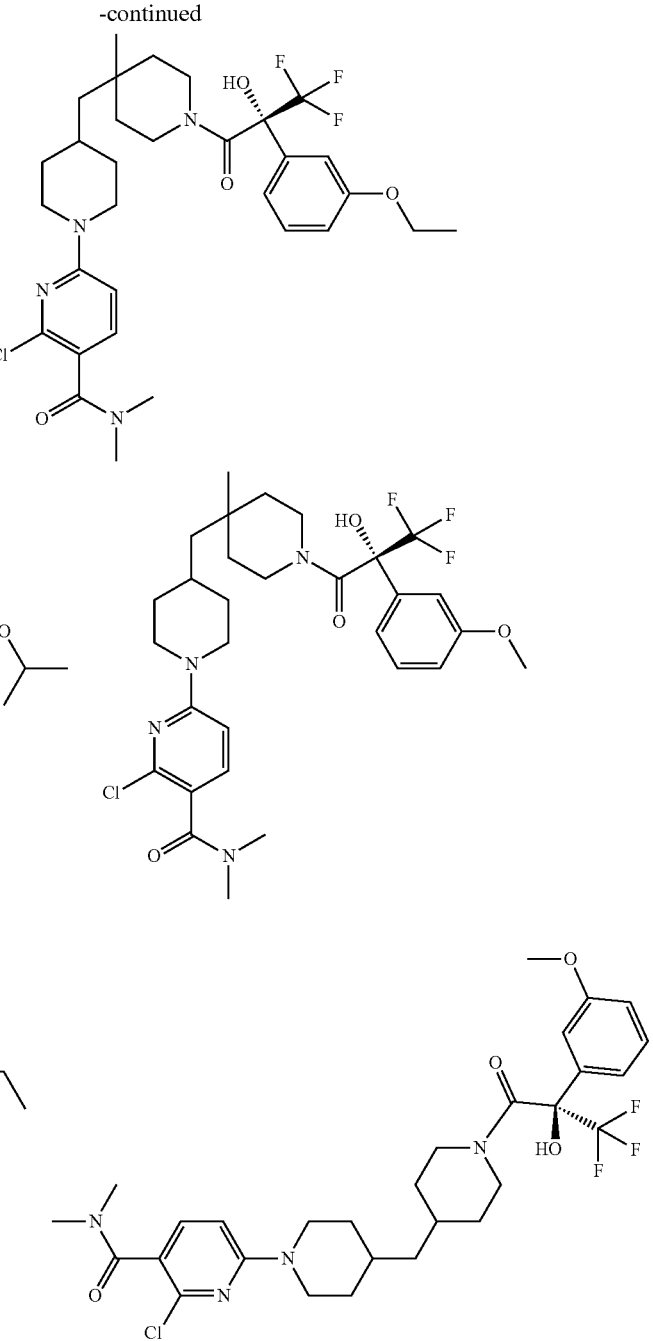
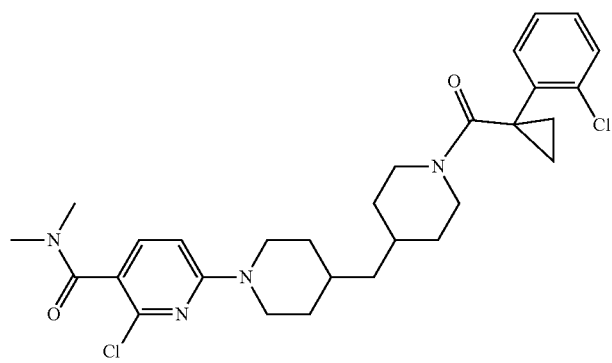

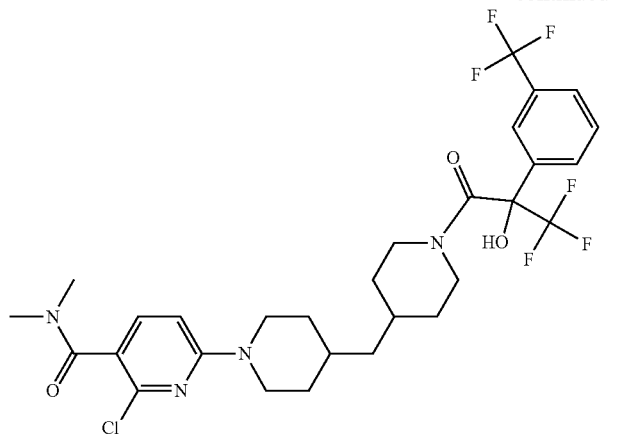
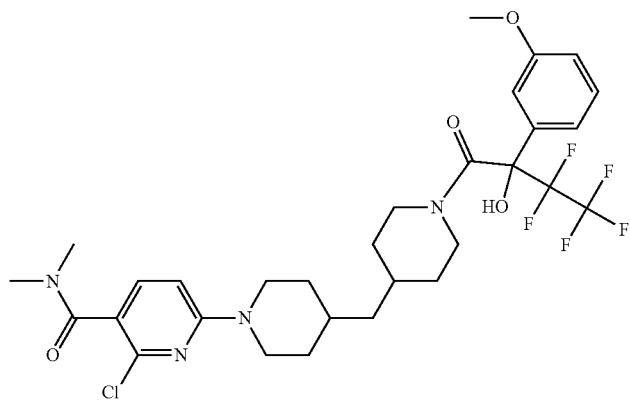
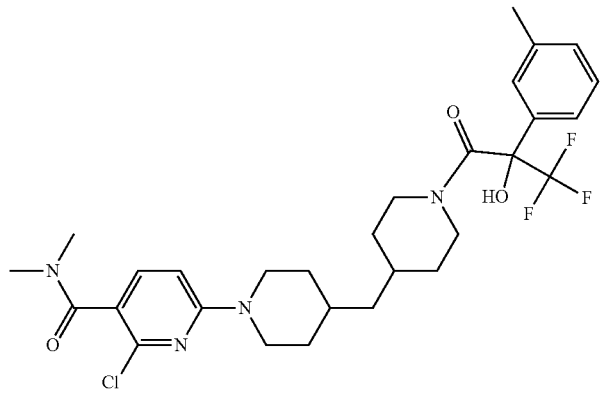
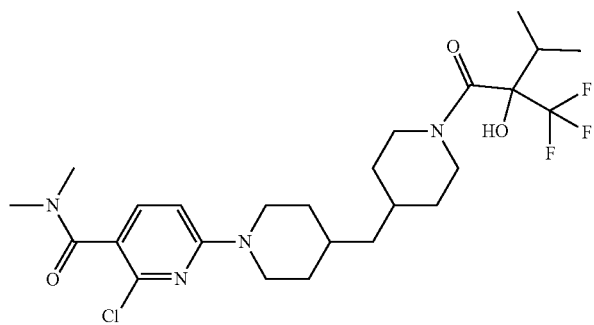

-continued
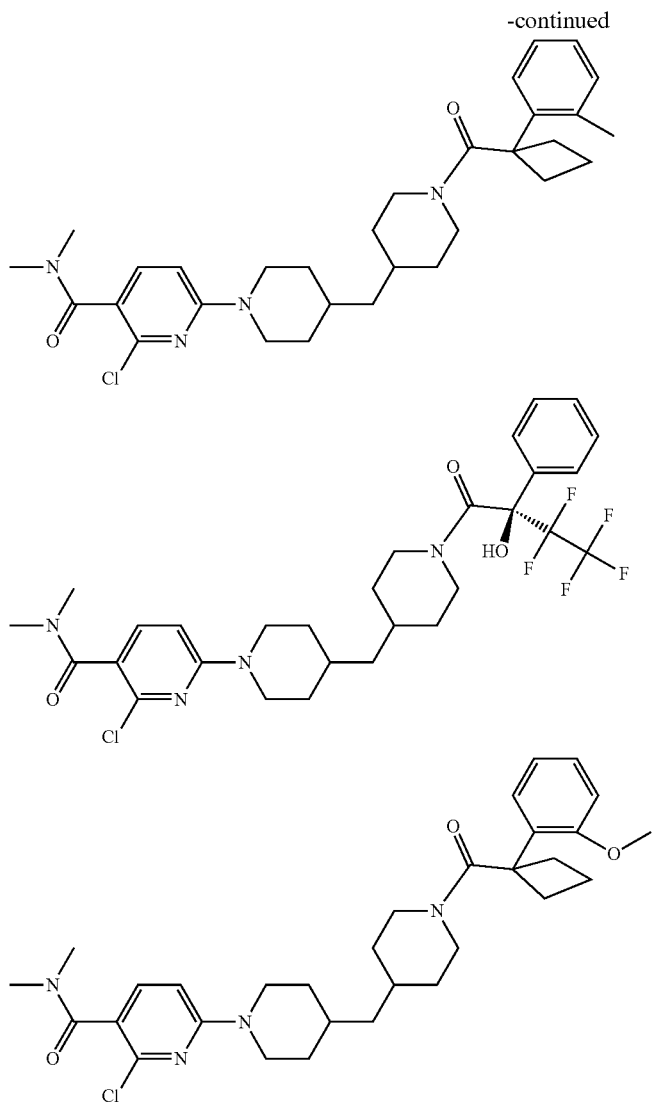
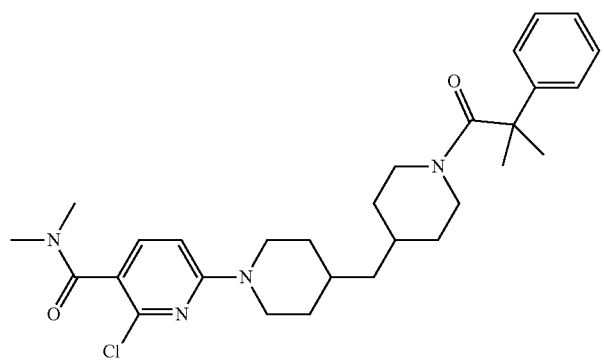

-continued
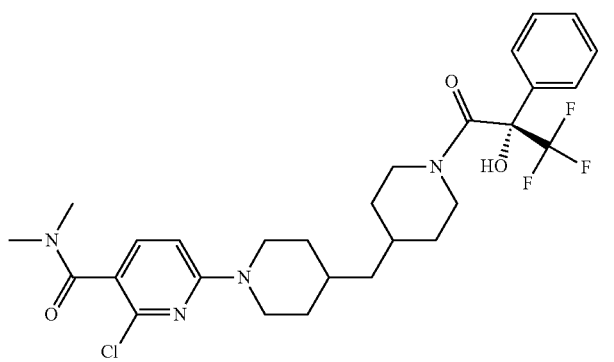
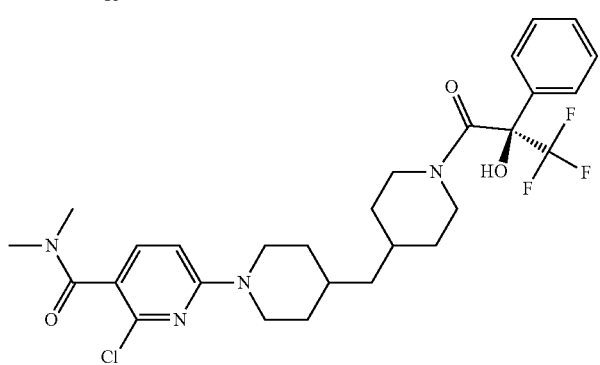
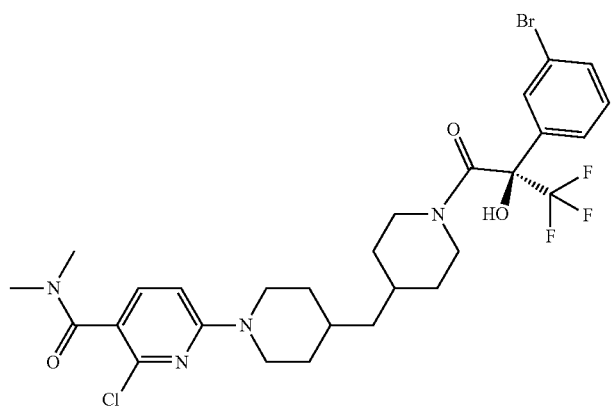
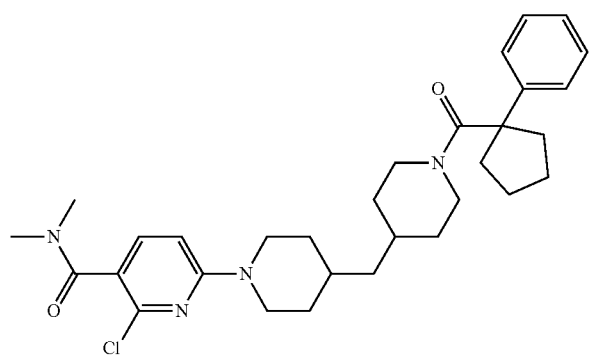

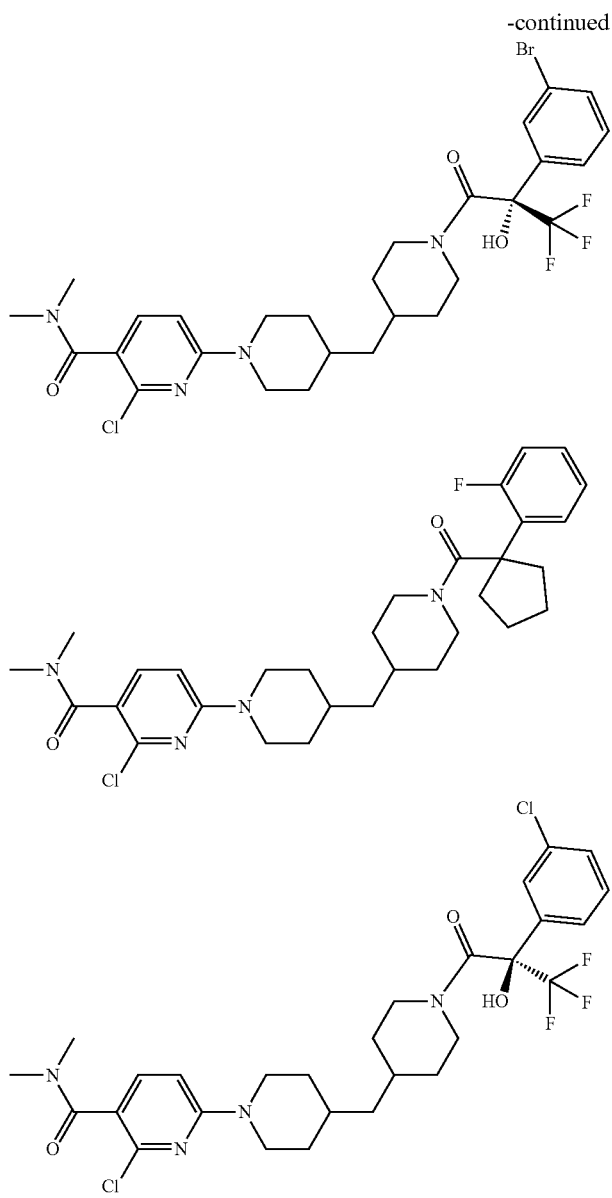
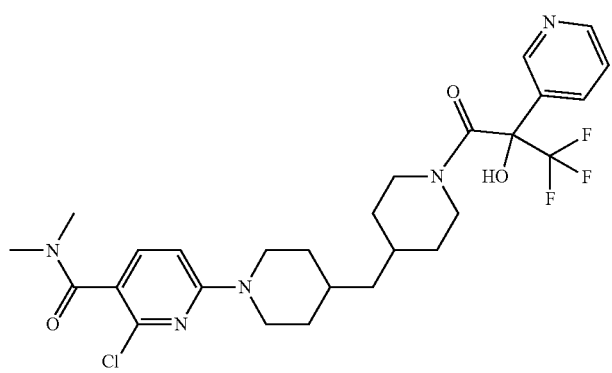

-continued
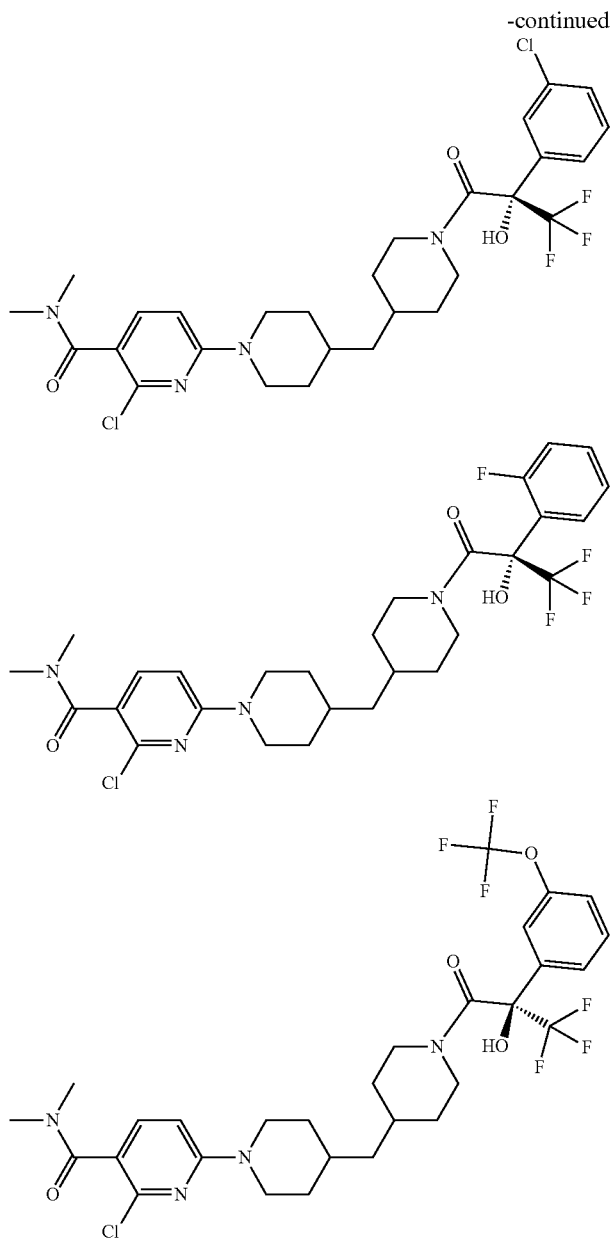
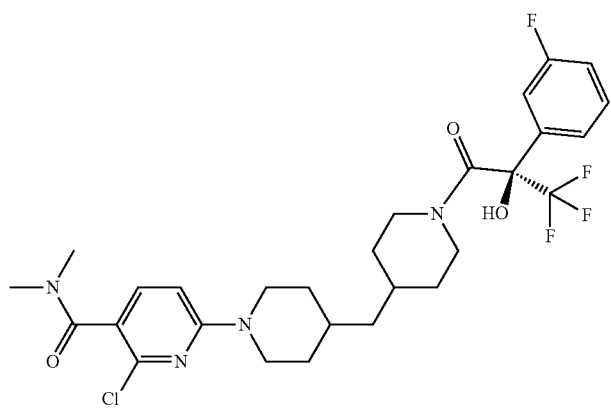

-continued
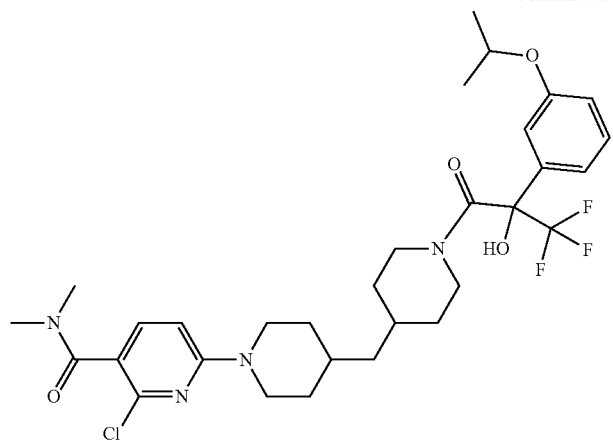
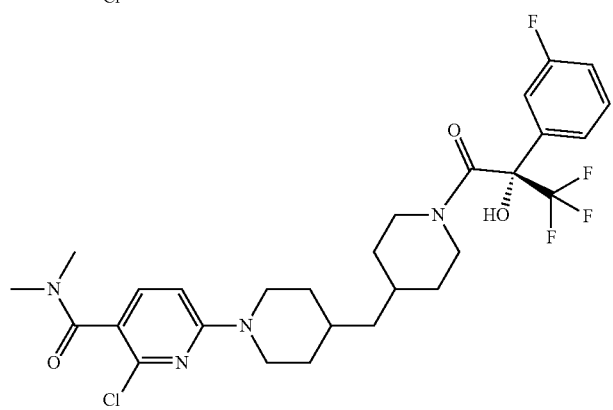
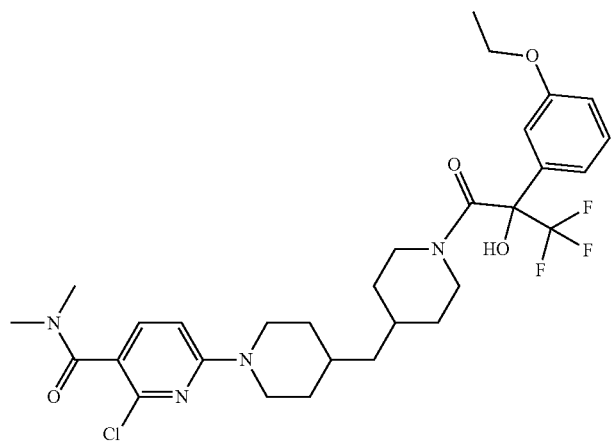
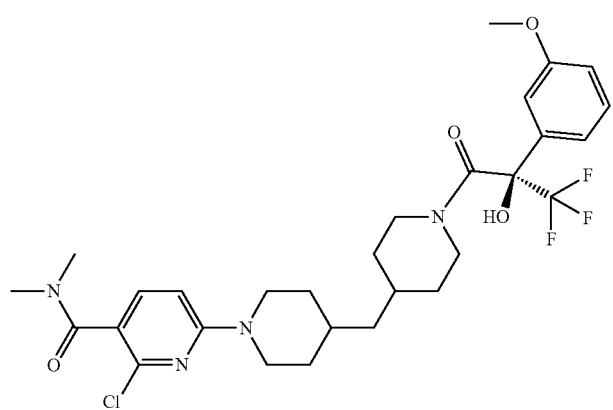

425
426
-continued
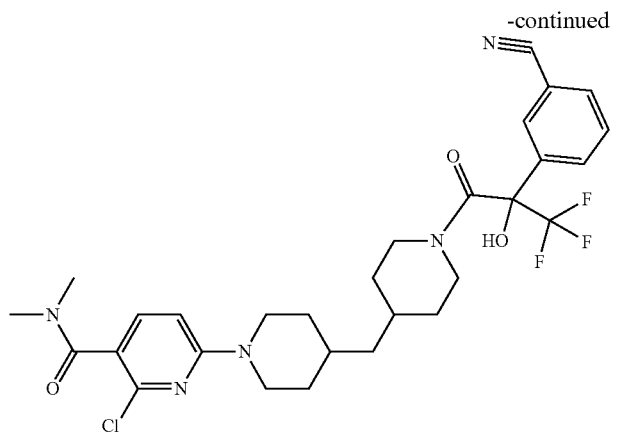
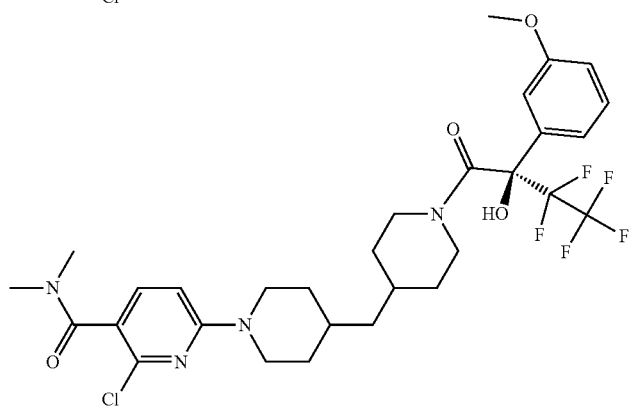
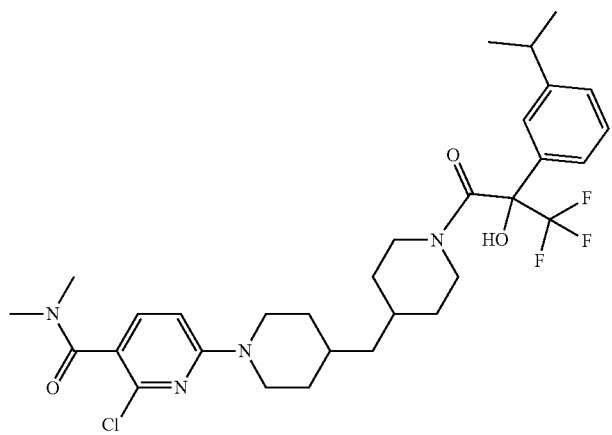
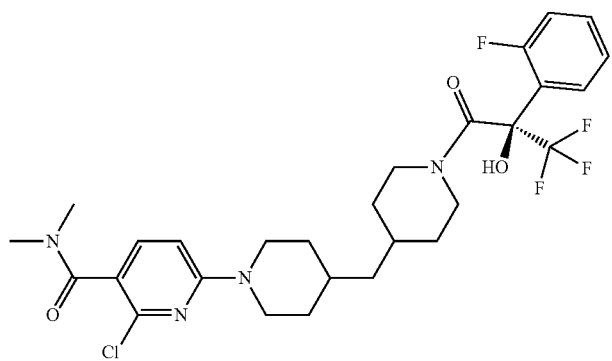

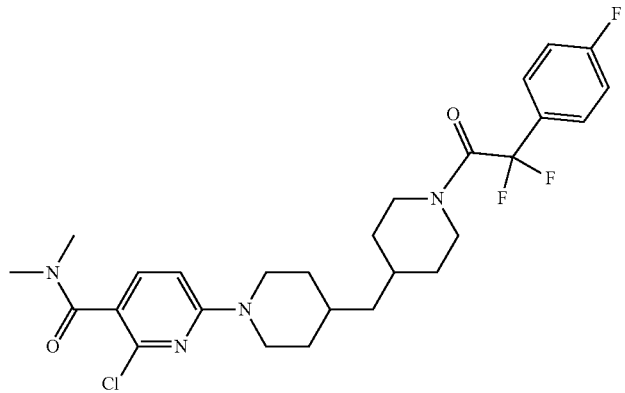
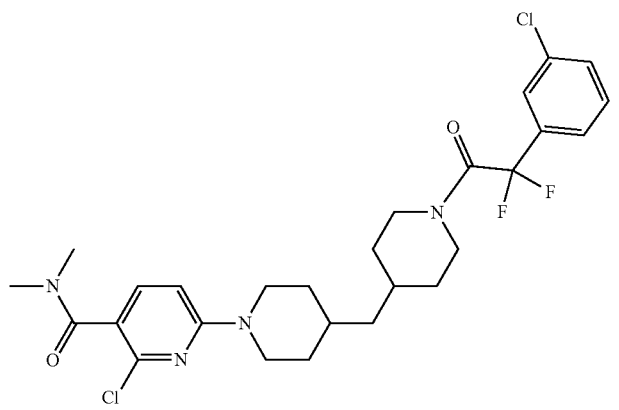
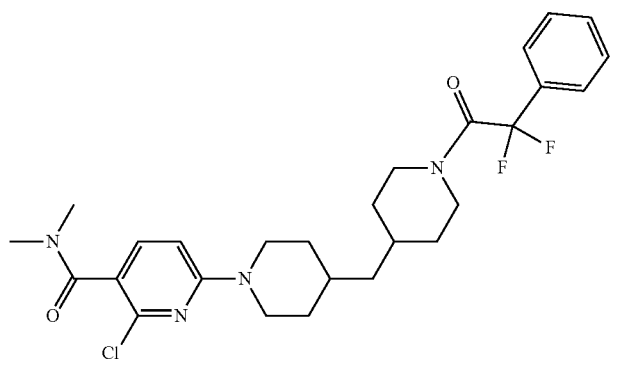
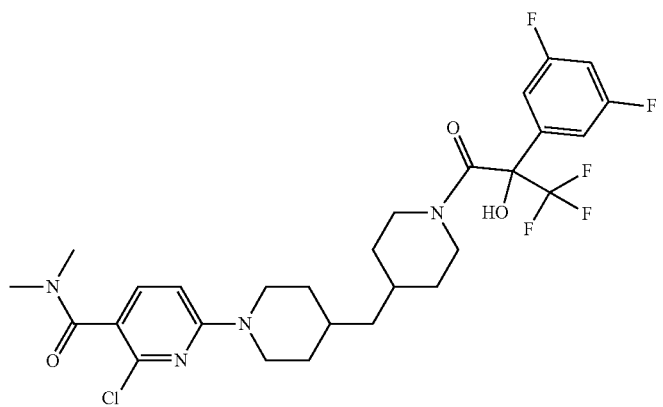

-continued
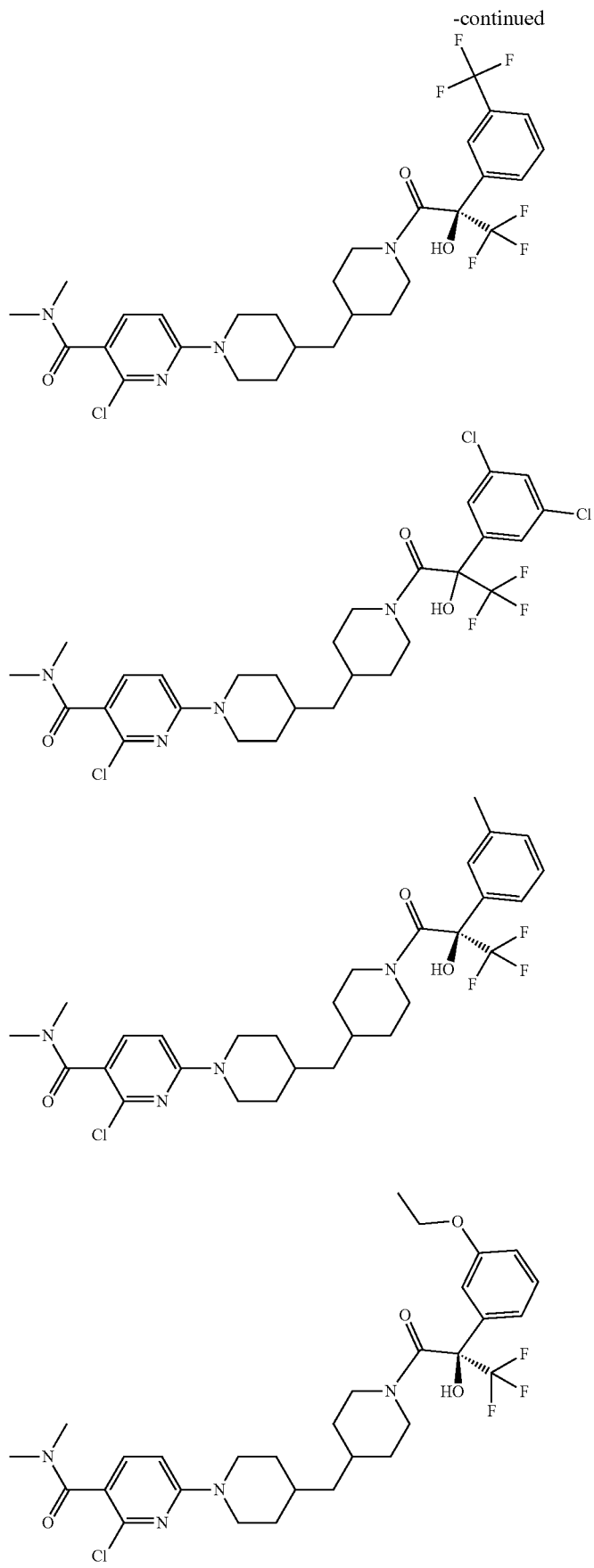

-continued
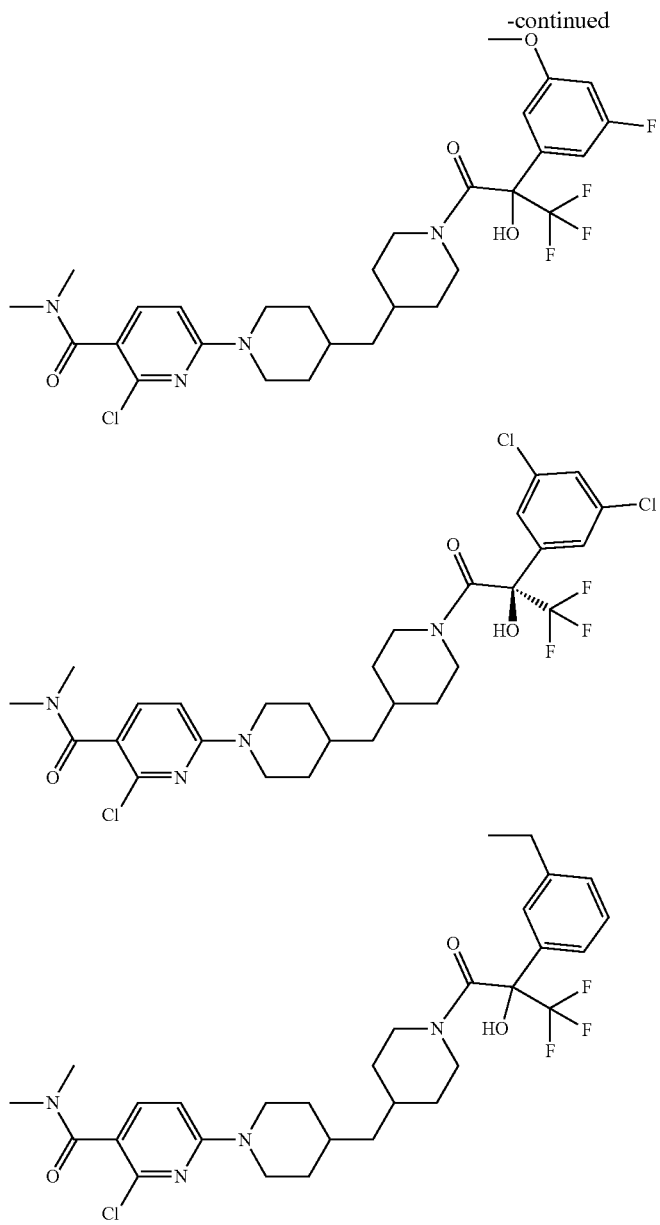
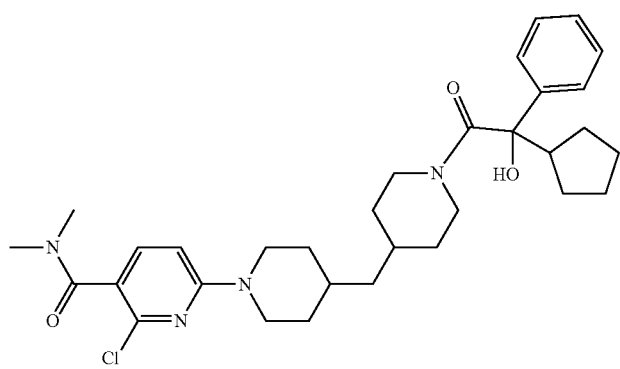

-continued
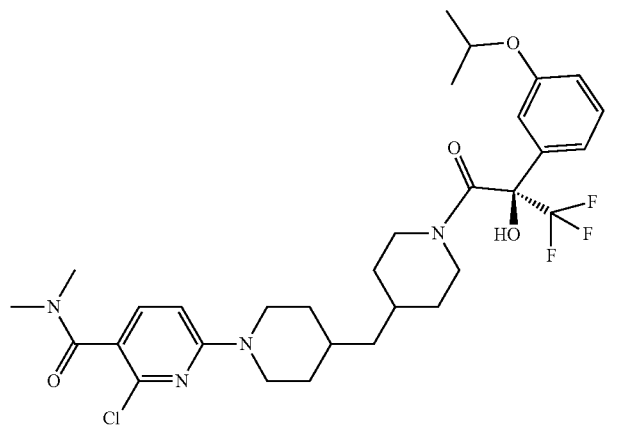
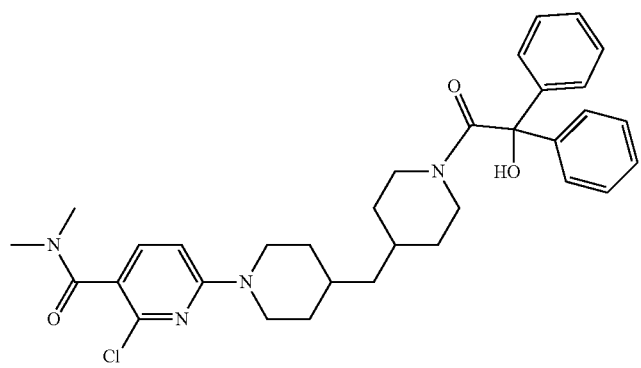
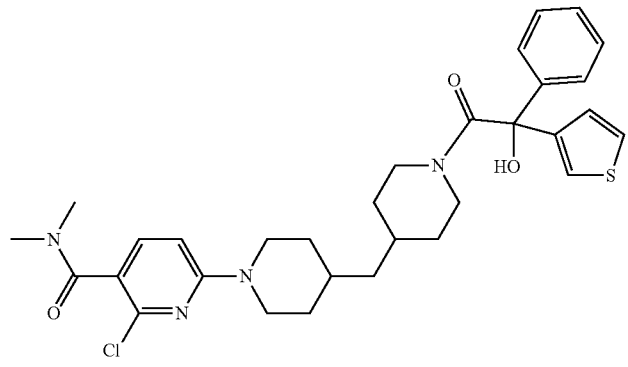
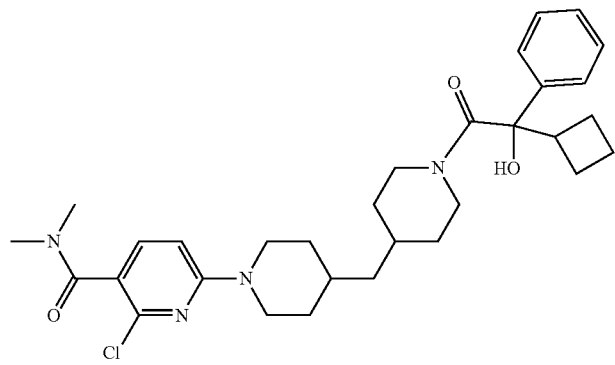

-continued
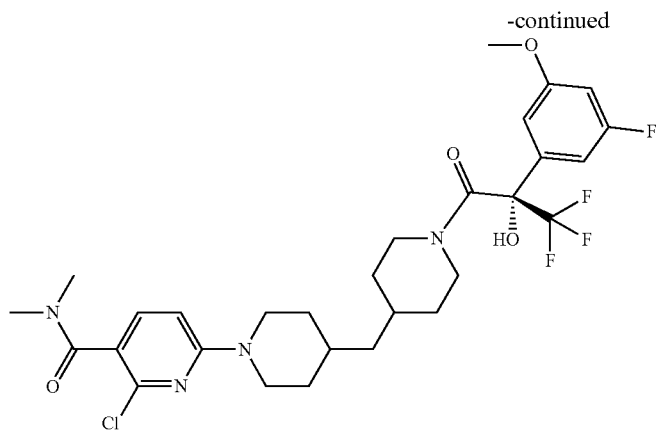
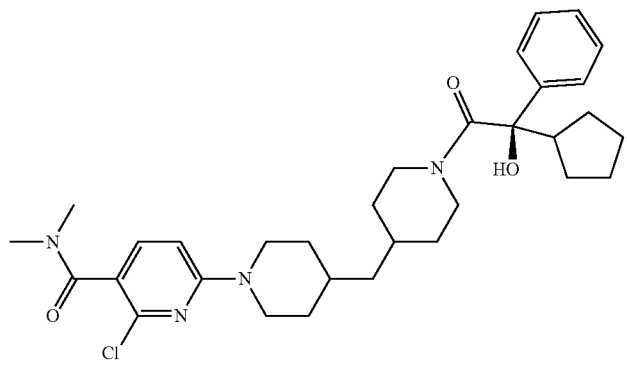
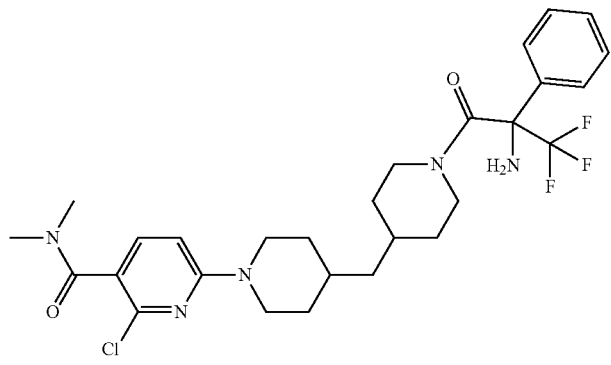
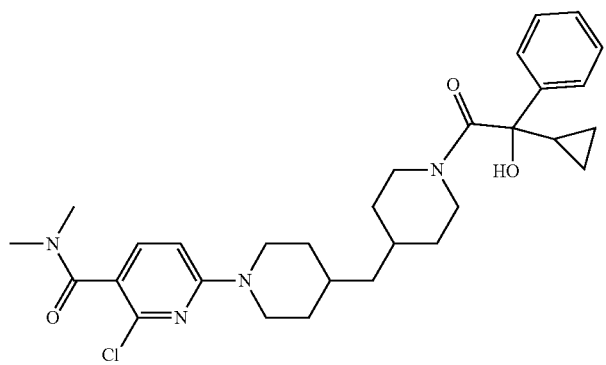

-continued
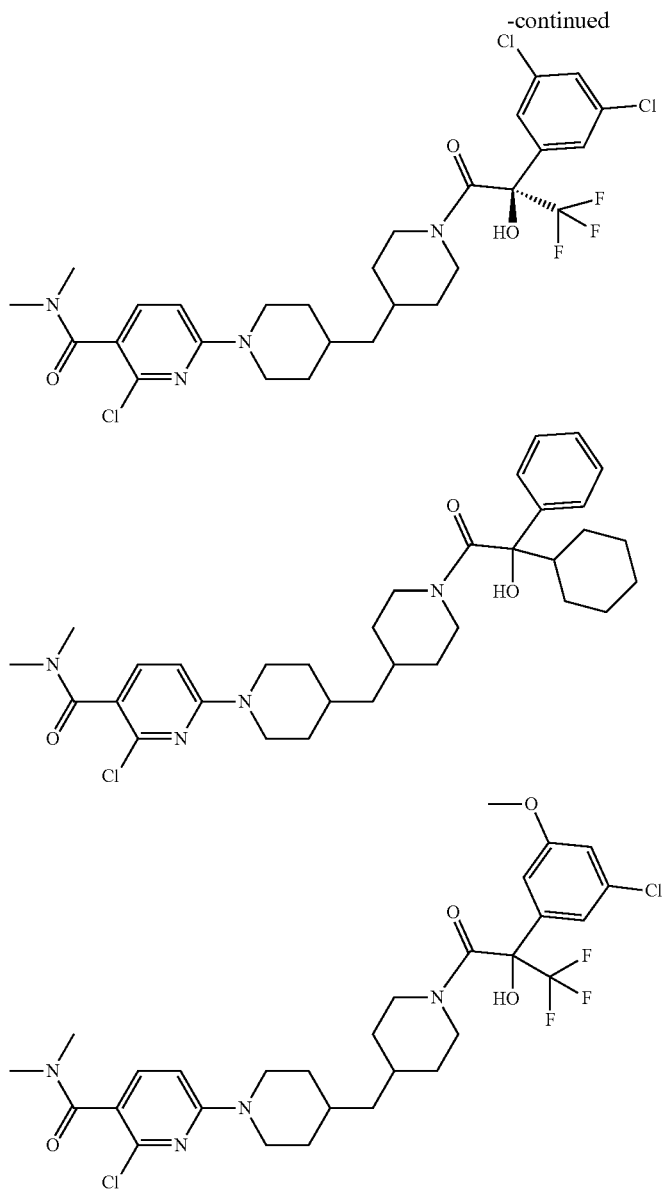
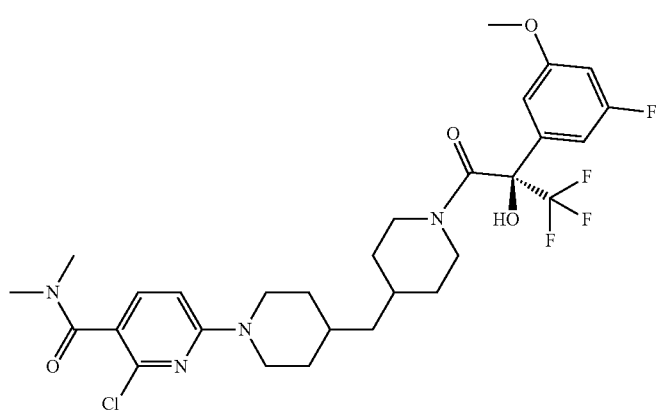

-continued
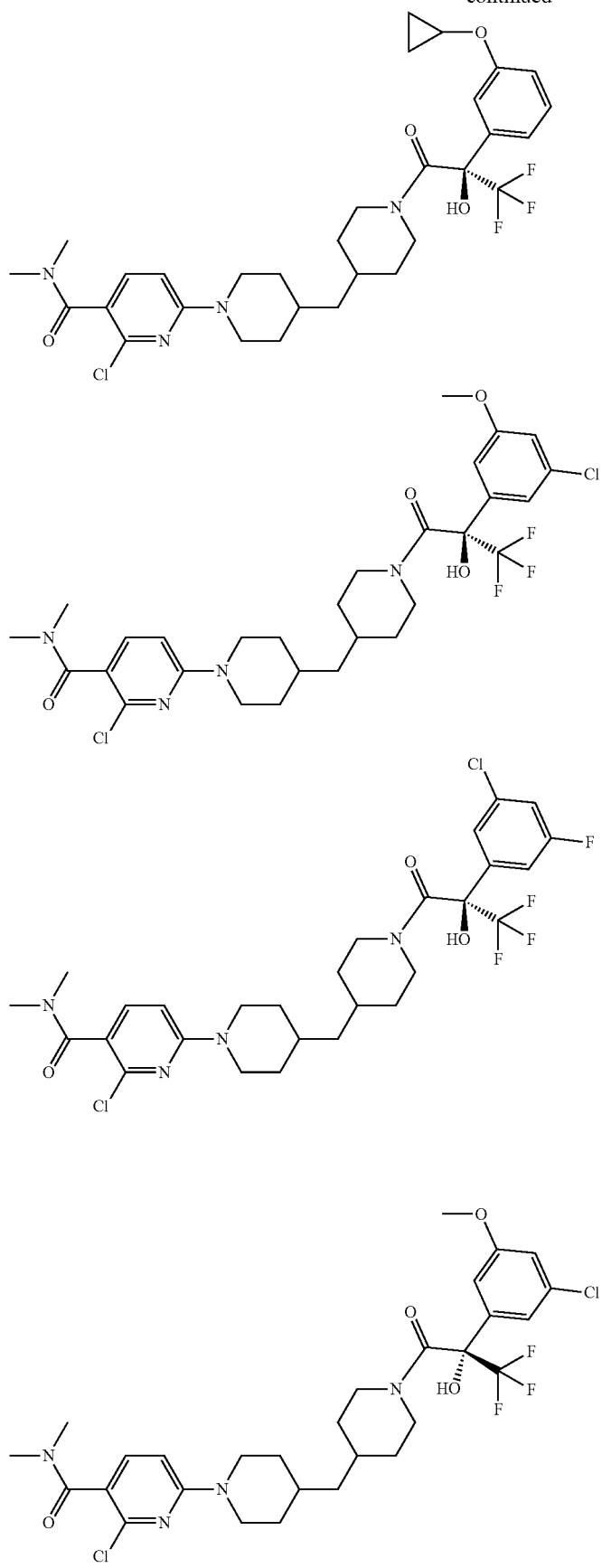

-continued
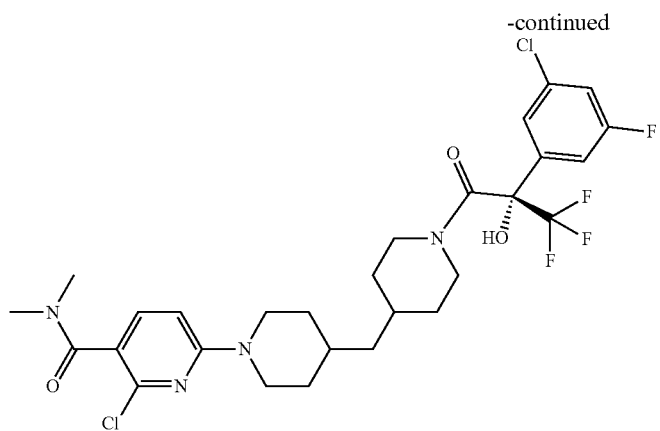
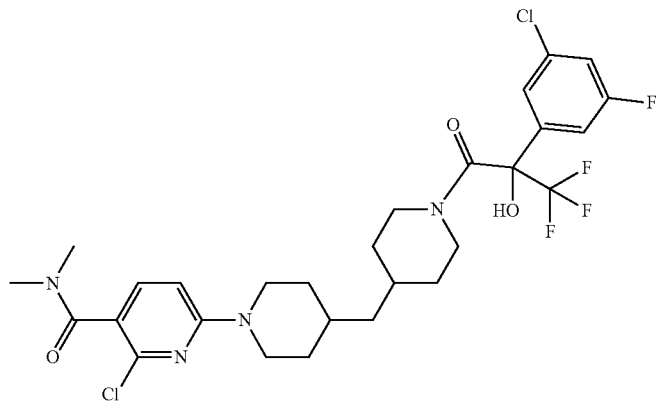
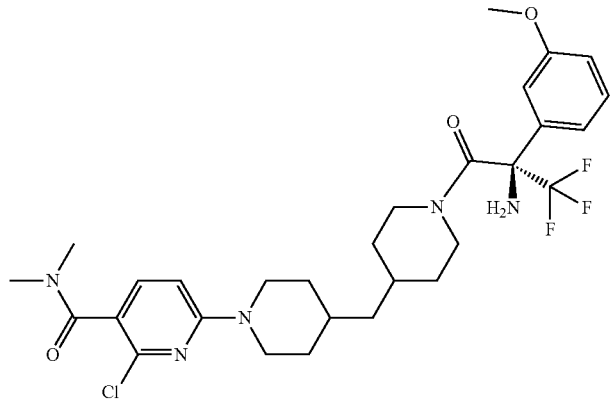
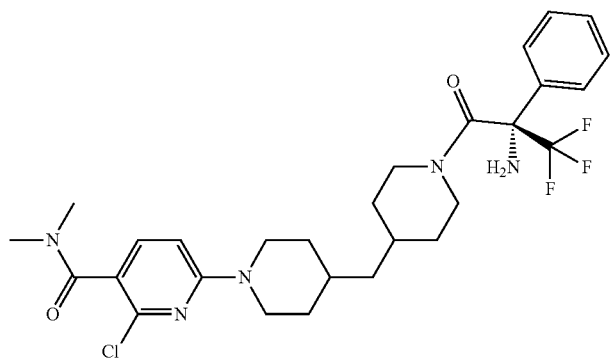

-continued
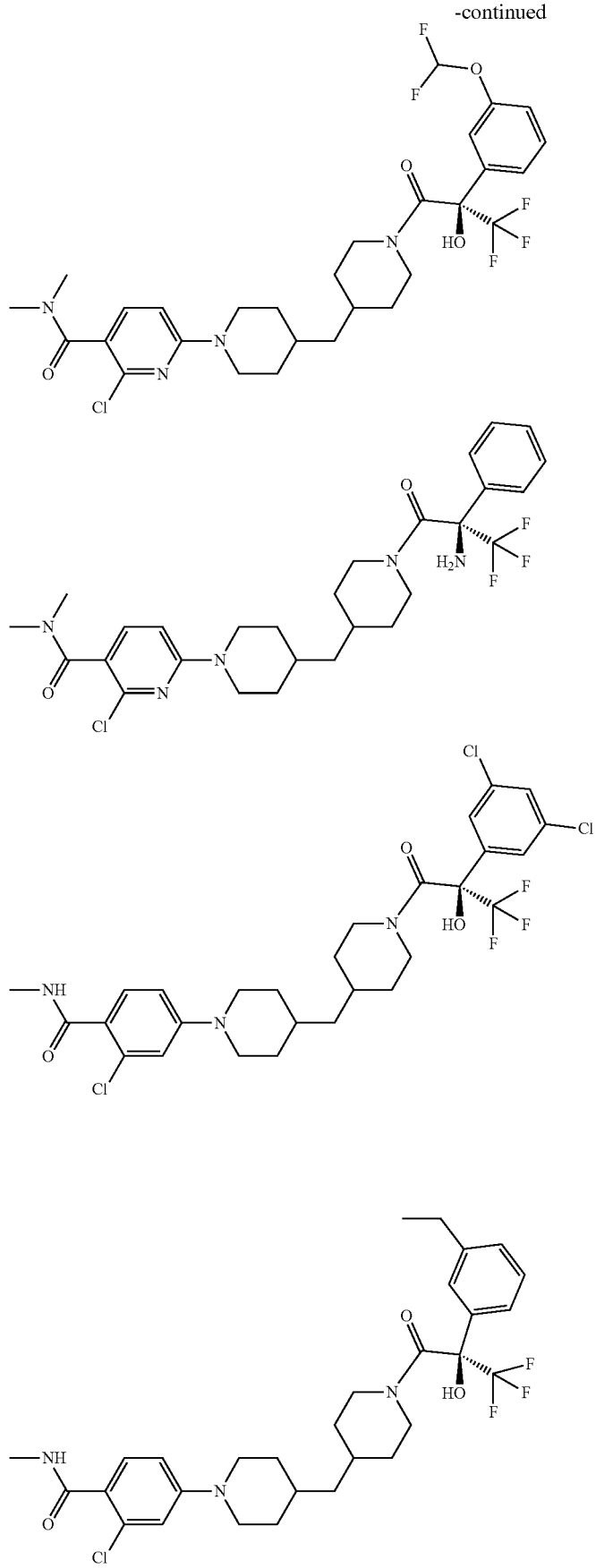

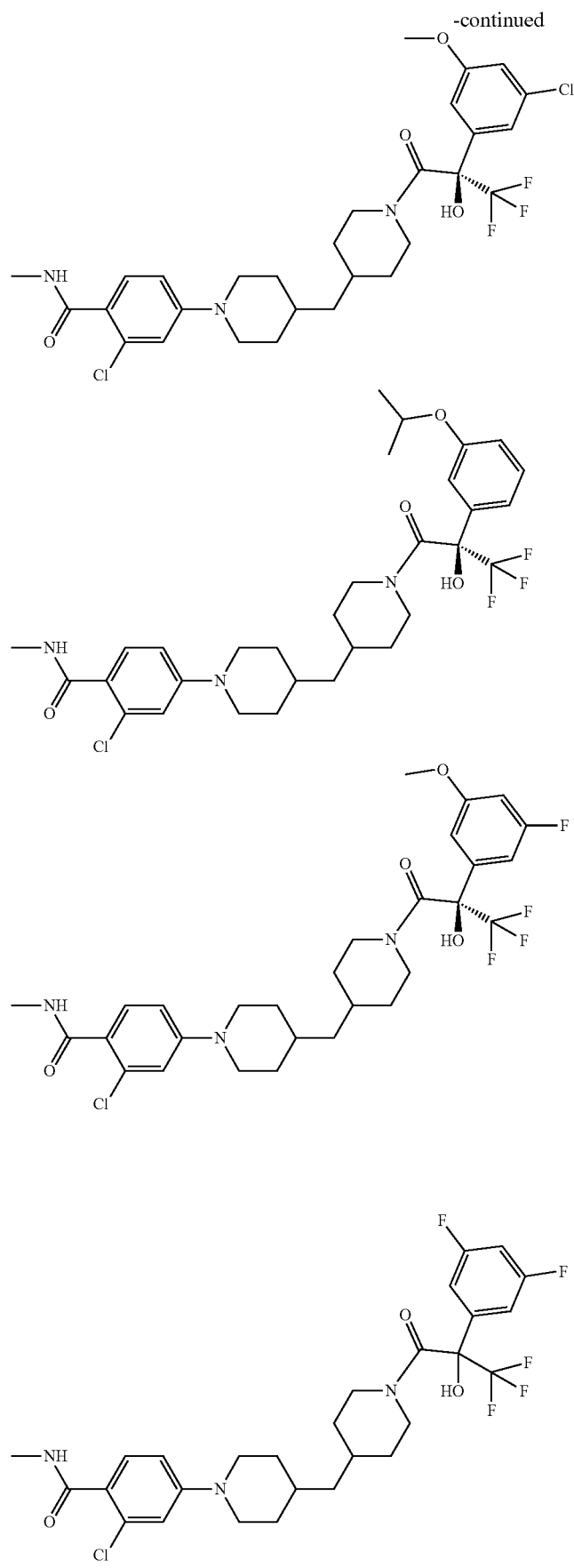

-continued
447
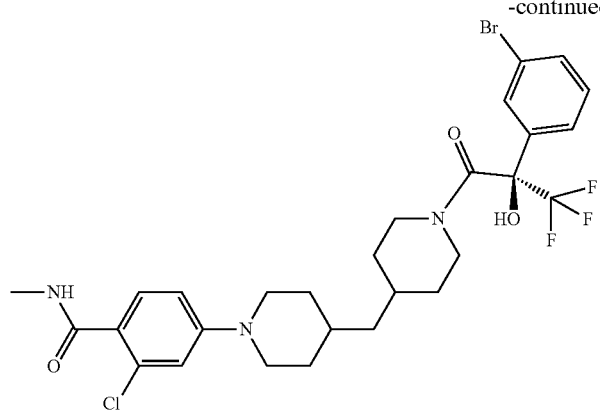
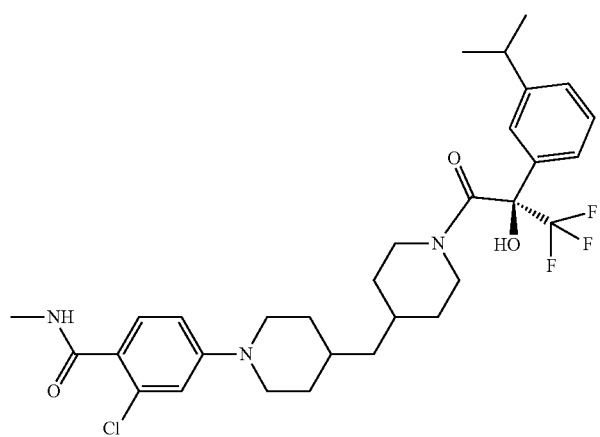
448
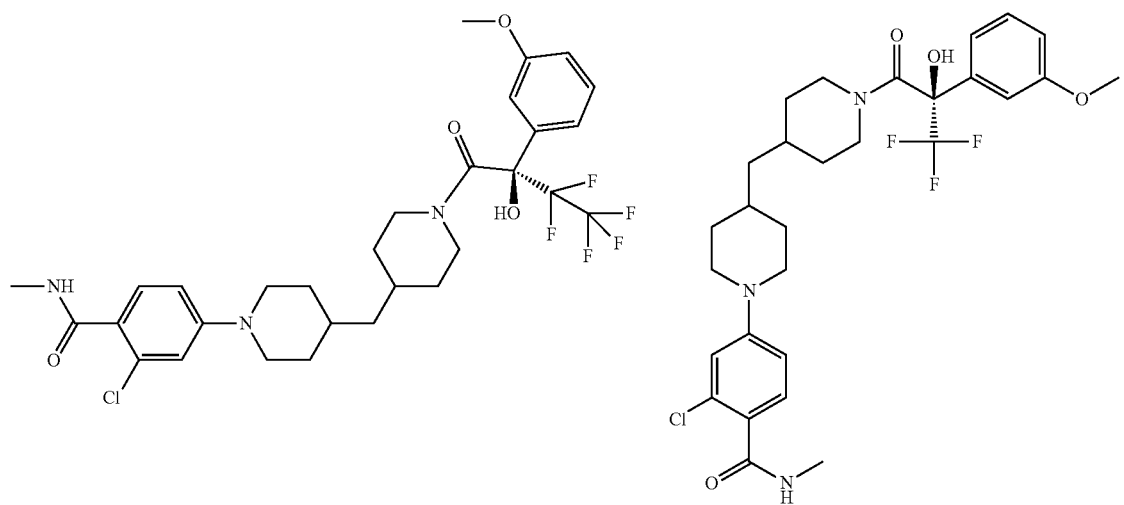

449 450
-continued
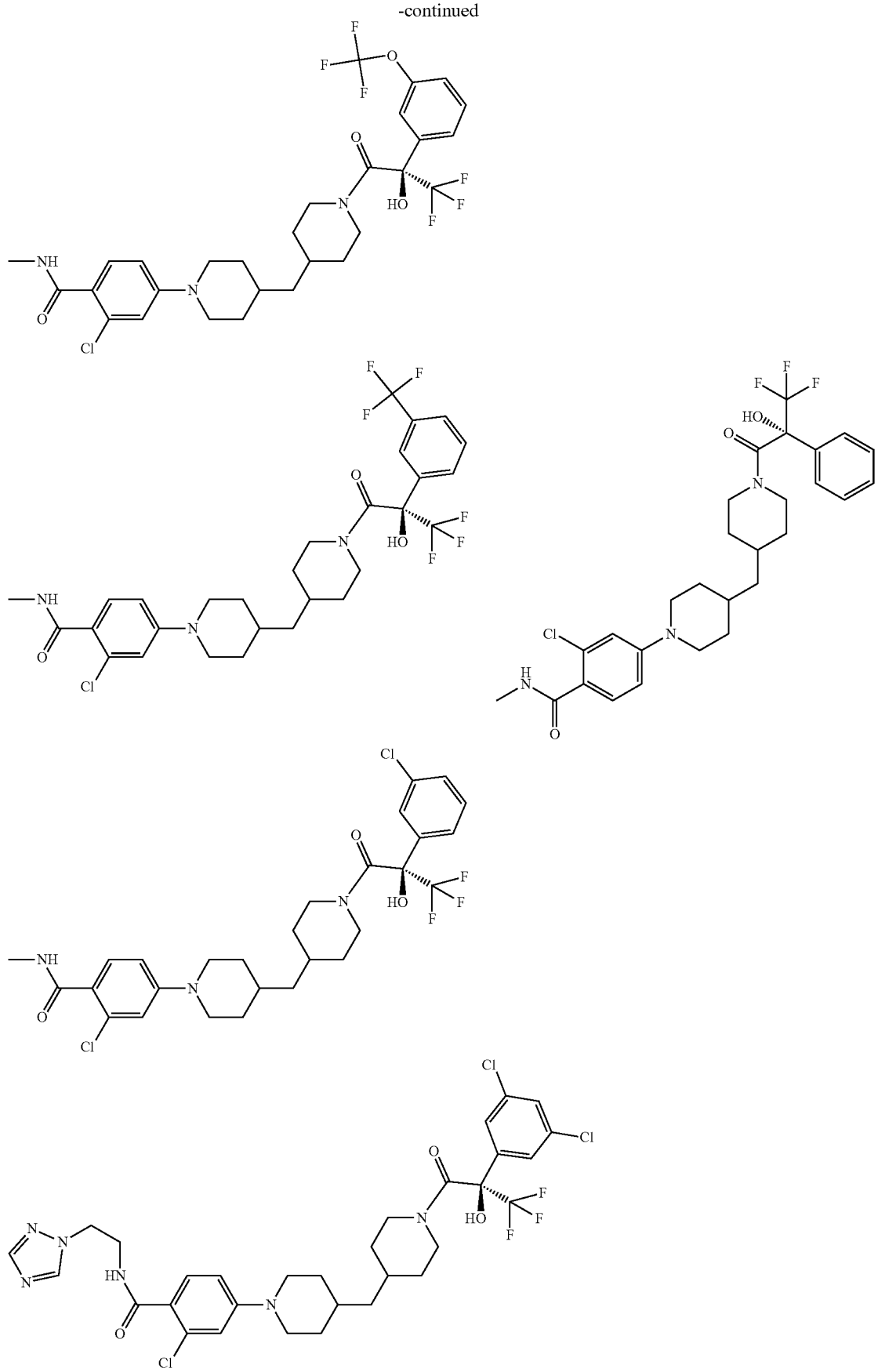

-continued
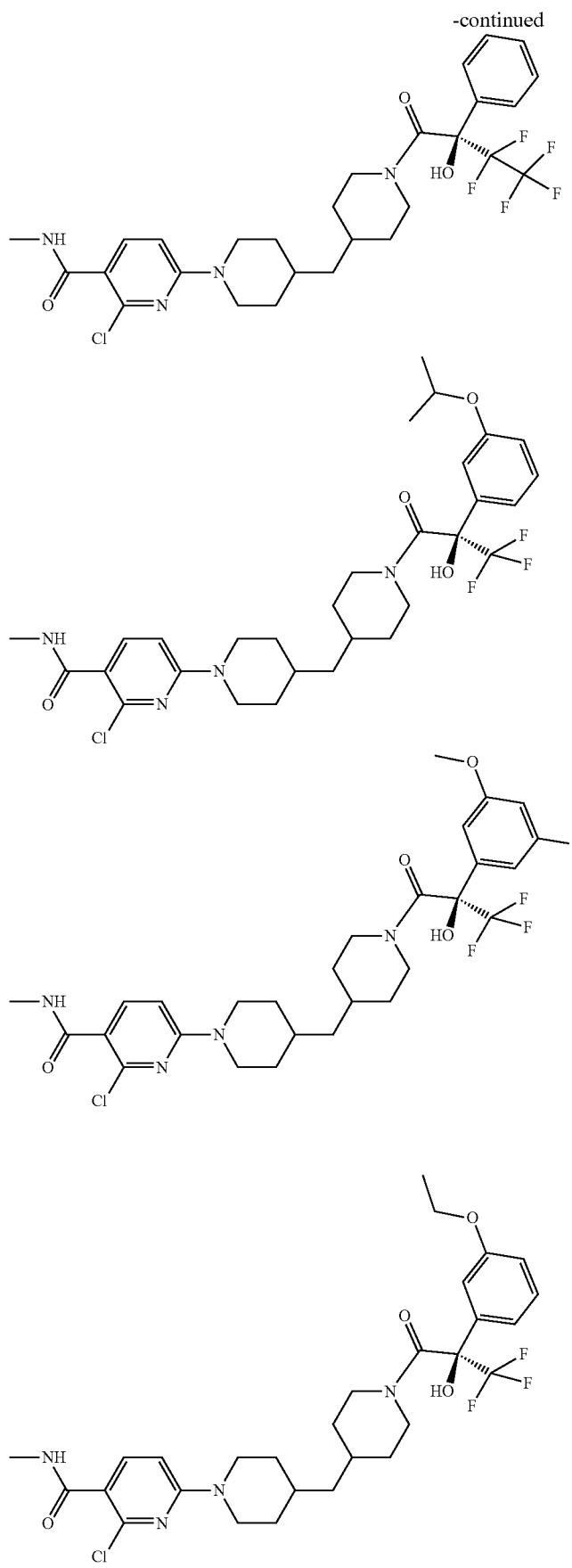

453
454
-continued
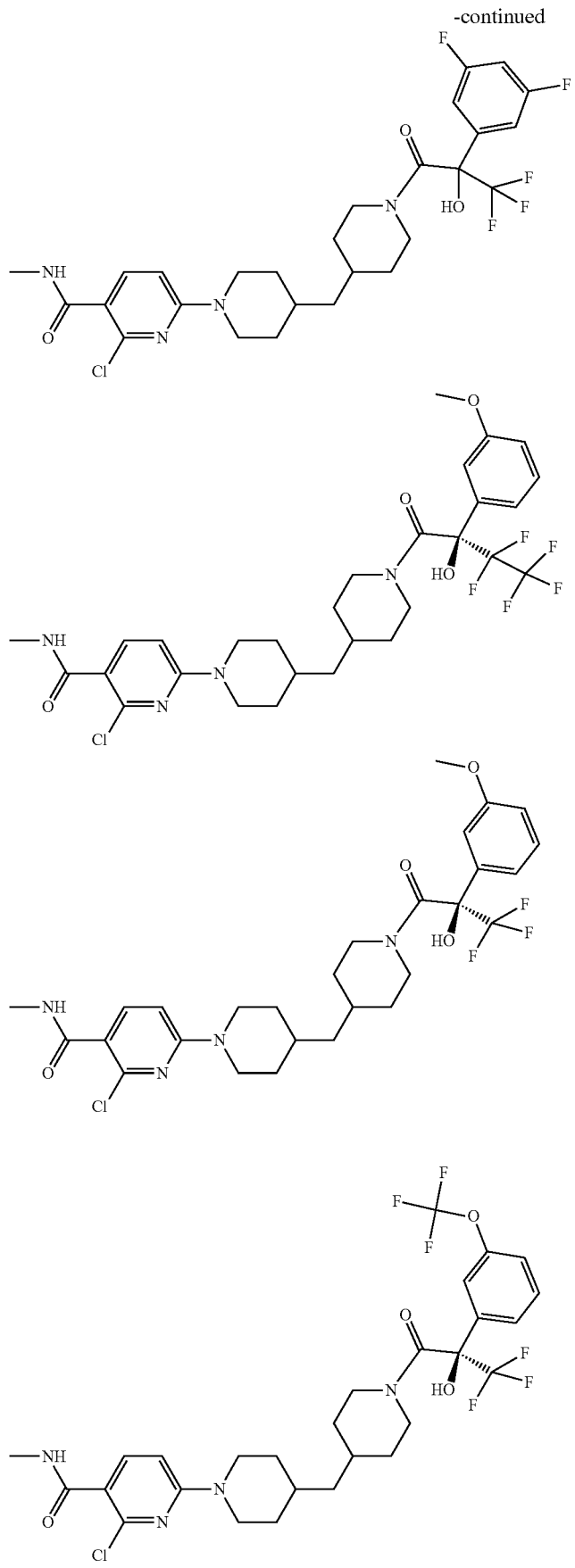

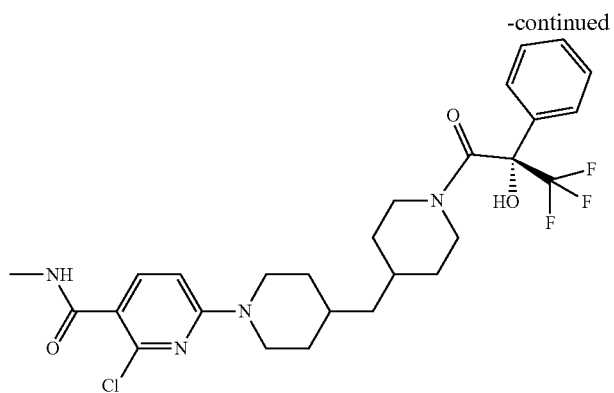
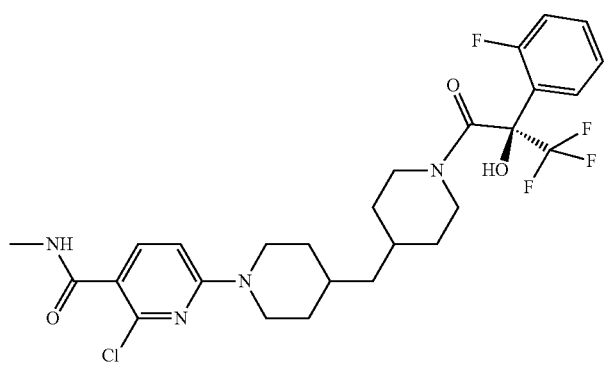
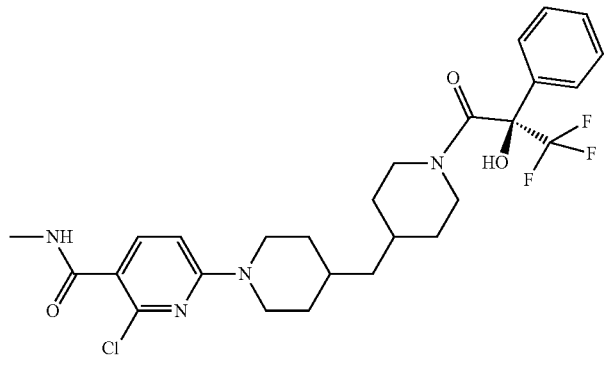
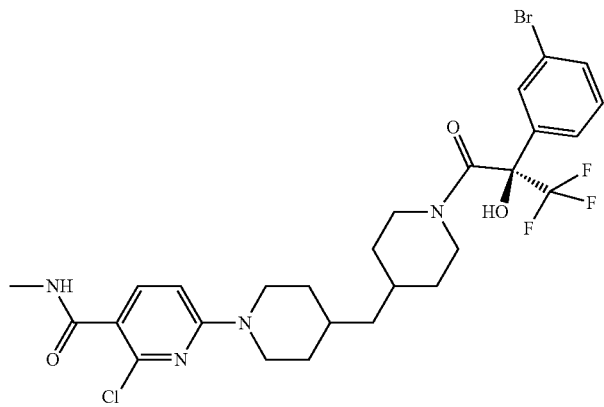

-continued
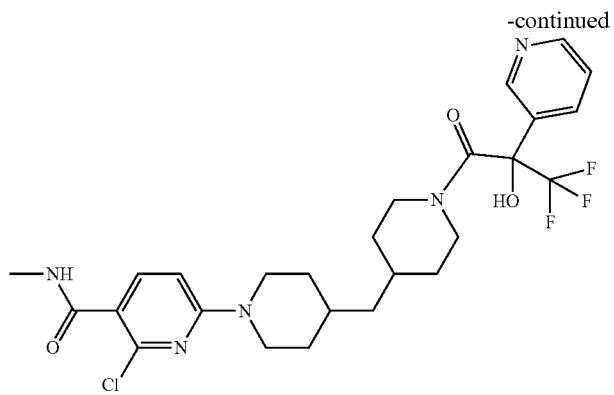
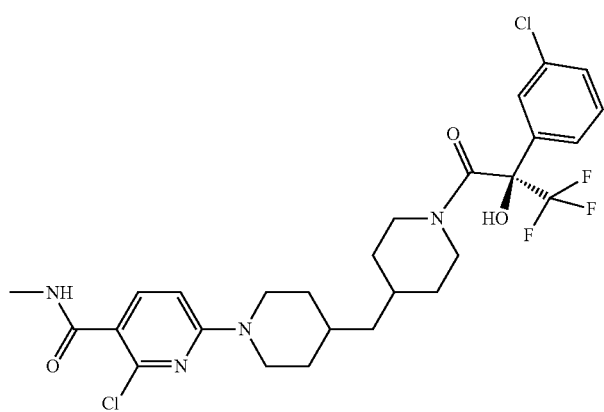
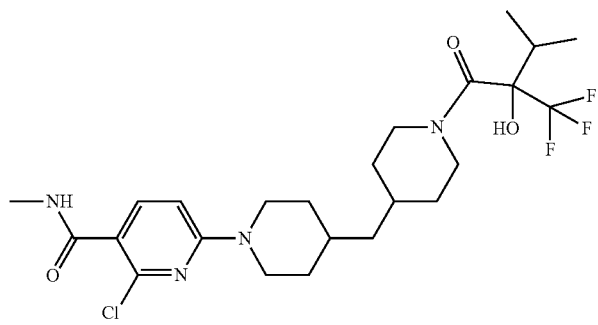
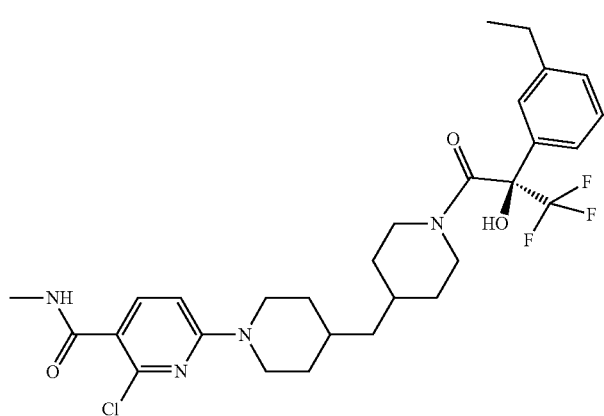

-continued
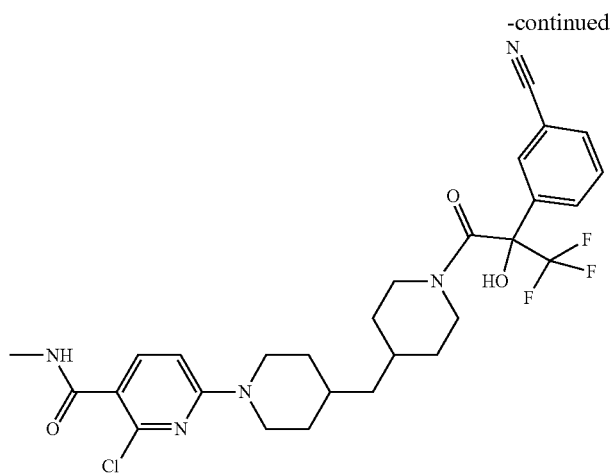
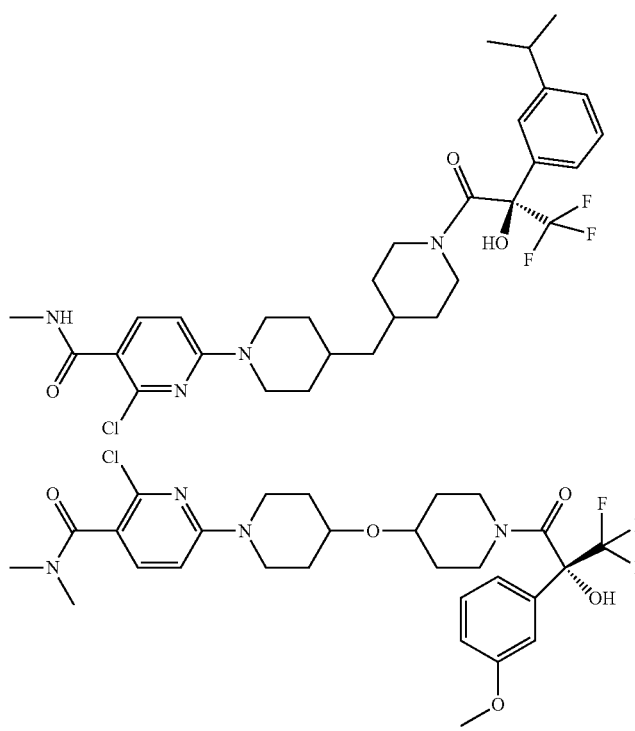
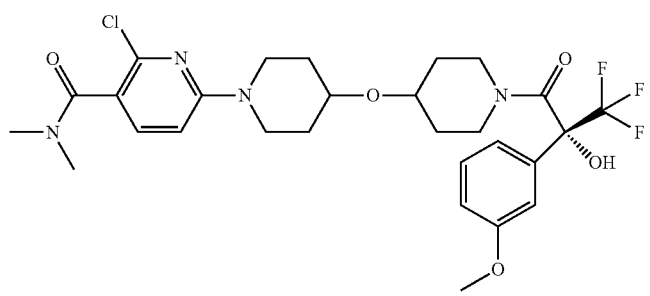

461 462
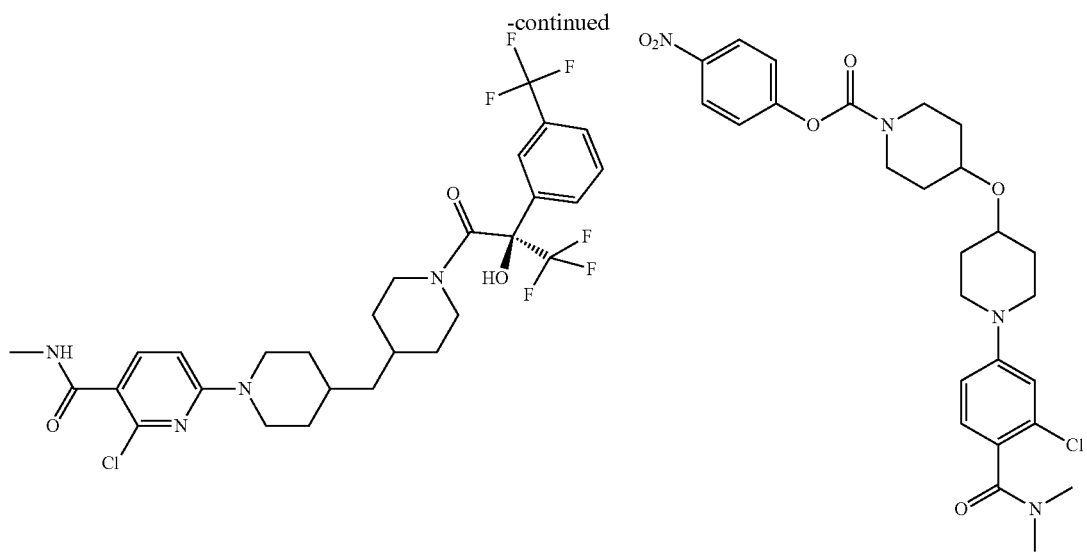
-continued
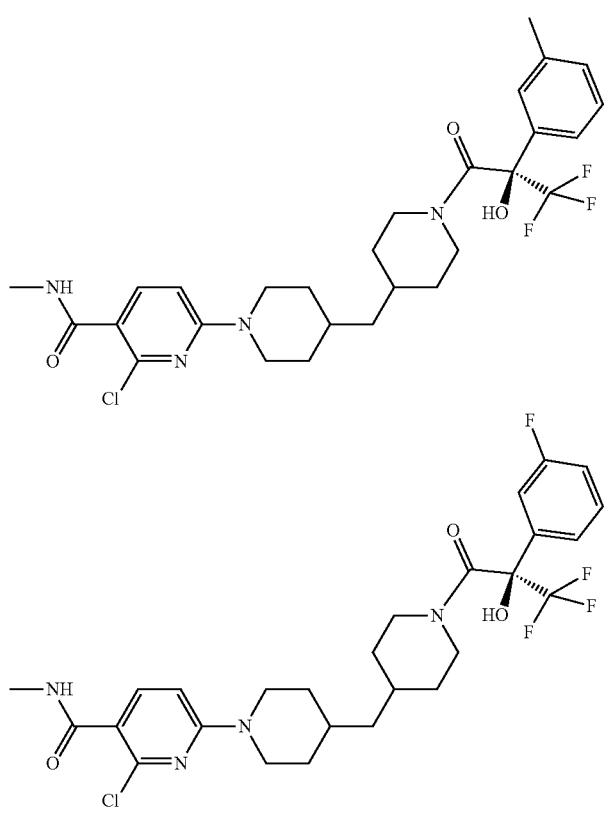
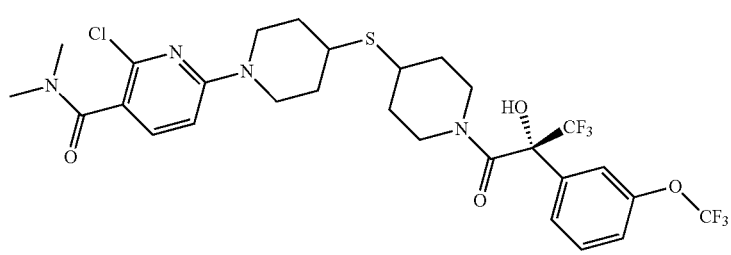

-continued
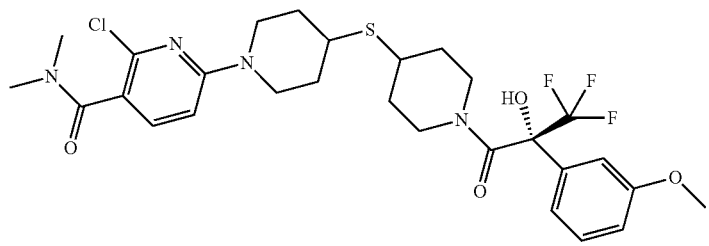
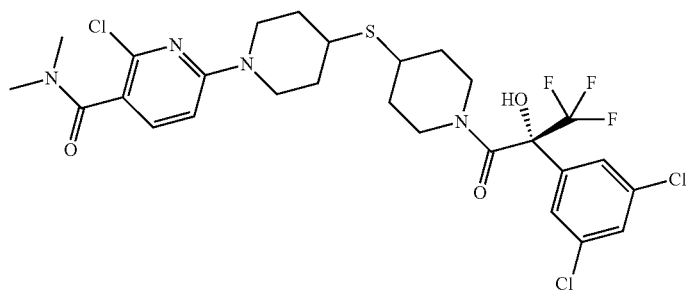
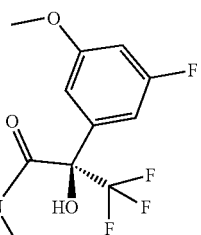
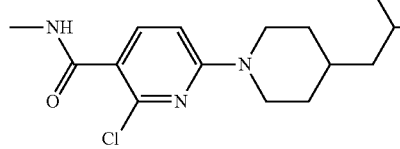
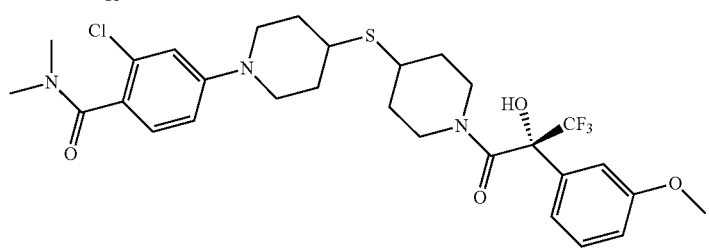
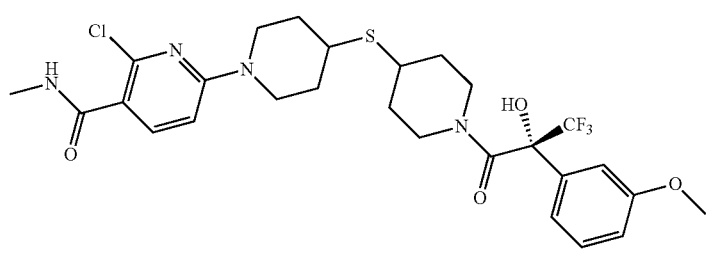

-continued
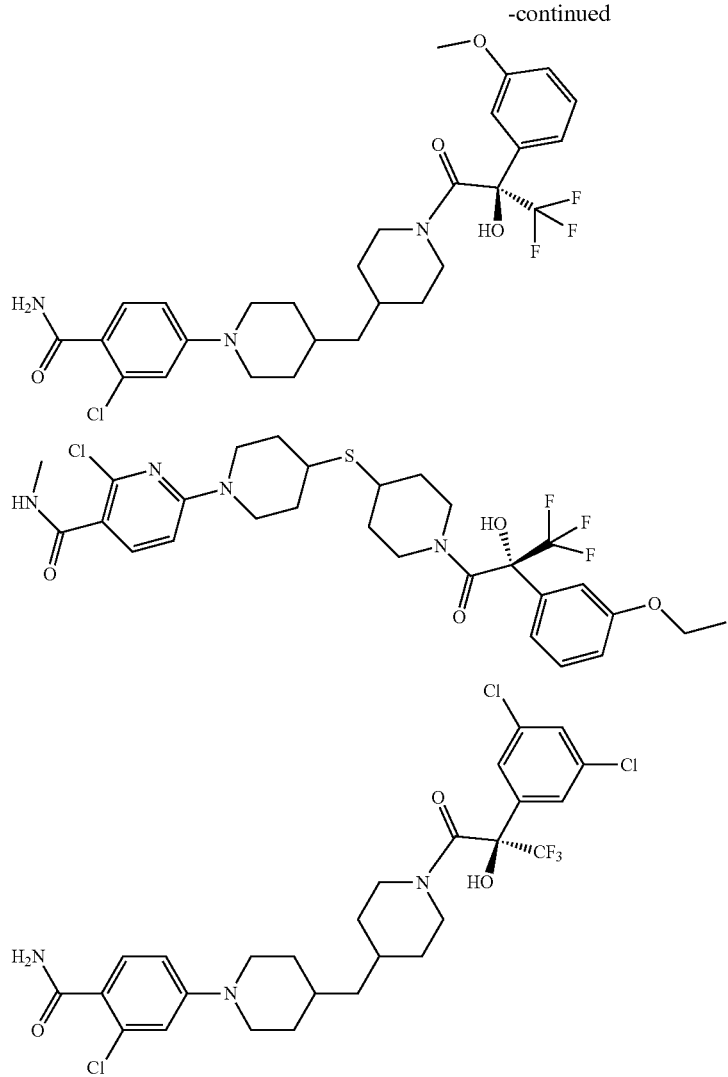
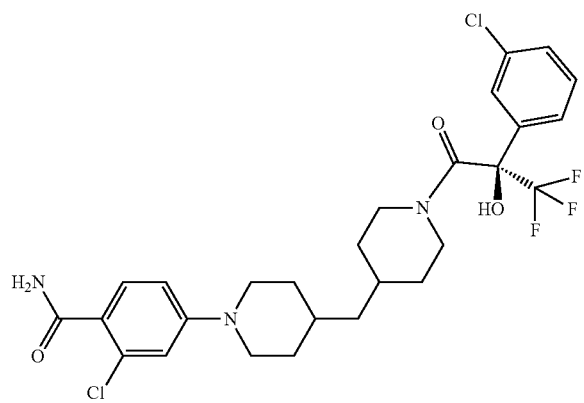

467 468
-continued
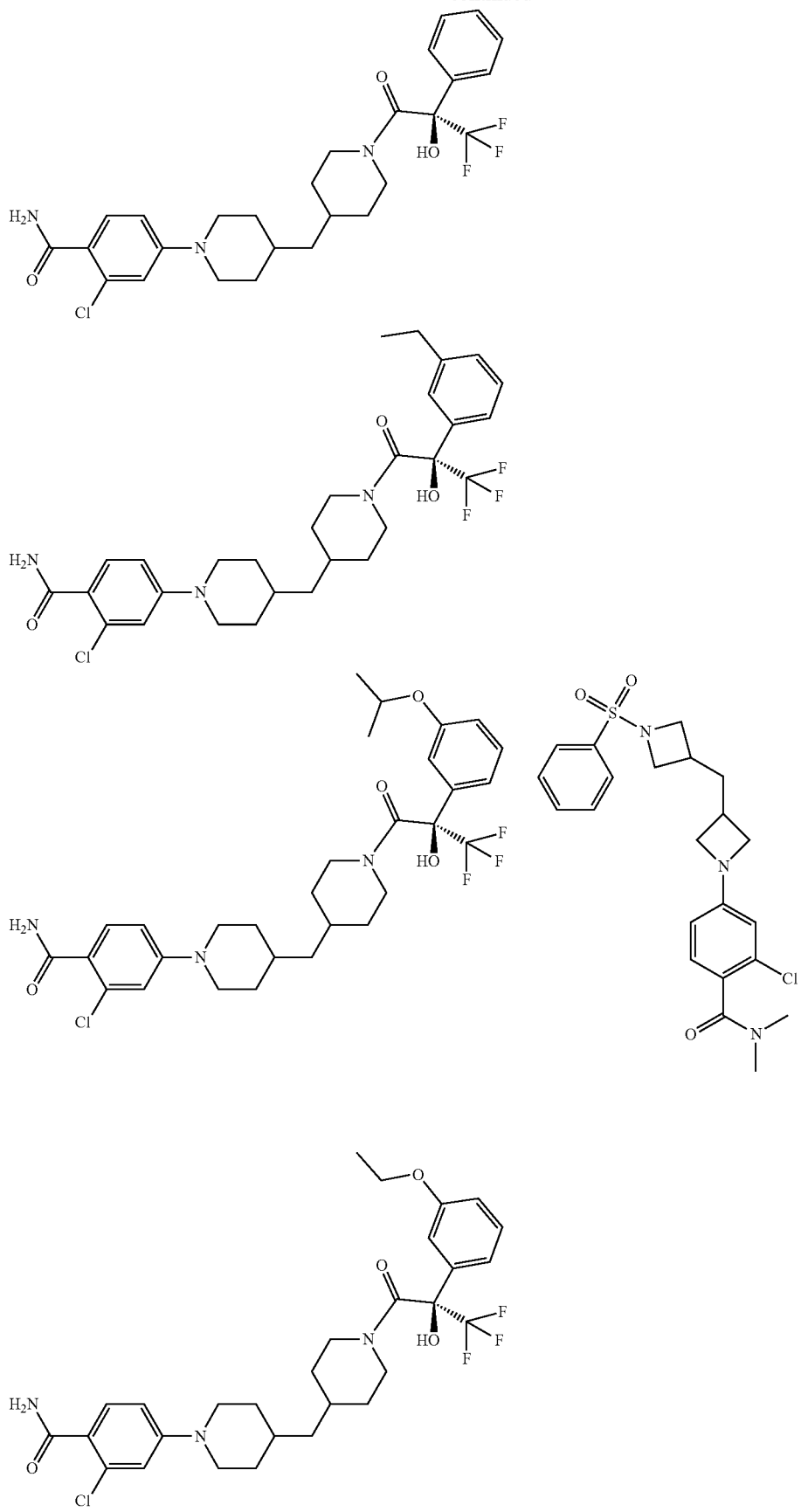

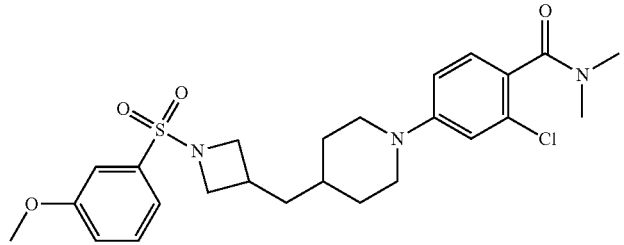
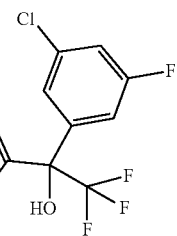
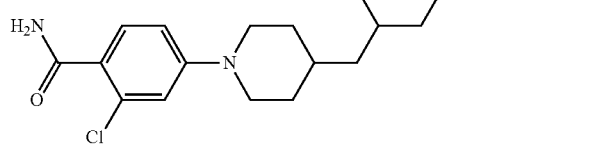
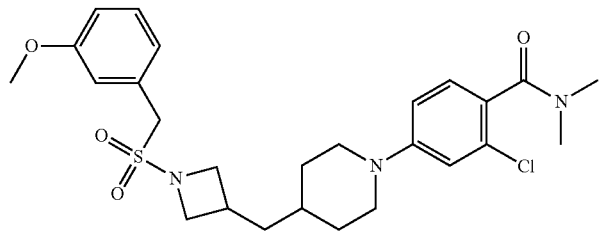
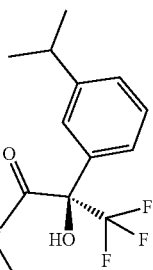
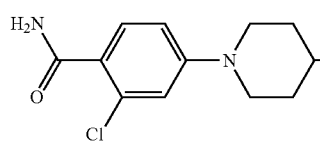
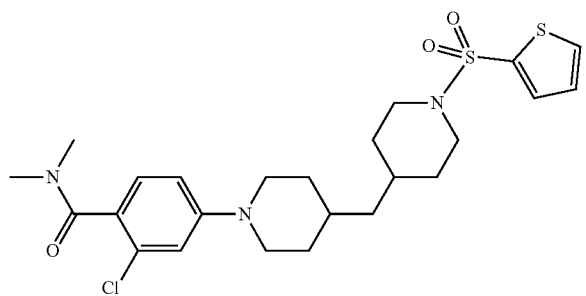

-continued
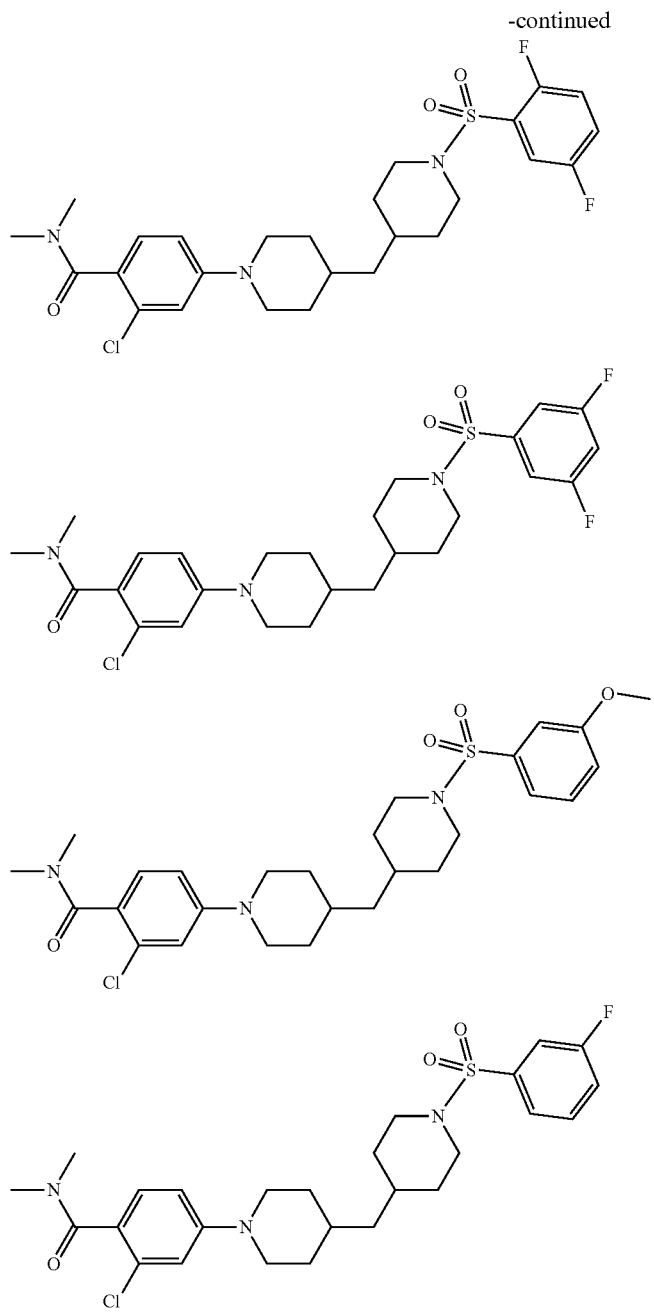
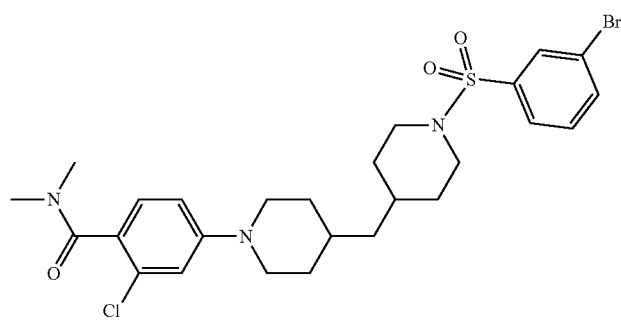

-continued
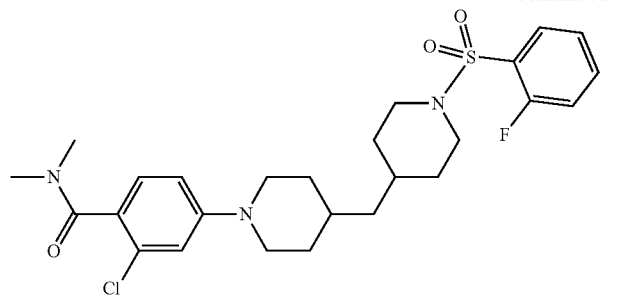
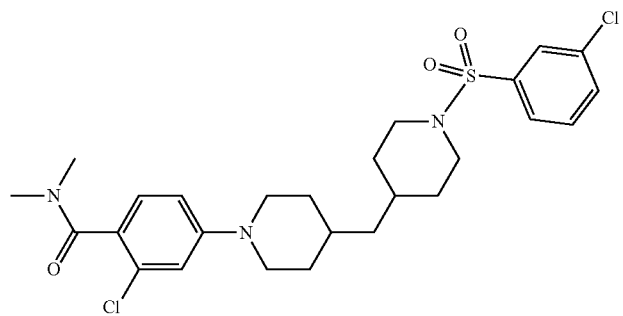
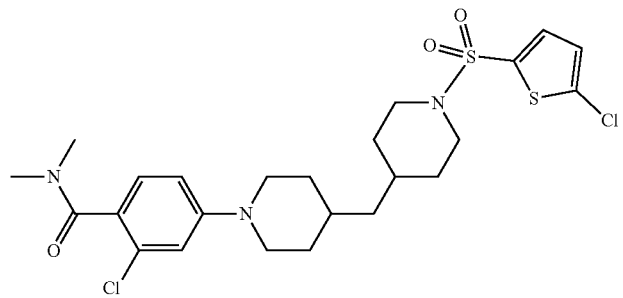
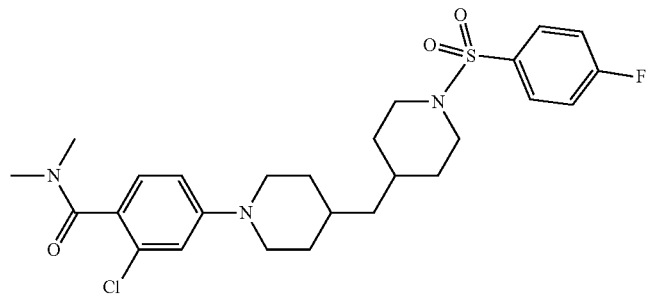
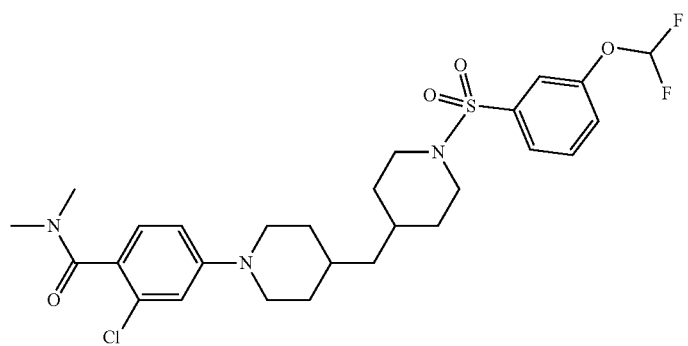

-continued
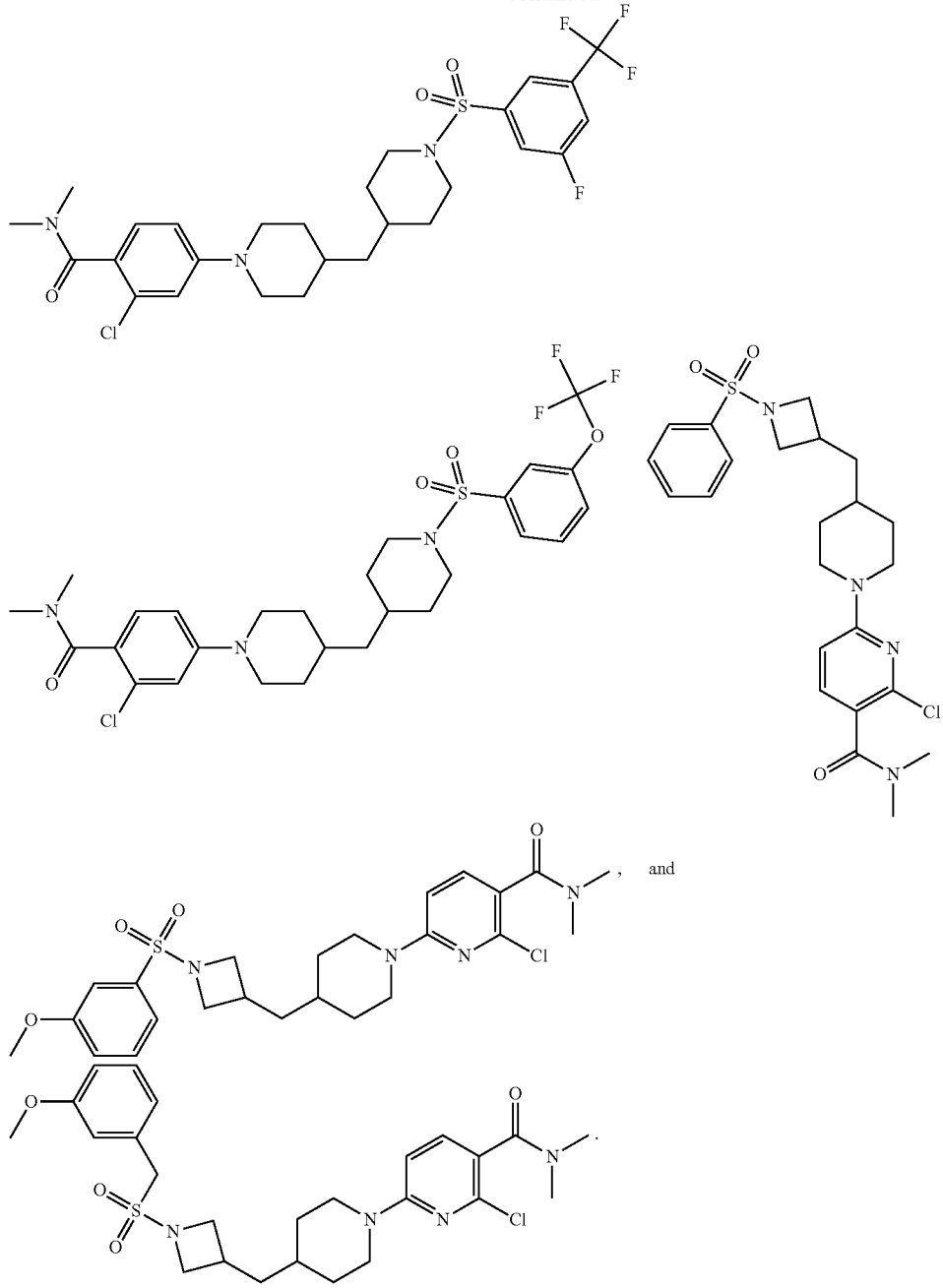
10. A pharmaceutical composition comprising a compound according to claim 1, a pharmaceutically acceptable salt thereof, and a pharmaceutically acceptable carrier or diluent.
* * * * *